(12) United States Patent
Gottschling et al.

(10) Patent No.: US 8,829,006 B2
(45) Date of Patent: Sep. 9, 2014

(54) COMPOUNDS

(75) Inventors: Dirk Gottschling, Mittelbiberach (DE);
Georg Dahmann, Attenweiler (DE);
Henri Doods, Warthausen (DE);
Annekatrin Heimann, Biberach (DE);
Stephan Georg Mueller, Warthausen (DE); Klaus Rudolf, Warthausen (DE);
Gerhard Schaenzle, Warthausen (DE);
Dirk Stenkamp, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 866 days.

(21) Appl. No.: 12/743,004

(22) PCT Filed: Nov. 21, 2008

(86) PCT No.: PCT/EP2008/065960
§ 371 (c)(1),
(2), (4) Date: Sep. 13, 2010

(87) PCT Pub. No.: WO2009/065919
PCT Pub. Date: May 28, 2009

(65) Prior Publication Data
US 2011/0195954 A1 Aug. 11, 2011

(30) Foreign Application Priority Data

Nov. 22, 2007 (EP) .................... 07121347

(51) Int. Cl.
*A61K 31/506* (2006.01)
*C07D 239/32* (2006.01)
*A61P 25/06* (2006.01)
*C07D 471/04* (2006.01)
*C07D 401/14* (2006.01)

(52) U.S. Cl.
CPC ............ *C07D 401/14* (2013.01); *C07D 471/04* (2013.01); *C07D 239/32* (2013.01); *A61K 31/506* (2013.01)
USPC .......... 514/256; 514/258.1; 544/328; 544/329

(58) Field of Classification Search
CPC ........................... A61K 31/506; C07D 239/32
USPC ......... 514/215, 221, 213.01, 264.1, 303, 256, 514/258.1; 544/328, 279, 229; 540/504; 546/118
See application file for complete search history.

(56) References Cited

U.S. PATENT DOCUMENTS

| | | | |
|---|---|---|---|
| 6,689,754 | B1 | 2/2004 | Chandrakumar et al. |
| 8,110,575 | B2 | 2/2012 | Gottschling et al. |
| 2007/0099903 | A1 | 5/2007 | Mueller et al. |
| 2011/0059954 | A1 | 3/2011 | Gottschling et al. |
| 2011/0172218 | A1 | 7/2011 | Gottschling et al. |
| 2011/0195954 | A1 | 8/2011 | Gottschling et al. |
| 2012/0149698 | A1 | 6/2012 | Gottschling et al. |
| 2012/0196872 | A1 | 8/2012 | Dreyer et al. |
| 2013/0029975 | A1 | 1/2013 | Gottschling et al. |

FOREIGN PATENT DOCUMENTS

| | | |
|---|---|---|
| CA | 2609392 A1 | 11/2006 |
| WO | 9952896 A1 | 10/1999 |
| WO | 0055154 A1 | 9/2000 |
| WO | 0132648 A1 | 5/2001 |
| WO | 0222592 A2 | 3/2002 |
| WO | 03040128 A1 | 5/2003 |
| WO | 2004037810 A1 | 5/2004 |
| WO | 2004037811 A1 | 5/2004 |
| WO | 2005030751 A2 | 4/2005 |
| WO | 2005100343 A1 | 10/2005 |
| WO | 2005103037 A2 | 11/2005 |
| WO | 2006031513 A2 | 3/2006 |
| WO | 2006100009 A1 | 9/2006 |
| WO | 2006127588 A2 | 11/2006 |
| WO | 2007000340 A2 | 1/2007 |
| WO | 2007045672 A1 | 4/2007 |
| WO | 2008020902 A1 | 2/2008 |
| WO | 2008070014 A2 | 6/2008 |
| WO | 2009034029 A2 | 3/2009 |
| WO | 2009050232 A1 | 4/2009 |

OTHER PUBLICATIONS

International Search Report, Form PCT/ISA/210, for corresponding PCT/EP2008/065960, Date of mailing Jul. 16, 2009.
Doods et al., CGRP antagonists: unravelling the role of CGRP in migraine, Trends in Pharmacological Sciences, 2007, vol. 28, No. 11, pp. 580-587.

*Primary Examiner* — Sreeni Padmanabhan
*Assistant Examiner* — Sahar Javanmard
(74) *Attorney, Agent, or Firm* — Michael P. Morris; Alan R. Stempel

(57) ABSTRACT

The present invention relates to new CGRP-antagonists of general formula I

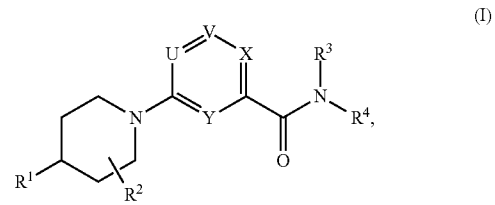

wherein U, V, X, Y, $R^1$, $R^2$, $R^3$ and $R^4$ are defined as mentioned in the description, the tautomers thereof, the isomers thereof, the diastereomers thereof, the enantiomers thereof, the hydrates thereof, the mixtures thereof and the salts thereof as well as the hydrates of the salts, particularly the physiologically acceptable salts thereof with inorganic or organic acids or bases, medicaments containing these compounds, the use thereof and processes for the preparation thereof.

22 Claims, No Drawings

COMPOUNDS

The present invention relates to new CGRP-antagonists of general formula I

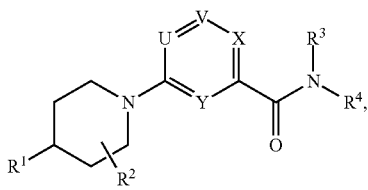

(I)

wherein U, V, X, Y, $R^1$, $R^2$, $R^3$ and $R^4$ are defined as mentioned hereinafter, the tautomers thereof, the isomers thereof, the diastereomers thereof, the enantiomers thereof, the hydrates thereof, the mixtures thereof and the salts thereof as well as the hydrates of the salts, particularly the physiologically acceptable salts thereof with inorganic or organic acids or bases, medicaments containing these compounds, the use thereof and processes for the preparation thereof.

DETAILED DESCRIPTION OF THE INVENTION

In the above general formula I in a first embodiment $R^1$ denotes a group of general formula II

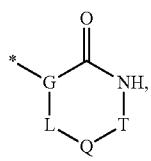

(II)

wherein

G-L denotes N,N—C($R^{5.1}$)$_2$, C=C($R^{5.1}$), C=N, C($R^{5.1}$), C($R^{5.1}$)—C($R^{5.1}$)$_2$, C($R^{5.1}$)—C($R^{5.1}$)$_2$—C($R^{5.1}$)$_2$, C=C($R^{5.1}$)—C($R^{5.1}$)$_2$, C($R^{5.1}$)—C($R^{5.1}$)=C($R^{5.1}$), C($R^{5.1}$)—C($R^{5.1}$)$_2$—N($R^{5.2}$), C=C($R^{5.1}$)—N($R^{5.2}$), C($R^{5.1}$)=C($R^{5.1}$)=N, C($R^{5.1}$)—N($R^{5.2}$)—C($R^{5.1}$)$_2$, C=N—C($R^{5.1}$)—N=C($R^{5.1}$), C($R^{5.1}$)—N=C($R^{5.1}$), C($R^{5.1}$)—N($R^{5.2}$)—N($R^{5.2}$), C=N—N($R^{5.2}$), N—C($R^{5.1}$)$_2$—C($R^{5.1}$)$_2$, N—C($R^{5.1}$)=C($R^{5.1}$), N—C($R^{5.1}$)$_2$—N($R^{5.2}$), N—C($R^{5.1}$)=N, N—N($R^{5.2}$)—C($R^{5.1}$)$_2$ or N—N=C($R^{5.1}$), Q-T denotes C($R^6$)$_2$—C($R^6$)$_2$, C($R^6$)=C($R^6$), N=C($R^6$), C($R^6$)$_2$—C(=O), C(=O)—C($R^6$)$_2$, C($R^6$)$_2$—S(O), or C($R^6$)$_2$—N($R^6$), while a group C($R^6$)$_2$ contained in Q-T may also denote a cyclic group, which is selected from among $C_{3-6}$-cycloalkyl, $C_{5-6}$-cycloalkenyl or heterocyclyl, or in a group C($R^6$)$_2$—C($R^6$)$_2$, C($R^6$)=C($R^6$) or C($R^6$)$_2$—N($R^6$) contained in Q-T in each case a group $R^6$ together with an adjacent group $R^6$ and the atoms to which these groups are attached may also denote a $C_{3-6}$-cycloalkyl, $C_{5-6}$-cycloalkenyl, heterocyclyl, aryl or heteroaryl group, which may be substituted independently of one another by 1, 2 or 3 substituents $R^{6.1}$, $R^2$ denotes
(a) H,
(b) F, —CN, $C_{1-3}$-alkyl, —$CO_2$—$R^{2.1}$ or
(c) a $C_{1-3}$-alkyl group wherein each methylene group is substituted by up to two fluorine atoms and each methyl group is substituted by up to three fluorine atoms, $R^{2.1}$ denotes H or $C_{1-6}$-alkyl, $R^3$ denotes
(a) H,
(b) $C_{1-6}$-alkylene-$R^{3.1}$,
(c) a $C_{3-6}$-cycloalkyl group substituted by one or two groups $R^{3.2}$,
(d) a $C_{5-7}$-cycloalkenyl group substituted by one or two groups $R^{3.2}$,
(e) an aryl group substituted by one or two groups $R^{3.2}$,
(f) a heterocyclyl group substituted by one or two groups $R^{3.2}$,
(g) a $C_{5-7}$-cycloalkyl group which may be fused to an aryl or heteroaryl group and is additionally substituted by one or two groups $R^{3.2}$,
(h) a heteroaryl group substituted by one or two groups $R^{3.2}$,
(i) a $C_{1-3}$-alkyl group wherein each methylene group is substituted by up to two fluorine atoms and each methyl group is substituted by up to three fluorine atoms, $R^{3.1}$ denotes
(a) H,
(b) an aryl group substituted by the groups $R^{3.1.1}$ and $R^{3.1.2}$,
(c) a heteroaryl group substituted by the groups $R^{3.1.1}$ and $R^{3.1.2}$, $R^{3.1.1}$ denotes
(a) H,
(b) halogen, $C_{1-3}$-alkyl, —OH, —CN, —O—$C_{1-3}$-alkyl, —O—C(O)—$C_{1-3}$-alkyl, —$NR^{3.1.1.1}R^{3.1.1.2}$, —S(O)$_-$—$C_{1-3}$-alkyl, —C(O)—$NR^{3.1.1.1}R^{3.1.1.2}$, —O—C(O)—$NR^{3.1.1.1}R^{3.1.1.2}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{3.1.1.1}$ denotes H, $C_{1-3}$-alkyl and
$R^{3.1.1.2}$ denotes H, $C_{1-3}$-alkyl, or
$R^{3.1.1.1}$ and $R^{3.1.1.2}$ together with the nitrogen atom to which they are attached also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{3.1.1.3}$ denotes H, $C_{1-3}$-alkyl, $R^{3.1.2}$ denotes
(a) H,
(b) halogen, $C_{1-3}$-alkyl, —OH, —CN, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, or $R^{3.2}$ independently of one another denote
(a) H,
(b) halogen, $C_{1-3}$-alkyl, —OH, —CN, —O—$C_{1-3}$-alkyl, —O—C(O)—$C_{1-3}$-alkyl, —$NR^{3.2.1}R^{3.2.2}$, —S(O)$_m$—$C_{1-3}$-alkyl, —$NR^{3.2.1}$—C(O)—$C_{1-3}$-alkyl, —C(O)—$NR^{3.2.1}R^{3.2.2}$, —C(O)—O—$R^{3.2.3}$, —$NR^{3.2.1}$—C(O)—O—$C_{1-3}$-alkyl, —O—C(O)—$NR^{3.2.1}R^{3.2.2}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{3.2.1}$ denotes H, $C_{1-3}$-alkyl and
$R^{3.2.2}$ denotes H, $C_{1-3}$-alkyl, or
$R^{3.2.1}$ and $R^{3.2.2}$ together with the nitrogen atom to which they are attached also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{3.2.3}$ denotes H, $C_{1-3}$-alkyl, $R^4$ denotes
- (a) H,
- (b) $C_{1-6}$-alkylene-$R^{4.1}$,
- (c) a $C_{3-6}$-cycloalkyl group substituted by one or two groups $R^{4.2}$,
- (d) a $C_{6-7}$-cycloalkenyl group substituted by one or two groups $R^{4.2}$,
- (e) an aryl group substituted by one or two groups $R^{4.2}$,
- (f) a heterocyclyl group substituted by one or two groups $R^{4.2}$,
- (g) a $C_{6-7}$-cycloalkyl group which may be fused to an aryl or heteroaryl group and is additionally substituted by one or two groups $R^{4.2}$,
- (h) a heteroaryl group substituted by one or two groups $R^{4.2}$,
- (i) a $C_{1-3}$-alkyl group wherein each methylene group is substituted by up to two fluorine atoms and each methyl group is substituted by up to three fluorine atoms, $R^{4.1}$ denotes
- (a) H,
- (b) an aryl group substituted by the groups $R^{4.1.1}$ and $R^{4.1.2}$,
- (c) a heteroaryl group substituted by the groups $R^{4.1.1}$ and $R^{4.1.2}$, $R^{4.1.1}$ denotes
- (a) H,
- (b) halogen, $C_{1-3}$-alkyl, —OH, —CN, —O—$C_{1-3}$-alkyl, —O—C(O)—$C_{1-3}$-alkyl, —$NR^{4.1.1.1}R^{4.1.1.2}$, —$S(O)_m$—$C_{1-3}$-alkyl, —$NR^{4.1.1.1}$-C(O)—$C_{1-3}$-alkyl, —C(O)—$NR^{4.1.1.1}R^{4.1.1.2}$, —C(O)—O—$R^{4.1.1.3}$, —$NR^{4.1.1.3}$,—$^{NR4.1.1.1}$-C(O)—O—$C_{1-3}$-alkyl, —O—C(O)—$NR^{4.1.1.1}R^{4.1.1.2}$,
- (c) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl and
$R^{4.1.1.2}$ denotes H, $C_{1-3}$-alkyl, or
$R^{4.1.1.1}$ and $R^{4.1.1.2}$ together with the nitrogen atom to which they are attached also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{4.1.1.3}$ denotes H, $C_{1-3}$-alkyl, $R^{4.1.2}$ denotes
- (a) H,
- (b) halogen, $C_{1-3}$-alkyl, —OH, —CN, —O—$C_{1-3}$-alkyl,
- (c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ independently of one another denote
- (a) H,
- (b) halogen, $C_{1-3}$-alkyl, —OH, —CN, —O—$C_{1-3}$-alkyl, —O—C(O)—$C_{1-3}$-alkyl, —$NR^{4.2.1}R^{4.2.2}$, —$S(O)_m$—$C_{1-3}$-alkyl, —$NR^{4.2.1}$-C(O)—$C_{1-3}$-alkyl, —C(O)—$NR^{4.2.1}R^{4.2.2}$, —C(O)—O—$R^{4.2.3}$, —$NR^{4.2.1}$-C(O)—O—$C_{1-3}$-alkyl, —O—C(O)—$NR^{4.2.1}R^{4.2.2}$,
- (c) a $C_{1-3}$-alkyl- or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are attached also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{4.2.3}$ denotes H, $C_{1-3}$-alkyl, $R^3$ and $R^4$ together with the nitrogen atom to which they are attached denote:
- (a) a saturated 5-, 6- or 7-membered heterocyclic group, which is substituted at a carbon atom by a group $R^{4.3}$ or by two groups $R^{4.3}$ and $R^{4.4}$,
- (b) a saturated 5-, 6- or 7-membered heterocyclic group, which is substituted at each of two adjacent carbon atoms by a group $R^{4.3}$ and $R^{4.4}$,
- (c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
- (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
- (e) a monounsaturated 5-, 6- or 7-membered heterocyclic group, which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
- (f) a heteroaryl group, which is substituted at 1, 2 or 3 carbon atoms by a group $R^{4.5}$ in each case, $R^{4.3}$ independently of one another denote
- (a) H, $C_{1-3}$-alkyl, $C_{2-4}$-alkenyl, $C_{2-6}$-alkynyl, aryl, —$C_{1-3}$-alkylene-$R^{4.3.1}$, $C_{1-3}$-alkyl-O—C(O), HO—C(O), F, —O—$C_{1-3}$-alkyl, —OH, —CN,
- (b) a $C_{1-3}$-alkyl or —O—$C_{1-3}$-alkyl group wherein each methylene group is substituted by up to two fluorine atoms and each methyl group is substituted by up to three fluorine atoms,
- (c) a 5- or 6-membered heteroaryl group,
- (d) aryl, $R^{4.3.1}$ denotes H, HO, $C_{1-3}$-alkyl-O—, $C_{1-3}$-alkyl-O—C(O)—, —CN, —$NH_2$, ($C_{1-4}$-alkyl)-NH—, ($C_{1-4}$-alkyl)$_2$N, $C_{3-6}$-cycloalkyl, heterocyclyl, heteroaryl, aryl, $R^{4.4}$ denotes
- (a) H, $C_{1-3}$-alkyl, —OH, —O—$C_{1-3}$-alkyl or
- (b) a $C_{1-3}$-alky-l or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached also denote a $C_{3-6}$-cycloalkyl-, $C_{5-6}$-cycloalkenyl- or heterocyclyl group, $R^{4.5}$ independently of one another denotes
- (a) H,
- (b) halogen, $C_{1-3}$-alkyl, —OH, —O—$C_{1-3}$-alkyl, —S(O)$_m$—$C_{1-3}$-alkyl, —NR$^{4.5.2}$R$^{4.5.3}$, —CN, —C(O)—O—R$^{4.5.1}$, —C(O)—NR$^{4.5.2}$R$^{4.5.3}$,
- (c) a $C_{1-3}$-alkyl- or —O—$C_{1-3}$-alkyl group wherein each methylene group is substituted by up to two fluorine atoms and each methyl group is substituted by up to three fluorine atoms,
- (d) aryl, heteroaryl, $R^{4.5.1}$ denotes H, $C_{1-3}$-alkyl,
$R^{4.5.2}$ denotes H, $C_{1-3}$-alkyl,
$R^{4.5.3}$ denotes H, $C_{1-3}$-alkyl, or
$R^{4.5.2}$ and $R^{4.5.3}$ together with the nitrogen atom to which they are attached also denote a group which is selected from morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{5.1}$ denotes
- (a) H,
- (b) $C_{1-6}$-alkyl, —CN, —OH, —O—$C_{1-3}$-alkyl,
- (c) a $C_{1-3}$-alkyl- or $C_{1-3}$-alkyl-O— group wherein each methylene group is substituted by up to two fluorine atoms and each methyl group is substituted by up to three fluorine atoms, $R^{5.2}$ denotes H or $C_{1-6}$-alkyl,
$R^6$ independently of one another denotes
- (a) H, $C_{1-6}$-alkyl, $C_{2-6}$-alkenyl, $C_{2-6}$-alkynyl, $C_{3-6}$-cycloalkyl,
- (b) an aryl group optionally substituted by 1, 2 or 3 substituents $R^{6.2}$, wherein the substituents $R^{6.2}$ may be identical or different,
- (c) a heteroaryl group optionally substituted by 1, 2 or 3 substituents $R^{6.2}$, wherein the substituents $R^{6.2}$ may be identical or different,
- (d) a heterocyclic group optionally substituted by 1, 2 or 3 substituents $R^{6.2}$, wherein the substituents $R^{6.2}$ may be identical or different, $R^{6.1}$ denotes
- (a) H, halogen, $C_{1-6}$-alkyl, $C_{3-6}$-cycloalkyl,
- (b) —O—$C_{1-6}$-alkylene-NR$^8$R$^9$, —O—R$^7$, —O—(CH$_2$)$_s$—O—R$^7$, —CO$_2$—R$^7$, —C(O)—NR$^8$R$^9$, —O—C(O)—NR$^8$R$^9$, —NR$^7$—C(O)—NR$^8$R$^9$, —NR$^8$—C(O)—R$^9$, —NR$^8$—C(O)—O—R$^9$, —SO$_2$—NR$^8$R$^9$, —NR$^8$—SO$_2$—R$^9$, —S(O)$_m$—R$^8$, —CN, —NR$^8$R$^9$, —NR$^7$—C(O)—NR$^8$R$^9$, —O—C(O)—R$^7$,
- (c) a $C_{1-3}$-alkyl- or $C_{1-3}$-alkyl-O— group wherein each methylene group is substituted by up to two fluorine atoms and each methyl group is substituted by up to three fluorine atoms,
- (d) an aryl group substituted by 1, 2 or 3 substituents $R^7$, wherein the substituents $R^7$ may be identical or different,
- (e) a heteroaryl group substituted by 1, 2 or 3 substituents $R^7$, wherein the substituents $R^7$ may be identical or different,
- (f) a heterocyclic group substituted by 1, 2 or 3 substituents $R^7$, wherein the substituents $R^7$ may be identical or different, $R^{6.2}$ denotes
- (a) halogen, $C_{1-6}$-alkyl, $C_{3-6}$-cycloalkyl,
- (b) —O—R$^7$, —O—(CH$_2$)$_s$—O—R$^7$, —CO$_2$R$^7$, —C(O)—NR$^8$R$^9$, —O—(CO)—NR$^8$R$^9$, —N(R$^7$)—C(O)—NR$^8$R$^9$, —N(R$^8$)—C(O)—R$^9$, —N(R$^8$)—C(O)—O—R$^9$, —SO$_2$—NR$^8$R$^9$, —N(R$^8$)—SO$_2$—R$^9$, —S(O)$_m$—R$^8$, —CN, —NR$^8$R$^9$, —N(R$^7$)—C(O)—NR$^8$R$^9$, —O—C(O)—R$^7$ or
- (c) a $C_{1-3}$-alkyl group wherein each methylene group is substituted by up to two fluorine atoms and each methyl group is substituted by up to three fluorine atoms, $R^7$ denotes
- (a) H,
- (b) $C_{1-6}$-alkyl, $C_{3-6}$-cycloalkyl, aryl, heteroaryl, benzyl, which may be substituted by a group $R^{7.1}$, or
- (c) a $C_{1-3}$-alkyl group wherein each methylene group is substituted by up to two fluorine atoms and each methyl group is substituted by up to three fluorine atoms, $R^{7.1}$ denotes halogen, HO— or $C_{1-6}$-alkyl-O—,
$R^8$ denotes
- (a) H,
- (b) $C_{1-6}$-alkyl, $C_{3-6}$-cycloalkyl, aryl, heteroaryl or benzyl, wherein the groups are unsubstituted or may be substituted by halogen, HO— or $C_{1-6}$-alkyl-O—, or
- (c) a $C_{1-3}$-alkyl-group wherein each methylene group is substituted by up to two fluorine atoms and each methyl group is substituted by up to three fluorine atoms, $R^9$ denotes
- (a) H,
- (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$ or fluorine, wherein the substituents $R^7$ are independent of one another, m denotes one of the numbers 0, 1 or 2,
s denotes one of the numbers 1, 2 or 3,
U denotes N,N-oxide or C—R$^{10}$,
V denotes N,N-oxide or C—R$^{11}$,
X denotes N,N-oxide or C—R$^{12}$,
Y denotes N or C—R$^{13}$,
while at most three of the previously mentioned groups U, V, X and Y simultaneously denote a nitrogen atom, $R^{10}$ denotes H, halogen, —CN, $C_{1-3}$-alkyl, —CF$_3$, $C_{2-6}$-alkynyl, HO—$C_{2-6}$-alkynylene,
$R^{11}$ denotes H, $C_1$, $C_{1-3}$-alkyl, —NR$^{11.1}$R$^{11.2}$ or —O—$C_{1-3}$-alkyl,
$R^{11.1}$ denotes H or $C_{1-6}$-alkyl,
$R^{11.2}$ denotes H or —SO$_2$—$C_{1-3}$-alkyl,
$R^{12}$ denotes H, halogen, —CN, $C_{1-3}$-alkyl, —CF$_3$, $C_{2-6}$-alkynyl and
$R^{13}$ denotes H, halogen or $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A second embodiment of the present invention consists in the compounds of the above general formula I, wherein U, V, X, Y, R$^2$, R$^3$ and R$^4$ are as hereinbefore defined in the first embodiment and $R^1$ denotes a group of general formula II

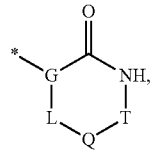

(II)

wherein

G-L denotes $N,N\text{—}C(R^{5.1})_2$, $C\text{=}C(R^{5.1})$, $C\text{=}N$, $C(R^{5.1})$, $C(R^{5.1})\text{—}C(R^{5.1})_2$, $C(R^{5.1})\text{—}C(R^{5.1})_2\text{—}C(R^{5.1})_2$, $C\text{=}C(R^{5.1})\text{—}C(R^{5.1})_2$, $C(R^{5.1})\text{—}C(R^{5.1})\text{=}C(R^{5.1})$, $C(R^{5.1})\text{—}C(R^{5.1})_2\text{—}N(R^{5.2})$, $C\text{=}C(R^{5.1})\text{—}N(R^{5.2})$, $C(R^{5.1})\text{—}C(R^{5.1})\text{=}N$, $C(R^{5.1})\text{—}N(R^{5.2})\text{—}C(R^{5.1})_2$, $C\text{=}N\text{—}C(R^{5.1})_2$, $C(R^{5.1})\text{—}N\text{=}C(R^{5.1})$, $C(R^{5.1})\text{—}N(R^{5.2})\text{—}N(R^{5.2})$, $C\text{=}N\text{—}N(R^{5.2})$, $N\text{—}C(R^{5.1})_2\text{—}C(R^{5.1})_2$, $N\text{—}C(R^{5.1})\text{=}C(R^{5.1})$, $N\text{—}C(R^{5.1})_2\text{—}N(R^{5.2})$, $N\text{—}C(R^{5.1})\text{=}N$, $N\text{—}N(R^{5.2})\text{—}C(R^{5.1})_2$ or $N\text{—}N\text{=}C(R^{5.1})$, Q-T denotes $C(R^6)_2\text{—}C(R^6)_2$, $C(R^6)\text{=}C(R^6)$, $N\text{=}C(R^6)$, $C(R^6)_2\text{—}C(\text{=}O)$, $C(\text{=}O)\text{—}C(R^6)_2$, $C(R^6)_2\text{—}S(O)_m$ or $C(R^6)_2\text{—}N(R^6)$, while a group $C(R^6)_2$ contained in Q-T may also denote a cyclic group, which is selected from among cyclobutyl, cyclopentyl, cyclohexyl, cyclopentenyl, cyclohexenyl, dioxanyl, morpholinyl, thiomorpholinyl, thiomorpholinyl-5-oxide, thiomorpholinyl-5-dioxide, azetidinyl, pyrrolidinyl, piperidinyl, tetrahydrofuranyl, tetrahydropyranyl and piperazinyl, or in a group $C(R^6)_2\text{—}C(R^6)_2$, $C(R^6)\text{=}C(R^6)$ or $C(R^6)_2\text{—}N(R^6)$ contained in Q-T in each case a group $R^6$ together with an adjacent group $R^6$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-5-oxide, thiomorpholinyl-5-dioxide, 1H-quinolinyl-2-on, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{6.1}$, $R^{5.1}$ denotes
(a) H,
(b) $C_{1-6}$-alkyl, —CN, —OH, —O—$C_{1-3}$-alkyl,
(c) a $C_{1-3}$-alkyl- or $C_{1-3}$-alkyl-O— group wherein each methylene group is substituted by up to two fluorine atoms and each methyl group is substituted by up to three fluorine atoms, $R^{5.2}$ denotes H or $C_{1-6}$-alkyl, $R^6$ independently of one another denote
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{6.2}$, wherein the substituents $R^{6.2}$ may be identical or different,
(c) a heteroaryl group optionally substituted by 1, 2 or 3 substituents $R^{6.2}$, wherein the substituents $R^{6.2}$ may be identical or different,
(d) a heterocyclic group optionally substituted by 1, 2 or 3 substituents $R^{6.2}$, wherein the substituents $R^{6.2}$ may be identical or different, $R^{6.1}$ denotes
(a) H, halogen, $C_{1-6}$-alkyl, $C_{3-6}$-cycloalkyl,
(b) —O—$C_{1-6}$-alkylene-$NR^8R^9$, —O—$R^7$, —O—$(CH_2)_s$—O—$R^7$, —$CO_2$—$R^7$, $C(O)$—$NR^8R^9$, —O—$C(O)$—$NR^8R^9$, —$NR^7$—$C(O)$—$NR^8R^9$, —$NR^8$—$C(O)$—$R^9$, —$NR^8$—$C(O)$—O—$R^9$, —$SO_2$—$NR^8R^9$, —$NR^8$—$SO_2$—$R^9$, —$S(O)_m$—$R^8$, —CN, —$NR^8R^9$, —$NR^7$—$C(O)$—$NR^8R^9$, —O—$C(O)$—$R^7$,
(c) a $C_{1-3}$-alkyl- or $C_{1-3}$-alkyl-O— group wherein each methylene group is substituted by up to two fluorine atoms and each methyl group is substituted by up to three fluorine atoms,
(d) an aryl group substituted by 1, 2 or 3 substituents $R^7$, wherein the substituents $R^7$ may be identical or different,
(e) a heteroaryl group substituted by 1, 2 or 3 substituents $R^7$, wherein the substituents $R^7$ may be identical or different,
(f) a heterocyclic group substituted by 1, 2 or 3 substituents $R^7$, wherein the substituents $R^7$ may be identical or different, $R^{6.2}$ denotes
(a) halogen, $C_{1-6}$-alkyl, $C_{3-6}$-cycloalkyl,
(b) —O—$R^7$, —O—$(CH_2)_s$—O—$R^7$, —$CO_2R^7$, —$C(O)$—$NR^8R^9$, —O—$(CO)$—$NR^8R^9$, —$N(R^7)$—$C(O)$—$NR^8R^9$, —$N(R^8)$—$C(O)$—$R^9$, —$N(R^8)$—$C(O)$—$O$—$R^9$, —$SO_2$—$NR^8R^9$, —$N(R^8)$—$SO_2$—$R^9$, —$S(O)_m$—$R^8$, CN, $NR^8R^9$, —$N(R^7)$—$C(O)$—$NR^8R^9$, —O—$C(O)$—$R^7$ or
(c) a $C_{1-3}$-alkyl group wherein each methylene group is substituted by up to two fluorine atoms and each methyl group is substituted by up to three fluorine atoms, $R^7$ denotes
(a) H,
(b) $C_{1-6}$-alkyl, $C_{3-6}$-cycloalkyl, aryl, heteroaryl, benzyl, which may be substituted by a group $R^{7.1}$, or
(c) a $C_{1-3}$-alkyl group wherein each methylene group is substituted by up to two fluorine atoms and each methyl group is substituted by up to three fluorine atoms, $R^{7.1}$ denotes halogen, HO— or $C_{1-6}$-alkyl-O—, $R^8$ denotes
(a) H,
(b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^9$ denotes
(a) H,
(b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$ or fluorine, wherein the substituents $R^7$ are independent of one another, m denotes one of the numbers 0, 1 or 2 and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A third embodiment of the present invention consists in the compounds of the above general formula I, wherein U, V, X, Y, $R^2$, $R^3$ and $R^4$ are as hereinbefore defined in the first embodiment and
$R^1$ denotes a group of general formulae

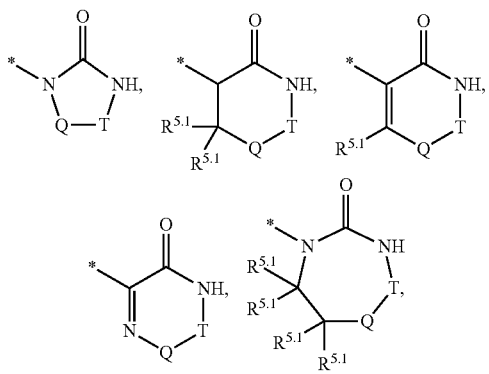

wherein
Q-T denotes $C(R^6)_2—C(R^6)_2$, $C(R^6)=C(R^6)$, $N=C(R^6)$, $C(R^6)_2—C(=O)$, $C(=O)—C(R^6)_2$, $C(R^6)_2—S(O)_m$ or $C(R^6)_2—N(R^6)$, while in a group $C(R^6)_2—C(R^6)_2$, $C(R^6)=C(R^6)$ or $C(R^6)_2—N(R^6)$ contained in Q-T in each case a group $R^6$ together with an adjacent group $R^6$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{6.1}$,
$R^{5.1}$ denotes
  (a) H,
  (b) $C_{1-6}$-alkyl, —CN, —OH, —O—$C_{1-3}$-alkyl,
  (c) a $C_{1-3}$-alkyl or $C_{1-3}$-alkyl-O— group wherein each methylene group is substituted by up to two fluorine atoms and each methyl group is substituted by up to three fluorine atoms,
$R^6$ independently of one another denotes
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{6.2}$, wherein the substituents $R^{6.2}$ may be identical or different,
  (c) a heteroaryl group optionally substituted by 1, 2 or 3 substituents $R^{6.2}$, wherein the substituents $R^{6.2}$ may be identical or different,
  (d) a heterocyclic group optionally substituted by 1, 2 or 3 substituents $R^{6.2}$, wherein the substituents $R^{6.2}$ may be identical or different,
$R^{6.1}$ denotes
  (a) H, halogen, $C_{1-6}$-alkyl, $C_{3-6}$-cycloalkyl,
  (b) —O—$C_{1-6}$-alkylene-$NR^8R^9$, —O—$R^7$, —$CO_2R^7$, —C(O)$NR^8R^9$, —$SO_2$—$NR^8R^9$, —$N(R^8)$—$SO_2$—$R^9$, —S(O)$_m$—$R^8$, —CN, —$NR^8R^9$, —O—C(O)—$R^7$ or
  (c) a $C_{1-3}$-alkyl group wherein each methylene group is substituted by up to two fluorine atoms and each methyl group is substituted by up to three fluorine atoms,
$R^{6.2}$ denotes
  (a) halogen, $C_{1-6}$-alkyl, $C_{3-6}$-cycloalkyl,
  (b) —O—$R^7$, —O—$(CH_2)_s$—O—$R^7$, —$CO_2R^7$, —S(O)$_m$—$R^8$, —CN, —O—C(O)—$R^7$ or
  (c) a $C_{1-3}$-alkyl group wherein each methylene group is substituted by up to two fluorine atoms and each methyl group is substituted by up to three fluorine atoms,
$R^7$ denotes
  (a) H,
  (b) $C_{1-6}$-alkyl, $C_{3-6}$-cycloalkyl, aryl, heteroaryl, benzyl, which may be substituted by a group $R^{7.1}$, or
  (c) a $C_{1-3}$-alkyl group wherein each methylene group is substituted by up to two fluorine atoms and each methyl group is substituted by up to three fluorine atoms,
$R^{7.1}$ denotes halogen, HO— or $C_{1-6}$-alkyl-O—,
$R^8$ denotes
  (a) H,
  (b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms,
$R^9$ denotes
  (a) H,
  (b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or
$R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$, wherein the substituents $R^7$ are independent of one another,
m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A fourth embodiment of the present invention consists in the compounds of the above general formula I, wherein U, V, X, Y, $R^2$, $R^3$ and $R^4$ are as hereinbefore defined in the first embodiment and
$R^1$ denotes a group of general formulae

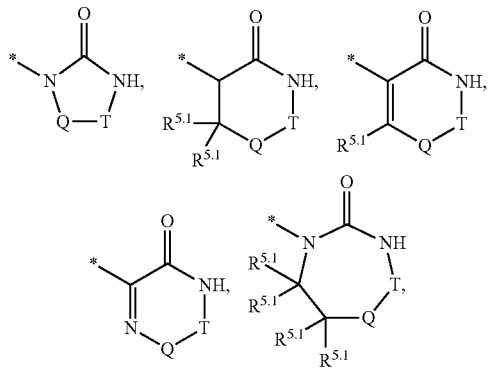

wherein

Q-T denotes C(R⁶)₂—C(R⁶)₂, C(R⁶)═C(R⁶), N═C(R⁶), C(R⁶)₂—C(═O), C(═O)—C(R⁶)₂, C(R⁶)₂—S(O)$_m$ or C(R⁶)₂—N(R⁶), while in a group C(R⁶)₂—C(R⁶)₂, C(R⁶)═C(R⁶) or C(R⁶)₂—N(R⁶) contained in Q-T in each case a group R⁶ together with an adjacent group R⁶ and the atoms to which these groups are attached may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another by 1, 2 or 3 substituents R⁶·¹, R⁵·¹ denotes
(a) H,
(b) $C_{1-6}$-alkyl, —CN, —OH, —O—$C_{1-3}$-alkyl,
(c) a $C_{1-3}$-alkyl or $C_{1-3}$-alkyl-O— group wherein each methylene group is substituted by up to two fluorine atoms and each methyl group is substituted by up to three fluorine atoms, R⁶ denotes
(a) H, $C_{1-6}$-alkyl, $C_{3-6}$-cycloalkyl,
(b) an aryl group optionally substituted by 1, 2 or 3 substituents R⁶·², wherein the substituents R⁶·² may be identical or different,
(c) a heteroaryl group optionally substituted by 1, 2 or 3 substituents R⁶·², wherein the substituents R⁶·² may be identical or different,
(d) a heterocyclic group optionally substituted by 1, 2 or 3 substituents R⁶·², wherein the substituents R⁶·² may be identical or different, R⁶·¹ denotes
(a) H, halogen, $C_{1-6}$-alkyl, $C_{3-6}$-cycloalkyl,
(b) —O—$C_{1-6}$-alkylene-NR⁸R⁹, —O—R⁷, —CO₂R⁷, —C(O)—NR⁸R⁹, —SO₂—NR⁸R⁹, —NR⁸—SO₂—R⁹, —S(O)$_m$—R⁸, —CN, —NR⁸R⁹, —O—C(O)—R⁷ or
(c) a $C_{1-3}$-alkyl group wherein each methylene group is substituted by up to two fluorine atoms and each methyl group is substituted by up to three fluorine atoms, R⁶·² denotes
(a) halogen, $C_{1-6}$-alkyl, $C_{3-6}$-cycloalkyl,
(b) —O—R⁷, —O—(CH₂)$_m$—OR⁷, —CO₂R⁷, —S(O)$_m$—R⁸, —CN, —O—C(O)—R⁷ or
(c) a $C_{1-3}$-alkyl group wherein each methylene group is substituted by up to two fluorine atoms and each methyl group is substituted by up to three fluorine atoms, R⁷ denotes
(a) H,
(b) $C_{1-6}$-alkyl, $C_{3-6}$-cycloalkyl, aryl, heteroaryl, benzyl, which may be substituted by a group R⁷¹, or
(c) a $C_{1-3}$-alkyl group wherein each methylene group is substituted by up to two fluorine atoms and each methyl group is substituted by up to three fluorine atoms, R⁷·¹ denotes halogen, HO— or $C_{1-6}$-alkyl-O—, R⁸ denotes
(a) H,
(b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, R⁹ denotes
(a) H,
(b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or R⁸ and R⁹ together may also form a ring which is selected from among azetidinyl, pyrrolidinyl, piperidinyl, piperazinyl and morpholinyl, wherein the ring may be unsubstituted or substituted by 1, 2 or 3 substituents R⁷, wherein the substituents R⁷ are independent of one another, m denotes one of the numbers 0, 1 or 2 and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifth embodiment of the present invention consists in the compounds of the above general formula I, wherein U, V, X, Y, R², R³ and R⁴ are as hereinbefore defined in the first embodiment and R¹ denotes a group of general formula

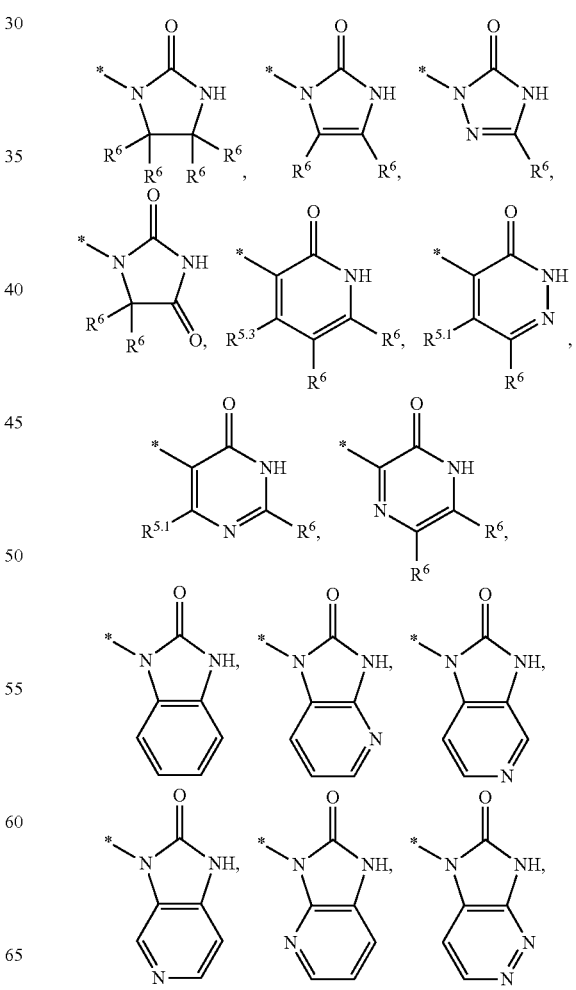

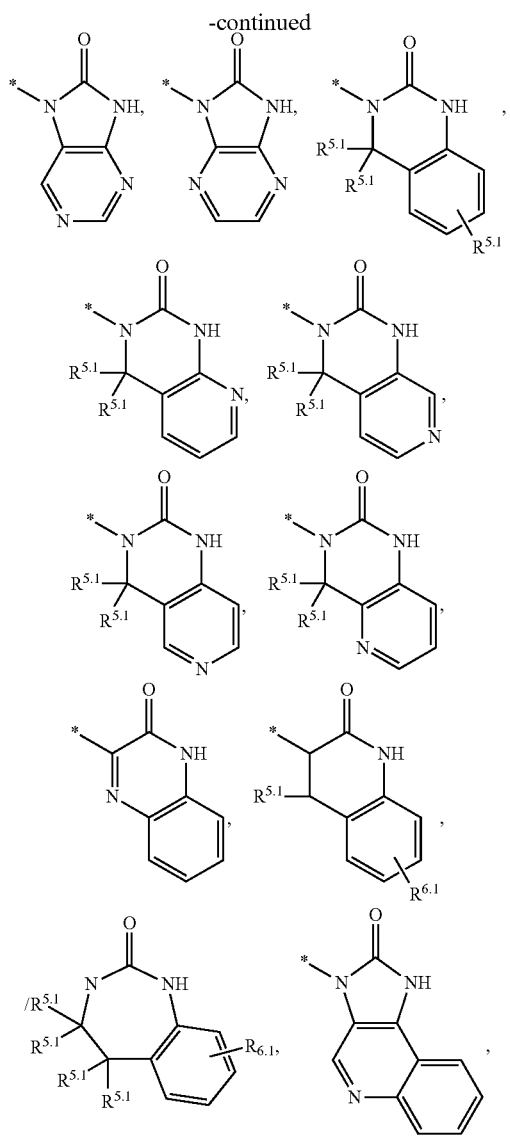

wherein
R^{5.1} denotes
 (a) H,
 (b) $C_{1-3}$-alkyl, —OH, —O—$C_{1-3}$-alkyl,
 (c) a $C_{1-3}$-alkyl or $C_{1-3}$-alkyl-O— group wherein each methylene group is substituted by up to two fluorine atoms and each methyl group is substituted by up to three fluorine atoms,
$R^6$ independently of one another denote
 (a) H, $C_{1-6}$-alkyl, $C_{3-6}$-cycloalkyl,
 (b) a phenyl group optionally substituted by 1, 2 or 3 substituents $R^{6.2}$, wherein the substituents $R^{6.2}$ may be identical or different,
 (c) a heteroaryl group optionally substituted by 1, 2 or 3 substituents $R^{6.2}$ which is selected from among benzimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents $R^{6.2}$ may be identical or different,
 (d) a heterocyclic group optionally substituted by 1, 2 or 3 substituents $R^{6.2}$, wherein the substituents $R^{6.2}$ may be $R^{6.1}$ denotes
 (a) H, halogen, $C_{1-6}$-alkyl, $C_{3-6}$-cycloalkyl,
 (b) —O—$C_{1-6}$-alkylene-$NR^8R^9$, —O—$R^7$, —$CO_2R^7$, —C(O)—$NR^8R^9$, —$SO_2$—$NR^8R^9$, —$NR^8$—$SO_2$—$R^9$, —$S(O)_m$—$R^8$, —CN, —$NR^8R^9$, —O—C(O)—$R^7$ or
 (c) a $C_{1-3}$-alkyl or $C_{1-3}$-alkyl-O— group wherein each methylene group is substituted by up to two fluorine atoms and each methyl group is substituted by up to three fluorine atoms,
$R^{6.2}$ denotes
 (a) halogen, $C_{1-6}$-alkyl, $C_{3-6}$-cycloalkyl,
 (b) —O—$R^7$, —O—$(CH_2)_s$—O—$R^7$, —$CO_2R^7$, —$S(O)_m$—$R^8$, —CN, —O—C(O)—$R^7$ or
 (c) a $C_{1-3}$-alkyl group wherein each methylene group is substituted by up to two fluorine atoms and each methyl group is substituted by up to three fluorine atoms,
$R^7$ denotes
 (a) H,
 (b) $C_{1-6}$-alkyl, $C_{3-6}$-cycloalkyl, aryl, heteroaryl, benzyl, which may be substituted by a group $R^{7.1}$, or
 (c) a $C_{1-3}$-alkyl group wherein each methylene group is substituted by up to two fluorine atoms and each methyl group is substituted by up to three fluorine atoms,
$R^{7.1}$ denotes HO— or $C_{1-6}$-alkyl-O—,
$R^8$ denotes
 (a) H,
 (b) $C_{1-3}$-alkyl, phenyl or benzyl, while the groups are unsubstituted or may be substituted by halogen, HO— or $H_3C$—O—,
$R^9$ denotes
 (a) H,
 (b) $C_{1-3}$-alkyl, phenyl or benzyl, while the groups are unsubstituted or may be substituted by halogen, HO— or $H_3C$—O—, or
$R^8$ and $R^9$ together may also form a ring which is selected from among azetidinyl, pyrrolidinyl, piperidinyl, piperazinyl and morpholinyl, while the ring may be unsubstituted or substituted by a substituent $R^7$,
m denotes one of the numbers 0, 1 or 2, and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A sixth embodiment of the present invention consists in the compounds of the above general formula I, wherein U, V, X, Y, $R^2$, $R^3$ and $R^4$ are as hereinbefore defined in the first embodiment and
$R^1$ denotes a group selected from

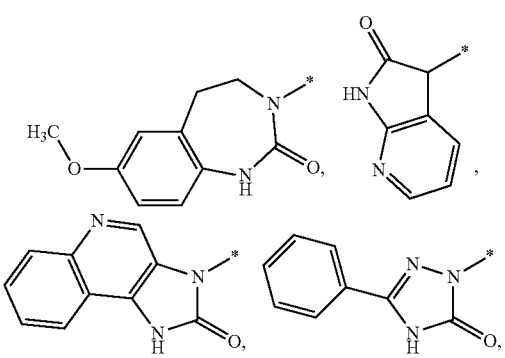

-continued

[chemical structures]

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventh embodiment of the present invention consists in the compounds of the above general formula I, wherein U, V, X, Y, $R^1$, $R^3$ and $R^4$ are as hereinbefore defined in the first, second, third, fourth, fifth or sixth embodiment and $R^2$ denotes a hydrogen atom, the tautomers, the diastereomers, the enantiomers, the hydrates, the mixtures thereof and the salts thereof as well as the hydrates of the salts, particularly the physiologically acceptable salts thereof with inorganic or organic acids or bases.

An eighth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes (a) H,
(b) $C_{1-6}$-alkyl,
(c) a $C_{3-6}$-cycloalkyl group substituted by one or two groups $R^{3.2}$,
(d) a $C_{1-3}$-alkyl group wherein each methylene group is substituted by up to two fluorine atoms and each methyl group is substituted by up to three fluorine atoms, $R^{3.2}$ independently of one another denote (a) H,
(b) halogen, $C_{1-3}$-alkyl, —OH, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes (a) H,
(b) $C_{1-6}$-alkylene-$R^{4.1}$,
(c) a $C_{3-6}$-cycloalkyl group substituted by one or two groups $R^{4.2}$,
(d) a $C_{6-7}$-cycloalkenyl group substituted by one or two groups $R^{4.2}$,
(e) an aryl group substituted by one or two groups $R^{4.2}$,
(f) a $C_{6-7}$-cycloalkyl group which may be fused to an aryl group and is additionally substituted by one or two groups $R^{4.2}$, or
(g) a heteroaryl group substituted by one or two groups $R^{4.2}$, $R^{4.1}$ denotes (a) H,
(b) a phenyl group substituted by the groups $R^{4.1.1}$ and $R^{4.1.2}$,
(c) a heteroaryl group substituted by the groups $R^{4.1.1}$ and $R^{4.1.2}$, $R^{4.1.1}$ denotes (a) H,
(b) halogen, $C_{1-3}$-alkyl, —OH, —CN, —O—$C_{1-3}$-alkyl, —$NR^{4.1.1.1}R^{4.1.1.2}$, —S—$C_{1-3}$-alkyl, —$NR^{4.1.1.1}$—C(O)—$C_{1-3}$-alkyl, —C(O)—$NR^{4.1.1.1}R^{4.1.1.2}$, C(O)—O—$R^{4.1.1.3}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl,
$R^{4.1.1.2}$ denotes H, $C_{1-3}$-alkyl, or
$R^{4.1.1.1}$ and $R^{4.1.1.2}$ together with the nitrogen atom to which they are attached also denote a group selected from morpholinyl, thiomorpholinyl, piperidinyl, piperazinyl, pyrrolidinyl and azetidinyl,
$R^{4.1.1.3}$ denotes H, $C_{1-3}$-alkyl,
$R^{4.1.2}$ denotes (a) H,
(b) halogen, $C_{1-3}$-alkyl, —OH, —O—$C_{1-3}$-alkyl,
(c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote (a) H,
(b) halogen, $C_{1-3}$-alkyl, —OH, —CN, —O—$C_{1-3}$-alkyl, —$NR^{4.2.1}R^{4.2.2}$, —S—$C_{1-3}$-alkyl, —$NR^{4.2.1}$—C(O)—$C_{1-3}$-alkyl, —C(O)—$NR^{4.2.1}R^{4.2.2}$, —C(O)—O—$R^{4.2.3}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are attached also denote a group which is selected from among morpholinyl, thiomorpholinyl, piperidinyl, piperidonyl, piperazinyl, pyrrolidinyl and azetidinyl, and which may additionally be substituted by one or two groups selected from F, —OH, —O—$C_{1-3}$-alkyl, —$OCF_3$, $C_{1-3}$-alkyl and $CF_3$,
$R^{4.2.3}$ denotes H, $C_{1-3}$-alkyl,
$R^3$ and $R^4$ together with the nitrogen atom to which they are attached denote:

(a) a saturated 5-, 6- or 7-membered heterocyclic group, which is substituted at a carbon atom by a group $R^{4.3}$ or by two groups $R^{4.3}$ and $R^{4.4}$,
(b) a saturated 5-, 6- or 7-membered heterocyclic group, which is substituted at each of two adjacent carbon atoms by a group $R^{4.3}$ and $R^{4.4}$,
(c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
(d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
(e) a monounsaturated 5-, 6- or 7-membered heterocyclic group, which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
(f) a heteroaryl group which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O), HO—C(O), F, —O—$C_{1-3}$-alkyl, —OH, —CN $R^{4.3.1}$ denotes H, HO, $C_{1-3}$-alkyl-O, cyclopropyl, $C_{1-3}$-alkyl-O—C(O), CN, —NH$_2$, ($C_{1-4}$-alkyl)-NH, ($C_{1-4}$-alkyl)$_2$N, heterocyclyl, $R^{4.4}$ denotes
 (a) H, $C_{1-3}$-alkyl, —OH, —O—$C_{1-3}$-alkyl or
 (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached also denote a $C_{3-6}$-cycloalkyl, $C_{5-6}$-cycloalkenyl or heterocyclyl group, $R^{4.5}$ independently of one another denote
 (a) H,
 (b) halogen, $C_{1-3}$-alkyl, —OH, —O—$C_{1-3}$-alkyl, —NH$_2$, —CN, —C(O)—O—$R^{4.5.1}$, —C(O)—N$R^{4.5.2}R^{4.5.3}$,
 (c) a $C_{1-3}$-alkyl- or —O—$C_{1-3}$-alkyl group wherein each methylene group is substituted by up to two fluorine atoms and each methyl group is substituted by up to three fluorine atoms,
 (d) phenyl, $R^{4.5.1}$ denotes H, $C_{1-3}$-alkyl,
$R^{4.5.2}$ denotes H, $C_{1-3}$-alkyl and
$R^{4.5.3}$ denotes H, $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A ninth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes
 (a) H,
 (b) $C_{1-6}$-alkyl,
 (c) a $C_{3-6}$-cycloalkyl substituted by one or two groups $R^{3.2}$, or
 (d) a $C_{1-3}$-alkyl group wherein each methylene group is substituted by up to two fluorine atoms and each methyl group is substituted by up to three fluorine atoms, $R^{3.2}$ independently of one another denote
 (a) H,
 (b) halogen, $C_{1-3}$-alkyl, —OH, —O—$C_{1-3}$-alkyl,
 (c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes
 (a) H,
 (b) $C_{1-6}$-alkylene-$R^{4.1}$,
 (c) a $C_{3-6}$-cycloalkyl group substituted by one or two groups $R^{4.2}$,
 (d) a $C_{3-7}$-cycloalkenyl group substituted by one or two groups $R^{4.2}$,
 (e) an aryl group substituted by one or two groups $R^{4.2}$,
 (f) a $C_{3-6}$-cycloalkyl group which may be fused to a phenyl group and which is additionally substituted by one or two groups $R^{4.2}$, $R^{4.1}$ denotes
 (a) H,
 (b) a phenyl group substituted by the groups $R^{4.1.1}$ and $R^{4.1.2}$, $R^{4.1.1}$ denotes
 (a) H,
 (b) halogen, $C_{1-3}$-alkyl, —OH, —O—$C_{1-3}$-alkyl, —CN, —C(O)—O—$R^{4.1.1.3}$,
 (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.3}$ denotes H, $C_{1-3}$-alkyl,
$R^{4.1.2}$ denotes
 (a) H,
 (b) halogen, $C_{1-3}$-alkyl, —OH, —O—$C_{1-3}$-alkyl,
 (c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ independently of one another denote
 (a) H,
 (b) halogen, $C_{1-3}$-alkyl, —OH, —O—$C_{1-3}$-alkyl, —CN, —O—C(O)—$C_{1-3}$-alkyl,
 (c) a $C_{1-3}$-alkyl- or —O—$C_{1-3}$-alkyl group wherein each methylene group is substituted by up to two fluorine atoms and each methyl group is substituted by up to three fluorine atoms, $R^3$ and $R^4$ together with the nitrogen atom to which they are attached denote:
 (a) a saturated 5- or 6-membered heterocyclic group, which is substituted at a carbon atom by a group $R^{4.3}$ or by two groups $R^{4.3}$ and $R^{4.4}$,
 (b) a saturated 5- or 6-membered heterocyclic group, which is substituted at two adjacent carbon atoms by in each case a group $R^{4.3}$ and $R^{4.4}$,
 (c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
 (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
 (e) a monounsaturated 5-, 6- or 7-membered heterocyclic group, which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

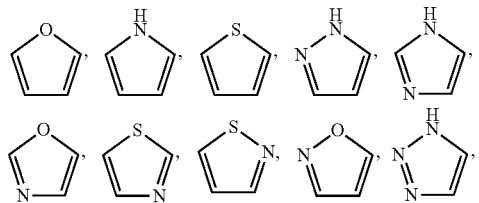

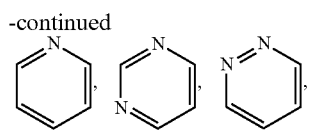

(f) a heteroaryl group which is substituted at 1, 2 or 3 carbon atoms by a group $R^{4.5}$ in each case, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN $R^{4.3.1}$ denotes H, HO, $C_{1-3}$-alkyl-O—, cyclopropyl, $C_{1-3}$-alkyl-O—C(O), CN, —$NH_2$, $(C_{1-4}$-alkyl$)_2$N—, morpholinyl, thiomorpholinyl, piperidinyl, pyrrolidinyl, azetidinyl, $R^{4.4}$ denotes
  (a) H, $C_{1-3}$-alkyl, —OH, —O—$C_{1-3}$-alkyl or
  (b) a $C_{1-3}$-alkyl or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl or heterocyclyl group, and $R^{4.5}$ independently of one another denotes
  (a) H,
  (b) halogen, $C_{1-3}$-alkyl, —OH, —O—$C_{1-3}$-alkyl, —$NH_2$, —CN,
  (c) a $C_{1-3}$-alkyl- or —O—$C_{1-3}$-alkyl group wherein each methylene group is substituted by up to two fluorine atoms and each methyl group is substituted by up to three fluorine atoms, or
  (d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A tenth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes
  (a) H,
  (b) $C_{1-6}$-alkyl,
  (c) a $C_{3-6}$-cycloalkyl group substituted by one or two groups $R^{3.2}$, or
  (d) a $C_{1-3}$-alkyl group wherein each methylene group is substituted by up to two fluorine atoms and each methyl group is substituted by up to three fluorine atoms, $R^{3.2}$ independently of one another denote
  (a) H,
  (b) halogen, $C_{1-3}$-alkyl, —OH, —O—$C_{1-3}$-alkyl,
  (c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) a phenyl group substituted by one or two groups $R^{4.2}$,
  (f) a $C_{5-6}$-cycloalkyl group which may be fused to a phenyl group and is additionally substituted by one or two groups $R^{4.2}$, $R^{4.1}$ denotes
  (a) H,
  (b) a phenyl group substituted by the groups $R^{4.1.1}$ and $R^{4.1.2}$, $R^{4.1.1}$ denotes
  (a) H,
  (b) halogen, $C_{1-3}$-alkyl, —OH, —O—$C_{1-3}$-alkyl, —CN, —C(O)—O—$R^{4.1.1.3}$,
  (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.3}$ denotes H, $C_{1-3}$-alkyl, $R^{4.1.2}$ denotes
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ denotes
  (a) H,
  (b) halogen, $C_{1-3}$-alkyl, —OH, —O—$C_{1-3}$-alkyl, —CN,
  (c) a $C_{1-3}$-alkyl- or —O—$C_{1-3}$-alkyl group wherein each methylene group is substituted by up to two fluorine atoms and each methyl group is substituted by up to three fluorine atoms, or $R^3$ and $R^4$ together with the nitrogen atom to which they are attached denote:
  (a) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$,
  (b) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at two adjacent carbon atoms by a group $R^{4.3}$ and $R^{4.4}$ in each case,
  (c) a saturated 5-, 6- or 7-membered heterocyclic group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, while the fused-on cycloalkyl or heterocyclyl group is substituted by 1, 2 or 3 groups $R^{4.5}$,
  (d) a monounsaturated 5-, 6- or 7-membered heterocyclic group, which is selected from among

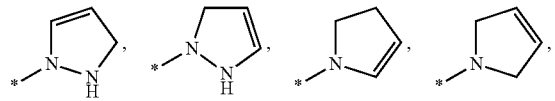

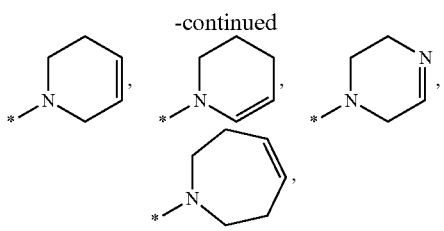

and which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, (e) a monounsaturated 5-, 6- or 7-membered heterocyclic group, which is selected from among

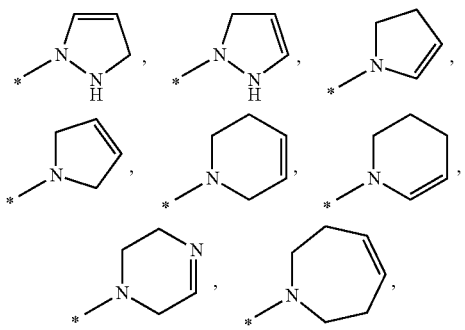

and which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

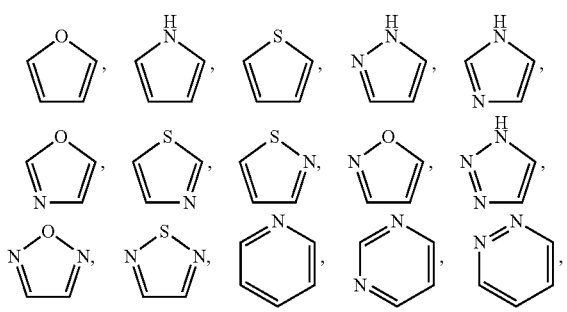

(f) a heteroaryl group, which is selected from among indole, isoindole, azaindole, indazole and benzimidazole, and which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl—O—C(O)—,HO—C(O)—, F, —O—$C_{1-3}$-alkyl, —OH, —CN, $R^{4.3.1}$ denotes H, HO, $C_{1-3}$-alkyl-O—, cyclopropyl, $C_{1-3}$-alkyl-O—C(O)—, CN, —$NH_2$, ($C_{1-4}$-alkyl)-NH—, ($C_{1-4}$-alkyl)$_2$N, morpholinyl, thiomorpholinyl, piperidinyl, pyrrolidinyl, azetidinyl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denotes (a) H, (b) halogen, $C_{1-3}$-alkyl, —OH, —O—$C_{1-3}$-alkyl, —$NH_2$, —CN, (c) a $C_{1-3}$-alkyl- or —O—$C_{1-3}$-alkyl group wherein each methylene group is substituted by up to two fluorine atoms and each methyl group is substituted by up to three fluorine atoms, or (d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

An eleventh embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes (a) H, (b) $C_{1-3}$-alkyl, (c) a $C_{1-3}$-alkyl group wherein each methylene group is substituted by up to two fluorine atoms and each methyl group is substituted by up to three fluorine atoms, and $R^4$ denotes H or a group selected from

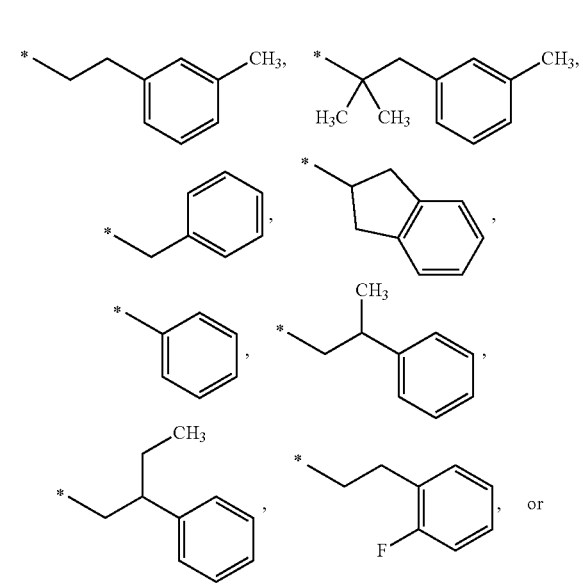

$R^3$ and $R^4$ together with the nitrogen atom to which they are attached denote a group selected from

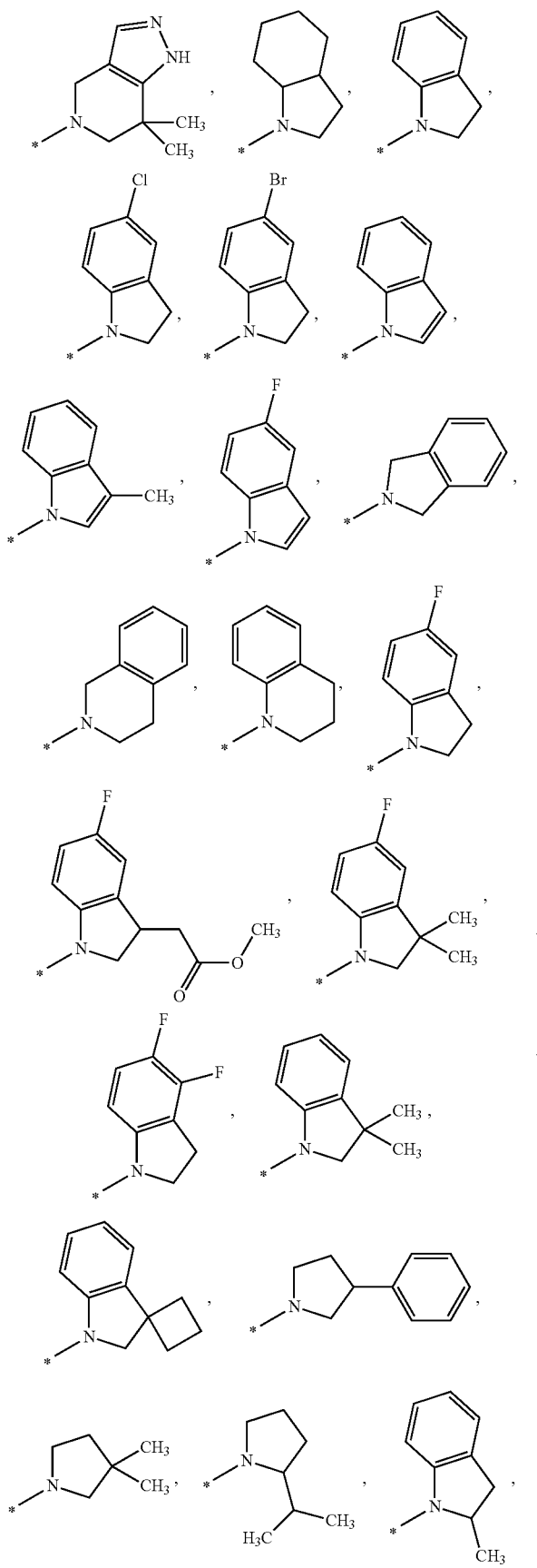
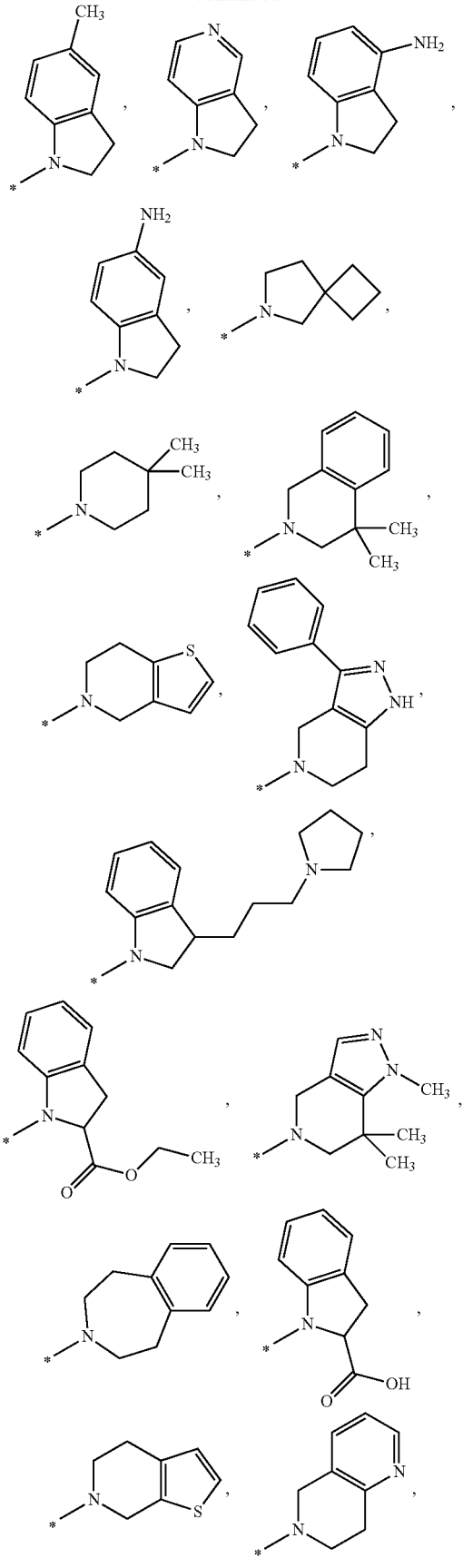

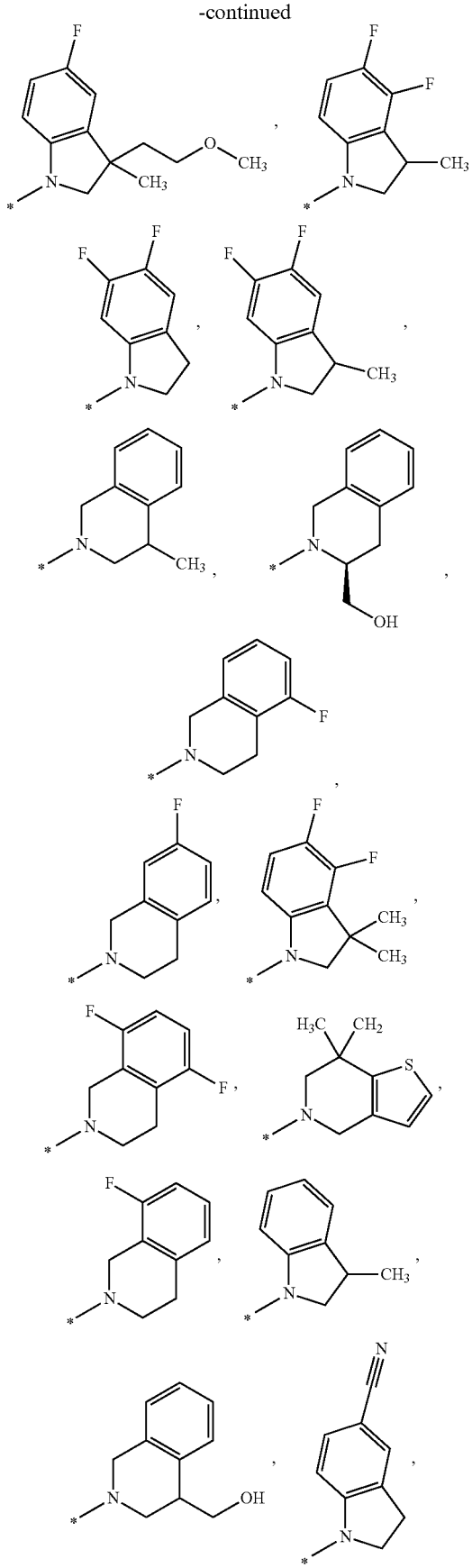
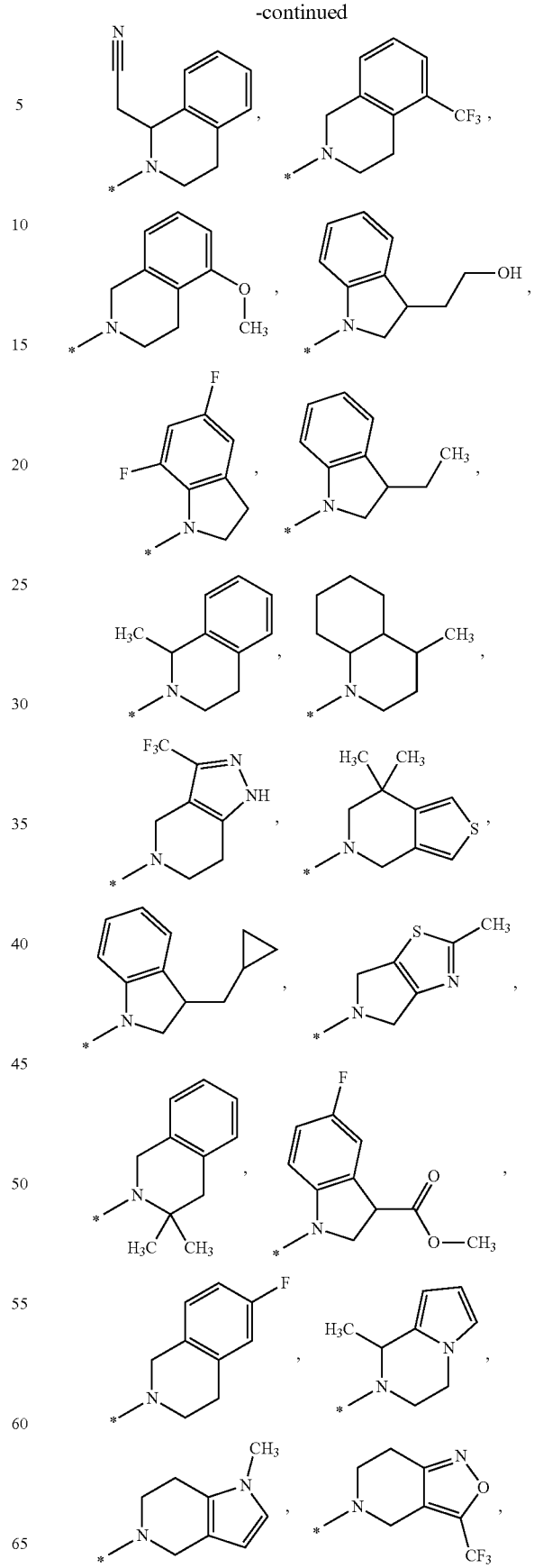

27
-continued
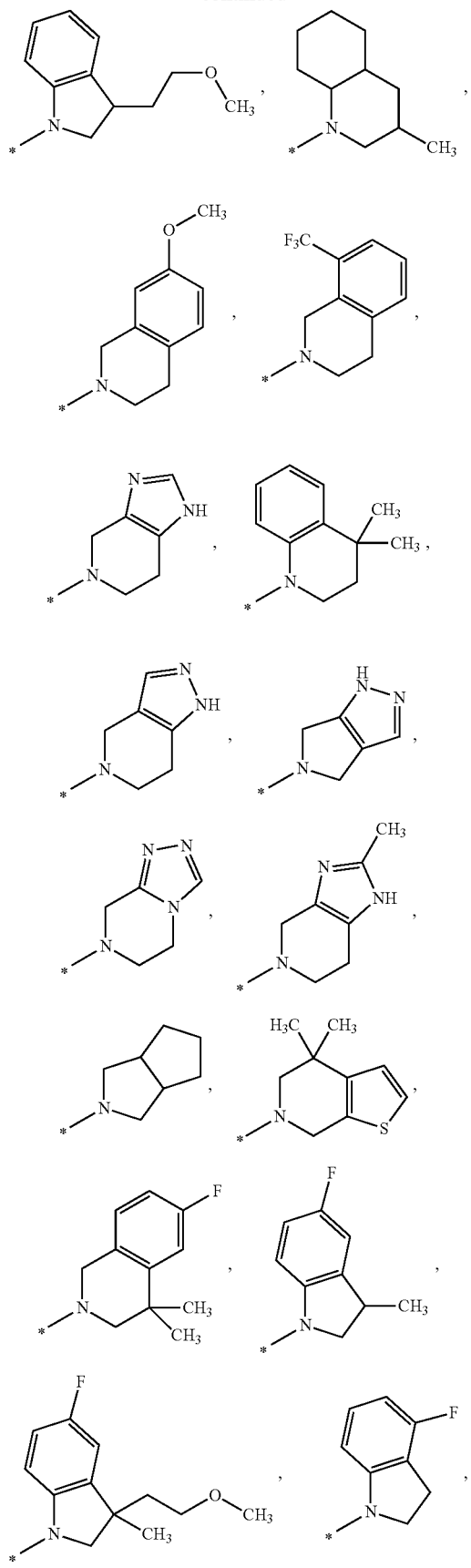
28
-continued
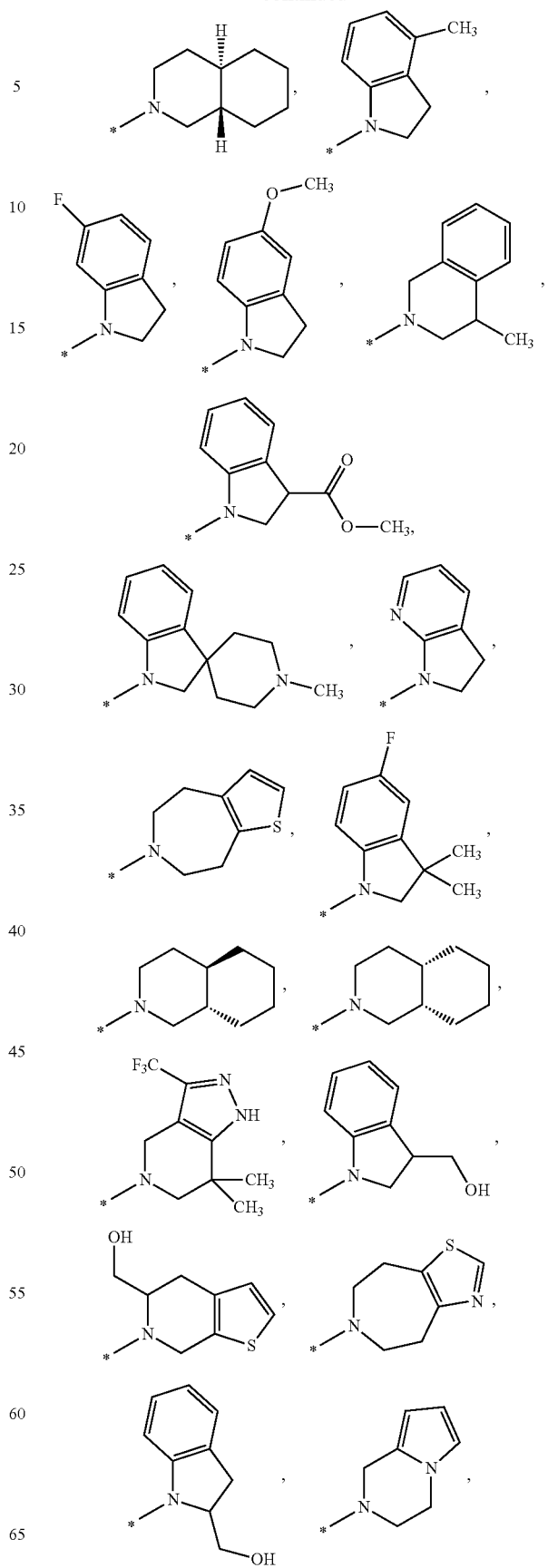

-continued

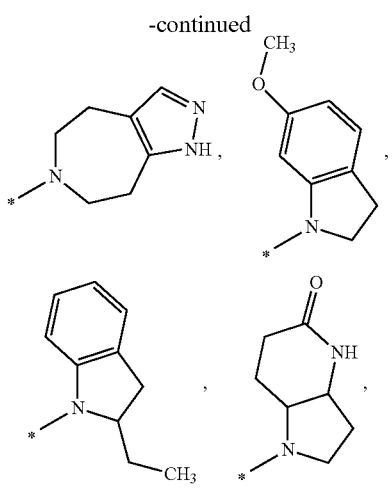

the tautomers, the diastereomers, the enantiomers, the hydrates, the mixtures thereof and the salts thereof as well as the hydrates of the salts, particularly the physiologically acceptable salts thereof with inorganic or organic acids or bases.

A twelfth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ and $R^4$ together with the nitrogen atom to which they are attached denote a monounsaturated 5-membered heterocyclic group, which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, HO, $C_{1-3}$-alkyl-O, $C_{1-3}$-alkyl-O—C(O)—, cyclopropyl, CN, —$NH_2$, ($C_{1-4}$-alkyl)-NH—, ($C_{1-4}$-alkyl)$_2$N, morpholinyl, thiomorpholinyl, piperidinyl, pyrrolidinyl, azetidinyl, $R^{4.4}$ denotes
(a) H, $C_{1-3}$-alkyl, —OH, —O—$C_{1-3}$-alkyl or
(b) a $C_{1-3}$-alkyl or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denotes
(a) H,
(b) halogen, $C_{1-3}$-alkyl, —OH, —O—$C_{1-3}$-alkyl, —$NH_2$, —CN, $NO_2$,
(c) a $C_{1-3}$-alkyl or —O—$C_{1-3}$-alkyl group wherein each methylene group is substituted by up to two fluorine atoms and each methyl group is substituted by up to three fluorine atoms, or
(d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A thirteenth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ and $R^4$ together with the nitrogen atom to which they are attached denote a group of general formula IIIa or IIIb

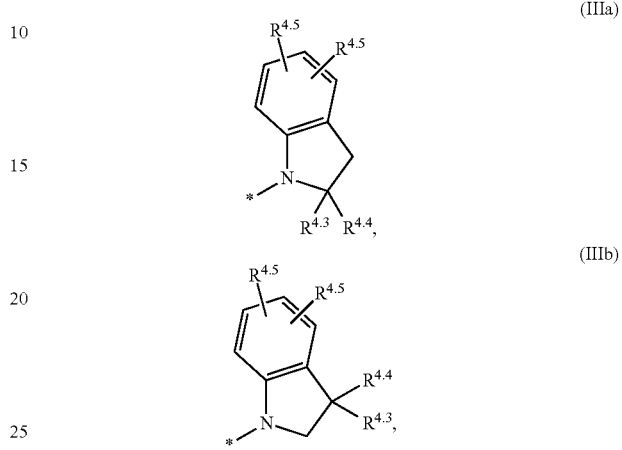

$R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, HO, $C_{1-3}$-alkyl-O—, $C_{1-3}$-alkyl-O—C(O), CN, —$NH_2$, ($C_{1-4}$-alkyl)-NH—, ($C_{1-4}$-alkyl)$_2$N, morpholinyl, thiomorpholinyl, piperidinyl, pyrrolidinyl, azetidinyl, $R^{4.4}$ denotes
(a) H, $C_{1-3}$-alkyl, —OH, —O—$C_{1-3}$-alkyl or
(b) a $C_{1-3}$-alkyl or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denotes
(a) H,
(b) halogen, $C_{1-3}$-alkyl, —OH, —O—$C_{1-3}$-alkyl, —$NH_2$, —CN, $NO_2$,
(c) a $C_{1-3}$-alkyl- or —O—$C_{1-3}$-alkyl group wherein each methylene group is substituted by up to two fluorine atoms and each methyl group is substituted by up to three fluorine atoms, or
(d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourteenth embodiment of the present invention consists in the compounds of the above general formula I, wherein U, V, X, Y, $R^1$ and $R^2$ are as hereinbefore defined in the third, fifth or seventh embodiment and $R^3$ and $R^4$ together with the nitrogen atom to which they are attached denote a group selected from

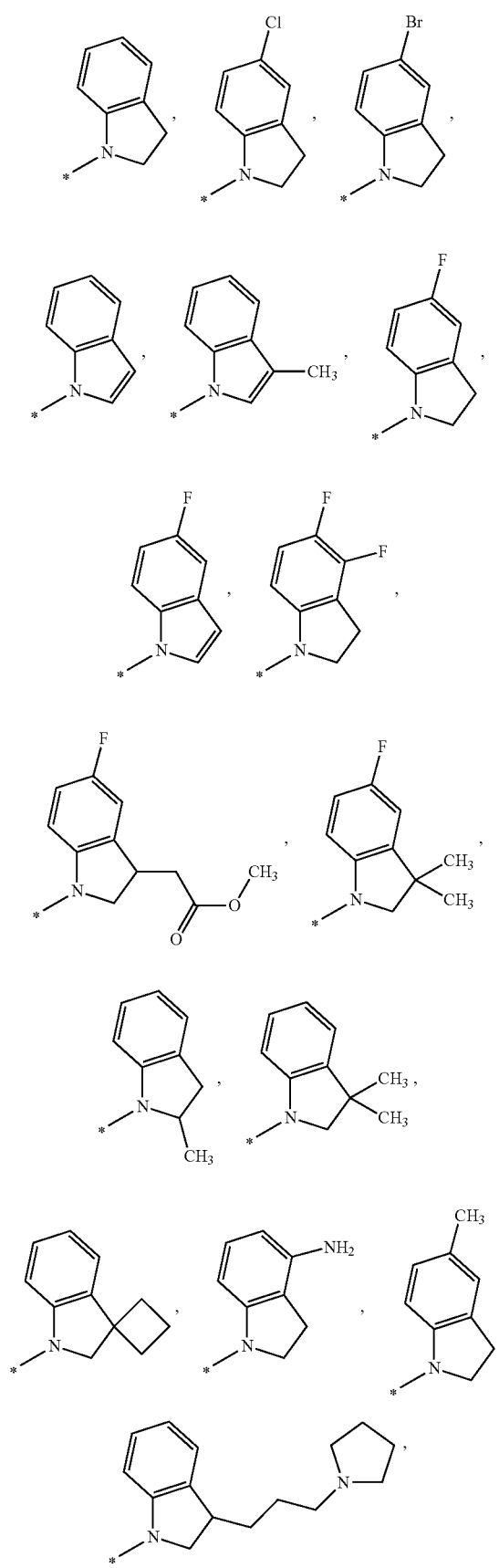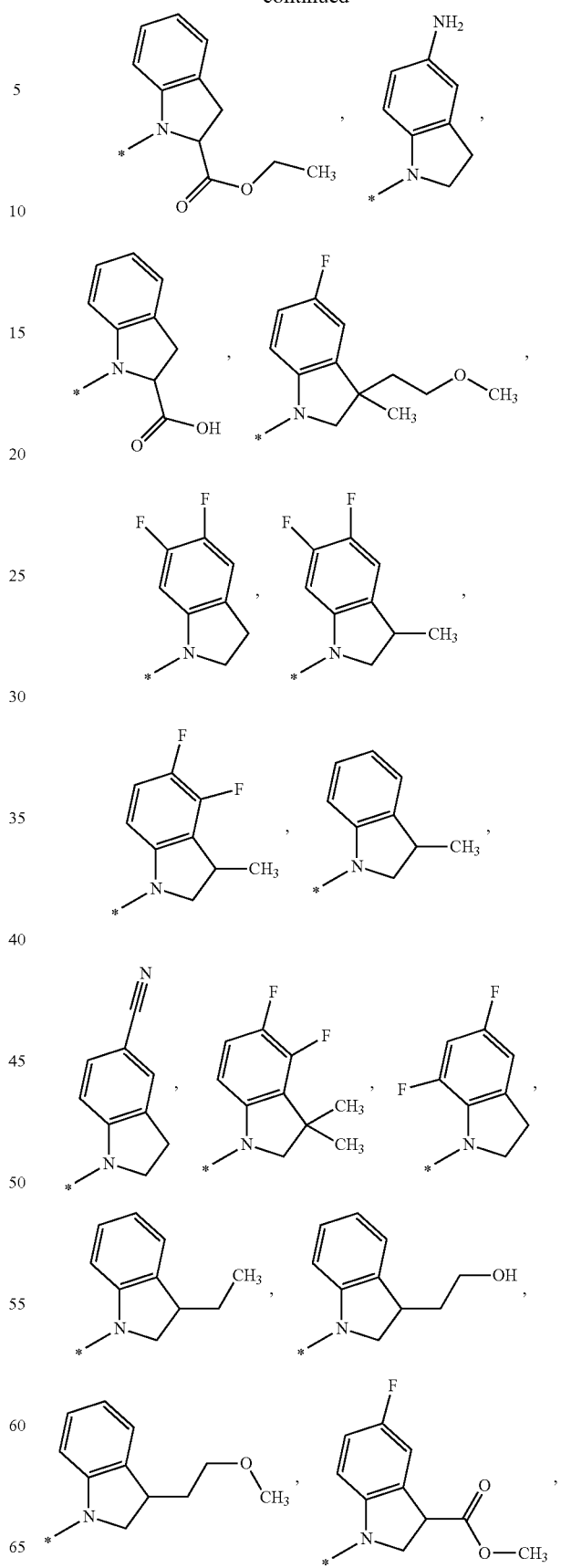

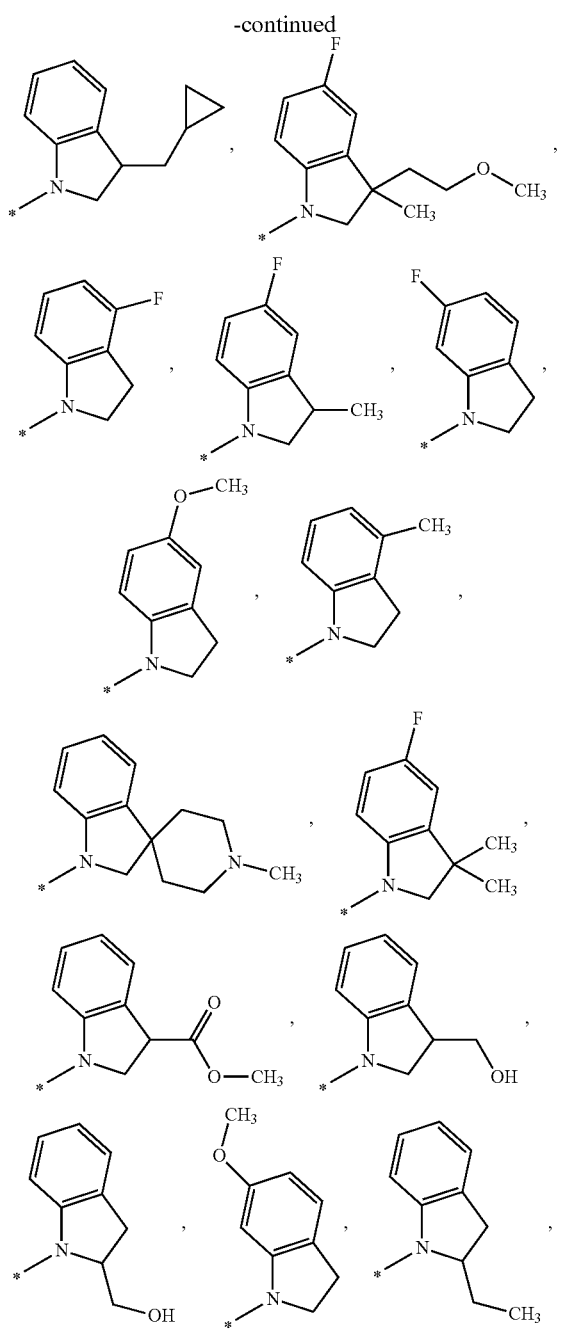

the tautomers, the diastereomers, the enantiomers, the hydrates, the mixtures thereof and the salts thereof as well as the hydrates of the salts, particularly the physiologically acceptable salts thereof with inorganic or organic acids or bases.

A fifteenth embodiment of the present invention consists in the compounds of the above general formula I, wherein $R^1$, $R^2$, $R^3$ and $R^4$ are as hereinbefore defined in the first, second, third, fourth, fifth, sixth, seventh, eighth, ninth, tenth, eleventh, twelfth, thirteenth or fourteenth embodiment and U—V—X denotes a group selected from
—N=N—(C—$R^{12}$)=, —N=(C—$R^{11}$)—N=, —N=(C—$R^{11}$)—(C—$R^{12}$)=, —(N-oxide)=(C—$R^{11}$)—(C—$R^{12}$)=, —(C—$R^{10}$)=N—N=, —(C—$R^{10}$)=N—(C—$R^{12}$)=, —(C—$R^{10}$)=N(oxide)-(C—$R^{12}$)=, —(C—$R^{10}$)=(C—$R^{11}$)—N=, —(C—$R^{10}$)=(C—$R^{11}$)—(N-oxide)=, —(C—$R^{10}$)=(C—$R^{11}$)—(C—$R^{12}$)=, $R^{10}$ denotes H, —CN, $R^{11}$ denotes H, —$NR^{11.1}R^{11.2}$ or —O—$C_{1-3}$-alkyl, $R^{11.1}$ denotes H or $C_{1-6}$-alkyl, $R^{11.2}$ denotes H or —$SO_2$—$C_{1-3}$-alkyl, $R^{12}$ denotes H, —CN and Y denotes N or CH, the tautomers, the diastereomers, the enantiomers, the hydrates, the mixtures thereof and the salts thereof as well as the hydrates of the salts, particularly the physiologically acceptable salts thereof with inorganic or organic acids or bases.

A further embodiment of the present invention comprises the compounds of the above general formula I, wherein $R^1$, $R^2$, $R^3$ and $R^4$ are as hereinbefore defined in the first, second, third, fourth, fifth, sixth, seventh, eighth, ninth, tenth, eleventh, twelfth, thirteenth or fourteenth embodiment and the ring

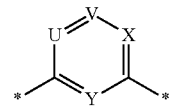

denotes a group selected from

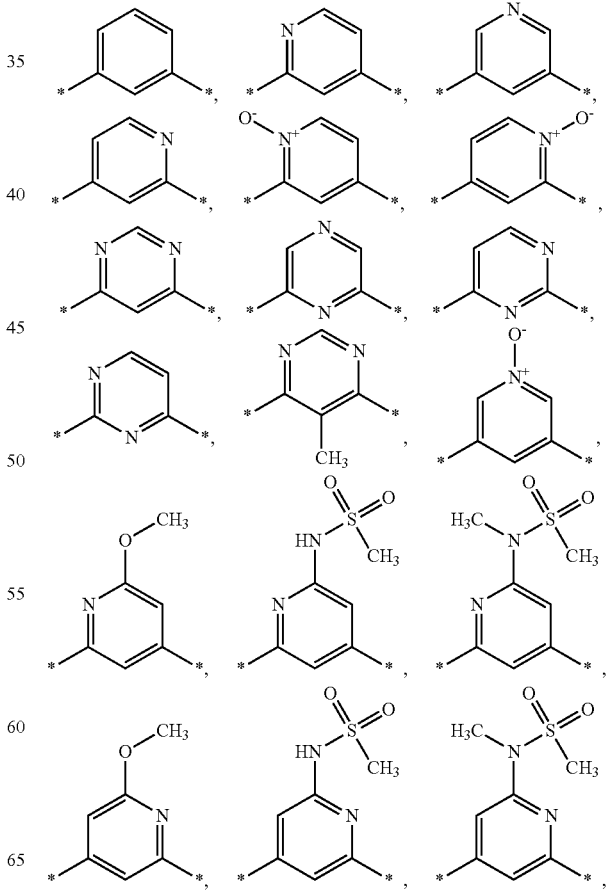

-continued

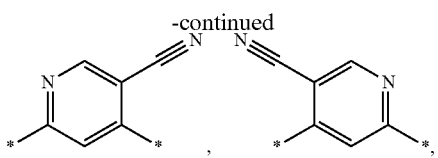

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventeenth embodiment of the present invention consists in the compounds of general formula I wherein $R^1$ denotes a group selected from

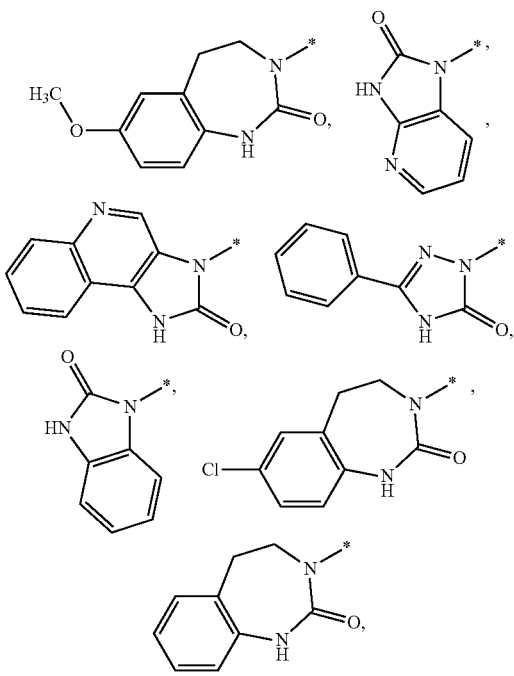

$R^2$ denotes H,
$R^3$ denotes
  (a) H,
  (b) $C_{1-3}$-alkyl,
  (c) a $C_{1-3}$-alkyl group wherein each methylene group is substituted by up to two fluorine atoms and each methyl group is substituted by up to three fluorine atoms, and
$R^4$ denotes H or a group selected from

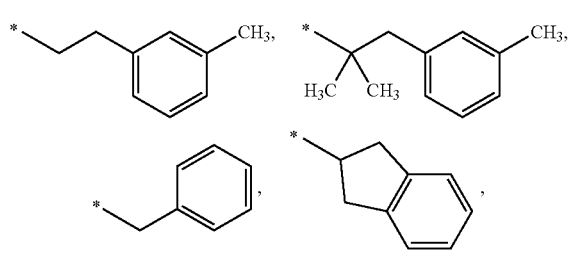

-continued

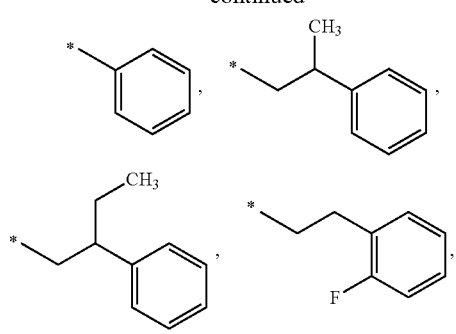

, or

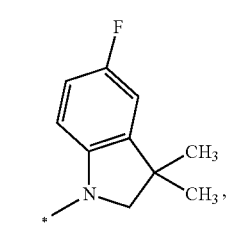

$R^3$ and $R^4$ together with the nitrogen atom to which they are attached denote a group selected from

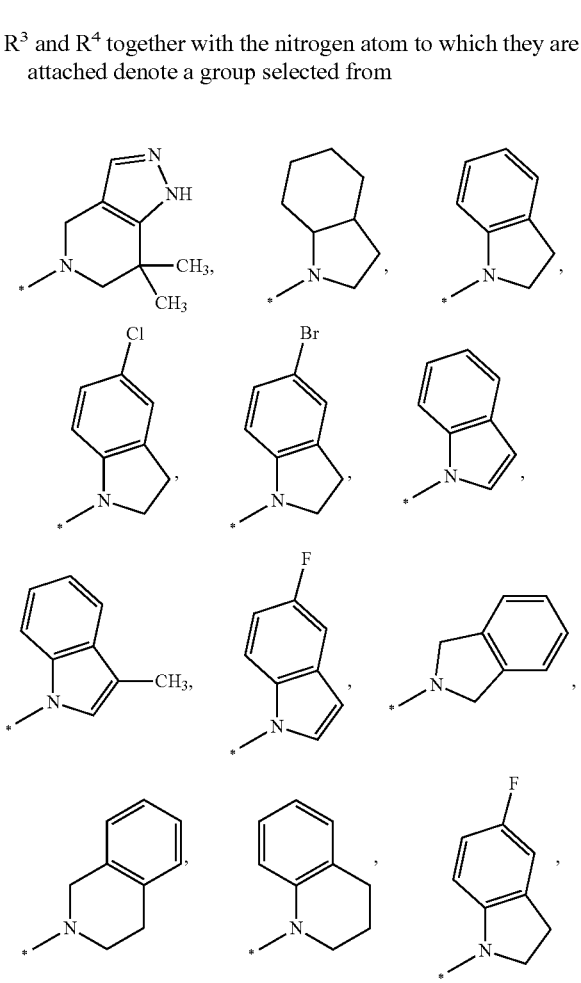

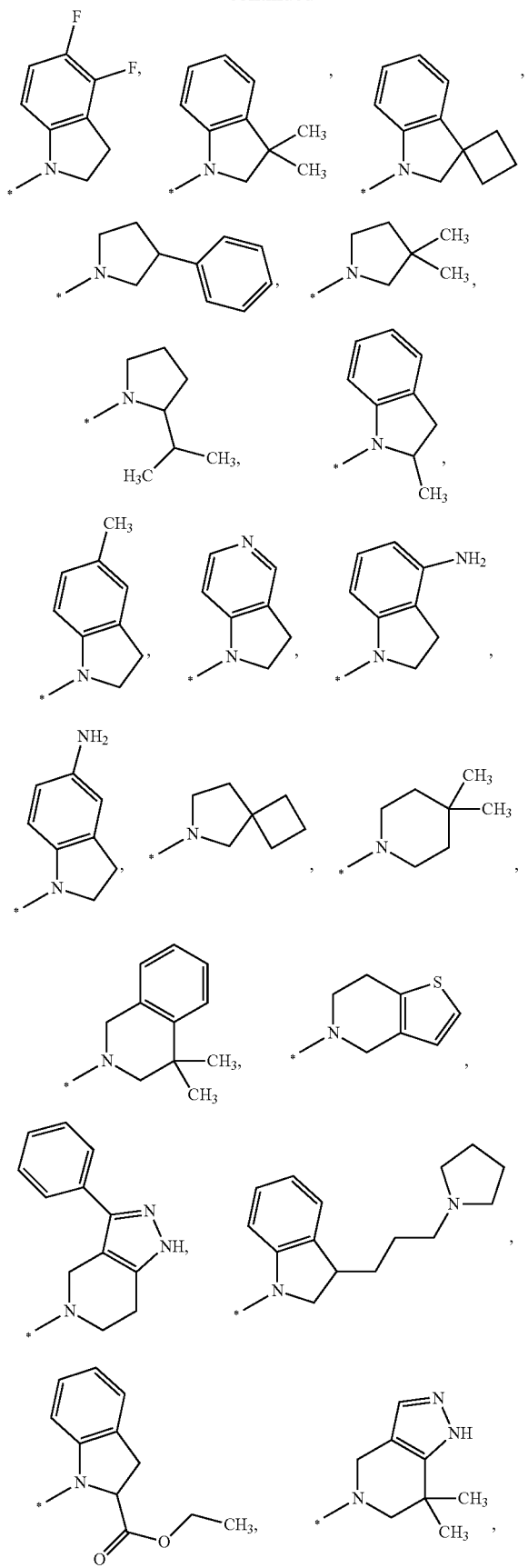
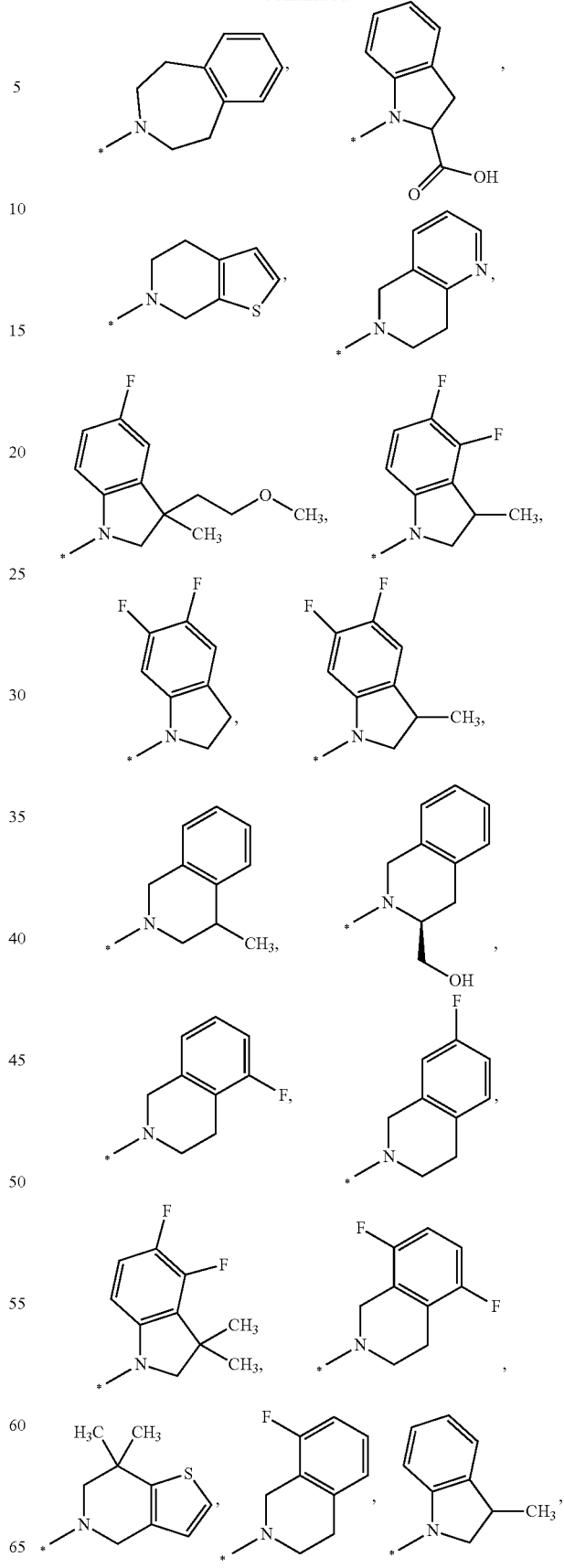

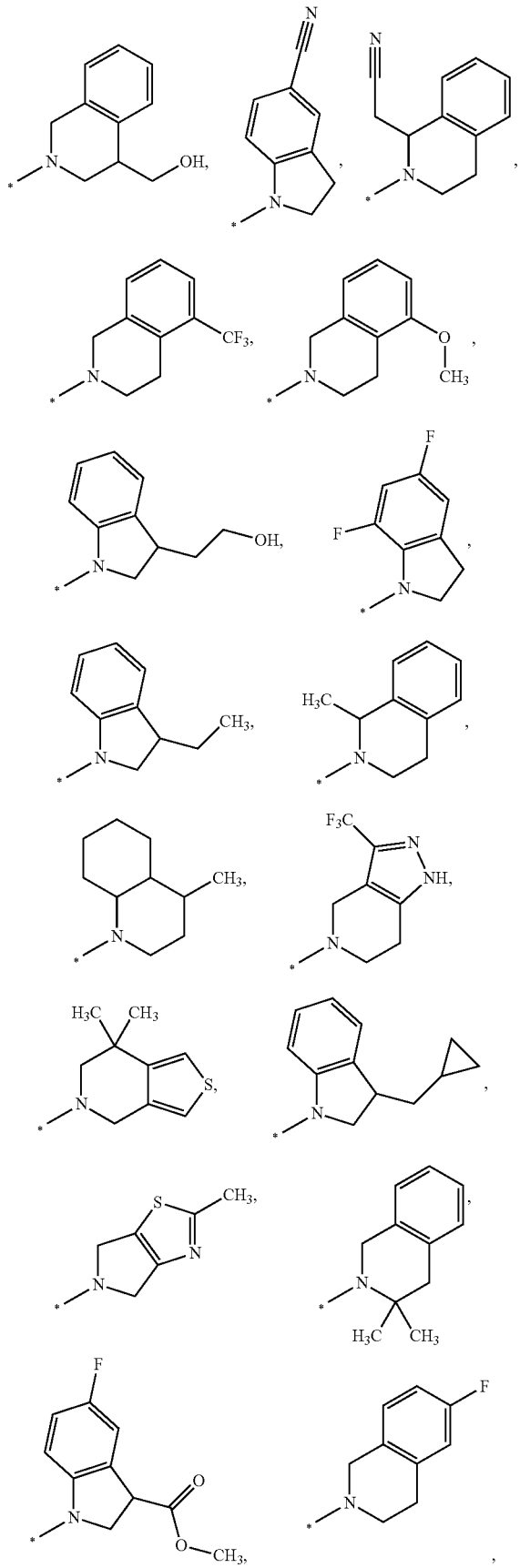
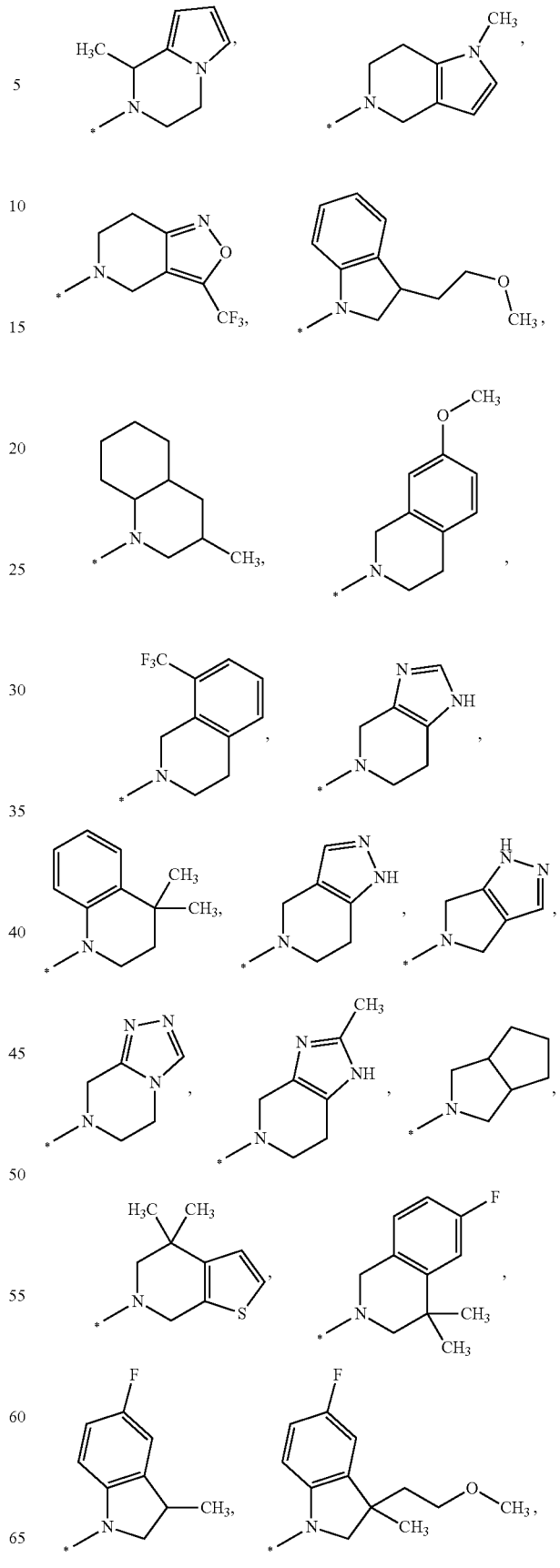

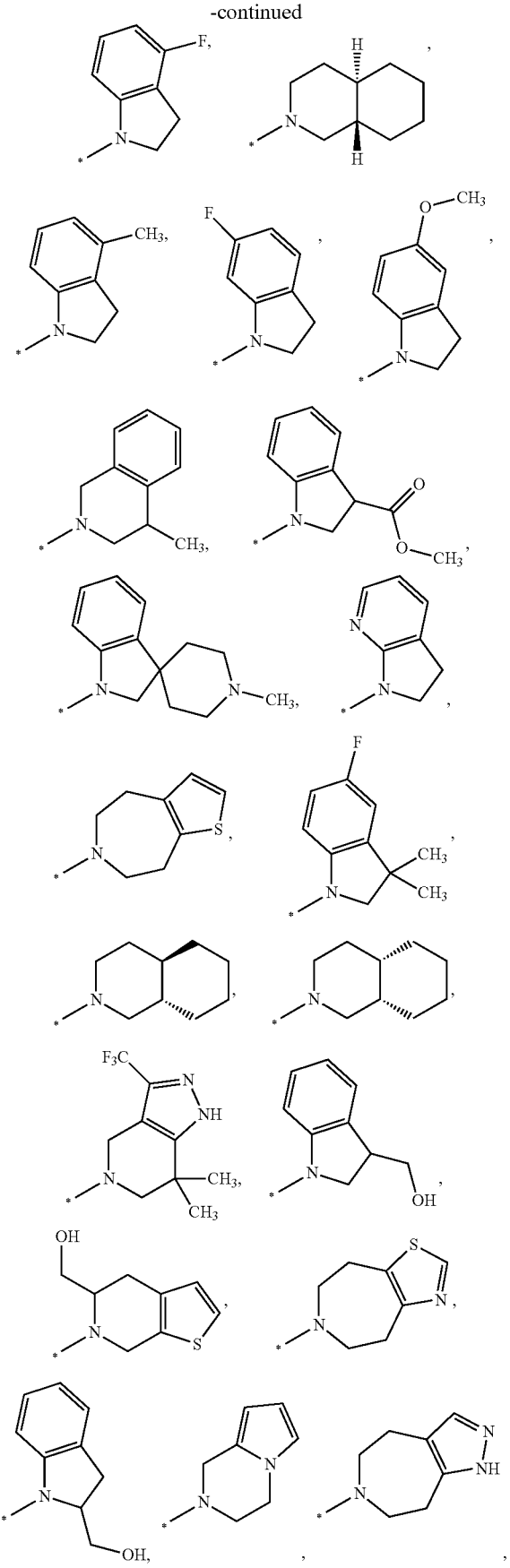
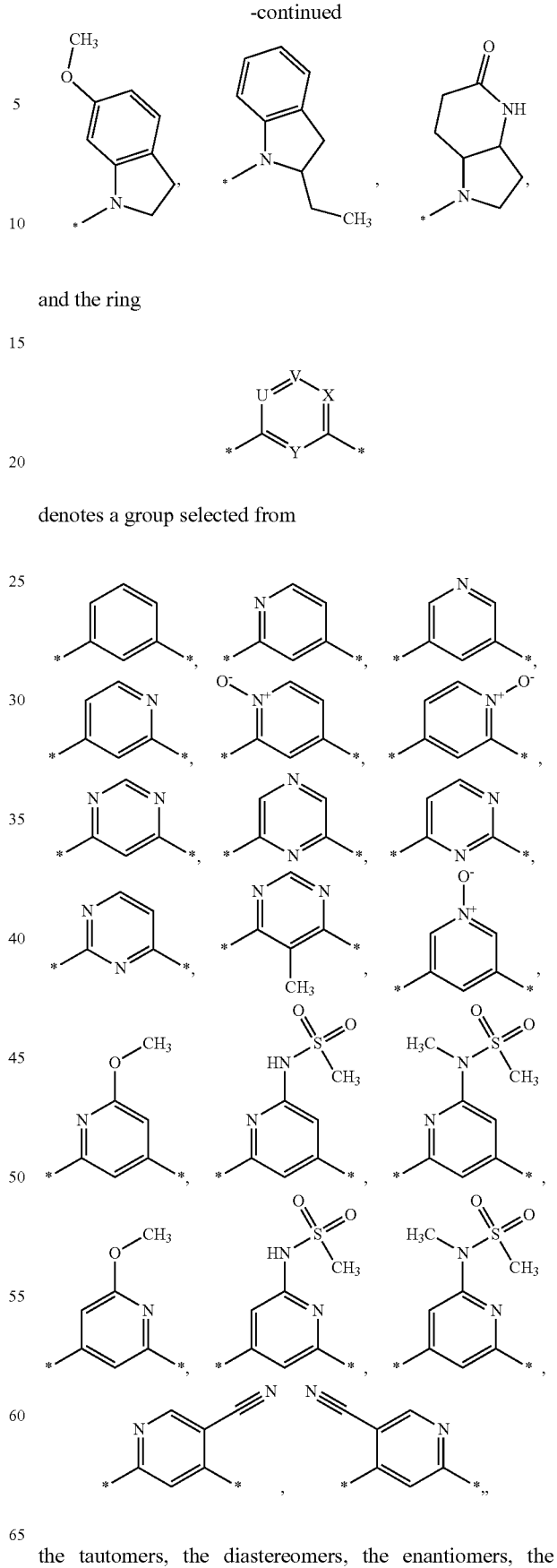
and the ring
denotes a group selected from
the tautomers, the diastereomers, the enantiomers, the hydrates, the mixtures thereof and the salts thereof as well as the hydrates of the salts, particularly the physiologically acceptable salts thereof with inorganic or organic acids or bases.

An eighteenth embodiment of the present invention consists in the compounds of general formula I wherein R¹ denotes a group selected from

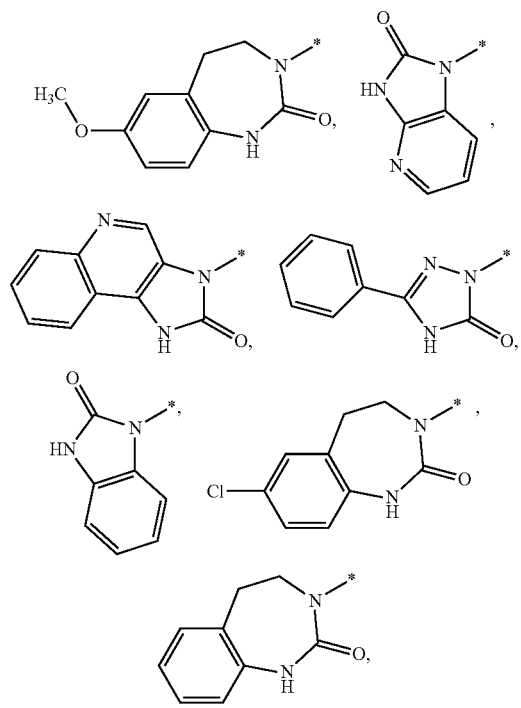

R³ and R⁴ together with the nitrogen atom to which they are attached denote a group selected from

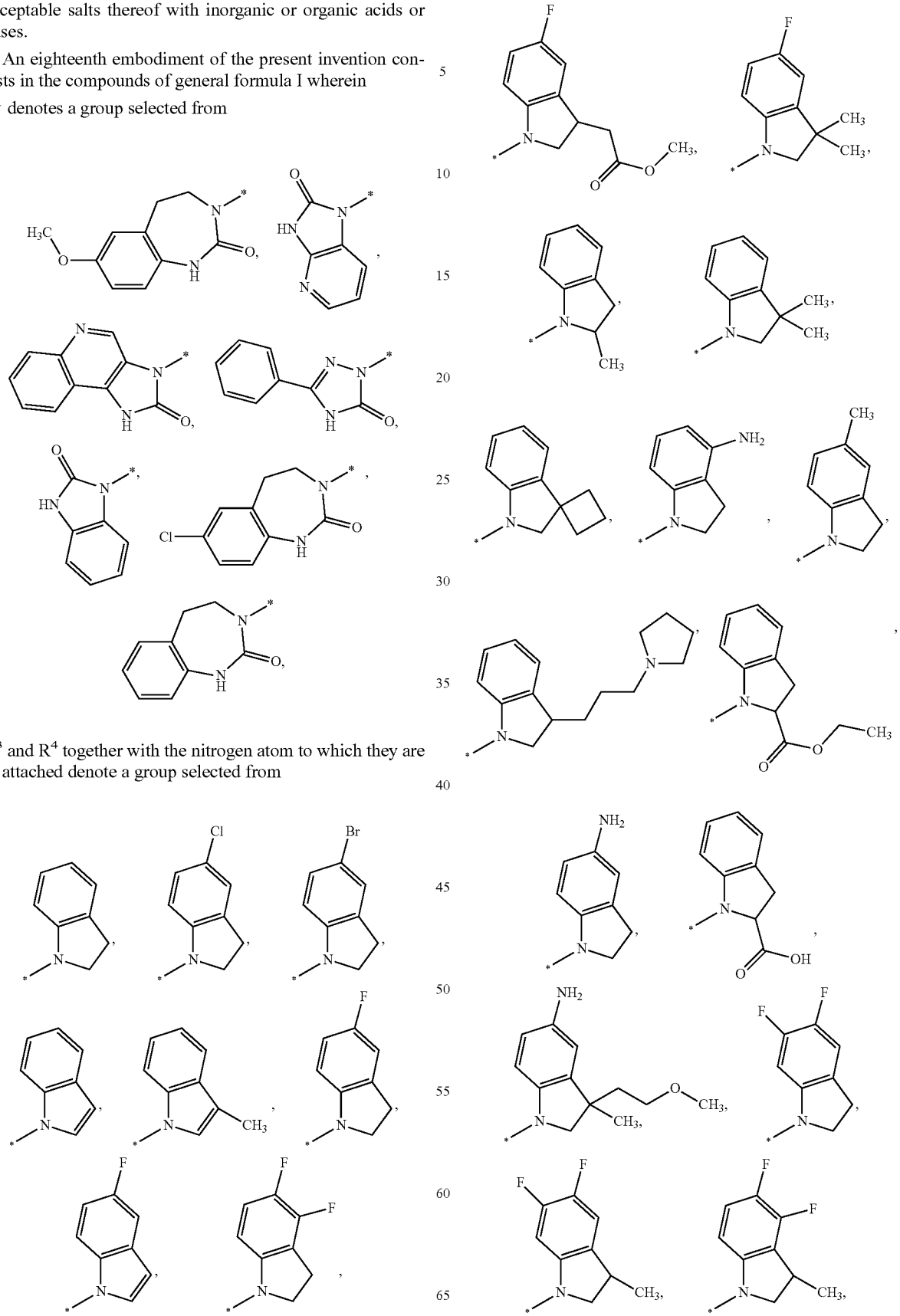

45
-continued
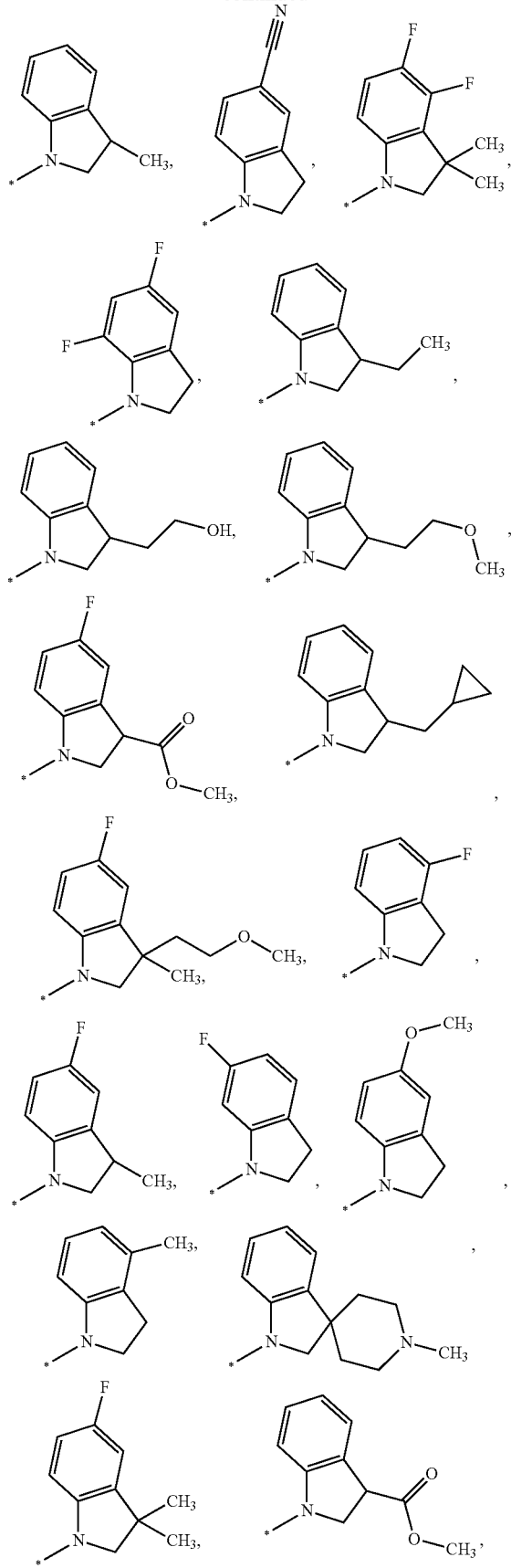
46
-continued
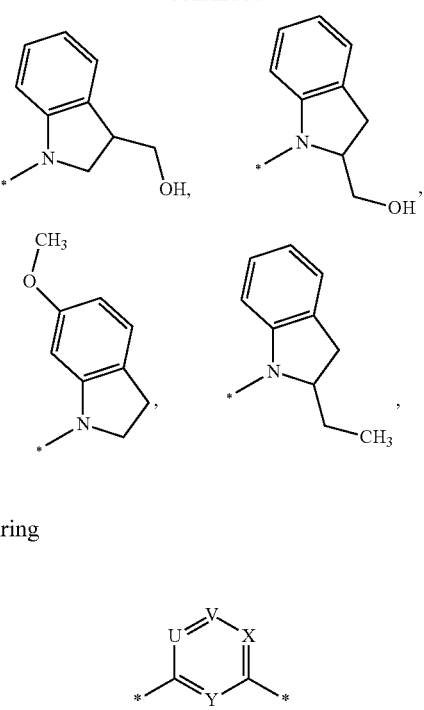
and the ring
denotes a group selected from

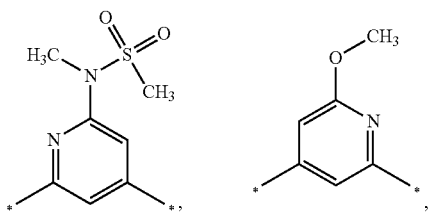
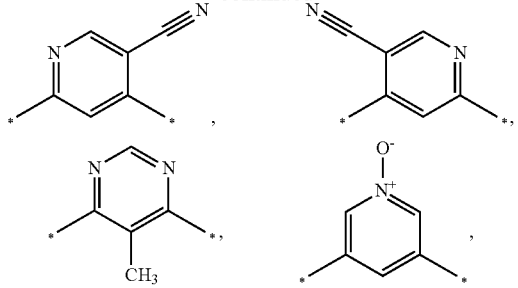
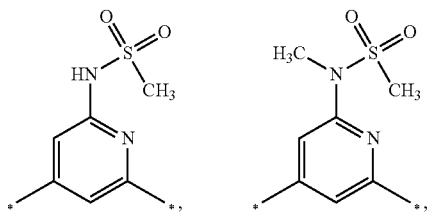

the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned as examples of most particularly preferred compounds of the above general formula I:

| No. | Structure |
|---|---|
| (1) | 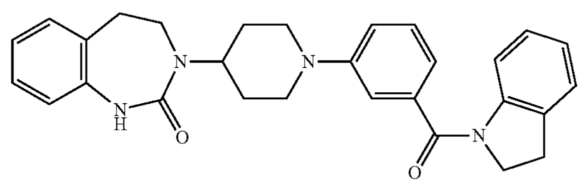 [SMILES: O=C(c1cccc(N2CCC(N3CCc4ccccc4NC3=O)CC2)c1)N1CCc2ccccc21] |
| (2) | 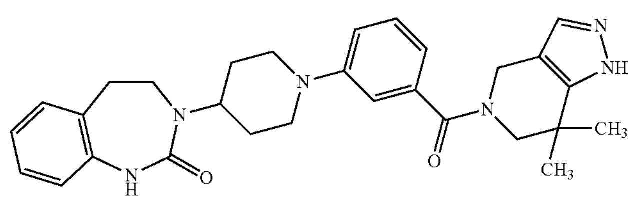 [SMILES: CC1(C)CN(C(=O)c2cccc(N3CCC(N4CCc5ccccc5NC4=O)CC3)c2)Cc2cn[nH]c21] |
| (3) | 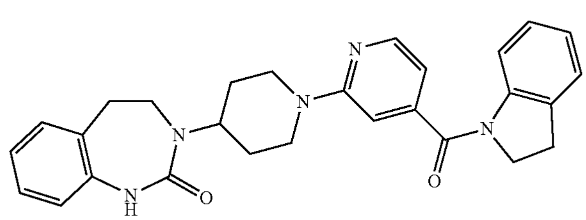 [SMILES: O=C(c1ccnc(N2CCC(N3CCc4ccccc4NC3=O)CC2)c1)N1CCc2ccccc21] |
| (4) | 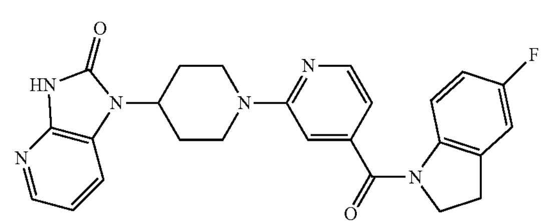 [SMILES: O=C(c1ccnc(N2CCC(n3c(=O)[nH]c4ncccc43)CC2)c1)N1CCc2cc(F)ccc21] |

-continued
| No. | Structure |
|---|---|
| (5) | 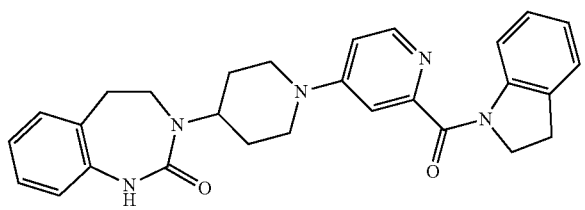 [SMILES: O=C(c1cc(N2CCC(N3CCc4ccccc4NC3=O)CC2)ccn1)N1CCc2ccccc21] |
| (6) | 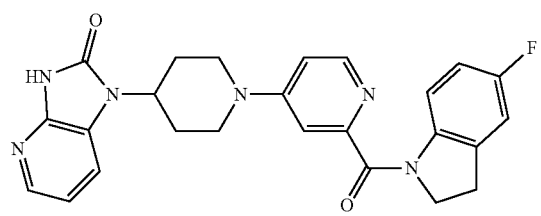 [SMILES: O=C(c1cc(N2CCC(n3c(=O)[nH]c4ncccc43)CC2)ccn1)N1CCc2cc(F)ccc21] |
| (7) | 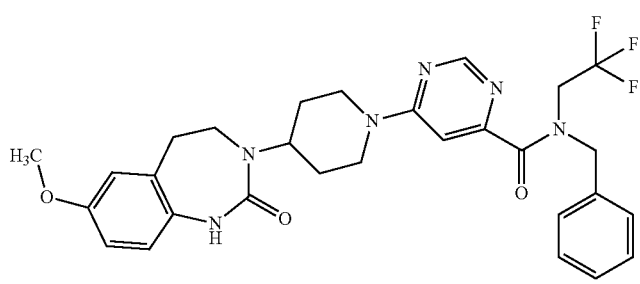 [SMILES: COc1ccc2c(c1)CCN(C1CCN(c3cc(C(=O)N(Cc4ccccc4)CC(F)(F)F)ncn3)CC1)C(=O)N2] |
| (8) | 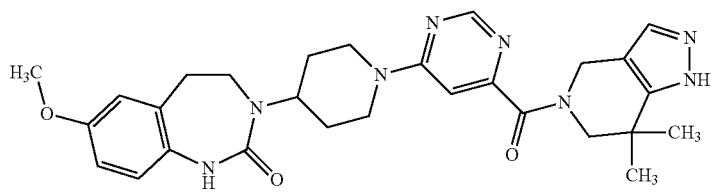 [SMILES: COc1ccc2c(c1)CCN(C1CCN(c3cc(C(=O)N4Cc5cn[nH]c5C(C)(C)C4)ncn3)CC1)C(=O)N2] |
| (9) | 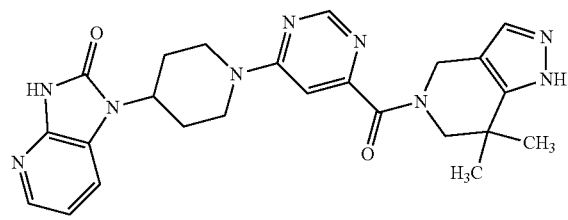 [SMILES: CC1(C)CN(C(=O)c2cc(N3CCC(n4c(=O)[nH]c5ncccc54)CC3)ncn2)Cc2cn[nH]c21] |
| (10) | 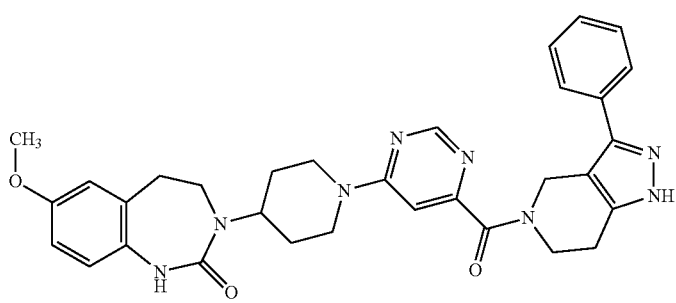 [SMILES: COc1ccc2c(c1)CCN(C1CCN(c3cc(C(=O)N4CCc5[nH]nc(-c6ccccc6)c5C4)ncn3)CC1)C(=O)N2] |

-continued
| No. | Structure |
|---|---|
| (11) | 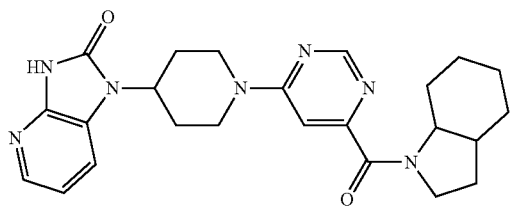 [SMILES: O=C(c1cc(N2CCC(n3c(=O)[nH]c4ncccc43)CC2)ncn1)N1CCC2CCCCC21] |
| (12) | 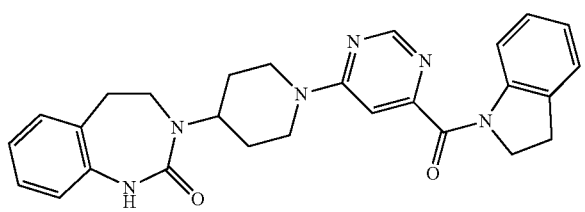 [SMILES: O=C(c1cc(N2CCC(N3CCc4ccccc4NC3=O)CC2)ncn1)N1CCc2ccccc21] |
| (13) | 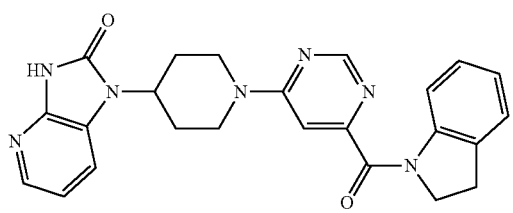 [SMILES: O=C(c1cc(N2CCC(n3c(=O)[nH]c4ncccc43)CC2)ncn1)N1CCc2ccccc21] |
| (14) | 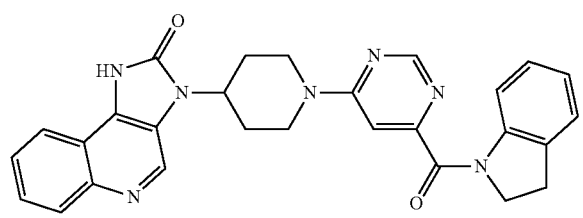 [SMILES: O=C(c1cc(N2CCC(n3c(=O)[nH]c4c5ccccc5ncc43)CC2)ncn1)N1CCc2ccccc21] |
| (15) | 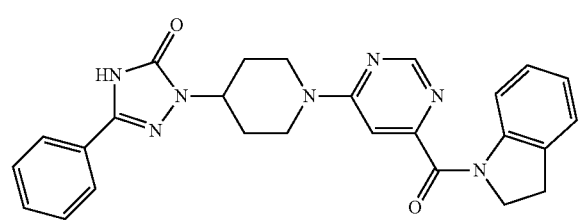 [SMILES: O=C(c1cc(N2CCC(n3nc(-c4ccccc4)[nH]c3=O)CC2)ncn1)N1CCc2ccccc21] |
| (16) | 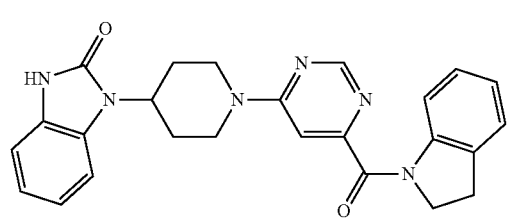 [SMILES: O=C(c1cc(N2CCC(n3c(=O)[nH]c4ccccc43)CC2)ncn1)N1CCc2ccccc21] |
| (17) | 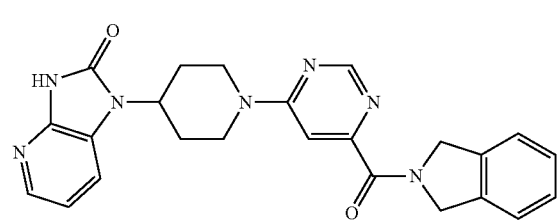 [SMILES: O=C(c1cc(N2CCC(n3c(=O)[nH]c4ncccc43)CC2)ncn1)N1Cc2ccccc2C1] |

-continued
| No. | Structure |
|---|---|
| (18) | 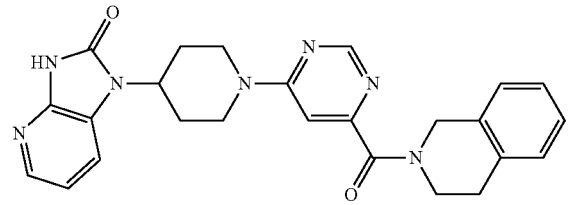 [SMILES: O=C(c1cc(N2CCC(n3c(=O)[nH]c4ncccc43)CC2)ncn1)N1CCc2ccccc2C1] |
| (19) | 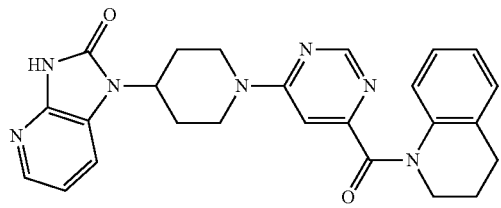 [SMILES: O=C(c1cc(N2CCC(n3c(=O)[nH]c4ncccc43)CC2)ncn1)N1CCCc2ccccc21] |
| (20) | 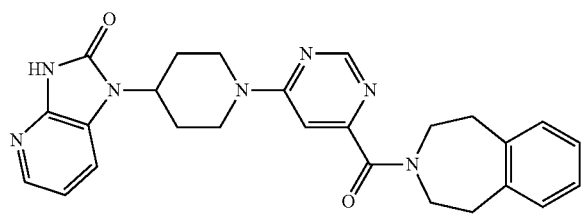 [SMILES: O=C(c1cc(N2CCC(n3c(=O)[nH]c4ncccc43)CC2)ncn1)N1CCc2ccccc2CC1] |
| (21) | 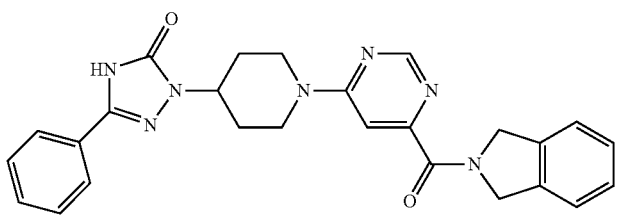 [SMILES: O=C(c1cc(N2CCC(n3nc(-c4ccccc4)[nH]c3=O)CC2)ncn1)N1Cc2ccccc2C1] |
| (22) | 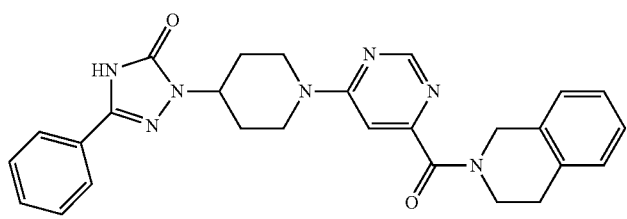 [SMILES: O=C(c1cc(N2CCC(n3nc(-c4ccccc4)[nH]c3=O)CC2)ncn1)N1CCc2ccccc2C1] |
| (23) | 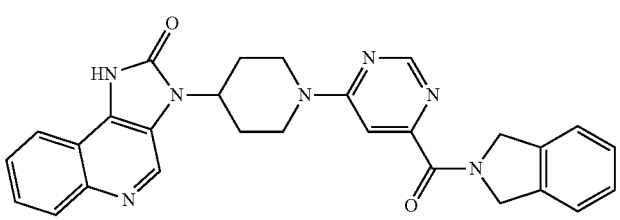 [SMILES: O=C(c1cc(N2CCC(n3c(=O)[nH]c4c5ccccc5ncc43)CC2)ncn1)N1Cc2ccccc2C1] |
| (24) | 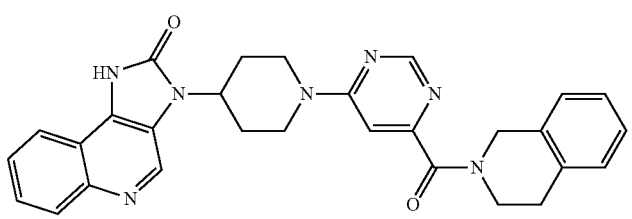 [SMILES: O=C(c1cc(N2CCC(n3c(=O)[nH]c4c5ccccc5ncc43)CC2)ncn1)N1CCc2ccccc2C1] |

| No. | Structure |
|---|---|
| (25) | 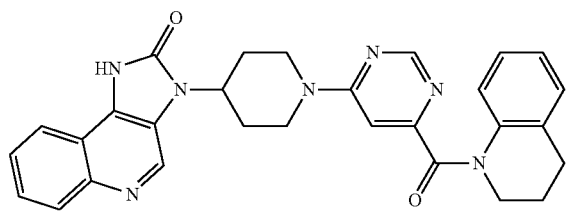 [SMILES: O=C(c1cc(N2CCC(n3c(=O)[nH]c4c5ccccc5ncc43)CC2)ncn1)N1CCCc2ccccc21] |
| (26) | 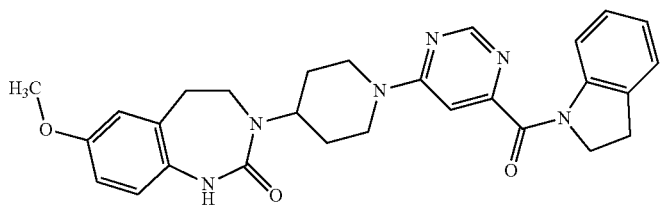 [SMILES: COc1ccc2c(c1)CCN(C1CCN(c3cc(C(=O)N4CCc5ccccc54)ncn3)CC1)C(=O)N2] |
| (27) | 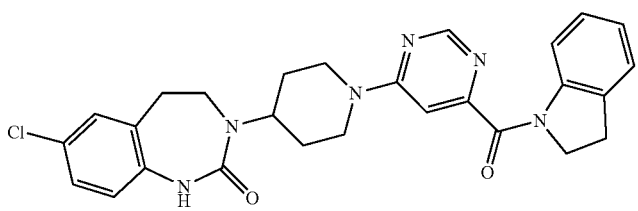 [SMILES: O=C(c1cc(N2CCC(N3CCc4cc(Cl)ccc4NC3=O)CC2)ncn1)N1CCc2ccccc21] |
| (28) | 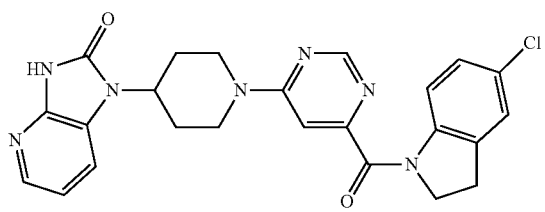 [SMILES: O=C(c1cc(N2CCC(n3c(=O)[nH]c4ncccc43)CC2)ncn1)N1CCc2cc(Cl)ccc21] |
| (29) | 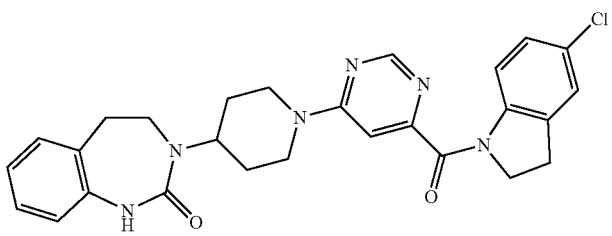 [SMILES: O=C(c1cc(N2CCC(N3CCc4ccccc4NC3=O)CC2)ncn1)N1CCc2cc(Cl)ccc21] |
| (30) | 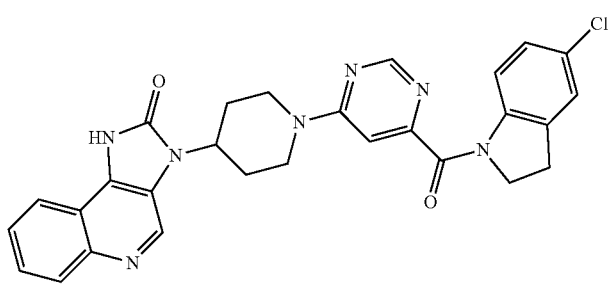 [SMILES: O=C(c1cc(N2CCC(n3c(=O)[nH]c4c5ccccc5ncc43)CC2)ncn1)N1CCc2cc(Cl)ccc21] |
| (31) | 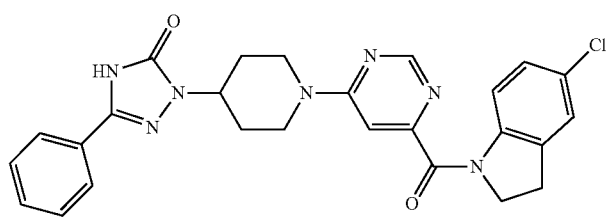 [SMILES: O=C(c1cc(N2CCC(n3nc(-c4ccccc4)[nH]c3=O)CC2)ncn1)N1CCc2cc(Cl)ccc21] |

| No. | Structure |
|---|---|
| (32) | 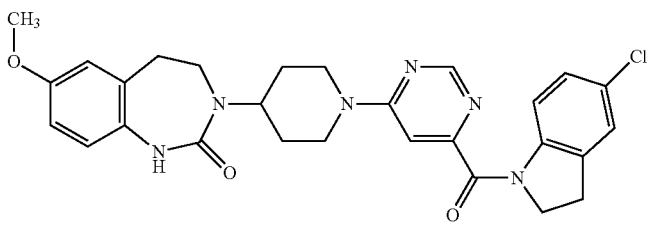 [SMILES: COc1ccc2c(c1)CCN(C1CCN(c3cc(C(=O)N4CCc5cc(Cl)ccc54)ncn3)CC1)C(=O)N2] |
| (33) | 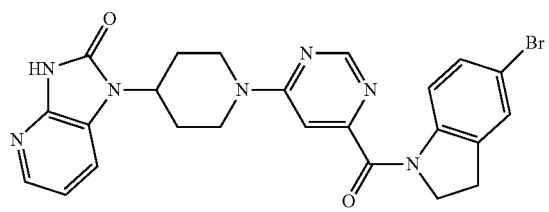 [SMILES: O=C(c1cc(N2CCC(n3c(=O)[nH]c4ncccc43)CC2)ncn1)N1CCc2cc(Br)ccc21] |
| (34) | 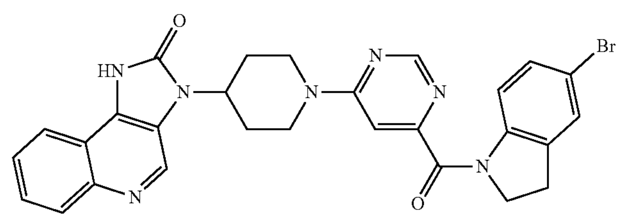 [SMILES: O=C(c1cc(N2CCC(n3c(=O)[nH]c4c5ccccc5ncc43)CC2)ncn1)N1CCc2cc(Br)ccc21] |
| (35) | 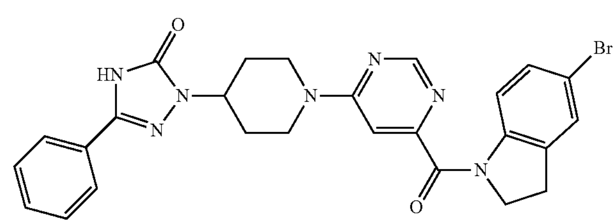 [SMILES: O=C(c1cc(N2CCC(n3nc(-c4ccccc4)[nH]c3=O)CC2)ncn1)N1CCc2cc(Br)ccc21] |
| (36) | 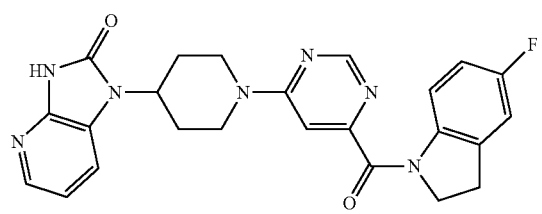 [SMILES: O=C(c1cc(N2CCC(n3c(=O)[nH]c4ncccc43)CC2)ncn1)N1CCc2cc(F)ccc21] |
| (37) | 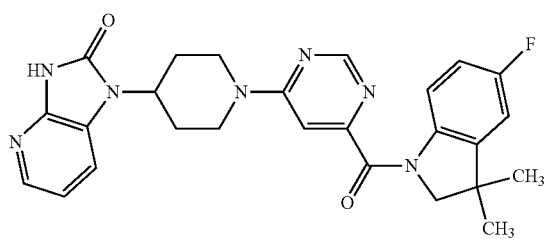 [SMILES: CC1(C)CN(C(=O)c2cc(N3CCC(n4c(=O)[nH]c5ncccc54)CC3)ncn2)c2ccc(F)cc21] |

-continued
| No. | Structure |
|---|---|
| (38) | 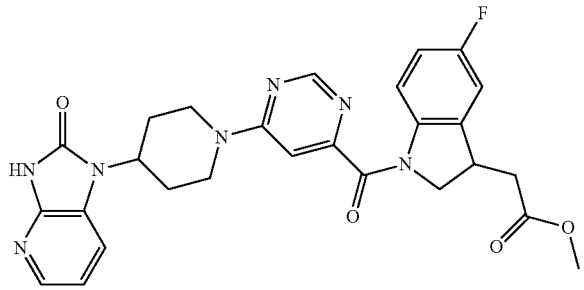 [SMILES: COC(=O)CC1CN(C(=O)c2cc(N3CCC(n4c(=O)[nH]c5ncccc54)CC3)ncn2)c2ccc(F)cc21] |
| (39) | 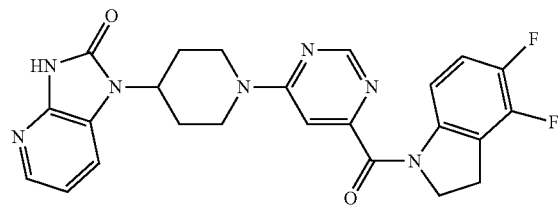 [SMILES: O=C(c1cc(N2CCC(n3c(=O)[nH]c4ncccc43)CC2)ncn1)N1CCc2c1ccc(F)c2F] |
| (40) | 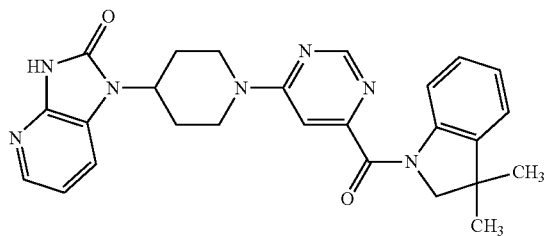 [SMILES: CC1(C)CN(C(=O)c2cc(N3CCC(n4c(=O)[nH]c5ncccc54)CC3)ncn2)c2ccccc21] |
| (41) | 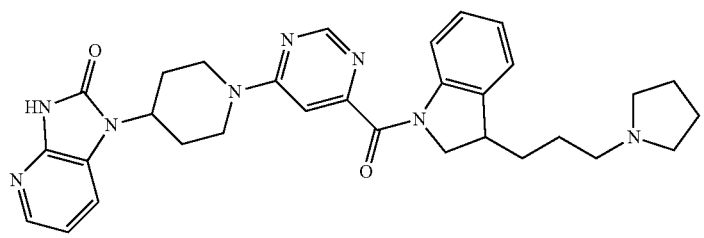 [SMILES: O=C(c1cc(N2CCC(n3c(=O)[nH]c4ncccc43)CC2)ncn1)N1CC(CCCN2CCCC2)c2ccccc21] |
| (42) | 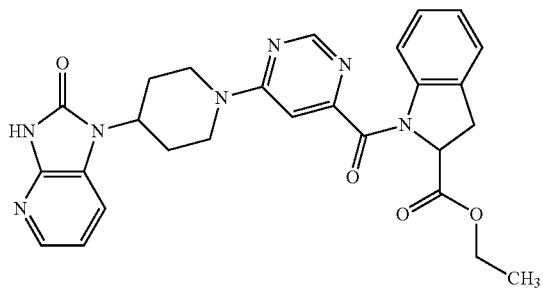 [SMILES: CCOC(=O)C1Cc2ccccc2N1C(=O)c1cc(N2CCC(n3c(=O)[nH]c4ncccc43)CC2)ncn1] |
| (43) | 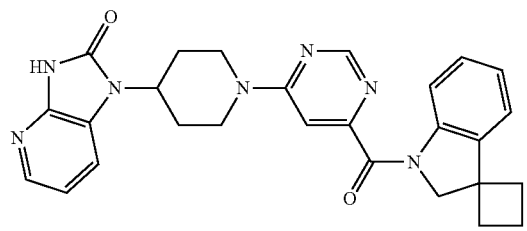 [SMILES: O=C(c1cc(N2CCC(n3c(=O)[nH]c4ncccc43)CC2)ncn1)N1CC2(CCC2)c2ccccc21] |

| No. | Structure |
|---|---|
| (44) | 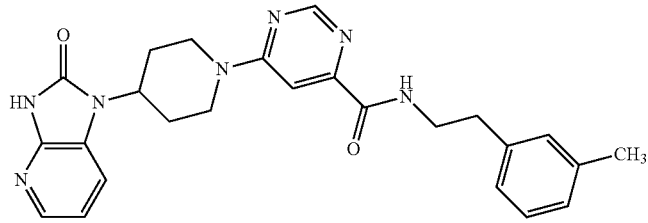 [SMILES: Cc1cccc(CCNC(=O)c2cc(N3CCC(n4c(=O)[nH]c5ncccc54)CC3)ncn2)c1] |
| (45) | 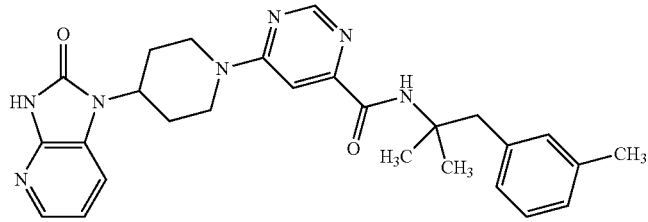 [SMILES: Cc1cccc(CC(C)(C)NC(=O)c2cc(N3CCC(n4c(=O)[nH]c5ncccc54)CC3)ncn2)c1] |
| (46) | 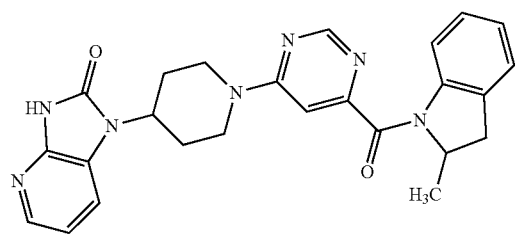 [SMILES: CC1Cc2ccccc2N1C(=O)c1cc(N2CCC(n3c(=O)[nH]c4ncccc43)CC2)ncn1] |
| (47) | 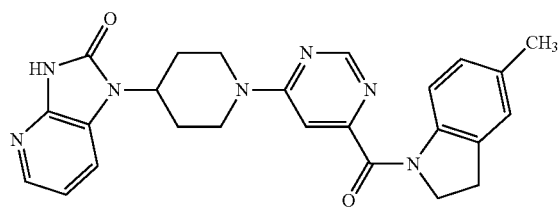 [SMILES: Cc1ccc2c(c1)CCN2C(=O)c1cc(N2CCC(n3c(=O)[nH]c4ncccc43)CC2)ncn1] |
| (48) | 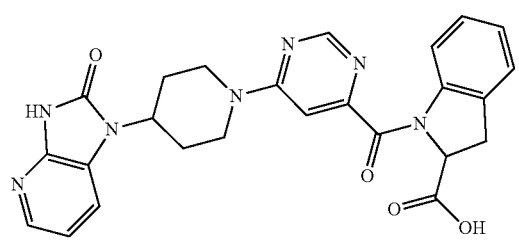 [SMILES: O=C(O)C1Cc2ccccc2N1C(=O)c1cc(N2CCC(n3c(=O)[nH]c4ncccc43)CC2)ncn1] |
| (49) | 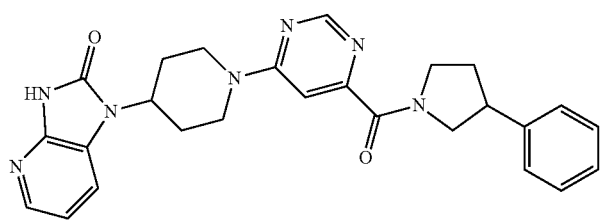 [SMILES: O=C(c1cc(N2CCC(n3c(=O)[nH]c4ncccc43)CC2)ncn1)N1CCC(c2ccccc2)C1] |

-continued
| No. | Structure |
|---|---|
| (50) | 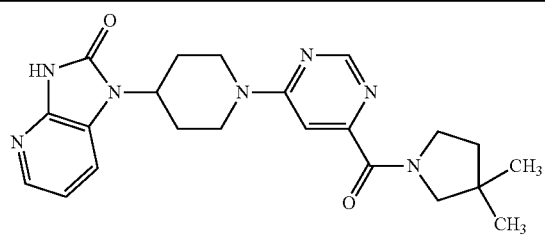 |
| (51) | 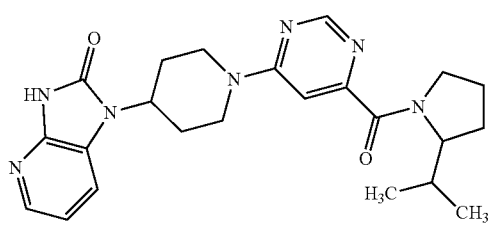 [SMILES: CC(C)C1CCCN1C(=O)c1cc(N2CCC(n3c(=O)[nH]c4ncccc43)CC2)ncn1] |
| (52) | 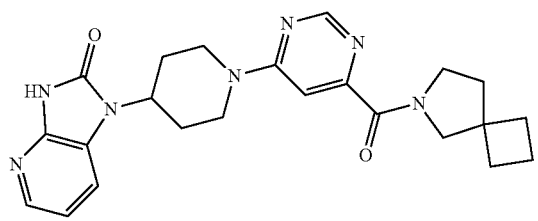 [SMILES: O=C(c1cc(N2CCC(n3c(=O)[nH]c4ncccc43)CC2)ncn1)N1CCC2(CCC2)C1] |
| (53) | 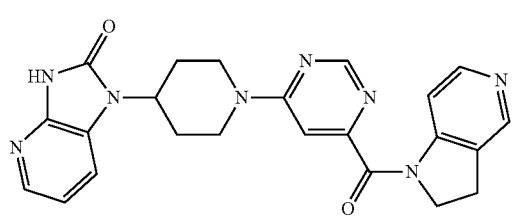 |
| (54) | 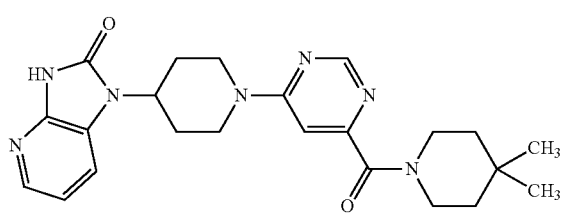 [SMILES: CC1(C)CCN(C(=O)c2cc(N3CCC(n4c(=O)[nH]c5ncccc54)CC3)ncn2)CC1] |
| (55) | 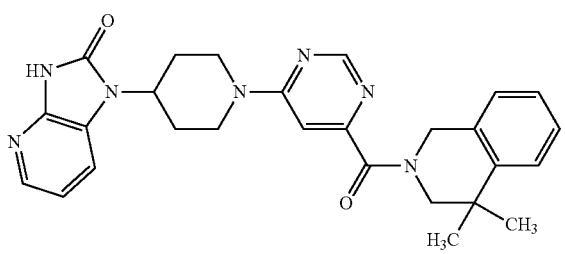 [SMILES: CC1(C)CN(C(=O)c2cc(N3CCC(n4c(=O)[nH]c5ncccc54)CC3)ncn2)Cc2ccccc21] |
| (56) | 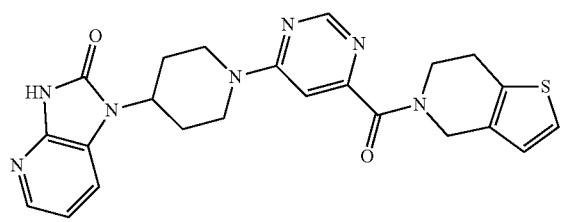 [SMILES: O=C(c1cc(N2CCC(n3c(=O)[nH]c4ncccc43)CC2)ncn1)N1CCc2sccc2C1] |

-continued
| No. | Structure |
|---|---|
| (57) | 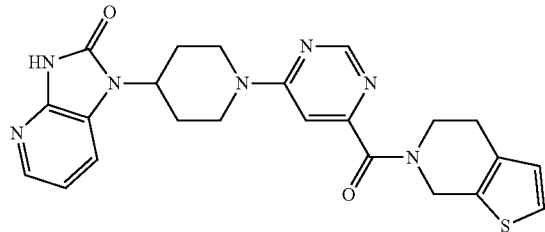 [SMILES: O=C(c1cc(N2CCC(n3c(=O)[nH]c4ncccc43)CC2)ncn1)N1CCc2ccsc2C1] |
| (58) | 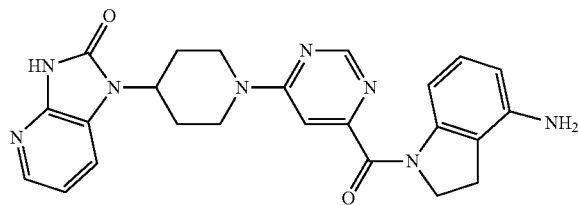 [SMILES: Nc1cccc2c1CCN2C(=O)c1cc(N2CCC(n3c(=O)[nH]c4ncccc43)CC2)ncn1] |
| (59) | 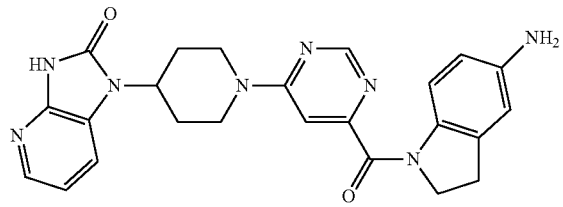 [SMILES: Nc1ccc2c(c1)CCN2C(=O)c1cc(N2CCC(n3c(=O)[nH]c4ncccc43)CC2)ncn1] |
| (60) | 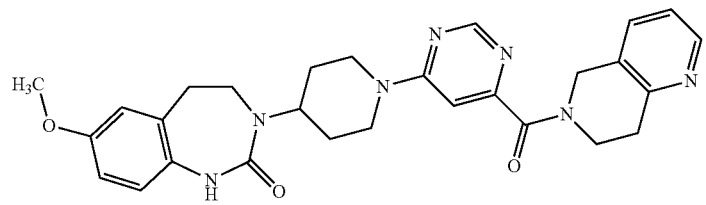 [SMILES: COc1ccc2c(c1)CCN(C1CCN(c3cc(C(=O)N4CCc5ncccc5C4)ncn3)CC1)C(=O)N2] |
| (61) | 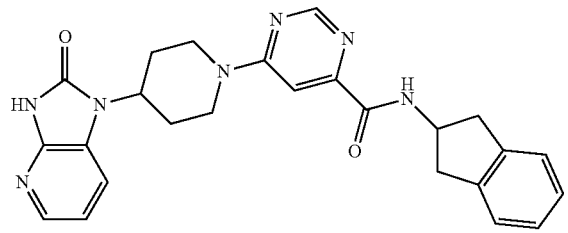 [SMILES: O=C(NC1Cc2ccccc2C1)c1cc(N2CCC(n3c(=O)[nH]c4ncccc43)CC2)ncn1] |
| (62) | 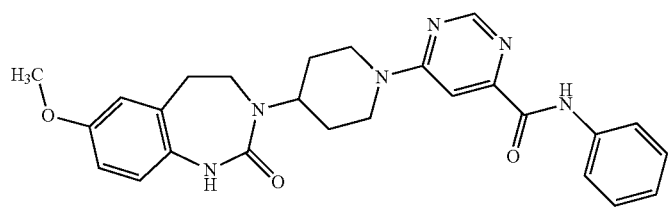 [SMILES: COc1ccc2c(c1)CCN(C1CCN(c3cc(C(=O)Nc4ccccc4)ncn3)CC1)C(=O)N2] |
| (63) | 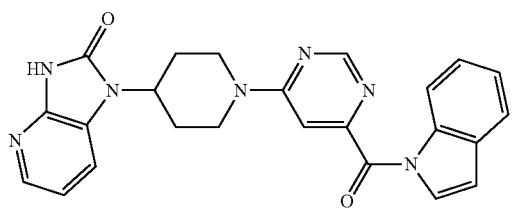 [SMILES: O=C(c1cc(N2CCC(n3c(=O)[nH]c4ncccc43)CC2)ncn1)n1ccc2ccccc21] |

| No. | Structure |
|---|---|
| (64) | 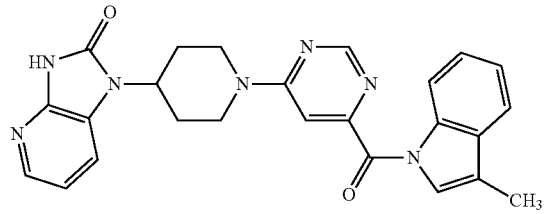 [SMILES: Cc1cn(C(=O)c2cc(N3CCC(n4c(=O)[nH]c5ncccc54)CC3)ncn2)c2ccccc12] |
| (65) | 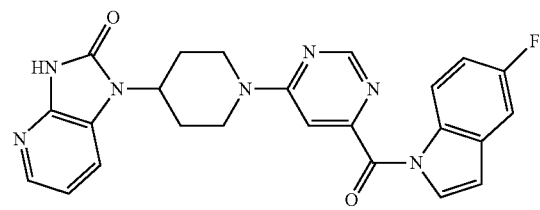 [SMILES: O=C(c1cc(N2CCC(n3c(=O)[nH]c4ncccc43)CC2)ncn1)n1ccc2cc(F)ccc21] |
| (66) | 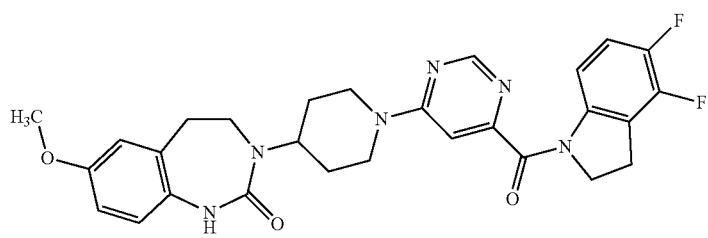 [SMILES: COc1ccc2c(c1)CCN(C1CCN(c3cc(C(=O)N4CCc5c4ccc(F)c5F)ncn3)CC1)C(=O)N2] |
| (67) | 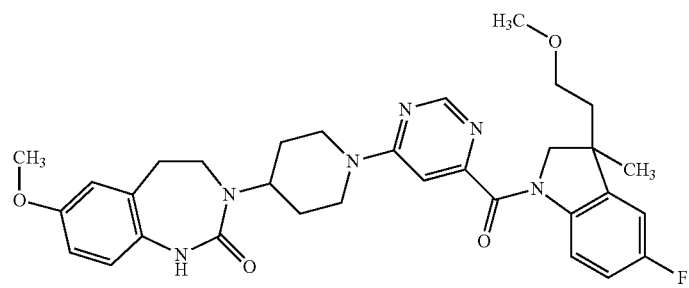 [SMILES: COCCC1(C)CN(C(=O)c2cc(N3CCC(N4CCc5cc(OC)ccc5NC4=O)CC3)ncn2)c2ccc(F)cc21] |
| (68) | 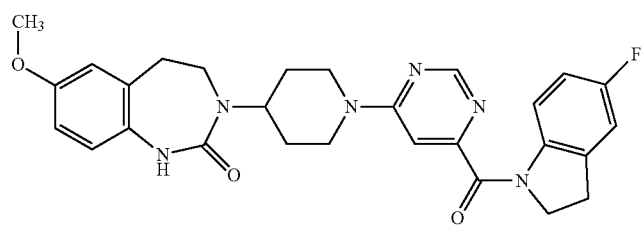 [SMILES: COc1ccc2c(c1)CCN(C1CCN(c3cc(C(=O)N4CCc5cc(F)ccc54)ncn3)CC1)C(=O)N2] |
| (69) | 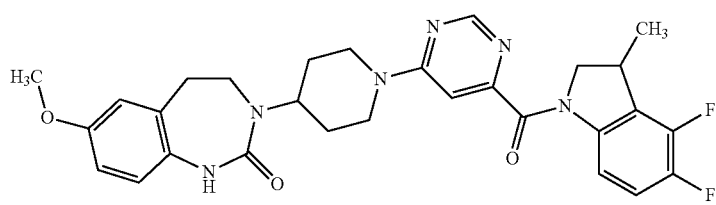 [SMILES: COc1ccc2c(c1)CCN(C1CCN(c3cc(C(=O)N4CC(C)c5c4ccc(F)c5F)ncn3)CC1)C(=O)N2] |

| No. | Structure |
|---|---|
| (70) | 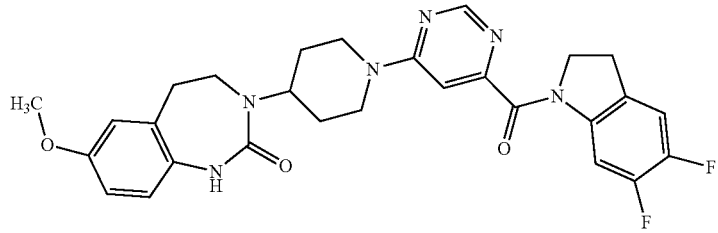 [SMILES: COc1ccc2c(c1)CCN(C1CCN(c3cc(C(=O)N4CCc5cc(F)c(F)cc54)ncn3)CC1)C(=O)N2] |
| (71) | 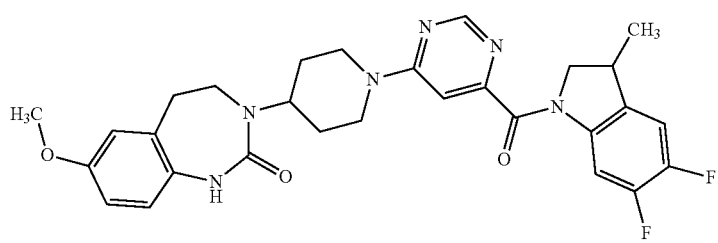 [SMILES: COc1ccc2c(c1)CCN(C1CCN(c3cc(C(=O)N4CC(C)c5cc(F)c(F)cc54)ncn3)CC1)C(=O)N2] |
| (72) | 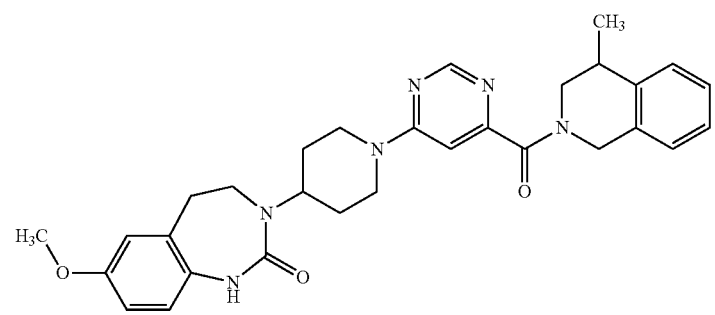 [SMILES: COc1ccc2c(c1)CCN(C1CCN(c3cc(C(=O)N4Cc5ccccc5C(C)C4)ncn3)CC1)C(=O)N2] |
| (73) | 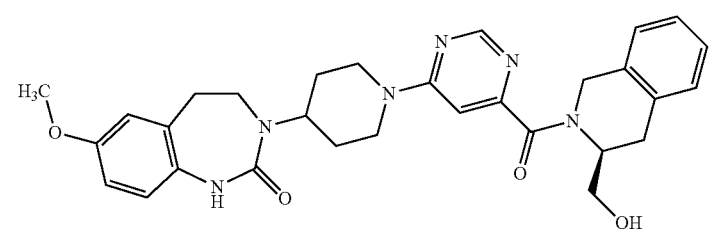 [SMILES: COc1ccc2c(c1)CCN(C1CCN(c3cc(C(=O)N4Cc5ccccc5C[C@H]4CO)ncn3)CC1)C(=O)N2] |
| (74) | 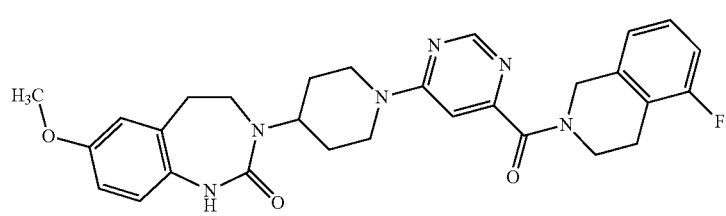 [SMILES: COc1ccc2c(c1)CCN(C1CCN(c3cc(C(=O)N4CCc5c(F)cccc5C4)ncn3)CC1)C(=O)N2] |
| (75) | 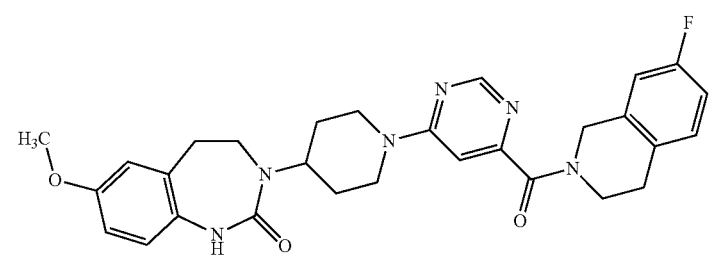 [SMILES: COc1ccc2c(c1)CCN(C1CCN(c3cc(C(=O)N4CCc5ccc(F)cc5C4)ncn3)CC1)C(=O)N2] |

| No. | Structure |
|---|---|
| (76) | 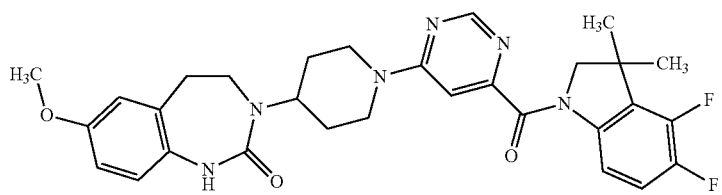 [SMILES: COc1ccc2c(c1)CCN(C1CCN(c3cc(C(=O)N4CC(C)(C)c5c4ccc(F)c5F)ncn3)CC1)C(=O)N2] |
| (77) | 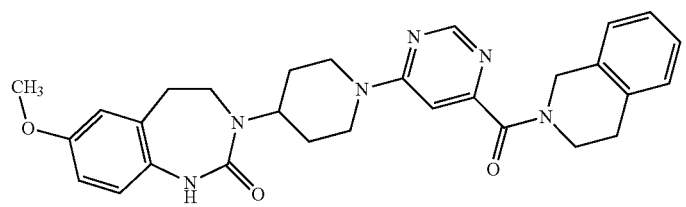 [SMILES: COc1ccc2c(c1)CCN(C1CCN(c3cc(C(=O)N4CCc5ccccc5C4)ncn3)CC1)C(=O)N2] |
| (78) | 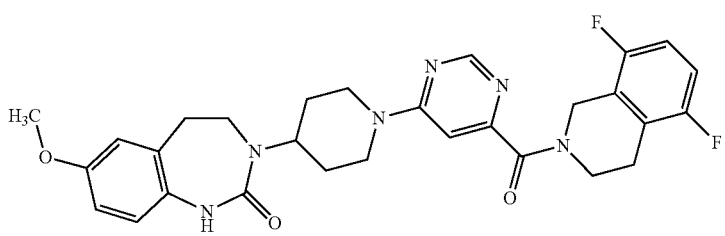 [SMILES: COc1ccc2c(c1)CCN(C1CCN(c3cc(C(=O)N4CCc5c(F)ccc(F)c5C4)ncn3)CC1)C(=O)N2] |
| (79) | 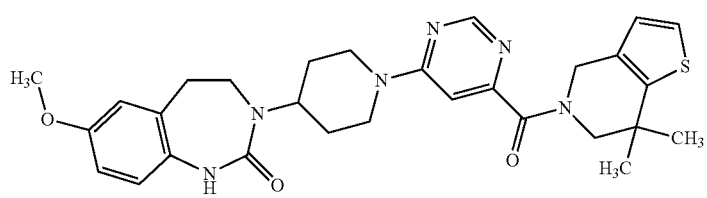 [SMILES: COc1ccc2c(c1)CCN(C1CCN(c3cc(C(=O)N4Cc5ccsc5C(C)(C)C4)ncn3)CC1)C(=O)N2] |
| (80) | 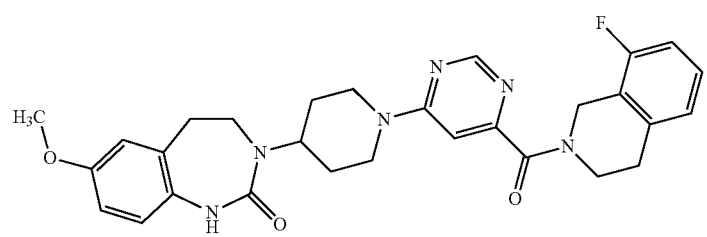 [SMILES: COc1ccc2c(c1)CCN(C1CCN(c3cc(C(=O)N4CCc5cccc(F)c5C4)ncn3)CC1)C(=O)N2] |
| (81) | 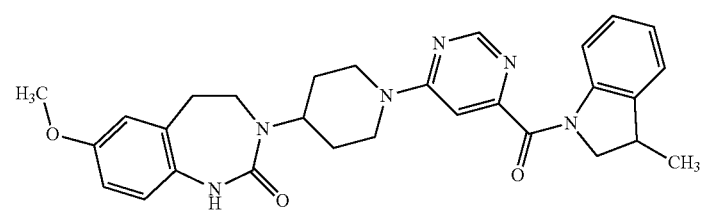 |
| (82) | 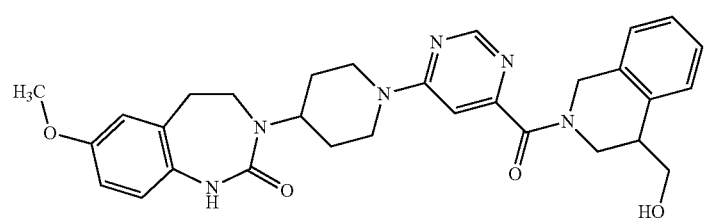 [SMILES: COc1ccc2c(c1)CCN(C1CCN(c3cc(C(=O)N4Cc5ccccc5C(CO)C4)ncn3)CC1)C(=O)N2] |

-continued
| No. | Structure |
|---|---|
| (83) | 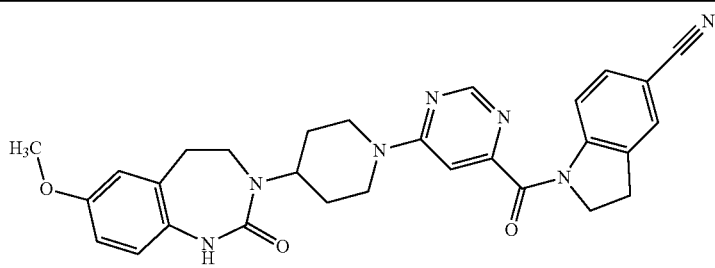 |
| (84) | 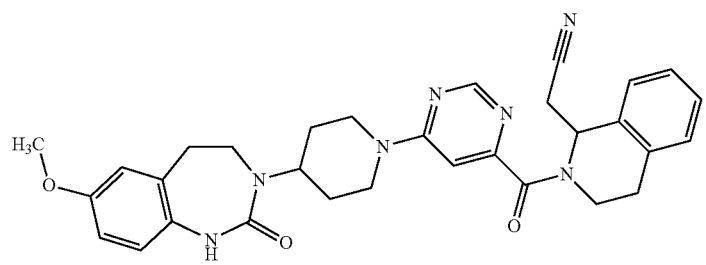 [SMILES: COc1ccc2c(c1)CCN(C1CCN(c3cc(C(=O)N4CCc5ccccc5C4CC#N)ncn3)CC1)C(=O)N2] |
| (85) | 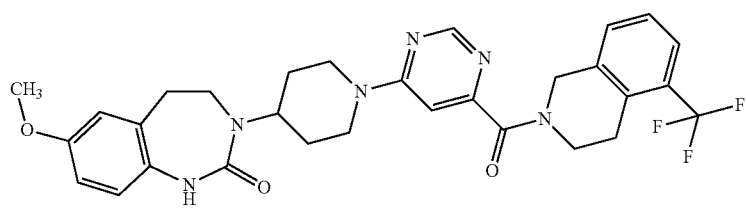 [SMILES: COc1ccc2c(c1)CCN(C1CCN(c3cc(C(=O)N4CCc5c(cccc5C(F)(F)F)C4)ncn3)CC1)C(=O)N2] |
| (86) | 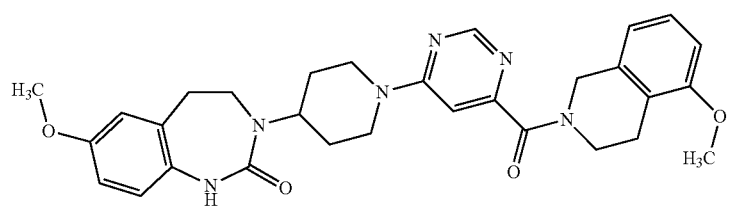 [SMILES: COc1ccc2c(c1)CCN(C1CCN(c3cc(C(=O)N4CCc5c(cccc5OC)C4)ncn3)CC1)C(=O)N2] |
| (87) | 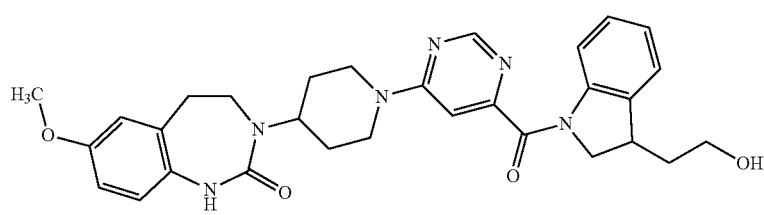 [SMILES: COc1ccc2c(c1)CCN(C1CCN(c3cc(C(=O)N4CC(CCO)c5ccccc54)ncn3)CC1)C(=O)N2] |
| (88) | 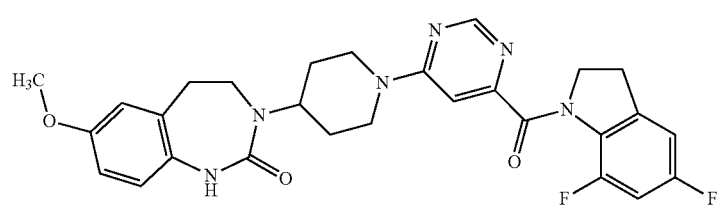 [SMILES: COc1ccc2c(c1)CCN(C1CCN(c3cc(C(=O)N4CCc5cc(F)cc(F)c54)ncn3)CC1)C(=O)N2] |
| (89) | 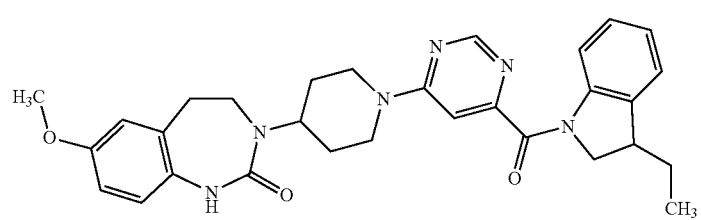 [SMILES: CCC1CN(C(=O)c2cc(N3CCC(N4CCc5cc(OC)ccc5NC4=O)CC3)ncn2)c2ccccc21] |

| No. | Structure |
|---|---|
| (90) | 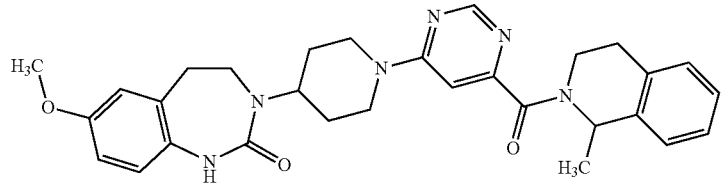 [SMILES: COc1ccc2c(c1)CCN(C1CCN(c3cc(C(=O)N4CCc5ccccc5C4C)ncn3)CC1)C(=O)N2] |
| (91) | 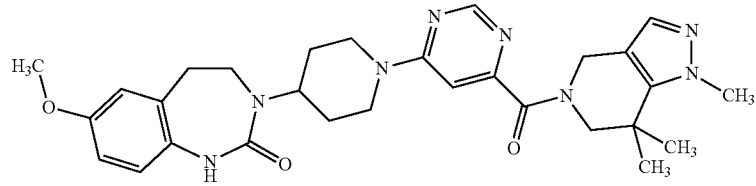 |
| (92) | 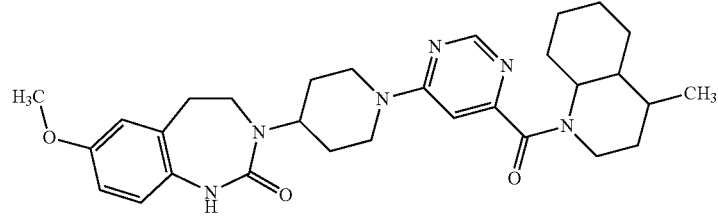 |
| (93) | 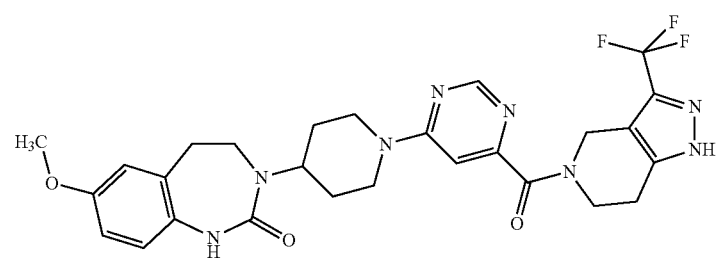 [SMILES: COc1ccc2c(c1)CCN(C1CCN(c3cc(C(=O)N4CCc5[nH]nc(C(F)(F)F)c5C4)ncn3)CC1)C(=O)N2] |
| (94) | 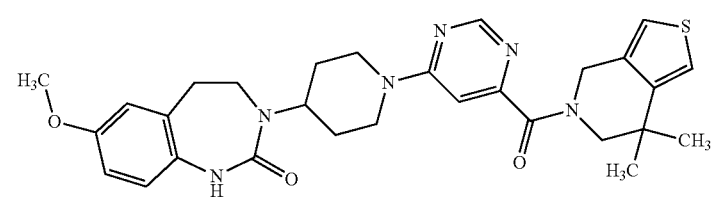 [SMILES: COc1ccc2c(c1)CCN(C1CCN(c3cc(C(=O)N4Cc5cscc5C(C)(C)C4)ncn3)CC1)C(=O)N2] |
| (95) | 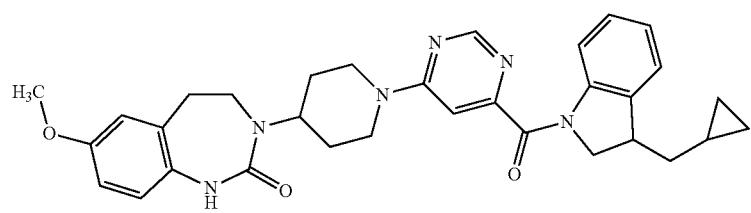 [SMILES: COc1ccc2c(c1)CCN(C1CCN(c3cc(C(=O)N4CC(CC5CC5)c5ccccc54)ncn3)CC1)C(=O)N2] |
| (96) | 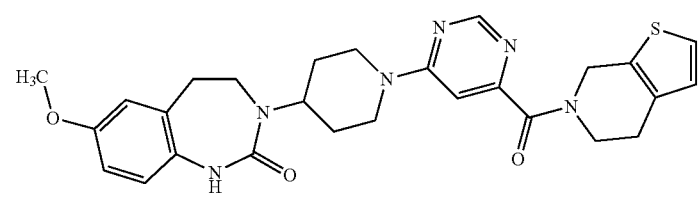 [SMILES: COc1ccc2c(c1)CCN(C1CCN(c3cc(C(=O)N4CCc5ccsc5C4)ncn3)CC1)C(=O)N2] |

| No. | Structure |
|---|---|
| (97) | 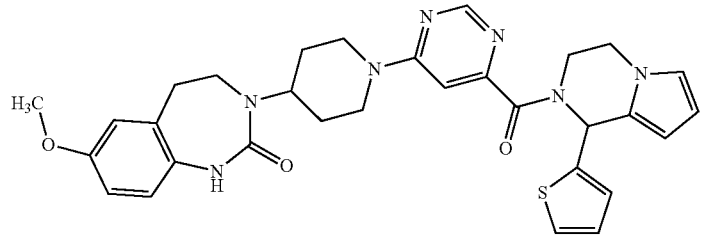 [SMILES: COc1ccc2c(c1)CCN(C1CCN(c3cc(C(=O)N4CCn5cccc5C4c4cccs4)ncn3)CC1)C(=O)N2] |
| (98) | 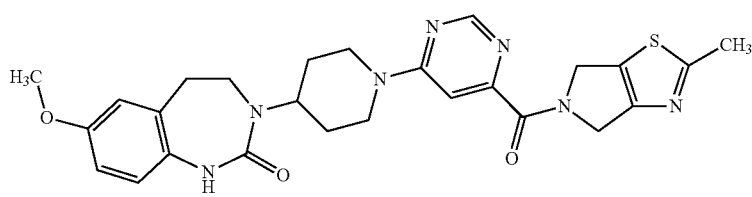 |
| (99) | 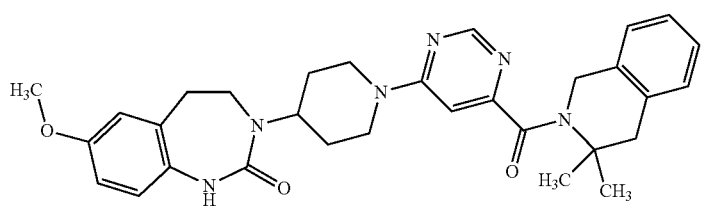 [SMILES: COc1ccc2c(c1)CCN(C1CCN(c3cc(C(=O)N4Cc5ccccc5CC4(C)C)ncn3)CC1)C(=O)N2] |
| (100) | 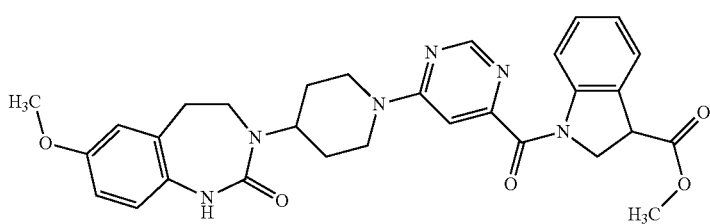 [SMILES: COC(=O)C1CN(C(=O)c2cc(N3CCC(N4CCc5cc(OC)ccc5NC4=O)CC3)ncn2)c2ccccc21] |
| (101) | 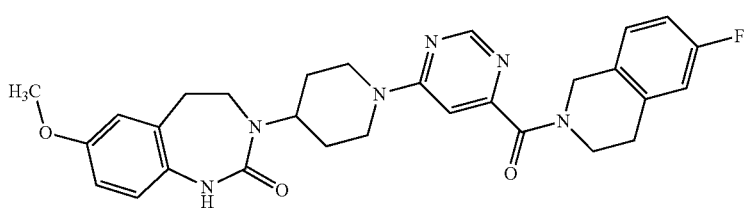 [SMILES: COc1ccc2c(c1)CCN(C1CCN(c3cc(C(=O)N4CCc5cc(F)ccc5C4)ncn3)CC1)C(=O)N2] |
| (102) | 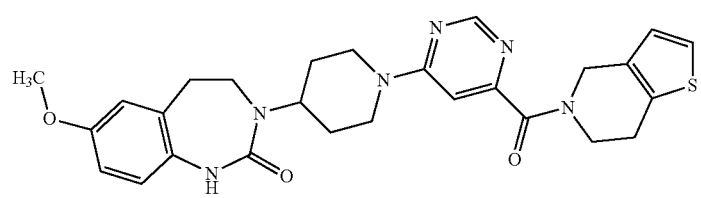 [SMILES: COc1ccc2c(c1)CCN(C1CCN(c3cc(C(=O)N4CCc5sccc5C4)ncn3)CC1)C(=O)N2] |
| (103) | 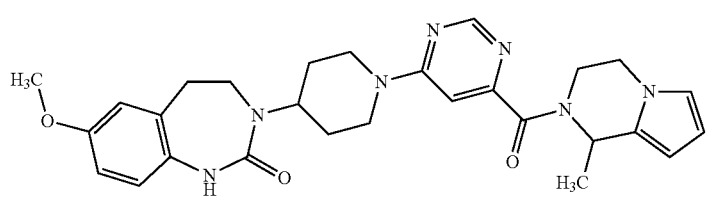 [SMILES: COc1ccc2c(c1)CCN(C1CCN(c3cc(C(=O)N4CCn5cccc5C4C)ncn3)CC1)C(=O)N2] |

US 8,829,006 B2
79                                                                80
-continued
| No.   | Structure |
|-------|-----------|
| (104) | 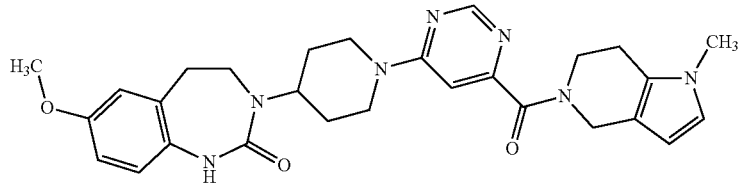 |
| (105) | 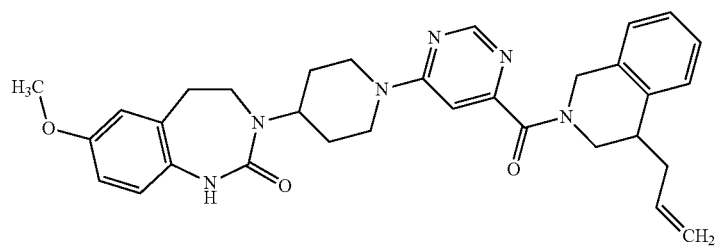 [SMILES: C=CCC1CN(C(=O)c2cc(N3CCC(N4CCc5cc(OC)ccc5NC4=O)CC3)ncn2)Cc2ccccc21] |
| (106) | 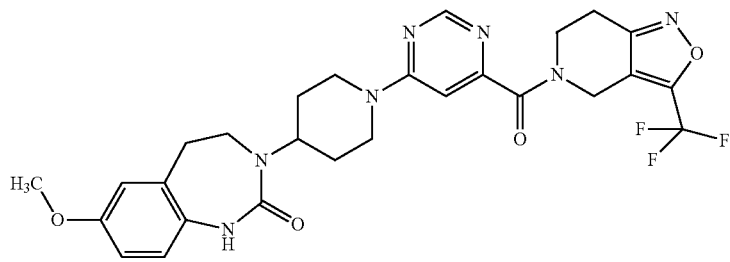 [SMILES: COc1ccc2c(c1)CCN(C1CCN(c3cc(C(=O)N4CCc5noc(C(F)(F)F)c5C4)ncn3)CC1)C(=O)N2] |
| (107) | 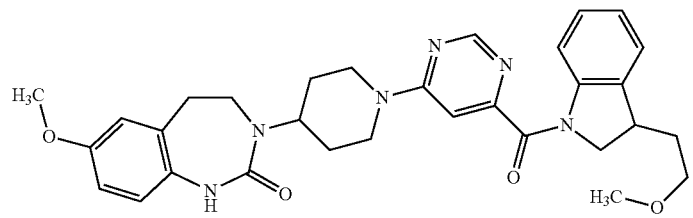 [SMILES: COCCC1CN(C(=O)c2cc(N3CCC(N4CCc5cc(OC)ccc5NC4=O)CC3)ncn2)c2ccccc21] |
| (108) | 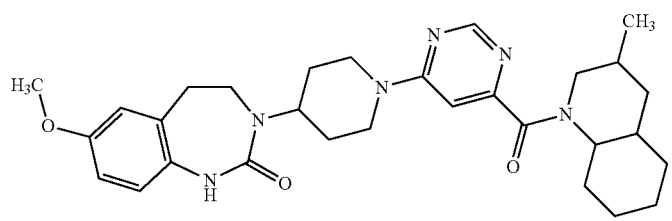 [SMILES: COc1ccc2c(c1)CCN(C1CCN(c3cc(C(=O)N4CC(C)CC5CCCCC54)ncn3)CC1)C(=O)N2] |
| (109) | 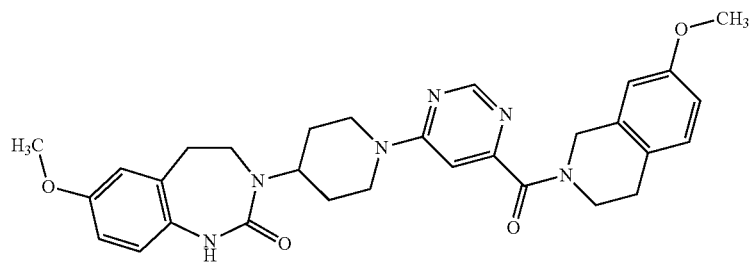 |

-continued
| No. | Structure |
|---|---|
| (110) | 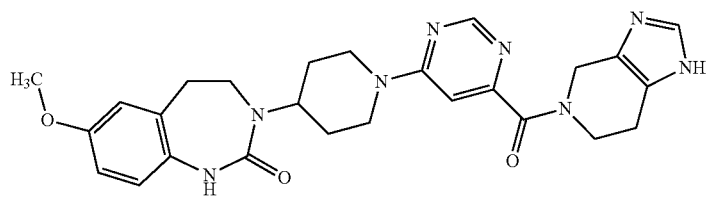 [SMILES: COc1ccc2c(c1)CCN(C1CCN(c3cc(C(=O)N4CCc5[nH]cnc5C4)ncn3)CC1)C(=O)N2] |
| (111) | 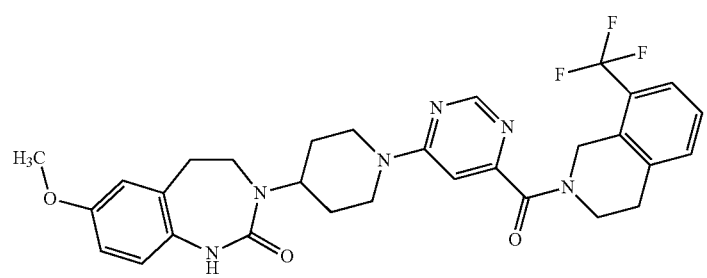 [SMILES: COc1ccc2c(c1)CCN(C1CCN(c3cc(C(=O)N4CCc5cccc(C(F)(F)F)c5C4)ncn3)CC1)C(=O)N2] |
| (112) | 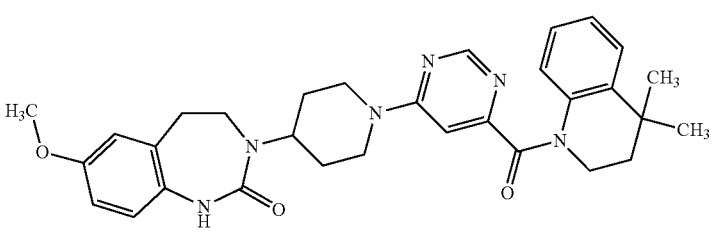 |
| (113) | 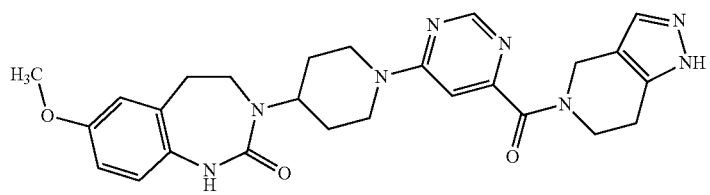 [SMILES: COc1ccc2c(c1)CCN(C1CCN(c3cc(C(=O)N4CCc5[nH]ncc5C4)ncn3)CC1)C(=O)N2] |
| (114) | 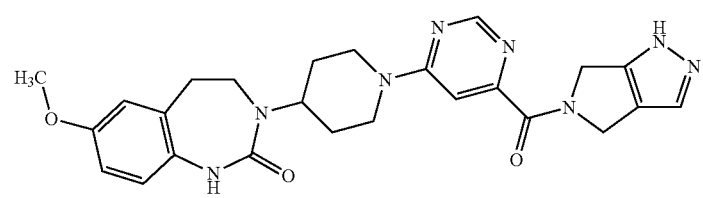 [SMILES: COc1ccc2c(c1)CCN(C1CCN(c3cc(C(=O)N4Cc5cn[nH]c5C4)ncn3)CC1)C(=O)N2] |
| (115) | 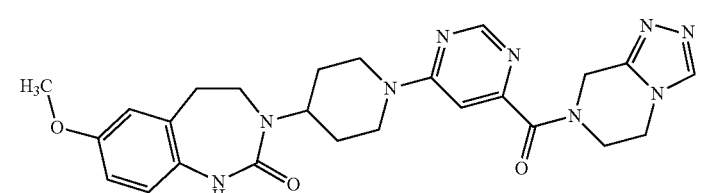 |
| (116) | 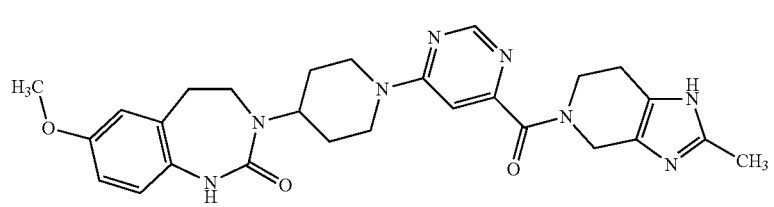 |

-continued
| No. | Structure |
|---|---|
| (117) | 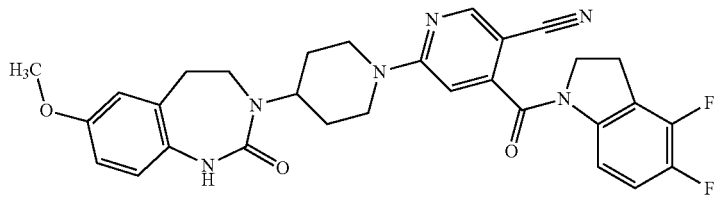 [SMILES: COc1ccc2c(c1)CCN(C1CCN(c3cc(C(=O)N4CCc5c4ccc(F)c5F)c(C#N)cn3)CC1)C(=O)N2] |
| (118) | 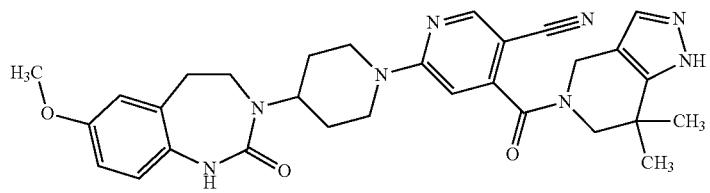 [SMILES: COc1ccc2c(c1)CCN(C1CCN(c3cc(C(=O)N4Cc5cn[nH]c5C(C)(C)C4)c(C#N)cn3)CC1)C(=O)N2] |
| (119) | 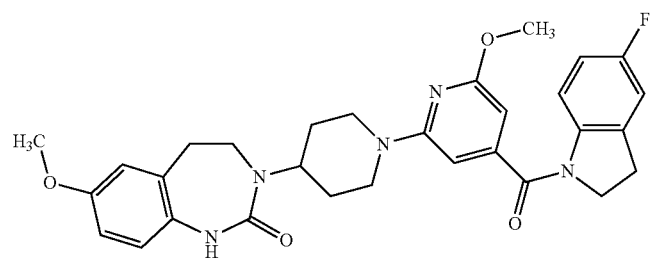 [SMILES: COc1ccc2c(c1)CCN(C1CCN(c3cc(C(=O)N4CCc5cc(F)ccc54)cc(OC)n3)CC1)C(=O)N2] |
| (120) | 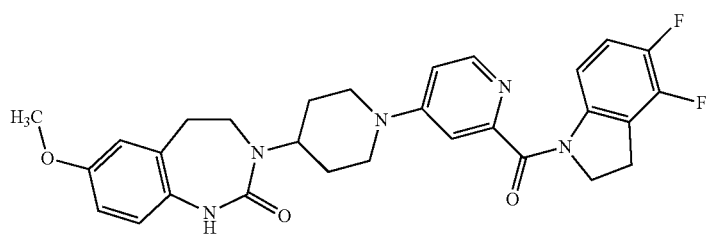 |
| (121) | 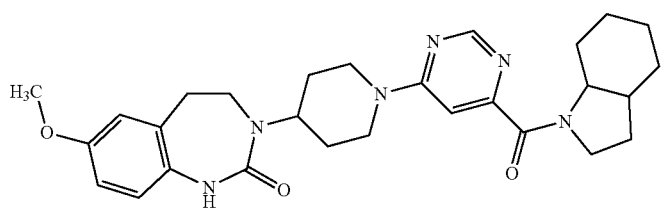 [SMILES: COc1ccc2c(c1)CCN(C1CCN(c3cc(C(=O)N4CCC5CCCCC54)ncn3)CC1)C(=O)N2] |
| (122) | 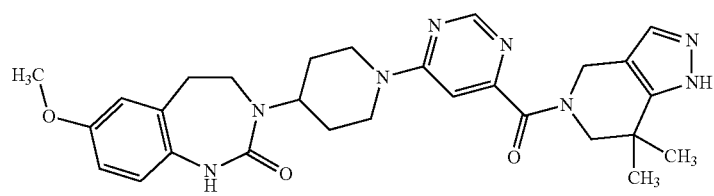 [SMILES: COc1ccc2c(c1)CCN(C1CCN(c3cc(C(=O)N4Cc5cn[nH]c5C(C)(C)C4)ncn3)CC1)C(=O)N2] |
| (123) | 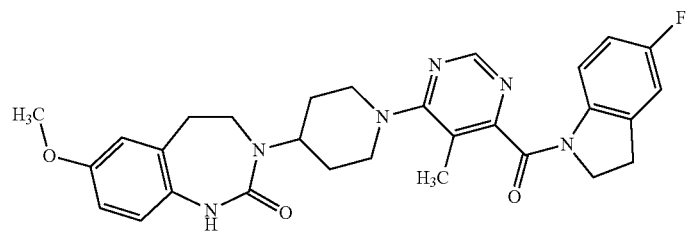 [SMILES: COc1ccc2c(c1)CCN(C1CCN(c3ncnc(C(=O)N4CCc5cc(F)ccc54)c3C)CC1)C(=O)N2] |

| No. | Structure |
|---|---|
| (124) | 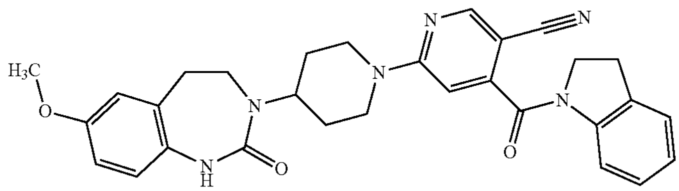 [SMILES: COc1ccc2c(c1)CCN(C1CCN(c3cc(C(=O)N4CCc5ccccc54)c(C#N)cn3)CC1)C(=O)N2] |
| (125) | 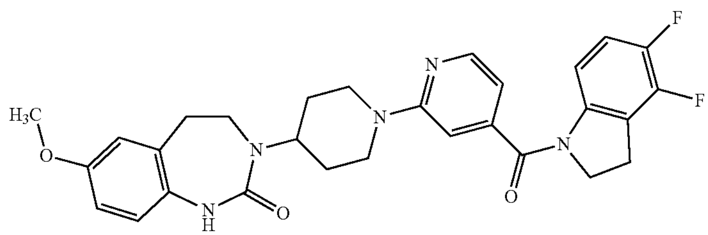 [SMILES: COc1ccc2c(c1)CCN(C1CCN(c3cc(C(=O)N4CCc5c4ccc(F)c5F)ccn3)CC1)C(=O)N2] |
| (126) | 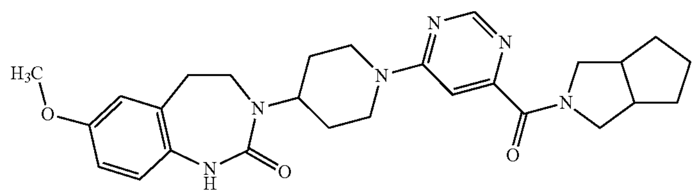 [SMILES: COc1ccc2c(c1)CCN(C1CCN(c3cc(C(=O)N4CC5CCCC5C4)ncn3)CC1)C(=O)N2] |
| (127) | 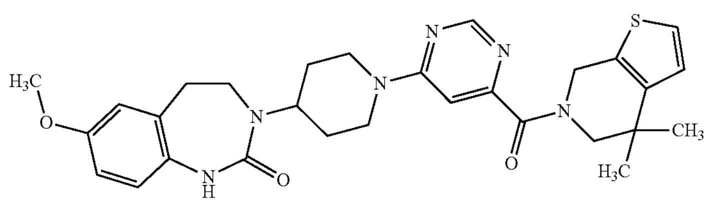 [SMILES: COc1ccc2c(c1)CCN(C1CCN(c3cc(C(=O)N4Cc5sccc5C(C)(C)C4)ncn3)CC1)C(=O)N2] |
| (128) | 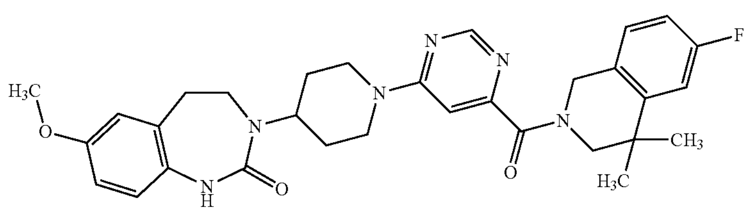 [SMILES: COc1ccc2c(c1)CCN(C1CCN(c3cc(C(=O)N4Cc5ccc(F)cc5C(C)(C)C4)ncn3)CC1)C(=O)N2] |
| (129) | 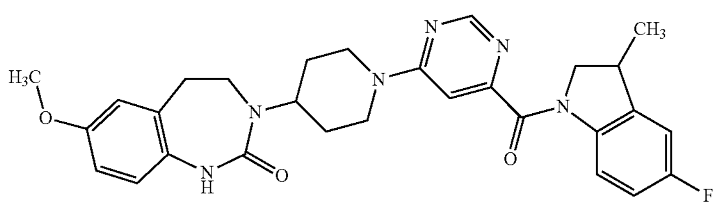 [SMILES: COc1ccc2c(c1)CCN(C1CCN(c3cc(C(=O)N4CC(C)c5cc(F)ccc54)ncn3)CC1)C(=O)N2] |
| (130) | 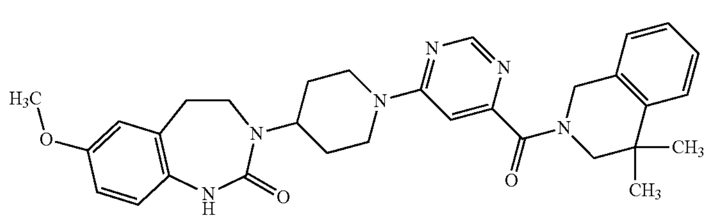 [SMILES: COc1ccc2c(c1)CCN(C1CCN(c3cc(C(=O)N4Cc5ccccc5C(C)(C)C4)ncn3)CC1)C(=O)N2] |

-continued
| No. | Structure |
|---|---|
| (131) | 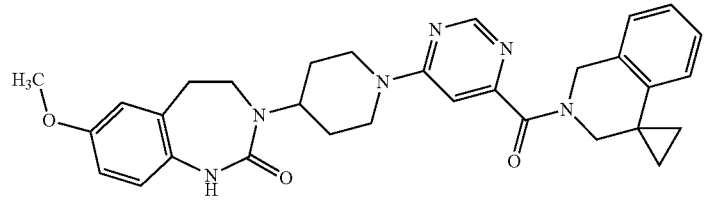 [SMILES: COc1ccc2c(c1)CCN(C1CCN(c3cc(C(=O)N4Cc5ccccc5C5(CC5)C4)ncn3)CC1)C(=O)N2] |
| (132) | 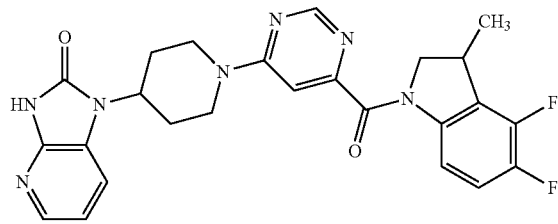 [SMILES: CC1CN(C(=O)c2cc(N3CCC(n4c(=O)[nH]c5ncccc54)CC3)ncn2)c2ccc(F)c(F)c21] |
| (133) | 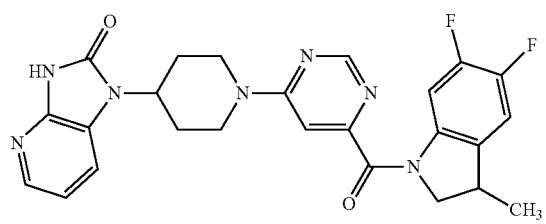 |
| (134) | 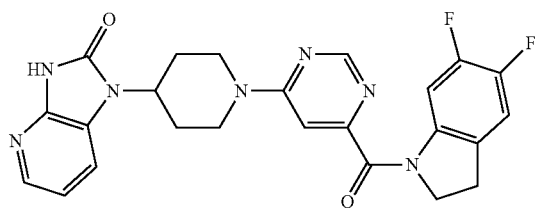 [SMILES: O=C(c1cc(N2CCC(n3c(=O)[nH]c4ncccc43)CC2)ncn1)N1CCc2cc(F)c(F)cc21] |
| (135) | 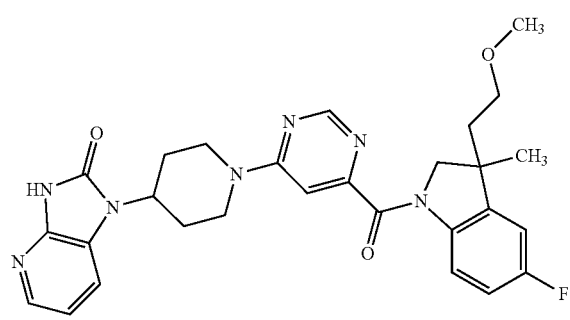 [SMILES: COCCC1(C)CN(C(=O)c2cc(N3CCC(n4c(=O)[nH]c5ncccc54)CC3)ncn2)c2ccc(F)cc21] |
| (136) | 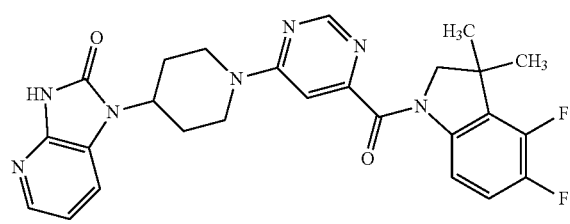 [SMILES: CC1(C)CN(C(=O)c2cc(N3CCC(n4c(=O)[nH]c5ncccc54)CC3)ncn2)c2ccc(F)c(F)c21] |

-continued
| No. | Structure |
|---|---|
| (137) | 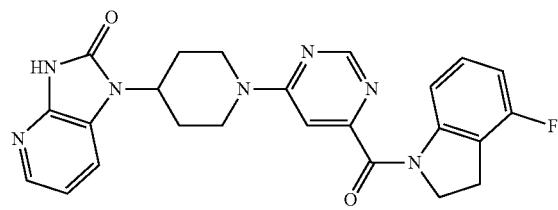 [SMILES: O=C(c1cc(N2CCC(n3c(=O)[nH]c4ncccc43)CC2)ncn1)N1CCc2c(F)cccc21] |
| (138) | 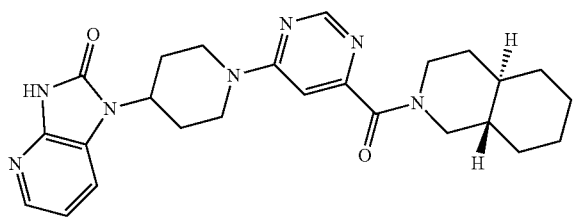 [SMILES: O=C(c1cc(N2CCC(n3c(=O)[nH]c4ncccc43)CC2)ncn1)N1CC[C@H]2CCCC[C@@H]2C1] |
| (139) | 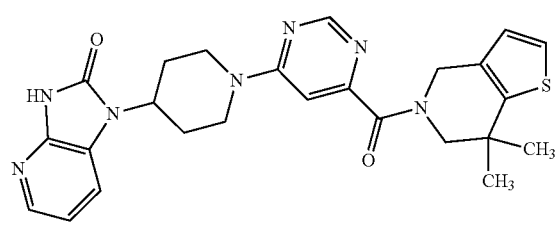 [SMILES: CC1(C)CN(C(=O)c2cc(N3CCC(n4c(=O)[nH]c5ncccc54)CC3)ncn2)Cc2ccsc21] |
| (140) | 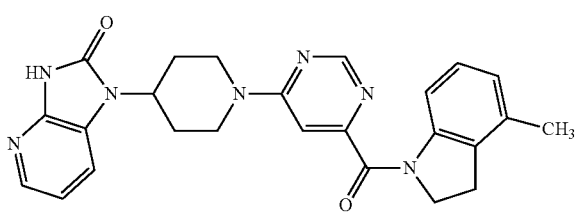 [SMILES: Cc1cccc2c1CCN2C(=O)c1cc(N2CCC(n3c(=O)[nH]c4ncccc43)CC2)ncn1] |
| (141) | 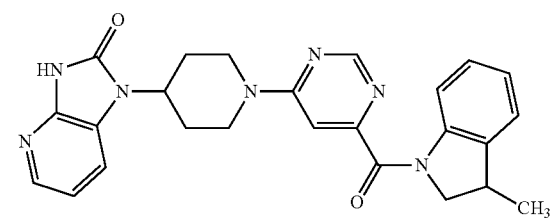 |
| (142) | 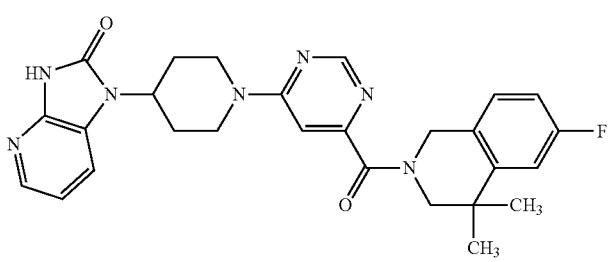 [SMILES: CC1(C)CN(C(=O)c2cc(N3CCC(n4c(=O)[nH]c5ncccc54)CC3)ncn2)Cc2ccc(F)cc21] |
| (143) | 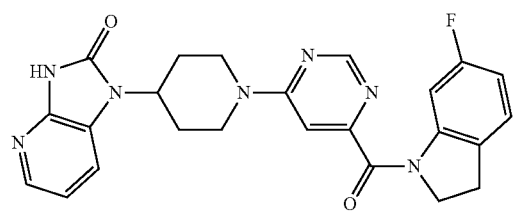 [SMILES: O=C(c1cc(N2CCC(n3c(=O)[nH]c4ncccc43)CC2)ncn1)N1CCc2ccc(F)cc21] |

-continued
| No. | Structure |
|---|---|
| (144) | 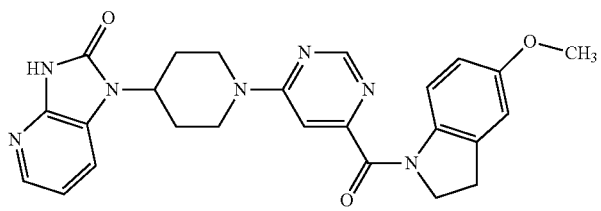 [SMILES: COc1ccc2c(c1)CCN2C(=O)c1cc(N2CCC(n3c(=O)[nH]c4ncccc43)CC2)ncn1] |
| (145) | 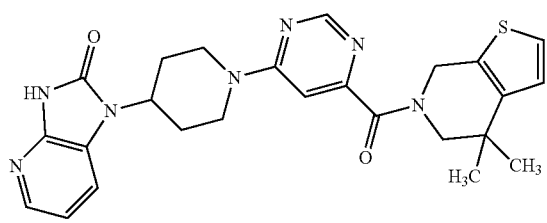 [SMILES: CC1(C)CN(C(=O)c2cc(N3CCC(n4c(=O)[nH]c5ncccc54)CC3)ncn2)Cc2sccc21] |
| (146) | 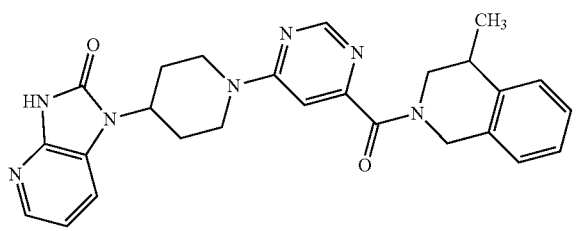 [SMILES: CC1CN(C(=O)c2cc(N3CCC(n4c(=O)[nH]c5ncccc54)CC3)ncn2)Cc2ccccc21] |
| (147) | 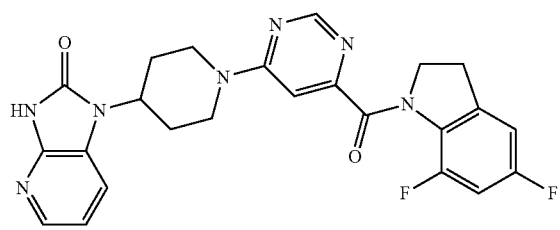 [SMILES: O=C(c1cc(N2CCC(n3c(=O)[nH]c4ncccc43)CC2)ncn1)N1CCc2cc(F)cc(F)c21] |
| (148) | 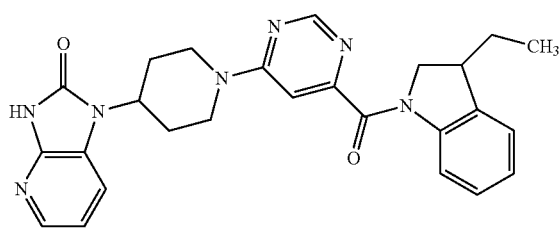 [SMILES: CCC1CN(C(=O)c2cc(N3CCC(n4c(=O)[nH]c5ncccc54)CC3)ncn2)c2ccccc21] |
| (149) | 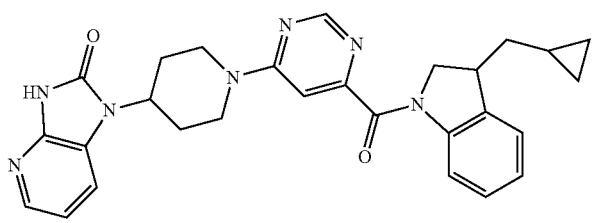 [SMILES: O=C(c1cc(N2CCC(n3c(=O)[nH]c4ncccc43)CC2)ncn1)N1CC(CC2CC2)c2ccccc21] |

| No. | Structure |
|---|---|
| (150) | 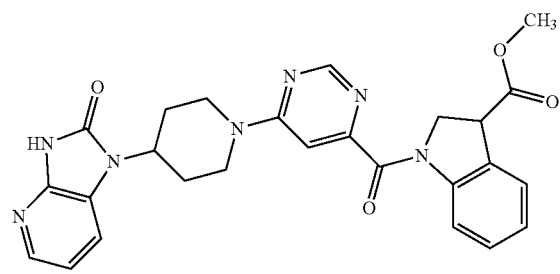 [SMILES: COC(=O)C1CN(C(=O)c2cc(N3CCC(n4c(=O)[nH]c5ncccc54)CC3)ncn2)c2ccccc21] |
| (151) | 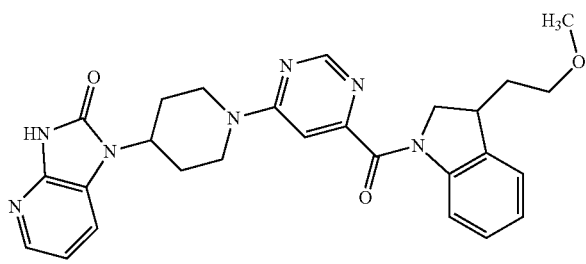 [SMILES: COCCC1CN(C(=O)c2cc(N3CCC(n4c(=O)[nH]c5ncccc54)CC3)ncn2)c2ccccc21] |
| (152) | 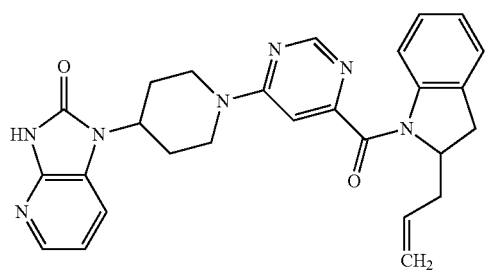 [SMILES: C=CCC1Cc2ccccc2N1C(=O)c1cc(N2CCC(n3c(=O)[nH]c4ncccc43)CC2)ncn1] |
| (153) | 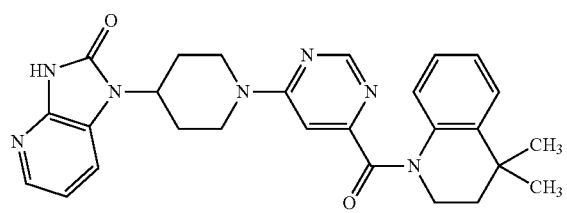 [SMILES: CC1(C)CCN(C(=O)c2cc(N3CCC(n4c(=O)[nH]c5ncccc54)CC3)ncn2)c2ccccc21] |
| (154) | 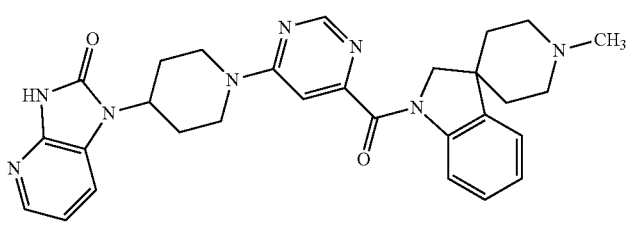 [SMILES: CN1CCC2(CC1)CN(C(=O)c1cc(N3CCC(n4c(=O)[nH]c5ncccc54)CC3)ncn1)c1ccccc12] |
| (155) | 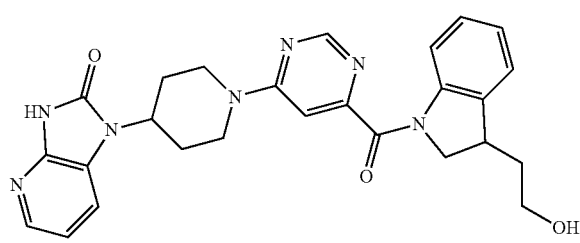 [SMILES: O=C(c1cc(N2CCC(n3c(=O)[nH]c4ncccc43)CC2)ncn1)N1CC(CCO)c2ccccc21] |

-continued
| No. | Structure |
|---|---|
| (156) | 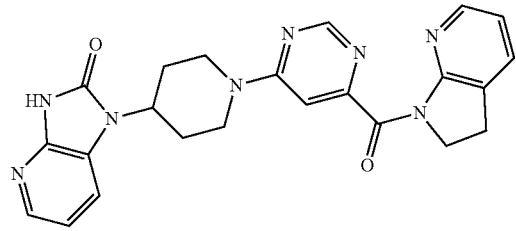 [SMILES: O=C(c1cc(N2CCC(n3c(=O)[nH]c4ncccc43)CC2)ncn1)N1CCc2cccnc21] |
| (157) | 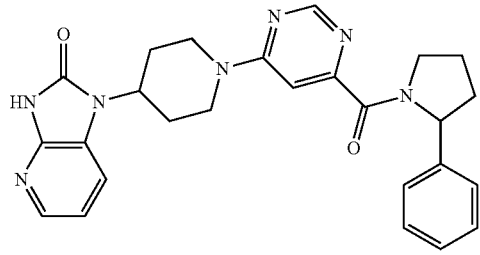 [SMILES: O=C(c1cc(N2CCC(n3c(=O)[nH]c4ncccc43)CC2)ncn1)N1CCCC1c1ccccc1] |
| (158) | 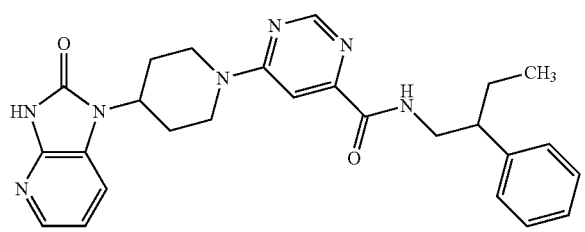 [SMILES: CCC(CNC(=O)c1cc(N2CCC(n3c(=O)[nH]c4ncccc43)CC2)ncn1)c1ccccc1] |
| (159) | 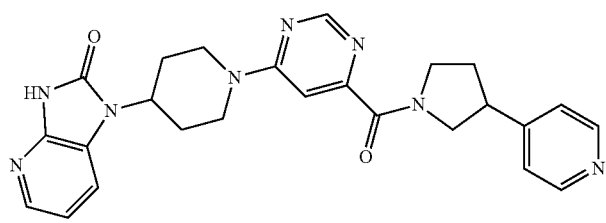 [SMILES: O=C(c1cc(N2CCC(n3c(=O)[nH]c4ncccc43)CC2)ncn1)N1CCC(c2ccncc2)C1] |
| (160) | 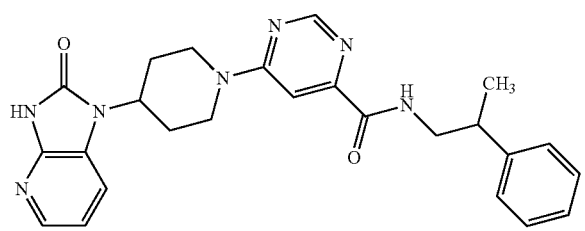 [SMILES: CC(CNC(=O)c1cc(N2CCC(n3c(=O)[nH]c4ncccc43)CC2)ncn1)c1ccccc1] |
| (161) | 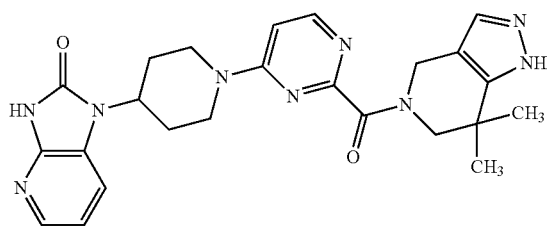 [SMILES: CC1(C)CN(C(=O)c2nccc(N3CCC(n4c(=O)[nH]c5ncccc54)CC3)n2)Cc2cn[nH]c21] |

-continued
| No. | Structure |
|---|---|
| (162) | 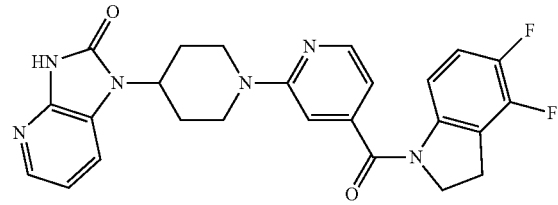 [SMILES: O=C(c1ccnc(N2CCC(n3c(=O)[nH]c4ncccc43)CC2)c1)N1CCc2c1ccc(F)c2F] |
| (163) | 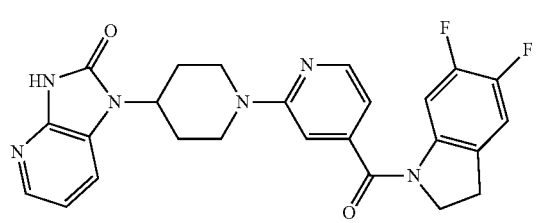 [SMILES: O=C(c1ccnc(N2CCC(n3c(=O)[nH]c4ncccc43)CC2)c1)N1CCc2cc(F)c(F)cc21] |
| (164) | 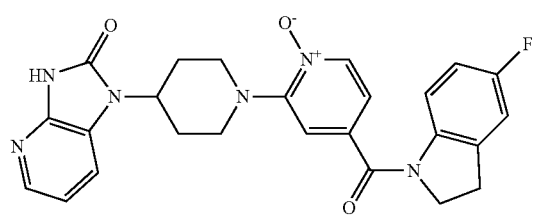 [SMILES: O=C(c1cc[n+]([O-])c(N2CCC(n3c(=O)[nH]c4ncccc43)CC2)c1)N1CCc2cc(F)ccc21] |
| (165) | 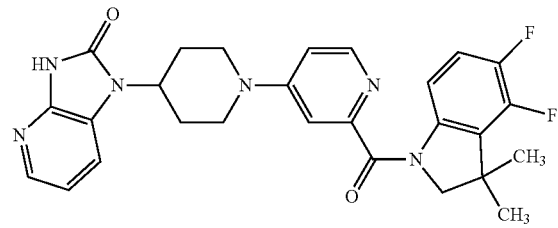 [SMILES: CC1(C)CN(C(=O)c2cc(N3CCC(n4c(=O)[nH]c5ncccc54)CC3)ccn2)c2ccc(F)c(F)c21] |
| (166) | 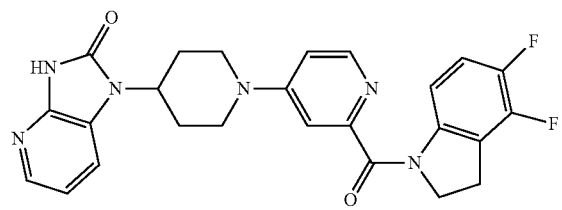 [SMILES: O=C(c1cc(N2CCC(n3c(=O)[nH]c4ncccc43)CC2)ccn1)N1CCc2c1ccc(F)c2F] |
| (167) | 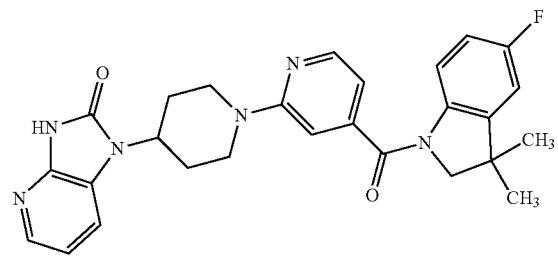 [SMILES: CC1(C)CN(C(=O)c2ccnc(N3CCC(n4c(=O)[nH]c5ncccc54)CC3)c2)c2ccc(F)cc21] |
| (168) | 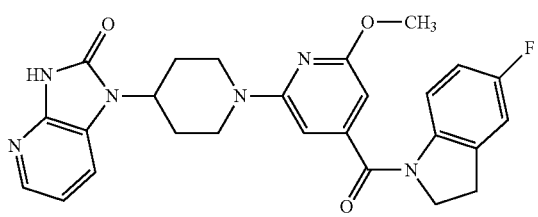 [SMILES: COc1cc(C(=O)N2CCc3cc(F)ccc32)cc(N2CCC(n3c(=O)[nH]c4ncccc43)CC2)n1] |

| No. | Structure |
|---|---|
| (169) | 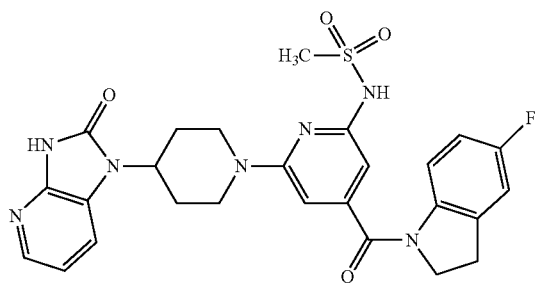 [SMILES: CS(=O)(=O)Nc1cc(C(=O)N2CCc3cc(F)ccc32)cc(N2CCC(n3c(=O)[nH]c4ncccc43)CC2)n1] |
| (170) | 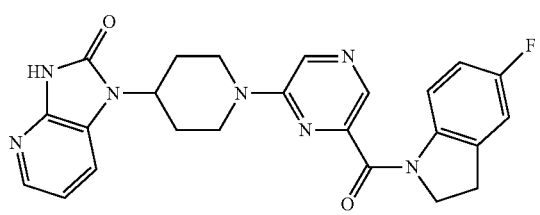 [SMILES: O=C(c1cncc(N2CCC(n3c(=O)[nH]c4ncccc43)CC2)n1)N1CCc2cc(F)ccc21] |
| (171) | 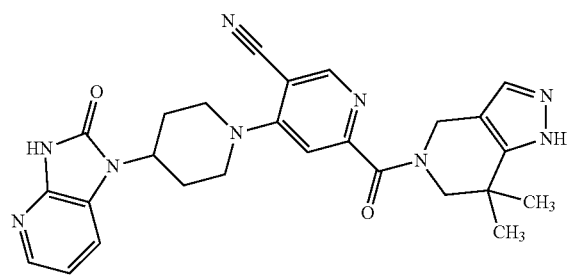 [SMILES: CC1(C)CN(C(=O)c2cc(N3CCC(n4c(=O)[nH]c5ncccc54)CC3)c(C#N)cn2)Cc2cn[nH]c21] |
| (172) | 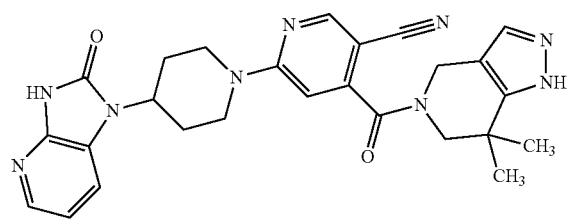 [SMILES: CC1(C)CN(C(=O)c2cc(N3CCC(n4c(=O)[nH]c5ncccc54)CC3)ncc2C#N)Cc2cn[nH]c21] |
| (173) | 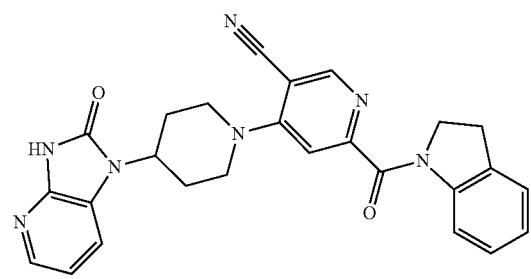 [SMILES: N#Cc1cnc(C(=O)N2CCc3ccccc32)cc1N1CCC(n2c(=O)[nH]c3ncccc32)CC1] |
| (174) | 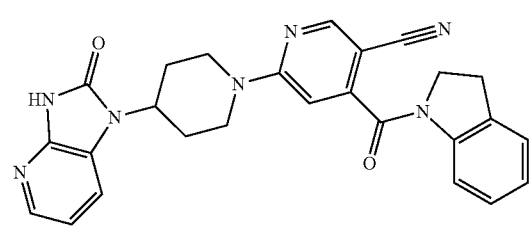 [SMILES: N#Cc1cnc(N2CCC(n3c(=O)[nH]c4ncccc43)CC2)cc1C(=O)N1CCc2ccccc21] |

-continued
| No. | Structure |
|---|---|
| (175) | 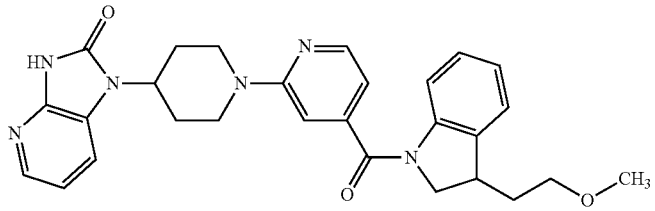 [SMILES: COCCC1CN(C(=O)c2ccnc(N3CCC(n4c(=O)[nH]c5ncccc54)CC3)c2)c2ccccc21] |
| (176) | 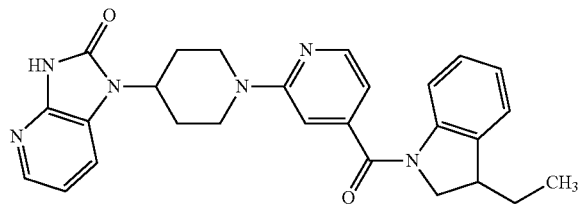 [SMILES: CCC1CN(C(=O)c2ccnc(N3CCC(n4c(=O)[nH]c5ncccc54)CC3)c2)c2ccccc21] |
| (177) | 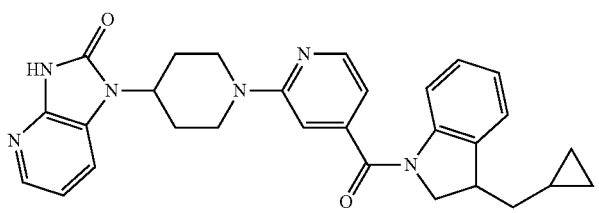 [SMILES: O=C(c1ccnc(N2CCC(n3c(=O)[nH]c4ncccc43)CC2)c1)N1CC(CC2CC2)c2ccccc21] |
| (178) | 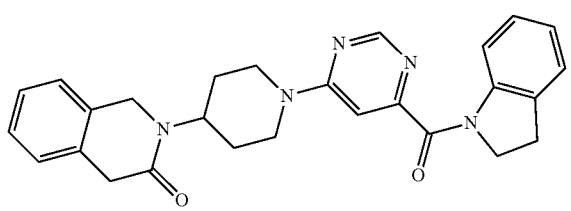 [SMILES: O=C(c1cc(N2CCC(N3Cc4ccccc4CC3=O)CC2)ncn1)N1CCc2ccccc21] |
| (179) | 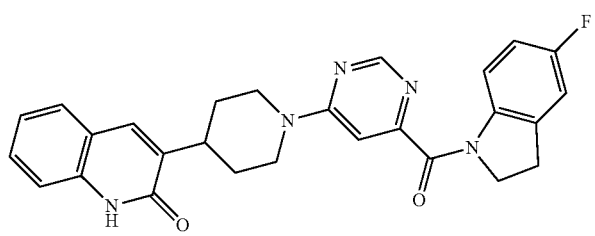 [SMILES: O=C(c1cc(N2CCC(c3cc4ccccc4[nH]c3=O)CC2)ncn1)N1CCc2cc(F)ccc21] |
| (180) | 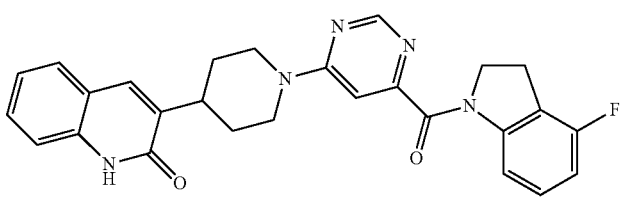 [SMILES: O=C(c1cc(N2CCC(c3cc4ccccc4[nH]c3=O)CC2)ncn1)N1CCc2c(F)cccc21] |
| (181) | 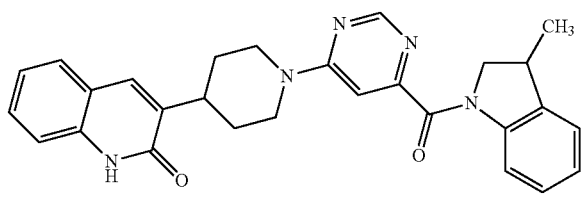 [SMILES: CC1CN(C(=O)c2cc(N3CCC(c4cc5ccccc5[nH]c4=O)CC3)ncn2)c2ccccc21] |

-continued
| No. | Structure |
|---|---|
| (182) | 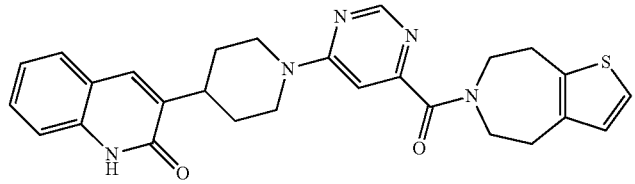 [SMILES: O=C(c1cc(N2CCC(c3cc4ccccc4[nH]c3=O)CC2)ncn1)N1CCc2ccsc2CC1] |
| (183) | 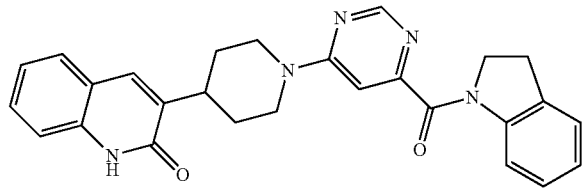 [SMILES: O=C(c1cc(N2CCC(c3cc4ccccc4[nH]c3=O)CC2)ncn1)N1CCc2ccccc21] |
| (184) | 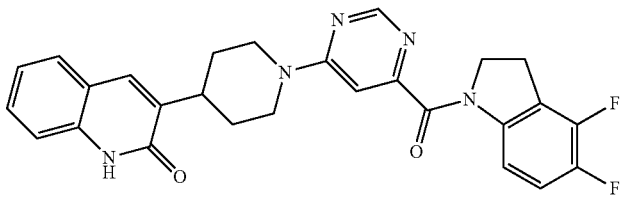 [SMILES: O=C(c1cc(N2CCC(c3cc4ccccc4[nH]c3=O)CC2)ncn1)N1CCc2c1ccc(F)c2F] |
| (185) | 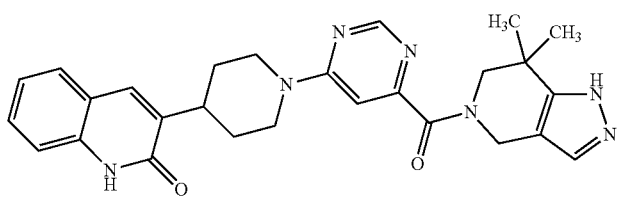 [SMILES: CC1(C)CN(C(=O)c2cc(N3CCC(c4cc5ccccc5[nH]c4=O)CC3)ncn2)Cc2cn[nH]c21] |
| (186) | 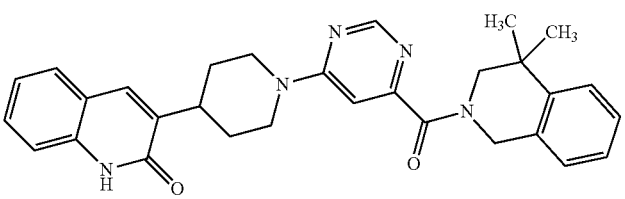 [SMILES: CC1(C)CN(C(=O)c2cc(N3CCC(c4cc5ccccc5[nH]c4=O)CC3)ncn2)Cc2ccccc21] |
| (187) | 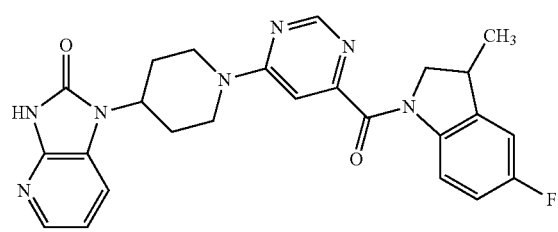 [SMILES: CC1CN(C(=O)c2cc(N3CCC(n4c(=O)[nH]c5ncccc54)CC3)ncn2)c2ccc(F)cc21] |
| (188) | 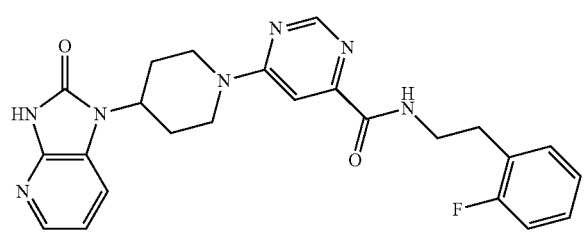 [SMILES: O=C(NCCc1ccccc1F)c1cc(N2CCC(n3c(=O)[nH]c4ncccc43)CC2)ncn1] |

-continued
| No. | Structure |
|---|---|
| (189) | 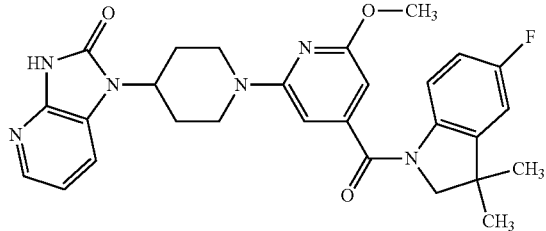 [SMILES: COc1cc(C(=O)N2CC(C)(C)c3cc(F)ccc32)cc(N2CCC(n3c(=O)[nH]c4ncccc43)CC2)n1] |
| (190) | 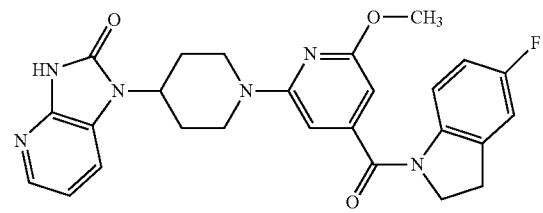 [SMILES: COc1cc(C(=O)N2CCc3cc(F)ccc32)cc(N2CCC(n3c(=O)[nH]c4ncccc43)CC2)n1] |
| (191) | 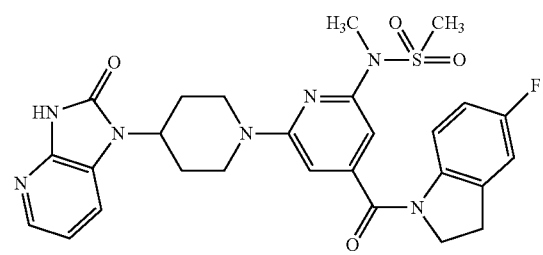 [SMILES: CN(c1cc(C(=O)N2CCc3cc(F)ccc32)cc(N2CCC(n3c(=O)[nH]c4ncccc43)CC2)n1)S(C)(=O)=O] |
| (192) | 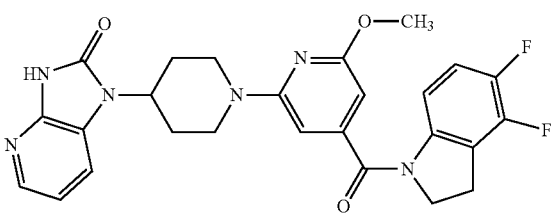 [SMILES: COc1cc(C(=O)N2CCc3c2ccc(F)c3F)cc(N2CCC(n3c(=O)[nH]c4ncccc43)CC2)n1] |
| (193) | 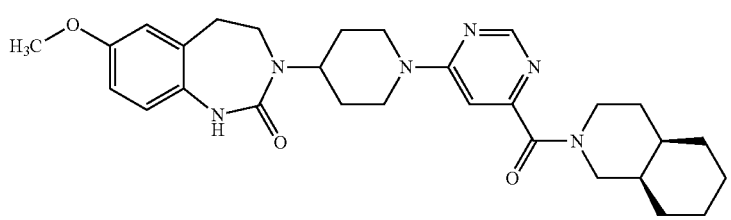 [SMILES: COc1ccc2c(c1)CCN(C1CCN(c3cc(C(=O)N4CC[C@H]5CCCC[C@H]5C4)ncn3)CC1)C(=O)N2] |
| (194) | 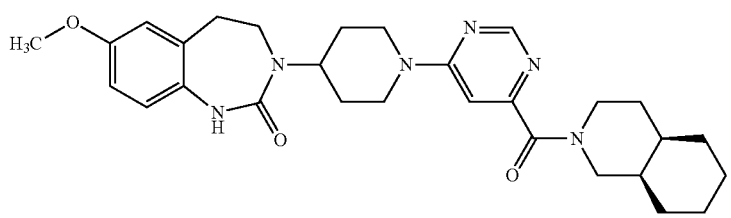 [SMILES: COc1ccc2c(c1)CCN(C1CCN(c3cc(C(=O)N4CC[C@H]5CCCC[C@H]5C4)ncn3)CC1)C(=O)N2] |
| (195) | 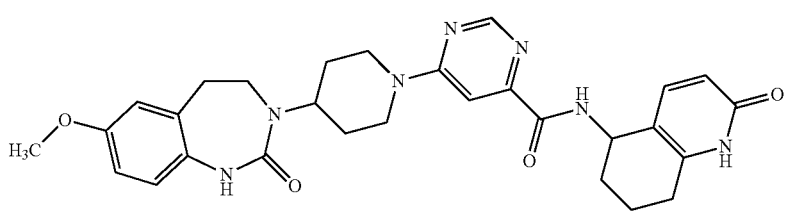 [SMILES: COc1ccc2c(c1)CCN(C1CCN(c3cc(C(=O)NC4CCCc5[nH]c(=O)ccc54)ncn3)CC1)C(=O)N2] |

| No. | Structure |
|---|---|
| (196) | 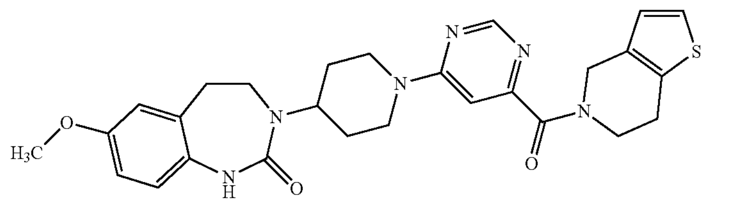 [SMILES: COc1ccc2c(c1)CCN(C1CCN(c3cc(C(=O)N4CCc5sccc5C4)ncn3)CC1)C(=O)N2] |
| (197) | 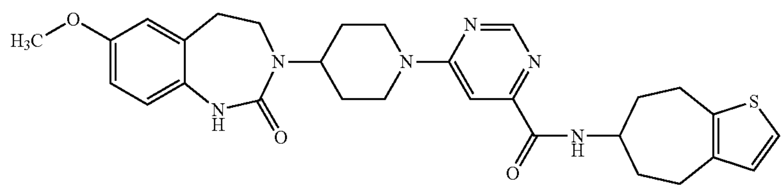 [SMILES: COc1ccc2c(c1)CCN(C1CCN(c3cc(C(=O)NC4CCc5ccsc5CC4)ncn3)CC1)C(=O)N2] |
| (198) | 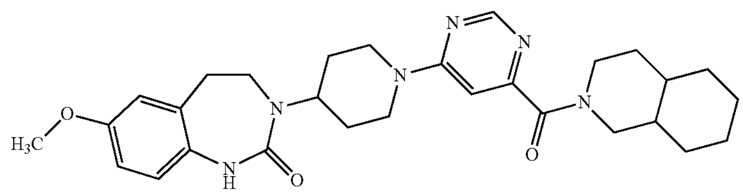 [SMILES: COc1ccc2c(c1)CCN(C1CCN(c3cc(C(=O)N4CCC5CCCCC5C4)ncn3)CC1)C(=O)N2] |
| (199) | 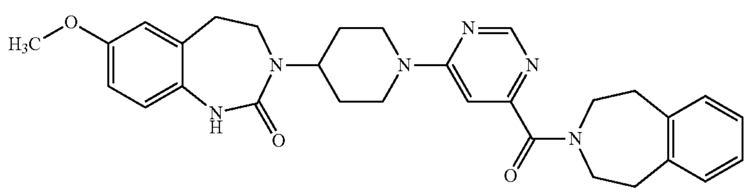 [SMILES: COc1ccc2c(c1)CCN(C1CCN(c3cc(C(=O)N4CCc5ccccc5CC4)ncn3)CC1)C(=O)N2] |
| (200) | 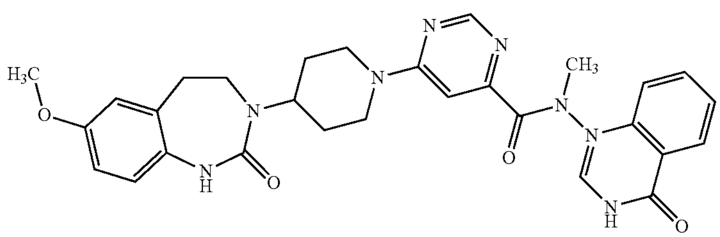 |
| (201) | 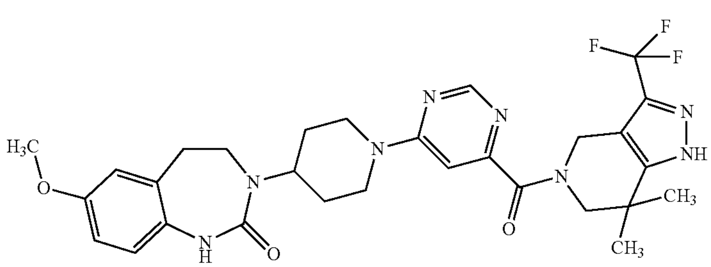 [SMILES: COc1ccc2c(c1)CCN(C1CCN(c3cc(C(=O)N4Cc5c(C(F)(F)F)n[nH]c5C(C)(C)C4)ncn3)CC1)C(=O)N2] |
| (202) | 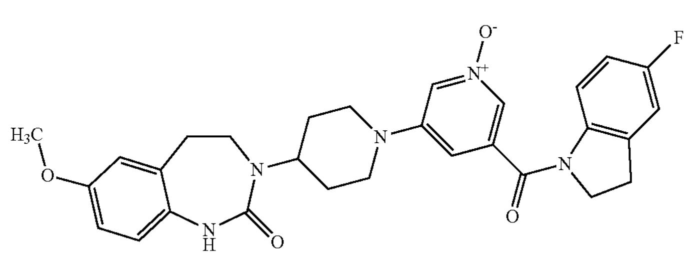 [SMILES: COc1ccc2c(c1)CCN(C1CCN(c3cc(C(=O)N4CCc5cc(F)ccc54)c[n+]([O-])c3)CC1)C(=O)N2] |

-continued
| No. | Structure |
|---|---|
| (203) | 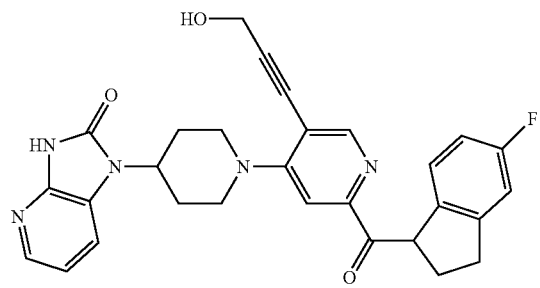 [SMILES: O=C(c1cc(N2CCC(n3c(=O)[nH]c4ncccc43)CC2)c(C#CCO)cn1)C1CCc2cc(F)ccc21] |
| (204) | 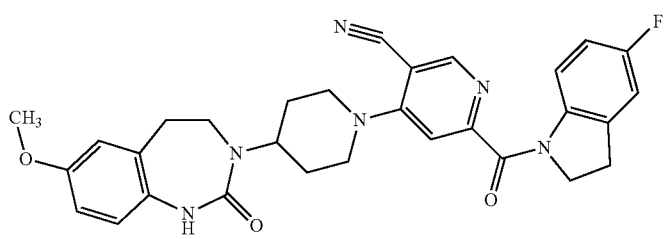 [SMILES: COc1ccc2c(c1)CCN(C1CCN(c3cc(C(=O)N4CCc5cc(F)ccc54)ncc3C#N)CC1)C(=O)N2] |
| (205) | 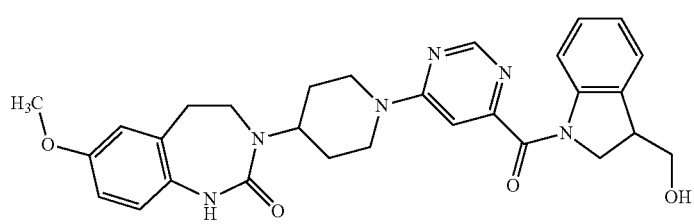 [SMILES: COc1ccc2c(c1)CCN(C1CCN(c3cc(C(=O)N4CC(CO)c5ccccc54)ncn3)CC1)C(=O)N2] |
| (206) | 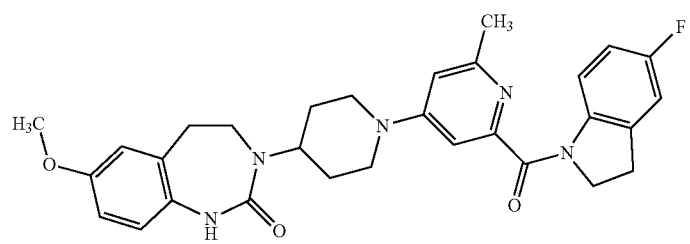 [SMILES: COc1ccc2c(c1)CCN(C1CCN(c3cc(C)nc(C(=O)N4CCc5cc(F)ccc54)c3)CC1)C(=O)N2] |
| (207) | 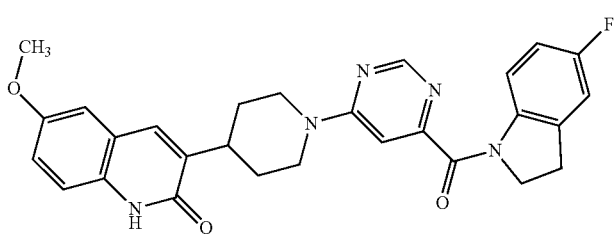 [SMILES: COc1ccc2[nH]c(=O)c(C3CCN(c4cc(C(=O)N5CCc6cc(F)ccc65)ncn4)CC3)cc2c1] |
| (208) | 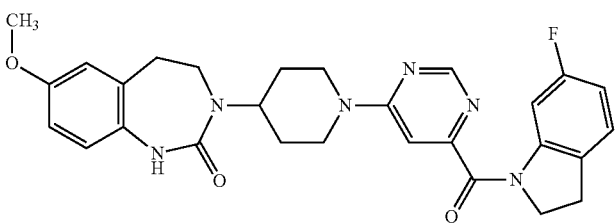 [SMILES: COc1ccc2c(c1)CCN(C1CCN(c3cc(C(=O)N4CCc5ccc(F)cc54)ncn3)CC1)C(=O)N2] |

US 8,829,006 B2
111                                                                                                                   112
-continued
| No. | Structure |
|---|---|
| (209) | 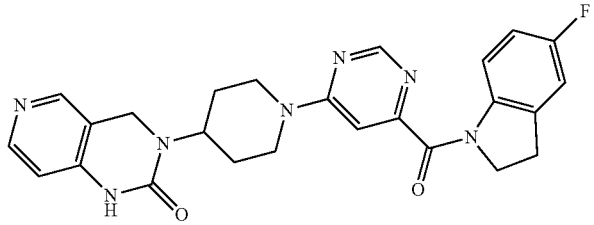 [SMILES: O=C(c1cc(N2CCC(N3Cc4cnccc4NC3=O)CC2)ncn1)N1CCc2cc(F)ccc21] |
| (210) | 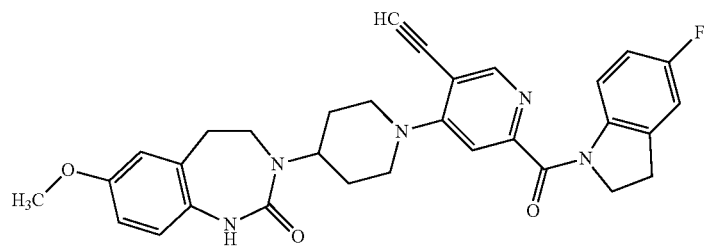 [SMILES: C#Cc1cnc(C(=O)N2CCc3cc(F)ccc32)cc1N1CCC(N2CCc3cc(OC)ccc3NC2=O)CC1] |
| (211) | 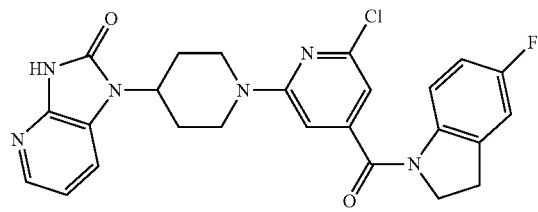 [SMILES: O=C(c1cc(Cl)nc(N2CCC(n3c(=O)[nH]c4ncccc43)CC2)c1)N1CCc2cc(F)ccc21] |
| (212) | 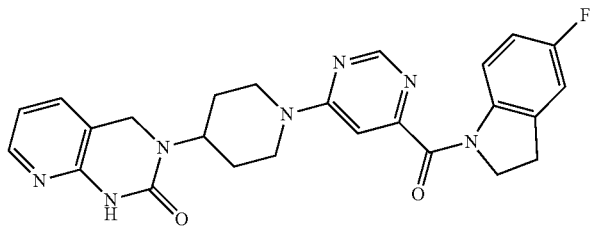 [SMILES: O=C(c1cc(N2CCC(N3Cc4cccnc4NC3=O)CC2)ncn1)N1CCc2cc(F)ccc21] |
| (213) | 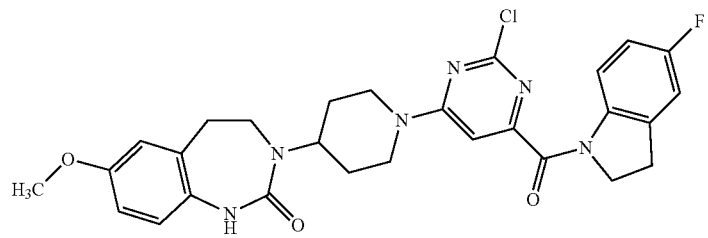 [SMILES: COc1ccc2c(c1)CCN(C1CCN(c3cc(C(=O)N4CCc5cc(F)ccc54)nc(Cl)n3)CC1)C(=O)N2] |
| (214) | 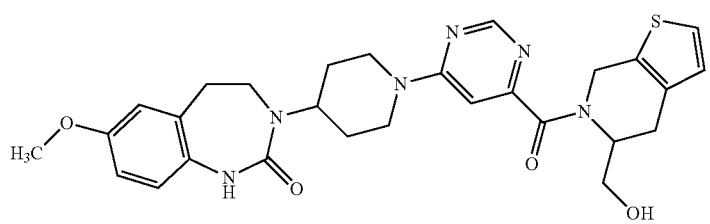 [SMILES: COc1ccc2c(c1)CCN(C1CCN(c3cc(C(=O)N4Cc5sccc5CC4CO)ncn3)CC1)C(=O)N2] |

-continued
| No. | Structure |
|---|---|
| (215) | 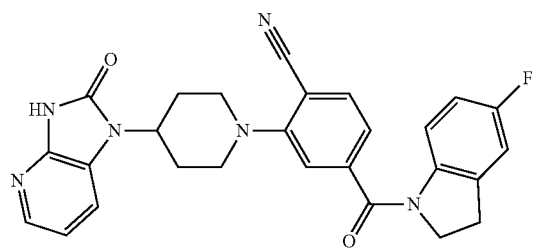 [SMILES: N#Cc1ccc(C(=O)N2CCc3cc(F)ccc32)cc1N1CCC(n2c(=O)[nH]c3ncccc32)CC1] |
| (216) | 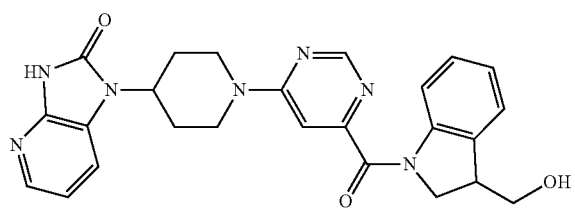 [SMILES: O=C(c1cc(N2CCC(n3c(=O)[nH]c4ncccc43)CC2)ncn1)N1CC(CO)c2ccccc21] |
| (217) | 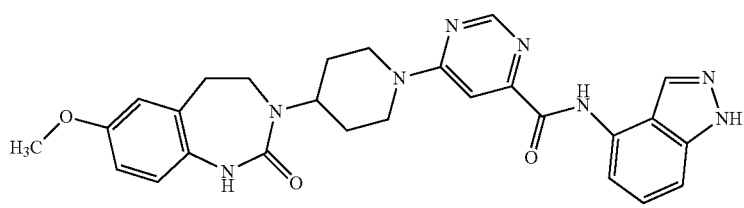 [SMILES: COc1ccc2c(c1)CCN(C1CCN(c3cc(C(=O)Nc4cccc5[nH]ncc45)ncn3)CC1)C(=O)N2] |
| (218) | 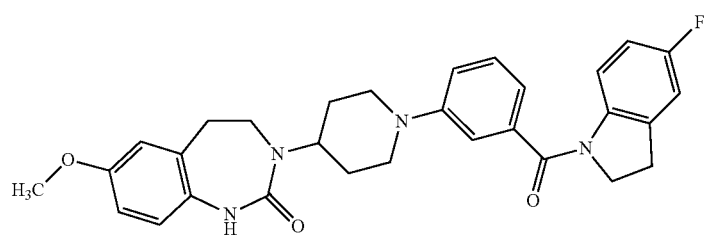 [SMILES: COc1ccc2c(c1)CCN(C1CCN(c3cccc(C(=O)N4CCc5cc(F)ccc54)c3)CC1)C(=O)N2] |
| (219) | 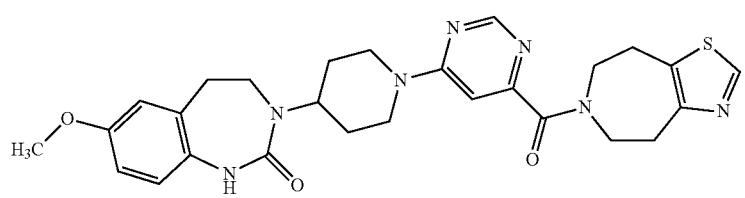 [SMILES: COc1ccc2c(c1)CCN(C1CCN(c3cc(C(=O)N4CCc5ncsc5CC4)ncn3)CC1)C(=O)N2] |
| (220) | 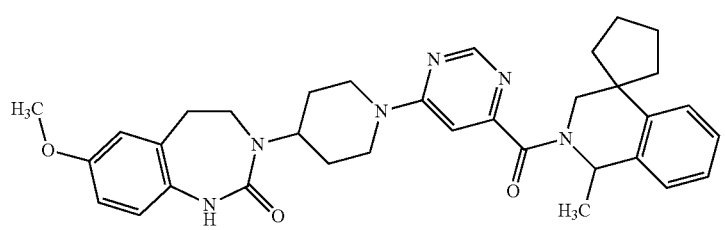 [SMILES: COc1ccc2c(c1)CCN(C1CCN(c3cc(C(=O)N4CC5(CCCC5)c5ccccc5C4C)ncn3)CC1)C(=O)N2] |
| (221) | 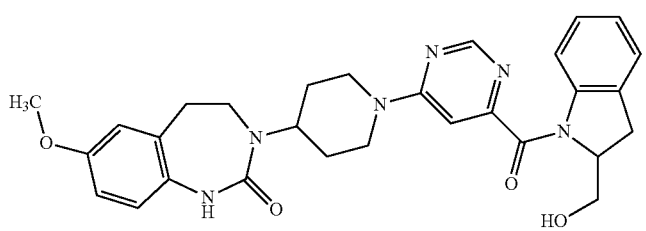 [SMILES: COc1ccc2c(c1)CCN(C1CCN(c3cc(C(=O)N4c5ccccc5CC4CO)ncn3)CC1)C(=O)N2] |

-continued

| No. | Structure |
|---|---|
| (222) | 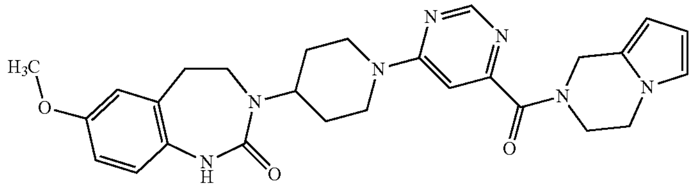 [SMILES: COc1ccc2c(c1)CCN(C1CCN(c3cc(C(=O)N4CCn5cccc5C4)ncn3)CC1)C(=O)N2] |
| (223) | 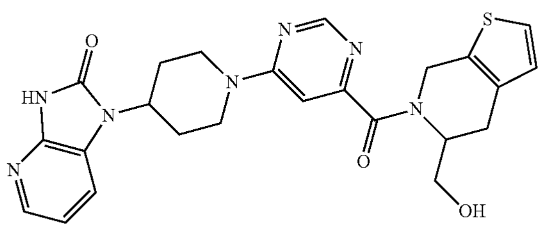 [SMILES: O=C(c1cc(N2CCC(n3c(=O)[nH]c4ncccc43)CC2)ncn1)N1Cc2sccc2CC1CO] |
| (224) | 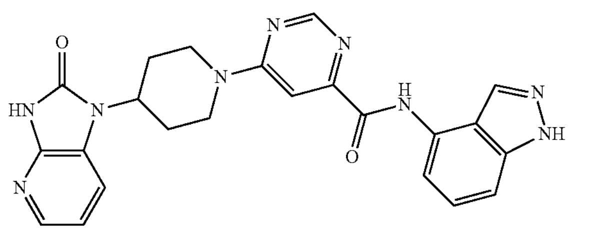 [SMILES: O=C(Nc1cccc2[nH]ncc12)c1cc(N2CCC(n3c(=O)[nH]c4ncccc43)CC2)ncn1] |
| (225) | 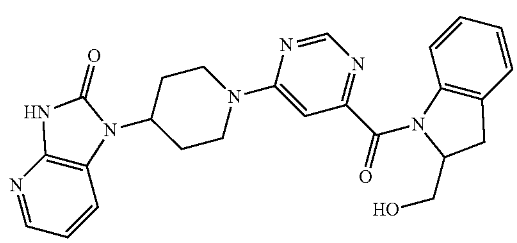 [SMILES: O=C(c1cc(N2CCC(n3c(=O)[nH]c4ncccc43)CC2)ncn1)N1c2ccccc2CC1CO] |
| (226) | 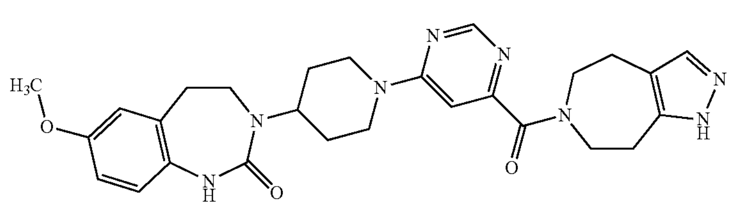 [SMILES: COc1ccc2c(c1)CCN(C1CCN(c3cc(C(=O)N4CCc5cn[nH]c5CC4)ncn3)CC1)C(=O)N2] |
| (227) | 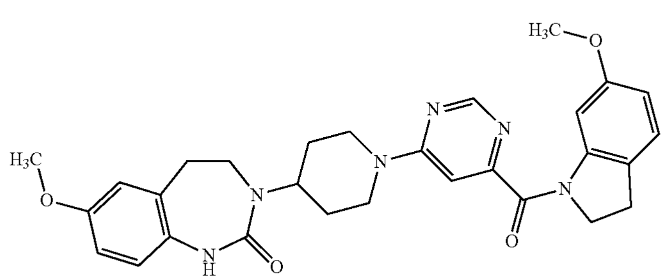 [SMILES: COc1ccc2c(c1)CCN(C1CCN(c3cc(C(=O)N4CCc5ccc(OC)cc54)ncn3)CC1)C(=O)N2] |

-continued

| No. | Structure |
|---|---|
| (228) | 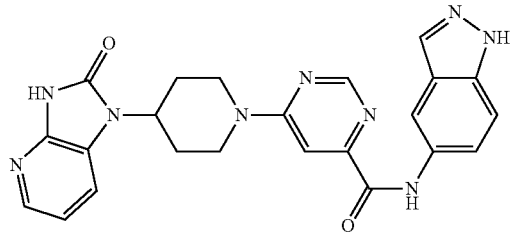 [SMILES: O=C(Nc1ccc2[nH]ncc2c1)c1cc(N2CCC(n3c(=O)[nH]c4ncccc43)CC2)ncn1] |
| (229) | 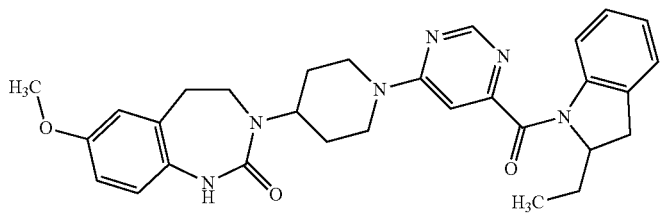 [SMILES: CCC1Cc2ccccc2N1C(=O)c1cc(N2CCC(N3CCc4cc(OC)ccc4NC3=O)CC2)ncn1] |
| (230) | 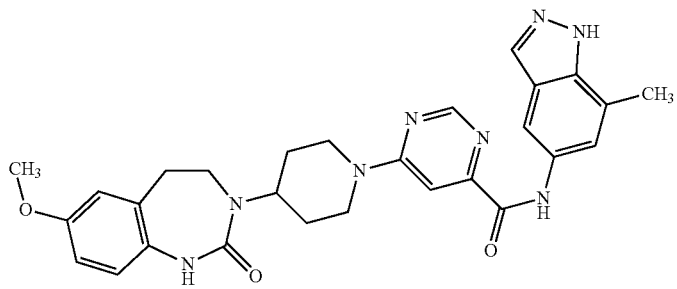 |
| (231) | 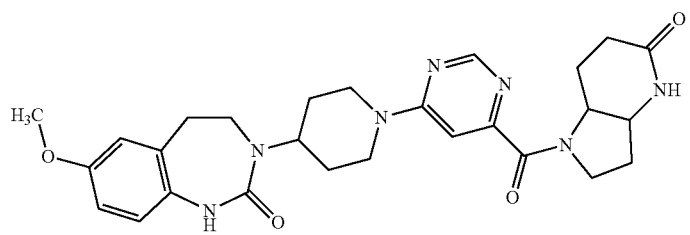 [SMILES: COc1ccc2c(c1)CCN(C1CCN(c3cc(C(=O)N4CCC5NC(=O)CCC54)ncn3)CC1)C(=O)N2] | the enantiomers, the diastereomers, the hydrates, the mixtures thereof and the salts thereof as well as the hydrates of the salts, particularly the physiologically acceptable salts thereof with inorganic or organic acids or bases.

Terms and Definitions Used

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

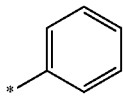 [SMILES: *c1ccccc1]

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms and by the term "$C_{1-3}$-alkylene" are meant branched and unbranched alkylene groups with 1 to 3 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1,1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms, by the term "$C_{5-6}$-cycloalkyl" are meant cyclic alkyl groups with 5 to 6 carbon atoms and by the term "$C_{5-7}$-cycloalkyl" are meant cyclic alkyl groups with 5 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems which do not form an aromatic ring system in at least one ring and besides carbon atoms may carry one to four heteroatoms, which are selected from among nitrogen, oxygen and sulphur. Both nitrogen atoms and sulphur atoms may optionally be oxidised and nitrogen atoms may be quaternised. The heterocyclic ring may contain one or two carbonyl, thiocarbonyl or cyanoimino groups adjacent to a nitrogen atom. The heterocycles mentioned previously may be attached to the rest of the molecule via a carbon atom or a nitrogen atom. Unless otherwise stated, the heterocycles may be substituted by one or more groups selected from among:

(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, COO—$C_{1-3}$-alkyl, preferably CO—O-methyl or CO—O-ethyl, while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholinyl-S-oxide, thiomorpholinyl-S-dioxide, thiomorpholine, dihydroxazine, morpholinedione, morpholinethione, perhydrothiazinedioxide, ε-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzthiophene, tetrahydrothieno-pyridine, tetrahydrobenzofuran, tetrahydrooxazolopyridine, tetrahydro-isoxazolopyridine.

The following heterocycles are preferred according to the invention:

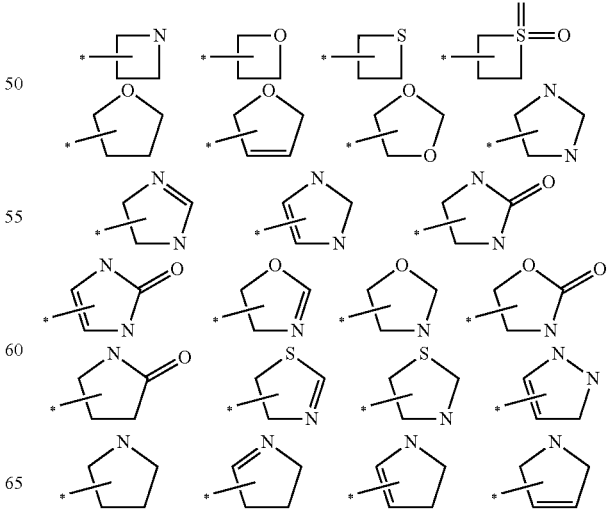

-continued

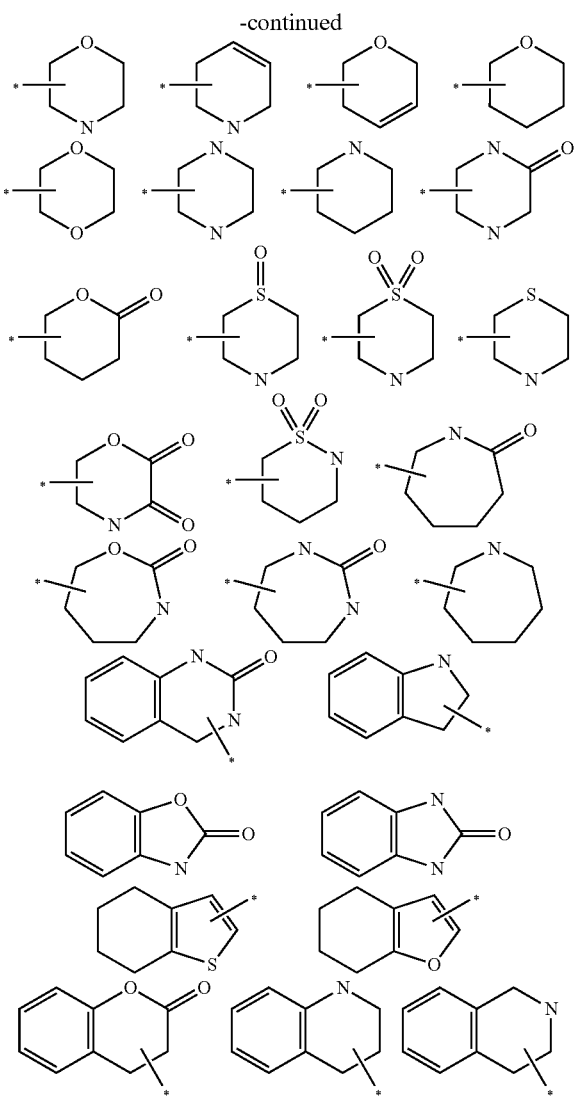

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:
- (a) OH, NO$_2$, CN, OCF$_3$, OCHF$_2$, OCH$_2$F, NH$_2$,
- (b) halogen, preferably fluorine or chlorine,
- (c) C$_{1-6}$-alkyl, preferably C$_{1-3}$-alkyl, particularly preferably ethyl, methyl, iso-propyl or tert-butyl,
- (d) —SO$_2$—O—C$_{1-3}$-alkyl, preferably —O-methyl,
- (e) —O—C$_{1-3}$-alkyl, preferably —O-methyl or —O-ethyl,
- (f) COOH, CO—O—C$_{1-3}$-alkyl, preferably CO—O-methyl or CO—O-ethyl, while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:

furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

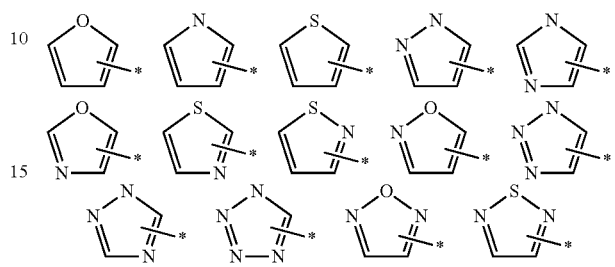

The following six-membered heterocyclic aromatic groups are preferred according to the invention:

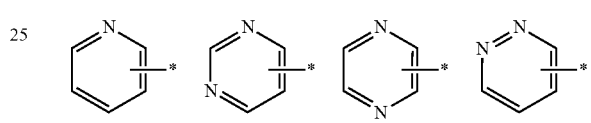

Examples of 9- or 10-membered bicyclic heteroaryl rings are as follows, but the invention is not restricted to these:

indole, isoindole, indazole, indolizine, benzofuran, benzothiophene, benzimidazole, benzoxazole, benzothiazole, benzotriazole, benzisoxazole, benzisothiazole, quinoline, isoquinoline, cinnoline, phthalazine, quinoxaline, quinazoline, pyridopyrimidine, pyridopyrazine, pyridopyridazine, pyrimidopyrimidine, pteridine, purine, quinolizine, benzoxazolecarbonitrile, quinoline, isoquinoline, quinolizine, pteridine, purine, quinolizine, benzoxazole-carbonitrile.

The following bicyclic heteroaryl rings are preferred according to this invention:

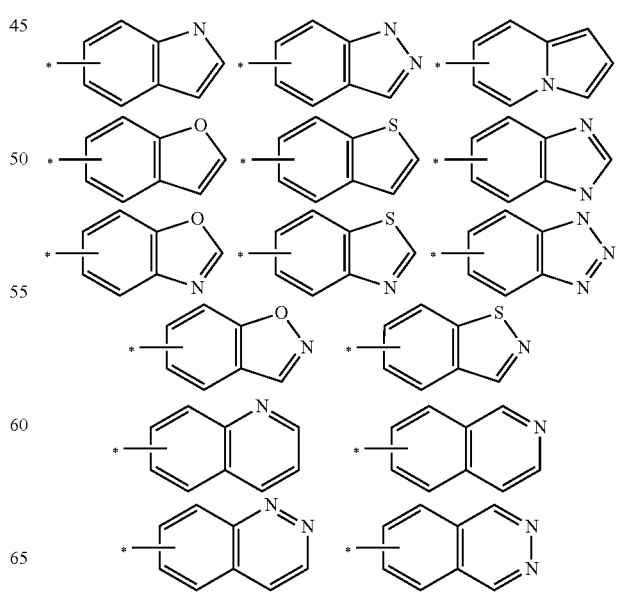

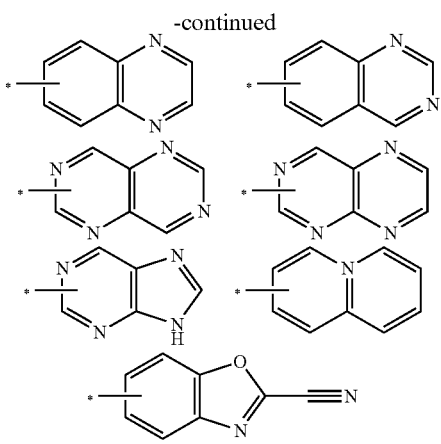

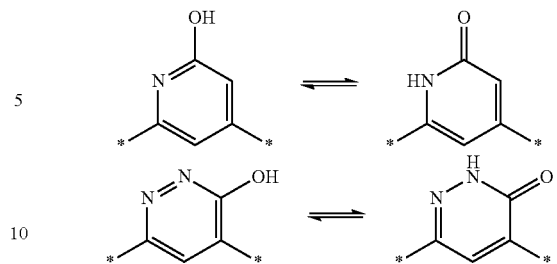

Unless otherwise stated, the heteroaryls previously mentioned may be substituted by one or more groups selected from among:

(a) OH, $NO_2$, CN, $OCF_3$, $OCHF_2$, $OCH_2F$, $NH_2$, (b) halogen, preferably fluorine or chlorine, (c) $C_{1-6}$-alkyl, preferably $C_{1-3}$-alkyl, particularly preferably ethyl, methyl, iso-propyl or tert-butyl, (d) —$SO_2$—O—$C_{1-3}$-alkyl, preferably —O-methyl, (e) —O—$C_{1-3}$-alkyl, preferably —O-methyl or —O-ethyl, (f) COOH, CO—O—$C_{1-3}$-alkyl, preferably CO—O-methyl or CO—O-ethyl, while the groups may be identical or different.

Bicyclic heteroaryl rings may preferably be substituted in the phenyl group.

By the term "halogen" are meant fluorine, chlorine, bromine or iodine atoms.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

Compounds with a carbon-double bond may be present in both the E- and the Z-form.

If a compound may be present in different tautomeric forms, the compound prepared is not limited to one tautomeric form, but encompasses all tautomeric forms. This is also true in particular of nitrogen-containing heteroaryls:

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs. (1986), Elsevier)

This invention also includes those metabolites that are derived from the compounds of general formula I. By metabolites are meant, in this context, compounds that are formed in-vivo from the compound of general formula I after administration. Examples of metabolites include:

methyl groups of the compound of general formula I may be converted into the corresponding hydroxymethyl groups (—$CH_3$->—$CH_2OH$)

alkoxy groups of the compound of general formula I may be converted into the corresponding hydroxyl groups (—OR->—OH)

secondary amines of the compound of general formula I may be converted into the corresponding primary amines (—$NR_1R_2$->—$NHR_1$, or —$NHR_2$)

nitrogen atoms of the compound of general formula I may be converted into the corresponding nitrogen oxides (=N—->=$N^+$—($O^-$)—)

Methods of Preparation

The invention also relates to a process for preparing the compounds of general formula I, wherein the substituents U, V, X, Y, $R^1$, $R^2$, $R^3$ and $R^4$ are as hereinbefore defined.

Some methods of preparing the compounds of general formula I according to the invention

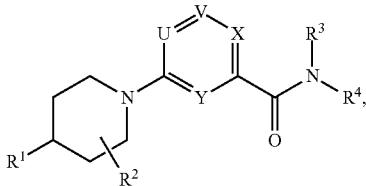

(I)

wherein U, V, X, Y, $R^1$, $R^2$, $R^3$ and $R^4$ are as hereinbefore defined, are illustrated in the following synthesis schemes and Examples.

In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

The compounds according to the invention may be prepared according to the schemes and specific examples provided or corresponding modifications. Modifications to these reactions which are known to the skilled man but not described in detail here may also be implemented.

The general methods of preparing the compounds of general formula I will be apparent to anyone skilled in the art from a study of the following schemes.

The starting compounds are commercially available or are prepared by methods described in the literature, known to the skilled man in the field or described herein. Before the reaction is carried out any corresponding functional groups in the compounds may be protected by conventional protective groups. These protective groups may be cleaved again at a suitable stage within the reaction sequence using methods known in the art.

In the reactions described below, any reactive groups present such as hydroxy, carboxy, amino, alkylamino, amide or imino groups may be protected during the reaction by conventional protective groups that are cleaved again after the reaction.

For example a suitable protective group for a hydroxy group may be the methoxy, benzyloxy, trimethylsilyl, acetyl, benzoyl, tert.-butyl, trityl, benzyl or tetrahydropyranyl group, suitable protective groups for a carboxyl group may be the trimethylsilyl, methyl, ethyl, tert.-butyl, benzyl or tetrahydropyranyl group, and suitable protective groups for an amide group may be the N-methoxymethyl-(MOM), N-benzyloxymethyl (BOM), N-(trimethylsilyl)ethoxymethyl (SEM), N-tert-butyldimethylsiloxymethyl, N-tert-butyldimethylsilyl (TBDMS), N-triisopropylsilyl-(TIPS), N-benzyl, N-4-methoxybenzyl (PMB), N-triphenylmethyl (Trt), N-tert-butoxycarbonyl (BOC), N-benzyloxycarbonyl (Cbz) or N-trimethylsilylethylsulphonyl (SES)

a suitable protective group for an amino, alkylamino or imino group may be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their cleavage are described in T. W. Greene, P. G. M. Wuts, "Protective Groups in Organic Synthesis", Wiley, 1991 and 1999.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of TBAF and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine at temperatures between 0 and 100° C., preferably at ambient temperature and under an inert gas, or by treating with a catalytic amount of tris-(triphenylphosphine)-rhodium (I) chloride in a solvent such as aqueous ethanol and optionally in the presence of a base such as 1,4-diazabicyclo[2,2,2] octane at temperatures between 20 and 70° C.

The following methods of preparing the compounds of general formula I according to the invention and their precursors have proved particularly suitable:

Scheme 1:

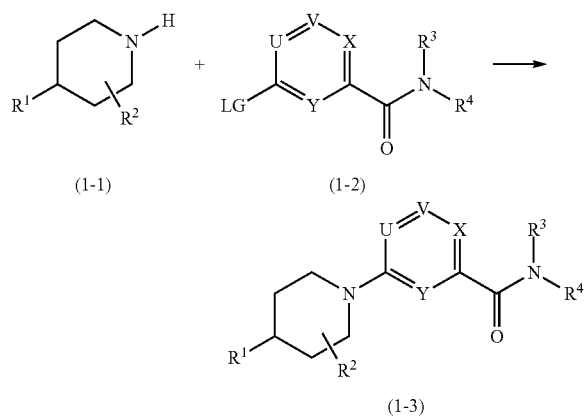

A compound of general formula (I-3), wherein U, V, X, Y, $R^1$, $R^2$, $R^3$ and $R^4$ are as hereinbefore defined, may be prepared by reacting an amine or aniline of general formula (1-1), wherein $R^1$ and $R^2$ are as hereinbefore defined, with an electron-poor compound of general formula (1-2), wherein U, V, X, Y, $R^3$ and $R^4$ are as hereinbefore defined and LG denotes a leaving group. Halides, preferably chlorides and bromides, $-SO_2CH_3$, $-OSO_2CH_3$, $-OSO_2C_6H_4-CH_3$ or $-S-CH_3$ ($-S-CH_3$ requires further reaction with an organic peroxide in order to be converted into the actual leaving group) etc. may act as the leaving group LG, but it is not restricted to this list. The use of chlorides is most particularly preferred.

The reaction may be carried out by nucleophilic aromatic substitution in an inert solvent using an auxiliary base in a temperature range of from 0° C. to the reflux temperature of the solvent. Nucleophilic aromatic substitutions are carried out in a suitable inert solvent, such as tetrahydrofuran, toluene, xylene, dialkylformamide (particularly preferably dimethylformamide), cyclic amide (particularly preferably N-methyl-pyrrolidone), 1,4-dioxane, acetonitrile or in solvent mixtures. Suitable auxiliary bases include tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. The reaction is preferably carried out in dimethylformamide, at temperatures between ambient temperature and the reflux temperature of the solvent, in the presence of a tertiary amine base.

Alternatively, structures of general formula (I-3) wherein U, V, X, Y, $R^1$, $R^2$, $R^3$ and $R^4$ are as hereinbefore defined may be synthesised by transition metal-catalysed reactions. An amine or aniline of general formula (1-1), wherein $R^1$ and $R^2$ are as hereinbefore defined, may react with a compound of general formula (1-2) wherein U, V, X, Y, $R^3$ and $R^4$ are as hereinbefore defined and LG denotes a leaving group, in an inert solvent in the presence of a catalyst and an auxiliary base. In addition, a suitable ligand may be used for the catalyst. Chlorides, bromides, iodides, trifluoroacetates, trifluoromethanesulphonates, methanesulphonates and toluenesulphonates may act as the leaving group LG, but this list is not restrictive. Xylene, tetrahydrofuran, dimethylformamide, dimethoxyethane, toluene, benzene, tert-butanol, 1,4-dioxane, acetonitrile or solvent mixtures may be used as inert solvents. The preferred solvent is xylene. Suitable bases are particularly amine bases such as e.g. triethylamine or diisopropylethylamine or also inorganic bases such as caesium carbonate, caesium acetate, potassium carbonate, potassium-tert-butoxide, sodium carbonate, sodium-tert-butoxide or potassium phosphate. Preferred reaction temperatures are from RT to the reflux temperature of the solvent at normal pressure. Typical catalysts are e.g. Transition metal catalysts, such as e.g. palladium catalysts of the tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium(II)-chloride type. Typical ligands are e.g. triphenylphosphine, triphenylarsene, BINAP, XPhos, XantPhos, or 2-(di-tert-butylphosphino)biphenyl.

Scheme 2:

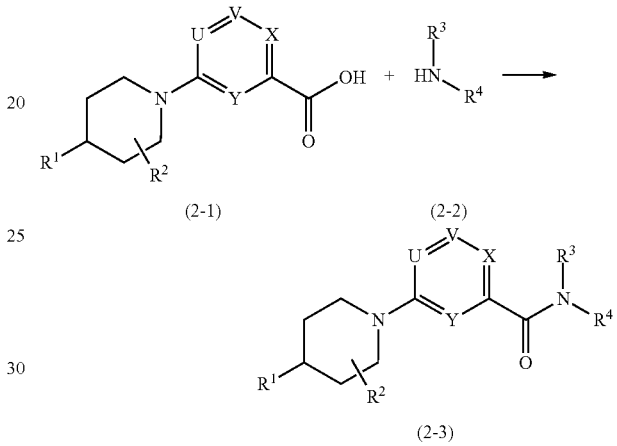

A compound of general formula (2-3), wherein U, V, X, Y, $R^1$, $R^2$, $R^3$ and $R^4$ are as hereinbefore defined, may be prepared as shown in Scheme 2 by coupling a compound of general formula (2-2), wherein $R^3$ and $R^4$ are as hereinbefore defined, with a carboxylic acid of general formula (2-1), wherein U, V, X, Y, $R^1$ and $R^2$ are as hereinbefore defined, using standard peptide-coupling reagents and a base in an inert solvent (cf. e.g. Houben-Weyl, Methoden der Organischen Chemie, vol. 15/2).

The inert solvents used may be dimethylformamide, N-methylpyrrolidone, dimethoxyethane, dichloromethane, acetonitrile or solvent mixtures. The preferred solvent is dimethylformamide. Suitable bases are especially amine bases such as e.g. triethylamine or diisopropylethylamine. Suitable coupling reagents include for example 1H-benzotriazol-1-yloxy-tripyrrolidino-phosphonium-hexafluorophosphate (PyBOP), dicyclohexylcarbodiimide (DCC), diisopropylcarbodiimide (DIC), ethyl-(3-dimethylaminopropyl)-carbodiimide, O-(1H-benzotriazol-1-yl)-N,N—N,N-tetramethyluronium-hexafluorophosphate (HBTU) or -tetrafluoroborate (TBTU) or 1H-benzotriazol-1-yl-oxy-tris-(dimethylamino)-phosphonium-hexafluorophosphate (BOP). It is particularly preferred to use TBTU. The activation of the carboxyl group may alternatively also be carried out using a corresponding acid anhydride or acid chloride. The reaction is generally carried out in a temperature range from −20° C. to the reflux temperature of the solvent at normal pressure. Reactions are preferably carried out at ambient temperature. The speed of the reaction can be increased by the addition of 1-hydroxybenzotriazole (HOBt) or of 3-hydroxy-4-oxo-3,4-dihydro-1,2,3-benzotriazine (HOOBt). Other standard coupling conditions may also be used in the synthesis of these amides.

The compounds of general formula (3-4), wherein U, V, X, Y, $R^1$ and $R^2$ are as hereinbefore defined, may be synthesised either by methods known to the skilled man or by reactions illustrated in Scheme 3 by way of example.

Scheme 3:

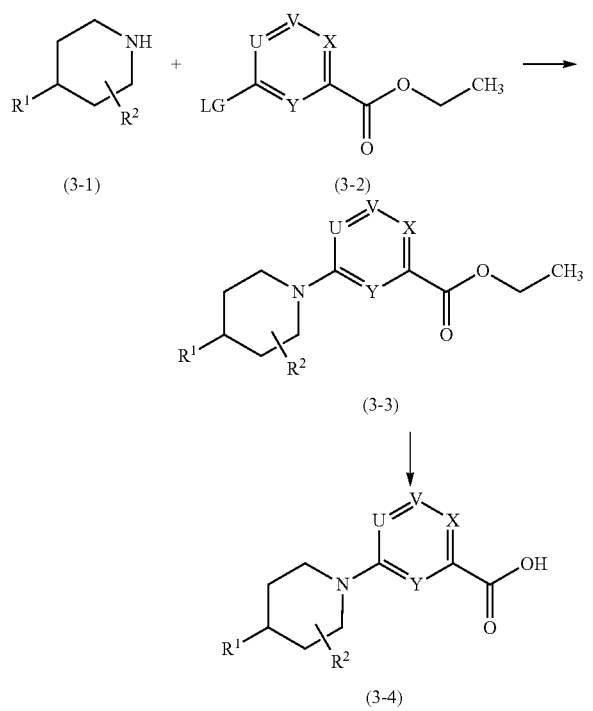

A compound of general formula (3-1), wherein $R^1$ and $R^2$ are as hereinbefore defined, may be reacted with an electron-poor compound of general formula (3-2), wherein U, V, X and Y are as hereinbefore defined and LG denotes a leaving group. Halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be converted into the actual leaving group) etc. may act as the leaving group LG, but it is not restricted to this list. The use of chlorides is most particularly preferred. The reaction may be carried out in an inert solvent using an auxiliary base in a temperature range from 0° C. to the reflux temperature of the solvent. The inert solvent may be tetrahydrofuran, toluene, xylene, dialkylformamide (dimethylformamide is particularly preferred), cyclic amide (N-methylpyrrolidone is particularly preferred), 1,4-dioxane, acetonitrile or solvent mixtures. Suitable auxiliary bases are especially tertiary amines such as triethylamine or ethyldiisopropylamine and alkali metal carbonates such as potassium carbonate or sodium carbonate. Preferably the reaction is carried out in dimethylformamide, at temperatures between ambient temperature and the reflux temperature of the solvent, in the presence of a tertiary amine base.

Esters of general formula (3-3), wherein U, V, X, Y, $R^1$ and $R^2$ are as hereinbefore defined, may be converted by basic or acid hydrolysis (J. March, Advanced Organic Chemistry (New York: J. Wiley and Sons, 1985) or by reaction with alkali metal salts (preferably LiI or NaCN) in an inert solvent into the acid of general formula (3-4). Inert solvents may be dialkylformamide (N,N-dimethylformamide is particularly preferred), dialkylacetamide (N,N-dimethylacetamide is particularly preferred), cyclic amide (N-methylpyrrolidone is particularly preferred). Alkaline saponification with alkali metal hydroxides such as sodium hydroxide or lithium hydroxide in inert solvents is particularly preferred. Suitable inert solvents are water and cyclic ethers such as 1,4-dioxane or tetrahydrofuran as well as solvent mixtures.

The compounds of general formula (4-3), wherein U, V, X, Y, $R^3$ and $R^4$ are as hereinbefore defined and LG denotes a leaving group, may be synthesised analogously to Scheme 4.

Scheme 4:

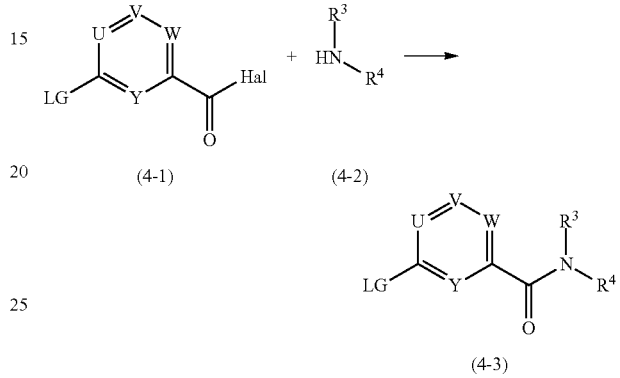

Carboxylic acid halides of general formula (4-1), wherein U, V, X and Y are as hereinbefore defined, LG denotes a leaving group, for example a halide, and Hal denotes a chlorine or bromine, may be reacted with compounds of general formula (4-2), wherein $R^3$ and $R^4$ are as hereinbefore defined. The reaction may be carried out in an inert solvent or without a solvent. Similarly, the reaction may also be carried out with or without a base. The inert solvents used may be halogen-containing hydrocarbons (the use of dichloromethane or dichloroethane is particularly preferred), dialkylethers (diethyl ether is preferred), cyclic ethers (1,4-dioxane or tetrahydrofuran is preferred) and aromatic hydrocarbons. Bases that may be used are tertiary amines (triethylamine or diisopropylethylamine is preferred) and aromatic amines (pyridine is preferred).

The compounds of general formula (5-3) wherein U, V, X, Y, $R^3$ and $R^4$ are as hereinbefore defined and LG denotes a leaving group may be synthesised analogously to Scheme 5.

Scheme 5:

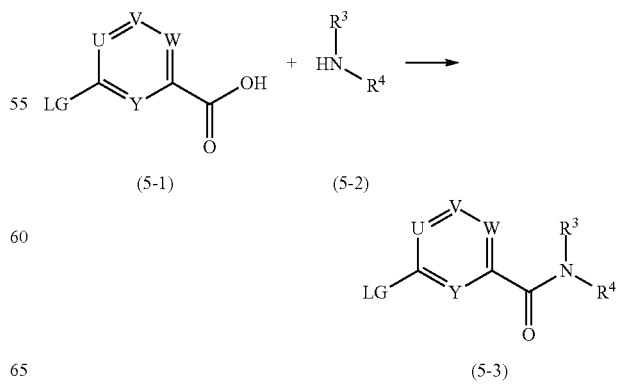

Carboxylic acids of general formula (5-1), wherein U, V, X and Y are as hereinbefore defined and LG denotes a leaving group, may be reacted with compounds of general formula (5-2), wherein $R^3$ and $R^4$ are as hereinbefore defined, using standard peptide coupling reagents and a base in an inert solvent to form amides of general formula (5-3), wherein U, V, X, Y, $R^3$ and $R^4$ are as hereinbefore defined and LG denotes a leaving group (cf. e.g. Houben-Weyl, Methoden der Organischen Chemie, vol. 15/2). Halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be converted into the actual leaving group) may act as the leaving group LG, but it is not restricted to this list. The use of chlorides is most particularly preferred. The inert solvents used may be dimethylformamide, N-methylpyrrolidone, dimethoxyethane, dichloromethane, acetonitrile or solvent mixtures. The preferred solvent is dimethylformamide. Suitable bases are especially amine bases such as e.g. triethylamine or diisopropylethylamine. Suitable coupling reagents include for example 1H-benzotriazol-1-yl-oxy-tripyrrolidino-phosphonium-hexafluorophosphate (PyBOP), dicyclohexylcarbodiimide (DCC), diisopropylcarbodiimide (DIC), ethyl-(3-dimethylamino-propyl)-carbodiimide, O-(1H-benzotriazol-1-yl)-N,N—N,N-tetramethyl-uronium-hexafluorophosphate (HBTU) or -tetrafluoroborate (TBTU) or 1H-benzotriazol-1-yl-oxy-tris-(dimethylamino)-phosphonium-hexafluorophosphate (BOP). Particularly preferred is the use of TBTU. The activation of the carboxyl group may also be carried out using a corresponding acid anhydride or acid chloride. The reaction is generally carried out in a temperature range from −20° C. to the reflux temperature of the solvent at normal pressure. Particularly preferred is the use of diisopropylethylamine as base and dimethylformamide as solvent.

Compounds of general formula (6-3), wherein U, V, X, Y, W and $R^2$ are as hereinbefore defined, may be prepared analogously to Scheme 6.

Scheme 6:

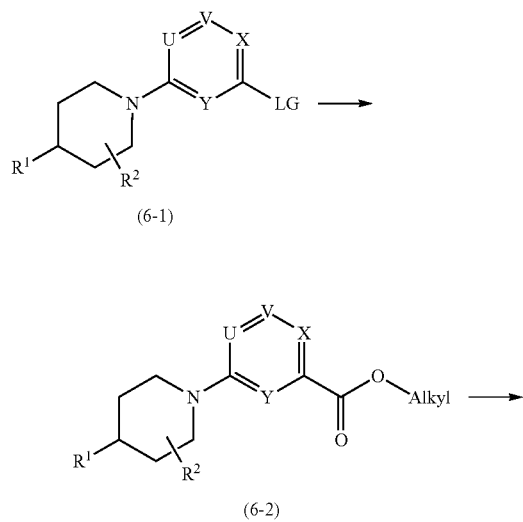

(6-1)

(6-2)

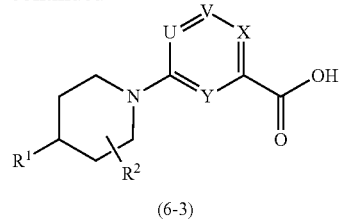

(6-3)

Here, a compound of general formula (6-1), wherein U, V, X, Y, $R^1$ and $R^2$ are as hereinbefore defined and LG denotes a leaving group, may be reacted with an alcohol and carbon monoxide in the presence of a catalyst and an auxiliary base. A suitable ligand may additionally be used for the catalyst. Chlorides, bromides, iodides, trifluoroacetates, trifluoromethanesulphonates, methanesulphonates and toluenesulphonates may serve as the leaving group LG, but this list is not restrictive. The alcohols used are preferably methanol and ethanol, but this list is not restrictive. Suitable bases are especially amine bases such as e.g. triethylamine or diisopropylethylamine or also inorganic bases such as caesium carbonate, caesium acetate, potassium carbonate, potassium-tert-butoxide, sodium carbonate, sodium acetate, sodium-tert-butoxide or potassium phosphate. Typical catalysts are e.g. transition metal catalysts, such as e.g. palladium catalysts such as tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium (II)-chloride. Typical ligands are e.g. triphenylphosphine, tricyclohexylphosphine, tri-(tert-butyl)phosphine, 1,4-bis (diphenylphosphino)butane (dppb), 1,1'-bis (diphenylphosphino)ferrocene (dppf), 1,3-bis (diisopropylphosphino)-propane, 1,3-bis (diphenylphosphino)propane(dppp), 1,4-bis (dicyclohexylphosphino)butane, 1,1"-bis (dicyclohexylphosphino)ferrocene. The pressure of carbon monoxide in the reaction vessel is from 1 bar to 100 bar, while elevated carbon monoxide pressures of 10 to 30 bar are preferred. The reactions may be carried out in a temperature range from RT to 200° C. Particularly preferred is a temperature range from 100° C. to 150° C. (M. Beller, W. Magerlein, A. F. Indolese, Ch. Fischer, Synthesis (2001) 7, 1098-1109 and literature cited therein). Esters of general formula (6-2), wherein U, V, X, Y, $R^1$ and $R^2$ are as hereinbefore defined and alkyl denotes a $C_{1-3}$-alkyl group, may be converted by basic or acid hydrolysis (J. March, Advanced Organic Chemistry (New York: J. Wiley and Sons, 1985) or by reaction with alkali metal salts (preferably LiI or NaCN) in an inert solvent into the acid of general formula (6-3). Inert solvents may be dialkylformamides (N,N-dimethylformamide is particularly preferred), dialkylacetamides (N,N-dimethylacetamide is particularly preferred), cyclic amides (N-methylpyrrolidone is particularly preferred). Alkaline saponification with alkali metal hydroxides such as sodium hydroxide or lithium hydroxide in inert solvents is particularly preferred. Suitable inert solvents are water and cyclic ethers such as 1,4-dioxane or tetrahydrofuran as well as solvent mixtures.

In some cases the end product may be further derivatised, e.g. by manipulation of the substituents. These manipulations may be, inter alia, those which are generally known to the skilled man, such as oxidation, reduction, alkylation, acylation and hydrolysis, but need not be restricted to the above.

The new compounds of general formula I according to the invention may contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC membranes (~20 µg protein) are incubated for 180 minutes at ambient temperature with 50 pM $^{125}$I-iodotyrosyl-Calcitonin-Gene-Related Peptide and increasing concentrations of the test substances in a total volume of 250 µl (assay buffer: 10 mM tris, 50 mM NaCl, 5 mM MgCl$_2$, 1 mM EDTA, pH=7.4). The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 µM BIBN4096BS during incubation.

The concentration binding curves are analysed using computer-aided non-linear curve fitting.

The compounds mentioned hereinbefore show $K_i$ values ≤50 µm in the test described.

B. CGRP Antagonism in SK-N-MC Cells

SK-N-MC cells (~1000 cells per well) are incubated for 30 minutes in the presence of increasing concentrations of CGRP and different concentrations of the test substance.

The cAMP contents of the samples are determined using an AlphaScreen cAMP assay kit (Perkin Elmer) and the pA$_2$ values of antagonistically acting substances are determined graphically.

The compounds according to the invention exhibit CGRP-antagonistic properties in the in vitro test model described, in a dosage range between $10^{-12}$ and $10^{-4}$ M.

To demonstrate that the compounds of general formula I exhibit good to very good CGRP-antagonistic activities with different structural elements, the following Table gives the $K_i$ values obtained according to the test procedure described above. It should be noted that the compounds were selected for their different structural elements and not in order to emphasise specific compounds:

| Example | $K_i$ [nM] |
|---|---|
| (8) | 4 |
| (11) | 34 |
| (15) | 21 |
| (17) | 117 |
| (36) | 5 |
| (37) | 2 |
| (41) | 21 |
| (50) | 690 |
| (55) | 3 |

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, 5-$HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Experimental Section

As a rule IR, $^1$H-NMR and/or mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The ratios given for the eluants relate to units by volume of the particular solvents. The units by volume given for $NH_3$ relate to a concentrated solution of $NH_3$ in water. Eluant systems used for TLC:
eluant A: DCM/cyclohexane/MeOH/$NH_4OH$=70/15/15/2
eluant B: petroleum ether/ethyl acetate=2/1

Unless stated otherwise, the acid, base and salt solutions used in working up the reaction solutions are aqueous systems of the specified concentrations. Silica gel made by Millipore (MATREX™, 35-70 μm) is used for chromatographic purifications. The HPLC data provided are measured under the parameters listed below and using the columns mentioned:
Columns Used:
(column temperature: 30° C.; injection volume: 5 μL; detection at 254 nm)

| | |
|---|---|
| S1 | Zorbax column (Agilent Technologies), SB (Stable Bond) C18; 3.5 μm; 4.6 × 75 mm |
| S2 | Waters Sunfire, SB (Stable Bond) C18; 3.5 μm; 4.6 × 75 mm |
| S3 | Agilent Bonus C18; 5 μm, 4.6 × 75 mm |
| S4 | Zorbax column (Agilent Technologies), SB (Stable Bond) C18; 1.8 μm; 3.0 × 30 mm |
| S5 | Zorbax column (Agilent Technologies), SB (Stable Bond) C18; 5 μm; 4.6 × 75 mm |
| S6 | Waters Symmetry C18; 3.5 μm; 4.6 × 75 mm |
| S7 | Waters XBridge C18; 3.5 μm; 4.6 × 75 mm (basic column) |
| S8 | WatersSunfire C18; 2.5 μm; 3.0 × 30 mm |

Solvents Used:
for the columns S1 to S6 (acid conditions) the following solvents were used:
solvent A: water (with 0.1% formic acid)
solvent B: acetonitrile (with 0.1% formic acid)
for the column S7 (basic conditions) the following solvents were used:
solvent A: water (with 0.1% $NH_4OH$)
solvent B: acetonitrile (with 0.1% $NH_4OH$)
(the percentages given relate to the total volume)
Gradients:

| gradient (flow) | time [min] | % A | % B |
|---|---|---|---|
| G1 (0.8 mL/min) | 0.0 | 95 | 5 |
| | 8.0 | 50 | 50 |
| | 9.0 | 10 | 90 |
| | 10.0 | 10 | 90 |
| | 11.0 | 95 | 5 |

| gradient | time [min] | % A | % B |
|---|---|---|---|
| G2 (1.6 mL/min) | 0.00 | 95 | 5 |
| | 0.10 | 95 | 5 |
| | 1.75 | 5 | 95 |
| | 1.90 | 5 | 95 |
| | 1.95 | 95 | 5 |
| | 2.00 | 95 | 5 |

| gradient | time [min] | % A | % B |
|---|---|---|---|
| G3 (1.6 mL/min) | 0.00 | 95 | 5 |
| | 4.50 | 10 | 90 |
| | 5.00 | 10 | 90 |
| | 5.50 | 95 | 5 |

| gradient | time [min] | % A | % B |
|---|---|---|---|
| G4 (1.6 mL/min) | 0.00 | 95 | 5 |
| | 4.00 | 50 | 50 |

| gradient | time [min] | % A | % B |
|---|---|---|---|
| | 4.50 | 10 | 90 |
| | 5.00 | 10 | 90 |
| | 5.50 | 95 | 5 |
| G5 (1.6 mL/min) | 0.00 | 90 | 10 |
| | 4.50 | 10 | 90 |
| | 5.50 | 10 | 90 |

| gradient (flow) | time [min] | % A | % B |
|---|---|---|---|
| G6 (0.8 mL/min) | 0.0 | 95 | 5 |
| | 9.0 | 10 | 90 |
| | 10.0 | 10 | 90 |
| | 11.0 | 95 | 5 |

| gradient | time [min] | % A | % B |
|---|---|---|---|
| G7 (1.6 mL/min) | 0.00 | 95 | 5 |
| | 2.00 | 50 | 50 |
| | 2.25 | 10 | 90 |
| | 2.50 | 10 | 90 |
| | 2.75 | 95 | 5 |

Methods:

| | column | gradient |
|---|---|---|
| method A | S1 | G4 |
| method B | S2 | G4 |
| method C | S4 | G2 |
| method D | S6 | G4 |
| method E | S1 | G3 |
| method F | S3 | G3 |
| method G | S5 | G4 |
| method H | S1 | G5 |
| method K | S2 | G3 |
| method L | S1 | G2 |
| method M | S7 | G3 |
| method N | S2 | G1 |
| method O | S2 | G6 |
| method Q | S5 | G5 |
| method R | S4 | G7 |
| method S | S8 | G7 |

In preparative HPLC purifications, the products are collected either under mass control or by UV detection. The fractions containing product are combined and freeze-dried. The following columns may be used for preparative HPLC separations:

| | |
|---|---|
| S8 | Agilent Zorbax SB C18, 50 × 150 mm, 5 μm |
| S9 | Agilent Zorbax Stable Bond, 50 × 140 mm, 7 μm |
| S10 | Waters Sunfire C18, 30 × 100 mm, 5 μm |
| S11 | Waters Symmetry 50 × 140 mm, 7 μm |
| S12 | Agilent Zorbax Stable Bond C18, 30 × 100 mm, 5 μm, |

The Following Solvent Systems May be Used for the Preparative HPLC Separation:

solvent A: water (with 0.1% formic acid)
solvent B: acetonitrile (with 0.1% formic acid)
solvent A: water (with 0.15% formic acid)
solvent B: acetonitrile (with 0.15% formic acid)
solvent A: water (with 0.3% formic acid)
solvent B: acetonitrile
solvent A: water (with 0.3% formic acid)
solvent B: acetonitrile (with 0.3% formic acid)
solvent A: water (with 0.1% $NH_4OH$)
solvent B: acetonitrile (with 0.1% $NH_4OH$)

The percentages given relate in each case to the total volume.

In the absence of any more information regarding the configuration, it is unclear whether there are pure enantiomers involved or whether partial or even total racemisation has taken place.

The following abbreviations are used in the test descriptions:

ACN acetonitrile
AcOH acetic acid
BINAP 2,2'-bis-(diphenylphosphino)-1,1'-binaphthyl
BOC tert.-butyloxycarbonyl
CAD circulating air dryer
CDI 1,1'-carbonyldiimidazole
CO carbon monoxide
conc. concentrated
Cyc cyclohexane
DC drying cupboard
DCM dichloromethane
DIPE diisopropylether
DIPEA diisopropylethylamine
DMAP 4-dimethylaminopyridine
DMF N,N-dimethylformamide
dppf 1,1'-bis-(diphenylphosphino)ferrocene
of theoretical of theory
d-water deionised water
EI electron jet ionisation (in MS)
Eq equivalent
ESI electrospray ionisation (in MS)
EtOAc ethyl acetate
EtOH ethanol
GWM General Working Method
HATU [dimethylamino-(1,2,3-triazolo[4,5-b]pyridin-3-yloxy)-methylen]-dimethyl-ammonium-hexafluorophosphate
HCl hydrogen chloride
HPLC High Performance Liquid Chromatography
HPLC-MS HPLC coupled mass spectrometry
i.vac. in vacuo (under vacuum)
MeOH methanol
MS mass spectrometry
MW molecular weight [g/mol]
NaOAc sodium acetate
NaOH sodium hydroxide
$NH_4OH$ ammonium hydroxide (aqueous ammonia solution, 30%)
NMP N-methyl-2-pyrrolidine
Pd/C palladium on charcoal
$Pd_2 dba_3$ bis(dibenzylideneacetone) palladium (0)
PE petroleum ether
$R_f$ retention index (bei DC)
RT ambient temperature
$R_t$ retention time (in HPLC)
TBME tert.-butyl-methylether
TBTU O-(benzotriazol-1-yl)-N,N,N,N-tetramethyluronium tetrafluoroborate
TEA triethylamine
TFA trifluoroacetic acid
THF tetrahydrofuran
XantPhos 4,5-bis(diphenylphosphino)-9.9-dimethylxanthene
XPhos 2-dicyclohexylphosphino-2',4',6'-triisopropylbiphenyl

Preparation of the Starting Compounds

Intermediate 1a 1-piperidin-4-yl-1,3-dihydroimidazo[4,5-b]pyridin-2-one dihydrochloride

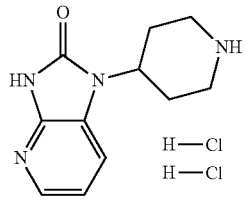

This compound and its precursors were synthesised as described in International application PCT/US2004/020209.
ESI-MS: m/z=219 (M+H)$^+$
$R_f$: 0.11 (silica gel, DCM/MeOH/NH$_4$OH=80:20:2)

Intermediate 1b 1-piperidin-4-yl-1,3-dihydroimidazo[4,5-b]pyridin-2-one

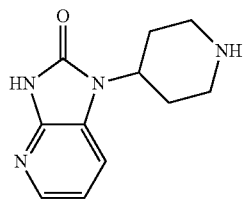

Step 1: benzyl 4-(2-chloro-pyridin-3-yl-amino)-piperidine-1-carboxylate

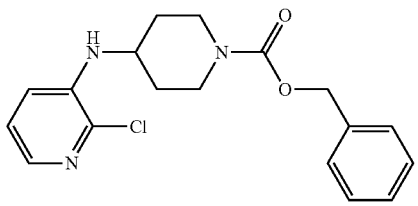 [SMILES: O=C(OCc1ccccc1)N1CCC(Nc2cccnc2Cl)CC1]

560 mL (7.25 mol) TFA were added dropwise at approx. 15° C. to 930 g (3.99 mol) N-benzyloxy carbonyl-4-piperidone and 466 g (3.63 mol) 2-chloro-3-aminopyridine in 9.5 L isopropyl acetate. 922 g (4.35 mol) sodium triacetoxyborohydride were added batchwise. The mixture was stirred until the reaction was complete. At RT the reaction mixture was combined with 860 mL sodium hydroxide solution (2 mol/L). The organic phase was separated off, washed with 5 L water and evaporated down.
Yield: 1250 g (crude, quant.)
ESI-MS: m/z=346 (M+H)$^+$

Step 2: benzyl 4-[1-(2-chloro-pyridin-3-yl)-ureido]-piperidine-1-carboxylate

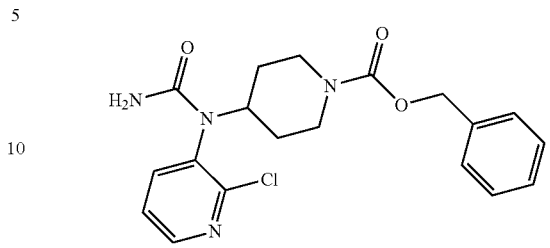

530 mL (6.1 mol) chlorosulphonyl isocyanate were placed in 6 L THF and cooled to −15° C. Then a solution of 1.25 kg (3.63 mol) benzyl 4-(2-chloro-pyridin-3-yl-amino)-piperidine-1-carboxylate in 7 L THF was added dropwise to this mixture within one hour such that the temperature of the reaction mixture did not exceed −7° C. The mixture was stirred for a further 90 minutes at approx. −8° C. and then 700 mL water was added dropwise within 30 minutes. The mixture was stirred for another 30 minutes at approx. 10° C. and then slowly combined with 8.1 L sodium hydroxide solution (2 mol/L). The reaction mixture was then heated to 50° C. and the phases were separated. The organic phase was washed with 2 L water. Then 10 L solvent were distilled off from the organic phase, 15 L butyl acetate were added to the residue and another 8 L were distilled off. By slow cooling to 0° C. the product was crystallised. The precipitate was suction filtered, washed with 2 L butyl acetate and dried at 40° C.
Yield: 1108 g (79% of theory)
ESI-MS: m/z=389/391 (M+H)$^+$

Step 3: benzyl 4-(2-oxo-2,3-dihydro-imidazo[4,5-b]pyridin-1-yl)-piperidine-1-carboxylate

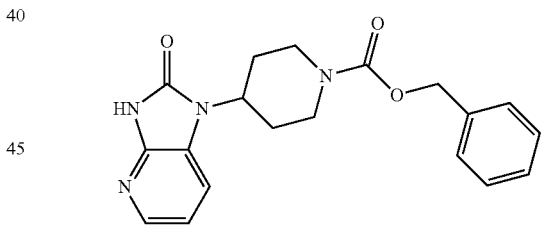

1108 g (2.85 mol) benzyl 4-[1-(2-chloro-pyridin-3-yl)-ureido]-piperidine-1-carboxylate were refluxed with 720 g (8.57 mol) sodium hydrogen carbonate in 14.5 L tert-amylalcohol. 3 L of solvent were distilled off. The reaction mixture was cooled to 35° C. and mixed with 11 mL water. Then 13 g (0.058 mol) palladium acetate and 49 g (0.115 mol) 1,4-bis-(diphenylphosphino)-butane (DPPB) were added and the mixture was refluxed. It was stirred at 100° C. until the reaction was complete, cooled to RT and 7.5 L water were added. The organic phase was separated off, washed with 5 L water and then evaporated down. The oily residue was twice combined with 3 L isopropyl acetate and distilled off. Then the residue was dissolved hot in 7 L isopropyl acetate and slowly cooled to ambient temperature. The solid that crystallised out was suction filtered, washed with 2 L isopropyl acetate and tert.-butyl-methylether and dried at 50° C.
Yield: 690 g (69% of theory)
ESI-MS: m/z=353 (M+H)$^+$

Step 4: 1-piperidin-4-yl-1,3-dihydro-imidazo[4,5-b]pyridin-2-one

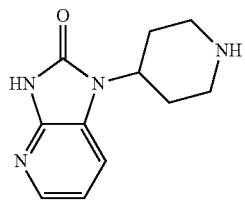 [SMILES: O=c1[nH]c2ncccc2n1C1CCNCC1]

690 g (1.96 mol) benzyl 4-(2-oxo-2,3-dihydro-imidazo[4,5-b]pyridin-1-yl-piperidine-1-carboxylate were dissolved in 5.4 L methanol and hydrogenated with the addition of 46 g Pd/C (10%; 6.6% by weight) at 60° C. and a hydrogen pressure of 60 psi until the uptake of hydrogen was complete. The catalyst was filtered off. 4 L methanol were distilled off from the filtrate. 2 L methylcyclohexane were added and a further 1.5 L solvent were distilled off. The suspension thus obtained was suction filtered, the residue was washed with methylcyclohexane and dried at 40° C.

Yield: 446 g (100% of theory)
ESI-MS: m/z=219 (M+H)$^+$

Intermediate 2

3-piperidin-4-yl-1,3,4,5-tetrahydro-1,3-benzodiazepin-2-one

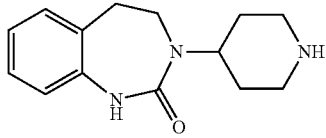 [SMILES: O=C1Nc2ccccc2CCN1C1CCNCC1]

This compound and its precursors were synthesised as described in European Patent Application No. EP 1 619 187.
ESI-MS: m/z=246 (M+H)$^+$

Intermediate 3

7-chloro-3-piperidin-4-yl-1,3,4,5-tetrahydro-1,3-benzodiazepin-2-one

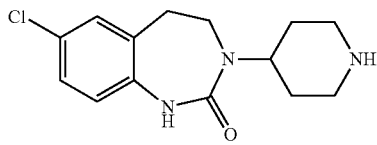 [SMILES: O=C1Nc2ccc(Cl)cc2CCN1C1CCNCC1]

801 mg (6.0 mmol) N-chlorosuccinimide were added to 1.23 g (5.0 mmol) 3-piperidin-4-yl-1,3,4,5-tetrahydro-1,3-benzodiazepin-2-one in 10 mL carbon tetrachloride and the reaction mixture was refluxed for 3 days. The solvent was evaporated down using the rotary evaporator and the residue was purified by flash chromatography. The product fractions were combined and the solvent was eliminated using the rotary evaporator. For further purification the product fractions were purified by preparative HPLC. The product fractions were combined and evaporated to dryness using the rotary evaporator.

Yield: 420 mg (30% of theory)
ESI-MS: m/z=280/282 (M+H)$^+$
$R_t$ (HPLC-MS): 2.04 min (method E)

Intermediate 4

7-methoxy-3-piperidin-4-yl-1,3,4,5-tetrahydro-1,3-benzodiazepin-2-one

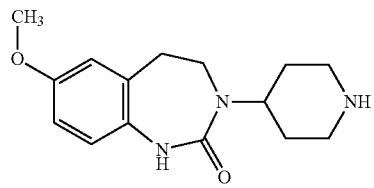 [SMILES: COc1ccc2c(c1)CCN(C1CCNCC1)C(=O)N2]

Step 1: (5-methoxy-2-nitrophenyl)-acetonitrile

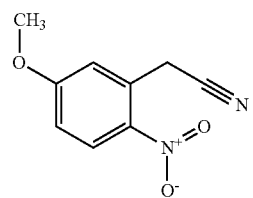

24.0 g (214 mmol) potassium-tert-butoxide in 100 mL DMF were slowly added dropwise to a solution of 13.2 g (86.0 mmol) 4-nitroanisole and 18.0 g (107 mmol) 4-chlorophenoxyacetonitrile in 50 mL DMF. The reaction mixture was stirred for 30 min at −10° C. and then poured into 300 g of a 1:1 mixture of conc. hydrochloric acid and ice. After extraction with EtOAc the organic phase was washed with water, dried and evaporated to dryness by rotary evaporation in vacuo with gentle heating. The residue was treated with a 1:1 mixture of petroleum ether/EtOAc and the product that crystallised out was suction filtered. After washing with a 1:1 mixture petroleum ether/EtOAc the crystals were dried in the air.

Yield: 6.5 g (39% of theoretical)
ESI-MS: m/z=210 (M+NH$_4$)$^+$
$R_f$: 0.45 (silica gel; PE/EtOAc=1:1)

Step 2: 2-(5-methoxy-2-nitrophenyl)-ethylamine

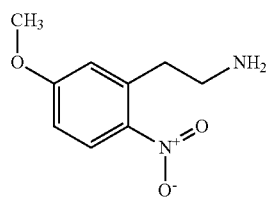

Under a nitrogen atmosphere 200 mL (200 mmol) of a 1M borane in THF solution were slowly added dropwise at RT to 12.6 g (65.7 mmol) (5-methoxy-2-nitrophenyl)-acetonitrile in 380 mL THF. The reaction mixture was refluxed for 2 h. After cooling 30 mL methanol were added dropwise within 20 min. During this time the temperature was maintained at 10° C. to 20° C. with an ice bath. The reaction mixture was stirred for 30 min at RT and then 45 mL of a 2M aqueous hydrochloric acid solution was added dropwise thereto within 30 min. The reaction mixture was concentrated by rotary evaporation i. vac. with gentle heating. The residue was diluted with water to approx. 200 mL and extracted with 200 mL EtOAc. The aqueous phase was made alkaline with a 15% (w/v) aqueous potassium carbonate solution and continuously extracted overnight with a rotary perforator according to Ludwig (Messrs. Normag) with diethyl ether. The organic extract was evaporated to dryness by rotary evaporation.

Yield: 9.98 g (77% of theoretical)
ESI-MS: m/z=197 (M+H)$^+$
$R_f$(HPLC): 2.1 min (method E)

Step 3:(1-benzylpiperidin-4-yl)-[2-(5-methoxy-2-nitrophenyl)-ethyl]-amine

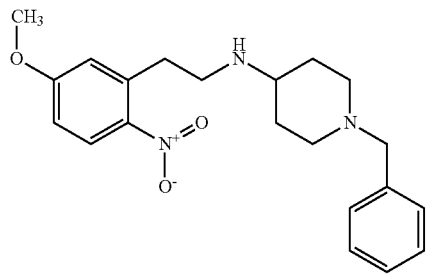 [SMILES: COc1ccc([N+](=O)[O-])c(CCNC2CCN(Cc3ccccc3)CC2)c1]

Under a nitrogen atmosphere a mixture of 9.98 g (50.9 mmol) 2-(5-methoxy-2-nitrophenyl)-ethylamine, 9.8 mL (54.9 mmol) N-benzylpiperidone and 6.3 mL (114 mmol) acetic acid in 270 mL dichloromethane was cooled to 0° C. in an ice bath. At this temperature 14.2 g (67.0 mmol) sodium triacetoxyborohydride were added batchwise within 20 min. The reaction mixture was left for a further 4 h at 0° C. with stirring and heated to RT overnight. Then the mixture was combined with 400 mL of a 15% (w/v) aqueous potassium carbonate solution and stirred for 1 h at RT. The organic phase was separated off, dried and concentrated by rotary evaporation.

Yield: 18.8 g (quantitative)
ESI-MS: m/z=370 (M+H)$^+$
$R_f$(HPLC): 1.9 min (method E)

Step 4:[2-(2-amino-5-methoxy-phenyl)-ethyl]-(1-benzylpiperidin-4-yl)-amine

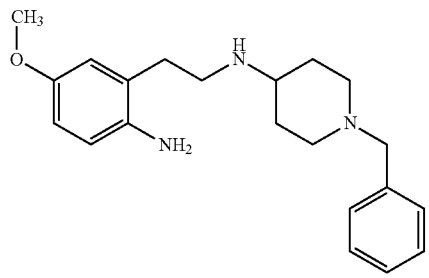 [SMILES: COc1ccc(N)c(CCNC2CCN(Cc3ccccc3)CC2)c1]

26.0 g (70.3 mmol) (1-benzylpiperidin-4-yl)-[2-(5-methoxy-2-nitrophenyl)-ethyl]-amine were hydrogenated with 5.0 g (2.45 mmol) rhodium charcoal (5%, moistened with water) in 350 mL methanol in a 3 bar hydrogen atmosphere for 3 h at RT. The catalyst was removed by suction filtering and the solution concentrated by rotary evaporation. The residue was immediately reacted further without any further purification.

Yield: 23.9 g (quantitative)
$R_f$(HPLC): $R_f$=0.99 min (method A)

Step 5:3-(1-benzylpiperidin-4-yl)-7-methoxy-1,3,4,5-tetrahydro-1,3-benzodiazepin-2-one

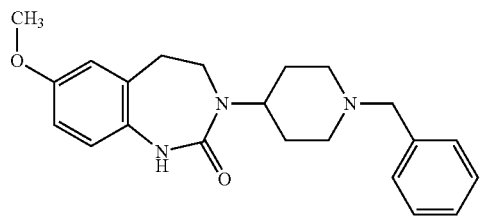 [SMILES: COc1ccc2c(c1)CCN(C1CCN(Cc3ccccc3)CC1)C(=O)N2]

35.0 g (216 mmol) N,N'-carbonyldiimidazole were added to 23.9 g (70.3 mmol) [2-(2-amino-5-methoxyphenyl)-ethyl]-(1-benzylpiperidin-4-yl)-amine in 175 mL DMF and the mixture was stirred for 2 h at 100° C. The reaction mixture was poured onto approx. 1 kg ice water and stirred overnight. The precipitated product was suction filtered, washed with 100 mL water and dried. The residue was stirred with 150 mL DIPE and suction filtered. The solid product was washed with 50 mL DIPE and dried.

Yield: 21.6 g (84% of theoretical)
ESI-MS: m/z=366 (M+H)$^+$
$R_f$(HPLC): 2.12 min (method E)

Step 6:7-methoxy-3-piperidin-4-yl-1,3,4,5-tetrahydro-1,3-benzodiazepin-2-one

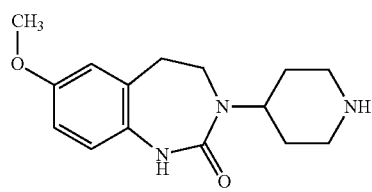 [SMILES: COc1ccc2c(c1)CCN(C1CCNCC1)C(=O)N2]

A mixture of 21.6 g (59.2 mmol) 3-(1-benzylpiperidin-4-yl)-7-methoxy-1,3,4,5-tetrahydro-1,3-benzodiazepin-2-one and 2.5 g palladium on charcoal (10%) in 300 mL methanol was hydrogenated in a 3 bar hydrogen atmosphere at 50° C. until the reaction was complete. The catalyst was removed by suction filtering and the mother liquor concentrated by rotary evaporation. The residue was triturated with 150 mL DIPE, suction filtered, washed with 100 mL DIPE and dried.

Yield: 13.2 g (81% of theoretical)
ESI-MS: m/z=276 (M+H)$^+$
$R_f$(HPLC): 0.73 min (method L)

Intermediate 5

3-piperidin-4-yl-1,3-dihydroimidazo[4,5-c]quinolin-2-one

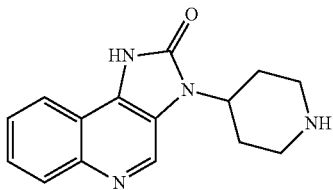 [SMILES: O=c1[nH]c2c3ccccc3ncc2n1C1CCNCC1]

Step 1: 3-bromoquinoline-1-oxide

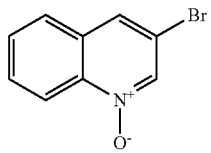 [SMILES: [O-][n+]1cc(Br)cc2ccccc21]

A solution of 72% 3-chloroperbenzoic acid (97.8 g (0.408 mol) dissolved in 1 L DCM, dried on sodium sulphate and filtered off) was added dropwise to a solution of 85.0 g 0.41 mol) 3-bromoquinoline in 100 mL DCM cooled to 5° C. Care was taken to ensure that the temperature of the reaction mixture did not rise above 10° C. After the addition had ended the mixture was stirred for 5 h, then a solution of 72% 3-chloroperbenzoic acid (25.0 g, 0.104 mol) dissolved in 200 mL DCM, dried on sodium sulphate and filtered off) was again added dropwise and the mixture was stirred overnight at RT. Saturated aqueous sodium carbonate solution was added, the phases were separated and the organic phase was dried on sodium sulphate. The solution was filtered through activated charcoal and then evaporated down i. vac.

Yield: 91 g (99% of theoretical)
MS: m/z=223/225 (M)$^+$
R$_f$: 0.15 (silica gel, eluant B)

Step 2: 3-bromo-4-nitroquinoline-1-oxide

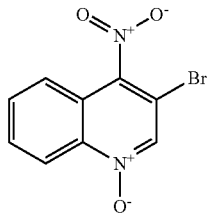 [SMILES: O=[N+]([O-])c1c(Br)c[n+]([O-])c2ccccc12]

A solution of 190 g (0.85 mol) 3-bromoquinoline-1-oxide in 500 mL concentrated sulphuric acid was heated to 90° C. Then 120 g (1.19 mol) potassium nitrate were added in small batches over a period of 100 min such that the temperature of the reaction did not rise above 95° C. The mixture was stirred for 3 h at 90° C.; it was left to cool to RT and the mixture was poured onto ice. The precipitated product was filtered off and the filter cake washed with water. The residue was dissolved in DCM and washed with saturated aqueous sodium hydrogen carbonate solution, until the solution reacted in alkaline manner. The phases were separated and the aqueous phase was again extracted with DCM. The combined organic phases were dried on sodium sulphate and evaporated down i. vac. After comminution of the residue and exhaustive drying i. vac. the product was obtained.

Yield: 104 g (46% of theoretical)
MS: m/z=268/270 (M)$^+$
R$_f$: 0.77 (silica gel, EtOAc)

Step 3: (1-benzylpiperidin-4-yl)-(4-nitro-1-oxyquinolin-3-yl)-amine

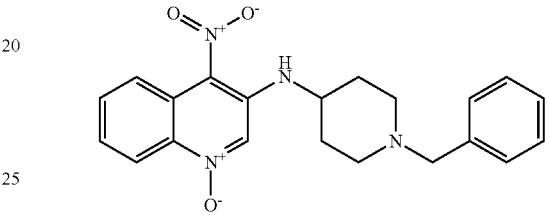

104 g (0.387 mol) 3-bromo-4-nitroquinoline-1-oxide were added to 320 mL (1.54 mol) 4-amino-1-benzylpiperidine. Then 500 mL THF were added and the mixture was hated until the substances were fully dissolved. Then it was stirred for 3 h at 70° C. and the reaction mixture was then evaporated down i. vac. The residue obtained was dissolved in 2.5 L DCM and washed with saturated aqueous sodium hydrogen carbonate solution. The aqueous phase was again extracted with 300 mL DCM. Then the organic phases were combined, dried on sodium sulphate and evaporated down i. vac. The residue was dissolved in 250 mL methanol. The product precipitated as a solid was suction filtered and dried i. vac.

Yield: 104 g (71% of theoretical)
ESI-MS: m/z=379 (M+H)$^+$
R$_f$: 0.75 (silica gel, EtOAc)

Step 4: N$^3$-(1-benzylpiperidin-4-yl)quinoline-3,4-diamine

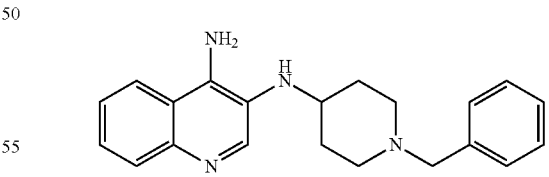

12.0 g rhodium charcoal (5%, moistened with water) were added to a solution of 76.0 g (0.20 mol) (1-benzylpiperidin-4-yl)-(4-nitro-1-oxyquinolin-3-yl)-amine in 1.0 L THF. The reaction was shaken for 4.5 h under a hydrogen atmosphere (50 psi) at RT. The catalyst was filtered off and the solvent was eliminated i. vac. Because of its proneness to oxidation the crude product was used immediately for the next step.

Yield: 66.0 g (99% of th.)
R$_f$: 0.30 (silica gel, eluant A)

Step 5: 3-(1-benzylpiperidin-4-yl)-1,3-dihydroimidazo[4,5-c]quinolin-2-one

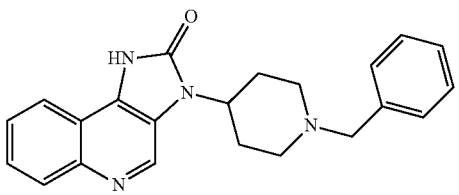 [SMILES: O=c1[nH]c2c3ccccc3ncc2n1C1CCN(Cc2ccccc2)CC1]

22.6 g (139 mmol) 1,1'-carbonyldiimidazole were added to a solution of 9.0 g (27.1 mmol) N³-(1-benzylpiperidin-4-yl)-quinoline-3,4-diamine in 100 mL DMF. The mixture was heated to 100° C. and stirred for 1.5 h at this temperature. After cooling the reaction mixture it was poured onto 300 mL water. The precipitated solid was filtered off, washed with water and dried at 30° C. i. vac. The residue was triturated with diethyl ether, suction filtered and the solid product was dried i. vac.

Yield: 7.42 g (77% of theoretical)
ESI-MS: m/z=359 (M+H)⁺
R$_t$(HPLC): 1.6 min (method E)

Step 6: 3-piperidin-4-yl-1,3-dihydroimidazo[4,5-c]quinolin-2-one

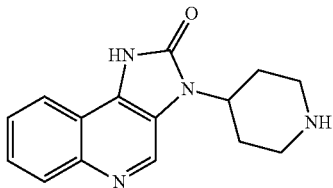 [SMILES: O=c1[nH]c2c3ccccc3ncc2n1C1CCNCC1]

A mixture of 44.0 g (0.123 mol) 3-(1-benzylpiperidin-4-yl)-1,3-dihydroimidazo[4,5-c]quinolin-2-one and 10.0 g palladium (Pd/C 10%) in 500 mL methanol was hydrogenated for 16 h at 50 C in a hydrogen atmosphere of 50 psi. After filtration of the reaction mixture the solvent was eliminated in vacuo. The product was precipitated out by the addition of isopropanol. It was filtered off and dried.

Yield: 31.2 g (95% of theoretical)
ESI-MS: m/z=269 (M+H)⁺
R$_f$: 0.20 (silica gel, eluant A)

Intermediate 6

6-chloropyrimidine-4-carboxylic acid chloride

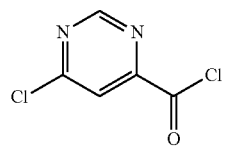

Step 1: 6-hydroxypyrimidine-4-carboxylic acid

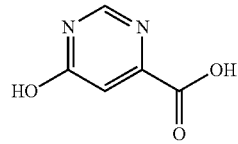

63.5 g (0.29 mol) sodium diethyloxalacetate and 30.2 g (0.29 mol) formamidine acetate were added to 24.1 g (0.6 mol) NaOH in 3.6 L water. The mixture was stirred overnight at RT. Then activated charcoal was added and the mixture was refluxed for 1 h. It was filtered off hot and after cooling acidified with aqueous hydrochloric acid. The solution was evaporated to dryness by rotary evaporation. The residue contained the desired product and was used in the next step without any further purification.

Yield: 83.0 g

Step 2: 6-chloropyrimidine-4-carboxylic acid chloride

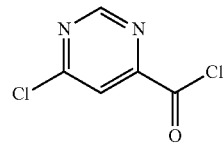

50.0 g (0.35 mol) 6-hydroxypyrimidine-4-carboxylic acid was taken and 500 mL phosphorus oxychloride were added. Then 150 g (0.720 mol) phosphorus pentachloride was added batchwise with stirring. The reaction mixture was refluxed for 5 h. The phosphorus oxychloride was distilled off and the residue was purified by vacuum distillation through a column.

Yield: 51.9 g (83% of theoretical)
MS: m/z=176/178/180 (M)⁺

Intermediate 7 ethyl 6-chloropyrimidine-4-carboxylate

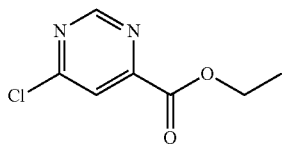

1.0 g (5.65 mmol) 6-chloropyrimidine-4-carboxylic acid chloride and 0.4 mL (6.94 mmol) ethanol were combined in 30 mL dichloromethane and stirred overnight at RT. The solvent was eliminated i.vac.

Yield: 1.0 g (95% of theoretical)
ESI-MS: m/z=187/189 (M+H)⁺
R$_f$: 0.85 (silica gel, EtOAc)

Intermediate 8 benzoate ethyl 3-[4-(2-oxo-1,2,4,5-tetrahydro-1,3-benzodiazepin-3-yl)-piperidin-1-yl]-

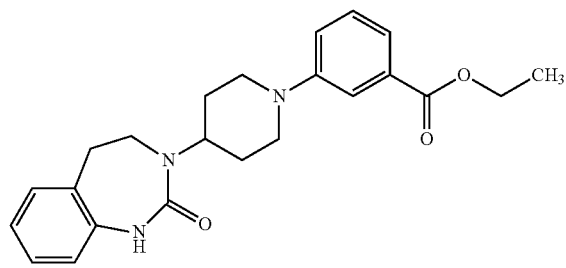 [SMILES: CCOC(=O)c1cccc(N2CCC(N3CCc4ccccc4NC3=O)CC2)c1]

Under a nitrogen atmosphere 1.06 g (4.32 mmol) 3-piperidin-4-yl-1,3,4,5-tetrahydro-1,3-benzodiazepin-2-one, 2.15 g (6.60 mmol) caesium carbonate, 100 mg (0.45 mmol) palladium-(II)-acetate and 280 mg (0.45 mmol) BINAP were stirred in 40 mL xylene for 10 min at RT. 850 μL (5.20 mmol) of ethyl 3-bromobenzoate were added and the mixture was stirred overnight at 120° C. Then the insoluble solid was suction filtered and the filtrate was evaporated down i. vac. The residue was purified by flash chromatography. The combined product fractions were evaporated down i. vac. The residue was stirred with diisopropylether and suction filtered. The solid was dried at 50° C. in the CAD.

Yield: 650 mg (38% of theoretical)

ESI-MS: m/z=394 (M+H)$^+$

R$_f$: 0.81 (silica gel, eluant A)

Intermediate 9

3-[4-(2-oxo-1,2,4,5-tetrahydro-1,3-benzodiazepin-3-yl)-piperidin-1-yl]-benzoic acid

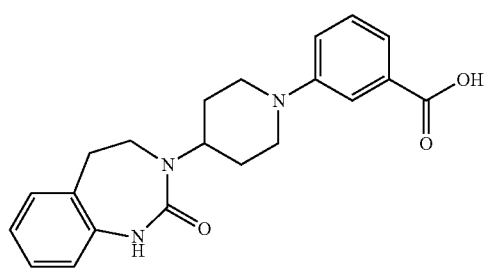 [SMILES: O=C(O)c1cccc(N2CCC(N3CCc4ccccc4NC3=O)CC2)c1]

650 mg (1.65 mmol) ethyl 3-[4-(2-oxo-1,2,4,5-tetrahydro-1,3-benzodiazepin-3-yl)-piperidin-1-yl]-benzoate, 10 mL THF, 2 mL water and 2 mL (8.00 mmol) of an aqueous 4M sodium hydroxide solution were stirred at RT until the reaction was complete. Then the THF was eliminated i. vac. The aqueous residue was acidified with a 4M hydrochloric acid solution. After several hours' stirring at RT the precipitate was suction filtered and dried.

Yield: 540 mg (90% of theoretical)

ESI-MS: m/z=366 (M+H)$^+$

R$_f$: 0.20 (silica gel, eluant A)

Intermediate 10 ethyl 6-[4-(2-oxo-1,2,4,5-tetrahydro-1,3-benzodiazepin-3-yl)-piperidin-1-yl]-pyrimidine-4-carboxylate

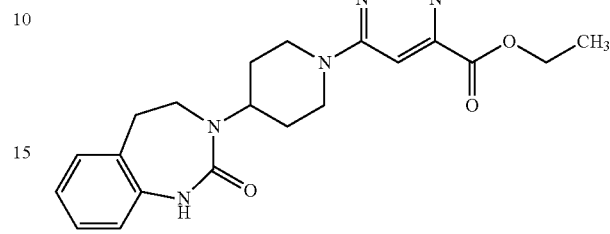

700 mg (2.85 mmol) 3-piperidin-4-yl-1,3,4,5-tetrahydro-1,3-benzodiazepin-2-one and 470 μL (2.73 mmol) DIPEA were added to 500 mg (2.68 mmol) ethyl 6-chloropyrimidine-4-carboxylate in 10 mL DMF and the reaction mixture was stirred for 1 h at RT. The reaction mixture was diluted with water and stirred for 30 min. The precipitate was suction filtered, washed with water and dried at 50° C. in the CAD.

Yield: 620 mg (59% of theoretical)

ESI-MS: m/z=396 (M+H)$^+$

R$_f$: 0.48 (silica gel, eluant A)

Intermediate 11

6-[4-(2-oxo-1,2,4,5-tetrahydro-1,3-benzodiazepin-3-yl)-piperidin-1-yl]-pyrimidine-4-carboxylic acid

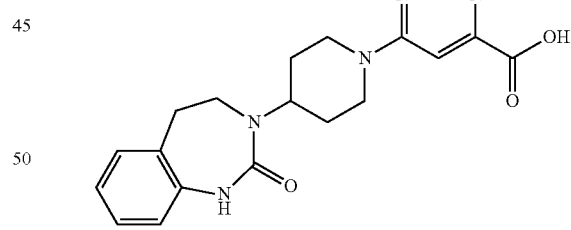

590 mg (1.49 mmol) ethyl 6-[4-(2-oxo-1,2,4,5-tetrahydro-1,3-benzodiazepin-3-yl)-piperidin-1-yl]-pyrimidine-4-carboxylate, 20 mL ethanol, 1 mL water and 1 mL (4.0 mmol) of a 4M NaOH solution were stirred for 2 h at RT. The reaction mixture was diluted with water until the precipitate had dissolved. 1 mL of a 4M hydrochloric acid solution were added and the ethanol was eliminated i. vac. The reaction mixture was stirred for 30 min at RT, the precipitate was suction filtered and dried at 50° C. in the CAD.

Yield: 500 mg (91% of theoretical)

MS: m/z=367 (M)$^+$

R$_f$: 0.13 (silica gel, eluant A)

Intermediate 12 ethyl 6-[4-(7-methoxy-2-oxo-1,2,4,5-tetrahydro-1,3-benzodiazepin-3-yl)-piperidin-1-yl]-pyrimidine-4-carboxylate

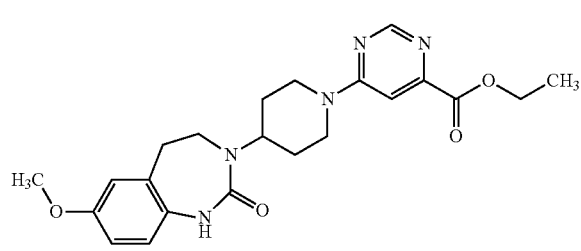 [SMILES: CCOC(=O)c1cc(N2CCC(N3CCc4cc(OC)ccc4NC3=O)CC2)ncn1]

2.80 g (10.2 mmol) 7-methoxy-3-piperidin-4-yl-1,3,4,5-tetrahydro-1,3-benzodiazepin-2-one and 6.00 mL (34.9 mmol) DIPEA were added to 1.90 g (10.2 mmol) ethyl 6-chloropyrimidine-4-carboxylate in 60 mL DMF and the reaction mixture was stirred for 3 h at RT. After elimination of the solvent i. vac. the residue was combined with 70 mL water and stirred for 10 min. 5 mL ethyl acetate were added. After vigorous stirring the solid was suction filtered and dried in the CAD.

Yield: 2.55 g (59% of theoretical)

ESI-MS: m/z=426 (M+H)$^+$ $R_f$: 0.63 (silica gel, eluant A)

Intermediate 13

6-[4-(7-methoxy-2-oxo-1,2,4,5-tetrahydro-1,3-benzodiazepin-3-O-piperidin-1-yl]-pyrimidine-4-carboxylic acid

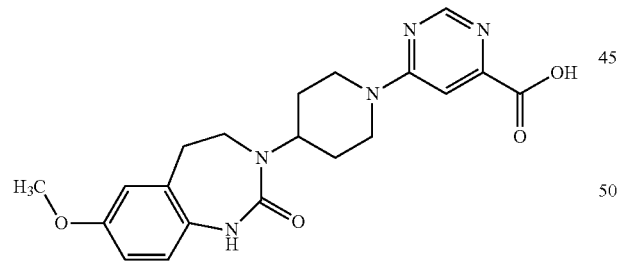

2.55 g (5.99 mmol) ethyl 6-[4-(7-methoxy-2-oxo-1,2,4,5-tetrahydro-1,3-benzodiazepin-3-yl)-piperidin-1-yl]-pyrimidine-4-carboxylate, 50 mL THF and 5 mL (20.0 mmol) of a 4M NaOH solution were stirred overnight at RT. After elimination of THF i. vac. The aqueous residue was combined with 5 mL of a 4 M hydrochloric acid solution. The supernatant solution was decanted off, the oily residue was again mixed with 50 mL water and stirred overnight at RT. The precipitate was suction filtered and dried at 50° C. in the CAD.

Yield: 2.05 g (86% of theoretical)

MS: m/z=397 (M)$^+$ $R_f$: 0.23 (silica gel, eluant A)

Intermediate 14 ethyl 6-[4-(2-oxo-2,3-dihydro-imidazo[4,5-b]pyridin-1-yl)-piperidin-1-yl]-pyrimidine-4-carboxylate

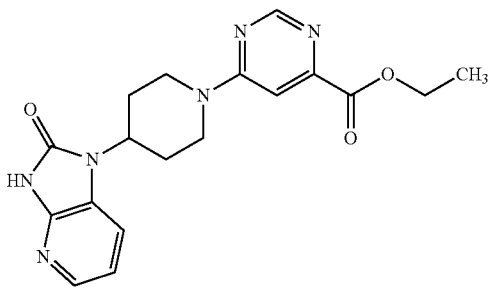 [SMILES: CCOC(=O)c1cc(N2CCC(n3c(=O)[nH]c4ncccc43)CC2)ncn1]

5.40 g (18.6 mmol) 1-piperidin-4-yl-1,3-dihydro-imidazo[4,5-b]pyridin-2-one dihydrochloride and 11 mL (63.93 mmol) DIPEA were added to 3.40 g (18.2 mmol) ethyl 6-chloropyrimidine-4-carboxylate in 80 mL DMF. After 3 h stirring at RT the solvent was eliminated i.vac. The residue was combined with 70 mL water and stirred for 10 min. 5 mL ethyl acetate were added and the mixture was stirred vigorously. The precipitated solid was suction filtered and dried at 40° C. in the circulating air dryer.

Yield: 5.50 g (82% of theoretical)

ESI-MS: m/z=369 (M+H)$^+$ $R_f$: 0.48 (silica gel; eluant A)

Intermediate 15

6-[4-(2-oxo-2,3-dihydroimidazo[4,5-b]pyridin-1-yl)-piperidin-1-yl]-pyrimidine-4-carboxylic acid

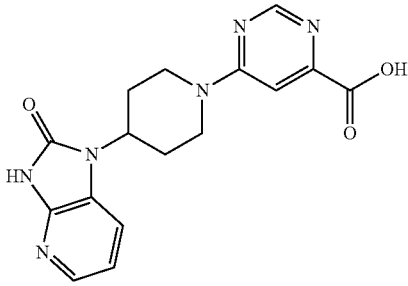 [SMILES: O=C(O)c1cc(N2CCC(n3c(=O)[nH]c4ncccc43)CC2)ncn1]

9.0 mL (36.0 mmol) of a 4M NaOH solution were added to 5.50 g (14.9 mmol) ethyl 6-[4-(2-oxo-2,3-dihydro-imidazo[4,5-b]pyridin-1-yl)-piperidin-1-yl]-pyrimidine-4-carboxylate, 25 mL water in 150 mL THF. After 3 h stirring at RT the THF was eliminated i. vac. The aqueous residue was combined with 9 mL of a 4M hydrochloric acid solution. After 3 h stirring at RT the precipitate was suction filtered and dried in the CAD at 60 C.

Yield: 4.5 g (89% of theoretical)

ESI-MS: m/z=341 (M+H)$^+$ $R_f$: 0.07 (silica gel; eluant A)

Intermediate 16

(2-chloropyridin-4-yl)-(2,3-dihydroindol-1-yl)-methanone

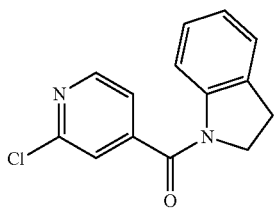 [SMILES: O=C(c1ccnc(Cl)c1)N1CCc2ccccc21]

400 µL (3.53 mmol) 2,3-dihydro-1H-indole were added to 500 mg (3.17 mmol) 2-chloroisonicotinic acid, 600 µL (3.49 mmol) DIPEA and 1.10 g (3.43 mmol) TBTU in 20 mL THF. The reaction mixture was stirred overnight, diluted with ethyl acetate and washed with 15% potassium carbonate solution (1×), water (1×) and 1M hydrochloric acid (1×). The organic phase was dried on magnesium sulphate, filtered and evaporated down i. vac. The residue was triturated with diisopropylether and suction filtered. The solid was dried at 40° C. in the circulating air dryer.

Yield: 700 mg (85% of theory)
ESI-MS: 259/261 (M+H)$^+$
$R_f$: 0.38 (silica gel, eluant B)

Intermediate 17

(2-chloropyridin-4-yl)-(5-fluoro-2,3-dihydroindol-1-yl)-methanone

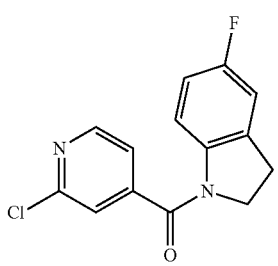 [SMILES: O=C(c1ccnc(Cl)c1)N1CCc2cc(F)ccc21]

174 mg (1.27 mmol) 5-fluoro-2,3-dihydro-1H-indole were added to 198 mg (1.26 mmol) 2-chloroisonicotinic acid, 351 µL (2.50 mmol) triethylamine and 434 mg (1.35 mmol) TBTU in 3 mL DMF. The reaction mixture was stirred overnight at RT. Purification was carried out by preparative HPLC. The product fractions were combined and evaporated down i. vac.

Yield: 230 mg (66% of theory)
ESI-MS: 277/279 (M+H)$^+$
$R_t$ (HPLC-MS): 4.0 min (method E)

Intermediate 18

(4-chloropyridin-2-yl)-(2,3-dihydroindol-1-yl)-methanone

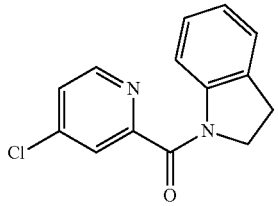 [SMILES: O=C(c1cc(Cl)ccn1)N1CCc2ccccc21]

800 µL (7.07 mmol) 2,3-dihydro-1H-indole were added to 1.0 g (6.35 mmol) 4-chloropyridine-2-carboxylic acid, 1.0 mL (7.12 mmol) triethylamine and 2.20 g (6.85 mmol) TBTU in 100 mL THF. The reaction mixture was stirred for 3 h at RT, diluted with ethyl acetate (100 mL) and washed with 15% potassium carbonate solution (2×50 mL), saturated sodium chloride solution (1×50 mL) and 1M hydrochloric acid (2×30 mL). The organic phase was dried on magnesium sulphate, filtered and evaporated down i. vac.

Yield: 850 mg (52% of theory)
ESI-MS: 259/261 (M+H)$^+$
$R_f$: 0.88 (silica gel, EtOAc)

Intermediate 19

(4-chloropyridin-2-yl)-(5-fluoro-2,3-dihydroindol-1-yl)-methanone

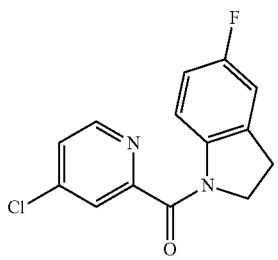 [SMILES: O=C(c1cc(Cl)ccn1)N1CCc2cc(F)ccc21]

174 mg (1.27 mmol) 5-fluoro-2,3-dihydro-1H-indole were added to 200.0 mg (1.27 mmol) 4-chloropyridine-2-carboxylic acid, 351 µL (2.50 mmol) triethylamine and 434.0 mg (1.35 mmol) TBTU in 3 mL DMF. The reaction mixture was stirred overnight at RT. Purification was carried out by preparative HPLC. The product fractions were combined and evaporated down i. vac.

Yield: 300 mg (85% of theory)
ESI-MS: 277/279 (M+H)$^+$
$R_t$ (HPLC-MS): 4.1 min (method E)

Intermediate 20

(6-chloropyrimidin-4-yl)-(octahydroindol-1-yl)-methanone

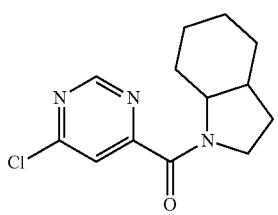 [SMILES: O=C(c1cc(Cl)ncn1)N1CCC2CCCCC21]

0.517 g (2.92 mmol) 6-chloropyrimidine-4-carboxylic acid chloride in 10 mL dichloromethane were combined with 1.07 mL (6.00 mmol) DIPEA. 0.73 g (2.92 mmol) octahydroindole in 10 mL DCM was slowly added dropwise. After 2 h stirring at RT the mixture was diluted with dichloromethane and extracted with water. The organic phase was separated off, dried on sodium sulphate, filtered, evaporated down i. vac. and dried.

The product thus obtained was reacted without further purification.

Yield: 800 mg (quant.)
ESI-MS: 266/268 (M+H)$^+$
$R_t$ (HPLC-MS): 3.62 min (method E)

Intermediate 21

(6-chloropyrimidin-4-yl)-(2,3-dihydroindol-1-yl)-methanone

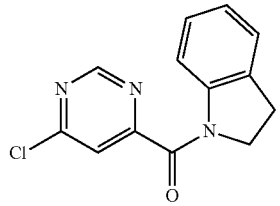 [SMILES: O=C(c1cc(Cl)ncn1)N1CCc2ccccc21]

500 mg (2.83 mmol) 6-chloropyrimidine-4-carboxylic acid chloride in 20 mL dichloromethane were cooled with a bath of ice/ethanol and mixed with 0.300 mL (2.68 mmol) 2,3-dihydro-1H-indole. 2.70 mL (2.70 mmol) of a 1M sodium hydroxide solution were added dropwise. The reaction mixture was stirred for 2 h while being cooled and for 1 h at RT. Then 50 mL of an aqueous saturated sodium hydrogen carbonate solution were added. After 10 min stirring the organic phase was separated off and extracted with water (1×30 mL) and with 1 M hydrochloric acid (1×50 mL). The organic phase was dried on magnesium sulphate, filtered and evaporated down i. vac.

Yield: 570 mg (78% of theoretical)
ESI-MS: m/z=260/262 (M+H)$^+$
$R_f$: 0.59 (silica gel, eluant B)

General method of reacting 6-chloropyrimidine-4-carboxylic acid chloride with heterocycles containing nitrogen:

1.50 g (8.48 mmol) 6-chloropyrimidine-4-carboxylic acid chloride in 50 mL dichloromethane were cooled with a bath of ice/ethanol and combined with the amount of a nitrogen-containing heterocyclic group specified in each case. 7.90 mL (7.90 mmol) of a 1M sodium hydroxide solution were added dropwise. The reaction mixture was stirred for 2 h while being cooled and for 1 h at RT. Then 50 mL of a saturated sodium hydrogen carbonate solution were added. After 10 min stirring the organic phase was separated off and extracted with water (1×30 mL) and then with 1 M hydrochloric acid (1×50 mL). The organic phase was dried on magnesium sulphate, filtered and evaporated down i. vac. The product was reacted without further purification.

| Intermediate | Structure | N heterocycle [amount of N heterocycle] Yield | Analytical data |
|---|---|---|---|
| 22 | (6-chloropyrimidin-4-yl)-(1,3-dihydroisoindol-2-yl)-methanone | 2,3-dihydro-1H-isoindole 0.89 mL (7.84 mmol) 1.8 g (82% of theory) | ESI-MS: m/z = 260/262 (M + H)$^+$ $R_f$ = 0.57 eluant B |
| 23 | (6-chloropyrimidin-4-yl)-(3,4-dihydro-1H-isoquinolin-2-yl)-methanone | 1,2,3,4-tetrahydro-isoquinoline 0.978 mL (7.81 mmol) 1.7 g (73% of theory) | ESI-MS: m/z = 274/276 (M + H)$^+$ $R_f$ = 0.46 eluant B |
| 24 | (6-chloropyrimidin-4-yl)-(3,4-dihydro-2H-quinolin-1-yl)-methanone | 2,3,4,5-tetrahydro-1H-1-benzazepine 1.15 g (7.81 mmol) 2.0 g (82% of theory) | ESI-MS: m/z = 288/290 (M + H)$^+$ $R_f$ = 0.61 eluant A |

Intermediate 25

(5-chloro-2,3-dihydroindol-1-yl)-(6-chloropyrimidin-4-yl)-methanone

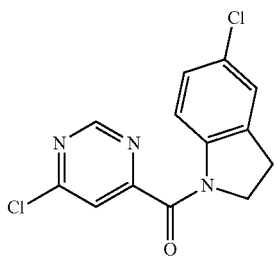 [SMILES: O=C(c1cc(Cl)ncn1)N1CCc2cc(Cl)ccc21]

1.50 g (8.48 mmol) 6-chloropyrimidine-4-carboxylic acid chloride in 50 mL dichloromethane were cooled with a bath of ice/ethanol and combined with 1.20 g (7.81 mmol) 5-chloro-2,3-dihydro-1H-indole. 7.90 mL (7.90 mmol) of a 1M sodium hydroxide solution were added dropwise. The reaction mixture was stirred for 2 h while being cooled and for 1 h at RT. Then 50 mL of an aqueous saturated sodium hydrogen carbonate solution were added. After 10 min stirring the organic phase was separated off and extracted with water (1×30 mL) and with 1 M hydrochloric acid (1×50 mL). The organic phase was dried on magnesium sulphate, filtered and evaporated down i. vac.

Yield: 2.00 g (80% of theoretical)
ESI-MS: m/z=294/296/298 (M+H)$^+$
R$_f$: 0.65 (silica gel, eluant B)

Intermediate 26

(5-bromo-2,3-dihydroindol-1-yl)-(6-chloropyrimidin-4-yl)-methanone

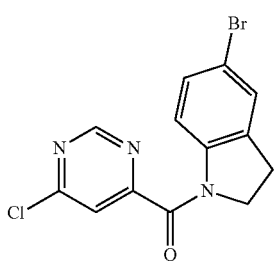 [SMILES: O=C(c1cc(Cl)ncn1)N1CCc2cc(Br)ccc21]

2.0 g (11.3 mmol) 6-chloropyrimidine-4-carboxylic acid chloride in 50 mL dichloromethane were cooled with a bath of ice/ethanol and combined with 2.2 g (10.9 mmol) 5-bromo-2,3-dihydro-1H-indole. 10.9 mL (10.9 mmol) of a 1M sodium hydroxide solution were added dropwise. The reaction mixture was stirred for 2 h while being cooled. After the mixture had warmed up to RT, 50 mL of a saturated aqueous sodium hydrogen carbonate solution was added. The organic phase was separated off and extracted with water (1×) and with 1 M hydrochloric acid (1×). The organic phase was dried on magnesium sulphate, filtered and evaporated down i. vac. The residue was triturated with diisopropylether, suction filtered and dried at 50° C. in the CAD.

Yield: 620 mg (16% of theoretical)
MS: m/z=337/339/341 (M)$^+$
R$_f$: 0.89 (silica gel, EtOAc)

Intermediate 27 methyl (5-fluoro-2,3-dihydro-1H-indol-3-yl)-acetate

Step 1: methyl (5-fluoro-1H-indol-3-yl)-acetate

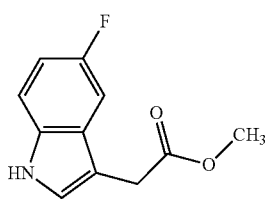

1.0 g (5.2 mmol) 5-fluoroindole-3-acetic acid was stirred in 60 mL methanolic HCl at RT for 2h. The solvent was eliminated using the rotary evaporator. The product was reacted without further purification.

Yield: 1.0 g (93% of theory)
ESI-MS: m/z=208 (M+H)$^+$
R$_t$ (HPLC): 3.18 min (method E)

Step 2: methyl (5-fluoro-2,3-dihydro-1H-indol-3-yl)-acetate

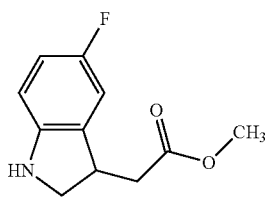

Under a nitrogen atmosphere 910 mg (14.5 mmol) sodium cyanoborohydride was added batchwise to 1.0 g (4.83 mmol) methyl (5-fluoro-1H-indol-3-yl)-acetate in 12.5 g acetic acid while cooling slightly. After 2 h stirring at RT another 910 mg (14.5 mmol) sodium cyanoborohydride was added batchwise while cooling slightly. After 3 h stirring at RT the solvent was evaporated down using the rotary evaporator. The residue was taken up in 4M hydrochloric acid and stirred for 30 min. Then the reaction solution was made alkaline with solid potassium carbonate and extracted with dichloromethane (3×). The combined organic phases were dried on sodium sulphate, filtered and evaporated down using the rotary evaporator. The product thus obtained was reacted directly.

Yield: 300 mg (30% of theory)
ESI-MS: m/z=210 (M+H)$^+$

Intermediate 28

5-fluoro-3,3-dimethyl-2,3-dihydro-1H-indole

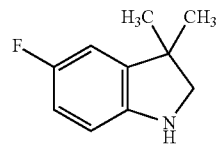

Step 1: 1-acetyl-5-fluoro-1,3-dihydro-indol-2-one

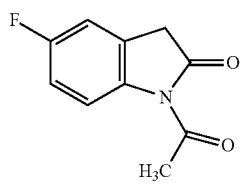

At 170° C. 3.0 g (20 mmol) 5-fluoroindolinone were stirred for 3 h in 10 mL (98 mmol) acetic anhydride. After cooling to RT the mixture was poured onto 200 mL ice water, the precipitated substance was suction filtered and washed with 100 mL water. The solid was recrystallised from 100 mL water and 50 mL ethanol at boiling temperature. The precipitated product was suction filtered, washed with 30 mL water and dried in the CAD.

Yield: 2.4 g (63% of theory)
ESI-MS: m/z=192 (M+H)$^+$
R$_t$ (HPLC): 1.2 min (method C)

Step 2: 1-acetyl-5-fluoro-3,3-dimethyl-1,3-dihydro-indol-2-one

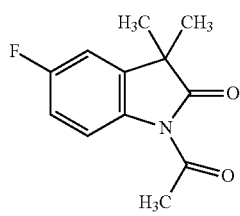

At 0° C. to 5° C., 1.14 g (26.0 mmol) 55% sodium hydride in oil was added batchwise under an argon atmosphere to 2.40 g (12.4 mmol) 1-acetyl-5-fluoro-1,3-dihydroindol-2-one in 30 mL DMF and stirred for 1 h. Then 1.91 mL (31.0 mmol) methyl iodide were added dropwise and the mixture was stirred overnight at RT. The reaction mixture was poured onto 200 mL water and the precipitated substance was suction filtered. The solid was washed with 50 mL water and dried in the CAD.

Yield: 2.1 g (76% of theory)
ESI-MS: m/z=222 (M+H)$^+$
R$_t$ (HPLC): 1.48 min (method C)

Step 3: 5-fluoro-3,3-dimethyl-1,3-dihydroindol-2-one

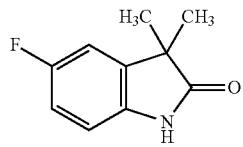

2.10 g (9.49 mmol) 1-acetyl-5-fluoro-3,3-dimethyl-1,3-dihydro-indol-2-one in 20 mL isopropanol were refluxed with 50 mL of an aqueous 6N hydrochloric acid solution for 1 h. After cooling the isopropanol was eliminated i. vac. The residue was diluted with 100 mL water and cooled with ice. The precipitated substance was suction filtered and washed with 30 mL water. The solid was dried in the CAD.

Yield: 1.40 g (82% of theory)
ESI-MS: m/z=180 (M+H)$^+$
R$_t$ (HPLC): 1.14 min (method C)

Step 4: 5-fluoro-3,3-dimethyl-2,3-dihydro-1H-indole

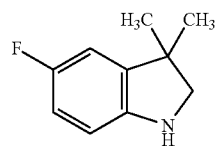

Under an argon atmosphere a solution of 9.30 mL (9.30 mmol) of a 1M solution lithium aluminium hydride in THF and 10 mL THF was slowly added dropwise to 1.40 g (7.81 mmol) 5-fluoro-3,3-dimethyl-1,3-dihydroindol-2-one in 50 mL THF. Then the reaction mixture was heated to 70° C. for 1 h. After cooling 2 mL water were added. The solution was dried on sodium sulphate and filtered off. The solvent was eliminated i. vac.

Yield: 1.30 g (quant)
ESI-MS: m/z=166 (M+H)$^+$
R$_t$ (HPLC): 0.75 min (method C)

Intermediate 29

3,3-dimethyl-2,3-dihydro-1H-indole

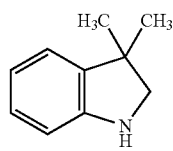

Step 1: 1-acetyl-1,3-dihydroindol-2-one

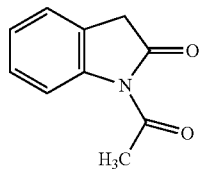

The compound was synthesised as in US Patent Application 2003/0069299.

Step 2: 1-acetyl-3,3-dimethyl-1,3-dihydroindol-2-one

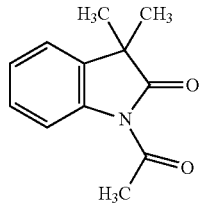

At 0° C. to 5° C. 2.75 g (63.0 mmol) 55% sodium hydride in oil was added batchwise under an argon atmosphere to 5.30 g (30.0 mmol) 1-acetyl-1,3-dihydroindol-2-one in 50 mL DMF and stirred for 1 h. Then 4.70 mL (75 mmol) methyl iodide were added dropwise and the mixture was stirred overnight at RT. The reaction mixture was poured onto water and extracted several times with tert-butylmethylether. The combined organic phases were dried and evaporated down i. vac. The residue was purified on a silica gel column. The product fractions were combined and evaporated to dryness by rotary evaporation.

Yield: 3.60 g (59% of theory)
ESI-MS: m/z=204 (M+H)+
$R_f$: 0.9 ((silica gel, petroleum ether/dichloromethane/ethyl acetate=5/4/1)

Step 3: 3,3-dimethyl-1,3-dihydroindol-2-one

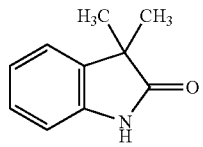

3.50 g (17.2 mmol) 1-acetyl-3,3-dimethyl-1,3-dihydro-indol-2-one were refluxed in 50 mL of a 6N hydrochloric acid solution for 1h. After cooling the reaction mixture was divided between tert-butylmethylether and water. The organic phase was washed with water, dried and evaporated down. The residue was crystallised from PE. The solid was suction filtered and dried at 80° C. in the CAD.

Yield: 2.40 g (87% of theory)
ESI-MS: m/z=162 (M+H)+
$R_f$ 0.3 (silica gel, petroleum ether/dichloromethane/ethyl acetate=5/4/1)

Step 4: 3,3-dimethyl-2,3-dihydro-1H-indole

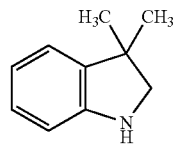

Under a nitrogen atmosphere a solution of 6.20 mL (6.20 mmol) of a 1M solution lithium aluminium hydride in THF and 10 mL THF was slowly added dropwise to 1.00 g (6.20 mmol) 3,3-dimethyl-1,3-dihydro-indol-2-one in 50 mL THF. Then the reaction mixture was heated to 60° C. for 1 h. After cooling to 0° C., 3 mL ice water were slowly added dropwise. 20 g sodium sulphate were added and the mixture was suction filtered. The solution was evaporated down i. vac.

Yield: 0.80 g (88% of theory)
ESI-MS: m/z=148 (M+H)+
$R_t$ (HPLC): 0.7 min (method C)

Intermediate 30

Spiro[cyclobutan-1.3'-indoline]

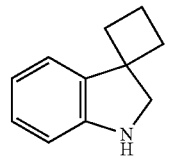 [SMILES: c1ccc2c(c1)NCC21CCC1]

Step 1: Cyclobutanecarboxylic acid N'-phenylhydrazide

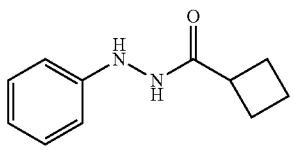 [SMILES: O=C(NNc1ccccc1)C1CCC1]

3.54 mL (31.0 mmol) cyclobutanecarboxylic acid chloride were added dropwise at RT to 3.00 mL (30.2 mmol) phenyl-hydrazine and 4.75 mL (60.0 mmol) pyridine in 30 mL DMF. The mixture was stirred for 1 h at RT and poured onto 200 mL of a 1M hydrochloric acid solution. The precipitated solid was suction filtered, washed with 50 mL water and dried i. vac. The product was extracted with 50 mL ether and suction filtered. The solid was washed with 20 mL ether and dried in the air.

Yield: 3.00 g (52% of theory)
ESI-MS: m/z=191 (M+H)+
$R_t$ (HPLC-MS): 1.05 min (method C)

Step 2: spiro[cyclobutan-1,3'-indolin]-2'-one

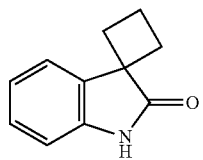 [SMILES: O=C1Nc2ccccc2C12CCC2]

Under a nitrogen atmosphere 1.50 g (7.89 mmol) cyclobutanecarboxylic acid N-phenylhydrazide and 530 mg (12.6 mmol) calcium hydride were mixed thoroughly and heated to 230° C. The mixture was stirred for 30 min at 230° C. and then cooled to RT again. The reaction mixture was carefully mixed with a solution of 7 mL water and 16 mL methanol. It was stirred for 1 h until no more hydrogen was released. Then the pH was adjusted to 1 with concentrated hydrochloric acid solution and the mixture was stirred for 1 h at 100° C. Using 4M sodium hydroxide solution the pH was adjusted to 3 and stirred overnight at RT. The precipitated substance was suction filtered and washed with 10 mL water. The mother liquor was evaporated down i.vac. and the residue was purified by preparative HPLC. The product fractions were combined, evaporated down i.vac. and dried.

Yield: 100 mg (7% of theory)
ESI-MS: m/z=174 (M+H)$^+$
R$_t$ (HPLC-MS): 1.18 min (method C)

Step 3: spiro[cyclobutan-1,3'-indoline]

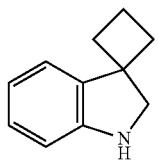 [SMILES: c1ccc2c(c1)NCC21CCC1]

Under a nitrogen atmosphere 0.60 mL (0.60 mmol) of a 1M solution of lithium aluminium hydride in THF was added dropwise to 100 mg (0.58 mmol) spiro[cyclobutan-1,3'-indolin]-2'-one in 20 mL THF. Then the reaction mixture was stirred for 1 h at 65° C. After cooling 1 mL water was added and the mixture was stirred for 10 min. The organic phase was dried on sodium sulphate and evaporated down. The product was reacted without further purification.

Yield: 100 mg (quant)
ESI-MS: m/z=160 (M+H)$^+$
R$_t$ (HPLC-MS): 0.77 min (method C)

Intermediate 31

3-(3-pyrrolidin-1-yl-propyl)-2,3-dihydro-1H-indole

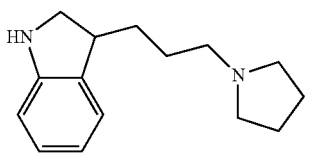 [SMILES: c1ccc2c(c1)NCC2CCCN1CCCC1]

Step 1: 3-(1H-indol-3-yl)-1-pyrrolidin-1-yl-propan-1-one

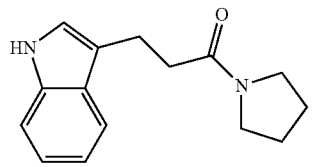 [SMILES: O=C(CCc1c[nH]c2ccccc12)N1CCCC1]

681 mg (3.60 mmol) 3-(1H-indol-3-yl)-propionic acid, 0.3 mL (3.60 mmol) pyrrolidine, 1.13 g (3.50 mmol) TBTU and 0.98 mL (7.00 mmol) triethylamine in 5.0 mL DMF were stirred overnight at RT. The mixture was purified by preparative HPLC. The product fractions were combined and evaporated down i. vac.

Yield: 670 mg (77% of theory)
ESI-MS: m/z=243 (M+H)$^+$
R$_t$ (HPLC-MS): 3.33 min (method E)

Step 2: 3-(3-pyrrolidin-1-yl-propyl)-1H-indole

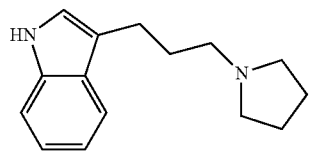 [SMILES: c1ccc2c(CCCN3CCCC3)c[nH]c2c1]

Under a nitrogen atmosphere 3.40 mL (3.40 mmol) of a 1M lithium aluminium hydride solution in THF was slowly added dropwise to 670 mg (2.77 mmol) 3-(1H-indol-3-yl)-1-pyrrolidin-1-yl-propan-1-one in 30 mL THF. The reaction mixture was stirred for 1 h at 65 C and after cooling combined with 1 mL water. After 10 min stirring at RT the organic phase was dried on sodium sulphate and evaporated down i. vac. The product was reacted further without any further purification.

Yield: 600 mg (95% of theory)
ESI-MS: m/z=229 (M+H)$^+$
R$_t$ (HPLC-MS): 0.9 min (method C)

Step 3: 3-(3-pyrrolidin-1-yl-propyl)-2,3-dihydro-1H-indole

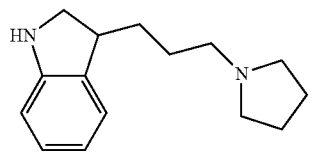 [SMILES: c1ccc2c(c1)NCC2CCCN1CCCC1]

At 15° C. 508 mg (8.10 mmol) sodium cyanoborohydride was added to 600 mg (2.63 mmol) 3-(3-pyrrolidin-1-yl-propyl)-1H-indole in 7.50 g acetic acid and the mixture was stirred for 1 h at 15° C. After this time another 600 mg sodium cyanoborohydride were added and the mixture was stirred at 15° C. for 3 h. The reaction mixture was evaporated down using the rotary evaporator and combined with 40 mL of a 4M hydrochloric acid solution. The reaction mixture was stirred for 1h at RT. Then the mixture was made basic with potassium carbonate and extracted with ethyl acetate (2×50 mL). The combined organic phases were dried and evaporated down i. vac. The product was reacted further without any further purification.

Yield: 600 mg (99% of theory)
ESI-MS: m/z=231 (M+H)$^+$
R$_t$ (HPLC-MS): 0.25 min (method C)

Intermediate 32 ethyl 2,3-dihydro-1H-indole-2-carboxylate hydrochloride

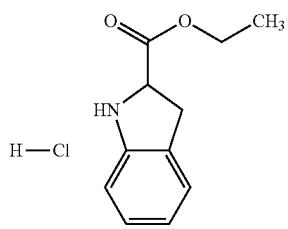

1.50 g (9.19 mmol) 2,3-dihydro-1H-indole-2-carboxylic acid in 50 mL ethanolic hydrochloric acid were stirred overnight at RT. The solvent was eliminated using the rotary evaporator.

Yield: 2.10 g (quant)
ESI-MS: m/z=192 (M+H)$^+$

Intermediate 33

7,7-dimethyl-4,5,6,7-tetrahydro-1H-pyrazol[4,3-c]pyridine-dihydrochloride

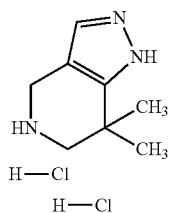

At 0° C. 5 mL trifluoroacetic acid was added to 1.60 g (6.05 mmol) tert-butyl 7,7-dimethyl-1,4,6,7-tetrahydro-pyrazolo[4,3-c]pyridine-5-carboxylate (synthesised analogously to WO2005/065779) in 15 mL dichloromethane and the reaction mixture was stirred for 2 h at RT. Then the solvent was eliminated i. vac. The residue was combined with ethanol and evaporated down again i. vac. The residue was dissolved in ethanol and 12 mL of a 1.25 M ethanolic HCl solution were added. The mixture was again evaporated down i. vac. The residue was triturated with ethanol. The solid was suction filtered and dried.

Yield: 1.24 g (92% of theoretical)
ESI-MS: m/z=152 (M+H)$^+$
R$_t$ (HPLC): 0.65 min (method N)

Intermediate 34

1,1-dimethyl-2-m-tolyl-ethylamine

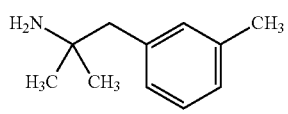

Step 1: ethyl m-tolyl-acetate

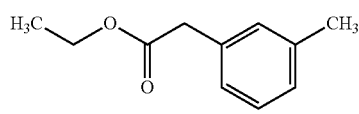

50 mL ethanolic hydrochloric acid were added to 25.5 g (169 mmol) m-tolylacetic acid in 200 mL ethanol and the mixture was stirred overnight at RT. After elimination of the solvent using the rotary evaporator the residue was combined with 250 mL EtOAc and extracted with 150 mL of a 15% potassium carbonate solution. The organic phase was dried on magnesium sulphate, filtered and evaporated to dryness using the rotary evaporator.

Yield: 25.6 g (85% of theory)
MS: m/z=178 (M)$^+$
R$_f$: 0.76 (silica gel, PE/EtOAc=8/2)

Step 2: 2-methyl-1-m-tolylpropan-2-ol

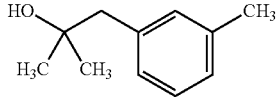

At 10° C., 17.8 g (99.87 mmol) ethyl m-tolyl-acetate in 400 mL THF was slowly added dropwise to 100 mL (300.0 mmol) of a 3M solution of methylmagnesium bromide in THF over an hour. The reaction mixture was heated for 30 min at RT and refluxed for 3 h. After cooling 250 mL of a saturated ammonium chloride solution were slowly added dropwise. The mixture was left to stand overnight. 300 mL of a 0.5 M hydrochloric acid solution were added and it was briefly stirred. The phases were separated and the aqueous phase was extracted with EtOAc. The combined organic phases were washed with saturated sodium chloride solution, dried on magnesium sulphate, filtered and evaporated down i. vac.

Yield: 14.7 g (90% of theory)
R$_f$: 0.39 (silica gel, PE/EtOAc=8/2)

Step 3: N-(1,1-dimethyl-2-m-tolylethyl)-formamide

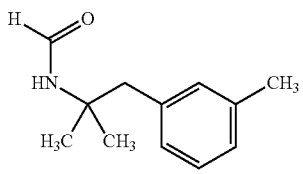

While cooling with ice 5.20 g (106 mmol) sodium cyanide were added to 60 mL glacial acetic acid. After brief stirring 40 mL conc. Sulphuric acid was added dropwise at 0° C. such that the reaction temperature did not rise above 20° C. After brief stirring 14.5 g (88.3 mmol) 2-methyl-1-m-tolylpropan-2-ol in 40 mL glacial acetic acid were added dropwise at 0° C. such that the reaction temperature did not rise above 20° C. The reaction mixture was stirred for 10 min at 0° C. and overnight at RT. The reaction mixture was poured onto ice and neutralised with 40% sodium hydroxide solution. The aqueous phase was extracted with EtOAc (3×150 mL). The combined organic phases were washed with 15% potassium carbonate solution, dried, filtered and evaporated down i. vac.

Yield: 14.4 g (85% of theory)
ESI-MS: m/z=192 (M+H)$^+$
R$_f$: 0.31 (silica gel, PE/EtOAc=8/2)

Step 4: 1,1-dimethyl-2-m-tolylethylamine

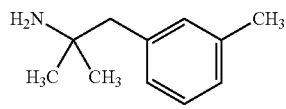

1.80 g (9.41 mmol) N-(1,1-dimethyl-2-m-tolylethyl)-formamide, 20 mL water and 20 mL conc. hydrochloric acid were refluxed for 2 h. The reaction mixture was diluted with 20 mL ice water and made alkaline with saturated potassium carbonate solution. The aqueous phase was extracted with DCM (2×20 mL). The organic phase was washed with water, dried on sodium sulphate and evaporated down i. vac. The residue was co-evaporated with toluene (2×).

Yield: 1.30 g (85% of theory)
ESI-MS: m/z=164 (M+H)$^+$

Intermediate 35

3,3-dimethylpyrrolidine hydrochloride

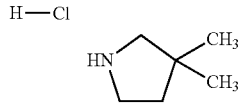

Step 1: 1-benzyl-3,3-dimethylpyrrolidin-2,5-dione

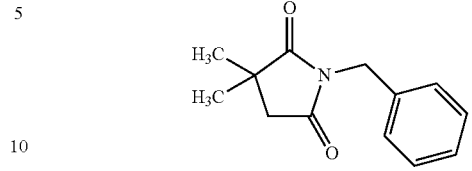

25.0 g (171 mmol) 2,2-dimethylsuccinic acid and 20.6 mL (188 mmol) benzylamine were refluxed for 1.5 h with stirring in an apparatus with water separator. The xylene was evaporated off by rotary evaporation and the residue was divided between 300 mL EtOAc and 150 mL of a 5% sodium hydrogen carbonate solution. The organic phase was dried on sodium sulphate, suction filtered and concentrated by rotary evaporation. The residue was crystallised from isopropanol in a bath of dry ice.

Yield: 34.6 g (93% of theory)
ESI-MS: m/z=218 (M+H)$^+$
R$_f$ 0.58 (silica gel, PE/EtOAc=4/1)

Step 2: 1-benzyl-3,3-dimethylpyrrolidine

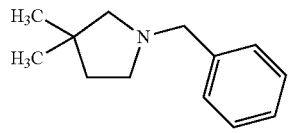

34.5 g (158.8 mmol) 1-benzyl-3,3-dimethyl-pyrrolidin-2,5-dione in 200 mL THF was slowly added dropwise at 10° C. to 20° C. within 1.5 h to 400 mL (400 mmol) of a 1M lithium aluminium hydride solution in THF while cooling with dry ice/isopropanol. The reaction mixture was stirred overnight at RT. While cooling with isopropanol/dry ice 120 mL of a 3:1 mixture of THF:water were added dropwise at 10° C. to 20° C. The reaction mixture was diluted with 600 mL THF. After total decomposition the precipitate was suction filtered and washed with THF. The filtrate was evaporated down using the rotary evaporator, combined with 100 mL of a 5% sodium hydrogen carbonate solution and extracted with 300 mL EtOAc. The organic phase was dried on sodium sulphate, suction filtered and concentrated by rotary evaporation.

Yield: 28.7 g (96% of theory)
ESI-MS: m/z=190 (M+H)$^+$
R$_f$: 0.16 (silica gel, DCM/EtOH=50/1)

Step 3: 3,3-dimethylpyrrolidine hydrochloride

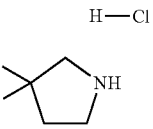

28.7 g (151 mmol) 1-benzyl-3,3-dimethylpyrrolidine and 2.0 g palladium on charcoal (10%) in 100 mL methanol were hydrogenated in a hydrogen atmosphere for 3 days at 3 bars of hydrogen pressure. During this time 3×300 mg palladium on charcoal (20%) were added to the reaction. Then the catalyst was suction filtered and the filtrate was combined with 100 mL ethereal 2N HCl solution and concentrated by rotary evaporation. The product was dried in vacuo in the desiccator on phosphorus pentoxide.

Yield: 20.9 g (quant.)

ESI-MS: m/z=100 (M+H)+

$R_f$ 0.34 (silica gel, DCM/MeOH/NH$_4$OH=8/2/0.2)

Intermediate 36

2,3-dihydro-1H-pyrrolo[3,2-c]pyridine

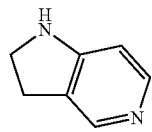

1.50 g (12.7 mmol) 5-azaindole and 0.75 g Raney nickel in 70 mL ethanol were hydrogenated in a hydrogen atmosphere at 3 bar hydrogen pressure for 3 days at 70° C. Then the catalyst was suction filtered and the solution was evaporated down i. vac. The residue was purified through a silica gel column. The product fractions were combined and evaporated down using the rotary evaporator.

Yield: 620 mg (41% of theoretical)

ESI-MS: m/z=121 (M+H)+

$R_f$ 0.12 (silica gel, DCM/MeOH/NH$_4$OH=80/20/2)

Intermediate 37

(6-chloropyrimidin-4-O-indol-1-yl-methanone

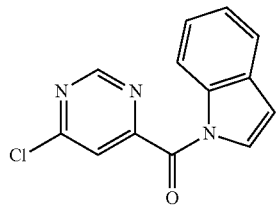 [SMILES: O=C(c1cc(Cl)ncn1)n1ccc2ccccc21]

Under a nitrogen atmosphere 120 mg (3.00 mmol) sodium hydride (60% in mineral oil) were added batchwise to 350 mg (2.96 mmol) indole in 15 mL THF and stirred for 30 min at RT. 500 mg (2.83 mmol) 6-chloropyrimidine-4-carboxylic acid chloride was added batchwise and then the reaction mixture was stirred for 2 h at RT. Then 50 mL EtOAc were added and the mixture was washed with 50 mL saturated sodium hydrogen carbonate solution (1×), 30 mL water and with 50 mL 1 M hydrochloric acid. The organic phase was dried on magnesium sulphate, filtered and then evaporated down i. vac. The residue was purified on silica gel. The product fractions were combined and evaporated down i. vac.

Yield: 200 mg (28% of theoretical)

MS: m/z=257/259 (M)+

$R_f$: 0.80 (silica gel, PE/EtOAc=7/3)

Intermediate 38

(6-chloropyrimidin-4-yl)-(3-methylindol-1-yl)-methanone

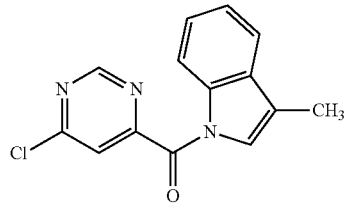 [SMILES: Cc1cn(C(=O)c2cc(Cl)ncn2)c2ccccc12]

Under a nitrogen atmosphere 120 mg (3.00 mmol) sodium hydride (60% in mineral oil) were added batchwise to 380 mg (2.90 mmol) 3-methylindole in 15 mL THF and the mixture was stirred for 30 min at RT. 500 mg (2.83 mmol) 6-chloropyrimidine-4-carboxylic acid chloride were added batchwise and then the reaction mixture was stirred for 2 h at RT. Then 50 mL EtOAc were added and the mixture was washed with 50 mL saturated sodium hydrogen carbonate solution (1×), 30 mL water and with 50 mL 1 M hydrochloric acid. The organic phase was dried on sodium sulphate, filtered and then evaporated down i. vac. The product was used in the next step without further purification.

Yield: 300 mg (39% of theoretical)

Intermediate 39

(6-chloropyrimidin-4-yl)-(5-fluoroindol-1-yl)-methanone

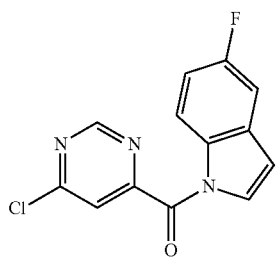 [SMILES: O=C(c1cc(Cl)ncn1)n1ccc2cc(F)ccc21]

Under a nitrogen atmosphere 120 mg (3.00 mmol) sodium hydride (60% in mineral oil) were added batchwise to 400 mg (2.90 mmol) 5-fluoroindole in 15 mL THF and the mixture was stirred for 30 min at RT. 500 mg (2.83 mmol) 6-chloropyrimidine-4-carboxylic acid chloride were added batchwise and then the reaction mixture was stirred for 2 h at RT. Then 50 mL EtOAc were added and the mixture was washed with 50 mL saturated sodium hydrogen carbonate solution (1×), 30 mL water and with 50 mL 1 M hydrochloric acid. The organic phase was dried on magnesium sulphate, filtered and then evaporated down i. vac. The residue was combined with a little EtOAc, the product precipitated was suction filtered and the filtrate was purified on silica gel. The product fractions were combined and evaporated down i. vac.

Yield: 70 mg (9% of theoretical)

$R_f$: 0.39 (silica gel, PE/EtOAc=4/1)

Intermediate 40

6-chloro-pyrimidine-4-carboxylic acid-benzyl-(2,2,2-trifluorethyl)-amide

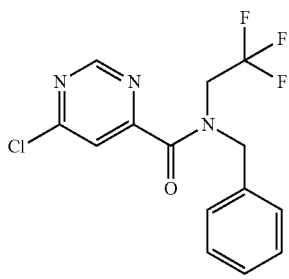 [SMILES: O=C(c1cc(Cl)ncn1)N(Cc1ccccc1)CC(F)(F)F]

Step 1: benzyl-(2,2,2-trifluorethyl)-amine

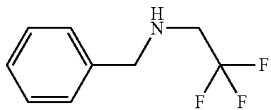

2.17 g (9.4 mmol) 2,2,2-trifluoroethyltrifluoromethanesulphonate were added to 2.00 g (18.7 mmol) benzylamine in 50 mL xylene and the reaction mixture was refluxed overnight. After cooling the reaction mixture was suction filtered, washed with DIPE and the filtrate was evaporated down using the rotary evaporator. The residue was purified by flash chromatography. The product fractions were combined and evaporated down using the rotary evaporator.

Yield: 2.30 g (65% of theory)
ESI-MS: m/z=190.0 (M+H)$^+$

Step 2: 6-chloropyrimidine-4-carboxylic acid-benzyl-(2,2,2-trifluoro-ethyl)-amide

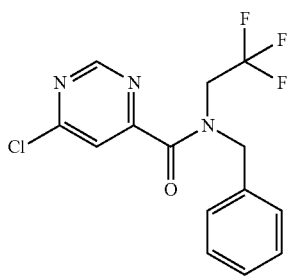 [SMILES: O=C(c1cc(Cl)ncn1)N(Cc1ccccc1)CC(F)(F)F]

1.04 g (5.50 mmol) benzyl-(2,2,2-trifluorethyl)-amine and 5.50 mL (5.50 mmol) of a 1M sodium hydroxide solution were added dropwise while cooling with a bath of ice/ethanol to 1.00 g (5.65 mmol) 6-chloropyrimidine-4-carboxylic acid chloride in 20 mL dichloromethane. The mixture was first stirred for 2 h while being cooled and then for a further 1 h at RT. 50 mL of a saturated sodium hydrogen carbonate solution were added and the mixture was stirred for 10 min. The organic phase was separated off, washed with water (1×30 mL) and 1M hydrochloric acid (1×50 mL), dried on sodium sulphate, filtered and evaporated down i. vac. The product was reacted further without any further purification.

Yield: 1.20 g (64% of theory)
ESI-MS: m/z=330/332 (M+H)$^+$
R$_t$ (HPLC-MS): 1.56 min (method C)

Intermediate 41

1-{1-[6-(4-nitro-2,3-dihydroindole-1-carbonyl)-pyrimidin-4-yl]-piperidin-4-yl}-1,3-dihydro-imidazo[4,5-b]pyridin-2-one

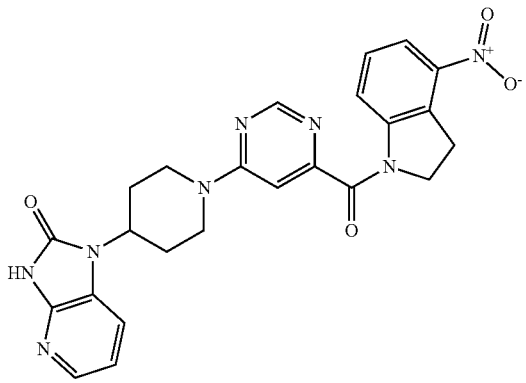 [SMILES: O=C(c1cc(N2CCC(n3c(=O)[nH]c4ncccc43)CC2)ncn1)N1CCc2c1cccc2[N+](=O)[O-]]

150 mg (0.470 mmol) TBTU were added to 150 mg (0.44 mmol) 6-[4-(2-oxo-2,3-dihydro-imidazo[4,5-b]pyridin-1-yl)-piperidin-1-yl]-pyrimidine-4-carboxylic acid, 75 mg (0.46 mmol) 4-nitro-2,3-dihydro-1H-indole, 100 μL (0.712 mmol) triethylamine in 1.5 mL DMF and the mixture was stirred overnight at RT. The reaction mixture was poured onto 30 mL water. The aqueous phase was extracted with DCM (3×20 mL). The combined organic phases were dried on magnesium sulphate, filtered and evaporated down i. vac. The residue was dissolved in 3 mL DMF, filtered through a syringe filter and purified by preparative HPLC. The product fractions were combined and lyophilised.

Yield: 30 mg (14% of theoretical)
ESI-MS: m/z=487 (M+H)$^+$
R$_f$: 0.54 (silica gel, eluant A)

Intermediate 42

1-{1-[6-(5-nitro-2,3-dihydro-indole-1-carbonyl)-pyrimidin-4-yl]-piperidin-4-yl}-1,3-dihydro-imidazo[4,5-b]pyridin-2-one

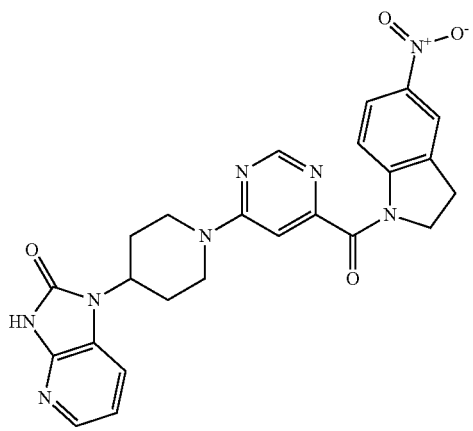 [SMILES: O=C(c1cc(N2CCC(n3c(=O)[nH]c4ncccc43)CC2)ncn1)N1CCc2cc([N+](=O)[O-])ccc21]

150 mg (0.47 mmol) TBTU were added to 150 mg (0.44 mmol) 6-[4-(2-oxo-2,3-dihydro-imidazo[4,5-b]pyridin-1-yl)-piperidin-1-yl]-pyrimidine-4-carboxylic acid, 75 mg (0.46 mmol) 5-nitro-2,3-dihydro-1H-indole, 100 μL and (0.712 mmol) triethylamine in 1.5 mL DMF and the mixture was stirred overnight at RT. The reaction mixture was poured onto 30 mL water. The precipitated product was suction filtered and dried at 50° C. in the CAD.

Yield: 130 mg (61% of theoretical)
ESI-MS: m/z=487 (M+H)$^+$
R$_f$: 0.61 (silica gel, eluant A)

Intermediate 43

3-{1-[6-(3-bromo-7,8-dihydro-5H-1,6-naphthyridin-6-carbonyl)-pyrimidin-4-yl]-piperidin-4-yl}-7-methoxy-1,3,4,5-tetrahydro-1,3-benzodiazepin-2-one

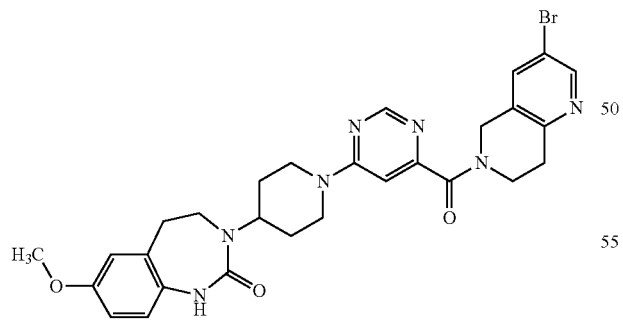

90 mg (0.24 mmol) TBTU were added to 80 mg (0.20 mmol) 6-[4-(7-methoxy-2-oxo-1,2,4,5-tetrahydro-1,3-benzodiazepin-3-yl)-piperidin-1-yl]-pyrimidine-4-carboxylic acid, 70 mg (0.28 mmol) 3-bromo-5,6,7,8-tetrahydro-1,6-naphthyridine-hydrochloride and 120 μL (0.86 mmol) triethylamine in 0.9 mL DMF and the mixture was stirred overnight at RT. The reaction mixture was combined with 1 mL methanol, 1 mL saturated sodium hydrogen carbonate solution and 8 mL ice water. The precipitate was suction filtered, washed with water and diethyl ether and dried.

Yield: 94 mg (75% of th.)
ESI-MS: m/z=592/594 (M+H)$^+$
R$_t$ (HPLC-MS): 3.06 min (method E)

Intermediate 44

3-ethyl-2,3-dihydro-1H-indole

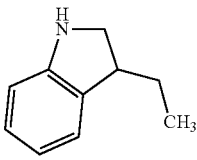

Step 1: 3-ethylidene-1,3-dihydro-indol-2-one

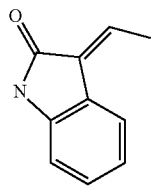

0.85 mL (15 mmol) acetaldehyde were added dropwise to 2.0 g (15 mmol) indolin-2-one and 0.20 mL piperidine in 20 mL methanol. The reaction mixture was refluxed for 3 h and then evaporated down. The residue was triturated in diisopropylether and suction filtered.

Yield: 2.2 g (92% of theory)
ESI-MS: m/z=158 (M–H)$^-$
R$_t$ (HPLC): 1.19 min (method C)

Step 2: 3-ethyl-2,3-dihydro-1H-indole

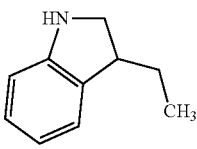

Under a nitrogen atmosphere 41 mL (41 mmol) of a 1M borane in THF solution was added dropwise to 2.2 g (14 mmol) 3-ethylidene-1,3-dihydro-indol-2-one in 50 mL THF. The reaction mixture was refluxed for 3 h and then at 0° C. mixed with 10 mL methanol followed by 15 mL semi-concentrated hydrochloric acid solution. The reaction mixture was refluxed for 3 h with stirring, cooled and washed twice with ethyl acetate. The aqueous phase was made alkaline with aqueous 4M sodium hydroxide solution and extracted three times with ethyl acetate. The organic phases were combined, dried on sodium sulphate and evaporated down.

Yield: 1.7 g (84% of theory)
ESI-MS: m/z=148 (M+H)$^+$
R$_t$(HPLC): 2.21 min (method E)

Intermediate 45

3-cyclopropylmethyl-2,3-dihydro-1H-indole

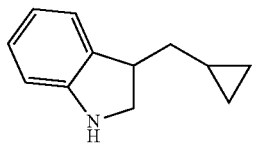 [SMILES: c1ccc2c(c1)NCC2CC1CC1]

Step 1
3-cyclopropylmethylene-1,3-dihydro-indol-2-one

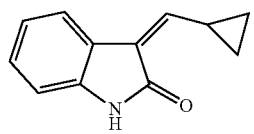 [SMILES: O=C1Nc2ccccc2/C1=C/C1CC1]

2.0 g (15 mmol) 1,3-dihydro-indol-2-one and 0.20 mL piperidine were placed in 20 mL methanol. 1.1 mL (15 mmol) cyclopropanecarboxaldehyde were added dropwise, the reaction mixture was refluxed for 3 h and then concentrated to dryness by rotary evaporation. The residue was triturated with diisopropylether and the solid remaining was suction filtered and dried.

Yield: 2.7 g (97% of theory)
ESI-MS: m/z=186 (M+H)$^+$
$R_t$ (HPLC-MS): 1.27 min (method C)

Step 2 3-cyclopropylmethyl-2,3-dihydro-1H-indole

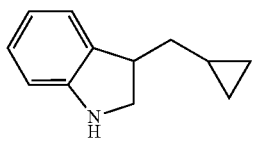 [SMILES: c1ccc2c(c1)NCC2CC1CC1]

1.0 g (5.4 mmol) 3-cyclopropylmethylene-1,3-dihydro-indol-2-one were placed in 50 mL THF. 12 mL (12 mmol) 1M borane in THF was slowly added dropwise. The reaction mixture was refluxed for 3 h. After cooling to RT 10 mL methanol and 15 mL semi-concentrated aqueous hydrochloric acid solution were successively added dropwise and then the mixture was refluxed for 3 h. After cooling to RT it was extracted with EtOAc. The aqueous phase was made alkaline with aqueous 4M sodium hydroxide solution and extracted once again with EtOAc. The organic phase was dried, filtered and evaporated down.

Yield: 0.23 g (25% of theory)
ESI-MS: m/z=174 (M+H)$^+$ $R_t$ (HPLC-MS): 1.01 min (method C)

Intermediate 46

7,7-dimethyl-4,5,6,7-tetrahydro-thieno[3,4-c]pyridine

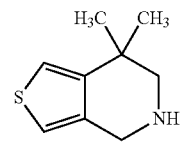

Step 1 methylene-(2-methyl-2-thiophene-3-yl-propyl)-amine

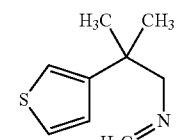

5.75 g (37.0 mmol) 2-methyl-2-thiophene-3-yl-propylamine and 3.61 mL (44.4 mmol) formaldehyde were stirred overnight at RT together with 2.0 g molecular sieve (4 Å powder). The reaction mixture was filtered and the filtrate was concentrated to dryness by rotary evaporation.

Yield: 6.00 g (97% of theory)
ESI-MS: m/z=168 (M+H)$^+$

Step 2 7,7-dimethyl-4,5,6,7-tetrahydro-thieno[3,4-c]pyridine

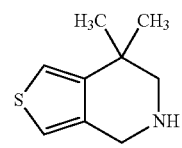

6.00 g (35.9 mmol) methylene-(2-methyl-2-thiophene-3-yl-propyl)-amine, 11.3 mL (45.3 mmol) 4M HCl and 11.8 mL (142 mmol) conc. HCl were stirred at RT over the weekend. The reaction mixture was made alkaline with 4M NaOH solution. The precipitate formed was suction filtered, washed with water and dried. The substance was purified through Alox. The product-containing fractions were combined and concentrated to dryness by rotary evaporation.

Yield: 740 mg (12% of theory)
$R_t$ (HPLC-MS): 1.24 min (method K)

Intermediate 47

1,7,7-trimethyl-4,5,6,7-tetrahydro-1H-pyrazolo[4,3-c]pyridinium trifluoroacetate

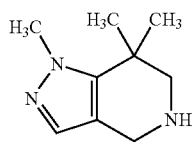 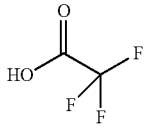

Step 1 tert. butyl 1,7,7-trimethyl-1,4,6,7-tetrahydro-pyrazolo[4,3-c]pyridine-5-carboxylate

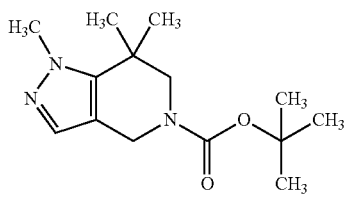 [SMILES: Cn1ncc2c1C(C)(C)CN(C(=O)OC(C)(C)C)C2]

2.10 g (8.36 mmol) tert. butyl 7,7-dimethyl-1,4,6,7-tetrahydro-pyrazolo[4,3-c]pyridine-5-carboxylate were placed in 25 mL DMF. While cooling with ice, 350 mg (8.75 mmol) sodium hydride (55%) were added. The reaction mixture was stirred for 30 min, then 0.540 mL (8.67 mmol) iodomethane were added and the mixture was stirred for 1 h at 0° C. The reaction mixture was concentrated to dryness by rotary evaporation and the residue was mixed with water and extracted with EtOAc. The organic phase was dried, filtered and concentrated to dryness by rotary evaporation. The residue was purified by HPLC. The product-containing fractions were combined and organic solvent was eliminated by rotary evaporation. The aqueous residue was extracted with DCM. The organic phase was dried, filtered and concentrated to dryness by rotary evaporation.

Yield: 100 mg (4% of theory)

$R_t$ (HPLC-MS): 3.64 min (method E)

Step 2 1,7,7-trimethyl-4,5,6,7-tetrahydro-1H-pyrazolo[4,3-c]pyridinium-trifluoro-acetate

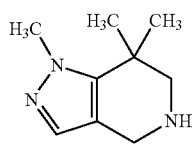 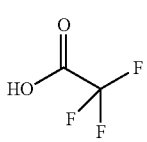

0.10 g (0.34 mmol) tert. butyl 1,7,7-trimethyl-1,4,6,7-tetrahydro-pyrazolo[4,3-c]pyridine-5-5-carboxylate and 1.0 mL TFA were stirred in 2.0 mL DCM for 2 h at RT. The reaction mixture was concentrated to dryness by rotary evaporation.

Yield: 125 mg (99% of theory)

ESI-MS: m/z=166 (M+H)$^+$

Intermediate 48

(1,2,3,4-tetrahydro-isoquinolin-4-yl)-methanol

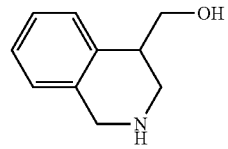 [SMILES: OCC1CNCc2ccccc21]

0.50 mg (3.1 mmol) isoquinolin-4-yl-methanol, 75 mg platinum dioxide and 3.2 mL 1N hydrochloric acid solution were hydrogenated in 50 mL methanol for 4 h at RT under a hydrogen atmosphere at 50 psi. The reaction mixture was filtered and the filtrate was concentrated to dryness by rotary evaporation.

Yield: 0.51 g (quantitative)

$R_t$ (HPLC-MS): 1.12 min (method O)

Intermediate 49

4,5-difluoro-3,3-dimethyl-2,3-dihydro-1H-indole

Step 1 1-acetyl-4,5-difluoro-1,3-dihydro-indol-2-one

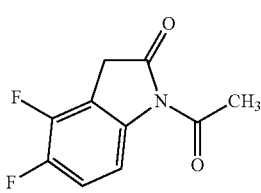

2.00 g (11.8 mmol) 4,5-difluoro-1,3-dihydro-indol-2-one I were stirred in 6.62 mL (55.0 mmol) acetic anhydride for 2 h at 150° C. The reaction mixture was added to ice water, the precipitated solid was suction filtered and washed with water. The product was recrystallised from a mixture of water and ethanol, suction filtered and dried.

Yield: 1.00 g (40% of theory)

ESI-MS: m/z=210 (M−H)$^-$ $R_t$ (HPLC-MS): 1.40 min (method C)

181

Step 2 4,5-difluoro-3,3-dimethyl-
1,3-dihydro-indol-2-one

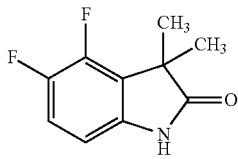

0.50 g (2.4 mmol) 1-acetyl-4,5-difluoro-1,3-dihydro-indol-2-one were placed in 10 mL DMF under argon. 0.22 g (5.1 mmol) sodium hydride (55%) were added at 0° C. and the reaction mixture was stirred for 1 h. Then 0.32 mL (5.1 mmol) iodomethane were added dropwise. The reaction mixture was stirred overnight at RT, poured onto water and extracted with EtOAc. The organic phase was dried, filtered and concentrated to dryness by rotary evaporation. The residue was purified by HPLC. The product-containing fractions were combined and concentrated to dryness by rotary evaporation.

Yield: 0.15 g (32% of theory)
ESI-MS: m/z=198 (M+H)$^+$
R$_t$ (HPLC-MS): 1.26 min (method C)

Step 3 4,5-difluoro-3,3-dimethyl-
2,3-dihydro-1H-indole

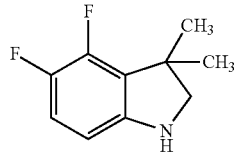

0.15 mg (0.76 mmol) 4,5-difluoro-3,3-dimethyl-1,3-dihydro-indol-2-one were placed in 20 mL THF under argon. 0.91 mL (0.91 mmol) of a 1M lithium aluminium hydride solution in 10 mL THF were added dropwise. The reaction mixture was stirred for 1 h at 70° C., cooled and mixed with water. The reaction mixture was dried, filtered and concentrated to dryness by rotary evaporation.

Yield: 160 mg (quantitative)
R$_t$ (HPLC-MS): 1.24 min (method C)

Intermediate 50

5,6-difluoro-3-methyl-2,3-dihydro-1H-indole

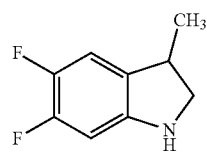

182

Step 1 5,6-difluoro-3-methyl-
1,3-dihydro-indol-2-one

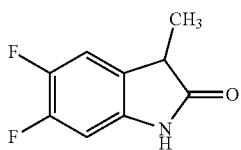

1.5 g (9.0 mmol) 5,6-difluoro-1,3-dihydro-indol-2-one were stirred with 1.0 g Raney nickel in 50 mL methanol 3 h at 200° C. in an autoclave. The catalyst was filtered off and the filtrate was concentrated to dryness by rotary evaporation.

Yield: 1.6 g (99% of theory)
ESI-MS: m/z=184 (M+H)$^+$
R$_t$ (HPLC-MS): 3.2 min (method E)

Step 2 5,6-difluoro-3-methyl-2,3-dihydro-1H-indole

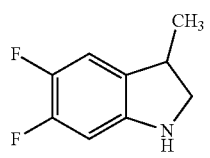

Under an argon atmosphere 1.6 g (8.7 mmol) 5,6-difluoro-3-methyl-1,3-dihydro-indol-2-one were placed in 50 mL THF. 18 mL (18 mmol) 1 M borane in THF were slowly added dropwise. The reaction mixture was stirred for 2 h at 70° C. After cooling to RT 10 mL methanol and 30 mL semiconc. HCl were successively added dropwise and then the mixture was refluxed for 1 h. After cooling to RT it was extracted with EtOAc. The aqueous phase was made alkaline with 4M NaOH solution and extracted with DCM. The organic phase was dried, filtered and evaporated down.

Yield: 0.7 mg (47% of theory)
ESI-MS: m/z=170 (M+H)$^+$
R$_t$ (HPLC-MS): 2.7 min (method E)

Intermediate 51

4,5-difluoro-3-methyl-2,3-dihydro-1H-indole

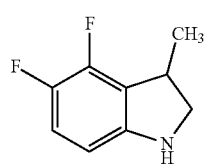

Prepared analogously to 5,6-difluoro-3-methyl-2,3-dihydro-1H-indol was 4,5-difluoro-3-methyl-2,3-dihydro-1H-indole from 1.50 g (8.87 mmol) 4,5-difluoro-1,3-dihydro-indol-2-one.

Yield: 320 mg (41% of theory)
ESI-MS: m/z=170 (M+H)$^+$
R$_t$ (HPLC-MS): 2.97 min (method E)

Intermediate 52

5-fluoro-3-(2-methoxy-ethyl)-3-methyl-2,3-dihydro-1H-indole

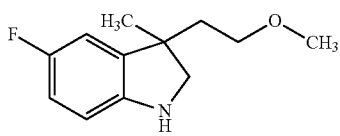

Step 1 5-fluoro-3-methyl-1,3-dihydro-indol-2-one

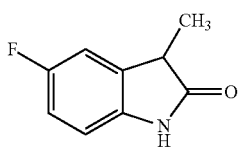

3.0 g (20 mmol) 5-fluoro-1,3-dihydro-indol-2-one were stirred with 2.0 g Raney nickel in 50 mL methanol for 1.5 h at 200° C. in an autoclave. The catalyst was filtered off and the filtrate was concentrated to dryness by rotary evaporation. The residue was recrystallised from methanol, suction filtered and dried.

Yield: 2.8 g (85% of theory)

ESI-MS: m/z=166 (M+H)$^+$ $R_t$ (HPLC-MS): 1.1 min (method C)

Step 2 5-fluoro-3-(2-methoxy-ethyl)-3-methyl-1,3-dihydro-indol-2-one

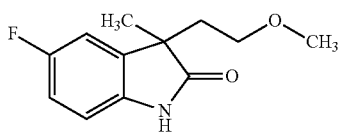 [SMILES: COCCC1(C)C(=O)Nc2ccc(F)cc21]

0.50 mg (3.0 mmol) 5-fluoro-3-methyl-1,3-dihydro-indol-2-one were placed in 10 mL DMF under a nitrogen atmosphere. 0.13 g (3.0 mmol) sodium hydride (55%) were added at 0° C. and the reaction mixture was stirred for 30 min. Then 0.28 mL (3 mmol) 2-(bromomethyl)-methylether in 1.0 mL DMF were added dropwise. The reaction mixture was stirred overnight at RT. The substance was purified by HPLC and the product-containing fractions were combined and concentrated to dryness by rotary evaporation.

Yield: 130 mg (19% of theory)

ESI-MS: m/z=224 (M+H)$^+$ $R_t$ (HPLC-MS): 1.24 min (method C)

Step 3 5-fluoro-3-(2-methoxy-ethyl)-3-methyl-2,3-dihydro-1H-indole

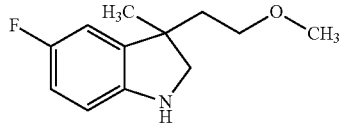

Under an argon atmosphere 0.12 g (0.54 mmol) 5-fluoro-3-(2-methoxy-ethyl)-3-methyl-1,3-dihydro-indol-2-one were placed in 20 mL THF. 0.56 mL (0.56 mmol) of a 1M lithium aluminium hydride solution in 10 mL THF were added dropwise. The reaction mixture was stirred for 1 h at 70° C., then mixed with water and dried, filtered and concentrated to dryness by rotary evaporation.

Yield: 160 mg (quantitative)

ESI-MS: m/z=210 (M+H)$^+$ $R_t$ (HPLC-MS): 0.94 min (method C)

Intermediate 53

5'-cyano-4-(7-methoxy-2-oxo-1,2,4,5-tetrahydro-benzo[d][1,3]diazepin-3-yl)-3,4,5,6-tetra-hydro-2H-[1,2']-bipyridinyl-4'-carboxylic acid

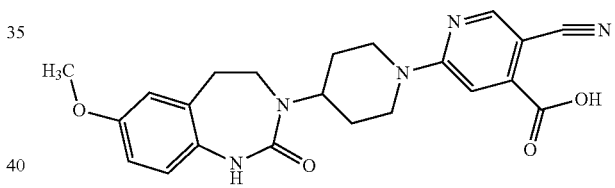

Step 1 4'-chloro-4-(7-methoxy-2-oxo-1,2,4,5-tetrahydro-benzo[d][1,3]diazepin-3-yl)-3,4,5,6-tetrahydro-2H-[1,2']bipyridinyl-5'-carbonitrile

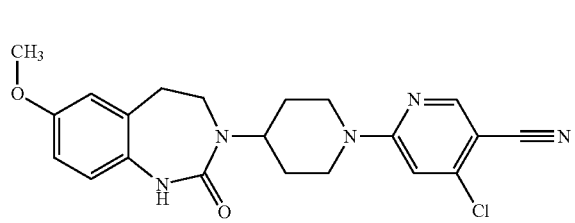 [SMILES: COc1ccc2c(c1)CCN(C1CCN(c3cc(Cl)c(C#N)cn3)CC1)C(=O)N2]

3.00 g (10.9 mmol) 7-methoxy-3-piperidin-4-yl-1,3,4,5-tetrahydro-1,3-benzodiazepin-2-one and 7.59 mL (43.6 mmol) DIPEA were placed in 90 mL ethanol. 1.89 g (10.9 mmol) 4,6-dichloro-nicotinonitrile and 3 spatula tips of DMAP were added and the reaction mixture was stirred for 4 h at RT. The precipitated solid was suction filtered and dried.

Yield: 3.70 g (82% of theory)

$R_t$ (HPLC-MS): 1.44 min (method C)

Step 2 methyl 5'-cyano-4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylate

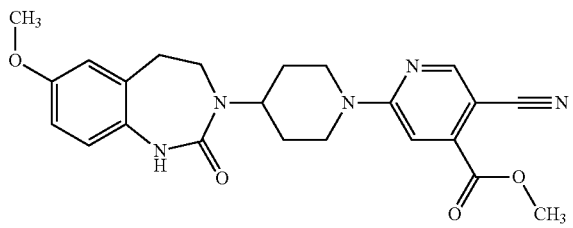 [SMILES: COC(=O)c1cc(N2CCC(N3CCc4cc(OC)ccc4NC3=O)CC2)ncc1C#N]

3.70 g (8.98 mmol) 6'-chloro-4-(7-methoxy-2-oxo-1,2,4,5-tetrahydro-1,3-benzodiazepin-3-yl)-3,4,5,6-tetrahydro-2H-[1,4']bipyridinyl-3'-carbonitrile, 345 mg (0.900 mmol) PdCl$_2$(PhCN)$_2$, 498 mg (0.900 mmol) dppf and 1.52 mL (10.8 mmol) TEA were stirred in 100 mL methanol under a carbon monoxide atmosphere for 4 h at 130° C. and 25 bar. The catalyst was removed by suction filtering and the filtrate was concentrated to dryness by rotary evaporation.
Yield: 3.4 g (87% of theory)
R$_t$ (HPLC-MS): 1.28 min (method C)

Step 3 5'-cyano-4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid

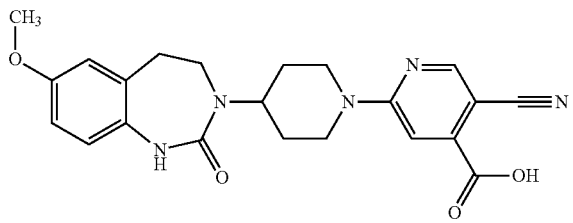 [SMILES: COc1ccc2c(c1)CCN(C1CCN(c3cc(C(=O)O)c(C#N)cn3)CC1)C(=O)N2]

3.40 g (7.81 mmol) methyl 5'-cyano-4-(7-methoxy-2-oxo-1,2,4,5-tetrahydro-1,3-benzodiazepin-3-yl)-3,4,5,6-tetrahydro-2H-[1,4']bipyridinyl-2'-carboxylate and 6 mL of a 4M NaOH solution were stirred overnight at RT in 50 mL THF and 6 mL water. The organic solvent was eliminated by rotary evaporation and the precipitated solid was suction filtered. The filtrate was acidified with a 4M HCl solution and the precipitated solid was suction filtered and dried.
Yield: 560 mg (17% of theory)
R$_t$ (HPLC-MS): 1.27 min (method C)

Intermediate 54

(4-chloro-pyridin-2-yl)-(4,5-difluoro-2,3-dihydro-indol-1-yl)-methanone

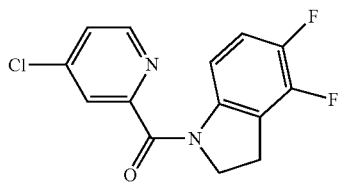 [SMILES: O=C(c1cc(Cl)ccn1)N1CCc2c1ccc(F)c2F]

0.50 g (3.2 mmol) 4-chloropicolinic acid, 1.1 g (3.4 mmol) TBTU and 0.91 mL (6.5 mmol) TEA were placed in 10 mL DMF. 0.63 g (3.3 mmol) 4,5-difluoroindoline hydrochloride were added. The reaction mixture was stirred overnight at RT and then extracted successively with a 15% potassium carbonate solution, water, a 1M HCl solution and EtOAc. The organic phase was dried, filtered and concentrated to dryness by rotary evaporation. The residue was stirred with diisopropylether and the undissolved solid was suction filtered and dried.
Yield: 850 mg (91% of theory)
ESI-MS: m/z=295/297 (Cl) (M+H)$^+$
R$_t$ (HPLC-MS): 1.56 min (method C)

Intermediate 55

(2-chloro-pyridin-4-yl)-(4,5-difluoro-2,3-dihydro-indol-1-yl)-methanone

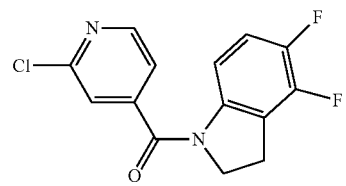 [SMILES: O=C(c1ccnc(Cl)c1)N1CCc2c1ccc(F)c2F]

Analogously to (4-chloro-pyridin-2-yl)-(4,5-difluoro-2,3-dihydro-indol-1-yl)-methanone this compound was prepared from 500 mg (3.17 mmol) 2-chloroisonicotinic acid and 1.0 eq 4,5-difluoroindoline hydrochloride.
Yield: 900 mg (96% of theory)
ESI-MS: m/z=295/297 (Cl) (M+H)$^+$
R$_t$ (HPLC-MS): 1.44 min (method C)

Intermediate 56

(2-chloro-6-methoxy-pyridin-4-yl)-(5-fluoro-2,3-dihydro-indol-1-yl)-methanone

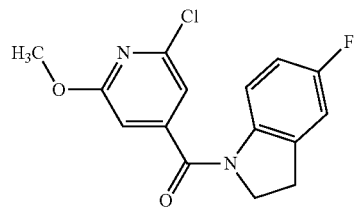 [SMILES: COc1cc(C(=O)N2CCc3cc(F)ccc32)cc(Cl)n1]

0.50 g (2.7 mmol) 2-chloro-6-methoxyisonicotinic acid, 0.37 g (2.7 mmol) 5-fluoroindoline and 0.42 mL (3 mmol) TEA were in 10 mL DMF placed. 0.97 g (3.0 mmol) TBTU were added and the reaction mixture was 2 h stirred at RT. The substance was purified by HPLC. The product-containing fractions were combined and freeze-dried.
Yield: 700 mg (86% of theory)
ESI-MS: m/z=307/309 (Cl) (M+H)$^+$
R$_t$ (HPLC-MS): 1.6 min (method C)

Intermediate 57

(2-chloro-6-methoxy-pyridin-4-yl)-(4,5-difluoro-2,3-dihydro-indol-1-yl)-methanone

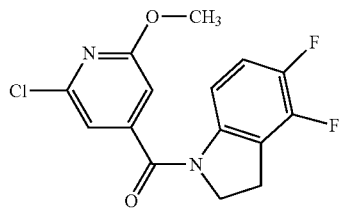 [SMILES: COc1cc(C(=O)N2CCc3c2ccc(F)c3F)cc(Cl)n1]

1.2 g (3.8 mmol) TBTU were added at RT to 0.69 g (3.7 mmol) 2-chloro-6-methoxyisonicotinic acid, 0.70 g (3.7 mmol) 4,5-fluoroindoline-dihydrochloride and 1.1 mL (8.0 mmol) triethylamine in 10 mL DMF. The mixture was stirred for 2 h at RT and then poured onto 200 mL of a 15% aqueous potassium carbonate solution. The precipitate formed was suction filtered, washed with water and dried.

Yield: 1.05 g (89% of theory)
ESI-MS: m/z=325/327 (M+H)$^+$ (Cl)
R$_t$(HPLC): 1.66 min (method C)

Intermediate 58

4-[4-(7-methoxy-2-oxo-1,2,4,5-tetrahydro-1,3-benzodiazepin-3-yl)-piperidin-1-yl]-[1,3,5]triazine-2-carboxylic acid

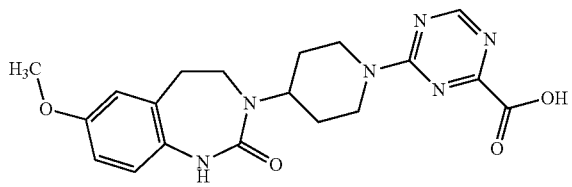 [SMILES: COc1ccc2c(c1)CCN(C1CCN(c3ncnc(C(=O)O)n3)CC1)C(=O)N2]

Step 1 3-[1-(4-chloro-[1,3,5]triazin-2-yl)-piperidin-4-yl]-7-methoxy-1,3,4,5-tetrahydro-1,3-benzodiazepin-2-one

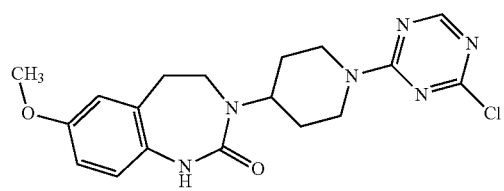 [SMILES: COc1ccc2c(c1)CCN(C1CCN(c3ncnc(Cl)n3)CC1)C(=O)N2]

1.84 g (6.67 mmol) 7-methoxy-3-piperidin-4-yl-1,3,4,5-tetrahydro-1,3-benzodiazepin-2-one and 4.54 mL (26.7 mmol) DIPEA were placed in 50 mL ethanol. 1.00 g (6.67 mmol) 2,4-dichloro-[1,3,5]triazine were added and the reaction mixture was stirred overnight at RT. The precipitated solid was suction filtered and dried, Yield: 1.76 g (68% of theory)
ESI-MS: m/z=389 (M+H)$^+$
R$_t$ (HPLC-MS): 1.35 min (method C)

Step 2 methyl 4-[4-(7-methoxy-2-oxo-1,2,4,5-tetrahydro-1,3-benzodiazepin-3-yl)-piperidin-1-yl]-[1,3,5]triazine-2-carboxylate

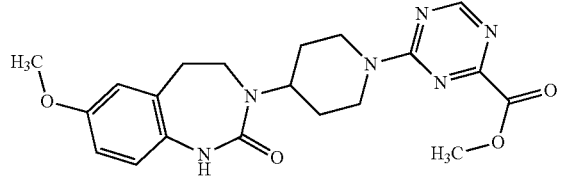 [SMILES: COC(=O)c1ncnc(N2CCC(N3CCc4cc(OC)ccc4NC3=O)CC2)n1]

In a CO atmosphere 400 mg (1.03 mmol) 3-[1-(4-chloro-[1,3,5]triazin-2-yl)-piperidin-4-yl]-7-methoxy-1,3,4,5-tetrahydro-1,3-benzodiazepin-2-one, 39.5 mg (0.1 mmol) PdCl$_2$(PhCN)$_2$, 57.0 mg (0.1 mmol) dppf and 0.173 mL (1.23 mmol) TEA in 30 mL methanol were carbonylated for 16 h at 130° C. The catalyst was suction filtered and the filtrate was concentrated to dryness by rotary evaporation. The residue was mixed with isopropanol and the precipitated solid was suction filtered and dried.

Yield: 265 mg (63% of theory)
ESI-MS: m/z=413 (M+H)$^+$
R$_t$ (HPLC-MS): 1.22 min (method C)

Step 3 4-[4-(7-methoxy-2-oxo-1,2,4,5-tetrahydro-1,3-benzodiazepin-3-yl)-piperidin-1-yl]-[1,3,5]triazine-2-carboxylic acid

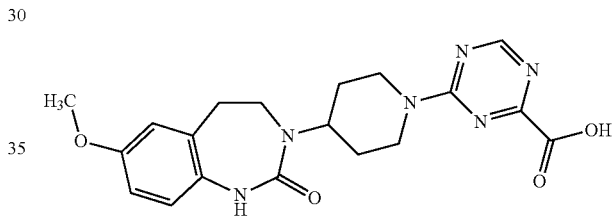

0.27 g (0.64 mmol) methyl 4-[4-(7-methoxy-2-oxo-1,2,4,5-tetrahydro-1,3-benzodiazepin-3-yl)-piperidin-1-yl]-[1,3,5]triazine-2-carboxylate and 0.5 mL (2 mmol) of a 4M NaOH solution were stirred in 0.5 mL water and 4.0 mL THF for 3 days at RT. The organic solvent was eliminated by rotary evaporation and the reaction mixture was combined with 0.5 mL of a 4M HCl solution. The precipitated solid was suction filtered and dried.

Yield: 210 mg (82% of theory)
R$_t$ (HPLC-MS): 0.94 min (method C)

Intermediate 59

6-[4-(7-methoxy-2-oxo-1,2,4,5-tetrahydro-1,3-benzodiazepin-3-yl)-piperidin-1-yl]-5-methyl-pyrimidine-4-carboxylic acid

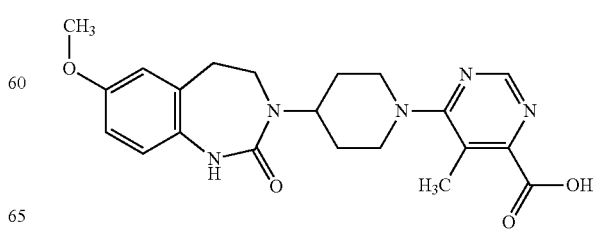

Step 1 tert. butyl 6-[4-(7-methoxy-2-oxo-1,2,4,5-tetrahydro-1,3-benzodiazepin-3-yl)-piperidin-1-yl]-5-methyl-pyrimidine-4-carboxylate

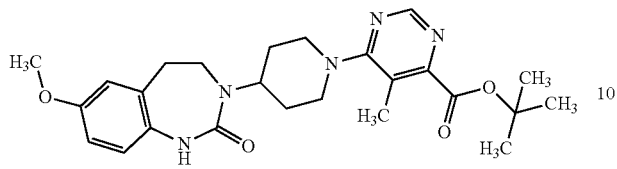

0.20 g (0.73 mmol) 7-methoxy-3-piperidin-4-yl-1,3,4,5-tetrahydro-1,3-benzodiazepin-2-one and 0.14 mL (0.80 mmol) DIPEA were placed in 3.0 mL DMF. 0.17 g (0.74 mmol) tert. butyl 6-chloro-5-methyl-pyrimidine-4-carboxylate were added and the reaction mixture was stirred for 3 h at RT. The reaction mixture was mixed with water and extracted with DCM. The organic phase was dried, filtered and concentrated to dryness by rotary evaporation. The residue was combined with diisopropylether and the precipitated solid was suction filtered and dried.

Yield: 140 mg (41% of theory)
ESI-MS: m/z=468 (M+H)+
R$_t$ (HPLC-MS): 1.95 min (method C)

Step 2 6-[4-(7-methoxy-2-oxo-1,2,4,5-tetrahydro-1,3-benzodiazepin-3-yl)-piperidin-1-yl]-5-methyl-pyrimidine-4-carboxylic acid

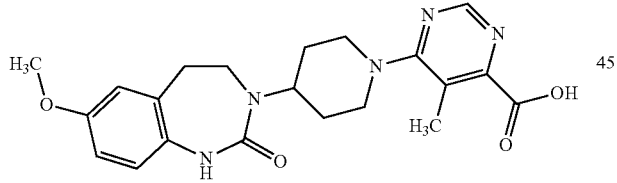

70 mg (0.17 mmol) tert. butyl 6-[4-(7-methoxy-2-oxo-1,2,4,5-tetrahydro-1,3-benzodiazepin-3-yl)-piperidin-1-yl]-5-methyl-pyrimidin-4-carboxylate, 26 mg (0.19 mmol) 5-fluoroindoline, 61 mg (0.19 mmol) TBTU and 27 μL (0.19 mmol) TEA were stirred in 1.0 mL DMF for 3 h at RT. The reaction mixture was purified by HPLC. The product-containing fractions were combined and freeze-dried.

Yield: 58 mg (64% of theory)
ESI-MS: m/z=531 (M+H)+
R$_t$ (HPLC-MS): 1.45 min (method C)

Intermediate 60

Isomer mixture of 5'-cyano-4-(2-oxo-2,3-dihydro-imidazo[4,5-b]pyridin-1-yl)-3,4,5,6-tetrahydro-2H-[1,2']bipyridinyl-4'-carboxylic acid and 5'-cyano-4-(2-oxo-2,3-dihydro-imidazo[4,5-b]pyridin-1-yl)-3,4,5,6-tetrahydro-2H-[1,4']bipyridinyl-2'-carboxylic acid

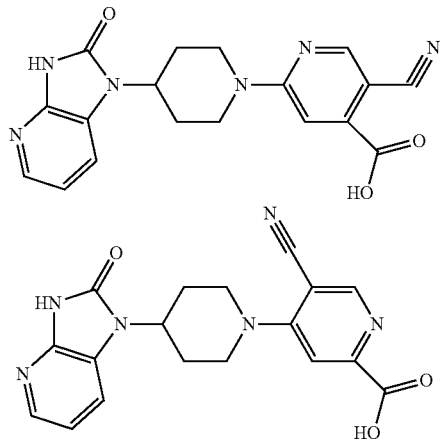

Step 1: Isomer mixture of 4'-chloro-4-(2-oxo-2,3-dihydro-imidazo[4,5-b]pyridin-1-yl)-3,4,5,6-tetrahydro-2H-[1,2']bipyridinyl-5'-carbonitrile and 6'-chloro-4-(2-oxo-2,3-dihydro-imidazo[4,5-b]pyridin-1-yl)-3,4,5,6-tetrahydro-2H-[1,4']bipyridinyl-3'-carbonitrile

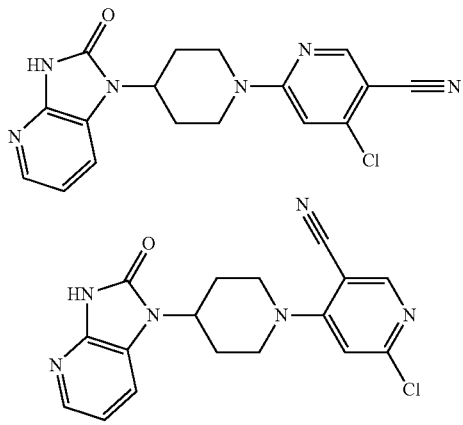

1.50 g (5.15 mmol) 1-piperidin-4-yl-1,3-dihydroimidazo[4,5-b]pyridin-2-one-dihydrochloride and 3.59 mL (20.6 mmol) DIPEA were placed in 45 mL ethanol. 891 mg (5.00 mmol) 4,6-dichloro-nicotinonitrile and 3 spatula tips of DMAP were added and the reaction mixture was stirred for 4 h at RT. The precipitated solid was suction filtered, washed with ethanol and dried.

Yield: 1.41 g (77% of theory)
ESI-MS: m/z=355/357 (Cl) (M+H)+
R$_t$ (HPLC-MS): 1.15 min (method C)

Step 2 Isomer mixture of methyl 5'-cyano-4-(2-oxo-2,3-dihydro-imidazo[4,5-b]pyridin-1-yl)-3,4,5,6-tetrahydro-2H-[1,2']bipyridinyl-4'-carboxylate and methyl 5'-cyano-4-(2-oxo-2,3-dihydro-imidazo[4,5-b]pyridin-1-yl)-3,4,5,6-tetrahydro-2H-[1,4']bipyridinyl-2'-carboxylate

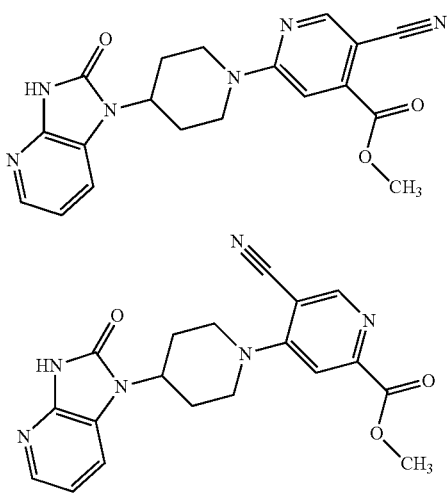

In a CO atmosphere 717 mg (2.02 mmol) of an isomer mixture of 4'-chloro-4-(2-oxo-2,3-dihydro-imidazo[4,5-b]pyridin-1-yl)-3,4,5,6-tetrahydro-2H-[1,2']bipyridinyl-5'-carbonitrile and 6'-chloro-4-(2-oxo-2,3-dihydro-imidazo[4,5-b]pyridin-1-yl)-3,4,5,6-tetrahydro-2H-[1,4']bipyridinyl-3'-carbonitrile, 78 mg (0.20 mmol) PdCl$_2$(PhCN)$_2$, 112 mg (0.20 mmol) dppf and 0.34 mL (2.4 mmol) TEA in 30 mL methanol were carbonylated for 4 h at 130° C. and 25 bar. The catalyst was removed by suction filtering and the filtrate was concentrated to dryness by rotary evaporation. The residue was combined with isopropanol and the precipitated solid was suction filtered and dried.

Yield: 112 mg (15% of theory)
R$_t$ (HPLC-MS): 1.05 min (method C)

Step 3 Isomer mixture of 5'-cyano-4-(2-oxo-2,3-dihydro-imidazo[4,5-b]pyridin-1-yl)-3,4,5,6-tetrahydro-2H-[1,2']-bipyridinyl-4'-carboxylic acid and 5'-cyano-4-(2-oxo-2,3-dihydro-imidazo[4,5-b]pyridin-1-yl)-3,4,5,6-tetrahydro-2H-[1,4']bipyridinyl-2'-carboxylic acid

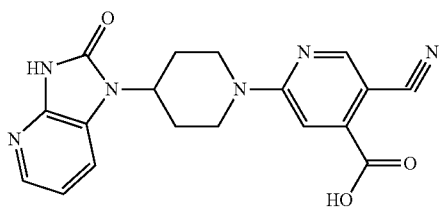

-continued

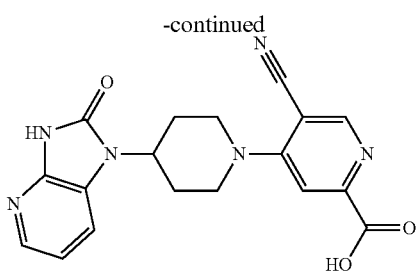

272 mg (0.720 mmol) of an isomer mixture of methyl 5'-cyano-4-(2-oxo-2,3-dihydro-imidazo[4,5-b]pyridin-1-yl)-3,4,5,6-tetrahydro-2H-[1,2']bipyridinyl-4'-carboxylate and methyl 5'-cyano-4-(2-oxo-2,3-dihydro-imidazo[4,5-b]pyridin-1-yl)-3,4,5,6-tetrahydro-2H-[1,4']bipyridinyl-2'-carboxylate were stirred overnight in 4.0 mL THF, 0.54 mL (2.1 mmol) of a 4M NaOH solution and 0.54 mL water at RT. The organic solvent was eliminated by rotary evaporation and the aqueous phase was combined with 50 mL water and 25 mL of a 4M HCl solution. The reaction mixture was stirred for one hour at RT, then the precipitated solid was suction filtered and dried.

Yield: 210 mg (80% of theory)
ESI-MS: m/z=365 (M+H)$^+$
R$_t$ (HPLC-MS): 3.65 min (method C)

Intermediate 61

4-(2-oxo-2,3-dihydro-imidazo[4,5-b]pyridin-1-yl)-3,4,5,6-tetrahydro-2H-[1,2']bipyridinyl-4'-carboxylic acid

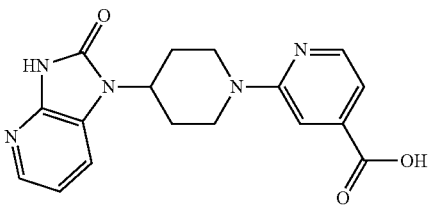 [SMILES: O=C(O)c1ccnc(N2CCC(n3c(=O)[nH]c4ncccc43)CC2)c1]

0.50 g (2.4 mmol) 2-bromopyridine-4-carboxylic acid and 1.1 g (5.0 mmol) 1-piperidin-4-yl-1,3-dihydro-imidazo[4,5-b]pyridin-2-one were mixed and melted for 10 min using the hot air blower. The reaction mixture was cooled, mixed with water and made basic with ammonia. It was extracted with EtOAc. The aqueous phase was concentrated and purified by HPLC. The product-containing fractions were combined and concentrated to dryness by rotary evaporation.

Yield: 200 mg (25% of theory)
ESI-MS: m/z=340 (M+H)$^+$
R$_t$ (HPLC-MS): 0.74 min (method C)

Intermediate 62

6-[4-(2-oxo-1,2-dihydro-quinolin-3-yl)-piperidin-1-yl]-pyrimidine-4-carboxylic acid

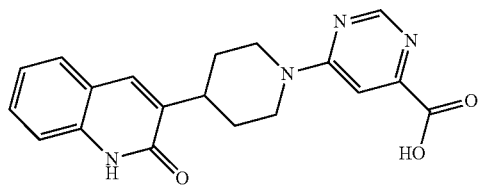 [SMILES: O=C(O)c1cc(N2CCC(c3cc4ccccc4[nH]c3=O)CC2)ncn1]

Step 1: 1-benzyl-4-(2-chloro-quinolin-3-yl)-piperidin-4-ol

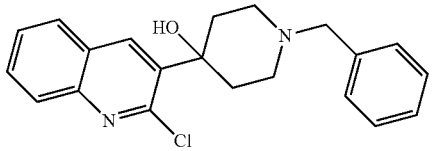 [SMILES: OC1(c2cc3ccccc3nc2Cl)CCN(Cc2ccccc2)CC1]

Under an argon atmosphere 22.3 g (136 mmol) 2-chloroquinoline in 60 mL THF was slowly added dropwise at −78° C. to 68.0 mL (136 mmol) of a 2M lithium diisopropylamide (in THF) solution in 280 mL THF. The reaction mixture was stirred for 1 h at −78° C. and then 24.3 mL (136 mmol) N-benzylpiperidone in 50 mL of THF were added dropwise. The reaction mixture was stirred for 40 min at −70° C. and for 3 h at RT. The reaction mixture was cooled to −20° C., and 200 mL water were added dropwise. The reaction mixture was allowed to come up to RT and extracted with EtOAc. The organic phase was dried, filtered and concentrated to dryness by rotary evaporation. The product was purified using an Alox column. The product-containing fractions were combined and concentrated to dryness by rotary evaporation.

Yield: 15.5 g (32% of theory)
ESI-MS: m/z=353 (M+H)$^+$
$R_t$ (HPLC-MS): 1.05 min (method C)

Step 2: 3-(1-benzyl-1,2,3,6-tetrahydro-pyridin-4-yl)-quinolin-2-ol

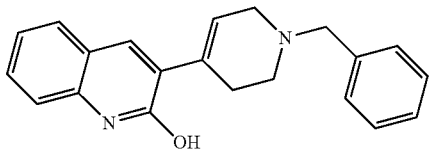 [SMILES: Oc1nc2ccccc2cc1C1=CCN(Cc2ccccc2)CC1]

15.5 g (43.9 mmol) 1-benzyl-4-(2-chloro-quinolin-3-yl)-piperidin-4-ol were refluxed for 8 h in 150 mL of a 6M aqueous hydrochloric acid solution. 100 mL water were added dropwise to the reaction mixture and the precipitated solid was suction filtered, dried and then stirred into 150 mL of a 15%, aqueous potassium carbonate solution. After the precipitate had been suction filtered the product was obtained as a free base and dried.

Yield: 6.20 g (45% of theory)
ESI-MS: m/z=317 (M+H)$^+$
$R_t$ (HPLC-MS): 1.00 min (method C)

Step 3: 3-piperidin-4-yl-1H-quinolin-2-one

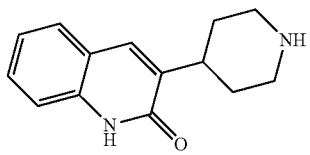 [SMILES: O=c1[nH]c2ccccc2cc1C1CCNCC1]

5.70 g (18.0 mmol) 3-(1-benzyl-1,2,3,6-tetrahydro-pyridin-4-yl)-quinolin-2-ol were placed in 200 mL methanol. 1.00 g palladium on charcoal (10%) were added and the reaction mixture was hydrogenated for 3 h at 50° C. under a hydrogen atmosphere. The catalyst was removed by suction filtering and the mother liquor was concentrated to dryness by rotary evaporation. The residue was triturated with diethyl ether and the undissolved solid was suction filtered and dried.

Yield: 3.7 g (90% of theory)
ESI-MS: m/z=229 (M+H)$^+$
$R_t$ (HPLC-MS): 0.77 min (method C)

Step 4: ethyl 6-[4-(2-oxo-1,2-dihydro-quinolin-3-yl)-piperidin-1-yl]-pyrimidine-4-carboxylate

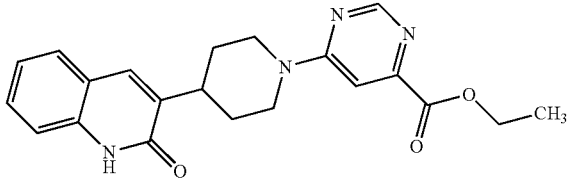 [SMILES: CCOC(=O)c1cc(N2CCC(c3cc4ccccc4[nH]c3=O)CC2)ncn1]

730 mg (3.91 mmol) ethyl 6-chloropyrimidine-4-carboxylate were placed in 10 mL DMF. 900 mg (3.94 mmol) 3-piperidin-4-yl-1,2-dihydro-quinolin-2-ol and 2.30 mL (13.4 mmol) DIPEA were added and the reaction mixture was stirred overnight at RT. The reaction mixture was mixed with 60 mL water and stirred for 30 min. The precipitated solid was suction filtered and dried.

Yield: 1.15 g (78% of theory)
ESI-MS: m/z=379 (M+H)$^+$
$R_t$ (HPLC-MS): 2.93 min (method E)

Step 5: 6-[4-(2-oxo-1,2-dihydro-quinolin-3-yl)-piperidin-1-yl]-pyrimidine-4-carboxylic acid

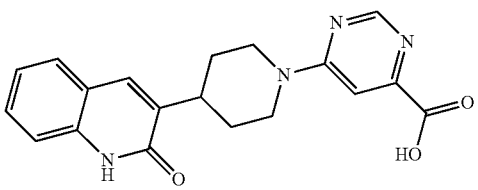 [SMILES: O=C(O)c1cc(N2CCC(c3cc4ccccc4[nH]c3=O)CC2)ncn1]

1.10 g (2.91 mmol) ethyl 6-[4-(2-hydroxy-1,2-dihydro-quinolin-3-yl)-piperidin-1-yl]-pyrimidine-4-carboxylate were stirred overnight at RT in 20 mL THF, 1.5 mL water and 1.5 mL of a 4 M NaOH solution. The organic solvent was eliminated by rotary evaporation and the precipitated solid was suction filtered. The filtrate was acidified with a 4 M HCl solution and the precipitated solid was suction filtered and dried.

Yield: 1 g (98% of theory)
ESI-MS: m/z=351 (M+H)$^+$
$R_t$ (HPLC-MS): 0.98 min (method C)

Intermediate 63

6-methoxy-3-piperidin-4-yl-1H-quinolin-2-one

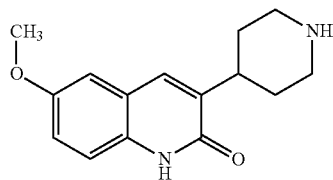

Step 1: 1-benzyl-4-(2-chloro-6-methoxy-quinolin-3-yl)-piperidin-4-ol

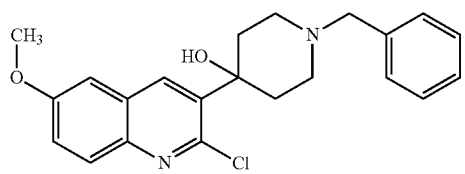 [SMILES: COc1ccc2nc(Cl)c(C3(O)CCN(Cc4ccccc4)CC3)cc2c1]

Under an argon atmosphere 5.0 g (25 mmol) 2-chloro-6-methoxyquinoline in a small amount of THF were added dropwise at −78° C. to 14 mL (28 mmol) of a 2 M lithium diisopropylamide solution (in THF) in 50 mL THF. Then the mixture was stirred for 1.5 h at −78° C. and 4.5 mL (25 mmol) N-benzylpiperidone was added dropwise. The mixture was stirred for a further 15 min with cooling before slowly being heated to RT. The reaction mixture was stirred overnight, evaporated down and purified by flash chromatography on aluminium oxide. The product-containing fractions were combined and evaporated down.

Yield: 2.1 g (13% of theory)
ESI-MS: m/z=383 (M+H)$^+$
$R_t$(HPLC): 1.14 min (method C)

Step 2: 3-(1-benzyl-1,2,3,6-tetrahydro-pyridin-4-yl)-6-methoxy-quinolin-2-ol

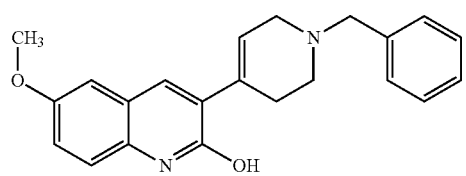 [SMILES: COc1ccc2nc(O)c(C3=CCN(Cc4ccccc4)CC3)cc2c1]

1.90 g (4.96 mmol) 1-benzyl-4-(2-chloro-6-methoxy-quinolin-3-yl)-piperidin-4-ol were stirred overnight at 100° C. in 25 mL of a 4N aqueous hydrochloric acid solution. Then 15 mL of a concentrated aqueous hydrochloric acid solution were slowly added dropwise and again the mixture was stirred overnight. After the reaction mixture had been evaporated down by half the remaining half was diluted with water and extracted with EtOAc. The organic phase was dried on sodium sulphate, filtered and evaporated down. The residue was triturated with PE/EtOAc.

Yield: 165 mg (8% of theory)
ESI-MS: m/z=347 (M+H)$^+$

Step 3: 6-methoxy-3-piperidin-4-yl-1H-quinolin-2-one

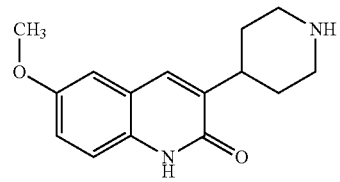 [SMILES: COc1ccc2[nH]c(=O)c(C3CCNCC3)cc2c1]

In a hydrogen atmosphere 160 mg (0.46 mmol) 3-(1-benzyl-1,2,3,6-tetrahydro-pyridin-4-yl)-6-methoxy-quinolin-2-ol and 20 mg palladium on charcoal (10%) in 30 mL MeOH were hydrogenated for 17.5 h at 50° C. at 50 psi. Then another 10 mL THF and catalyst were added and the mixture was hydrogenated for a further 2 h. Catalyst was added again and the mixture was hydrogenated overnight at 50° C. in a hydrogen atmosphere of 60 psi. After filtration of the reaction mixture the filter cake was washed with DMF and the filtrate was evaporated down. The residue was added to EtOAc, triturated with PE and filtered. The precipitate was washed with diisopropylether and dried.

Yield: 56 mg (35% of theory)
ESI-MS: m/z=259 (M+H)$^+$
$R_t$(HPLC): 0.90 min (method C)

Intermediate 64

7,7-dimethyl-3-trifluoromethyl-4,5,6,7-tetrahydro-1H-pyrazolo[4,3-c]pyridine

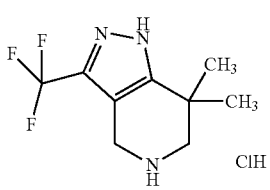

Step 1: tert. butyl 3,3-dimethyl-4-oxo-piperidine-1-carboxylate

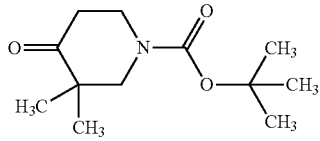

20 g (0.10 mol) tert. butyl 4-oxo-piperidine-1-carboxylate in 500 mL THF were cooled to 0° C. and mixed batchwise with 8.2 g (0.21 mol) sodium hydride (55%). The reaction mixture was stirred for 15 min before 15 mL (0.24 mol) iodomethane was added dropwise and was then stirred overnight at RT. Then the reaction mixture was evaporated down and the residue was taken up in diethyl ether. The organic phase was washed with water and saturated sodium chloride solution, dried and evaporated down. The residue was recrystallised from PE.

Yield: 10.05 g (37% of theory)
ESI-MS: m/z=172 (M-tert.butyl+H)+
$R_t$ (HPLC-MS): 1.44 min (method C)

Step 2: tert. butyl 3,3-dimethyl-4-oxo-5-(2,2,2-trifluoro-acetyl)-piperidine-1-carboxylate

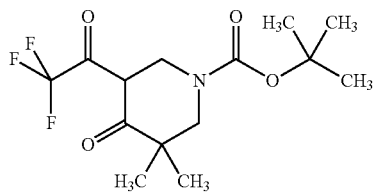 [SMILES: CC(C)(C)OC(=O)N1CC(C(=O)C(F)(F)F)C(=O)C(C)(C)C1]

Under a nitrogen atmosphere 4.20 mL (4.2 mmol) of a 1 M lithium bis(trimethylsilyl)amide solution were added to 1.00 g (3.96 mmol) tert. butyl 3,3-dimethyl-4-oxo-piperidine-1-carboxylate in 10 mL toluene at 0° C., the mixture was stirred for 1 min and then 0.56 mL (4.00 mmol) trifluoroacetic anhydride was added. The cooling bath was removed, the mixture was stirred for another 2 min and combined with 10 mL water and 1.2 mL acetic acid. The reaction mixture was stirred for 15 min. After extracting with diethyl ether the organic phase was dried and evaporated down. The residue was purified by flash chromatography.

Yield: 300 mg (23% of theory)
ESI-MS: m/z=322 (M−H)−
$R_t$ (HPLC-MS): 1.84 min (method C)

Step 3: tert. butyl 7,7-dimethyl-3-trifluoromethyl-1,4,6,7-tetrahydro-pyrazolo[4,3-c]pyridine-5-carboxylate

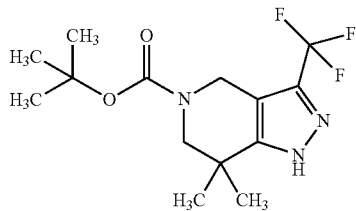 [SMILES: CC(C)(C)OC(=O)N1Cc2c(C(F)(F)F)n[nH]c2C(C)(C)C1]

480 mg (1.41 mmol) tert. butyl 3,3-dimethyl-4-oxo-5-(2,2,2-trifluoro-acetyl)-piperidine-1-carboxylate in 5.00 mL EtOH were combined with 0.15 mL hydrazine hydrate, 0.18 mL acetic acid and 1.00 g molecular sieve (3A) and left to stand for 48 h at RT. Then the reaction mixture was refluxed for 3 h and cooled overnight. In addition a spatula tip of p-toluenesulphonic acid was also added and the mixture was refluxed first of all for 1 h and then for a further 3 h. After cooling the reaction mixture was filtered and evaporated down. The residue was purified by flash chromatography. A mixture of tert. butyl 7,7-dimethyl-3-trifluoromethyl-1,4,6,7-tetrahydro-pyrazolo[4,3-c]pyridine-5-carboxylate and tert. butyl 4-hydrazone-3,3-dimethyl-5-(2,2,2-trifluoro-acetyl)-piperidine-1-carboxylate was obtained in the ratio 3:2.

Yield: 370 mg (37% of theory)
ESI-MS: m/z=318 (M−H)−

Step 4: 7,7-dimethyl-3-trifluoromethyl-4,5,6,7-tetrahydro-1H-pyrazolo[4,3-c]-pyridin-hydrochloride

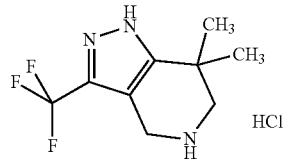

0.37 g (0.52 mmol) of a mixture of tert. butyl 7,7-dimethyl-3-trifluoromethyl-1,4,6,7-tetrahydro-pyrazolo[4,3-c]pyridine-5-carboxylate and tert. butyl 4-hydrazone-3,3-dimethyl-5-(2,2,2-trifluoro-acetyl)-piperidine-1-carboxylate in 8.0 mL DCM was combined with 4.0 mL trifluoroacetic acid and stirred for 2 h at RT. Then the reaction mixture was evaporated down, the residue was dissolved in EtOH, mixed with 0.90 mL (1.1 mmol) of a 1.25 molar ethanolic hydrochloric acid and co-evaporated again. The residue was triturated with diethyl ether, suction filtered and dried.

Yield: 270 mg (77% of theory)
ESI-MS: m/z=220 (M+H)+
$R_t$ (HPLC-MS): 0.43 min (method R)

Intermediate 65

4,4-dimethyl-4,5,6,7-tetrahydro-thieno[2,3-c]pyridine

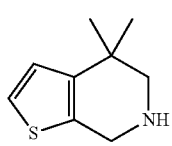

Step 1: methylene-(2-methyl-2-thiophen-3-yl-propyl)-amine

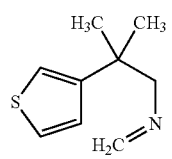

5.8 g (37 mmol) 2-methyl-2-thiophene-3-yl-propylamine and 3.6 mL (44 mmol) formaldehyde were stirred together with 2.0 g molecular sieve (4A powders) overnight at RT. The reaction mixture was filtered and the filtrate was concentrated to dryness by rotary evaporation.

Yield: 6.0 g (97% of theory)
ESI-MS: m/z=168 (M+H)$^+$

Step 2: 4,4-dimethyl-4,5,6,7-tetrahydro-thieno[2,3-c]pyridine

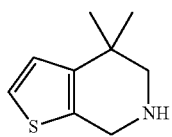

6.0 g (36 mmol) methylene-(2-methyl-2-thiophene-3-yl-propyl)-amine, 11 mL (45 mmol) of a 4M HCl solution and 12 mL (0.14 mol) conc. HCl were stirred at RT over the weekend. The reaction mixture was made alkaline with a 4M sodium hydroxide solution. The precipitate formed was suction filtered, washed with water and dried. The substance was purified on Alox. The product-containing fractions were combined and concentrated to dryness by rotary evaporation.

Yield: 0.74 g (12% of theory)
R$_t$ (HPLC-MS): 1.24 min (method K)

Intermediate 66

5,6-difluoro-2,3-dihydro-1H-indole

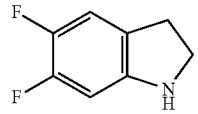

Under an argon atmosphere 0.30 g (1.8 mmol) 5,6-difluoro-1,3-dihydro-indol-2-one were dissolved in 10 mL THF and 3.0 mL of a 1 M borane in THF solution were added dropwise. Then the reaction mixture was heated for 2 h to 70° C. and then cooled. After the addition of 3 mL MeOH a further 5 mL of a 4N aqueous hydrochloric acid solution were added and the mixture was refluxed for 1 h. The organic phase was evaporated down, the aqueous phase was washed with DCM and then made alkaline with a 4N aqueous sodium hydroxide solution and extracted several times with EtOAc. The combined organic phases were dried on sodium sulphate, filtered and evaporated down.

Yield: 160 mg (47% of theory)
ESI-MS: m/z=156 (M+H)$^+$
R$_t$ (HPLC-MS): 0.73 min (method C)

Intermediate 67

(2,3-dihydro-1H-indol-3-yl)-methanol

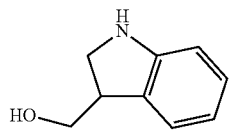 [SMILES: OCC1CNc2ccccc21]

Step 1: ethyl 2,3-dihydro-1H-indol-3-carboxylate hydrochloride

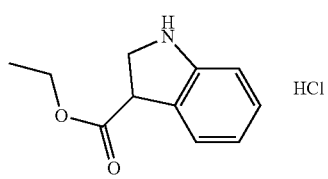

This compound was synthesised analogously to WO 2007/054453.

Step 2: (2,3-dihydro-1H-indol-3-yl)-methanol

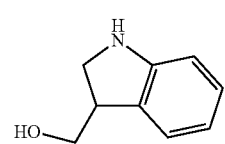 [SMILES: OCC1CNc2ccccc21]

0.79 g (3.5 mmol) ethyl 2,3-dihydro-1H-indol-3-carboxylate were added batchwise at RT to 7.8 mL (7.8 mmol) of a 1 M lithium aluminium hydride solution (in THF) in 40 mL THF and refluxed for 1 h. Then the reaction mixture was combined with water while being cooled, the precipitate formed was filtered off and the filtrate was evaporated down.

Yield: 52 mg (95% of theory)
ESI-MS: m/z=150 (M+H)$^+$
R$_t$ (HPLC-MS): 0.31 min (method R)

Intermediate 68

6-fluoro-2,3-dihydro-1H-indole

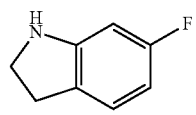

Under a nitrogen atmosphere 0.29 g (4.6 mmol) sodium cyanoborohydride were added batchwise to 0.54 g (4.0 mmol) 6-fluoroindole in 5.0 mL glacial acetic acid and the mixture was stirred for 30 min. Then the reaction mixture was poured onto a 4N aqueous sodium hydroxide solution and extracted with EtOAc. The combined organic phases were washed several times with saturated sodium hydrogen carbonate solution, dried on sodium sulphate and evaporated down.

Yield: 0.56 g (97% of theory)
ESI-MS: m/z=138 (M+H)$^+$
R$_t$ (HPLC-MS): 0.74 min (method C)

Intermediate 69

4-methyl-1,2,3,4-tetrahydro-isoquinolin hydrochloride

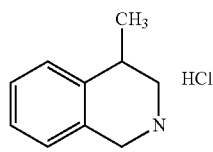

In a hydrogen atmosphere 0.50 g (3.5 mmol) 4-methyl-isoquinoline, 50 mg platinum dioxide in 50 mL methanol and 3.5 mL 1M aqueous hydrochloric acid solution were hydrogenated at RT and 3 bar for 4 h. After removal of the catalyst by suction filtering the reaction mixture was evaporated down. A mixture of educt and product was obtained, which was reacted further without any further purification.

Yield: 0.60 g (94% of theory)
ESI-MS: m/z=148 (M+H)$^+$
R$_t$ (HPLC-MS): 0.70 min (method C)

Intermediate 70

3-methyl-decahydro-quinoline hydrochloride

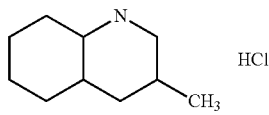

In a hydrogen atmosphere 500 mg (3.5 mmol) 3-methyl-decahydro-quinoline, 75 mg platinum dioxide in 50 mL methanol and 3.5 mL 1M aqueous hydrochloric acid solution were hydrogenated at RT and 50 psi for 4 h. After removal of the catalyst by suction filtering the reaction mixture was evaporated down.

Yield: 0.60 g (94% of theory)
ESI-MS: m/z=148 (M+H)$^+$
R$_t$ (HPLC-MS): 0.70 min (method C)

Intermediate 71

1,2,2a,5-tetrahydro-3H-pyrrolo[4,3,2-de]quinolin-4-one

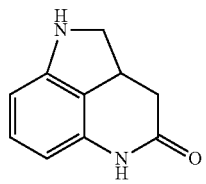 [SMILES: O=C1CC2CNc3cccc(c32)N1]

Step 1: methyl oxo-pyrrolidin-1-yl-acetate

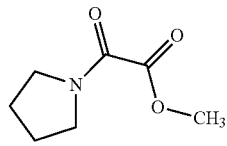

30 mL (0.33 mol) methyloxalyl chloride in 220 mL diethyl ether were added dropwise to 33 mL (0.40 mol) pyrrolidine and 55 mL (0.40 mol) TEA in 500 mL diethyl ether while cooling with an ice bath. After heating to RT the mixture was stirred for a further 2 h at RT. The precipitate formed was suction filtered and the filtrate was evaporated down. The residue was subjected to fractional distillation under a high vacuum.

Yield: 41.8 g (82% of theory)
MS: m/z=180 (M+Na)$^+$
R$_f$: 0.3 (silica gel, PE/EtOAc 1/1)

Step 2: methyl (4-nitro-1H-indol-3-yl)-oxo-acetate

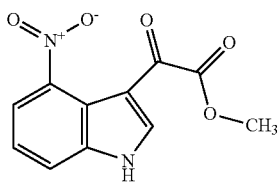 [SMILES: COC(=O)C(=O)c1c[nH]c2cccc([N+](=O)[O-])c12]

9.4 mL (68 mmol) diphosphoryl chloride were slowly added dropwise to 10 g (62 mmol) 4-nitroindole and 11 g (68 mmol) methyl oxo-pyrrolidin-1-yl-acetate with stirring and while cooling with ice. The reaction mixture was heated to RT and stirred for 3 h at RT. Then first of all 10 mL MeOH were added dropwise at 0° C. and then saturated sodium hydrogen carbonate solution was added dropwise at 0° C. After repeated extraction with DCM the organic phase was dried and evaporated down to 100 mL. This residue was left to stand at RT and the precipitate formed was suction filtered, washed and dried in the air.
Yield: 2.30 g (15% of theory)
ESI-MS: m/z=249 (M+H)$^+$
$R_t$ (HPLC-MS): 1.23 min (method C)

Step 3: methyl (4-nitro-2,3-dihydro-1H-indol-3-yl)-acetate

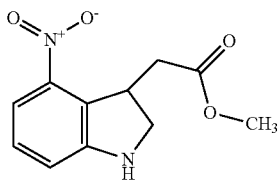 [SMILES: COC(=O)CC1CNc2cccc([N+](=O)[O-])c21]

Under an argon atmosphere 16 mL (0.10 mmol) triethylsilane were slowly added dropwise to 2.3 g (9.3 mmol) methyl (4-nitro-1H-indol-3-yl)-oxo-acetate in 18 mL trifluoroacetic acid while cooling with ice. Then the mixture was stirred for a further 3 h at RT and evaporated down. The residue was dried and then triturated with diisopropylether, suction filtered and dried in the air.
Yield: 2.0 g (91% of theory)
ESI-MS: m/z=237 (M+H)$^+$
$R_t$ (HPLC-MS): 1.34 min (method C)

Step 4: methyl (4-amino-2,3-dihydro-1H-indol-3-yl)acetate

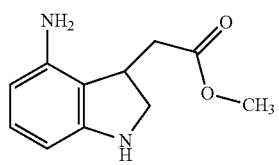

2.0 g (8.5 mmol) methyl (4-nitro-2,3-dihydro-1H-indol-3-yl)-acetate in 70 mL MeOH were combined with 0.30 g Raney nickel and hydrogenated for 2 h in a hydrogen atmosphere. The catalyst was removed by suction filtering and the solution was concentrated by rotary evaporation. The residue was immediately reacted further without further purification.
Yield: 1.80 g (quantitative)
ESI-MS: m/z=237 (M+H)$^+$
$R_t$ (HPLC-MS): 0.40 min (method C)

Step 5: 1,2,2a,5-tetrahydro-3H-pyrrolo[4,3,2-de]quinolin-4-one

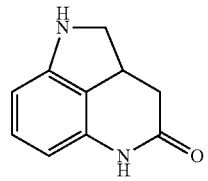 [SMILES: O=C1CC2CNc3cccc(c32)N1]

1.80 g (8.73 mmol) methyl (4-amino-2,3-dihydro-1H-indol-3-yl)acetate in 100 mL xylene were refluxed for 30 h. The reaction mixture was evaporated down and purified by flash chromatography. The product-containing fractions were combined and evaporated down.
Yield: 0.21 g (14% of theory)
ESI-MS: m/z=175 (M+H)$^+$
$R_t$ (HPLC-MS): 0.03 min (method C)

Intermediate 72

5,6,7,8-tetrahydro-4H-thiazolo[4,5-d]azepine hydrochloride

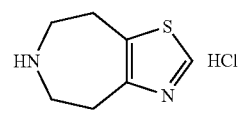

Step 1: ethyl 3-benzylamino-propionate

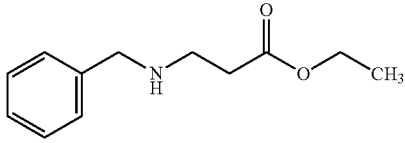

25 g (0.23 mol) benzylamine and 21 g (0.21 mol) ethyl acrylate in 125 mL EtOH were stirred at RT for 15 h. Then the solvent was evaporated down and the crude product was used in the next step without further purification.
Yield: 30 g (62% of theory)
ESI-MS: m/z=208 (M+H)$^+$
$R_f$: 0.5 (silica gel, EtOAc/PE 50%)

Step 2: ethyl 4-[(benzyl-(2-ethoxycarbonyl-ethyl)-amino]-propanecarboxylate

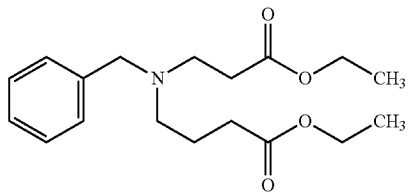 [SMILES: CCOC(=O)CCCN(CCC(=O)OCC)Cc1ccccc1]

71 g (0.36 mol) ethyl 4-bromobutyrate were slowly added dropwise at RT to 50 g (0.24 mol) ethyl 3-benzylaminopropionate and 83 g (0.60 mol) potassium carbonate in 1.0 L acetonitrile. Then the reaction mixture was stirred for 12 h at 90° C. After cooling the reaction mixture was diluted with EtOAc and the organic phase was separated off. This was washed with water and saturated sodium chloride solution and then dried on sodium sulphate. After filtration the filtrate was evaporated down and the residue was purified by flash chromatography (on aluminium oxide).

Yield: 55 g (68% of theory)
$R_f$: 0.7 (silica gel, EtOAc/PE 2%)

Step 3: 1-benzyl-azepan-4-one

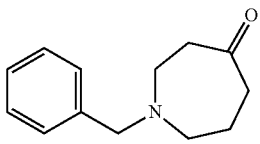 [SMILES: O=C1CCCN(Cc2ccccc2)CC1]

Under an argon atmosphere 1.0 L xylene were heated at 145° C. for 1 to 2 h with a Dean-Stark apparatus. The solvent was cooled to 65° C., combined with 21 g (0.19 mol) potassium-tert-butoxide and heated to 145° C. for a further 1 to 2 h. Then 30 g (93 mmol) ethyl 4-[benzyl-(2-ethoxycarbonyl-ethyl)-amino]-butyrate in xylene were added dropwise over a period of 1 h to the reaction mixture and this was then stirred for 2 to 3 h at 145° C. After cooling to 0° C. the reaction mixture was mixed with 0.45 L of a 6 N aqueous hydrochloric acid solution, the aqueous phase was separated off and refluxed for 2 h. Then it was cooled to 0° C. again, the reaction mixture was made alkaline with aqueous sodium hydroxide solution and extracted with EtOAc. The combined organic phases were dried on sodium sulphate, filtered and evaporated down. The residue was purified by flash chromatography (aluminium oxide).

Yield: 5.5 g (29% of theory)
ESI-MS: m/z=204 (M+H)$^+$
$R_f$: 0.4 (silica gel, EtOAc/PE 30%)

Step 4: 1-benzyl-5-bromo-azepan-4-one-hydrobromide

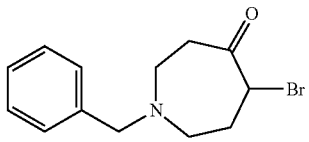

5.7 mL HBr in acetic acid (33%) were added dropwise at RT to 10 g (49 mmol) 1-benzyl-azepan-4-one in 28 mL acetic acid. Then another 9.5 g (60 mmol) bromine were added at RT and the mixture was stirred for 1.5 h at RT. After evaporation of the reaction mixture under 35° C. the residue was added to EtOAc and refluxed for approx. 1 h. The supernatant organic phase was decanted off from the precipitated solid, then combined again with EtOAc and refluxed for approx. 1 h. The precipitated solid was filtered, washed with EtOAc and dried.

Yield: 6.0 g (34% of theory)
$R_f$: 0.6 (silica gel, EtOAc/PE 30%)

Step 5: 6-benzyl-5,6,7,8-tetrahydro-4H-thiazolo[4,5-d]azepine-hydrochloride

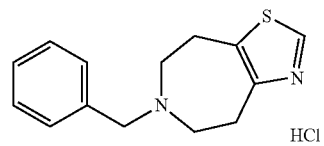 [SMILES: c1ccc(CN2CCc3ncsc3CC2)cc1 ; Cl]

2.1 g (9.7 mmol) phosphorus pentasulphide and 1.9 g (41 mmol) formamide in dioxane were stirred for a total of 2.5 h at 100° C. After cooling to RT 10 g (28 mmol) 1-benzyl-5-bromo-azepan-4-one hydrobromide were added and the mixture was stirred for 5 h at 100° C. Then the solvent was evaporated down, the residue was added to saturated sodium bicarbonate solution and extracted with EtOAc. The combined organic phases were washed with water, aqueous sodium bicarbonate solution and saturated sodium chloride solution. The organic phase was dried on sodium sulphate, filtered and evaporated down. The residue was purified by flash chromatography. The product-containing fractions were combined and evaporated down. The free base was mixed with methanolic hydrochloric acid solution. The precipitate formed was filtered off.

Yield: 3.50 g (45% of theory)
ESI-MS: m/z=245 (M+H)$^+$
$R_f$: 0.5 (silica gel, MeOH/chloroform 10%)

Step 6: ethyl 4,5,7,8-tetrahydro-thiazolo[4,5-d]azepine-6-carboxylate

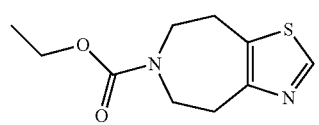

1.4 g (9.8 mmol) 1-chloroethylchloroformate were added dropwise at −20° C. to 2.0 g (8.2 mmol) 6-benzyl-5,6,7,8-tetrahydro-4H-thiazolo[4,5-d]azepine in 100 mL DCM and the mixture was stirred for 30 min. The organic solvent was evaporated down and the residue was reacted further without any further purification.
Yield: 1.5 g (81% of theory)
$R_f$: 0.6 (silica gel, EtOAc/PE 20%)

Step 7: 5,6,7,8-tetrahydro-4H-thiazolo[4,5-d]azepine hydrochloride

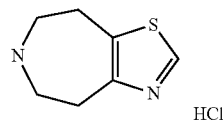

1.5 g (6.6 mmol) ethyl 4,5,7,8-tetrahydro-thiazolo[4,5-d]azepine-6-carboxylate were refluxed in 50 mL MeOH for 3 h. After evaporation of the organic solvent the residue was purified by flash chromatography. The product-containing fractions were combined and evaporated down. The free base was mixed with 5.0 mL (12.5 mmol) of a 2.5 molar methanolic hydrochloric acid solution and the excess solvent was evaporated down.
Yield: 0.70 g (55% of theory)
ESI-MS: m/z=155 (M+H)⁺
$R_f$: 0.2 (silica gel, MeOH/chloroform 20%)

Intermediate 73

6-fluoro-4,4-dimethyl-1,2,3,4-tetrahydro-isoquinoline hydrochloride

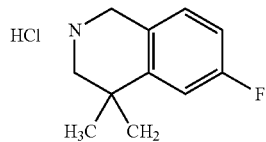

Step 1: 2-(3-fluoro-phenyl)-2-methyl-propionitrile

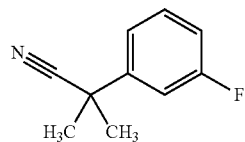

Under an argon atmosphere 77 mL (77 mmol) of a 1M lithium bis(trimethylsilyl)amide solution was added dropwise at −70° C. to 5.0 g (37 mmol) (3-fluoro-phenyl)-acetonitrile in 150 mL THF. The mixture was allowed to come up to −50° C. and was then stirred at this temperature for 1 h. Then at −50° C. 4.8 mL (78 mmol) methyl iodide were added. The reaction mixture was heated to RT overnight. The reaction mixture was slowly combined with saturated aqueous ammonium chloride solution and extracted with ethyl acetate. The organic phase was dried on sodium sulphate and evaporated down.

Yield: 5.6 g (93% of theory)
ESI-MS: m/z=163 (M+H)⁺
$R_t$(HPLC): 1.54 min (method C)

Step 2: 243-fluoro-phenyl)-2-methyl-propylamine

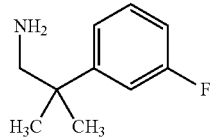

Under an argon atmosphere 69 mL (69 mmol) of a 1M lithium aluminium hydride solution in THF were slowly added dropwise at 0° C. to 5.6 g (34 mmol) 2-(3-fluoro-phenyl)-2-methyl-propionitrile in 40 mL THF. The reaction mixture was stirred for 30 min at 0° C. and overnight at RT. At 0° C. ethyl acetate and then water was added dropwise. The reaction mixture was filtered through Celite®, the organic phase was separated off and evaporated down. The residue was purified by flash chromatography.
Yield: 1.7 g (30% of theory)
ESI-MS: m/z=168 (M+H)⁺
$R_t$(HPLC): 0.86 min (method C)

Step 3: 2,2,2-trifluoro-N-1-[2-(3-fluoro-phenyl)-2-methyl-propyl]-acetamide

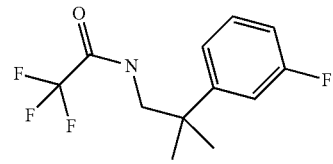 [SMILES: CC(C)(CNC(=O)C(F)(F)F)c1cccc(F)c1]

At 0° C. 1.7 mL (12 mmol) trifluoroacetic anhydride were added dropwise to 1.7 g (10 mmol) 2-(3-fluoro-phenyl)-2-methyl-propylamine and 5.4 mL (31 mmol) DIPEA in 35 mL dichloromethane. The reaction mixture was stirred for 3 h at RT, mixed with water and extracted with dichloromethane. The organic phase was dried and evaporated down.
Yield: 2.7 g (97% of theory)
ESI-MS: m/z=262 (M−Hy
$R_t$(HPLC): 1.54 min (method C)

Step 4: 6-fluoro-4,4-dimethyl-1,2,3,4-tetrahydro-isoquinoline hydrochloride

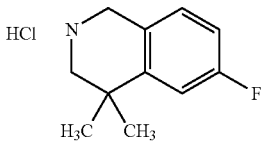

1.0 g (3.8 mmol) 2,2,2-trifluoro-N-[2-(3-fluoro-phenyl)-2-methyl-propyl]-acetamide and 0.18 g (6.1 mmol) formaldehyde in 5.0 mL acetic acid and 3.5 mL concentrated sulphuric acid were stirred for 16 h at RT. The reaction mixture was poured onto water and extracted with dichloromethane. The organic phase was extracted with an aqueous sodium hydrogen carbonate solution. The organic phase was dried and evaporated down. The residue was mixed with aqueous 0.1 M hydrochloric acid and extracted with ethyl acetate. The aqueous phase was evaporated down. The product was reacted without further purification.
Yield: 0.14 g (17% of theory)
$R_f$(HPLC): 0.86 min (method C)

Intermediate 74

2',3'-dihydro-1'H-spiro[cyclopropane-1,4'-isoquinoline]

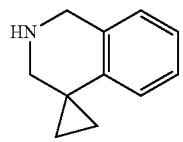

Step 1: 1'H-spiro[cyclopropane-1,4'-isoquinoline]-1',3'(2'H)-dione

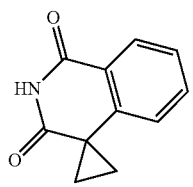 [SMILES: O=C1NC(=O)C2(CC2)c2ccccc21]

3.0 g (19 mmol) isoquinoline-1,3(2H,4H)-dione, 15.4 mL (0.19 mol) 1-bromo-2-chloroethane and 5.1 g (37 mmol) potassium carbonate in 35 mL DMF were stirred at RT over the weekend. Then 200 mL water were added and the mixture was extracted with ethyl acetate. The organic phase was dried and evaporated down.
Yield: 3.0 g (86% of theory)
ESI-MS: m/z=188 (M+H)$^+$
$R_f$(HPLC): 2.95 min (method E)

Step 2: 2',3'-dihydro-1'H-spiro[cyclopropane-1,4'-isoquinoline]

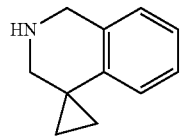

0.5 g (2.7 mmol) 1'H-spiro[cyclopropane-1,4'-isoquinoline]-1',3'(2'H)-dione in 50 mL THF were heated to the reflux temperature of the solvent. 11 mL (11 mmol) of a 1M borane in THF solution were added dropwise and the mixture was refluxed for 3 h. The reaction mixture was cooled to 0° C. and mixed with 50 mL methanol. The reaction mixture was evaporated down, the residue was combined with 15 mL of a 4M hydrochloric acid solution and refluxed for 30 min. After neutralisation with 15 mL of an aqueous 4M sodium hydroxide solution the mixture was extracted twice with ethyl acetate. The combined organic phases were dried and evaporated down. The product was purified by HPLC. The product-containing fractions were combined and evaporated down.
Yield: 20 mg (5% of theory)
ESI-MS: m/z=160 (M+H)$^+$
$R_f$(HPLC): 0.74 min (method C)

Intermediate 75

3-(2-methoxy-ethyl)-2,3-dihydro-1H-indole

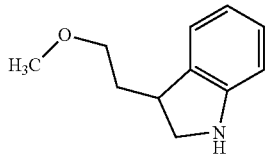

Step 1: 3-(2-methoxy-ethyl)-1,3-dihydro-indol-2-one

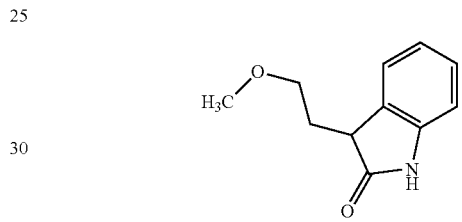

2.0 g (15 mmol) indolin-2-one, 5 mL (63 mmol) 2-methoxyethanol and 1.5 g Raney nickel in 20 mL THF were stirred for 4 h at 200° C. in an autoclave. After the catalyst had been filtered off the mother liquor was evaporated down, the residue was triturated with diisopropylether, suction filtered and dried
Yield: 1.2 g (42% of theory)
ESI-MS: m/z=190 (M−H)$^-$
$R_f$(HPLC): 2.87 min (method E)

Step 2: 3-(2-methoxy-ethyl)-2,3-dihydro-1H-indole

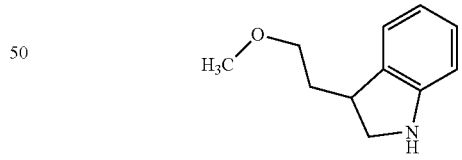

Under a nitrogen atmosphere 12.6 mL (12.6 mmol) of a 1M borane in THF solution was added dropwise to 1.2 g (6.3 mmol) 3-(2-methoxy-ethyl)-1,3-dihydro-indol-2-one in 50 mL THF. The reaction mixture was refluxed for 3 h, cooled to 0° C. and combined with 10 mL methanol and then with 15 mL semi-concentrated hydrochloric acid solution. The reaction mixture was refluxed for 3 h with stirring, cooled and washed twice with ethyl acetate. The aqueous phase was made alkaline with an aqueous 4M sodium hydroxide solution and extracted three times with ethyl acetate. The organic phases were combined, dried on sodium sulphate and evaporated down.

Yield: 0.95 g (85% of theory)
ESI-MS: m/z=178 (M+H)+
R$_t$(HPLC): 0.76 min (method C)

Intermediate 76

5-fluoro-3-methyl-2,3-dihydro-1H-indole

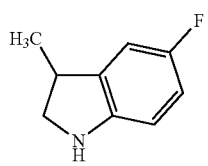

Step 1: 5-fluoro-3-methyl-1,3-dihydro-indol-2-one

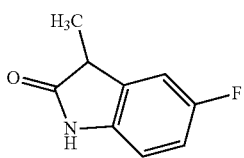

3.0 g (20 mmol) 5-fluoro-1,3-dihydro-indol-2-one, 50 mL methanol and 2.0 g Raney nickel were stirred for 1.5 h at 200° C. in an autoclave. After the catalyst had been filtered off the mother liquor was evaporated down and the residue was recrystallised from methanol.
Yield: 2.8 g (85% of theory)
ESI-MS: m/z=166 (M+H)+
R$_t$(HPLC): 1.1 min (method C)

Step 2: 5-fluoro-3-methyl-2,3-dihydro-1H-indole

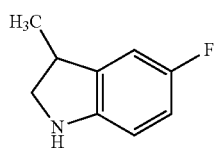

Under an argon atmosphere 18 mL (18 mmol) of a 1M borane in THF solution was added dropwise to 1.5 g (9.1 mmol) 5-fluoro-3-methyl-1,3-dihydro-indol-2-one in 50 mL THF. The reaction mixture was stirred for 2 h at 70° C., cooled to 0° C. and combined with 10 mL methanol and then with 30 mL semi-concentrated hydrochloric acid solution. The reaction mixture was refluxed for 1 h with stirring, cooled and the organic phase was eliminated using the rotary evaporator. The aqueous phase was extracted with ethyl acetate. The aqueous phase was made alkaline with an aqueous 4M sodium hydroxide solution and extracted with dichloromethane. The organic phase was dried on sodium sulphate, filtered off and evaporated down.
Yield: 0.50 g (36% of theory)
ESI-MS: m/z=152 (M+H)+
R$_t$(HPLC): 1.85 min (method E)

Intermediate 77

(2-chloro-pyridin-4-yl)-(5,6-difluoro-2,3-dihydro-indol-1-yl)-methanone

0.35 g (2.2 mmol) 2-chloroisonicotinic acid, 0.34 g (2.2 mmol) 5,6-difluoro-2,3-dihydro-1 H-indole, 0.70 mL (5.0 mmol) TEA and 10 mL DMF were mixed with 0.77 g (2.4 mmol) TBTU and stirred for 2 h at RT. The reaction mixture was purified by HPLC. The product fractions were combined and evaporated down.
Yield: 0.45 g (69% of theory)
ESI-MS: m/z=295/297 (M+H)+ Cl R$_t$ (HPLC-MS): 1.5 min (method C)

Intermediate 78

(2-chloro-1-oxy-pyridin-4-yl)-(5-fluoro-2,3-dihydro-indol-1-yl)-methanone

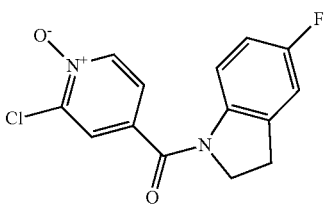 [SMILES: O=C(c1cc[n+]([O-])c(Cl)c1)N1CCc2cc(F)ccc21]

0.12 g (0.43 mmol) (2-chloro-pyridin-4-yl)-(5-fluoro-2,3-dihydro-indol-1-yl)-methanone and 0.22 g (0.90 mmol) 3-chloroperoxybenzoic acid in 5.0 mL chloroform were stirred for 48 h at 40° C. The mixture was diluted with 50 mL dichloromethane and washed twice with 50 mL 15% aqueous potassium carbonate solution. The organic phase was dried and evaporated down.
Yield: 0.14 g (quantitative)
R$_t$ (HPLC-MS): 1.11 min (method C)

Intermediate 79

(2-chloro-pyridin-4-yl)-(5-fluoro-3,3-dimethyl-2,3-dihydro-indol-1-yl)-methanone

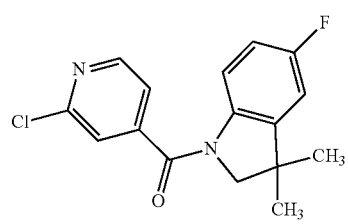 [SMILES: CC1(C)CN(C(=O)c2ccnc(Cl)c2)c2ccc(F)cc21]

0.17 g (1.1 mmol) 2-chloroisonicotinic acid, 0.18 g (1.1 mmol) 5-fluoro-3,3-dimethyl-2,3-di-hydro-1H-indole, 0.28 mL (2.0 mmol) TEA and 3.0 mL DMF were combined with 0.39 g (1.2 mmol) TBTU and stirred overnight at RT. The reaction mixture was purified by HPLC.

The product fractions were combined and evaporated down.

Yield: 0.12 g (36% of theory)
ESI-MS: m/z=305/307 (M+H)+ Cl
$R_t$ (HPLC-MS): 1.55 min (method C)

Intermediate 80

(4-chloro-pyridin-2-yl)-(5-fluoro-3,3-dimethyl-2,3-dihydro-indol-1-yl)-methanone

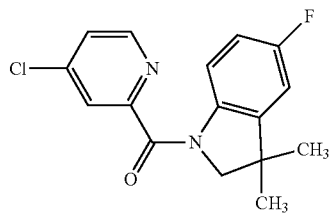 [SMILES: CC1(C)CN(C(=O)c2cc(Cl)ccn2)c2ccc(F)cc21]

0.17 g (1.1 mmol) 4-chloro-pyridine-2-carboxylic acid, 0.18 g (1.1 mmol) 5-fluoro-3,3-dimethyl-2,3-dihydro-1H-indole, 0.28 mL (2.0 mmol) TEA and 3.0 mL DMF were combined with 0.39 g (1.2 mmol) TBTU and stirred overnight at RT. The reaction mixture was purified by HPLC. The product fractions were combined and evaporated down.

Yield: 120 mg (36% of theory)
ESI-MS: m/z=305/307 (M+H)+ Cl
$R_t$ (HPLC-MS): 1.66 min (method C)

Intermediate 81

N-[6-chloro-4-(5-fluoro-2,3-dihydro-indole-1-carbonyl)-pyridin-2-yl]-methanesulphonamide

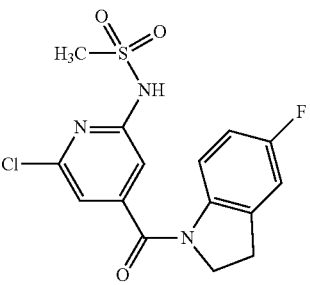 [SMILES: CS(=O)(=O)Nc1cc(C(=O)N2CCc3cc(F)ccc32)cc(Cl)n1]

Step 1: methyl 2-chloro-6-methanesulphonylamino-isonicotinate

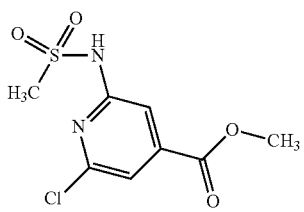 [SMILES: COC(=O)c1cc(Cl)nc(NS(C)(=O)=O)c1]

Under a nitrogen atmosphere 10 g (49 mmol) methyl 2,6-dichloro-isonicotinate, 5.6 g (59 mmol) methanesulphonamide, 14 g (68 mmol) potassium phosphate, 1.7 g (2.9 mmol) Xantphos and 0.90 g tris(dibenzylideneacetone)dipalladium in 300 mL dioxane were stirred for 5 h at 100° C. The mixture was suction filtered through kieselguhr and evaporated down. The residue was stirred with ethanol and the solid was suction filtered.

Yield: 4.4 g (34% of theory)
ESI-MS: m/z=265/266 (M+H)+ (Cl)

Step 2: 2-chloro-6-methanesulphonylamino-isonicotinic acid

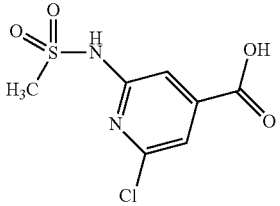

0.29 g (1.1 mmol) methyl 2-chloro-6-methanesulphonylamino-isonicotinate in 5.0 mL tetrahydrofuran and 1 mL water were mixed with 79 mg (3.3 mmol) lithium hydroxide and stirred overnight at RT. The reaction mixture was acidified with 1M aqueous hydrochloric acid and evaporated down. The product was reacted without further purification.

Yield: 300 mg (quantitative)
$R_t$ (HPLC-MS): 0.93 min (method C)

Step 3: N-[6-chloro-4-(5-fluoro-2,3-dihydro-indole-1-carbonyl)-pyridin-2-yl]-methanesulphonamide

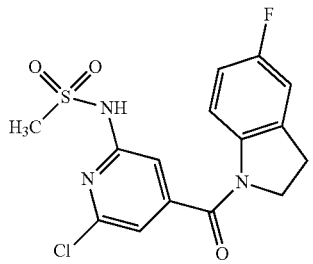 [SMILES: CS(=O)(=O)Nc1cc(C(=O)N2CCc3cc(F)ccc32)cc(Cl)n1]

0.28 g (1.1 mmol) 2-chloro-6-methanesulphonylamino-isonicotinic acid, 0.16 g (1.1 mmol) 5-fluoro-2,3-dihydro-1H-indole, 0.31 mL (2.2 mmol) TEA in 4.0 mL DMF were mixed with 0.39 g (1.2 mmol) TBTU and stirred for 2 h at RT. The reaction mixture was purified by HPLC. The product fractions were combined and evaporated down.

Yield: 340 mg (81% of theory)
ESI-MS: m/z=370/372 (M+H)$^+$ (Cl)
R$_t$ (HPLC-MS): 1.4 min (method C)

Intermediate 82

N-[6-chloro-4-(5-fluoro-2,3-dihydro-indole-1-carbonyl)-pyridin-2-yl]-N-methyl-methane-sulphonamide

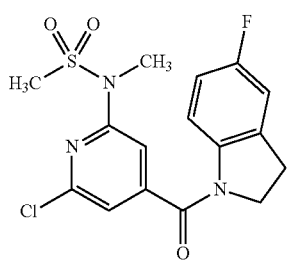 [SMILES: CN(c1cc(C(=O)N2CCc3cc(F)ccc32)cc(Cl)n1)S(C)(=O)=O]

0.30 g (1.1 mmol) 2-chloro-6-(methanesulphonyl-methyl-amino)-isonicotinic acid, 0.16 g (1.1 mmol) 5-fluoro-2,3-dihydro-1H-indole, 0.31 mL (2.2 mmol) TEA in 4.0 mL DMF were mixed with 0.39 g (1.2 mmol) TBTU and stirred for 2 h at RT. The reaction mixture was purified by HPLC. The product fractions were combined and evaporated down.

Yield: 360 mg (83% of theory)
ESI-MS: m/z=384/386 (M+H)$^+$ (Cl)
R$_t$ (HPLC-MS): 1.55 min (method C)

Intermediate 83

(6-chloro-pyrazin-2-yl)-(5-fluoro-2,3-dihydro-indol-1-yl)-methanone

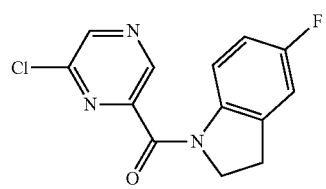 [SMILES: O=C(c1cncc(Cl)n1)N1CCc2cc(F)ccc21]

0.18 g (1.1 mmol) 6-chloro-pyrazine-2-carboxylic acid, 0.15 g (1.1 mmol) 5-fluoro-2,3-dihydro-1H-indole, 0.31 mL (2.2 mmol) TEA in 3.0 mL DMF were mixed with 0.39 g (1.2 mmol) TBTU and stirred for 1 h at RT. The reaction mixture was mixed with water and stirred for 5 min. The precipitated solid was filtered, washed with water and dried.

Yield: 235 mg (66% of theory)
EI-MS: m/z=277 (M+H)$^+$ (Cl)
R$_t$ (HPLC-MS): 1.48 min (method C)

Intermediate 84

(2-chloro-6-methoxypyridin-4-yl)-(5-fluoro-3,3-dimethyl-2,3-dihydroindol-1-yl)-methanone

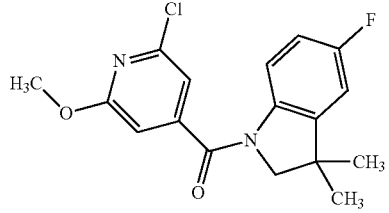 [SMILES: COc1cc(C(=O)N2CC(C)(C)c3cc(F)ccc32)cc(Cl)n1]

This compound was obtained analogously to (2-chloro-6-methoxypyridin-4-yl)-(5-fluoro-2,3-dihydroindol-1-yl)-methanone from 0.50 g (2.7 mmol) 2-chloro-6-methoxy-isonicotinic acid, 0.44 g (2.7 mmol) 5-fluoro-3,3-dimethyl-2,3-dihydro-1H-indole and 0.42 mL (3.0 mmol) triethylamine in 10 mL DMF.

Yield: 0.60 g (67% of theory)
ESI-MS: m/z=335/337 (M+H)$^+$ (Cl)
R$_t$(HPLC): 1.73 min (method C)

Intermediate 85

(6-chloro-pyrimidin-4-yl)-(2-ethyl-2,3-dihydro-indol-1-yl)-methanone

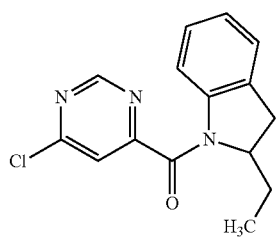 [SMILES: CCC1Cc2ccccc2N1C(=O)c1cc(Cl)ncn1]

Step 1: 1-benzenesulphonyl-1H-indole

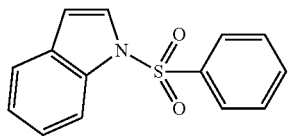 [SMILES: O=S(=O)(c1ccccc1)n1ccc2ccccc21]

0.89 g (22 mmol) sodium hydride (60%) were added to 2.0 g (17 mmol) indole in 30 mL THF while cooling with an ice bath and the mixture was stirred for 15 min at this temperature. Then 2.2 mL (17 mmol) benzenesulphonic acid chloride were added and stirred overnight at RT. The reaction mixture was combined with water and EtOAc and extracted several times with EtOAc. The combined organic phases were dried on sodium sulphate and evaporated down.

Yield: 4.6 g (quantitative)
ESI-MS: m/z=275 (M+H)$^+$

Step 2: 1-benzenesulphonyl-2-ethyl-1H-indole

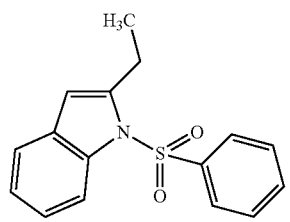 [SMILES: CCc1cc2ccccc2n1S(=O)(=O)c1ccccc1]

Under an argon atmosphere 6.7 mL (12 mmol) of a 1.8 molar lithium diisopropylamide solution in THF were slowly added dropwise to 2.8 g (11 mmol) 1-benzenesulphonyl-1H-indole in 25 mL THF at −78° C. Then the cooling was removed, the reaction mixture was heated to RT and stirred for a further hour at RT. The reaction mixture was cooled to −78° C. again and combined with 1.0 mL (12 mmol) iodoethane. Then the reaction mixture was heated to RT again and stirred overnight. As the reaction was unfinished the reaction mixture was again cooled to −78° C., mixed with 3.3 mL (6.0 mmol) of a 1.8 molar lithium diisopropylamide solution in THF and once the addition had ended heated to RT. Then the reaction mixture was poured onto ice water and extracted with EtOAc. The organic phase was dried on sodium sulphate and evaporated down. The residue was purified by flash chromatography. The product-containing fractions were combined, evaporated down and dried under HV.

Yield: 0.75 g (24% of theory)
$R_f$: 0.61 (silica gel, PE/EtOAc 3/1)

Step 3: 2-ethyl-1H-indole

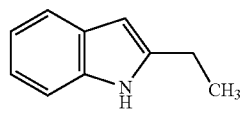

1.2 g (4.2 mmol) 1-benzenesulphonyl-2-ethyl-1H-indole in 10 mL EtOH were combined with 5 mL of a (20 mmol) 4 N aqueous sodium hydroxide solution and refluxed for 8 h. Then the solvent was eliminated using the rotary evaporator and the residue was diluted with ice water. After acidifying with semi-concentrated aqueous hydrochloric acid the grease precipitated was extracted with ethyl acetate. The organic phase was dried on sodium sulphate, filtered off, evaporated down and dried.

Yield: 0.66 g (quantitative)
ESI-MS: m/z=146 (M+H)$^+$

Step 4: 2-ethyl-2,3-dihydro-1H-indole

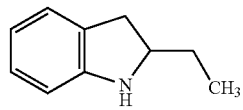

0.66 g (4.2 mmol) 2-ethyl-1H-indole in 10 mL acetic acid were mixed with 1.3 g (20 mmol) sodium cyanoborohydride and stirred for one day at RT. The reaction mixture was evaporated down using the rotary evaporator, combined with 20 mL aqueous 4N hydrochloric acid and stirred for 1 h at RT. While cooling with ice 45 mL of an aqueous 4N sodium hydroxide solution were then added and the mixture was extracted with ethyl acetate. The organic phase was dried on sodium sulphate, filtered, evaporated down and the residue was dried in vacuo.

Yield: 0.80 g (quantitative)

Step 5: (6-chloro-pyrimidin-4-yl)-(2-ethyl-2,3-dihydro-indol-1-yl)-methanone

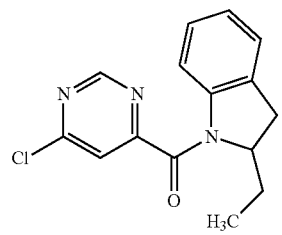 [SMILES: CCC1Cc2ccccc2N1C(=O)c1cc(Cl)ncn1]

0.80 g (4.5 mmol) 6-chloropyrimidine-4-carboxylic acid chloride in 30 mL DCM were cooled in a bath of ice/ethanol and mixed with 0.62 g (4.2 mmol) 2-ethyl-2,3-dihydro-1H- indole in DCM and 4.7 mL (4.7 mmol) of a 1M aqueous sodium hydroxide solution. Then the mixture was stirred for 30 min with cooling and for 1 h at RT. After the addition of 50 mL of a saturated sodium hydrogen carbonate solution the mixture was stirred for a further 10 min. The organic phase was separated off, washed with water and evaporated down. The residue was purified by flash chromatography. The product-containing fractions were combined, evaporated down and dried.

Yield: 0.25 g (19% of theory)
$R_f$: 0.54 (silica gel, PE/EtOAc 4/1)

Intermediate 86

3-bromo-5-(5-fluoroindoline-1-carbonyl)pyridine-1-oxide

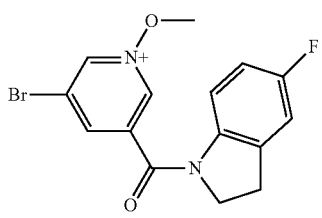 [SMILES: CO[n+]1cc(Br)cc(C(=O)N2CCc3cc(F)ccc32)c1]

Step 1: (5-bromo-pyridin-3-yl)-(5-fluoro-2,3-dihydro-indol-1-yl)-methanone

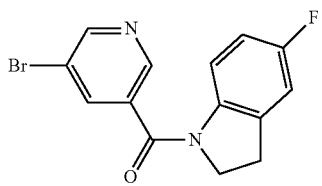 [SMILES: O=C(c1cncc(Br)c1)N1CCc2cc(F)ccc21]

0.44 g (2.2 mmol) 5-bromonicotinic acid, 0.30 g (2.2 mmol) 5-fluoroindoline, 0.75 g (2.3 mmol) TBTU and 0.60 mL (4.3 mmol) TEA were combined in 3.0 mL DMF and stirred overnight at RT. Then the reaction mixture was added to water, the precipitate formed was suction filtered and dried.

Yield: 700 mg (quantitative)
ESI-MS: m/z=321/323 (Br) (M+H)$^+$
$R_t$ (HPLC-MS): 0.43 min (method C)

Step 2: 3-bromo-5-(5-fluoroindoline-1-carbonyl)pyridine-1-oxide

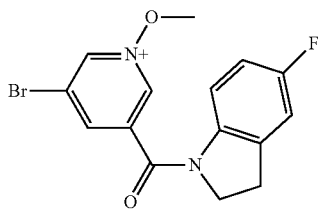 [SMILES: CO[n+]1cc(Br)cc(C(=O)N2CCc3cc(F)ccc32)c1]

0.19 g (1.1 mmol) m-chloroperbenzoic acid were added to 0.32 g (0.98 mmol) (5-bromo-pyridin-3-yl)-(5-fluoro-2,3-dihydro-indol-1-yl)-methanone in 5.0 mL DCM and the mixture was stirred for 4 h at RT. In addition, a further 95 mg (0.55 mmol) m-chloroperbenzoic acid were added to the reaction mixture and it was stirred for 48 h at RT. Then the reaction mixture was diluted with DCM and extracted with 1N aqueous sodium hydroxide solution. The organic phase was dried on sodium sulphate, evaporated down and dried under HV.

Yield: 330 mg (quantitative)
ESI-MS: m/z=337 (M+H)$^+$
$R_t$ (HPLC-MS): 1.22 min (method C)

Intermediate 87

(4-chloro-5-iodo-pyridin-2-yl)-(5-fluoro-2,3-dihydro-indol-1-yl)-methanone

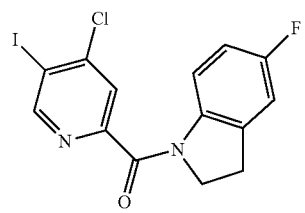 [SMILES: O=C(c1cc(Cl)c(I)cn1)N1CCc2cc(F)ccc21]

Step 1: 5-bromo-2-methylpyridine-1-oxide

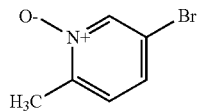

39 g (0.16 mol) 3-chloroperbenzoic acid in 450 mL DCM (dried on sodium sulphate) were added dropwise within 2 h to 25 g (0.15 mol) 5-bromo-2-methylpyridine in 50 mL DCM. Then the reaction mixture was stirred for 20 h at RT and extracted with 15% potassium carbonate solution. The organic phase was dried on sodium sulphate and evaporated down.

Yield: 21 g (76% of theory)
ESI-MS: m/z=337 (M+H)$^+$
$R_t$ (HPLC-MS): 0.75 min (method C)

Step 2: 5-bromo-2-methyl-4-nitropyridine-1-oxide

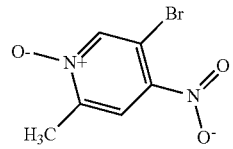

6.0 mL nitric acid were added dropwise to 6.0 mL conc. sulphuric acid while cooling with ice and stirring. Then 3.6 g (21 mmol) 5-bromo-2-methylpyridine-1-oxide were added batchwise and the reaction mixture was stirred for 18 h at 60° C. After cooling to RT the reaction mixture was added to ice water and neutralised with 4N aqueous sodium hydroxide solution. The precipitated solid was suction filtered and dried at 50° C.

Yield: 3.60 g (73% of theory)
ESI-MS: m/z=233 (M+H)$^+$
R$_t$ (HPLC-MS): 1.09 min (method C)

Step 3: 5-bromo-4-chloro-2-methylpyridine-1-oxide

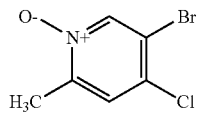

4.2 mL (46 mmol) phosphorus oxychloride in 20 mL DCM were added dropwise at 10° C. to 3.6 g (15 mmol) 5-bromo-2-methyl-4-nitropyridine-1-oxide in 30 mL DCM. The reaction mixture was then refluxed for 5 h, then added to ice water and adjusted to a pH of 10 with 4N aqueous sodium hydroxide solution. The organic phase was separated off and the aqueous phase was extracted twice more with DCM. The combined organic phases were dried on sodium sulphate and evaporated down. The residue was stirred into petroleum ether, the precipitate formed was suction filtered and dried.

Yield: 2.60 g (76% of theory)
R$_t$ (HPLC-MS): 1.08 min (method C)

Step 4: (5-bromo-4-chloro-pyridin-2-yl)-methanol

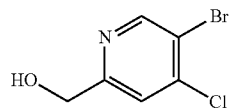

3.0 mL trifluoroacetic anhydride were added dropwise at 10° C. to 2.6 g (12 mmol) 5-bromo-4-chloro-2-methylpyridine-1-oxide in 30 mL DCM. The reaction mixture was stirred for 5 days at RT. After the addition of MeOH the reaction mixture was evaporated down, the residue was combined with 15% potassium carbonate solution and extracted several times with EtOAC. The combined organic phases were dried on sodium sulphate and evaporated down.

Yield: 2.15 g (83% of theory)
ESI-MS: m/z=222 (M+H)$^+$
R$_t$ (HPLC-MS): 1.10 min (method C)

Step 5: 5-bromo-4-chloro-pyridine-2-carboxylic acid

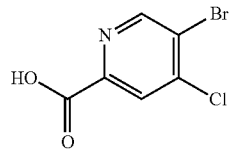 [SMILES: O=C(O)c1cc(Cl)c(Br)cn1]

0.50 g (2.3 mmol) (5-bromo-4-chloro-pyridin-2-yl)-methanol in 8 mL acetone were added dropwise at RT to 0.71 g (4.5 mmol) potassium permanganate in 10 mL acetone and then the mixture was stirred for 17 h at RT. Then 10 mL isopropanol were added and the mixture was stirred for a further 5 h at RT. The precipitated manganese dioxide was suction filtered and washed with water. The filtrate was partially evaporated down and the aqueous phase was adjusted to a pH of 3 with 1N aqueous hydrochloric acid solution. The precipitate formed was suction filtered.

Yield: 330 mg (62% of theory)
ESI-MS: m/z=234 (M−H)$^−$
R$_t$ (HPLC-MS): 1.09 min (method C)

Step 6: (5-bromo-4-chloro-pyridin-2-yl)-(5-fluoro-2,3-dihydro-indol-1-yl)-methanone

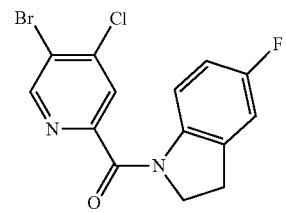 [SMILES: O=C(c1cc(Cl)c(Br)cn1)N1CCc2cc(F)ccc21]

0.75 mg (2.3 mmol) TBTU were added to 0.50 g (2.1 mmol) 5-bromo-4-chloro-pyridine-2-carboxylic acid, 0.29 g (2.1 mmol) 5-fluoro-2,3-dihydro-1H-indole and 0.62 mL (4.4 mmol) TEA in 11 mL DMF and the mixture was stirred overnight at RT. Then the reaction mixture was combined with water, the precipitate formed was suction filtered and dried.

Yield: 356 mg (85% of theory)
ESI-MS: m/z=355 (M+H)$^+$

Step 7: (4-chloro-5-iodo-pyridin-2-yl)-(5-fluoro-2,3-dihydro-indol-1-yl)-methanone

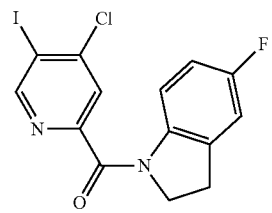 [SMILES: O=C(c1cc(Cl)c(I)cn1)N1CCc2cc(F)ccc21]

Under a nitrogen atmosphere 1.3 g (8.4 mmol) sodium iodide, 80 mg (0.42 mmol) copper iodide and 90 μL (0.84 mmol) N,N-dimethylene-ethylenediamine were added to 1.5 g (4.2 mmol) (5-bromo-4-chloro-pyridin-2-yl)-(5-fluoro-2,3-dihydro-indol-1-yl)-methanone in 15 mL 1,4-dioxane and the mixture was stirred for 5 days at 110° C. The reaction mixture was diluted with water, the precipitate formed was suction filtered and dried.

Yield: 1.57 g (92% of theory)
ESI-MS: m/z=403 (M+H)$^+$
R$_t$ (HPLC-MS): 1.80 min (method C)

Intermediate 88

(4-chloro-6-methoxy-pyridin-2-yl)-(5-fluoro-2,3-dihydro-indol-1-yl)-methanone

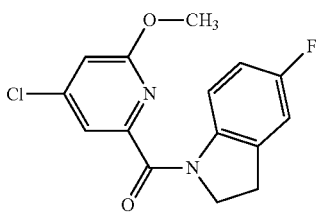 [SMILES: COc1cc(Cl)cc(C(=O)N2CCc3cc(F)ccc32)n1]

0.55 g (2.9 mmol) 4-chloro-6-methoxy-pyridine-2-carboxylic acid, 0.41 g (3.0 mmol) 5-fluoroindoline, 1.1 g (3.3 mmol) TBTU and 0.93 mL (6.6 mmol) triethylamine in 5.0 mL DMF were stirred for 3 h at RT. The reaction mixture was purified by HPLC. The product-containing fractions were combined and evaporated down using the rotary evaporator.

Yield: 450 mg (50% of theory)
ESI-MS: m/z=307/309 (M+H)+ (Cl)
$R_t$(HPLC): 1.7 min (method C)

Intermediate 89

4-chloro-6-(5-fluoro-2,3-dihydro-indole-1-carbonyl)-nicotinonitrile

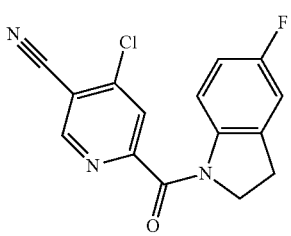 [SMILES: N#Cc1cnc(C(=O)N2CCc3cc(F)ccc32)cc1Cl]

Under a nitrogen atmosphere 45 mg (0.50 mmol) copper cyanide were added to 0.10 g (0.25 mmol) (4-chloro-5-iodo-pyridin-2-yl)-(5-fluoro-2,3-dihydro-indol-1-yl)-methanone in 1.5 mL DMF and the mixture was stirred for 2 h at RT. The reaction mixture was stirred overnight at 100° C. and then mixed with d-water. The precipitate formed was suction filtered and dried.

Yield: 75 mg (quantitative)
MS: m/z=301 (M+)
$R_t$ (HPLC-MS): 1.65 min (method C)

Intermediate 90

(4-chloro-6-methyl-pyridin-2-yl)-(5-fluoro-2,3-dihydro-indol-1-yl)-methanone

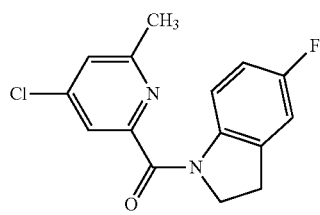 [SMILES: Cc1cc(Cl)cc(C(=O)N2CCc3cc(F)ccc32)n1]

0.10 g (0.58 mmol) 4-chloro-6-methyl-pyridine-2-carboxylic acid and 80 mg (0.58 mmol) 5-fluoro-2,3-dihydro-1H-indole in 0.17 mL (1.2 mmol) TEA and 2.0 mL DMF were combined with 0.19 g (0.58 mmol) TBTU and stirred overnight at RT. The reaction mixture was diluted with water, the precipitated solid was suction filtered and dried.

Yield: 125 mg (74% of theory)
ESI-MS: m/z=291 (M+H)+
$R_t$ (HPLC-MS): 0.31 min (method C)

Intermediate 91

(6-chloro-pyrimidin-4-yl)-(5-fluoro-2,3-dihydro-indol-1-yl)-methanone

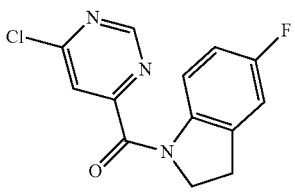 [SMILES: O=C(c1cc(Cl)ncn1)N1CCc2cc(F)ccc21]

0.92 g (4.9 mmol) 6-chloro-pyrimidine-4-carboxylic acid chloride in 40 mL DCM were cooled in a bath of ice/acetone and mixed with 0.67 g (4.9 mmol) 5-fluoro-2,3-dihydro-1H-indole. Then 5.0 mL (5.0 mmol) of a 1N aqueous sodium hydroxide solution were added dropwise and the mixture was stirred for 1 h with cooling. 50 mL of a saturated sodium hydrogen carbonate solution were added and the mixture was stirred for a further 10 min. The organic phase was separated off, extracted with a 1N aqueous hydrochloric acid solution and with water, dried and evaporated down.

Yield: 0.81 g (60% of theory)
ESI-MS: m/z=278 (M+H)+
$R_t$ (HPLC-MS): 1.50 min (method C)

Intermediate 92

(2,6-dichloro-pyridin-4-yl)-(5-fluoro-2,3-dihydro-indol-1-yl)-methanone

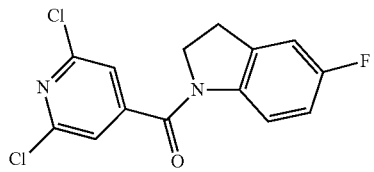 [SMILES: O=C(c1cc(Cl)nc(Cl)c1)N1CCc2cc(F)ccc21]

2.0 g (9.5 mmol) 2,6-dichloro-pyridine-4-carboxylic acid chloride in 50 mL DCM were cooled in the ice/EtOH bath and combined with 1.3 g (9.6 mmol) 5-fluoro-2,3-dihydro-1H-indole. In addition 9.6 mL (9.6 mmol) of a 1N aqueous sodium hydroxide solution were added dropwise and the mixture was stirred for 2 h while being cooled and for 1 h at RT. Then 50 mL of a saturated sodium hydrogen carbonate solution were added and the mixture was stirred for a further 10 min. The organic phase was separated off, extracted with 1N aqueous hydrochloric acid solution and with water, dried on sodium sulphate and evaporated down.

Yield: 2.85 g (96% of theory)
ESI-MS: m/z=311 (M+H)$^+$
$R_t$ (HPLC-MS): 4.57 min (method E)

Intermediate 93

(3-bromo-phenyl)-(5-fluoro-2,3-dihydro-indol-1-yl)-methanone

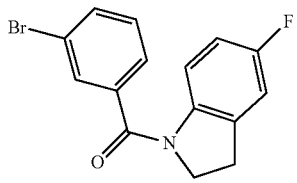 [SMILES: O=C(c1cccc(Br)c1)N1CCc2cc(F)ccc21]

0.40 g (2.0 mmol) 3-bromobenzoic acid and 0.28 g (2.0 mmol) 5-fluoro-2,3-dihydro-1H-indole in 0.55 mL (4.0 mmol) TEA and 10 mL DCM were combined with 0.64 mg (2.0 mmol) TBTU and stirred overnight at RT. The reaction mixture was extracted with saturated sodium hydrogen carbonate solution and DCM. The combined organic phases were dried on sodium sulphate, filtered and evaporated down. The residue was suspended in MeOH, suction filtered and dried.

Yield: 475 mg (71% of theory)
ESI-MS: m/z=320 (M+H)$^+$
$R_t$ (HPLC-MS): 1.64 min (method C)

Intermediate 94

4-(7-methoxy-2-oxo-1,2,4,5-tetrahydro-benzo[d][1,3]diazepin-3-yl)-3,4,5,6-tetrahydro-2H-[1,4']bipyridinyl-2'-carboxylic acid

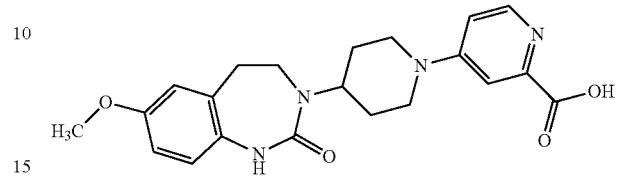

7.0 g (25 mmol) 7-methoxy-3-piperidin-4-yl-1,3,4,5-tetrahydro-1,3-benzodiazepin-2-one and 2.5 g (12 mmol) 4-bromopicolinic acid in 25 mL NMP were stirred for 2 h at 110° C. The reaction mixture was combined with some formic acid and purified by preparative HPLC-MS. The product-containing fractions were combined and evaporated down. The residue was stirred with MeOH, suction filtered and dried.

Yield: 0.95 g (19% of theory)
ESI-MS: m/z=397 (M+H)$^+$
$R_t$ (HPLC-MS): 1.25 min (method S)

Intermediate 95

4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid

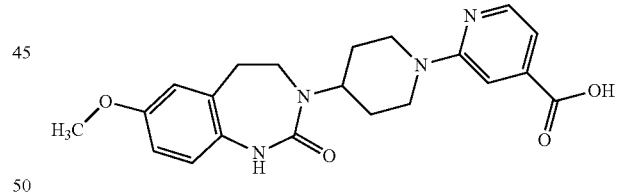

6.0 g (22 mmol) 7-methoxy-3-piperidin-4-yl-1,3,4,5-tetrahydro-1,3-benzodiazepin-2-one and 1.5 g (11 mmol) 2-fluoropyridine-4-carboxylic acid in 20 mL NMP were stirred overnight at 110° C. The reaction mixture was cooled and the precipitate formed was suction filtered. This was stirred with water, additionally combined with 15% potassium carbonate solution and extracted several times with DCM. The aqueous phase was acidified, the precipitate formed was suction filtered and dried.

Yield: 1.30 g (31% of theory)
ESI-MS: m/z=397 (M+H)$^+$
$R_t$ (HPLC-MS): 1.19 min (method S)

Intermediate 96

4-cyano-3-[4-(2-oxo-2,3-dihydro-imidazo[4,5-b]pyridin-1-O-piperidin-1-yl]-benzoic acid

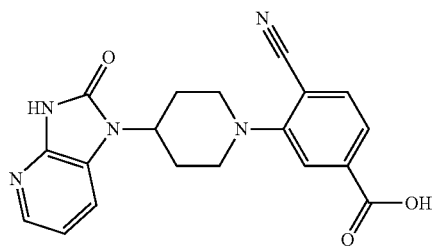 [SMILES: N#Cc1ccc(C(=O)O)cc1N1CCC(n2c(=O)[nH]c3ncccc32)CC1]

0.20 g (1.2 mmol) 4-cyano-3-fluorobenzoic acid and 0.53 g (2.4 mmol) 1-piperidin-4-yl-1,3-dihydroimidazo[4,5-b]pyridin-2-one were first of all mixed thoroughly before being melted for 10 minutes with the hot air blower. After the reaction mixture had cooled it was taken up in water, made basic with aqueous ammonia solution and extracted several times with EtOAc. The aqueous phase was evaporated down and purified by preparative HPLC-MS.

Yield: 0.20 g (41% of theory)

ESI-MS: m/z=364 (M+H)$^+$

R$_t$ (HPLC-MS): 1.28 min (method C)

Intermediate 97

1-[2'-(5-fluoro-2,3-dihydro-indole-1-carbonyl)-5'-iodo-3,4,5,6-tetrahydro-2H-[1,4']bipyridinyl-4-yl]-1,3-dihydro-imidazo[4,5-b]pyridin-2-one

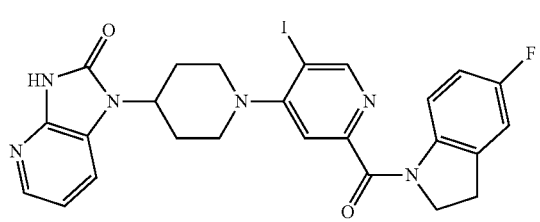 [SMILES: O=C(c1cc(N2CCC(n3c(=O)[nH]c4ncccc43)CC2)c(I)cn1)N1CCc2cc(F)ccc21]

0.50 g (1.2 mmol) (4-chloro-5-iodo-pyridin-2-yl)-(5-fluoro-2,3-dihydro-indol-1-yl)-methanone, 0.27 g (1.2 mmol) 1-piperidin-4-yl-1,3-dihydroimidazo[4,5-b]pyridin-2-one, 0.26 g (1.9 mmol) potassium carbonate and 3.5 mL NMP were combined and stirred at 130° C. for 10 h. After the addition of water the precipitate formed was suction filtered and dried.

Yield: 450 mg (62% of theory)

R$_t$ (HPLC-MS): 1.70 min (method C)

Intermediate 98

3-[2'-(5-fluoro-2,3-dihydro-indole-1-carbonyl)-5'-trimethylsilanylethynyl-3,4,5,6-tetrahydro-2H-[1,4']bipyridinyl-4-yl]-7-methoxy-1,3,4,5-tetrahydro-benzo[d][1,3]diazepin-2-one

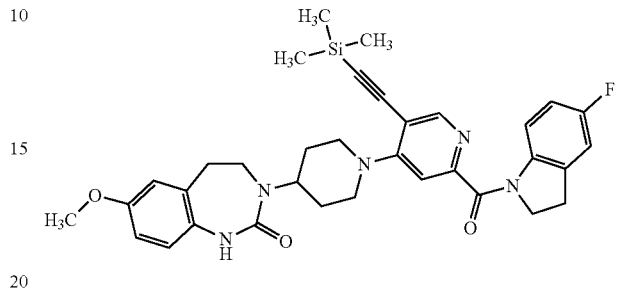

Step 1: 3-[5'-bromo-2'-(5-fluoro-2,3-dihydro-indole-1-carbonyl)-3,4,5,6-tetrahydro-2H-[1,4']bipyridinyl-4-yl]-7-methoxy-1,3,4,5-tetrahydro-benzo[d][1,3]-diazepin-2-one

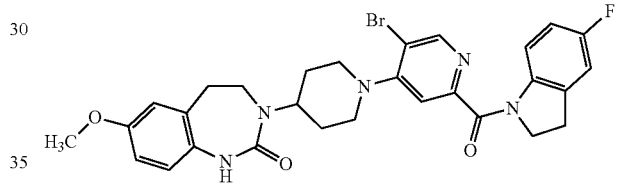

0.38 g (1.1 mmol) (5-bromo-4-chloro-pyridin-2-yl)-(5-fluoro-2,3-dihydro-indol-1-yl)-methanone, 0.29 g (1.1 mmol) 7-methoxy-3-piperidin-4-yl-1,3,4,5-tetrahydro-1,3-benzodiazepin-2-one, 0.22 g (1.6 mmol) potassium carbonate and 3.0 mL NMP were combined and stirred for 10 h at 130° C. Then the reaction mixture was combined with water and the precipitate formed was suction filtered and dried.

Yield: 0.47 g (74% of theory)

ESI-MS: m/z=594 (M+H)$^+$

R$_t$(HPLC): 1.72 min (method C)

Step 2: 3-[2'-(5-fluoro-2,3-dihydro-indole-1-carbonyl)-5'-iodo-3,4,5,6-tetrahydro-2H-[1,4']bipyridinyl-4-yl]-7-methoxy-1,3,4,5-tetrahydro-benzo[d][1,3]-diazepin-2-one

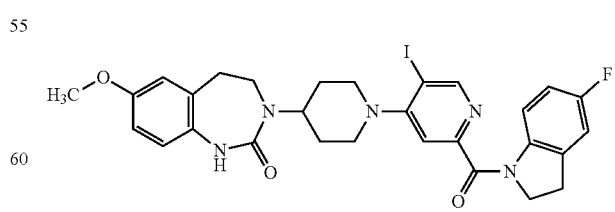

Under a nitrogen atmosphere 91 mg (0.61 mmol) sodium-iodide, 6 mg (0.03 mmol) copper iodide and 0.09 mL (0.01 mmol) N,N-dimethylene-ethylene-diamine were added to 0.18 g (0.30 mmol) 3-[5'-bromo-2'-(5-fluoro-2,3-dihydro-indole-1-carbonyl)-3,4,5,6-tetrahydro-2H-[1,4']bipyridinyl-4-yl]-7-methoxy-1,3,4,5-tetrahydro-benzo[d][1,3]diazepin-2-one in 1.0 mL 1,4-dioxane and the mixture was stirred overnight at 110° C. Then an additional 0.3 mL DMF was added and the reaction mixture was stirred for a further 10 days at 110° C. After being diluted with water the precipitate formed was suction filtered and dried.

Yield: 194 mg (75% of theory)
purity: 75%
$R_t$ (HPLC-MS): 1.79 min (method C)

Step 3: 3-[2'-(5-fluoro-2,3-dihydro-indole-1-carbonyl)-5'-trimethylsilanylethynyl-1-3,4,5,6-tetrahydro-2H-[1,4']bipyridinyl-4-yl]-7-methoxy-1,3,4,5-tetrahydro-benzo[d][1,3]diazepin-2-one

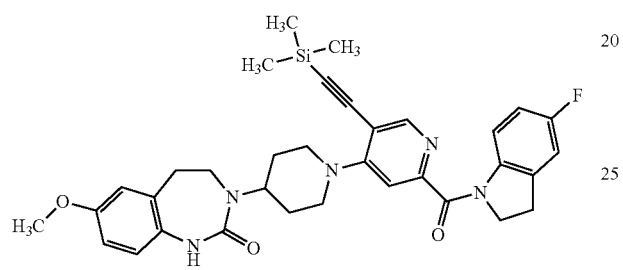

Under an argon atmosphere 22 mg (0.03 mmol) 1,1-bis(diphenylphosphino)ferrocene-dichloro-palladium (II) and 12 mg (0.06 mmol) copper iodide were added to 0.19 g (0.23 mmol) 3-[2'-(5-fluoro-2,3-dihydro-indole-1-carbonyl)-5'-iodo-3,4,5,6-tetrahydro-2H-[1,4']bipyridinyl-4-yl]-7-methoxy-1,3,4,5-tetrahydro-benzo[d][1,3]diazepin-2-one in 0.13 mL (0.91 mmol) TEA and 4.0 mL dioxane. Then another 0.42 mL (3.0 mmol) trimethyl-prop-1-ynyl-silane were added and the reaction mixture was stirred overnight at RT. After the addition of MeOH the precipitate formed was suction filtered and the filtrate was evaporated down. The residue was dissolved in DMF and acetonitrile and purified by preparative HPLC-MS. The product-containing fractions were combined and evaporated down.

Yield: 35 mg (25% of theory)
$R_t$ (HPLC-MS): 1.88 min (method C)

Intermediate 99

3-{1-[6-(5-benzyloxy-pyrrolo[3,2-b]pyridine-1-carbonyl)-pyrimidin-4-yl]-piperidin-4-yl}-7-methoxy-1,3,4,5-tetrahydro-benzo[d][1,3]diazepin-2-one

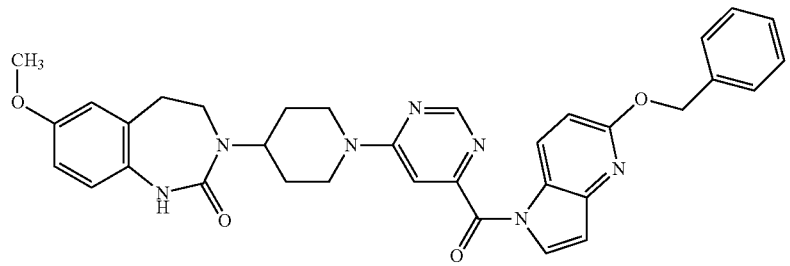 [SMILES: COc1ccc2c(c1)CCN(C1CCN(c3cc(C(=O)n4ccc5nc(OCc6ccccc6)ccc54)ncn3)CC1)C(=O)N2]

Step 1: 2-benzyloxy-5-nitro-pyridine

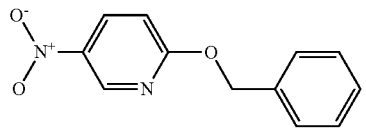 [SMILES: [O-][NH+](O)c1ccc(OCc2ccccc2)nc1]

32 g (0.20 mol) 2-chloro-5-nitropyridine in 120 mL toluene were combined with 200 mL (0.20 mmol) of a 1M sodium benzylate solution in benzylalcohol and stirred overnight at RT. The organic phase was washed with water and saturated sodium chloride solution, dried on sodium sulphate and the toluene was eliminated by distillation. The residue was cooled with ice, the precipitate formed was suction filtered and washed several times with tert.-butylmethylether.

Yield: 33.1 g (72% of theory)

Step 2: (6-benzyloxy-3-nitro-pyridin-2-yl)-acetonitrile

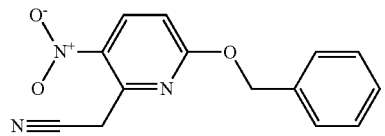 [SMILES: N#CCc1nc(OCc2ccccc2)ccc1[NH+]([O-])O]

Under a nitrogen atmosphere 11.5 g (50 mmol) 2-benzyloxy-5-nitro-pyridine and 9.2 g (55 mmol) 4-chlorophenoxy-acetonitrile in 100 mL DMF were added dropwise at −10° C. to 13.7 g (120 mmol) potassium tert. butoxide in 50 mL DMF. After one hour's stirring at −10° C. 120 mL of a 1N aqueous hydrochloric acid solution were added dropwise to the reaction mixture which was then stirred for 30 min at 0° C. The precipitate formed was suction filtered and purified by flash chromatography. The product-containing fractions were evaporated down and the residue was combined with diisopropylether/PE (1/1) and stirred. The precipitate formed was suction filtered, washed with diisopropylether and dried.

Yield: 10.9 g (81% of theory)
ESI-MS: m/z=268 (M−H)⁻
$R_f$: 0.75 (silica gel, DCM)

Step 3:
(3-amino-6-benzyloxy-pyridin-2-yl)-acetonitrile

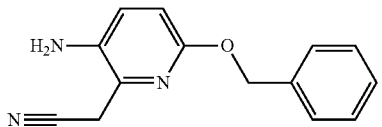 [SMILES: N#CCc1nc(OCc2ccccc2)ccc1N]

11 g (40 mmol) (6-benzyloxy-3-nitro-pyridin-2-yl)-acetonitrile and 1.7 g Raney nickel (washed with abs. EtOH) in 120 mL EtOH and 50 mL acetic acid were hydrogenated at RT in a hydrogen atmosphere of 3 bar. The catalyst was filtered off and the filtrate was evaporated down. The residue was combined with 30 mL water and adjusted to pH=10 with solid sodium carbonate. The aqueous phase was extracted several times with EtOAc. The combined organic phases were dried on magnesium sulphate, filtered and evaporated down. The residue was purified by flash chromatography. The product-containing fractions were combined and evaporated down.

Yield: 1.80 g (9% of theory)
ESI-MS: m/z=225 (M+H)+⁻
$R_t$ (HPLC-MS): 1.10 min (method C)

Step 4: (5-benzyloxy-pyrrolo[3,2-b]pyrimidin-1-yl)-(6-chloro-pyrimidin-4-yl)-methanone

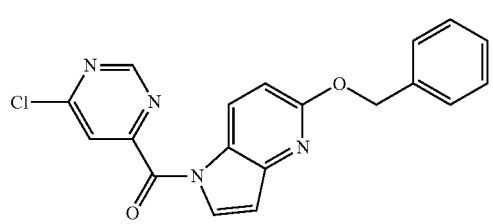 [SMILES: O=C(c1cc(Cl)ncn1)n1ccc2nc(OCc3ccccc3)ccc21]

Under a nitrogen atmosphere 0.11 g (2.8 mmol) sodium hydride (60%) were added batchwise to 0.60 g (2.7 mmol) (3-amino-6-benzyloxy-pyridin-2-yl)-acetonitrile in 15 mL THF and the mixture was stirred for 30 min at RT. 0.45 g (2.5 mmol) 6-chloro-pyrimidine-4-carboxylic acid chloride were added batchwise and the mixture was stirred for 2 h at RT. The reaction mixture was then diluted with 50 mL EtOAc and extracted with saturated sodium hydrogen carbonate solution, water and 1N aqueous hydrochloric acid solution. The organic phase was dried on magnesium sulphate, filtered and evaporated down. The residue was purified by flash chromatography. The product-containing fractions were combined and evaporated down.

Yield: 420 mg (45% of theory)
ESI-MS: m/z=364 (M+H)+⁻
$R_t$ (HPLC-MS): 1.79 min (method C)

Step 5: 3-{1-[6-(5-benzyloxy-pyrrolo[3,2-b]pyridine-1-carbonyl)-pyrimidin-4-yl]-piperidin-4-yl}-7-methoxy-1,3,4,5-tetrahydro-benzo[d][1,3]diazepin-2-one

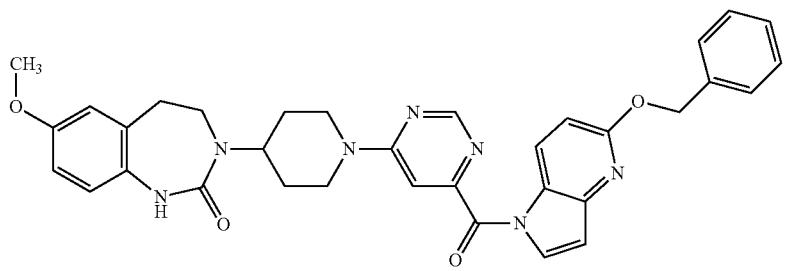 [SMILES: COc1ccc2c(c1)CCN(C1CCN(c3cc(C(=O)n4ccc5nc(OCc6ccccc6)ccc54)ncn3)CC1)C(=O)N2]

0.11 g (0.40 mmol) 7-methoxy-3-piperidin-4-yl-1,3,4,5-tetrahydro-1,3-benzodiazepin-2-one, 0.14 g (0.38 mmol) (5-benzyloxy-pyrrolo[3,2-b]pyrimidin-1-yl)-(6-chloro-pyrimidin-4-yl)-methanone and 0.10 mL (0.58 mmol) DIPEA in 5 mL DMF were stirred overnight at RT. The reaction mixture was diluted with water and stirred for 30 min. The precipitate formed was suction filtered, washed with water and MeOH and dried.

Yield: 210 mg (91% of theory)
ESI-MS: m/z=604 (M+H)⁺
$R_t$ (HPLC-MS): 1.75 min (method C Example 100

4-[4-(2-oxo-2,3-dihydro-imidazo[4,5-b]pyridin-1-yl)-piperidin-1-yl]-pyrimidine-2-carboxylic acid

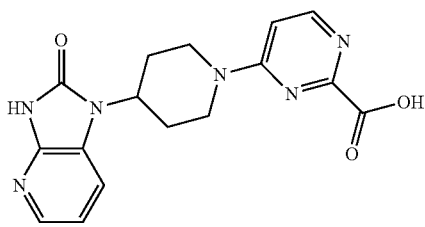

Step 1: 1-[1-(2-bromo-pyrimidin-4-yl)-piperidin-4-yl]-1,3-dihydro-imidazo[4,5-b]-pyridin-2-one

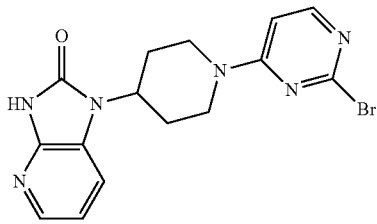 [SMILES: O=c1[nH]c2ncccc2n1C1CCN(c2ccnc(Br)n2)CC1]

1.4 g (4.8 mmol) 1-piperidin-4-yl-1,3-dihydro-imidazo[4,5-b]pyridin-2-one-dihydrochloride, 1.1 g (4.8 mmol) 2,4-dibromo-pyrimidine, a spatula tip of DMAP and 3.3 mL (19.1 mmol) DIPEA in 35 mL ethanol were stirred at RT. After the reaction had ended the precipitate was suction filtered, washed with a little ethanol and dried.
Yield: 1.6 g (90% of theory)
ESI-MS: m/z=375/377 (Br) (M+H)$^+$
R$_t$ (HPLC-MS): 1.08 min (method C)

Step 2: methyl 4-[4-(2-oxo-2,3-dihydro-imidazo[4,5-b]pyridin-1-yl)-piperidin-1-yl]-pyrimidine-2-carboxylate

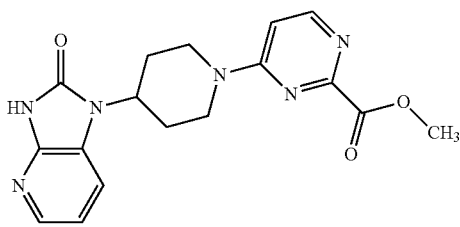 [SMILES: COC(=O)c1nccc(N2CCC(n3c(=O)[nH]c4ncccc43)CC2)n1]

In a carbon monoxide atmosphere 1.0 g (2.7 mmol) 1-[1-(2-bromo-pyrimidin-4-yl)-piperidin-4-yl]-1,3-dihydro-imidazo[4,5-b]pyridin-2-one, 0.10 g (0.27 mmol) bis-(benzonitrile)-palladium (II) chloride, 0.15 g (0.27 mmol) dppf and 0.45 mL triethylamine were carbonylated in 30 mL methanol for 13 h at 130° C. under 25 bar of CO pressure. The reaction mixture was evaporated down and the residue was stirred with methanol. The solid was suction filtered and dried.
Yield: 0.50 g (53% of theory)
ESI-MS: m/z=355 (M+H)$^+$
R$_t$ (HPLC-MS): 0.83 min (method C)

Step 3: 4-[4-(2-oxo-2,3-dihydro-imidazo[4,5-b]pyridin-1-yl)-piperidin-1-yl]-pyrimidine-2-carboxylic acid

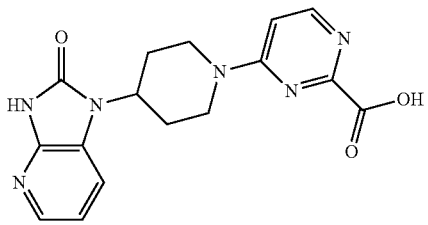 [SMILES: O=C(O)c1nccc(N2CCC(n3c(=O)[nH]c4ncccc43)CC2)n1]

0.50 g (1.4 mmol) methyl 4-[4-(2-oxo-2,3-dihydro-imidazo[4,5-b]pyridin-1-yl)-piperidin-1-yl]-pyrimidine-2-carboxylate, 1.1 mL d-water and 1.1 mL 4 M sodium hydroxide solution in 9.0 mL tetrahydrofuran was stirred overnight at RT. The organic solvent was removed and the residue was diluted with 250 mL water. After the addition of 25 mL 4M hydrochloric acid solution the mixture was stirred for 1 h. The precipitated solid was suction filtered, washed with water and dried.
Yield: 0.37 g (53% of theory)
ESI-MS: m/z=341 (M+H)$^+$
R$_t$ (HPLC-MS): 0.63 min (method C)

Intermediate 101

(S)-2-(3,5-difluorophenyl)-5,5-dimethylpiperidine

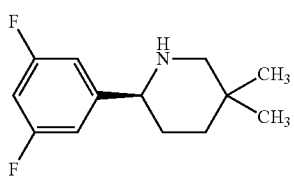

7.0 mL (7.0 mmol) of a 1 molar di-isobutyl-aluminium hydride solution in toluene were added to 0.48 g (2.0 mmol) (S)-6-(3,5-difluorophenyl)-3,3-dimethylpiperidin-2-one in 10 mL THF while cooling with ice and stirred for 20 h at RT. Then the reaction mixture was refluxed for 8 h. A 1M diisobutylaluminium hydride solution in toluene was added twice more and the mixture was refluxed for 8 h and 24 h in each case. After hydrolysis of the reaction mixture the precipitate formed was suction filtered and washed with THF. The filtrate was evaporated down and the residue was purified by flash chromatography (aluminium oxide).
Yield: 0.40 g (53% of theory)
ESI-MS: m/z=226 (M+H)$^+$
R$_t$ (HPLC-MS): 1.55 min (method C)

Intermediate 102 tert. butyl 6-chloro-5-methyl-pyrimidine-4-carboxylate

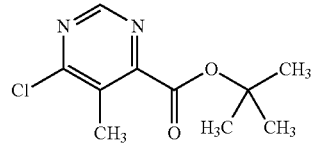

Step 1: ethyl 6-hydroxy-5-methyl-pyrimidine-4-carboxylate

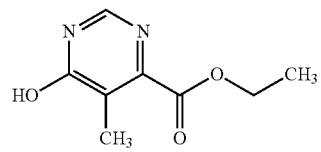

Under a nitrogen atmosphere 28.4 g (0.27 mol) formamidine acetate in 200 mL ethanol was added dropwise at −10° C.

to 6.2 g (0.27 mol) sodium in 150 mL ethanol. The reaction mixture was stirred for 5 min and the suspension was suction filtered. 50 mL of diethyloxal propionate was added dropwise to the filtrate at −10° C. The reaction mixture was stirred overnight in the ice bath. Then the reaction mixture was refluxed for 5 h. 300 mL tert.-butylmethylether were added to the suspension and this was cooled to 3° C. The suspension was suction filtered and washed with TBME. The filtrate was concentrated by rotary evaporation and the residue was combined with 300 mL ethyl acetate and Celite® and refluxed. At this temperature Celite® was suction filtered and washed with 150 mL boiling ethyl acetate. The filtrate was cooled with stirring and seed crystals were prepared in the test tube. The suspension was suction filtered, washed with ethyl acetate and dried.

Yield: 7.0 g (14% of theory)

ESI-MS: m/z=181 (M−H)⁻

Step 2: 6-hydroxy-5-methyl-pyrimidine-4-carboxylic acid

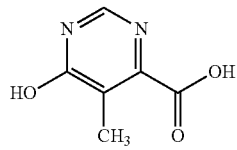

5.0 g (27 mmol) ethyl 6-hydroxy-5-methyl-pyrimidine-4-carboxylate were dissolved in 20 mL concentrated hydrochloric acid and stirred overnight at RT. Then the reaction mixture was heated to 75° C. and stirred for 6 h. The reaction mixture was cooled to 5° C., suction filtered, washed with 2 mL concentrated hydrochloric acid and dried.

Yield: 2.8 g (66% of theory)

ESI-MS: m/z=153 (M−H)⁻

Step 3: 6-chloro-5-methyl-pyrimidine-4-carboxylic acid chloride

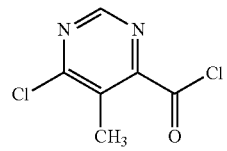

2.6 g (17 mmol) 6-hydroxy-5-methyl-pyrimidine-4-carboxylic acid, 6.7 mL thionyl chloride, 0.10 mL DMF in 16 mL acetonitrile were refluxed overnight. The reaction mixture was evaporated down and co-evaporated with toluene. The residue was combined with petroleum ether, the solid was suction filtered and dried.

Yield: 1.0 g (31% of theory)

Step 4: tert. butyl 6-chloro-5-methyl-pyrimidine-4-carboxylate

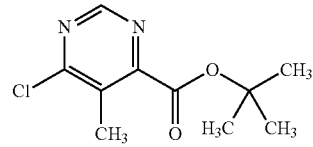

At 0° C. a solution of 5.8 mL pyridine and 15 mL tert.-butanol in 10 mL dichloromethane was added dropwise to 6.0 g 6-chloro-5-methyl-pyrimidine-4-carboxylic acid chloride in 10 mL dichloromethane. The reaction mixture was heated to RT and stirred for 30 min. The reaction mixture was diluted with dichloromethane and washed successively with a 2M sodium hydroxide solution, twice with a 10% aqueous citric acid solution and a sodium chloride solution. The organic phase was dried and evaporated down. The residue was taken up in dichloromethane and purified by flash chromatography. The product-containing fractions were evaporated down and dried.

Yield: 5.7 g (79% of theory)

Preparation of the End Compounds

Example 1

3-{1-[3-(2,3-dihydro-indole-1-carbonyl)-phenyl]-piperidin-4-yl}-1,3,4,5-tetrahydro-1,3-benzodiazepin-2-one

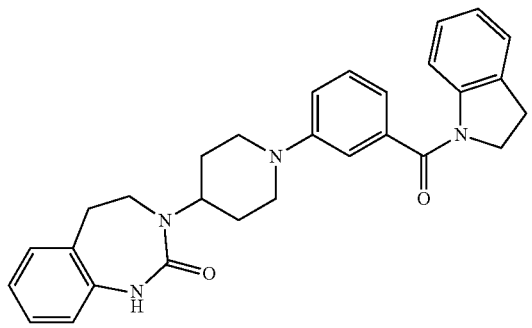 [SMILES: O=C(c1cccc(N2CCC(N3CCc4ccccc4NC3=O)CC2)c1)N1CCc2ccccc21]

110 mg (0.30 mmol) 3-[4-(2-oxo-1,2,4,5-tetrahydro-1,3-benzodiazepin-3-yl)-piperidin-1-yl]-benzoic acid, 40 µL (0.35 mmol) 2,3-dihydro-1H-indole, 50 µL (0.36 mmol) triethylamine and 100 mg (0.31 mmol) TBTU in 2 mL DMF were stirred overnight at RT. The reaction mixture was poured onto 25 mL water. The precipitated product was suction filtered, washed with water, dried and by purified using a silica gel column. The product fractions were combined and evaporated down i. vac. The residue was triturated with methanol, suction filtered and dried at 40° C. in the CAD.

Yield: 83 mg (59% of theoretical)

ESI-MS: m/z=467 (M+H)⁺

$R_f$: 0.66 (silica gel, DCM/MeOH/NH₄OH=75/25/5)

Example 2

3-{1-[3-(7,7-dimethyl-1,4,6,7-tetrahydropyrazolo[4,3-c]pyridin-5-carbonyl)-phenyl]-piperidin-4-yl}-1,3,4,5-tetrahydro-1,3-benzodiazepin-2-one

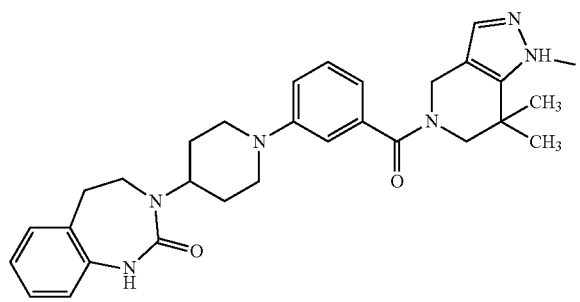 [SMILES: Cn1ncc2c1C(C)(C)CN(C(=O)c1cccc(N3CCC(N4CCc5ccccc5NC4=O)CC3)c1)C2]

70.0 mg (0.19 mmol) 3-[4-(2-oxo-1,2,4,5-tetrahydro-1,3-benzodiazepin-3-yl)-piperidin-1-yl]-benzoic acid, 60 mg (0.27 mmol) 7,7-dimethyl-4,5,6,7-tetrahydro-1H-pyrazolo[4,3-c]pyridine-dihydrochloride, 100 µL (0.71 mmol) triethylamine and 70.0 mg (0.22 mmol) TBTU in 1 mL DMF were stirred overnight at RT. The reaction mixture was combined with 1 mL methanol and 10 mL ice water. The precipitated product was suction filtered, washed with water and diethyl ether and purified by preparative HPLC. The product fractions were combined and evaporated down i. vac.

Yield: 36 mg (38% of theoretical)
ESI-MS: m/z=499 (M+H)+

Example 3

3-[4'-(2,3-dihydroindole-1-carbonyl)-3,4,5,6-tetrahydro-2H-1,2'-bipyridinyl-4-yl]-1,3,4,5-tetrahydro-1,3-benzodiazepin-2-one

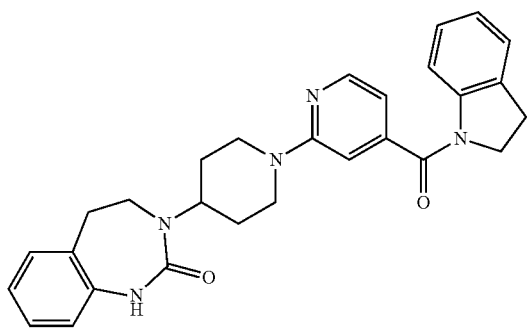 [SMILES: O=C(c1ccnc(N2CCC(N3CCc4ccccc4NC3=O)CC2)c1)N1CCc2ccccc21]

100 mg (0.41 mmol) 3-piperidin-4-yl-1,3,4,5-tetrahydro-1,3-benzodiazepin-2-one were added to 110 mg (0.43 mmol) (2-chloropyridin-4-yl)-(2,3-dihydro-indol-1-yl)-methanone and 3.0 mL (17.4 mmol) DIPEA. The reaction mixture was refluxed for 5 h with stirring. Then 1 mL DMF were added and the mixture was stirred overnight at 130 C. After cooling water was added, the precipitate formed was suction filtered and purified by preparative HPLC. The product fractions were combined and evaporated down i. vac.

Yield: 10 mg (5% of theoretical)
ESI-MS: m/z=468 (M+H)+
$R_f$: 0.74 (silica gel, eluant A)

Example 4

1-[4'-(5-fluoro-2,3-dihydroindole-1-carbonyl)-3,4,5,6-tetrahydro-2H-[1,2']bipyridinyl-4-yl]-1,3-dihydroimidazo[4,5-b]pyridin-2-one

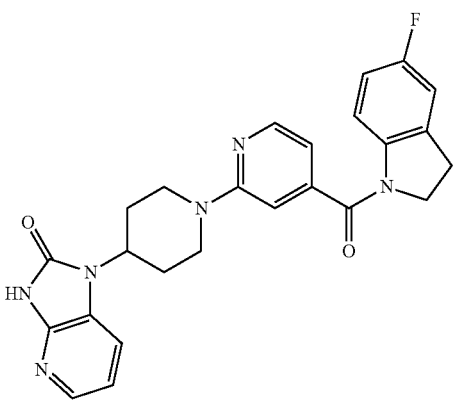 [SMILES: O=C(c1ccnc(N2CCC(n3c(=O)[nH]c4ncccc43)CC2)c1)N1CCc2cc(F)ccc21]

232 mg (0.8 mmol) 1-piperidin-4-yl-1,3-dihydro-imidazo[4,5-b]pyridin-2-one dihydrochloride were added to 220 mg (0.80 mmol) (2-chloropyridin-4-yl)-(5-fluoro-2,3-dihydro-indol-1-yl)-methanone and 0.52 mL (3.00 mmol) DIPEA in 3.0 mL N-methylpyrrolidone. The reaction mixture was stirred for 6 h at 130° C. After 4 h 400 mg potassium carbonate were added and the reaction mixture was stirred for a further 24 h at 130° C. Then the mixture was poured onto 100 mL water and extracted with EtOAc (3×100 mL). The combined organic phases were dried and evaporated down using the rotary evaporator. The residue was purified by preparative HPLC. The product fractions were combined and evaporated down i. vac. The residue was triturated with 30 mL diethyl ether. The precipitated solid was suction filtered and dried in the air.

Yield: 20 mg (6% of theoretical)
ESI-MS: m/z=459 (M+H)+
$R_t$ (HPLC-MS): 1.14 min (method C)

Example 5

3-[2'-(2,3-dihydroindole-1-carbonyl)-3,4,5,6-tetrahydro-2H-1,4'-bipyridinyl-4-yl]-1,3,4,5-tetrahydro-1,3-benzodiazepin-2-one

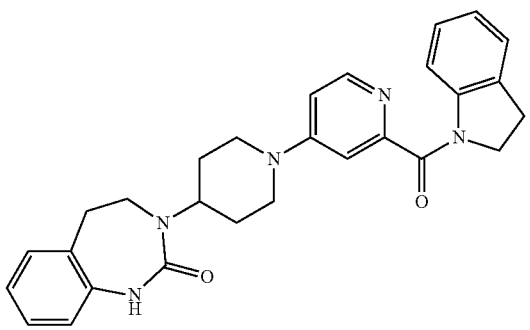 [SMILES: O=C(c1cc(N2CCC(N3CCc4ccccc4NC3=O)CC2)ccn1)N1CCc2ccccc21]

110 mg (0.43 mmol) (4-chloro-pyridin-2-yl)-(2,3-dihydro-indol-1-yl)-methanone, 150 mg (1.0 mmol) potassium carbonate and 100 mg (0.41 mmol) 3-piperidin-4-yl-1,3,4,5-tetrahydro-1,3-benzodiazepin-2-one in 10 mL THF were refluxed for 3 days. Then the reaction mixture was evaporated down using the rotary evaporator, taken up in 20 mL xylene and refluxed for a further 3 days. The solid was filtered off and the filtrate evaporated down i. vac. The residue was dissolved in DMF and purified by preparative HPLC. The product fractions were combined and lyophilised.

Yield: 45 mg (24% of theoretical)
ESI-MS: m/z=468 (M+H)⁺
R$_f$: 0.57 (silica gel, eluant A)

Example 6

1-[2'-(5-fluoro-2,3-dihydroindole-1-carbonyl)-3,4,5,6-tetrahydro-2H-[1,4']bipyridinyl-4-yl]-1,3-dihydroimidazo[4,5-b]pyridin-2-one

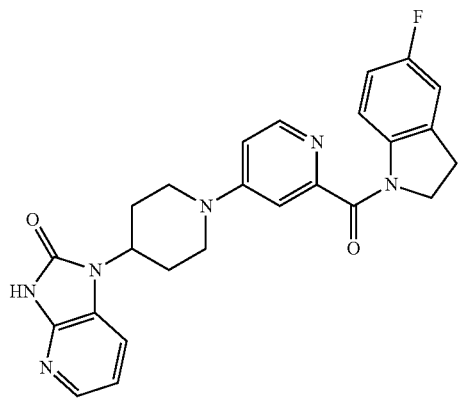 [SMILES: O=C(c1cc(N2CCC(n3c(=O)[nH]c4ncccc43)CC2)ccn1)N1CCc2cc(F)ccc21]

314 mg (1.08 mmol) 1-piperidin-4-yl-1,3-dihydroimidazo[4,5-b]pyridin-2-one dihydrochloride were added to 300 mg (1.08 mmol) (4-chloropyridin-2-yl)-(5-fluoro-2,3-dihydroindol-1-yl)-methanone and 373 mg (2.70 mmol) potassium carbonate in 5.0 mL N-methylpyrrolidone. The reaction mixture was stirred for 30 h at 130° C. Then the mixture was poured onto 100 mL water and extracted with EtOAc (3×100 mL). The combined organic phases were dried and evaporated down using the rotary evaporator. The residue was purified by preparative HPLC. The product fractions were combined and evaporated down i. vac. The residue was triturated with 30 mL diethyl ether. The precipitated solid was suction filtered and dried in the air.

Yield: 190 mg (38% of theoretical)
ESI-MS: m/z=459 (M+H)⁺
R$_t$ (HPLC-MS): 1.0 min (method C)

Example 7

6-[4-(7-methoxy-2-oxo-1,2,4,5-tetrahydro-1,3-benzodiazepin-3-yl)-piperidin-1-yl]-pyrimidine-4-carboxylic acid benzyl-(2,2,2-trifluorethyl)-amide

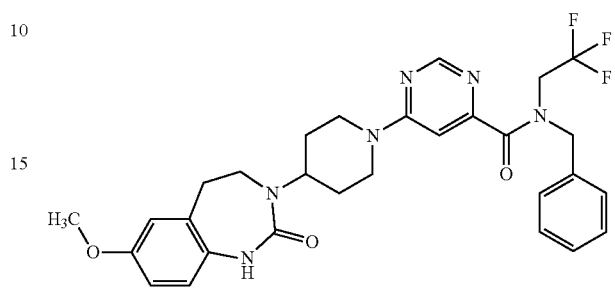

44 mg (0.16 mmol) 7-methoxy-3-piperidin-4-yl-1,3,4,5-tetrahydro-1,3-benzodiazepin-2-one were added to 50 mg (0.15 mmol) 6-chloropyrimidine-4-carboxylic acid-benzyl-(2,2,2-trifluorethyl)-amide and 34 µL (0.20 mmol) DIPEA in 5 mL DMF. The reaction mixture was stirred for 2 h at RT. The reaction mixture was purified by preparative HPLC-MS. The product fractions were combined and evaporated down i. vac.

Yield: 62 mg (72% of theoretical)
ESI-MS: m/z=569 (M+H)⁺
R$_t$ (HPLC-MS): 1.52 min (method C)

Example 8

3-{1-[6-(7,7-dimethyl-1,4,6,7-tetrahydro-pyrazolo[4,3-c]pyridin-5-carbonyl)-pyrimidin-4-yl]-piperidin-4-yl}-7-methoxy-1,3,4,5-tetrahydro-1,3-benzodiazepin-2-one

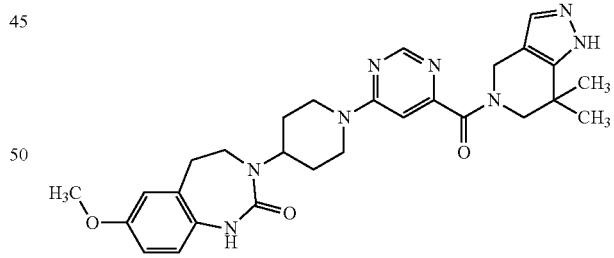

105 mg (0.28 mmol) TBTU were added to 100 mg (0.25 mmol) 6-[4-(7-methoxy-2-oxo-1,2,4,5-tetrahydro-1,3-benzodiazepin-3-yl)-piperidin-1-yl]-pyrimidine-4-carboxylic acid, 80.0 mg (0.36 mmol) 7,7-dimethyl-4,5,6,7-tetrahydro-1H-pyrazolo[4,3-c]pyridine dihydrochloride, 120.0 µL (0.86 mmol) triethylamine in 1.0 mL DMF and stirred overnight at RT. The reaction mixture was purified by preparative HPLC, the product fractions were combined and then lyophilised.

Yield: 22 mg (16% of theoretical)
ESI-MS: m/z=531 (M+H)⁺
R$_t$ (HPLC): 2.51 min (method E)

Example 9

1-{1-[6-(7,7-dimethyl-1,4,6,7-tetrahydropyrazolo[4,3-c]pyridin-5-carbonyl)-pyrimidin-4-yl]-piperidin-4-yl}-1,3-dihydroimidazo[4,5-b]pyridin-2-one

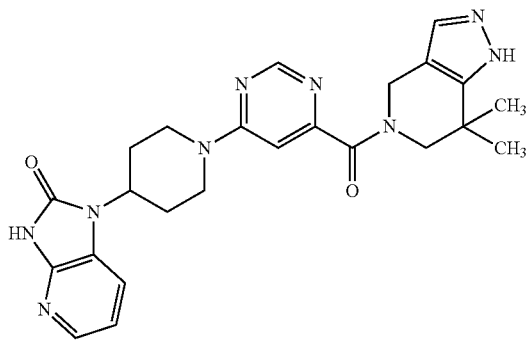 [SMILES: CC1(C)CN(C(=O)c2cc(N3CCC(n4c(=O)[nH]c5ncccc54)CC3)ncn2)Cc2cn[nH]c21]

100 mg (0.26 mmol) TBTU were added to 80 mg (0.24 mmol) 6-[4-(2-oxo-2,3-dihydroimidazo[4,5-b]pyridin-1-yl)-piperidin-1-yl]-pyrimidine-4-carboxylic acid, 70.0 mg (0.31 mmol) 7,7-dimethyl-4,5,6,7-tetrahydro-1H-pyrazolo[4,3-c]pyridine dihydrochloride, 120.0 µL (0.86 mmol) triethylamine in 1.0 mL DMF and the mixture was stirred overnight at RT. The reaction mixture was purified by preparative HPLC, the product fractions were combined and then lyophilised.

Yield: 34 mg (16% of theoretical)
ESI-MS: m/z=474 (M+H)$^+$
R$_t$ (HPLC): 2.03 min (method E)

Example 10

7-methoxy-3-{1-[6-(3-phenyl-1,4,6,7-tetrahydropyrazolo[4,3-c]pyridin-5-carbonyl)-pyrimidin-4-yl]-piperidin-4-yl}-1,3,4,5-tetrahydro-1,3-benzodiazepin-2-one

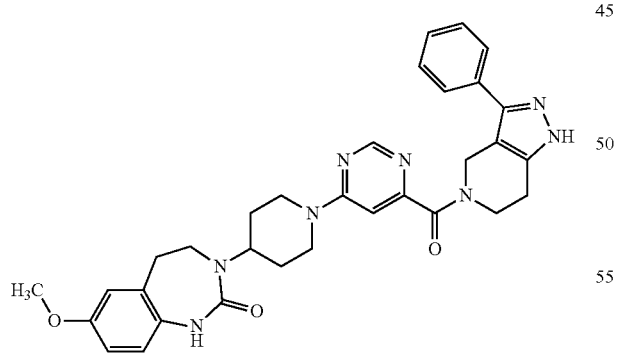

90 mg (0.24 mmol) TBTU were added to 80 mg (0.20 mmol) 6-[4-(7-methoxy-2-oxo-1,2,4,5-tetrahydro-1,3-benzodiazepin-3-yl)-piperidin-1-yl]-pyrimidine-4-carboxylic acid, 75 mg (0.28 mmol) 3-phenyl-4,5,6,7-tetrahydro-1H-pyrazolo[4,3-c]pyridine dihydrochloride, 120.0 µL (0.86 mmol) triethylamine in 0.9 mL DMF and stirred overnight at RT. The reaction mixture was combined with 1 mL methanol, 1 mL saturated sodium hydrogen carbonate solution and 8 mL ice water. The precipitate was suction filtered, washed with water and diethyl ether and dried.

Yield: 79 mg (68% of theoretical)
ESI-MS: m/z=579 (M+H)$^+$
R$_t$ (HPLC): 2.88 min (method E)

Example 11

1-{1-[6-(octahydroindole-1-carbonyl)-pyrimidin-4-yl]-piperidin-4-yl}-1,3-dihydroimidazo[4,5-b]pyridin-2-one

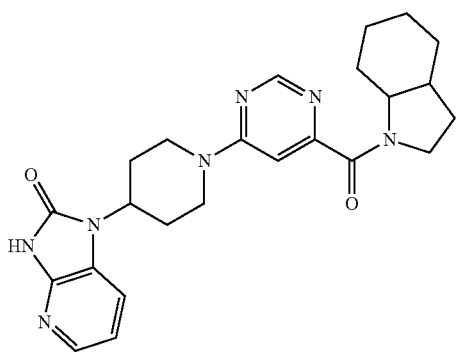 [SMILES: O=C(c1cc(N2CCC(n3c(=O)[nH]c4ncccc43)CC2)ncn1)N1CCC2CCCCC21]

201 mg (0.69 mmol) 1-piperidin-4-yl-1,3-dihydroimidazo[4,5-b]pyridin-2-on-dihydrochloride were added to 184 mg (0.69 mmol) (6-chloropyrimidin-4-yl)-(octahydroindol-1-yl)-methanone and 488 µL (2.8 mmol) DIPEA in 3 mL DMF. The reaction mixture was stirred at RT over the weekend and then purified by preparative HPLC-MS. The product fractions were combined and the organic solvent was removed using the rotary evaporator. The aqueous solution was neutralised with aqueous 1N NaOH solution and the precipitate obtained was suction filtered. The precipitate was washed with water and dried.

Yield: 50 mg (16% of theoretical)
ESI-MS: m/z=448 (M+H)$^+$
R$_t$ (HPLC-MSI): 2.69 min (method E)

Example 12

3-{1-[6-(2,3-dihydroindole-1-carbonyl)-pyrimidin-4-yl]-piperidin-4-yl}-1,3,4,5-tetrahydro-1,3-benzodiazepin-2-one

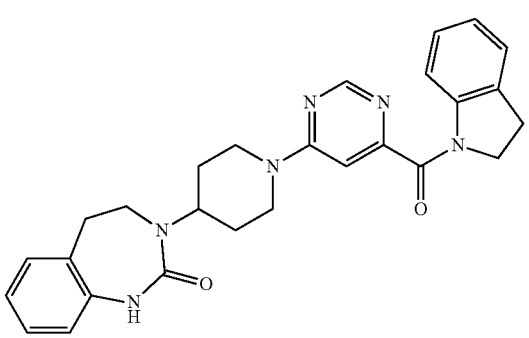 [SMILES: O=C(c1cc(N2CCC(N3CCc4ccccc4NC3=O)CC2)ncn1)N1CCc2ccccc21]

34 μL (0.30 mmol) 2,3-dihydro-1H-indole and 90.0 mg (0.28 mmol) TBTU was added to 100 mg (0.27 mmol) 6-[4-(2-oxo-1,2,4,5-tetrahydro-1,3-benzodiazepin-3-yl)-piperidin-1-yl]-pyrimidine-4-carboxylic acid and 42 μL (0.30 mmol) triethylamine in 4.0 mL DMF. The mixture was stirred for 1 h at RT and then poured onto 40 mL water. The precipitated product was suction filtered. The solid was stirred with methanol, suction filtered and dried.

Yield: 65 mg (51% of theoretical)
ESI-MS: m/z=469 (M+H)+
$R_f$: 0.48 (eluant A)

Example 13

1-{1-[6-(2,3-dihydroindole-1-carbonyl)-pyrimidin-4-yl]-piperidin-4-yl}-1,3-dihydro-imidazo[4,5-b]pyridin-2-one

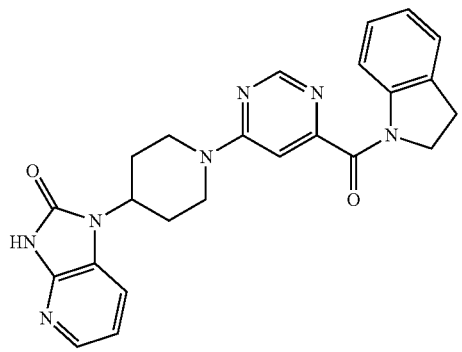 [SMILES: O=C(c1cc(N2CCC(n3c(=O)[nH]c4ncccc43)CC2)ncn1)N1CCc2ccccc21]

350 mg (1.20 mmol) 1-piperidin-4-yl-1,3-dihydroimidazo[4,5-t]pyridin-2-one dihydrochloride were added to 300 mg (1.16 mmol) (6-chloropyrimidin-4-yl)-(2,3-dihydro-indol-1-yl)-methanone and 750 μL (4.36 mmol) DIPEA in 10 mL DMF. The reaction mixture was stirred overnight at RT and then evaporated down i. vac. The residue was purified by preparative HPLC. The product fractions were combined and lyophilised.

Yield: 330 mg (65% of theoretical)
ESI-MS: m/z=442 (M+H)+
$R_f$: 0.52 (eluant A)

General Working Method 1 (GWM1) for Reacting (6-chloropyrimidin-4-yl)-(2,3-dihydroindol-1-yl)-methanone with an amine derivative The quantity of amine derivative specified in the Table was added to 100 mg (0.39 mmol) (6-chloropyrimidin-4-yl)-(2,3-dihydro-indol-1-yl)-methanone and 100 μL (0.58 mmol) DIPEA in 10 mL DMF. The reaction mixture was stirred for 2 h at RT. The working up could be done in various ways:

[A]: The reaction mixture was evaporated down using the rotary evaporator and the residue was mixed with 20 mL water and stirred for 30 min at RT. The precipitated product was suction filtered, stirred with methanol and suction filtered again. The product was dried in the CAD at 40° C.

[B] The reaction mixture was evaporated down using the rotary evaporator and the residue was mixed with 20 mL water and stirred for 30 min at RT. The precipitated product was suction filtered, stirred with diisopropylether and isopropanol and suction filtered again. The product was dried in the CAD at 40° C.

| Example method | Structure | amine derivative [amount of amine derivative] Yield | Analytical data |
|---|---|---|---|
| Example 14: GWM1[B] | 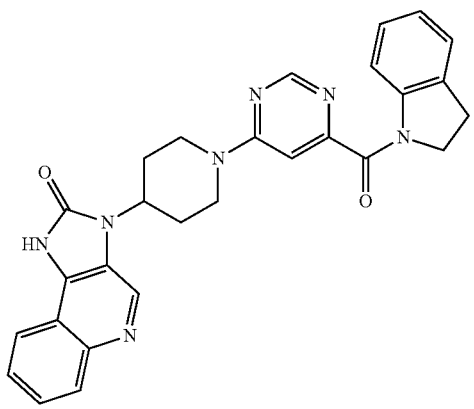 [SMILES: O=C(c1cc(N2CCC(n3c(=O)[nH]c4c5ccccc5ncc43)CC2)ncn1)N1CCc2ccccc21]<br>3-{1-[6-(2,3-dihydro-indole-1-carbonyl)-pyrimidin-4-yl]-piperidin-4-yl}-1,3-dihydro-imidazo[4,5-c]quinolin-2-one | 3-piperidin-4-yl-1,3-dihydro-imidazo[4,5-c]quinolin-2-one 110 mg (0.41 mmol) 125 mg (66% of theory) | ESI-MS: m/z = 492 [M + H]+ $R_f$ = 0.50 eluant A |

| Example method | Structure | amine derivative [amount of amine derivative] Yield | Analytical data |
|---|---|---|---|
| Example 15: GWM1[B] | 2-{1-[6-(2,3-dihydroindole-1-carbonyl)-pyrimidin-4-yl]-piperidin-4-yl}-5-phenyl-2,4-dihydro-1,2,4-triazol-3-one | 5-phenyl-2-piperidin-4-yl-2,4-dihydro-1,2,4-triazol-3-one 100 mg (0.41 mmol) 115 mg (64% of theory) | ESI-MS: m/z = 448 [M + H]+ $R_f$ = 0.53 eluant A |
| Example 16: GWM1[B] | 1-{1-[6-(2,3-dihydroindole-1-carbonyl)-pyrimidin-4-yl]-piperidin-4-yl}-1,3-dihydro-benzimidazole-2-one | 1-piperidin-4-yl-1,3-dihydro-benzimidazole-2-on 90 mg (0.41 mmol) 130 mg (77% of theory) | ESI-MS: m/z = 441 [M + H]+ $R_f$ = 0.54 eluant A |

General Working Method 2 (GWM2) for Reacting 1-piperidin-4-yl-1,3-dihydro-imidazo[4,5-b]pyridin-2-one dihydrochloride with (6-chloropyrimidin-4-yl)-methanone derivatives:

90 mg (0.31 mmol) 1-piperidin-4-yl-1,3-dihydro-imidazo[4,5-b]pyridin-2-one dihydrochloride were added to a (6-chloropyrimidin-4-yl)-methanone derivative and 100 μL (0.58 mmol) DIPEA in 10 mL DMF. The reaction mixture was stirred for 2 h at RT, then evaporated down and the residue was combined with 20 mL water and stirred for 30 min at RT. The precipitated product was suction filtered and purified by flash chromatography. The product fractions were combined and evaporated down using the rotary evaporator. The residue was triturated with diisopropylether and suction filtered. The product was dried at 40° C. in the CAD.

| Example | Structure | 6-chloropyrimidin-4-yl derivative [amount of 6-chloro-pyrimidin-4-yl derivative] Yield | Analytical data |
|---|---|---|---|
| Example 17: | 1-{1-[6-(1,3-dihydro-isoindole-2-carbonyl)-pyrimidin-4-yl]-piperidin-4-yl}-1,3-dihydro-imidazo[4,5-b]pyridin-2-one | (6-chloropyrimidin-4-yl)-(1,3-dihydro-isoindol-2-yl)-methanone 100 mg (0.39 mmol) 30 mg (22% of theory) | ESI-MS: m/z = 442 [M + H]$^+$ R$_f$ = 0.66 eluant A |
| Example 18: | 1-{1-[6-(3,4-dihydro-1H-isoquinoline-2-carbonyl)-pyrimidin-4-yl]-piperidin-4-yl}-1,3-dihydroimidazo[4,5-b]pyridin-2-one | (6-chloropyrimidin-4-yl)-(3,4-dihydro-1H-isoquinolin-2-yl)-methanone 100 mg (0.37 mmol) 35 mg (25% of theory) | ESI MS: m/z = 456 [M + H]$^+$ R$_f$ = 0.56 eluant A |
| Example 19: | 1-{1-[6-(3,4-dihydro-2H-quinoline-1-carbonyl)-pyrimidin-4-yl]-piperidin-4-yl}-1,3-dihydro-imidazo[4,5-b]pyridin-2-one | (6-chloropyrimidin-4-yl)-(3,4-dihydro-2H-quinolin-1-yl)-methanone 100 mg (0.37 mmol) 25 mg (18% of theory) | ESI-MS: m/z = 456 [M + H]$^+$ R$_f$ = 0.56 eluant A |

Example 20

1-{1-[6-(1,2,4,5-tetrahydro-3-benzazepin-3-carbonyl)-pyrimidin-4-yl]-piperidin-4-yl}-1,3-dihydroimidazo[4,5-b]pyridin-2-one

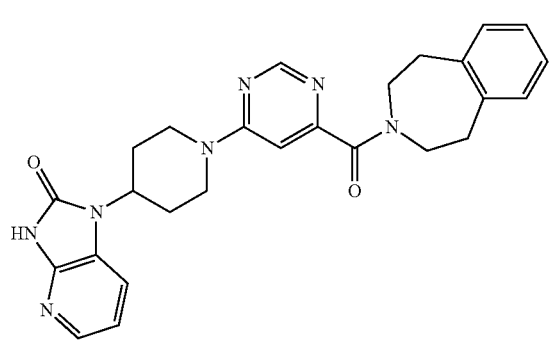 [SMILES: O=C(c1cc(N2CCC(n3c(=O)[nH]c4ncccc43)CC2)ncn1)N1CCc2ccccc2CC1]

100.0 mg (0.29 mmol) 6-[4-(2-oxo-2,3-dihydro-imidazo[4,5-b]pyridin-1-yl)-piperidin-1-yl]-pyrimidine-4-carboxylic acid, 50.0 mg (0.34 mmol) 2,3,4,5-tetrahydro-1H-3-benzazepine, 100 μL (0.71 mmol) triethylamine and 100.0 mg (0.31 mmol) TBTU in 1.5 mL DMF were stirred overnight at RT. The reaction mixture was filtered through a syringe filter and the solution was purified by preparative HPLC. The product fractions were combined and lyophilised.

Yield: 60 mg (44% of theoretical)
ESI-MS: m/z=470 (M+H)$^+$
R$_f$: 0.50 (silica gel, eluant A)

General Working Method 3 (GWM3) for Reacting 5-phenyl-2-piperidin-4-yl-2,4-dihydro-1,2,4-triazol-3-one with (6-chloropyrimidin-4-yl)-methanone derivatives 100 mg (0.41 mmol) 5-phenyl-2-piperidin-4-yl-2,4-dihydro-1,2,4-triazol-3-one were added to a corresponding amount of a (6-chloropyrimidin-4-yl)-methanone derivative (see Table) and 100 μL (0.58 mmol) DIPEA in 10 mL DMF. The reaction mixture was stirred for 2 h at RT, then evaporated down and the residue was combined with 20 mL water and stirred for 30 min at RT. The precipitated product was suction filtered, stirred with methanol and suction filtered again. The product was dried at 40° C. in the CAD.

| Example | Structure | 6-chloropyrimidin-4-yl derivative [amount of 6-chloropyrimidin-4-yl derivative] Yield | Analytical data |
|---|---|---|---|
| Example 21: | 2-{1-[6-(1,3-dihydro-isoindole-2-carbonyl)-pyrimidin-4-yl]-piperidin-4-yl}-5-phenyl-2,4-dihydro-1,2,4-triazol-3-on | (6-chloropyrimidin-4-yl)-(1,3-dihydro-isoindol-2-yl)-methanone 100 mg (0.39 mmol) 95 mg (53% of theory) | ESI-MS: m/z = 468 [M + H]$^+$ R$_f$ = 0.57 eluant A |

-continued

| Example | Structure | 6-chloropyrimidin-4-yl derivative [amount of 6-chloropyrimidin-4-yl derivative] Yield | Analytical data |
|---|---|---|---|
| Example 22: | 2-{1-[6-(3,4-dihydro-1H-isoquinolin-2-carbonyl)-pyrimidin-4-yl]-piperidin-4-yl}-5-phenyl-2,4-dihydro-1,2,4-triazol-3-one | (6-chloropyrimidin-4-yl)-(3,4-dihydro-1H-isoquinolin-2-yl)-methanone 100 mg (0.37 mmol) 60 mg (34% of theory) | ESI-MS: m/z = 482 [M + H]$^+$ R$_f$ = 0.58 eluant A |

General Working Method 4 (GWM4) for Reacting 3-piperidin-4-yl-1,3-dihydro-imidazo[4,5-c]quinolin-2-one with (6-chloropyrimidin-4-yl)-methanone derivatives 100 mg (0.37 mmol) 3-piperidin-4-yl-1,3-dihydro-imidazo[4,5-c]quinolin-2-one were added to a corresponding amount of a (6-chloropyrimidin-4-yl)-methanone derivative (see Table) and 100 µL (0.58 mmol) DIPEA in 10 mL DMF. The reaction mixture was stirred for 2 h at RT, then evaporated down i. vac. and the residue was combined with 20 mL water and stirred for 30 min at RT. The precipitated product was suction filtered, stirred with methanol and suction filtered again. The product was dried at 40° C. in the CAD.

| Example | Structure | 6-chloropyrimidin-4-yl)-(derivatives [amount of 6-chloropyrimidine derivative] Yield | Analytical data |
|---|---|---|---|
| Example 23: | 3-{1-[6-(1,3-dihydro-isoindole-2-carbonyl)-pyrimidin-4-yl]-piperidin-4-yl}-1,3-dihydro-imidazo[4,5-c]quinolin-2-one | (6-chloropyrimidin-4-yl)-(1,3-dihydro-isoindol-2-yl)-methanone 95 mg (0.37 mmol) 130 mg (72% of theory) | ESI-MS: m/z = 492 [M + H]$^+$ R$_f$ = 0.55 eluant A |

-continued

| Example | Structure | 6-chloropyrimidin-4-yl)-(derivatives [amount of 6-chloro-pyrimidine derivative] Yield | Analytical data |
|---|---|---|---|
| Example 24: | 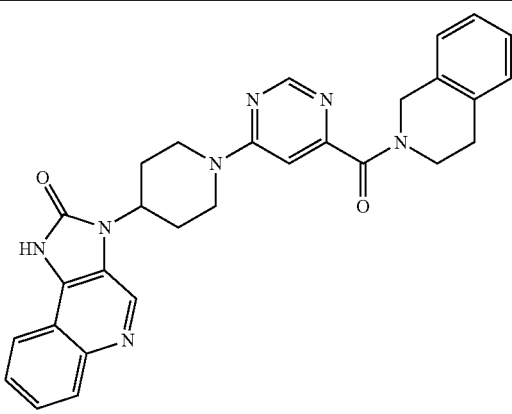<br>3-{1-[6-(3,4-[6-1H-isoquinolin-2-carbonyl)-pyrimidin-4-yl]-piperidin-4-yl}-1,3-dihydro-imidazo[4,5-c]quinolin-2-one | (6-chloropyrimidin-4-yl)-(3,4-dihydro-1H-isoquinolin-2-yl)-methanone 100 mg (0.37 mmol) 120 mg (65% of theory) | ESI MS: m/z = 506 [M + H]$^+$ R$_f$ = 0.56 eluant A |
| Example 25: | 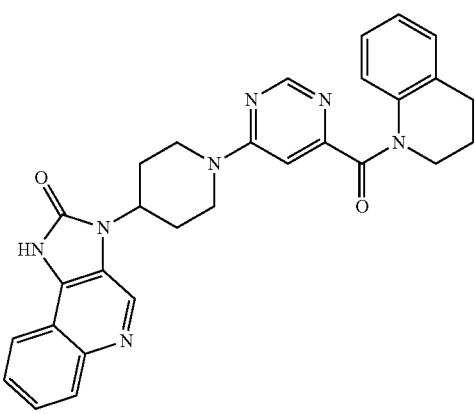 [SMILES: O=C(c1cc(N2CCC(n3c(=O)[nH]c4c5ccccc5ncc43)CC2)ncn1)N1CCCc2ccccc21]<br>3-{1-[6-(3,4-dihydro-2H-quinoline-1-carbonyl)-pyrimidin-4-yl]-piperidin-4-yl}-1,3-dihydro-imidazo[4,5-c]quinolin-2-one | (6-chloro-pyrimidin-4-yl)-(3,4-dihydro-2H-quinolin-1-yl)-methanone 100 mg (0.37 mmol) 55 mg (30% of theory) | ESI-MS: m/z = 506 [M + H]$^+$ R$_f$ = 0.53 eluant A |

Example 26

3-{1-[6-(2,3-dihydroindole-1-carbonyl)-pyrimidin-4-yl]-piperidin-4-yl}-7-methoxy-1,3,4,5-tetrahydro-1,3-benzodiazepin-2-one

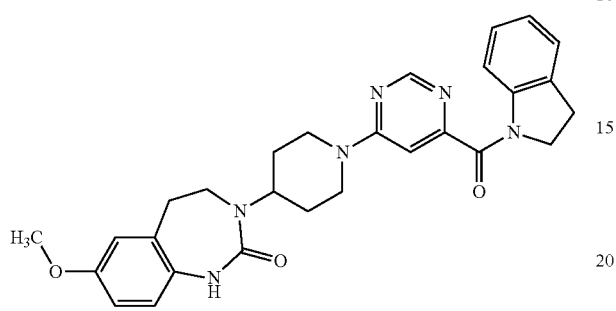

110 mg (0.4 mmol) 7-methoxy-3-piperidin-4-yl-1,3,4,5-tetrahydro-1,3-benzodiazepin-2-one were added to 100 mg (0.39 mmol) (6-chloropyrimidin-4-yl)-(2,3-dihydroindol-1-yl)-methanone and 100 µL (0.58 mmol) DIPEA in 10 mL DMF. The reaction mixture was stirred for 2 h at RT and then evaporated down i. vac. The residue was combined with 20 mL water and stirred for 30 min at RT. The precipitated product was suction filtered, stirred with methanol, suction filtered again and dried at 40° C. in the CAD.

Yield: 35 mg (18% of theoretical)
ESI-MS: m/z=499 (M+H)$^+$
$R_f$: 0.70 (silica gel, eluant A)

Example 27

7-chloro-3-{1-[6-(2,3-dihydroindole-1-carbonyl)-pyrimidin-4-yl]-piperidin-4-yl}-1,3,4,5-tetrahydro-1,3-benzodiazepin-2-one

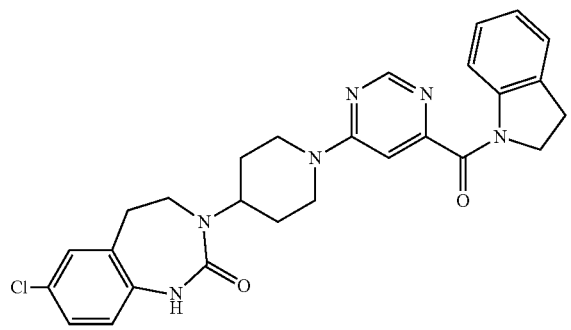 [SMILES: O=C(c1cc(N2CCC(N3CCc4cc(Cl)ccc4NC3=O)CC2)ncn1)N1CCc2ccccc21]

110 mg (0.36 mmol) 7-chloro-3-piperidin-4-yl-1,3,4,5-tetrahydro-1,3-benzodiazepin-2-one were added to 87.6 mg (0.34 mmol) (6-chloropyrimidin-4-yl)-(2,3-dihydro-indol-1-yl)-methanone and 63 µL (0.37 mmol) DIPEA in 2.5 mL DMF. The reaction mixture was stirred overnight at RT, then concentrated by rotary evaporation using the rotary evaporator and purified by preparative HPLC. The corresponding product fractions were combined and evaporated down using the rotary evaporator. The residue was taken up in DMF and combined with methanol. The substance was precipitated, suction filtered, washed with a little methanol and dried.

Yield: 117 mg (69% of theoretical)
ESI-MS: m/z=503/505 (M+H)$^+$
$R_t$ (HPLC-MS): 3.87 min (method E)

Example 28

1-{1-[6-(5-chloro-2,3-dihydroindole-1-carbonyl)-pyrimidin-4-yl]-piperidin-4-yl}-1,3-dihydro-imidazo[4,5-b]pyridin-2-one

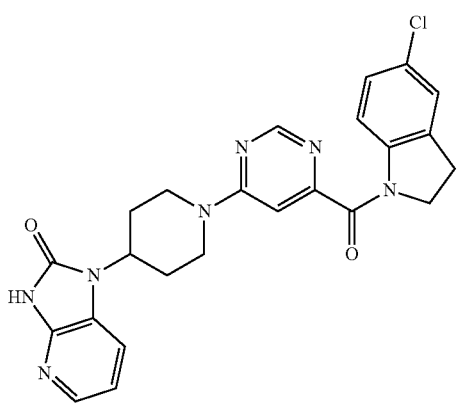

80 mg (0.27 mmol) 1-piperidin-4-yl-1,3-dihydro-imidazo[4,5-b]pyridin-2-one (dihydrochloride) were added to 100 mg (0.34 mmol) (5-chloro-2,3-dihydroindol-1-yl)-(6-chloro-pyrimidin-4-yl)-methanone and 100 µL (0.58 mmol) DIPEA in 10 mL DMF. The reaction mixture was stirred for 22 h at RT and then evaporated down i. vac. The residue was combined with 20 mL water and stirred for 30 min at RT. The precipitated product was suction filtered. The purification was carried out using a silica gel column. The product fractions were combined and the solvent was eliminated using the rotary evaporator. The residue was stirred with water, suction filtered and dried.

Yield: 30 mg (19% of theoretical)
ESI-MS: m/z=476/478 (M+H)$^+$
$R_f$: 0.44 (silica gel, eluant A)

General Working Method 5 (GWM5) for Reacting (5-chloro-2,3-dihydro-indol-1-O-(6-chloropyrimidin-4-yl)-methanone with amines A corresponding amount of an amine derivative (see Table) was added to 100 mg (0.34 mmol) (5-chloro-2,3-dihydro-indol-1-yl)-(6-chloropyrimidin-4-yl)-methanone and 100 µL (0.58 mmol) DIPEA in 10 mL DMF. The reaction mixture was stirred for 2 h at RT, then evaporated down i. vac. and the residue was mixed with 20 mL water and stirred for 30 min at RT. The precipitated product was suction filtered, stirred with methanol and suction filtered again. The product was dried in the CAD at 40° C. The following Examples were synthesised according to this general working method:

| Example | Structure | amine [amount of amine] Yield | Analytical data |
|---|---|---|---|
| Example 29: | 3-{1-[6-(5-chloro-2,3-dihydro-indole-1-carbonyl)-pyrimidin-4-yl]-piperidin-4-yl}-1,3,4,5-tetrahydro-1,3-benzodiazepin-2-one | 3-piperidin-4-yl-1,3,4,5-tetrahydro-1,3-benzodiazepin-2-one 90 mg (0.37 mmol) 145 mg (85% of theory) | ESI MS: m/z = 503/505 [M + H]$^+$ R$_f$ = 0.72 eluant A |
| Example 30: | 3-{1-[6-(5-chloro-2,3-dihydro-indole-1-carbonyl)-pyrimidin-4-yl]-piperidin-4-yl}-1,3-dihydroimidazo[4,5-c]quinolin-2-one | 3-piperidin-4-yl-1,3-dihydro-imidazo[4,5-c]quinolin-2-one 90 mg (0.34 mmol) 115 mg (64% of theory) | ESI-MS: m/z = 526/528 [M + H]$^+$ R$_f$ = 0.50 eluant A |
| Example 31: | 2-{1-[6-(5-chloro-2,3-dihydroindole-1-carbonyl)-pyrimidin-4-yl]-piperidin-4-yl}-5-phenyl-2,4-dihydro-1,2,4-triazol-3-one | 5-phenyl-2-piperidin-4-yl-2,4-dihydro-1,2,4-triazol-3-one 85 mg (0.35 mmol) 65 mg (38% of theory) | ESI-MS: m/z = 502/504 [M + H]$^+$ R$_f$ = 0.54 eluant A |

| Example | Structure | amine [amount of amine] Yield | Analytical data |
|---|---|---|---|
| Example 32: | 3-{1-[6-(5-chloro-2,3-dihydroindole-1-carbonyl)-pyrimidin-4-yl]-piperidin-4-yl}-7-methoxy-1,3,4,5-tetrahydro-1,3-benzodiazepin-2-one | 7-methoxy-3-piperidin-4-yl-1,3,4,5-tetrahydro-1,3-benzodiazepin-2-one 100 mg (0.36 mmol) 120 mg (66% of theory) | ESI-MS: m/z = 533/535 [M + H]$^+$ $R_f$ = 0.68 eluant A |

Example 33

1-{1-[6-(5-bromo-2,3-dihydro-indole-1-carbonyl)-pyrimidin-4-yl]-piperidin-4-yl}-1,3-dihydro-imidazo[4,5-b]pyridin-2-one

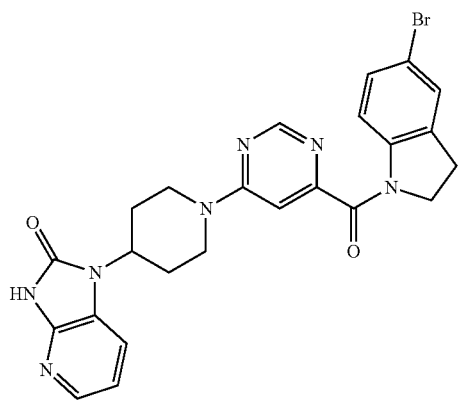

70 mg (0.24 mmol) 1-piperidin-4-yl-1,3-dihydroimidazo[4,5-b]pyridin-2-one dihydrochloride were added to 100 mg (0.30 mmol) (5-bromo-2,3-dihydroindol-1-yl)-(6-chloropyrimidin-4-yl)-methanone and 100 μL (0.58 mmol) DIPEA in 10 mL DMF. The reaction mixture was stirred for 22 h at RT and then evaporated down i. vac. The residue was combined with 20 mL water and stirred for 30 min at RT. The precipitated product was suction filtered. The purification was carried out using a silica gel column. The product fractions were combined and the solvent was eliminated using the rotary evaporator. The residue was stirred with water, suction filtered and dried at 40° C. in the CAD.

Yield: 55 mg (36% of theoretical)

ESI-MS: m/z=520/522 (M+H)$^+$ $R_f$: 0.44 (silica gel, eluant A)

General Working Method 6 (GWM6) for Reacting (5-bromo-2,3-dihydro-indol-1-yl)-(6-chloropyrimidin-4-yl)-methanone with amines 0.30 mmol of an amine derivative were added to 100 mg (0.30 mmol) (5-bromo-2,3-dihydroindol-1-yl)-(6-chloropyrimidin-4-yl)-methanone and 100 μL (0.58 mmol) DIPEA in 10 mL DMF. The reaction mixture was stirred for 2 h at RT, then evaporated down i. vac. and the residue was combined with 20 mL water and stirred for 30 min at RT. The precipitated product was suction filtered, stirred with methanol and suction filtered again. The product was dried in the CAD at 40° C. The following Examples were synthesised according to this general working method:

| Example | Structure | amine [amount of amine] Yield | Analytical data |
|---|---|---|---|
| Example 34: | -{1-[6-(5-bromo-2,3-dihydro-indole-1-carbonyl)-pyrimidin-4-yl]-piperidin-4-yl}-1,3-dihydro-imidazo[4,5-c]quinolin-2-one | 3-piperidin-4-yl-1,3-dihydro-imidazo[4,5-c]quinolin-2-one 80 mg (0.30 mmol) 85 mg (51% of theory) | ESI-MS: m/z = 570/572 [M + H]$^+$ R$_f$ = 0.43 eluant A |
| Example 35: | 2-{1-[6-(5-bromo-2,3-dihydroindole-1-carbonyl)-pyrimidin-4-yl]-piperidin-4-yl}-5-phenyl-2,4-dihydro-1,2,4-triazol-3-one | 5-phenyl-2-piperidin-4-yl-2,4-dihydro-1,2,4-triazol-3-one 75 mg (0.30 mmol) 30 mg (19% of theory) | ESI-MS: m/z = 546/548 [M + H]$^+$ R$_f$ = 0.52 eluant A |

Example 36

1-{1-[6-(5-fluoro-2,3-dihydroindole-1-carbonyl)-pyrimidin-4-yl]-piperidin-4-yl}-1,3-dihydro-imidazo[4,5-b]pyridin-2-one

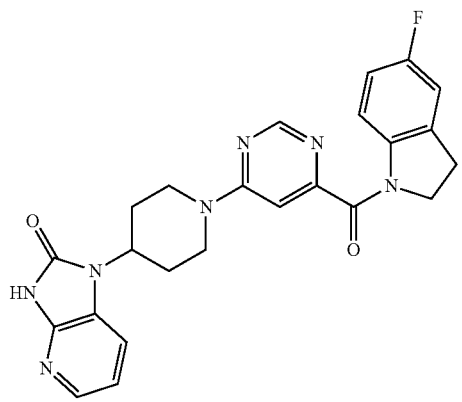

100 mg (0.294 mmol) 6-[4-(2-oxo-2,3-dihydroimidazo[4,5-b]pyridin-1-yl)-piperidin-1-yl]-pyrimidine-4-carboxylic acid, 42 mg (0.31 mmol) 5-fluoro-2,3-dihydro-1H-indole, 100 mg (0.311 mmol) TBTU and 45 µL (0.320 mmol) triethylamine in 10 mL DMF were stirred overnight at RT. The reaction mixture was evaporated down using the rotary evaporator. The residue was dissolved in 3 mL DMF and purified by preparative HPLC-MS. The product fractions were combined and lyophilised.

Yield: 50 mg (37% of theoretical)
ESI-MS: m/z=460 (M+H)$^+$
$R_f$: 0.52 (eluant A)

Example 37

1-{1-[6-(5-fluoro-3,3-dimethyl-2,3-dihydro-indole-1-carbonyl)-pyrimidin-4-yl]-piperidin-4-yl}-1,3-dihydroimidazo[4,5-t]pyridin-2-one

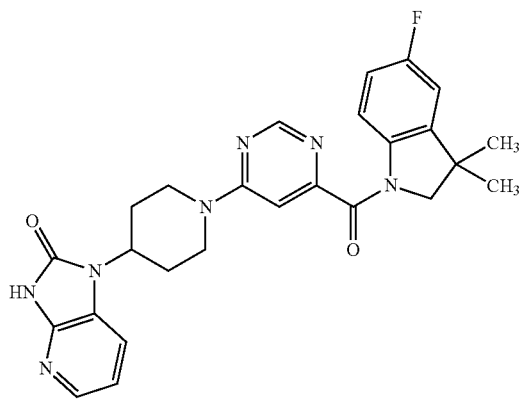 [SMILES: CC1(C)CN(C(=O)c2cc(N3CCC(n4c(=O)[nH]c5ncccc54)CC3)ncn2)c2ccc(F)cc21]

100 mg (0.294 mmol) 6-[4-(2-oxo-2,3-dihydro-imidazo[4,5-t]pyridin-1-yl)-piperidin-1-yl]-pyrimidine-4-carboxylic acid, 50 mg (0.300 mmol) 5-fluoro-3,3-dimethyl-2,3-dihydro-1H-indole, 106.1 mg (0.33 mmol) TBTU and 84 µL (0.60 mmol) triethylamine in 2 mL DMF were stirred overnight at RT. The reaction mixture was purified by preparative HPLC-MS. The product fractions were combined and lyophilised.

Yield: 100 mg (70% of theoretical)
ESI-MS: m/z=488 (M+H)$^+$
$R_t$ (HPLC): 3.5 min (method C)

Example 38

Methyl (5-fluoro-1-{6-[4-(2-oxo-2,3-dihydroimidazo[4,5-b]pyridin-1-yl)-piperidin-1-yl]-pyrimidine-4-carbonyl}-2,3-dihydro-1H-indol-3-yl)-acetate

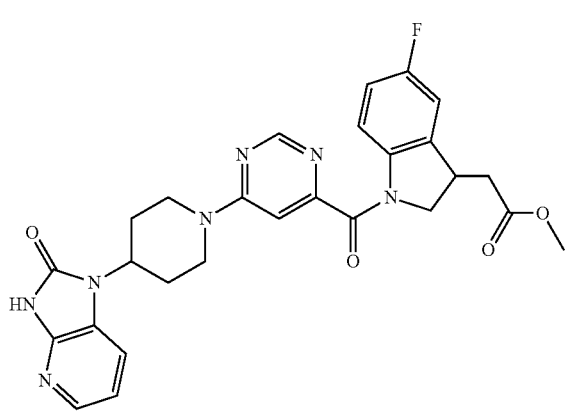 [SMILES: COC(=O)CC1CN(C(=O)c2cc(N3CCC(n4c(=O)[nH]c5ncccc54)CC3)ncn2)c2ccc(F)cc21]

150 mg (0.441 mmol) 6-[4-(2-oxo-2,3-dihydroimidazo[4,5-b]pyridin-1-yl)-piperidin-1-yl]-pyrimidine-4-carboxylic acid, 105 mg (0.500 mmol) methyl (5-fluoro-2,3-dihydro-1H-indol-3-yl)-acetate, 148 mg (0.460 mmol) TBTU and 112 µL (0.80 mmol) triethylamine in 2 mL DMF were stirred for 3 h at RT. The reaction mixture was purified by preparative HPLC-MS without any further working up. The product fractions were combined and lyophilised.

Yield: 116 mg (50% of theoretical)
ESI-MS: m/z=532 (M+H)$^+$
$R_t$ (HPLC-MS): 1.32 min (method C)

Example 39

1-{1-[6-(4,5-difluoro-2,3-dihydroindole-1-carbonyl)-pyrimidin-4-yl]-piperidin-4-yl}-1,3-dihydro-imidazo[4,5-t]pyridin-2-one

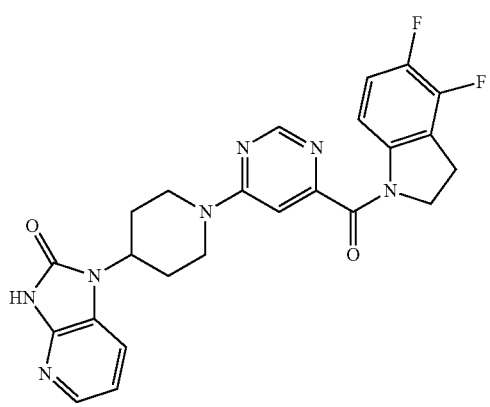 [SMILES: O=C(c1cc(N2CCC(n3c(=O)[nH]c4ncccc43)CC2)ncn1)N1CCc2c1ccc(F)c2F]

100 mg (0.294 mmol) 6-[4-(2-oxo-2,3-dihydroimidazo[4,5-b]pyridin-1-yl)-piperidin-1-yl]-pyrimidine-4-carboxylic acid, 60.0 mg (0.313 mmol) 4,5-difluoroindoline hydrochloride, 100 mg (0.311 mmol) TBTU and 45 μL (0.32 mmol) triethylamine in 10 mL DMF were stirred overnight at RT. The reaction mixture was concentrated by rotary evaporation using the rotary evaporator, with heating, under reduced pressure. The residue was dissolved in 3 mL DMF and purified by preparative HPLC. The product fractions were combined and lyophilised.

Yield: 85 mg (61% of theoretical)
ESI-MS: m/z=478 (M+H)+
$R_f$: 0.52 (eluant A)

Example 40

1-{1-[6-(3,3-dimethyl-2,3-dihydroindole-1-carbonyl)-pyrimidin-4-yl]piperidin-4-yl}-1,3-dihydro-imidazo[4,5-b]pyridin-2-one

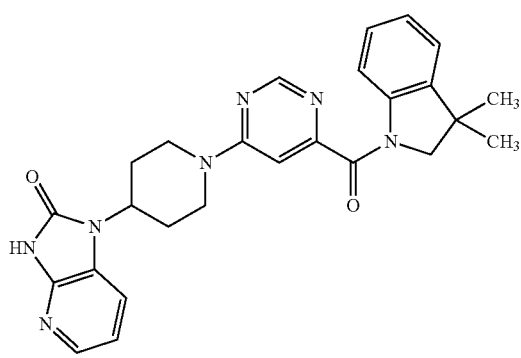 [SMILES: CC1(C)CN(C(=O)c2cc(N3CCC(n4c(=O)[nH]c5ncccc54)CC3)ncn2)c2ccccc21]

70 mg (0.21 mmol) 6-[4-(2-oxo-2,3-dihydroimidazo[4,5-b]pyridin-1-yl)-piperidin-1-yl]-pyrimidine-4-carboxylic acid, 30.33 mg (0.21 mmol) 3,3-dimethyl-2,3-dihydro-1H-indole, 71 mg (0.22 mmol) TBTU and 56 μL (0.40 mmol) triethylamine in 2 mL DMF were stirred overnight at RT. The mixture was separated by preparative HPLC. The product fractions were combined and lyophilised.

Yield: 55 mg (57% of theoretical)
ESI-MS: m/z=470 (M+H)+
$R_t$ (HPLC-MS): 3.5 min (method K)

Example 41

1-(1-{6-[3-(3-pyrrolidin-1-yl-propyl)-2,3-dihydroindole-1-carbonyl]-pyrimidin-4-yl}-piperidin-4-yl)-1,3-dihydro-imidazo[4,5-b]pyridin-2-one

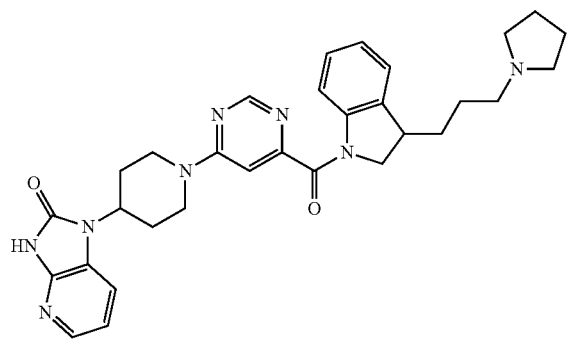 [SMILES: O=C(c1cc(N2CCC(n3c(=O)[nH]c4ncccc43)CC2)ncn1)N1CC(CCCN2CCCC2)c2ccccc21]

140 mg (0.41 mmol) 6-[4-(2-oxo-2,3-dihydroimidazo[4,5-b]pyridin-1-yl)-piperidin-1-yl]-pyrimidine-4-carboxylic acid, 94.4 mg (0.41 mmol) 3-(3-pyrrolidin-1-yl-propyl)-2,3-dihydro-1H-indole, 138.2 mg (0.43 mmol) TBTU and 112 μL (0.8 mmol) triethylamine in 4 mL DMF were stirred overnight at RT. The mixture was separated by preparative HPLC. The product fractions were combined and lyophilised.

Yield: 55 mg (24% of theoretical)
ESI-MS: m/z=553 (M+H)+
$R_t$ (HPLC-MS): 1.0 min (method C)

Example 42

Ethyl 1-{6-[4-(2-oxo-2,3-dihydroimidazo[4,5-b]pyridin-1-yl)-piperidin-1-yl]-pyrimidine-4-carbonyl}-2,3-dihydro-1H-indole-2-carboxylate

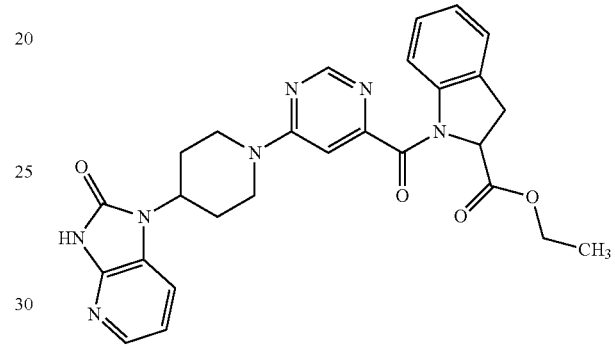

150 mg (0.44 mmol) 6-[4-(2-oxo-2,3-dihydroimidazo[4,5-b]pyridin-1-yl)-piperidin-1-yl]pyrimidine-4-carboxylic acid, 110 mg (0.48 mmol) ethyl 2,3-dihydro-1H-indole-2-carboxylate hydrochloride, 150.0 mg (0.47 mmol) TBTU and 150 μL (1.1 mmol) triethylamine in 2 mL DMF were stirred overnight at RT. The mixture was filtered through a syringe filter and the solution was purified by preparative HPLC. The product fractions were combined and lyophilised.

Yield: 35 mg (16% of theoretical)
ESI-MS: m/z=514 (M+H)+
$R_f$: 0.55 (silica gel, eluant A)

Example 43

1-(1-(6-(spiro[cyclobutan-1,3'-indolin]-1'-ylcarbonyl)pyrimidin-4-yl)piperidin-4-yl)-1H-imidazo[4,5-b]pyridin-2(3H)-one

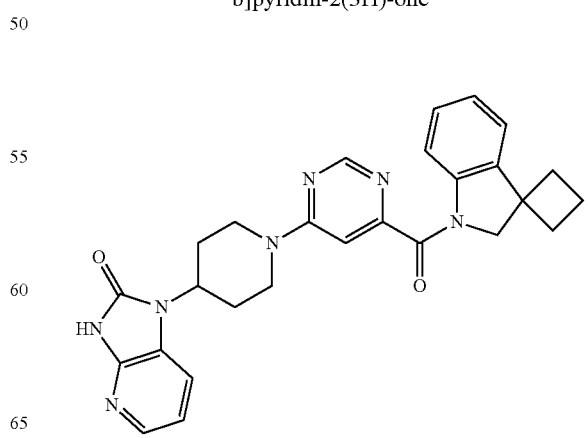

214 mg (0.63 mmol) 6-[4-(2-oxo-2,3-dihydro-imidazo[4,5-b]pyridin-1-yl)-piperidin-1-yl]-pyrimidine-4-carboxylic acid, 100 mg (0.628 mmol) spiro[cyclobutane-1,3'-indoline], 212 mg (0.66 mmol) TBTU and 168 µL (1.20 mmol) triethylamine in 4 mL DMF were stirred overnight at RT. The mixture was separated by preparative HPLC. The product fractions were combined and the acetonitrile was removed using the rotary evaporator. The precipitated substance was suction filtered, washed with 20 mL water and dried in the CAD at 50° C.

Yield: 187 mg (62% of theoretical)

ESI-MS: m/z=482 (M+H)$^+$

R$_t$ (HPLC-MS): 1.37 min (method C)

General Working Method 7 (GWM7) for Reacting 6-[4-(2-oxo-2,3-dihydro-imidazo[4,5-b]pyridin-1-yl)-piperidin-1-yl]-pyrimidine-4-carboxylic acid with amines 100 mg (0.31 mmol) TBTU were added to 100 mg (0.29 mmol) 6-[4-(2-oxo-2,3-dihydro-imidazo[4,5-b]pyridin-1-yl)-piperidin-1-yl]-pyrimidine-4-carboxylic acid, a corresponding amount of an amine (see Table) and 45 µL triethylamine in 10.0 mL DMF and stirred overnight at RT. The reaction mixture was evaporated down using the rotary evaporator. The residue was dissolved in 3 mL DMF and purified by preparative HPLC. The product fractions were combined and then lyophilised.

| Example | Structure | [amount of amine] amine Yield | Analytical data |
|---|---|---|---|
| Example 44: | 6-[4-(2-oxo-2,3-dihydro-imidazo[4,5-b]pyridin-1-yl)-piperidin-1-yl]-pyrimidine-4-carboxylic acid (2-m-tolylethyl)-amide | 40 mg (0.30 mmol) 3-methyl-phenethylamine 48 mg (36% of theory) | ESI-MS: m/z = 458 [M + H]$^+$ R$_f$ = 0.57 eluant A |
| Example 45: | [6-[4-(2-oxo-2,3-dihydro-imidazo[4,5-b]pyridin-1-yl)-piperidin-1-yl]-pyrimidine-4-carboxylic acid (1,1-dimethyl-2-m-tolyl-ethyl)-amide | 50 mg (0.31 mmol) 1,1-dimethyl-2-m-tolylethylamine 72 mg (51% of theory) | ESI-MS: m/z = 486 [M + H]$^+$ R$_f$ = 0.66 eluant A |
| Example 46: | 1-{1-[6-(2-methyl-2,3-dihydro-indole-1-carbonyl)-pyrimidin-4-yl]-piperidin-4-yl}-1,3-dihydroimidazo[4,5-b]pyridin-2-one | 40 µL (0.31 mmol) 2-methyl-2,3-dihydro-1H-indole 91 mg (68% of theory) | ESI-MS: m/z = 456 [M + H]$^+$ R$_f$ = 0.59 eluant A |

-continued

| Example | Structure | [amount of amine] amine Yield | Analytical data |
|---|---|---|---|
| Example 47: | 1-{1-[6-(5-methyl-2,3-dihydro-indole-1-carbonyl)-pyrimidin-4-yl]-piperidin-4-yl}-1,3-dihydroimidazo[4,5-b]pyridin-2-one | 40 µL (0.31 mmol) 5-methyl-2,3-dihydro-1H-indole 80 mg (60% of theory) | ESI-MS: m/z = 456 [M + H]$^+$ R$_f$ = 0.40 eluant A |

Example 48

1-{6-[4-(2-oxo-2,3-dihydroimidazo[4,5-b]pyridin-1-yl)-piperidin-1-yl]-pyrimidine-4-carbonyl}-2,3-dihydro-1H-indole-2-carboxylic acid

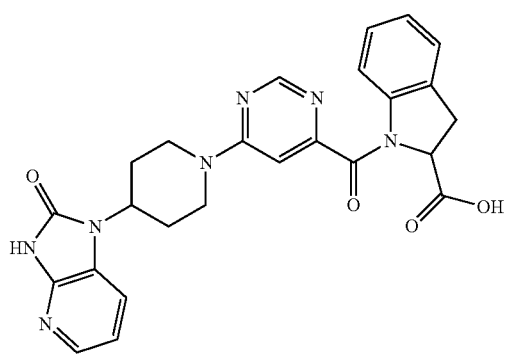 [SMILES: O=C(O)C1Cc2ccccc2N1C(=O)c1cc(N2CCC(n3c(=O)[nH]c4ncccc43)CC2)ncn1]

107 mg (0.31 mmol) 6-[4-(2-oxo-2,3-dihydroimidazo[4,5-b]pyridin-1-yl)-piperidin-1-yl]-pyrimidine-4-carboxylic acid, 65.0 mg (0.40 mmol) 2,3-dihydro-1H-indole-2-carboxylic acid, 107.0 mg (0.33 mmol) TBTU and 100 µL (0.71 mmol) triethylamine in 10 mL DMF were stirred overnight at RT. The mixture was evaporated down i. vac. and the residue was dissolved in 5 mL DMF. The purification was carried out by preparative HPLC. The product fractions were combined and lyophilised.

Yield: 10 mg (7% of theoretical)

ESI-MS: m/z=486 (M+H)$^+$

R$_f$: 0.07 (silica gel, eluant A)

General Working Method 8 (GWM8) for Reacting 6-[4-(2-oxo-2,3-dihydro-imidazo[4,5-b]pyridin-1-yl)-piperidin-1-yl]-pyrimidine-4-carboxylic acid with amines 100 mg (0.31 mmol) TBTU were added to 100 mg (0.29 mmol) 6-[4-(2-oxo-2,3-dihydroimidazo[4,5-b]pyridin-1-yl)-piperidin-1-yl]-pyrimidine-4-carboxylic acid, a corresponding amount of amine (see Table) and 100 µL (0.71 mmol) triethylamine in 1.5 mL DMF and the mixture was stirred overnight at RT. Working up was carried out by two different methods:

[A] The reaction mixture was diluted with 5 mL water and purified by preparative HPLC. The product fractions were combined and then lyophilised.

[B] The reaction mixture was filtered through a syringe filter and purified by preparative HPLC. The product fractions were combined and then lyophilised.

| Example method | Structure | [amount of amine] amine Yield | Analytical data |
|---|---|---|---|
| Example 49: GWM 8[A] | 1-{1-[6-(3-phenyl-pyrrolidin-1-carbonyl)-pyrimidin-4-yl]-piperidin-4-yl}-1,3-dihydroimidazo[4,5-b]pyridin-2-one | 55 mg (0.3 mmol) 3-phenyl-pyrrolidine-hydrochloride 55 mg (40% of theory) | ESI-MS: m/z = 470 [M + H]$^+$ $R_f$ = 0.59 eluant A |
| Example 50: GWM 8[A] | 1-{1-[6-(3,3-dimethylpyrrolidin-1-carbonyl)-pyrimidin-4-yl]-piperidin-4-yl}-1,3-dihydroimidazo[4,5-b]pyridin-2-one | 41 mg (0.3 mmol) 3,3-dimethyl-pyrrolidine-hydrochloride 65 mg (53% of theory) | ESI-MS: m/z = 422 [M + H]$^+$ $R_f$ = 0.57 eluant A |
| Example 51: GWM 8[A] | 1-{1-[6-(2-isopropyl-pyrrolidin-1-carbonyl)-pyrimidin-4-yl]-piperidin-4-yl}-1,3-dihydro-imidazo[4,5-b]pyridin-2-one | 45 mg (0.30 mmol) 2-(methylethyl)-pyrrolidine-hydrochloride 65 mg (51% of theory) | ESI-MS: m/z = 436 [M + H]$^+$ $R_f$ = 0.57 eluant A |
| Example 52: GWM 8[B] | 1-{1-[6-(6-aza-spiro[3,4]octane-6-carbonyl)-pyrimidin-4-yl]-piperidin-4-yl}-1,3-dihydro-imidazo[4,5-b]pyridin-2-one | 40 mg (0.36 mmol) 6-aza-spiro[3,4]octane 40 mg (31% of theory) | ESI-MS: m/z = 434 [M + H]$^+$ $R_f$ = 0.61 eluant A |

| Example method | Structure | [amount of amine] amine Yield | Analytical data |
|---|---|---|---|
| Example 53: GWM 8[B] | 1-{1-[6-(2,3-dihydro-pyrrolo[3,2-c]pyridin-1-carbonyl)-pyrimidin-4-yl]-piperidin-4-yl}-1,3-dihydroimidazo[4,5-b]pyridin-2-one | 40 mg (0.33 mmol) 2,3-dihydro-1H-pyrrolo[3,2-c]pyridine 60 mg (46% of theory) | ESI-MS: m/z = 443 [M + H]+ $R_f$ = 0.50 eluant A |

General Working Method 9 (GWM9) for Reacting 6-[4-(2-oxo-2,3-dihydro-imidazo[4,5-b]pyridin-1-yl)-piperidin-1-yl]-pyrimidine-4-carboxylic acid with amines 62 mg (0.19 mmol) TBTU were added to 60 mg (0.18 mmol) 6-[4-(2-oxo-2,3-dihydroimidazo[4,5-b]pyridin-1-yl)-piperidin-1-yl]-pyrimidine-4-carboxylic acid, 0.18 mmol amine and 52 µL (0.37 mmol) triethylamine in 1.5 mL DMF and the mixture was stirred for 4 h at RT. The reaction mixture was purified by preparative HPLC. The product fractions were combined and lyophilised.

| Example | Structure | [amount of amine] amine Yield | Analytical data |
|---|---|---|---|
| Example 54: | 1-{1-[6-(4,4-dimethyl-piperidine-1-carbonyl)-pyrimidin-4-yl]-piperidin-4-yl}-1,3-dihydroimidazo[4,5-b]pyridin-2-one | 31 mg (0.18 mmol) 4,4-dimethyl-piperidine 16 mg (21% of theory) | ESI-MS: m/z = 436 [M + H]+ $R_t$ = 1.12 min method C |

-continued

| Example | Structure | [amount of amine] amine Yield | Analytical data |
|---|---|---|---|
| Example 55: | 1-{1-[6-(4.4-dimethyl-3,4-dihydro-1 H-isoquinolin-2-carbonyl)-pyrimidin-4-yl]-piperidin-4-yl}-1,3-dihydroimidazo[4,5-b]pyridin-2-one | 28 mg (0.18 mmol) 4.4-dimethyl-1,2,3,4-tetrahydro-isoquinoline 35 mg (41% of theory) | ESI-MS: m/z = 484 [M + H]$^+$ R$_t$ = 1.25 min method C |
| Example 56: | 1-{1-[6-(6,7-dihydro-4H-thieno[3,2-c]pyridin-5-carbonyl)-pyrimidin-4-yl]-piperidin-4-yl}-1,3-dihydroimidazo[4,5-b]pyridin-2-one | 24.5 mg (0.18 mmol) 4,5,6,7-tetrahydro-thieno[3,2-c]pyridine 36 mg (44% of theory) | ESI-MS: m/z = 462 [M + H]$^+$ R$_t$ = 1.13 min method C |
| Example 57: | 1-{1-[6-(4.7-dihydro-5H-thieno[2,3-c]pyridin-6-carbonyl)-pyrimidin-4-yl]-piperidin-4-yl}-1,3-dihydro-imidazo[4,5-b]pyridin-2-one | 25 mg (0.18 mmol) 4,5,6,7-tetrahydro-thieno[2,3-c]pyridine 32 mg (39% of theory) | ESI-MS: m/z = 462 [M + H]$^+$ R$_t$ = 1.15 min method C |

Example 58

1-{1-[6-(4-amino-2,3-dihydroindole-1-carbonyl)-pyrimidin-4-yl]-piperidin-4-yl}-1,3-dihydro-imidazo[4,5-b]pyridin-2-one

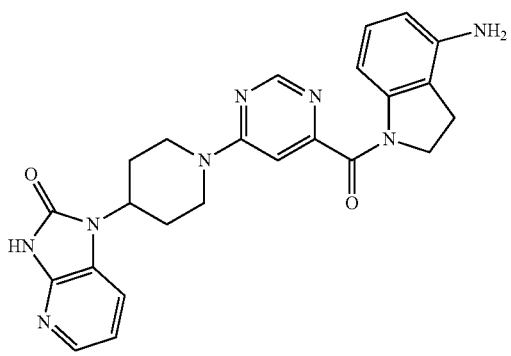 [SMILES: Nc1cccc2c1CCN2C(=O)c1cc(N2CCC(n3c(=O)[nH]c4ncccc43)CC2)ncn1]

Under a hydrogen atmosphere 130 mg (0.27 mmol) 1-{1-[6-(4-nitro-2,3-dihydroindole-1-carbonyl)-pyrimidin-4-yl]-piperidin-4-yl}-1,3-dihydroimidazo[4,5-b]pyridin-2-one and 25 mg palladium on charcoal (10%) were hydrogenated in a 1:1 mixture methanol:THF (15 mL of each) at RT and 3 bar hydrogen pressure. Then the catalyst was eliminated by suction filtering and the residue was washed with 50 mL DMF. The filtrate was evaporated down i. vac., the residue was stirred with methanol and suction filtered. The solid was dried at 50° C. in the CAD.

Yield: 40 mg (33% of theoretical)
ESI-MS: m/z=457 (M+H)+
$R_f$: 0.53 (silica gel, eluant A)

Example 59

1-{1-[6-(5-amino-2,3-dihydro-indole-1-carbonyl)-pyrimidin-4-yl]-piperidin-4-yl}-1,3-dihydro-imidazo[4,5-b]pyridin-2-one

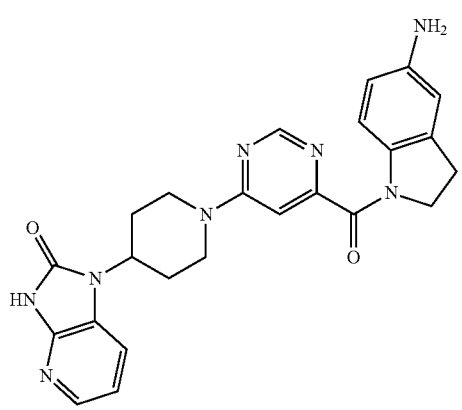

Under a hydrogen atmosphere 30 mg (0.06 mmol) 1-{1-[6-(5-nitro-2,3-dihydro-indole-1-carbonyl)-pyrimidin-4-yl]-piperidin-4-yl}-1,3-dihydro-imidazo[4,5-b]pyridin-2-one and 10 mg palladium on charcoal (10%) were hydrogenated in a 1:1 mixture methanol:THF (5 mL each) at RT and 3 bar hydrogen pressure. Then the catalyst was removed by suction filtering and the filtrate was evaporated down i. vac. The residue was dissolved in 1 mL DMF, filtered through a syringe filter and purified by preparative HPLC. The product fractions were combined and lyophilised.

Yield: 1 mg (4% of theoretical)
ESI-MS: m/z=457 (M+H)+
$R_f$: 0.51 (silica gel, eluant A)

Example 60

3-{1-[6-(7,8-dihydro-5H-1,6-naphthyridin-6-carbonyl)-pyrimidin-4-yl]-piperidin-4-yl}-7-methoxy-1,3,4,5-tetrahydro-1,3-benzodiazepin-2-one

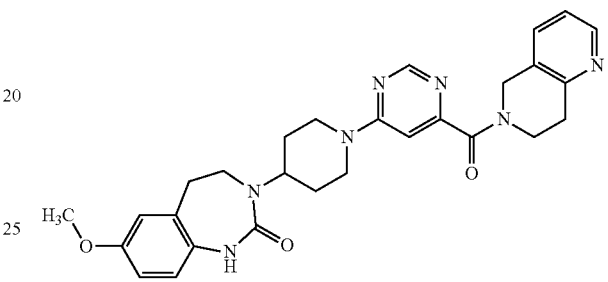

Under a hydrogen atmosphere 77 mg (0.12 mmol) 3-{1-[6-(3-bromo-7,8-dihydro-5H-1,6-naphthyridin-6-carbonyl)-pyrimidin-4-yl]-piperidin-4-yl}-7-methoxy-1,3,4,5-tetrahydro-1,3-benzodiazepin-2-one and 40 mg palladium on charcoal (10%) were hydrogenated in 10 mL methanol at 50° C. under 50 psi hydrogen pressure. Then the catalyst was removed by suction filtering and the filtrate was evaporated down i. vac. The residue was purified by preparative HPLC. The product fractions were combined and lyophilised.

Yield: 27 mg (43% of theoretical)
ESI-MS: m/z=514 (M+H)+
$R_t$ (HPLC-MS): 2.19 min (method E)

Example 61

6-[4-(2-oxo-2,3-dihydro-imidazo[4,5-t]pyridin-1-yl)-piperidin-1-yl]-pyrimidine-4-carboxylic acid-indan-2-ylamide

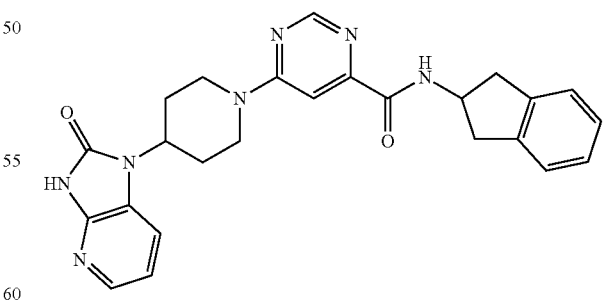

100 mg (0.29 mmol) 6-[4-(2-oxo-2,3-dihydro-imidazo[4,5-b]pyridin-1-yl)-piperidin-1-yl]-pyrimidine-4-carboxylic acid, 40.0 mg (0.30 mmol) indan-2-ylamine, 100 mg (0.31 mmol) TBTU and 45 μL (0.32 mmol) triethylamine in 10 mL DMF were stirred overnight at RT. The mixture was evaporated down i. vac., the residue was dissolved in 3 mL DMF and purified by preparative HPLC. The product fractions were combined and lyophilised.
Yield: 62 mg (46% of theoretical)
ESI-MS: m/z=456 (M+H)$^+$
$R_f$: 0.74 (silica gel, eluant A)

Example 62

6-[4-(7-methoxy-2-oxo-1,2,4,5-tetrahydro-1,3-benzodiazepin-3-yl)-piperidin-1-yl]-pyrimidine-4-carboxylic acid-phenylamide

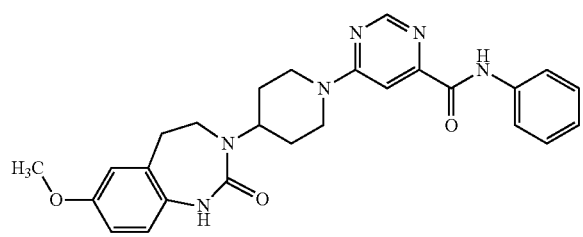 [SMILES: COc1ccc2c(c1)CCN(C1CCN(c3cc(C(=O)Nc4ccccc4)ncn3)CC1)C(=O)N2]

120.0 mg (0.30 mmol) 6-[4-(7-methoxy-2-oxo-1,2,4,5-tetrahydro-1,3-benzodiazepin-3-yl)-piperidin-1-yl]-pyrimidine-4-carboxylic acid, 30 µL (0.33 mmol) aniline, 120.0 mg (0.37 mmol) TBTU and 100 µL (0.71 mmol) triethylamine in 2 mL DMF were stirred overnight at RT. The mixture was filtered through a syringe filter and purified by preparative HPLC. The product fractions were combined and lyophilised.
Yield: 65 mg (46% of theoretical)
ESI-MS: m/z=473 (M+H)$^+$
$R_f$: 0.57 (silica gel, eluant A)

Example 63

1-{1-[6-(indole-1-carbonyl)-pyrimidin-4-yl]-piperidin-4-yl}-1,3-dihydro-imidazo[4,5-b]pyridin-2-one

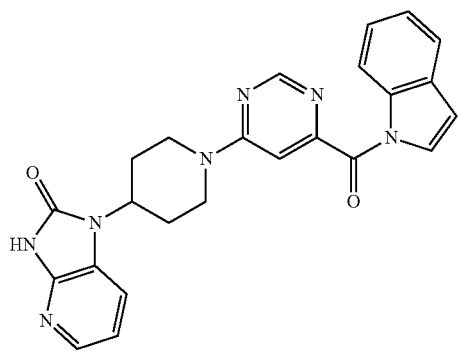 [SMILES: O=C(c1cc(N2CCC(n3c(=O)[nH]c4ncccc43)CC2)ncn1)n1ccc2ccccc21]

100 mg (0.34 mmol) 1-piperidin-4-yl-1,3-dihydro-imidazo[4,5-b]pyridin-2-one dihydrochloride and 200 µL (1.162 mmol) DIPEA were added to 100 mg (0.39 mmol) (6-chloropyrimidin-4-yl)-indol-1-yl-methanone in 30 mL DMF. The reaction mixture was stirred for 3 h at RT. The reaction mixture was evaporated down i. vac. The residue was combined with 20 mL water and stirred for 10 min. The solid was suction filtered and purified by flash chromatography. The product fractions were combined and evaporated down i. vac. The residue was triturated with diisopropylether and suction filtered. The solid was dried at 40° C. in the CAD.

Yield: 75 mg (44% of theoretical)
ESI-MS: m/z=440 (M+H)$^+$
$R_f$: 0.55 (silica gel, eluant A)

Example 64

1-{1-[6-(3-methyl-indole-1-carbonyl)-pyrimidin-4-yl]-piperidin-4-yl}-1,3-dihydro-imidazo[4,5-b]pyridin-2-one

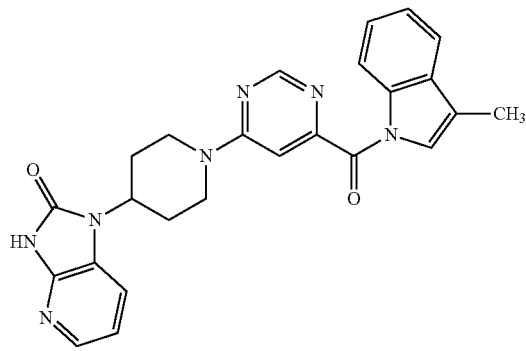 [SMILES: Cc1cn(C(=O)c2cc(N3CCC(n4c(=O)[nH]c5ncccc54)CC3)ncn2)c2ccccc12]

227 mg (0.78 mmol) 1-piperidin-4-yl-1,3-dihydro-imidazo[4,5-b]pyridin-2-one dihydrochloride were added to 200 mg (0.74 mmol) (6-chloropyrimidin-4-yl)-(3-methyl-indol-1-yl)-methanone and 413 µL (2.40 mmol) DIPEA in 5 mL DMF. The reaction mixture was stirred overnight at RT and then purified by preparative HPLC. The product fractions were combined and concentrated by rotary evaporation using the rotary evaporator. The residue was taken up in methanol and purified through a silica gel column. The product fractions were combined and concentrated by rotary evaporation using the rotary evaporator.
Yield: 210 mg (63% of theoretical)
ESI-MS: m/z=454 (M+H)$^+$
$R_t$ (HPLC-MS): 1.46 min (method C)

Example 65

1-{1-[6-(5-fluoroindole-1-carbonyl)-pyrimidin-4-yl]-piperidin-4-yl}-1,3-dihydro-imidazo[4,5-b]pyridin-2-one

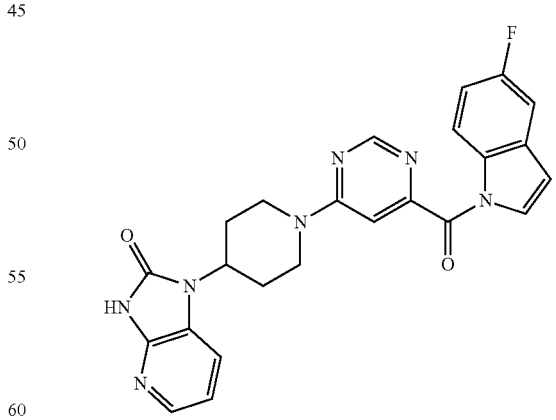

75.0 mg (0.26 mmol) 1-piperidin-4-yl-1,3-dihydro-imidazo[4,5-b]pyridin-2-one dihydrochloride and 150 µL (0.87 mmol) DIPEA were added to 70 mg (0.25 mmol) (6-chloropyrimidin-4-yl)-(5-fluoroindol-1-yl)-methanone in 5 mL DMF. The reaction mixture was stirred overnight at RT and then evaporated down i. vac. The residue was taken up in 20 mL water and stirred for 10 min. The precipitate was suction filtered, dissolved in 2.5 mL DMF and purified by preparative HPLC. The product fractions were combined and concentrated by rotary evaporation using the rotary evaporator.

Yield: 40 mg (34% of theoretical)
ESI-MS: m/z=458 (M+H)$^+$
$R_f$ (silica gel): 0.45 (eluant A)

Example 66

3-{1-[6-(4,5-difluoro-2,3-dihydro-indole-1-carbonyl)-pyrimidin-4-yl]-piperidin-4-yl}-7-methoxy-1,3,4,5-tetrahydro-1,3-benzodiazepin-2-one

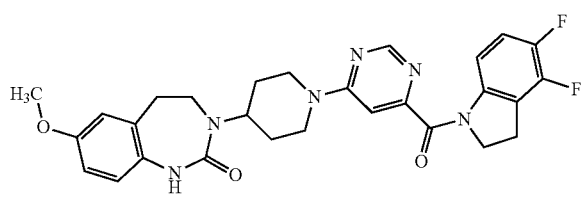 [SMILES: COc1ccc2c(c1)CCN(C1CCN(c3cc(C(=O)N4CCc5c4ccc(F)c5F)ncn3)CC1)C(=O)N2]

0.12 g (0.29 mmol) 6-[4-(7-methoxy-2-oxo-1,2,4,5-tetrahydro-1,3-benzodiazepin-3-yl)-piperidin-1-yl]-pyrimidine-4-carboxylic acid, 60 mg (0.31 mmol) 4,5-difluoroindoline-hydrochloride, 0.10 mL (0.71 mmol) TEA and 0.10 g (0.31 mmol) TBTU were stirred overnight in 10 mL DMF at RT. The reaction mixture was concentrated to dryness by rotary evaporation and then purified by HPLC. The product-containing fractions were combined and freeze-dried.

Yield: 58 mg (38% of theory)
ESI-MS: m/z=535 (M+H)$^+$
$R_f$ (silica gel): 0.70 (DCM/cyclohexane/MeOH/NH4OH=70:15:15:2)

Analogously to 3-{1-[6-(4,5-difluoro-2,3-dihydro-indole-1-carbonyl)-pyrimidin-4-yl]-piperidin-4-yl}-7-methoxy-1,3,4,5-tetrahydro-1,3-benzodiazepin-2-one the following compounds were prepared from in each case 0.15-0.44 mmol 6-[4-(7-methoxy-2-oxo-1,2,4,5-tetrahydro-1,3-benzodiazepin-3-yl)-piperidin-1-yl]-pyrimidine-4-carboxylic acid, 1.0 to 1.3 eq TBTU, 1.2 to 4.2 eq TEA and 1 to 1.5 eq of the respective amine in a suitable amount of solvent such as NMP or DMF:

| Ex. | Structure Name | [amount of amine] Amine Yield | Analytical data |
|---|---|---|---|
| 67 | 3-(1-{6-[5-fluoro-3-(2-methoxy-ethyl)-3-methyl-2,3-dihydro-indole-1-carbonyl]-pyrimidin-4-yl}-piperidin-4-yl)-7-methoxy-1,3,4,5-tetrahydro-1,3-benzodiazepin-2-one | 80 mg (0.38 mmol) 5-fluoro-3-(2-methoxy-ethyl)-3-methyl-2,3-dihydro-1 H-indole 110 mg (49% of theory) | ESI MS: m/z = 589 [M + H]$^+$ $R_t$ = 1.54 min method C |
| 68 | 3-{1-[6-(5-fluoro-2,3-dihydro-indole-1-carbonyl)-pyrimidin-4-yl]-piperidin-4-yl}-7-methoxy-1,3,4,5-tetrahydro-1,3-benzodiazepin-2-one | 45 mg (0.33 mmol) 5-fluoro-2,3-dihydro-1H-indole 94 mg (60% of theory) | ESI-MS: m/z = 517 [M + H]$^+$ $R_f$ = 0.75 silica gel, (eluant A |

-continued

| Ex. | Structure Name | [amount of amine] Amine Yield | Analytical data |
|---|---|---|---|
| 69 | 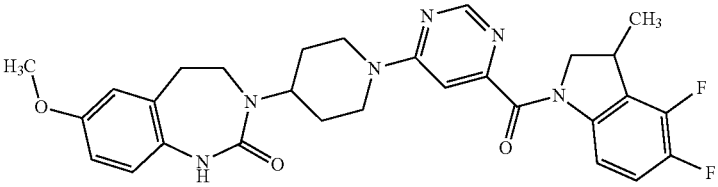 [SMILES: COc1ccc2c(c1)CCN(C1CCN(c3cc(C(=O)N4CC(C)c5c4ccc(F)c5F)ncn3)CC1)C(=O)N2]<br>3-{1-[6-(4,5-difluoro-3-methyl-2,3-dihydro-indole-1-carbonyl)-pyrimidin-4-yl]-piperidin-4-yl}-7-methoxy-1,3,4,5-tetrahydro-1,3-benzodiazepin-2-one | 37 mg (0.22 mmol) 4,5-difluoro-3-methyl-2,3-dihydro-1H-indole 70 mg (63% of theory) | ESI-MS: m/z = 549 [M + H]$^+$ R$_t$ = 4.2 min method K |
| 70 | 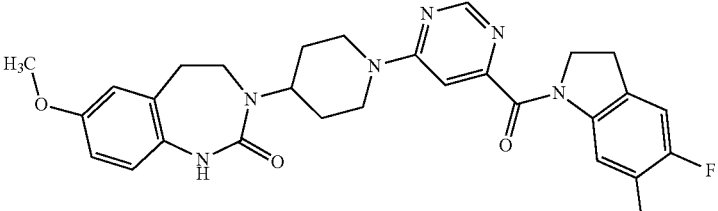<br>3-{1-[6-(5,6-difluoro-2,3-dihydro-indole-1-carbonyl)-pyrimidin-4-yl]-piperidin-4-yl}-7-methoxy-1,3,4,5-tetrahydro-benzodiazepin-2-one | 47 mg (0.30 mmol) 5,6-difluoro-2,3-dihydro-1 H-indole 66 mg (49% of theory) | ESI-MS: m/z = 535 [M + H]$^+$ R$_t$ = 1.5 min method C |
| 71 | 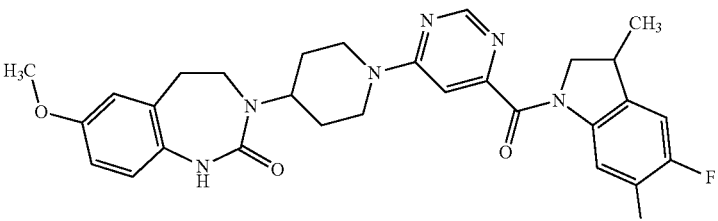<br>3-{1-[6-(5,6-difluoro-3-methyl-2,3-dihydro-indole-1-carbonyl)-pyrimidin-4-yl]-piperidin-4-yl}-7-methoxy-1,3,4,5-tetrahydro-1,3-benzodiazepin-2-one | 36 mg (0.21 mmol) 5,6-difluoro-3-methyl-2,3-dihydro-1H-indole 45 mg (41% of theory) | ESI-MS: m/z = 549 [M + H]$^+$ R$_t$ = 4.4 min method K |
| 72 | 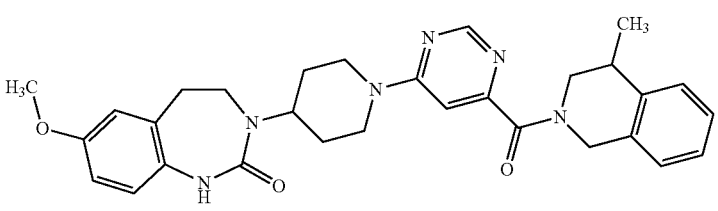 [SMILES: COc1ccc2c(c1)CCN(C1CCN(c3cc(C(=O)N4Cc5ccccc5C(C)C4)ncn3)CC1)C(=O)N2]<br>7-methoxy-3-{1-[6-(4-methyl-3,4-dihydro-1H-isoquinoline-2-carbonyl)-pyrimidin-4-yl]-piperidin-4-yl}-1,3,4,5-tetrahydro-1,3-benzodiazepin-2-one | 37 mg (0.20 mmol) 4-methyl-1,2,3,4-tetrahydro-isoquinoline hydrochloride 17 mg (18% of theory) | ESI-MS: m/z = 527 [M + H]$^+$ R$_t$ = 1.38 min method C |
| 73 | 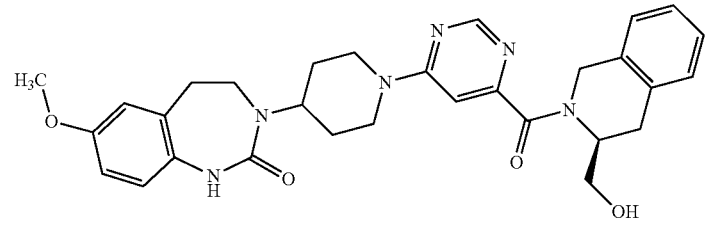 [SMILES: COc1ccc2c(c1)CCN(C1CCN(c3cc(C(=O)N4Cc5ccccc5C[C@H]4CO)ncn3)CC1)C(=O)N2]<br>(S)-3-{1-[6-(3-hydroxymethyl-3,4-dihydro-1H-isoquinoline-2-carbonyl)-pyrimidin-4-yl]-piperidin-4-yl}-7-methoxy-1,3,4,5-tetrahydro-1,3-benzodiazepin-2-one | 25 mg (0.15 mmol) S-(-)-(1,2,3,4-tetrahydro-isoquinolin-3-yl)-methanol 42 mg (51% of theory) | ESI-MS: m/z = 543 [M + H]$^+$ R$_t$ = 1.27 min method C |

| Ex. | Structure Name | [amount of amine] Amine Yield | Analytical data |
|---|---|---|---|
| 74 | 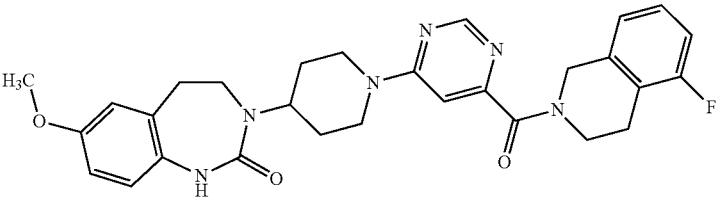 [SMILES: COc1ccc2c(c1)CCN(C1CCN(c3cc(C(=O)N4CCc5c(F)cccc5C4)ncn3)CC1)C(=O)N2]<br>3-{1-[6-(5-fluoro-3,4-dihydro-1H-iso-quinoline-2-carbonyl)-pyrimidin-4-yl]-piperidin-4-yl}-7-methoxy-1,3,4,5-tetrahydro-1,3-benzodiazepin-2-one | 28 mg (0.15 mmol) 5-fluoro-1,2,3,4-tetrahydro-isoquinoline hydrochloride 12 mg (15% of theory) | ESI-MS: m/z = 531 [M + H]$^+$ R$_t$ = 1.37 min method C |
| 75 | 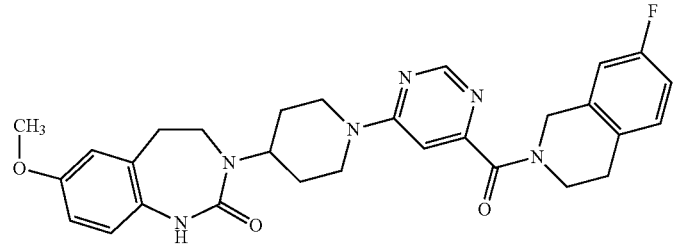 [SMILES: COc1ccc2c(c1)CCN(C1CCN(c3cc(C(=O)N4CCc5ccc(F)cc5C4)ncn3)CC1)C(=O)N2]<br>3-{1-[6-(7-fluoro-3,4-dihydro-1H-iso-quinoline-2-carbonyl)-pyrimidin-4-yl]-piperidin-4-yl}-7-methoxy-1,3,4,5-tetrahydro-1,3-benzodiazepin-2-one | 28 mg (0.15 mmol) 7-fluoro-1,2,3,4-tetrahydro-isoquinoline hydrochloride 12 mg (15% of theory) | ESI-MS: m/z = 531 [M + H]$^+$ R$_t$ = 1.36 min method C |
| 76 | 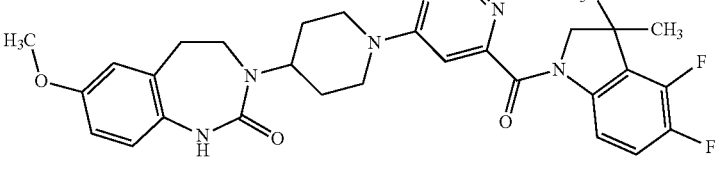<br>3-{1-[6-(4,5-difluoro-3,3-dimethyl-2,3-dihydro-indole-1-carbonyl)-pyrimidin-4-yl]-piperidin-4-yl}-7-methoxy-1,3,4,5-tetrahydro-1,3-benzodiazepin-2-one | 80 mg (0.44 mmol) 4,5-difluoro-3,3-dimethyl-2,3-dihydro-1H-indole 150 mg (61% of theory) | ESI-MS: m/z = 563 [M + H]$^+$ R$_t$ = 1.63 min method C |
| 77 | 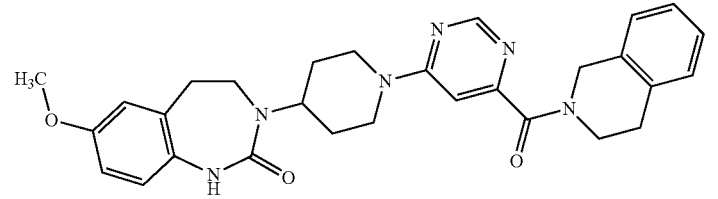 [SMILES: COc1ccc2c(c1)CCN(C1CCN(c3cc(C(=O)N4CCc5ccccc5C4)ncn3)CC1)C(=O)N2]<br>3-{1-[6-(3,4-dihydro-1H-isoquinoline-2-carbonyl)-pyrimidin-4-yl]-piperidin-4-yl}-7-methoxy-1,3,4,5-tetrahydro-1,3-benzodiazepin-2-one | 20 mg (0.15 mmol) 1,2,3,4-tetrahydro-isoquinoline 40 mg (52% of theory) | ESI-MS: m/z = 513 [M + H]$^+$ R$_t$ = 1.36 min method C |
| 78 | 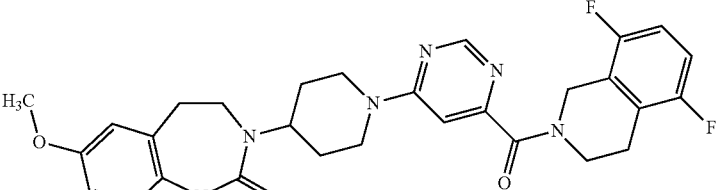<br>3-(1-[6-(5,8-difluoro-3,4-dihydro-1H-isoquinoline-2-carbonyl)-pyrimidin-4-yl]-piperidin-4-yl}-7-methoxy-1,3,4,5-tetrahydro-1,3-benzodiazepin-2-one | 31 mg (0.15 mmol) 5,8-difluoro-1,2,3,4-tetrahydro-isoquinoline 47 mg (57% of theory) | ESI-MS: m/z = 549 [M + H]$^+$ R$_t$ = 1.43 min method C |

| Ex. | Structure Name | [amount of amine] Amine Yield | Analytical data |
|---|---|---|---|
| 79 | 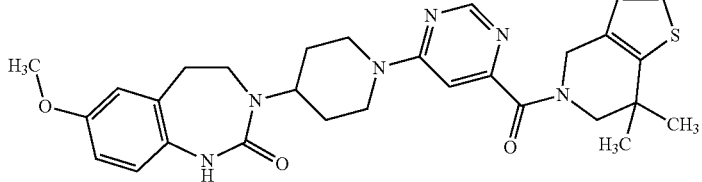<br>3-{1-[6-(7,7-dimethyl-6,7-dihydro-4H-thieno[3,2-c]pyridine-5-carbonyl)-pyrimidin-4-yl]-piperidin-4-yl}-7-methoxy-1,3,4,5-tetrahydro-1,3-benzodiazepin-2-one | 40 mg (0.21 mmol) 7,7-dimethyl-4,5,6,7-tetrahydro-thieno-[3,2-c]pyridine 29 mg (25% of theory) | ESI-MS: m/z = 547 [M + H]$^+$ R$_t$ = 3.94 min method K |
| 80 | 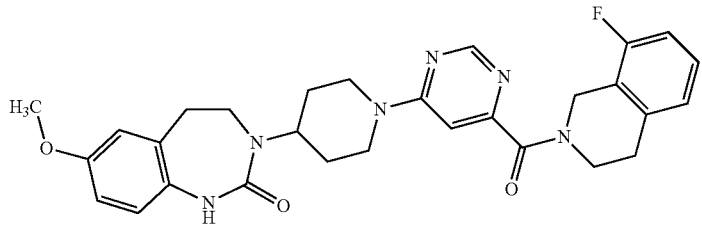 [SMILES: COc1ccc2c(c1)CCN(C1CCN(c3cc(C(=O)N4CCc5cccc(F)c5C4)ncn3)CC1)C(=O)N2]<br>3-{1-[6-(8-fluoro-3,4-dihydro-1H-iso-quinoline-2-carbonyl)-pyrimidin-4-yl]-piperidin-4-yl}-7-methoxy-1,3,4,5-tetrahydro-1,3-benzodiazepin-2-one | 28 mg (0.15 mmol) 8-fluoro-1,2,3,4-tetrahydro-isoquinoline hydrochloride 22 mg (28% of theory) | ESI-MS: m/z = 531 [M + H]$^+$ R$_t$ = 1.38 min method C |
| 81 | 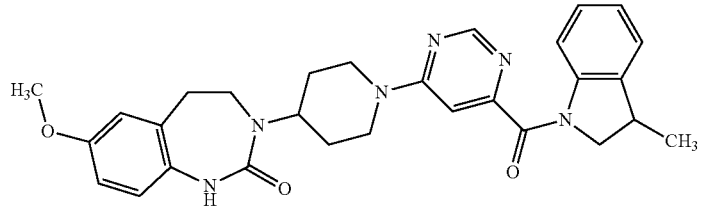<br>7-methoxy-3-{1-[6-(3-methyl-2,3-dihydro-indole-1-carbonyl)-pyrimidin-4-yl]-piperidin-4-yl}-1,3,4,5-tetrahydro-1,3-benzodiazepin-2-one | 40 mg (0.30 mmol) 3-methyl-2,3-dihydro-1H-indole 85 mg (66% of theory) | ESI-MS: m/z = 513 [M + H]$^+$ R$_f$ = 0.77 silica gel, (eluant A |
| 82 | 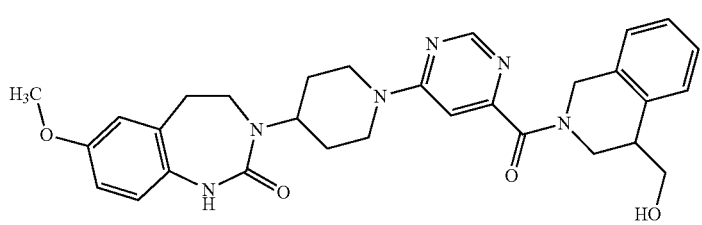 [SMILES: COc1ccc2c(c1)CCN(C1CCN(c3cc(C(=O)N4Cc5ccccc5C(CO)C4)ncn3)CC1)C(=O)N2]<br>3-{1-[6-(4-hydroxymethyl-3,4-dihydro-1H-isoquinoline-2-carbonyl)-pyrimidin-4-yl]-piperidin-4-yl}-7-methoxy-1,3,4,5-tetrahydro-1,3-benzodiazepin-2-one | 25 mg (0.15 mmol) (1,2,3,4-tetrahydro-isoquinolin-4-yl)-methanol 4 mg (5% of theory) | ESI-MS: m/z = 543 [M + H]$^+$ R$_t$ = 1.27 min method C |
| 83 | 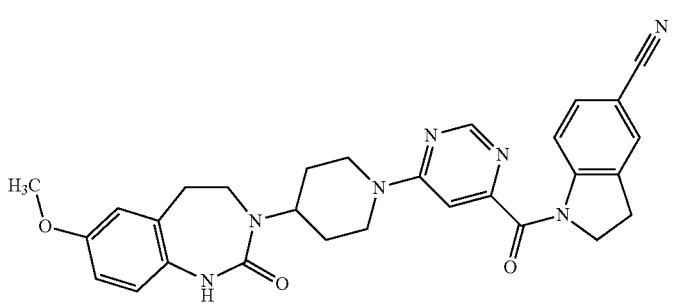 [SMILES: COc1ccc2c(c1)CCN(C1CCN(c3cc(C(=O)N4CCc5cc(C#N)ccc54)ncn3)CC1)C(=O)N2]<br>1-{6-[4-(7-methoxy-2-oxo-1,2,4,5-tetrahydro-benzo[d][1,3]diazepin-3-yl)-piperidin-1-yl]-pyrimidine-4-carbonyl}-2,3-dihydro-1H-indole-5-carbonitrile | 50 mg (0.35 mmol) 2,3-dihydro-1H-indole-5-carbonitrile 30 mg (19% of theory) | ESI-MS: m/z = 524 [M + H]$^+$ R$_f$ = 0.77 silica gel, (eluant A |

| Ex. | Structure Name | [amount of amine] Amine Yield | Analytical data |
|---|---|---|---|
| 84 | 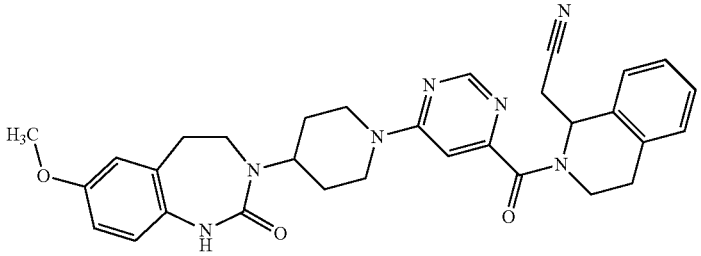 [SMILES: COc1ccc2c(c1)CCN(C1CCN(c3cc(C(=O)N4CCc5ccccc5C4CC#N)ncn3)CC1)C(=O)N2]<br>(2-{6-[4-(7-methoxy-2-oxo-1,2,4,5-tetrahydro-1,3-benzodiazepin-3-yl)-piperidin-1-yl]-pyrimidine-4-carbonyl}-1,2,3,4-tetrahydro-isoquinolin-1-yl)-acetonitrile | 32 mg (0.15 mmol) (1,2,3,4-tetrahydro-isoquinolin-1-yl)-acetonitrile hydrochloride 39 mg (47% of theory) | ESI MS: m/z = 552 [M + H]$^+$ R$_t$ = 1.39 min method C |
| 85 | 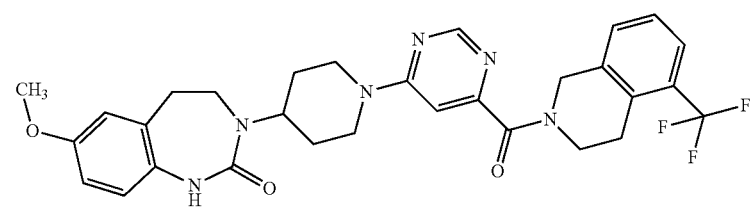 [SMILES: COc1ccc2c(c1)CCN(C1CCN(c3cc(C(=O)N4CCc5c(cccc5C(F)(F)F)C4)ncn3)CC1)C(=O)N2]<br>7-methoxy-3-{1-[6-(5-trifluoromethyl-3,4-dihydro-1H-isoquinoline-2-carbonyl)-pyrimidin-4-yl]-piperidin-4-yl}-1,3,4,5-tetrahydro-1,3-benzodiazepin-2-one | 36 mg (0.15 mmol) 5-trifluoromethyl-1,2,3,4-tetrahydro-isoquinoline hydrochloride 41 mg (47% of theory) | ESI-MS: m/z = 581 [M + H]$^+$ R$_t$ = 1.47 min method C |
| 86 | 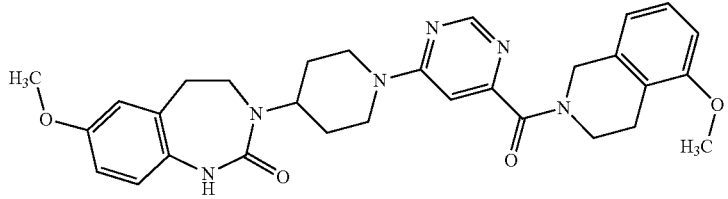 [SMILES: COc1ccc2c(c1)CCN(C1CCN(c3cc(C(=O)N4CCc5c(cccc5OC)C4)ncn3)CC1)C(=O)N2]<br>7-methoxy-3-{1-[6-(5-methoxy-3,4-dihydro-1H-isoquinoline-2-carbonyl)-pyrimidin-4-yl]-piperidin-4-yl}-1,3,4,5-tetrahydro-1,3-benzodiazepin-2-one | 30 mg (0.15 mmol) 5-methoxy-1,2,3,4-tetrahydro-isoquinoline hydrochloride 42 mg (51% of theory) | ESI-MS: m/z = 543 [M + H]$^+$ R$_t$= 1.39 min method C |
| 87 | 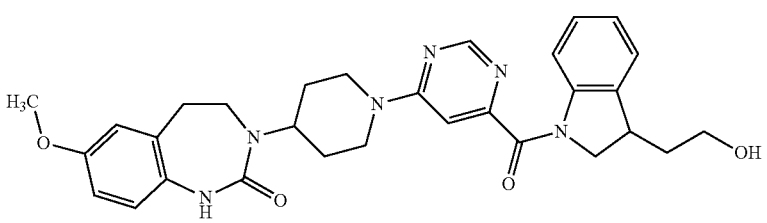 [SMILES: COc1ccc2c(c1)CCN(C1CCN(c3cc(C(=O)N4CC(CCO)c5ccccc54)ncn3)CC1)C(=O)N2]<br>3-(1-{6-[3-(2-hydroxy-ethyl)-2,3-dihydroindole-1-carbonyl]-pyrimidin-4-yl}-piperidin-4-yl)-7-methoxy-1,3,4,5-tetrahydro-benzo[d][1,3]-diazepin-2-one | 50 mg (0.31 mmol) 2-(2,3-dihydro-1H-indol-3-yl)-ethanol 90 mg (66% of theory) | ESI-MS: m/z = 543 [M + H]$^+$ R$_f$= 0.77 silica gel, eluant A |
| 88 | 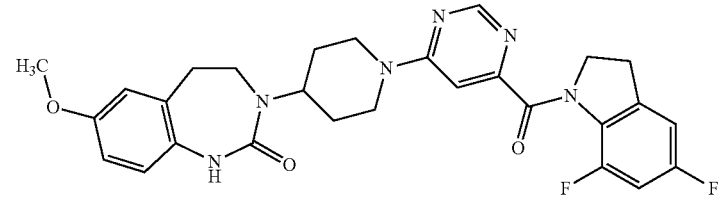 [SMILES: COc1ccc2c(c1)CCN(C1CCN(c3cc(C(=O)N4CCc5cc(F)cc(F)c54)ncn3)CC1)C(=O)N2]<br>3-{1-[6-(5,7-difluoro-2,3-dihydro-indole-1-carbonyl)-pyrimidin-4-yl]-piperidin-4-yl}-7-methoxy-1,3,4,5-tetrahydro-benzo[d][1,3]diazepin-2-one | 33 mg (0.21 mmol) 5,7-difluoro-2-dihydro-1H-indole 35 mg (33% of theory) | ESI-MS: m/z = 535 [M + H]$^+$ R$_t$ = 4.8 min method B |

-continued

| Ex. | Structure Name | [amount of amine] Amine Yield | Analytical data |
|---|---|---|---|
| 89 | 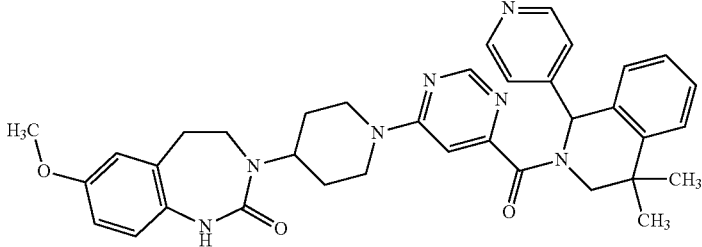 [SMILES: COc1ccc2c(c1)CCN(C1CCN(c3cc(C(=O)N4CC(C)(C)c5ccccc5C4c4ccncc4)ncn3)CC1)C(=O)N2]<br>3-{1-[6-(4,4-dimethyl-1-pyridin-4-yl-3,4-dihydro-1H-isoquinoline-2-carbonyl)-pyrimidin-4-yl]-piperidin-4-yl}-7-methoxy-1,3,4,5-tetrahydro-benzo-[d][1,3]diazepin-2-one | 36 mg (0.15 mmol) 4,4-dimethyl-1-pyridin-4-yl-1,2,3,4-tetrahydro-isoquinoline 34 mg (37% of theory) | ESI-MS: m/z = 618 [M + H]+ $R_t$ = 1.51 min method C |
| 90 | 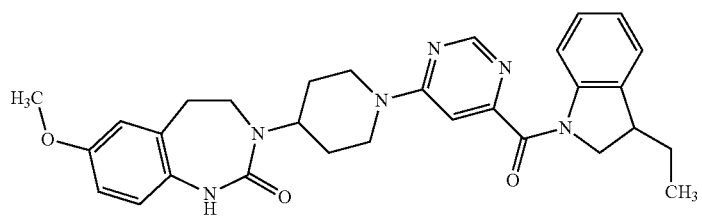 [SMILES: CCC1CN(C(=O)c2cc(N3CCC(N4CCc5cc(OC)ccc5NC4=O)CC3)ncn2)c2ccccc21]<br>3-{1-[6-(3-ethyl-2,3-dihydroindole-1-carbonyl)-pyrimidin-4-yl]-piperidin-4-yl}-7-methoxy-1,3,4,5-tetrahydro-benzo[d][1,3]diazepin-2-one | 34 mg (0.23 mmol) 3-ethyl-2,3-dihydro-1H-indole 29 mg (26% of theory) | ESI-MS: m/z = 527 [M + H]+ $R_t$ = 1.52 min method C |
| 91 | 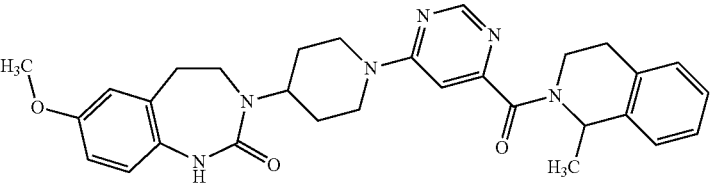 [SMILES: COc1ccc2c(c1)CCN(C1CCN(c3cc(C(=O)N4CCc5ccccc5C4C)ncn3)CC1)C(=O)N2]<br>7-methoxy-3-{1-[6-(1-methyl-3,4-dihydro-1H-isoquinoline-2-carbonyl)-pyrimidin-4-yl]-piperidin-4-yl}-1,3,4,5-tetrahydro-benzo[d][1,3]diazepin-2-one | 69 mg (0.15 mmol) 1-methyl-1,2,3,4-tetrahydro-isoquinoline hydrochloride 10 mg (13% of theory) | ESI-MS: m/z = 527 [M + H]+ $R_t$ = 1.44 min method C |
| 92 | 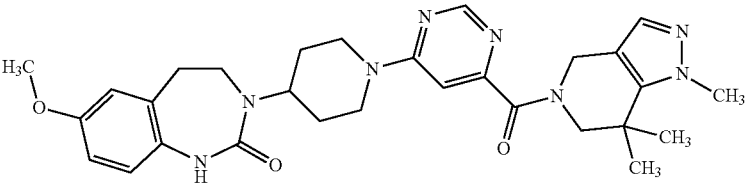<br>7-methoxy-3-{1-[6-(1,7,7-trimethyl-1,4,6,7-tetrahydro-pyrazolo[4,3-c]-pyridine-5-carbonyl)-pyrimidin-4-yl]-piperidin-4-yl}-1,3,4,5-tetrahydro-benzo[d][1,3]diazepin-2-one | 125 mg (0.34 mmol) 1,7,7-trimethyl-4,5,6,7-tetrahydro-1H-pyrazolo[4,3-c]-pyridinium trifluoroacetate 44 mg (29% of theory) | ESI-MS: m/z = 545 [M + H]+ $R_t$ = 2.75 min method E |
| 93 | 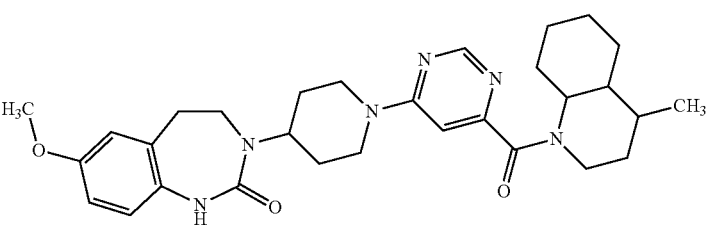<br>7-methoxy-3-{1-[6-(4-methyl-octahydro-quinoline-1-carbonyl)-pyrimidin-4-yl]-piperidin-4-yl}-1,3,4,5-tetrahydro-benzo[d][1,3]diazepin-2-one | 11 mg (0.08 mmol) 4-methyl-decahydro-quinoline 12 mg (15% of theory) | ESI-MS: m/z = 533 [M + H]+ $R_t$ = 1.45 min method C |

-continued

| Ex. | Structure Name | [amount of amine] Amine Yield | Analytical data |
|---|---|---|---|
| 94 | 7-methoxy-3-{1-[6-(3-trifluoromethyl-1,4,6,7-tetrahydro-pyrazolo[4,3-c]pyridine-5-carbonyl)-pyrimidin-4-yl]-piperidin-4-yl}-1,3,4,5-tetrahydro-benzo[d][1,3]diazepin-2-one | 50 mg (0.26 mmol) 3-trifluoromethyl-4,5,6,7-tetrahydro-1H-pyrazolo[4,3-c]pyridine 65 mg (57% of theory) | ESI-MS: m/z = 571 [M + H]$^+$ R$_t$ = 2.92 min method E |
| 95 | 3-{1-[6-(7,7-dimethyl-6,7-dihydro-4H-thieno[3,4-c]pyridine-5-carbonyl)-pyrimidin-4-yl]-piperidin-4-yl}-7-methoxy-1,3,4,5-tetrahydro-benzo[d][1,3]diazepin-2-one | 0.16 g (0.24 mmol) 7,7-dimethyl-4,5,6,7-tetrahydro-thieno[3,4c]pyridine 7.4 mg (6% of theory) | ESI-MS: m/z = 547 [M + H]$^+$ R$_t$ = 4.03 min method E |
| 96 | 3-{1-[6-(3-cyclopropylmethyl-2,3-dihydro-indole-1-carbonyl)-pyrimidin-4-yl]-piperidin-4-yl}-7-methoxy-1,3,4,5-tetrahydro-benzo[d][1,3]diazepin-2-one | 40 mg (0.23 mmol) 3-cyclopropyl-methyl-2,3-dihydro-1H-indole 76 mg (66% of theory) | ESI-MS: m/z = 553 [M + H]$^+$ R$_t$ = 1.62 min method C |
| 97 | 3-{1-[6-(4,7-dihydro-5H-thieno[2,3-c]pyridin-6-carbonyl)-pyrimidin-4-yl]-piperidin-4-yl}-7-methoxy-1,3,4,5-tetrahydro-benzo[d][1,3]diazepin-2-one | 21 mg (0.15 mmol) 4,5,6,7-tetrahydro-thieno[2,3-c]pyridine 38 mg (49% of theory) | ESI-MS: m/z = 519 [M + H]$^+$ R$_t$ = 1.31 min method C |
| 98 | 7-methoxy-3-{1-[6-(1-thiophene-2-yl-3,4-dihydro-1H-pyrrolo[1,2-a]pyrazine-2-carbonyl)-pyrimidin-4-yl]-piperidin-4-yl}-1,3,4,5-tetrahydro-benzo[d]-[1,3]diazepin-2-one | 31 mg (0.15 mmol) 1-thiophen-2-yl-1,2,3,4-tetrahydro-pyrrolo-[1,2-a]pyrazine 47 mg (53% of theory) | ESI-MS: m/z = 584 [M + H]$^+$ R$_t$ = 1.50 min method C |

| Ex. | Structure Name | [amount of amine] Amine Yield | Analytical data |
|---|---|---|---|
| 99 | 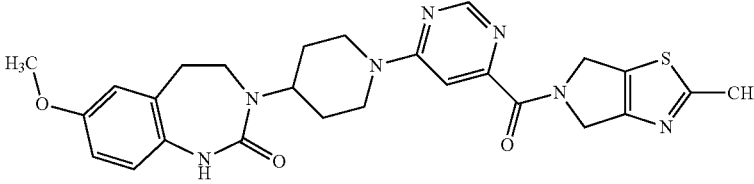<br>7-methoxy-3-{1-[6-(2-methyl-4,6-dihydro-pyrrolo[3,4-d]thiazole-5-carbonyl)-pyrimidin-4-yl]-piperidin-4-yl}-1,3,4,5-tetrahydro-benzo[d]-[1,3]diazepin-2-one | 55 mg (0.25 mmol) 2-methyl-5,6-dihydro-4H-pyrrolo[3,4-d]thiazole hydrobromide 62 mg (53% of theory) | ESI-MS: m/z = 520 [M + H]$^+$ R$_t$ = 2.95 min method E |
| 100 | 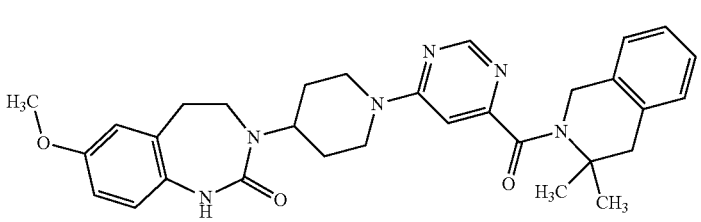 [SMILES: COc1ccc2c(c1)CCN(C1CCN(c3cc(C(=O)N4Cc5ccccc5CC4(C)C)ncn3)CC1)C(=O)N2]<br>3-{1-[6-(3,3-dimethyl-3,4-dihydro-1H-isoquinoline-2-carbonyl)-pyrimidin-4-yl]-piperidin-4-yl}-7-methoxy-1,3,4,5-tetrahydro-benzo[d]-[1,3]diazepin-2-one | 24 mg (0.15 mmol) 3,3-dimethyl-1,2,3,4-tetrahydro-isoquinoline 35 mg (43% of theory) | ESI-MS: m/z = 541 [M + H]$^+$ R$_t$ = 1.57 min method C |
| 101 | 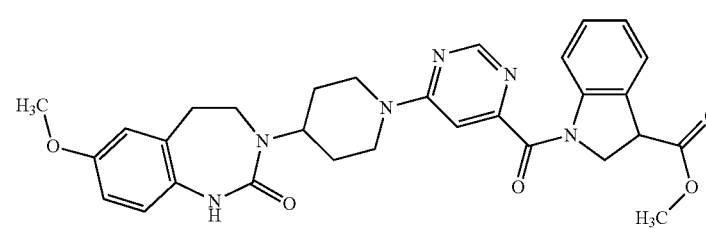<br>methyl 1-{6-[4-(7-methoxy-2-oxo-1,2,4,5-tetrahydro-benzo[d][1,3]diazepin-3-yl)-piperidin-1-yl]-pyrimidine-4-carbonyl}-2,3-dihydro-1H-indole-3-carboxylate | 110 mg (0.52 mmol) methyl 2,3-dihydro-1H-indole-3-carboxylate hydrochloride 20 mg (7% of theory) | ESI-MS: m/z = 557 [M + H]$^+$ R$_f$ = 0.78 silica gel, eluant A |
| 102 | 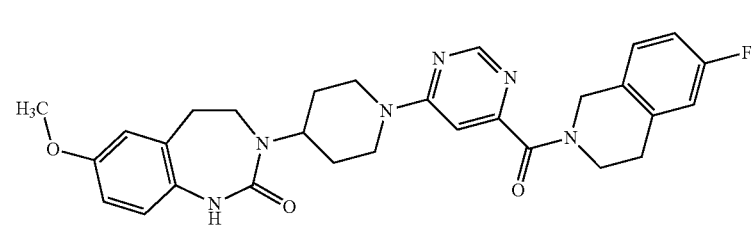 [SMILES: COc1ccc2c(c1)CCN(C1CCN(c3cc(C(=O)N4CCc5cc(F)ccc5C4)ncn3)CC1)C(=O)N2]<br>3-{1-[6-(6-fluoro-3,4-dihydro-1H-isoquinoline-2-carbonyl)-pyrimidin-4-yl]-piperidin-4-yl}-7-methoxy-1,3,4,5-tetrahydro-benzo[d]-[1,3]diazepin-2-one | 28 mg (0.15 mmol) 6-fluoro-1,2,3,4-tetrahydro-isoquinoline hydrochloride 41 mg (51% of theory) | ESI-MS: m/z = 531 [M + H]$^+$ R$_t$ = 1.36 min method C |
| 103 | 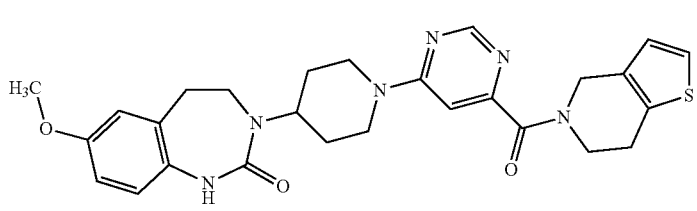 [SMILES: COc1ccc2c(c1)CCN(C1CCN(c3cc(C(=O)N4CCc5sccc5C4)ncn3)CC1)C(=O)N2]<br>3-{1-[6-(6,7-dihydro-4H-thieno[3,2-c]pyridine-5-carbonyl)-pyrimidin-4-yl]-piperidin-4-yl}-7-methoxy-1,3,4,5-tetrahydro-benzo[d]-[1,3]diazepin-2-one | 21 mg (0.15 mmol) 4,5,6,7-tetrahydro-thieno[3,2-c]pyridine 40 mg (51% of theory) | ESI-MS: m/z = 519 [M + H]$^+$ R$_t$ = 1.31 min method C |

| Ex. | Structure Name | [amount of amine] Amine Yield | Analytical data |
|---|---|---|---|
| 104 | 7-methoxy-3-{1-[6-(1-methyl-3,4-dihydro-1H-pyrrolo[1,2-a]pyrazine-2-carbonyl)-pyrimidin-4-yl]-piperidin-4-yl}-1,3,4,5-tetrahydro-benzo[d]-[1,3]diazepin-2-one | 21 mg (0.15 mmol) 1-methyl-1,2,3,4-tetrahydro-pyrrolo-[1,2-a]pyrazine 40 mg (51% of theory) | ESI-MS: m/z = 516 [M + H]$^+$ R$_t$ = 1.30 min method C |
| 105 | 7-methoxy-3-{1-[6-(1-methyl-1,4,6,7-tetrahydro-pyrrolo[3,2-c]pyridine-5-carbonyl)-pyrimidin-4-yl]-piperidin-4-yl}-1,3,4,5-tetrahydro-benzo[d]-[1,3]diazepin-2-one | 21 mg (0.15 mmol) 1-methyl-4,5,6,7-tetrahydro-1H-pyrrolo[3,2-c]pyridine 22 mg (28% of theory) | ESI-MS: m/z = 516 [M + H]$^+$ R$_t$ = 1.28 min method C |
| 106 | 3-{1-[6-(4-allyl-3,4-dihydro-1H-iso-quinoline-2-carbonyl)-pyrimidin-4-yl]-piperidin-4-yl}-7-methoxy-1,3,4,5-tetrahydro-benzo[d]-[1,3]diazepin-2-one | 26 mg (0.15 mmol) 4-allyl-1,2,3,4-tetrahydro-isoquinoline 18 mg (22% of theory) | ESI-MS: m/z = 553 [M + H]$^+$ R$_t$ = 1.63 min method C |
| 107 | 7-methoxy-3-{1-[6-(3-trifluoromethyl-6,7-dihydro-4H-isoxazolo[4,3-c]pyridine-5-carbonyl)-pyrimidin-4-yl]-piperidin-4-yl}-1,3,4,5-tetrahydro-benzo[d]-[1,3]diazepin-2-one | 45 mg (0.23 mmol) 3-trifluoromethyl-4,5,6,7-tetrahydro-isoxazolo-[4,3-c]pyridin 85 mg (74% of theory) | ESI-MS: m/z = 572 [M + H]$^+$ R$_t$ = 3.45 min method E |
| 108 | 7-methoxy-3-(1-{6-[3-(2-methoxy-ethyl)-2,3-dihydro-indole-1-carbonyl]-pyrimidin-4-yl}-piperidin-4-yl)-1,3,4,5-tetrahydro-benzo[d]-[1,3]diazepin-2-one | 41 mg (0.23 mmol) 3-(2-methoxy-ethyl)-2,3-dihydro-1H-indole 83 mg (71% of theory) | ESI-MS: m/z = 557 [M + H]$^+$ R$_t$ = 3.94 min method E |

-continued

| Ex. | Structure Name | [amount of amine] Amine Yield | Analytical data |
|---|---|---|---|
| 109 | 7-methoxy-3-{1-[6-(3-methyl-octahydro-quinoline-1-carbonyl)-pyrimidin-4-yl]-piperidin-4-yl}-1,3,4,5-tetrahydro-benzo[d]-[1,3]diazepin-2-one | 29 mg (0.15 mmol) 3-methyl-decahydro-quinoline hydrochloride 13 mg (16% of theory) | ESI-MS: m/z = 533 [M + H]+ $R_t$ = 1.48 min method C |
| 110 | 7-methoxy-3-{1-[6-(7-methoxy-3,4-dihydro-1H-isoquinoline-2-carbonyl)-pyrimidin-4-yl]-piperidin-4-yl}-1,3,4,5-tetrahydro-benzo[d]-[1,3]diazepin-2-one | 30 mg (0.15 mmol) 7-methoxy-1,2,3,4-tetrahydro-iso-quinoline hydrochloride 42 mg (51% of theory) | ESI-MS: m/z = 543 [M + H]+ $R_t$ = 1.36 min method C |
| 111 | 7-methoxy-3-{1-[6-(1,4,6,7-tetrahydro-imidazo[4,5-c]pyridine-5-carbonyl)-pyrimidin-4-yl]-piperidin-4-yl}-1,3,4,5-tetrahydro-benzo[d]-[1,3]diazepin-2-one | 60 mg (0.31 mmol) 4,5,6,7-tetrahydro-1H-imidazo[4,5-c]pyridine dihydro-chloride 32 mg (32% of theory) | ESI-MS: m/z = 503 [M + H]+ $R_t$ = 2.05 min method E |
| 112 | 7-methoxy-3-{1-[6-(8-trifluoromethyl-3,4-dihydro-1H-isoquinoline-2-carbonyl)-pyrimidin-4-yl]-piperidin-4-yl}-1,3,4,5-tetrahydro-benzo[d]-[1,3]diazepin-2-one | 36 mg (0.15 mmol) 8-trifluoromethyl-1,2,3,4-tetrahydro-isoquinoline hydrochloride 42 mg (48% of theory) | ESI-MS: m/z = 581 [M + H]+ $R_t$ = 1.45 min method C |
| 113 | 3-{1-[6-(4,4-dimethyl-3,4-dihydro-2H-quinoline-1-carbonyl)-pyrimidin-4-yl]-piperidin-4-yl}-7-methoxy-1,3,4,5-tetrahydro-benzo[d]-[1,3]diazepin-2-one | 69 mg (0.43 mmol) 4,4-dimethyl-1,2,3,4-tetrahydro-quinoline 0.12 g (59% of theory) | ESI-MS: m/z = 541 [M + H]+ $R_t$ = 3.75 min method K |

-continued

| Ex. | Structure Name | [amount of amine] Amine Yield | Analytical data |
|---|---|---|---|
| 114 | 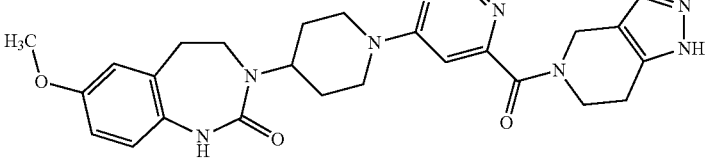<br>7-methoxy-3-{1-[6-(1,4,6,7-tetrahydro-pyrazolo[4,3-c]pyridine-5-carbonyl)-pyrimidin-4-yl]-piperidin-4-yl}-1,3,4,5-tetrahydro-benzo[d]-[1,3]diazepin-2-one | 75 mg (0.31 mmol) 4,5,6,7-tetrahydro-1H-pyrazolo[4,3-c]pyridine dihydrochloride dimethylether 40 mg (40% of theory) | ESI-MS: m/z = 503 [M + H]$^+$ R$_t$ = 2.24 min method E |
| 115 | 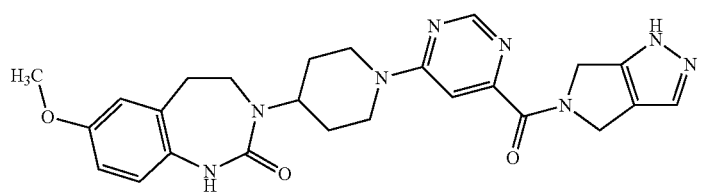 [SMILES: COc1ccc2c(c1)CCN(C1CCN(c3cc(C(=O)N4Cc5cn[nH]c5C4)ncn3)CC1)C(=O)N2]<br>3-{1-[6-(4,6-dihydro-1H-pyrrolo[3.4c]-pyrazole-5-carbonyl)-pyrimidin-4-yl]-piperidin-4-yl}-7-methoxy-1,3,4,5-tetra-hydrobenzo[d]-[1,3]diazepin-2-one | 50 mg (0.28 mmol) 1,4,5,6-tetrahydro-pyrrolo[3,4-c]pyrazole dihydrochloride 63 mg (64% of theory) | ESI-MS: m/z = 489 [M + H]$^+$ R$_t$ = 2.4 min method E |
| 116 | 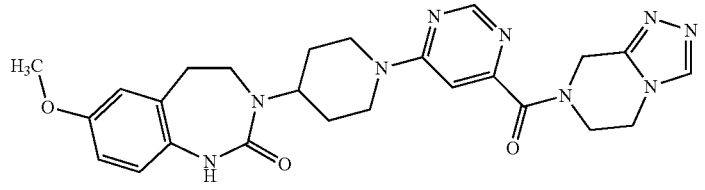 [SMILES: COc1ccc2c(c1)CCN(C1CCN(c3cc(C(=O)N4CCn5cnnc5C4)ncn3)CC1)C(=O)N2]<br>3-{1-[6-(5,6-dihydro-8H-[1,2,4]-triazolo[4,3-a]pyrazin-7-carbonyl)-pyrimidin-4-yl]-piperidin-4-yl}-7-methoxy-1,3,4,5-tetra-hydrobenzo[d]-[1,3]diazepin-2-one | 60 mg (0.37 mmol) 5,6,7,8-tetrahydro-[1,2,4]-triazolo[4.3a]-pyrazine hydrochloride 23 mg (23% of theory) | ESI-MS: m/z = 504 [M + H]$^+$ R$_t$ = 2.3 min method E |
| 117 | 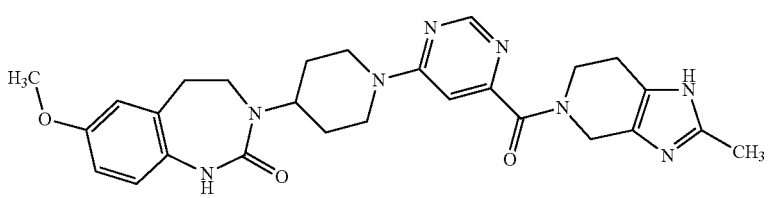<br>7-methoxy-3-{1-[6-(2-methyl-1,4,6,7-tetrahydro-imidazo[4,5-c]pyridine-5-carbonyl)-pyrimidin-4-yl]-piperidin-4-yl}-1,3,4,5-tetra-hydrobenzo[d]-[1,3]diazepin-2-one | 26 mg (0.15 mmol) 2-methyl-4,5,6,7-tetra-hydro-1H-imidazo[4,5-c]pyridine hydrochloride 27 mg (35% of theory) | ESI-MS: m/z = 517 [M + H]$^+$ R$_t$ = 1.19 min method C |

Example 118

4'-(4,5-difluoro-2,3-dihydroindole-1-carbonyl)-4-(7-methoxy-2-oxo-1,2,4,5-tetrahydro-benzo[d]-[1,3]diazepin-3-yl)-3,4,5,6-tetrahydro-2H-[1,2']bipyridinyl-5'-carbonitrile

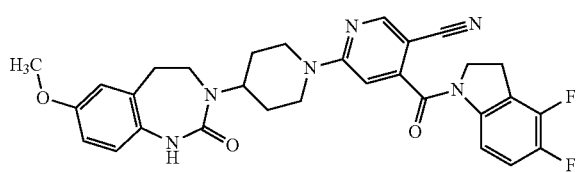 [SMILES: COc1ccc2c(c1)CCN(C1CCN(c3cc(C(=O)N4CCc5c4ccc(F)c5F)c(C#N)cn3)CC1)C(=O)N2]

0.10 g (0.24 mmol) 5'-cyano-4-(7-methoxy-2-oxo-1,2,4,5-tetrahydro-1,3-benzodiazepin-3-yl)-3,4,5,6-tetrahydro-2H-[1,4']bipyridinyl-2'-carboxylic acid, 45 mg (0.24 mmol) 4,5-difluoro-2,3-dihydro-1H-indole hydrochloride and 0.103 mL (0.74 mmol) TEA were placed in 2 mL DMF. 83.8 mg (0.26 mmol) TBTU were added, the reaction mixture was stirred overnight at RT and then purified by HPLC. The product-containing fractions were combined and freeze-dried.

Yield: 24 mg (18% of theory)
ESI-MS: m/z=559 (M+H)+
$R_t$ (HPLC-MS): 3.23 min (method O)

Example 119

4'-(7,7-dimethyl-1,4,6,7-tetrahydro-pyrazolo[4,3-c]pyridine-5-carbonyl)-4-(7-methoxy-2-oxo-1,2,4,5-tetrahydro-1,3-benzodiazepin-3-yl)-3,4,5,6-tetrahydro-2H-[1,2']bipyridinyl-5'-carbonitrile

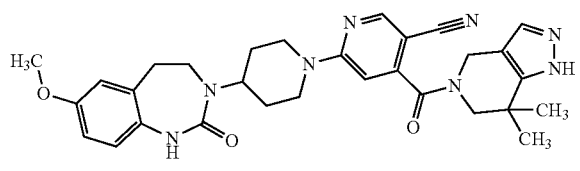 [SMILES: COc1ccc2c(c1)CCN(C1CCN(c3cc(C(=O)N4Cc5cn[nH]c5C(C)(C)C4)c(C#N)cn3)CC1)C(=O)N2]

100 mg (0.24 mmol) 5'-cyano-4-(7-methoxy-2-oxo-1,2,4,5-tetrahydro-1,3-benzodiazepin-3-yl)-3,4,5,6-tetrahydro-2H-[1,2']bipyridinyl-4'-carboxylic acid, 53.2 mg (0.24 mmol) 7,7-dimethyl-4,5,6,7-tetrahydro-1H-pyrazolo[4,3-c]pyridine dihydrochloride, 137 µL (0.97 mmol) TEA and 83.8 mg (0.26 mmol) TBTU were stirred in 2 mL DMF overnight at RT. The reaction mixture was purified by HPLC. The product-containing fractions were combined and freeze-dried.

Yield: 19 mg (14% of theory)
ESI-MS: m/z=555 (M+H)+
$R_t$ (HPLC-MS): 1.29 min (method C)

Example 120

3-[4'-(5-fluoro-2,3-dihydro-indole-1-carbonyl)-6'-methoxy-3,4,5,6-tetrahydro-2H-[1,2']bipyridinyl-4-yl]-7-methoxy-1,3,4,5-tetrahydro-benzo[d][1,3]diazepin-2-one

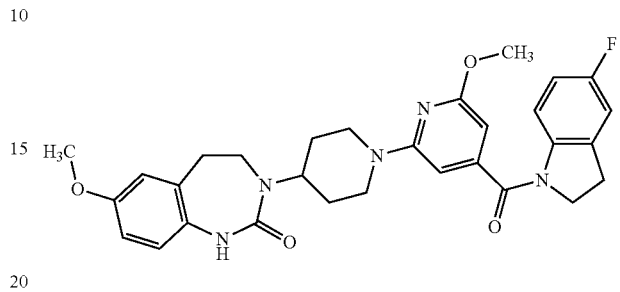

633 mg (2.3 mmol) 7-methoxy-3-piperidin-4-yl-1,3,4,5-tetrahydro-1,3-benzodiazepin-2-one, 700 mg (2.28 mmol) (2-chloro-6-methoxy-pyridin-4-yl)-(5-fluoro-2,3-dihydro-indol-1-yl)-methanone and 953.6 mg (6.9 mmol) potassium carbonate were stirred in 5 mL of NMP for 8 h at 130° C. The undissolved solid was filtered off and the filtrate was purified by HPLC. The product-containing fractions were combined and concentrated to dryness by rotary evaporation. For further purification the residue was combined with DMF and the undissolved solid was suction filtered and dried.

Yield: 490 mg (39% of theory)
ESI-MS: m/z=547 (M+H)+
$R_t$ (HPLC-MS): 1.5 min (method C)

Example 121

3-[2'-(4,5-difluoro-2,3-dihydro-indole-1-carbonyl)-3,4,5,6-tetrahydro-2H-[1,4']bipyridinyl-4-yl]-7-methoxy-1,3,4,5-tetrahydro-1,3-benzodiazepin-2-one

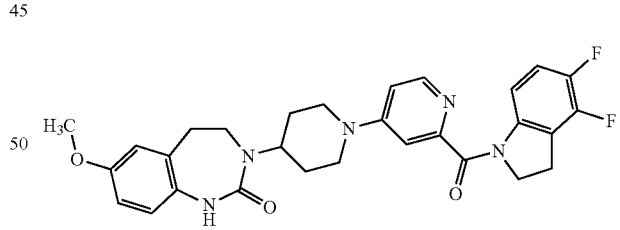

0.18 g (0.67 mmol) 7-methoxy-3-piperidin-4-yl-1,3,4,5-tetrahydro-1,3-benzodiazepin-2-one, 0.20 g (0.68 mmol) (4-chloro-pyridin-2-yl)-(4,5-difluoro-2,3-dihydro-indol-1-yl)-methanone and 97 mg (0.70 mmol) potassium carbonate were stirred in 3 mL of NMP for 4 h at 130° C. and overnight at RT. The reaction mixture was purified by HPLC. The product-containing fractions were combined and freeze-dried.

Yield: 55 mg (15% of theory)
ESI-MS: m/z=534 (M+H)+
$R_t$ (HPLC-MS): 1.40 min (method C)

Example 122

7-methoxy-3-{1-[6-(octahydro-indol-1-carbonyl)-pyrimidin-4-yl]piperidin-4-yl}-1,3,4,5-tetra-hydro-1,3-benzodiazepin-2-one

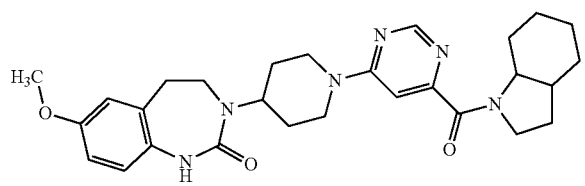 [SMILES: COc1ccc2c(c1)CCN(C1CCN(c3cc(C(=O)N4CCC5CCCCC54)ncn3)CC1)C(=O)N2]

705 mg (2.56 mmol) 7-methoxy-3-piperidin-4-yl-1,3,4,5-tetrahydro-1,3-benzodiazepin-2-one, 680 mg (2.56 mmol) (6-chloro-pyrimidin-4-yl)-(octahydro-indol-1-yl)-methanone and 0.871 mL (5 mmol) DIPEA were stirred in 10 mL DMF for 2 h at RT. The reaction mixture was purified by HPLC. The product-containing fractions were combined and the ACN was eliminated by rotary evaporation. The aqueous phase was made alkaline with 4M NaOH and extracted with EtOAc. The organic phase was dried, filtered and the filtrate was concentrated to dryness by rotary evaporation. The residue was crystallised from a mixture of MeOH and diethyl ether and the solid was suction filtered and dried.

Yield: 520 mg (40% of theory)

ESI-MS: m/z=505 (M+H)$^+$ $R_t$ (HPLC-MS): 3.28 min (method E)

Example 123

3-{1-[4-(7,7-dimethyl-1,4,6,7-tetrahydro-pyrazolo[4,3-c]pyridine-5-carbonyl)-[1,3,5]triazin-2-yl]-piperidin-4-yl}-7-methoxy-1,3,4,5-tetrahydro-1,3-benzodiazepin-2-one

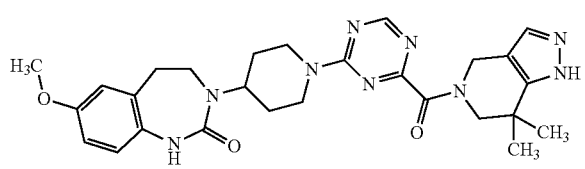 [SMILES: COc1ccc2c(c1)CCN(C1CCN(c3ncnc(C(=O)N4Cc5cn[nH]c5C(C)(C)C4)n3)CC1)C(=O)N2]

0.11 g (0.26 mmol) 4-[4-(7-methoxy-2-oxo-1,2,4,5-tetrahydro-1,3-benzodiazepin-3-yl)-piperidin-1-yl]-[1,3,5]triazine-2-carboxylic acid, 59 mg (0.26 mmol) 7,7-dimethyl-4,5,6,7-tetrahydro-1H-pyrazolo[4,3-c]pyridine dihydrochloride and 0.15 mL (1.1 mmol) TEA were placed in 1.5 mL DMF. 93 mg (0.29 mmol) TBTU were added and the reaction mixture was stirred for three days at RT. The substance was purified by HPLC-MS. The product-containing fractions were combined and freeze-dried.

Yield: 8 mg (6% of theory)

ESI-MS: m/z=532 (M+H)$^+$ $R_t$ (HPLC-MS): 3.11 min (method E)

Example 124

3-{1-[6-(5-fluoro-2,3-dihydro-indole-1-carbonyl)-5-methyl-pyrimidin-4-yl]-piperidin-4-yl}-7-methoxy-1,3,4,5-tetrahydro-1,3-benzodiazepin-2-one

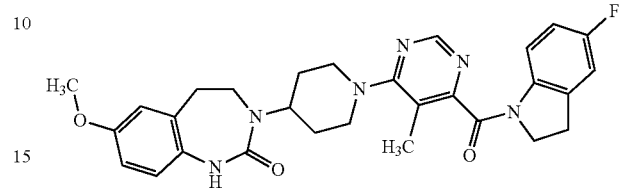

70 mg (0.17 mmol) 6-[4-(7-methoxy-2-oxo-1,2,4,5-tetrahydro-1,3-benzodiazepin-3-yl)-piperidin-1-yl]-5-methyl-pyrimidine-4-carboxylic acid, 26.1 mg (0.19 mmol) 5-fluoroindoline, 61 mg (0.19 mmol) TBTU and 0.027 mL (0.19 mmol) TEA were stirred in 1 mL DMF for 3 h at RT. The reaction mixture was purified by HPLC-MS. The product-containing fractions were combined and freeze-dried.

Yield: 58 mg (6% of theory)

ESI-MS: m/z=531 (M+H)$^+$ $R_t$ (HPLC-MS): 1.45 min (method C)

Example 125

4'-(2,3-dihydro-indole-1-carbonyl)-4-(7-methoxy-2-oxo-1,2,4,5-tetrahydro-1,3-benzo-diazepin-3-yl)-3,4,5,6-tetrahydro-2H-[1,2']bipyridinyl-5'-carbonitrile

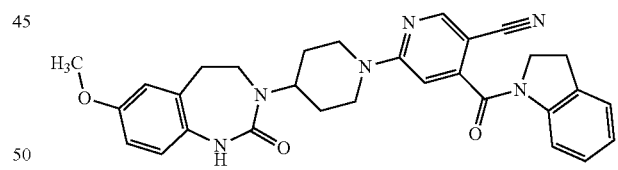

0.02 g (0.48 mmol) 5'-cyano-4-(7-methoxy-2-oxo-1,2,4,5-tetrahydro-1,3-benzodiazepin-3-yl)-3,4,5,6-tetrahydro-2H-[1,2']bipyridinyl-4'-carboxylic acid, 57 mg (0.48 mmol) 2,3-dihydro-1H-indole and 0.21 mL (1.5 mmol) TEA were placed in 3 mL DMF. 0.17 g (0.52 mmol) TBTU were added. The reaction mixture was stirred overnight at RT and then purified by HPLC. The product-containing fractions were combined and freeze-dried.

Yield: 38 mg (15% of theory)

ESI-MS: m/z=523 (M+H)$^+$ $R_t$ (HPLC-MS): 1.53 min (method C)

Example 126

3-[4'-(4,5-difluoro-2,3-dihydro-indole-1-carbonyl)-3,4,5,6-tetrahydro-2H-[1,2']bipyridinyl-4-yl]-7-methoxy-1,3,4,5-tetrahydro-1,3-benzodiazepin-2-one

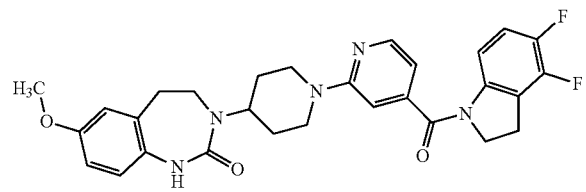 [SMILES: COc1ccc2c(c1)CCN(C1CCN(c3cc(C(=O)N4CCc5c4ccc(F)c5F)ccn3)CC1)C(=O)N2]

0.18 g (0.67 mmol) 7-methoxy-3-piperidin-4-yl-1,3,4,5-tetrahydro-1,3-benzodiazepin-2-one, 0.020 g (0.68 mmol) (2-chloro-pyridin-4-yl)-(4,5-difluoro-2,3-dihydro-indol-1-yl)-methanone and 97 mg (0.70 mmol) potassium carbonate were stirred in 3 mL NMP for 4 h at 130° C., then overnight at RT. The reaction mixture was purified by HPLC. The product-containing fractions were combined and freeze-dried.

Yield: 42 mg (12% of theory)

ESI-MS: m/z=534 (M+H)+

$R_t$ (HPLC-MS): 1.4 min (method C)

Example 127

3-{1-[6-(hexahydro-cyclopenta[c]pyrrol-2-carbonyl)-pyrimidin-4-yl]-piperidin-4-yl}-7-methoxy-1,3,4,5-tetrahydro-1,3-benzodiazepin-2-one

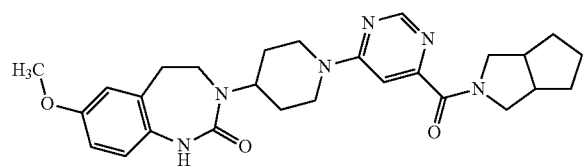 [SMILES: COc1ccc2c(c1)CCN(C1CCN(c3cc(C(=O)N4CC5CCCC5C4)ncn3)CC1)C(=O)N2]

80 mg (0.20 mmol) 6-[4-(7-methoxy-2-oxo-1,2,4,5-tetrahydro-1,3-benzodiazepin-3-yl)-piperidin-1-yl]-pyrimidine-4-carboxylic acid, 40 mg (0.27 mmol) octahydrocyclopenta[c]pyrrole hydrochloride, 0.080 mL (0.57 mmol) TEA and 80 mg (0.25 mmol) TBTU were stirred in 0.9 mL DMF overnight at RT. The reaction mixture was combined with saturated sodium hydrogen carbonate solution and ice water, and the precipitated solid was suction filtered and dried.

Yield: 74 mg (75% of theory)

ESI-MS: m/z=491 (M+H)+

$R_t$ (HPLC-MS): 3.14 min (method E)

Example 128

3-{1-[6-(4,4-dimethyl-4.7-dihydro-5H-thieno[2,3-c]pyridin-6-carbonyl)-pyrimidin-4-yl]-piperidin-4-yl}-7-methoxy-1,3,4,5-tetrahydro-1,3-benzodiazepin-2-one

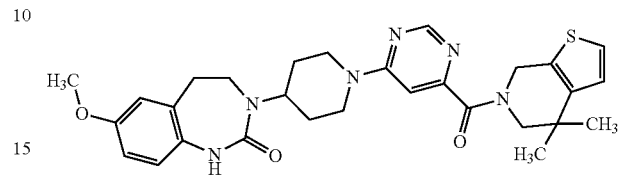

84 mg (0.21 mmol) 6-[4-(7-methoxy-2-oxo-1,2,4,5-tetrahydro-1,3-benzodiazepin-3-yl)-piperidin-1-yl]-pyrimidine-4-carboxylic acid, 40 mg (0.24 mmol) 4,4-dimethyl-4,5,6,7-tetra-hydro-thieno[2,3-c]pyridine, 34 µL (0.24 mmol) TEA and 77 mg (0.24 mmol) TBTU were stirred in 1 mL DMF overnight at RT. The reaction mixture was purified by HPLC. The product-containing fractions were combined and freeze-dried.

Yield: 62 mg (54% of theory)

ESI-MS: m/z=547 (M+H)+

$R_t$ (HPLC-MS): 3.57 min (method E)

Example 129

3-{1-[6-(6-fluoro-4,4-dimethyl-3,4-dihydro-1H-isoquinoline-2-carbonyl)-pyrimidin-4-yl]-piperidin-4-yl}-7-methoxy-1,3,4,5-tetrahydro-1,3-benzodiazepin-2-one

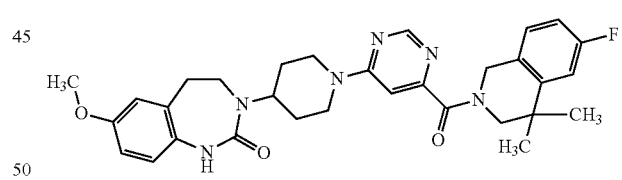

60 mg (0.15 mmol) 6-[4-(7-methoxy-2-oxo-1,2,4,5-tetrahydro-1,3-benzodiazepin-3-yl)-piperidin-1-yl]-pyrimidine-4-carboxylic acid, 33 mg (0.15 mmol) 6-fluoro-4,4-dimethyl-1,2,3,4-tetrahydro-isoquinoline hydrochloride, 66 µL (0.47 mmol) TEA and 54 mg (0.17 mmol) TBTU were stirred in 1.5 mL DMF overnight at RT. The reaction mixture was purified by HPLC. The product-containing fractions were combined and freeze-dried.

Yield: 22 mg (26% of theory)

ESI-MS: m/z=559 (M+H)+

$R_t$ (HPLC-MS): 1.49 min (method C)

Example 130

3-{1-[6-(5-fluoro-3-methyl-2,3-dihydro-indole-1-carbonyl)-pyrimidin-4-yl]-piperidin-4-yl}-7-methoxy-1,3,4,5-tetrahydro-1,3-benzodiazepin-2-one

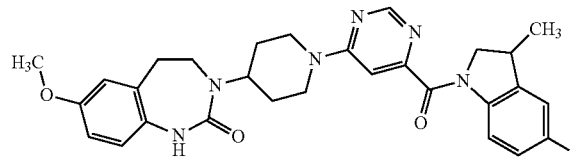

80 mg (0.21 mmol) 6-[4-(7-methoxy-2-oxo-1,2,4,5-tetrahydro-1,3-benzodiazepin-3-yl)-piperidin-1-yl]-pyrimidine-4-carboxylic acid, 32 mg (0.21 mmol) 5-fluoro-3-methyl-2,3-dihydro-1H-indole, 70 μL (0.50 mmol) TEA and 74 mg (0.23 mmol) TBTU were stirred in 1.8 mL DMF overnight at RT. The reaction mixture was purified by HPLC. The product-containing fractions were combined and freeze-dried.

Yield: 64 mg (60% of theory)
ESI-MS: m/z=531 (M+H)⁺
R$_t$ (HPLC-MS): 3.8 min (method K)

Example 131

3-{1-[6-(4,4-dimethyl-3,4-dihydro-1H-isoquinoline-2-carbonyl)-pyrimidin-4-yl]-piperidin-4-yl}-7-methoxy-1,3,4,5-tetrahydro-1,3-benzodiazepin-2-one

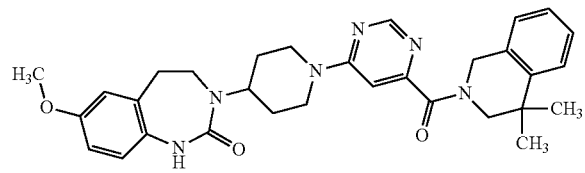 [SMILES: COc1ccc2c(c1)CCN(C1CCN(c3cc(C(=O)N4Cc5ccccc5C(C)(C)C4)ncn3)CC1)C(=O)N2]

0.10 g mg (0.25 mmol) 6-[4-(7-methoxy-2-oxo-1,2,4,5-tetrahydro-1,3-benzodiazepin-3-yl)-piperidin-1-yl]-pyrimidine-4-carboxylic acid, 57 mg (0.35 mmol) 4,4-dimethyl-1,2,3,4-tetra-hydro-isoquinoline, 75 μL (0.53 mmol) TEA and 0.11 (0.30 mmol) TBTU were stirred in 1.1 mL DMF overnight at RT. The reaction mixture was purified by HPLC. The product-containing fractions were combined and freeze-dried.

Yield: 81 mg (60% of theory)
ESI-MS: m/z=541 (M+H)⁺
R$_t$ (HPLC-MS): 3.59 min (method E)

Example 132

3-(1-(6-(2',3'-dihydro-1'H-spiro[cyclopropane-1,4'-isoquinolin]-2'-ylcarbonyl)pyrimidin-4-yl)-piperidin-4-yl)-7-methoxy-4,5-dihydro-1H-benzo[d][1,3]diazepin-2(3H)-one

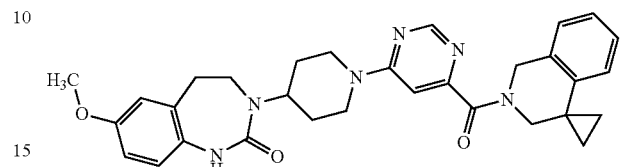

50 mg (0.13 mmol) 6-[4-(7-methoxy-2-oxo-1,2,4,5-tetrahydro-1,3-benzodiazepin-3-yl)-piperidin-1-yl]-pyrimidine-4-carboxylic acid, 20 mg (0.13 mmol) 2',3'-dihydro-1'H-spiro-[cyclopropane-1,4'-isoquinoline], 37 μL (0.26 mmol) TEA and 44.3 mg (0.14 mmol) TBTU were stirred in 1.5 mL DMF overnight at RT. The reaction mixture was purified by HPLC. The product-containing fractions were combined and freeze-dried.

Yield: 5 mg (7% of theory)
ESI-MS: m/z=539 (M+H)⁺
R$_t$ (HPLC-MS): 3.98 min (method E)

Example 133

1-{1-[6-(4,5-difluoro-3-methyl-2,3-dihydro-indole-1-carbonyl)-pyrimidin-4-yl]-piperidin-4-yl}-1,3-dihydro-imidazo[4,5-b]pyridin-2-one

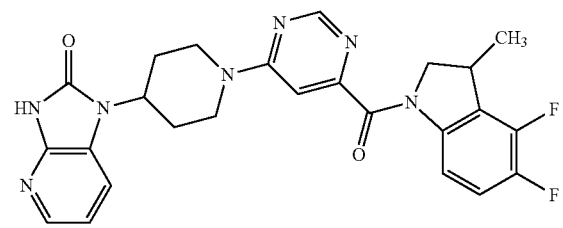 [SMILES: CC1CN(C(=O)c2cc(N3CCC(n4c(=O)[nH]c5ncccc54)CC3)ncn2)c2ccc(F)c(F)c21]

80 mg (0.24 mmol) 6-[4-(2-oxo-2,3-dihydroimidazo[4,5-b]pyridin-1-yl)-piperidin-1-yl]-pyrimidine-4-carboxylic acid, 43 mg (0.25 mmol) 4,5-difluoro-3-methyl-2,3-dihydro-1H-indole, 70 μL (0.50 mmol) TEA and 90 mg (0.28 mmol) TBTU were stirred in 1.8 mL DMF overnight at RT. The reaction mixture was purified by HPLC. The product-containing fractions were combined and freeze-dried.

Yield: 76 mg (66% of theory)
ESI-MS: m/z=492 (M+H)⁺
R$_t$ (HPLC-MS): 3.6 min (method K)

Analogously to 1-{1-[6-(4,5-difluoro-3-methyl-2,3-dihydro-indole-1-carbonyl)-pyrimidin-4-yl]piperidin-4-yl}-1,3-dihydro-imidazo[4,5-b]pyridin-2-one the following compounds were prepared from in each case 0.24-0.43 mmol-[4-(2-oxo-2,3-dihydroimidazo[4,5-b]pyridin-1-yl)-piperidin-1-yl]pyrimidine-4-carboxylic acid, 1 to 1.5 eq of the respective amine, 1.0 to 1.2 eq TBTU and 1.1 to 4.1 eq triethylamine in a suitable amount of DMF:

| Ex. | Structure Name | [Amount of amine] Amine Yield | Analytical data |
|---|---|---|---|
| 134 | 1-{1-[6-(5,6-difluoro-3-methyl-2,3-dihydro-indole-1-carbonyl)-pyrimidin-4-yl]-piperidin-4-yl}-1,3-dihydroimidazo[4,5-b]pyridin-2-one | 40 mg (0.24 mmol) 5,6-difluoro-3-methyl-2,3-dihydro-1H-indole 70 mg (61% of theory) | ESI-MS: m/z = 492 [M + H]$^+$ R$_t$ = 3.8 min method K |
| 135 | 1-{1-[6-(5,6-difluoro-2,3-dihydro-indole-1-carbonyl)-pyrimidin-4-yl]-piperidin-4-yl}-1,3-dihydro-imidazo[4,5-b]pyridin-2-one | 62 mg (0.40 mmol) 5,6-difluoro-2,3-dihydro-1H-indole 72 mg (51% of theory) | ESI-MS: m/z = 478 [M + H]$^+$ 1.4 min method C |
| 136 | 1-(1-{6-[5-fluoro-3-(2-methoxy-ethyl)-3-methyl-2,3-dihydro-indole-1-carbonyl]-pyrimidin-4-yl}-piperidin-4-yl)-1,3-dihydro-imidazo[4,5-b]pyridin-2-one | 80 mg (0.38 mmol) 5-fluoro-3-(2-methoxy-ethyl)-3-methyl-2,3-dihydro-1H-indole 83 mg (41% of theory) | ESI-MS: m/z = 530 [M + H]$^+$ 1.4 min method C |
| 137 | 1-{1-[6-(4,5-difluoro-3,3-dimethyl-2,3-dihydro-indole-1-carbonyl)-pyrimidin-4-yl]-piperidin-4-yl}-1,3-dihydroimidazo[4,5-b]pyridin-2-one | 80 mg (0.44 mmol) 4,5-difluoro-3,3-dimethyl-2,3-dihydro-1H-indole 0.10 g (45% of theory) | ESI-MS: m/z = 506 [M + H]$^+$ 1.4 min method C |
| 138 | 1-{1-[6-(4-fluoro-2,3-dihydroindole-1-carbonyl)-pyrimidin-4-yl]-piperidin-4-yl}-1,3-dihydro-imidazo[4,5-b]pyridin-2-one | 45 mg (0.33 mmol) 4-fluoro-2,3-dihydro-1H-indole 95 mg (70% of theory) | ESI-MS: m/z = 460 [M + H]$^+$ R$_f$ = 0.63 silica gel, eluant A) |

-continued

| Ex. | Structure Name | [Amount of amine] Amine Yield | Analytical data |
|---|---|---|---|
| 139 | 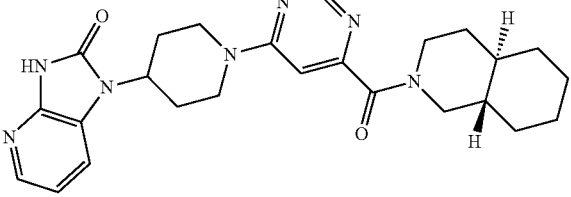<br>1-{1-[6-(octahydro-isoquinoline-2-carbonyl)-pyrimidin-4-yl]-piperidin-4-yl}-1,3-dihydro-imidazo[4,5-b]pyridin-2-one | 50 mg (0.36 mmol) decahydro-isoquinoline 33 mg (23% of theory) | ESI-MS: m/z = 462 [M + H]$^+$ 3.03 min method E |
| 140 | 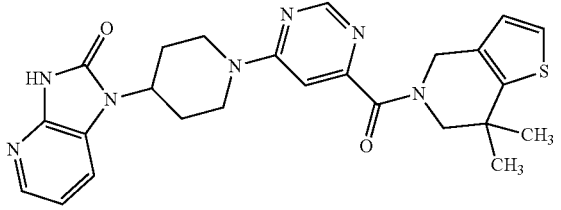 [SMILES: CC1(C)CN(C(=O)c2cc(N3CCC(n4c(=O)[nH]c5ncccc54)CC3)ncn2)Cc2ccsc21]<br>1-{1-[6-(7,7-dimethyl-6,7-dihydro-4H-thieno[3,2-c]pyridine-5-carbonyl)-pyrimidin-4-yl]-piperidin-4-yl}-1,3-dihydro-imidazo[4,5-b]pyridin-2-one | 40 mg (0.24 mmol) 7,7-dimethyl-4,5,6,7-tetrahydro-thieno[3,2-c]pyridine 12 mg (12% of theory) | ESI-MS: m/z = 490 [M + H]$^+$ 3.42 min method K |
| 141 | 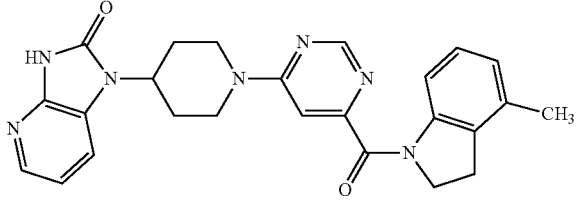 [SMILES: Cc1cccc2c1CCN2C(=O)c1cc(N2CCC(n3c(=O)[nH]c4ncccc43)CC2)ncn1]<br>1-{1-[6-(4-methyl-2,3-dihydro-indole-1-carbonyl)-pyrimidin-4-yl]-piperidin-4-yl}-1,3-dihydro-imidazo[4,5-b]pyridin-2-one | 50 mg (0.30 mmol) 4-methyl-2,3-dihydro-1H-indole hydrochloride 95 mg (71% of theory) | ESI-MS: m/z = 456 [M + H]$^+$ $R_f$ = 0.67 silica gel, eluant A |
| 142 | 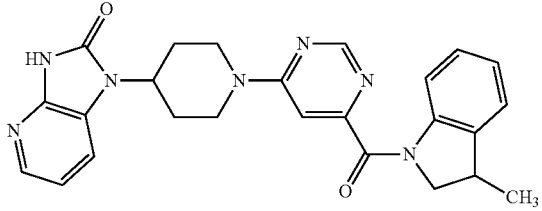 [SMILES: CC1CN(C(=O)c2cc(N3CCC(n4c(=O)[nH]c5ncccc54)CC3)ncn2)c2ccccc21]<br>1-{1-[6-(3-methyl-2,3-dihydro-indole-1-carbonyl)-pyrimidin-4-yl]-piperidin-4-yl}-1,3-dihydro-imidazo[4,5-b]pyridin-2-one | 40 mg (0.30 mmol) 3-methyl-2,3-dihydro-1H-indole 65 mg (54% of theory) | ESI-MS: m/z = 456 [M + H]$^+$ $R_f$ = 0.62 silica gel, eluant A) |
| 143 | 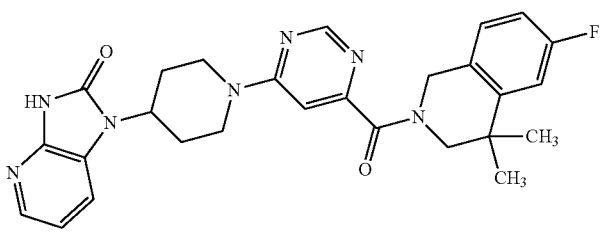 [SMILES: CC1(C)CN(C(=O)c2cc(N3CCC(n4c(=O)[nH]c5ncccc54)CC3)ncn2)Cc2ccc(F)cc21]<br>1-{1-[6-(6-fluoro-4,4-dimethyl-3,4-dihydro-1H-isoquinoline-2-carbonyl)-pyrimidn-4-yl]-piperidin-4-yl}-1,3-dihydro-imidazo[4,5-b]pyridin-2-one | 38 mg (0.18 mmol) 6-fluoro-4,4-dimethyl-1,2,3,4-tetrahydro-isoquinoline hydrochloride 5 mg (6% of theory) | ESI-MS: m/z = 502 [M + H]$^+$ 1.34 min method C |

-continued

| Ex. | Structure Name | [Amount of amine] Amine Yield | Analytical data |
|---|---|---|---|
| 144 | 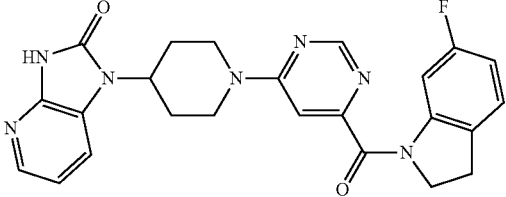 [SMILES: O=C(c1cc(N2CCC(n3c(=O)[nH]c4ncccc43)CC2)ncn1)N1CCc2ccc(F)cc21] 1-{1-[6-(6-fluoro-2,3-dihydro-indole-1-carbonyl)-pyrimidin-4-yl]-piperidin-4-yl}-1,3-dihydro-imidazo[4,5-b]pyridin-2-one | 45 mg (0.33 mmol) 6-fluoro-2,3-dihydro-1H-indole 0.10 g (74% of theory) | ESI-MS: m/z = 460 [M + H]$^+$ $R_f$ = 0.71 silica gel, eluant A |
| 145 | 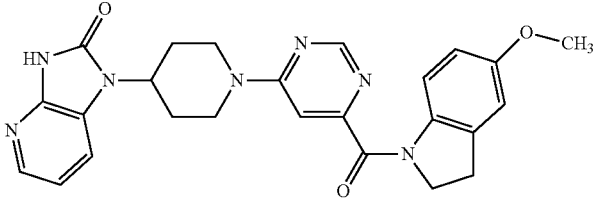 [SMILES: COc1ccc2c(c1)CCN2C(=O)c1cc(N2CCC(n3c(=O)[nH]c4ncccc43)CC2)ncn1] 1-{1-[6-(5-methoxy-2,3-dihydro-indole-1-carbonyl)-pyrimidin-4-yl]-piperidin-4-yl}-1,3-dihydro-imidazo[4,5-b]pyridin-2-one | 60 mg (0.32 mmol) 5-methoxy-2,3-dihydro-1H-indole hydrochloride 95 mg (69% of theory) | ESI-MS: m/z = 470 [M + H]$^+$ $R_f$ = 0.64 silica gel, eluant A |
| 146 | 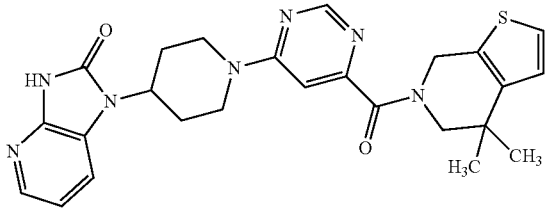 [SMILES: CC1(C)CN(C(=O)c2cc(N3CCC(n4c(=O)[nH]c5ncccc54)CC3)ncn2)Cc2sccc21] 1-{1-[6-(4,4-dimethyl-4,7-dihydro-5H-thieno[2,3-c]pyridin-6-carbonyl)-pyrimidn-4-yl]-piperidin-4-yl}-1,3-dihydro-imidazo[4,5-b]pyridin-2-one | 40 mg (0.24 mmol) 4,4-dimethyl-4,5,6,7-tetrahydro-thieno[2,3-c]pyrdine 31 mg (30% of theory) | ESI-MS: m/z 490 [M + H]$^+$ 3.03 min method E |
| 147 | 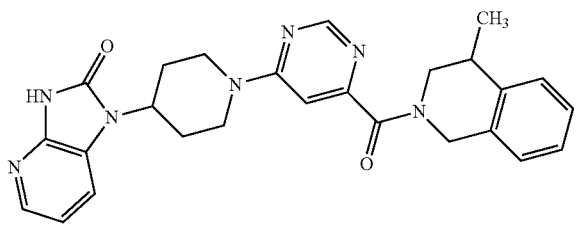 1-{1-[6-(4-methyl-3,4-dihydro-1H-isoquinoline-2-carbonyl)-pyrimidin-4-yl]-piperidin-4-yl}-1,3-dihydro-imidazo[4,5-b]pyridin-2-one | 42 mg (0.23 mmol) 4-methyl-1,2,3,4-tetra-hydroisoqinoline hydrochloride 25 mg (26% of theory) | ESI-MS: m/z = 578 [M + H]$^+$ 3.9 min method B |
| 148 | 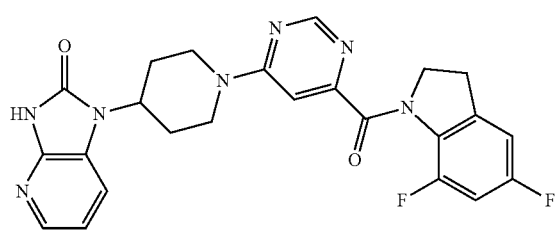 [SMILES: O=C(c1cc(N2CCC(n3c(=O)[nH]c4ncccc43)CC2)ncn1)N1CCc2cc(F)cc(F)c21] 1-{1-[6-(5,7-difluoro-2,3-dihydro-indole-1-carbonyl)-pyrimidin-4-yl]-piperdin-4-yl}-1,3-dihydro-imidazo[4,5-b]pyridin-2-one | 37 mg (0.2 mmol) 4-methyl-1,2,3,4-tetrahydro-isoquinoline 48 mg (43% of theory) | ESI-MS: m/z = 470 [M + H]$^+$ 1.2 min method C |

| Ex. | Structure Name | [Amount of amine] Amine Yield | Analytical data |
|---|---|---|---|
| 149 | 1-{1-[6-(3-ethyl-2,3-dihydro-indole-1-carbonyl)-pyrimidin-4-yl]-piperidin-4-yl}-1,3-dihydro-imidazo[4,5-b]pyridin-2-one | 34 mg (0.23 mmol) 3-ethyl-2,3-dihydro-1H-indole 22 mg (23% of theory) | ESI-MS: m/z = 470 [M + H]$^+$ 1.6 min method C |
| 150 | 1-{1-[6-(3-cyclopropylmethyl-2,3-dihydro-indole-1-carbonyl)-pyrimidin-4-yl]-piperidin-4-yl}-1,3-dihydro-imidazo[4,5-b]pyridin-2-one | 40 mg (0.23 mmol) 3-cyclopropyl-methyl-2,3-dihydro-1H-indole 45 mg (44% of theory) | ESI-MS: m/z = 496 [M + H]$^+$ 1.47 min (method C) |
| 151 | methyl 1-{6-[4-(2-oxo-2,3-dihydro-imidazo[4,5-b]pyridin-1-yl)-piperidin-1-yl]-pyrimidine-4-carbonyl}-2,3-dihydro-1H-indole-3-carboxylate | 130 mg (0.61 mmol) methyl 2,3-dihydro-1H-indole-3-carboxylate hydrochloride 160 mg (55% of theory) | ESI-MS: m/z = 500 [M + H]$^+$ R$_f$ = 0.64 silica gel, eluant A |
| 152 | 1-(1-{6-[3-(2-methoxy-ethyl)-2,3-dihydro-indole-1-carbonyl]-pyrimidin-4-yl}-piperidin-4-yl)-1,3-dihydro-imidazo[4,5-b]pyridin-2-one | 41 mg (0.23 mmol) 2-(2-methoxy-ethyl)-2,3-dihydro-1H-indole 72 mg (70% of theory) | ESI-MS: m/z = 500 [M + H]$^+$ 3.33 min method E |
| 153 | 1-{1-[6-(2-allyl-2,3-dihydro-indole-1-carbonyl)-pyrimidin-4-yl]-piperidin-4-yl}-1,3-dihydro-imidazo[4,5-b]pyridin-2-one | 60 mg (0.31 mmol) 2-allyl-2,3-dihydro-1H-indole hydrochloride 72 mg (51% of theory) | ESI-MS: m/z = 482 [M + H]$^+$ R$_f$ = 0.62 silica gel, eluant A |

| Ex. | Structure Name | [Amount of amine] Amine Yield | Analytical data |
|---|---|---|---|
| 154 | 1-{1-[6-(4,4-dimethyl-3,4-dihydro-2H-quinoline-1-carbonyl)-pyrimidin-4-yl]-piperidin-4-yl}-1,3-dihydro-imidazo[4,5-b]pyridin-2-one | 81 mg (0.5 mmol) 4,4-dimethyl-1,2,3,4-tetrahydro-quinoline 118 mg (55% of theory) | ESI-MS: m/z = 484 [M + H]$^+$ 3.17 min (method K) |
| 155 | 1-(1-(6-(1-methylspiro[indolin-3,4'-piperidin]-1-ylcarbonyl)-pyrimidin-4-yl)piperidin-4-yl)-1H-imidazo[4,5-b]pyridin-2(3H)-one | 62 mg (0.3 mmol) 1'-methylspiro[indoline-3,4'-piperidine] 118 mg (77% of theory) | ESI-MS: m/z = 525 [M + H]$^+$ 2.2 min (method K) |
| 156 | 1-(1-{6-[3-(2-hydroxy-ethyl)-2,3-dihydro-indole-1-carbonyl]-pyrimidin-4-yl}-piperidin-4-yl)-1,3-dihydro-imidazo[4,5-b]pyridin-2-one | 50 mg (0.31 mmol) 2-(2,3-dihydro-1H-indol-3-yl)-ethanol 85 mg (66% of theory) | ESI-MS: m/z = 486 [M + H]$^+$ $R_f$ = 0.59 silica gel, eluant A |
| 157 | 1-{1-[6-(2,3-dihydro-pyrrolo[2,3-b]pyridine-1-carbonyl)-pyrimidin-4-yl]-piperidin-4-yl}-1,3-dihydro-imidazo[4,5-b]pyridin-2-one | 45 mg (0.32 mmol) 2,3-dihydro-1H-pyrrolo[2,3-b]pyridine 50 mg (39% of theory) | ESI-MS: m/z = 443 [M + H]$^+$ $R_f$ = 0.54 silica gel, eluant A |
| 158 | 1-{1-[6-(2-phenyl-pyrrolidine-1-carbonyl)-pyrimidin-4-yl]-piperidine-4-yl}-1,3-dihydro-imidazo[4,5-b]pyridin-2-one | 45 mg (0.31 mmol) 2-phenylpyrrolidine 65 mg (47% of theory) | ESI-MS: m/z = 470 [M + H]$^+$ $R_f$ = 0.61 silica gel, eluant A |

| Ex. | Structure Name | [Amount of amine] Amine Yield | Analytical data |
|---|---|---|---|
| 159 | 6-[4-(2-oxo-2,3-dihydro-imidazo[4,5-b]pyridin-1-yl)-piperidin-1-yl]-pyrimidine-4-carboxylic acid (2-phenyl-butyl)-amide | 46 mg (0.31 mmol) 2-phenylbutan-1-amine 80 mg (58% of theory) | ESI-MS: m/z = 472 [M + H]$^+$ R$_f$ = 0.56 silica gel, eluant A |
| 160 | 1-{1-[6-(3-pyridin-4-yl-pyrrolidine-1-carbonyl)-pyrimidin-4-yl]-piperidin-4-yl}-1,3-dihydro-imidazo[4,5-b]pyridin-2-one | 45 mg (0.3 mmol) 4-pyrrolinin-3-ylpyridine 20 mg (15% of theory) | ESI-MS: m/z = 471 [M + H]$^+$ R$_f$ = 0.55 silica gel, eluant A |
| 161 | 6-[4-(2-oxo-2,3-dihydro-imidazo[4,5-b]pyridin-1-yl)-piperidin-1-yl]-pyrimidine-4-caboxylic acid (2-phenyl-propyl)-amide | 40 mg (0.3 mmol) Beta-methyl-phenethylamine 72 mg (54% of theory) | ESI-MS: m/z = 458 [M + H]$^+$ R$_f$ = 0.62 silica gel, eluant A |

Example 162

1-{1-[2-(7,7-dimethyl-1,4,6,7-tetrahydro-pyrazolo[4,3-c]pyridine-5-carbonyl)-pyrimidin-4-yl]-piperidin-4-yl}-1,3-dihydro-imidazo[4,5-b]pyridin-2-one

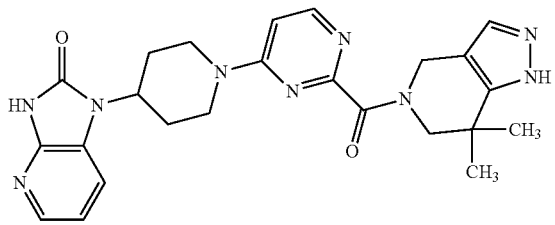 [SMILES: CC1(C)CN(C(=O)c2nccc(N3CCC(n4c(=O)[nH]c5ncccc54)CC3)n2)Cc2cn[nH]c21]

60 mg (0.18 mmol) 4-[4-(2-oxo-2,3-dihydro-imidazo[4,5-b]pyridin-1-yl)-piperidin-1-yl]-pyrimidine-2-carboxylic acid, 40 mg (0.18 mmol) 7,7-dimethyl-4,5,6,7-tetrahydro-1H-pyrazolo[4,3-c]pyridine dihydrochloride, 0.10 (0.72 mmol) triethylamine and 62 (0.19 mmol) TBTU in 1.5 mL DMF were stirred overnight at RT. The reaction mixture was purified by HPLC. The product-containing fractions were combined and freeze-dried.

Yield: 25 mg (30% of theory)
ESI-MS: m/z=474 (M+H)$^+$
R$_t$ (HPLC-MS): 0.91 min (method C)

Example 163

1-[4'-(4,5-difluoro-2,3-dihydro-indole-1-carbonyl)-3,4,5,6-tetrahydro-2H-[1,2']bipyridinyl-4-yl]-1,3-dihydro-imidazo[4,5-b]pyridin-2-one

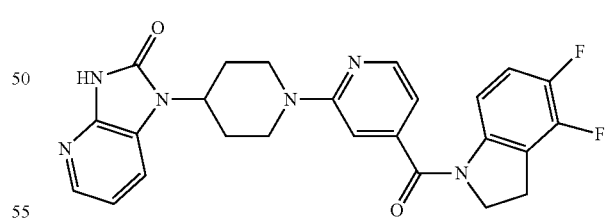

0.59 g (2.7 mmol) 1-piperidin-4-yl-1,3-dihydroimidazo[4,5-b]pyridin-2-one, 0.80 g (2.7 mmol) (2-chloro-pyridin-4-yl)-(4,5-difluoro-2,3-dihydro-indol-1-yl)-methanone and 0.39 g (2.8 mmol) potassium carbonate were stirred in 3 mL of NMP for 4 h at 130° C. The reaction mixture was purified by HPLC. The product-containing fractions were combined and freeze-dried.

Yield: 74 mg (6% of theory)
ESI-MS: m/z=477 (M+H)$^+$
R$_t$ (HPLC-MS): 1.26 min (method C)

Example 164

1-[4'-(5,6-difluoro-2,3-dihydro-indole-1-carbonyl)-3,4,5,6-tetrahydro-2H-[1,2']bipyridinyl-4-yl]-1,3-dihydro-imidazo[4,5-b]pyridin-2-one

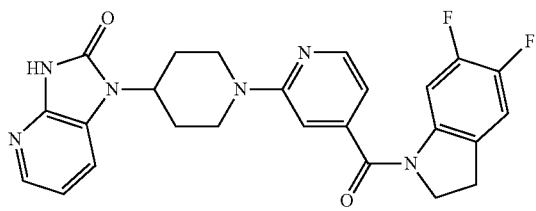

1.0 g (4.6 mmol) 1-piperidin-4-yl-1,3-dihydroimidazo[4,5-b]pyridin-2-one, 0.45 g (1.5 mmol) (2-chloro-pyridin-4-yl)-(5,6-difluoro-2,3-dihydro-indol-1-yl)-methanone were stirred in 4 mL of NMP for 4 h at 130° C. The reaction mixture was purified by HPLC. The product-containing fractions were combined and freeze-dried.

Yield: 46 mg (2% of theory)
ESI-MS: m/z=477 (M+H)$^+$
R$_t$ (HPLC-MS): 3.4 min (method E)

The following compounds were synthesised according to the following General Working Method:

0.4 to 1 mmol 1-piperidin-4-yl-1,3-dihydroimidazo[4,5-b]pyridin-2-one dihydrochloride, 1 eq of the respective chloro-pyridine and 3 eq potassium carbonate in 1 to 3 mL NMP were stirred for 4 to 12 h at 130° C. Purification was carried out by HPLC. Instead of the 1-piperidin-4-yl-1,3-dihydroimidazo[4,5-b]pyridin-2-one-dihydrochloride the free base was used, so only 1 eq potassium carbonate was used:

| Example | Structure Name | [Amount of pyridine] Amine Yield | Analytical data |
|---|---|---|---|
| 165 | 1-[4'-(5-fluoro-2,3-dihydro-indole-1-carbonyl)-1'-oxy-3,4,5,6-tetrahydro-2H-[1,2']bipyridinyl-4-yl]-1,3-dihydro-imidazo[4,5-b]pyridin-2-one | 140 mg (0.48 mmol) (2-chloro-1-oxy-pyridin-4-yl)-(5-fluoro-2,3-dihydro-indol-1-yl)-methanone 70 mg (30% of theory) | ESI-MS: m/z = 475 [M + H]$^+$ 3.84 min (method K) |
| 166 | 1-[2'-(5-fluoro-3,3-dimethyl-2,3-dihydro-indole-1-carbonyl)-3,4,5,6-tetrahydro-2H-[1,4']bipyridinyl-4-yl]-1,3-dihydro-imidazo[4,5-b]pyridin-2-one | 120 mg (0.39 mmol) (4-chloro-pyridin-2-yl)-(5-fluoro-3,3-dimethyl-2,3-dihydro-indol-1-yl)-methanone 80 mg (41% of theory) | ESI-MS: m/z = 487 [M + H]$^+$ 1.29 min (method C) |
| 167 | 1-[2'-(4,5-difluoro-2,3-dihydro-indole-1-carbonyl)-3,4,5,6-tetrahydro-2H-[1,4']bipyridinyl-4-yl]-1,3-dihydro-imidazo[4,5-b]pyridin-2-one | 200 mg (0.68 mmol) (4-chloro-pyridin-2-yl)-(4,5-difluoro-2,3-dihydro-indol-1-yl)-methanone 111 mg (35% of theory) | ESI-MS: m/z = 475 [M − H]$^−$ 1.23 min (method C) |

-continued

| Example | Structure Name | [Amount of pyridine] Amine Yield | Analytical data |
|---|---|---|---|
| 168 | 1-[4'-(5-fluoro-3,3-dimethyl-2,3-dihydro-indole-1-carbonyl)-3,4,5,6-tetrahydro-2H-[1,2']bipyridinyl-4-yl]-1,3-dihydro-imidazo[4,5-b]pyridin-2-one | 120 mg (0.4 mmol) (2-chloro-pyridin-4-yl)-(5-fluoro-3,3-dimethyl-2,3-dihydro-indol-1-yl)-methanone 42 mg (22% of theory) | ESI-MS: m/z = 487 [M + H]+ 1.25 min (method C) |
| 169 | 1-[4'-(5-fluoro-2,3-dihydro-indole-1-carbonyl)-6'-methoxy-3,4,5,6-tetrahydro-2H-[1,2']bipyridinyl-4-yl]-1,3-dihydro-imidazo[4,5-b]pyridin-2-one | 300 mg (0.98 mmol) (2-chloro-6-methoxy-pyridin-4-yl)-(5-fluoro-2,3-dihydro-indol-1-yl)-methanone 33 mg (7% of theory) | ESI-MS: m/z = 489 [M + H]+ 1.5 min (method C) |
| 170 | N-[4'-(5-fluoro-2,3-dihydro-indole-1-carbonyl)-4-(2-oxo-2,3-dihydro-imidazo[4,5-b]pyridin-1-yl)-3,4,5,6-tetrahydro-2H-[1,2']bipyridinyl-6'-yl]-methanesulphonamide | 340 mg (0.92 mmol) N-[6-chloro-4-(5-fluoro-2,3-dihydro-indole-1-carbonyl)-pyridin-2-yl]-methanesulphonamide 30 mg (6% of theory) | ESI-MS: m/z = 552 [M + H]+ 1.22 min (method C) |

Example 171

1-{1-[6-(5-fluoro-2,3-dihydro-indole-1-carbonyl)-pyrazin-2-yl]-piperidin-4-yl}-1,3-dihydro-imidazo[4,5-b]pyridin-2-one

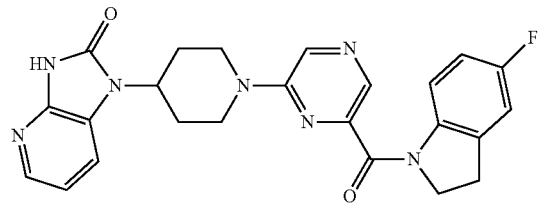 [SMILES: O=C(c1cncc(N2CCC(n3c(=O)[nH]c4ncccc43)CC2)n1)N1CCc2cc(F)ccc21]

0.10 g (0.34 mmol) 1-piperidin-4-yl-1,3-dihydroimidazo[4,5-b]pyridin-2-one dihydrochloride, 0.11 g (0.34 mmol) (6-chloro-pyrazin-2-yl)-(5-fluoro-2,3-dihydro-indol-1-yl)-methanone and 0.20 mL (1.1 mmol) DIPEA were stirred in 1.0 mL DMF overnight at 80° C. 10 mL water were added to the reaction solution, the precipitate formed was suction filtered. The precipitate was stirred into methanol, suction filtered and dried.

Yield: 74 mg (6% of theory)
ESI-MS: m/z=477 (M+H)$^+$
$R_t$ (HPLC-MS): 1.26 min (method C)

Example 172

6'-(7,7-dimethyl-1,4,6,7-tetrahydro-pyrazolo[4,3-c]pyridine-5-carbonyl)-4-(2-oxo-2,3-di-hydro-imidazo[4,5-b]pyridin-1-yl)-3,4,5,6-tetrahydro-2H-[1,4']bipyridinyl-3'-carbonitrile

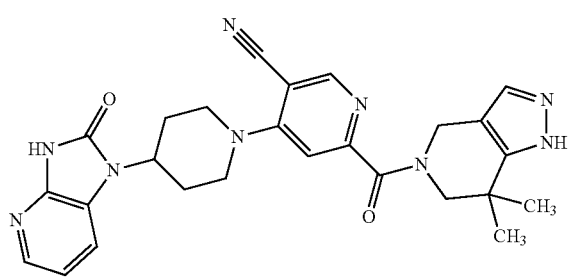 [SMILES: CC1(C)CN(C(=O)c2cc(N3CCC(n4c(=O)[nH]c5ncccc54)CC3)c(C#N)cn2)Cc2cn[nH]c21]

0.11 mg (0.29 mmol) of an isomer mixture of 5'-cyano-4-(2-oxo-2,3-dihydro-imidazo[4,5-b]pyridin-1-yl)-3,4,5,6-tetrahydro-2H-[1,2']bipyridinyl-4'-carboxylic acid and 5'-cyano-4-(2-oxo-2,3-dihydro-imidazo[4,5-b]pyridin-1-yl)-3,4,5,6-tetrahydro-2H-[1,4']bipyridinyl-2'-carboxylic acid, 65 mg (0.29 mmol) 7,7-dimethyl-4,5,6,7-tetrahydro-1H-pyrazolo[4,3-c]pyridine dihydrochloride and 0.17 mL (1.2 mmol) TEA were placed in 1.5 mL DMF. 0.10 g (0.32 mmol) TBTU were added. The reaction mixture was stirred over the weekend at RT. The purification and separation of the isomers were carried out by HPLC-MS. The product-containing fractions were combined and freeze-dried.

Yield: 23 mg (16% of theory)
ESI-MS: m/z=498 (M+H)$^+$
$R_t$ (HPLC-MS): 3.33 min (method B)

The following was obtained as the second product:

Example 173

4'-(7,7-dimethyl-1,4,6,7-tetrahydro-pyrazolo[4,3-c]pyridine-5-carbonyl)-4-(2-oxo-2,3-di-hydro-imidazo[4,5-b]pyridin-1-yl)-3,4,5,6-tetrahydro-2H-[1,2']bipyridinyl-5'-carbonitrile

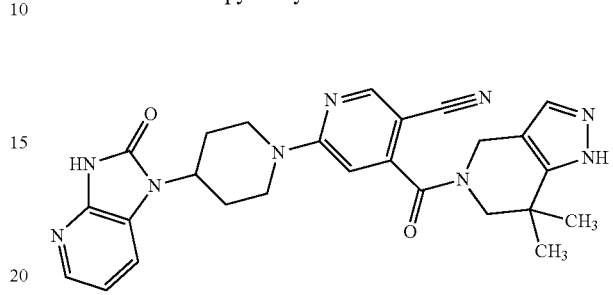

The compound was obtained as described for 6-(7,7-dimethyl-1,4,6,7-tetrahydro-pyrazolo[4,3-c]pyridine-5-carbonyl)-4-(2-oxo-2,3-dihydro-imidazo[4,5-b]pyridin-1-yl)-3,4,5,6-tetrahydro-2H-[1,4']bipyridinyl-3'-carbonitrile.

Yield: 16 mg (11% of theory)
ESI-MS: m/z=498 (M+H)$^+$
$R_t$ (HPLC-MS): 3.67 min (method B)

Example 174

6'-(2,3-dihydro-indole-1-carbonyl)-4-(2-oxo-2,3-dihydro-imidazo[4,5-b]pyridin-1-yl)-3,4,5,6-tetrahydro-2H-[1,4']bipyridinyl-3'-carbonitrile

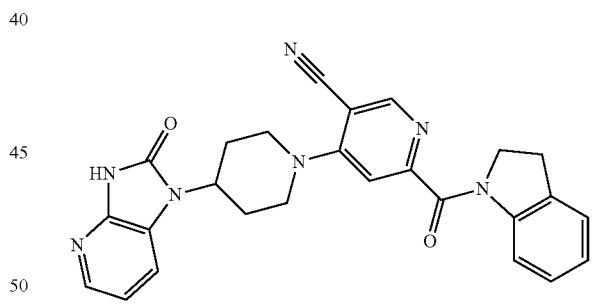

0.11 mg (0.29 mmol) of an isomer mixture of 5'-cyano-4-(2-oxo-2,3-dihydro-imidazo[4,5-b]pyridin-1-yl)-3,4,5,6-tetrahydro-2H-[1,2']bipyridinyl-4'-carboxylic acid and 5'-cyano-4-(2-oxo-2,3-dihydro-imidazo[4,5-b]pyridin-1-yl)-3,4,5,6-tetrahydro-2H-[1,4']bipyridinyl-2'-carboxylic acid, 34 mg (0.29 mmol) 2,3-dihydro-1H-indole and 90 µL (0.61 mmol) TEA were placed in 1.5 mL DMF. 0.10 g (0.32 mmol) TBTU were added. The reaction mixture was stirred over the weekend at RT. The purification and separation of the isomers were carried out by HPLC-MS. The product-containing fractions were combined and freeze-dried.

Yield: 18 mg (13% of theory)
ESI-MS: m/z=466 (M+H)$^+$
$R_t$ (HPLC-MS): 3.67 min (method E)

The following was obtained as the second product:

Example 175

4'-(2,3-dihydro-indole-1-carbonyl)-4-(2-oxo-2,3-dihydro-imidazo[4,5-b]-pyridin-1-yl)-3,4,5,6-tetrahydro-2H-[1,2']bipyridinyl-5'-carbonitrile

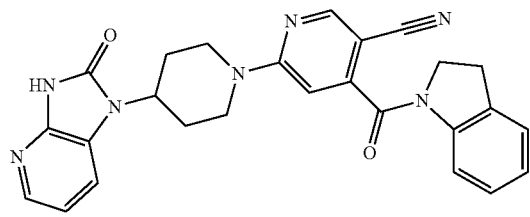 [SMILES: N#Cc1cnc(N2CCC(n3c(=O)[nH]c4ncccc43)CC2)cc1C(=O)N1CCc2ccccc21]

This compound was obtained as described for 6'-(2,3-dihydro-indole-1-carbonyl)-4-(2-oxo-2,3-dihydro-imidazo[4,5-b]pyridin-1-yl)-3,4,5,6-tetrahydro-2H-[1,4']bipyridinyl-3'-carbonitrile.

Yield: 5 mg (4% of theory)
ESI-MS: m/z=466 (M+H)$^+$
$R_t$ (HPLC-MS): 3.77 min (method E)

Example 176

1-{4'-[3-(2-methoxy-ethyl)-2,3-dihydro-indole-1-carbonyl]-3,4,5,6-tetrahydro-2H-[1,2']bipyridinyl-4-yl}-1,3-dihydro-imidazo[4,5-b]pyridin-2-one

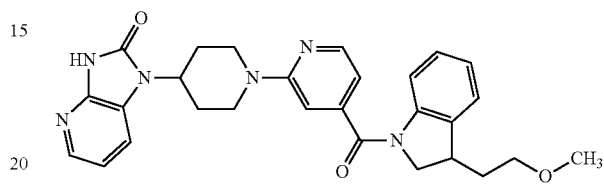

60 mg (0.18 mmol) 4-(2-oxo-2,3-dihydro-imidazo[4,5-b]pyridin-1-yl)-3,4,5,6-tetrahydro-2H-[1,2']bipyridinyl-4'-carboxylic acid, 36 mg (0.2 mmol) 3-(2-methoxy-ethyl)-2,3-dihydro-1H-indole and 28 µL (0.2 mmol) TEA were placed in 1 mL DMF. 64 mg (0.2 mmol) TBTU were added and the reaction mixture was stirred for 3 h at RT. The reaction mixture was purified by HPLC. The product-containing fractions were combined and freeze-dried.

Yield: 35 mg (40% of theory)
ESI-MS: m/z=499 (M+H)$^+$
$R_t$ (HPLC-MS): 1.24 min (method C)

Analogously to 1-{4'-[3-(2-methoxy-ethyl)-2,3-dihydro-indole-1-carbonyl]-3,4,5,6-tetrahydro-2H-[1,2']bipyridinyl-4-yl}-1,3-dihydro-imidazo[4,5-b]pyridin-2-one the following compounds were prepared from in each case 0.18 mmol 4-(2-oxo-2,3-dihydro-imidazo[4,5-b]pyridin-1-yl)-3,4,5,6-tetrahydro-2H-[1,2']bipyridinyl-4'-carboxylic acid, 1.1 eq triethylamine, 1.1 eq TBTU and 1 equivalent of the respective amine in 1 mL DMF:

| Ex. | Structure Name | [Amount of amine] Amine Yield | Analytical data |
|---|---|---|---|
| 177 | ![structure] 1-[4'-(3-ethyl-2,3-dihydro-indole-1-carbonyl)-3,4,5,6-tetrahydro-2H-[1,2']bipyridinyl-4-yl]-1,3-dihydro-imidazo[4,5-b]pyridin-2-one | 29 mg (0.2 mmol) 3-ethyl-2,3-dihydro-1H-indole 6 mg (7% of theory) | ESI-MS: m/z = 469 [M + H]$^+$ $R_t$ = 1.34 min (method C) |

| Ex. | Structure Name | [Amount of amine] Amine Yield | Analytical data |
|---|---|---|---|
| 178 | 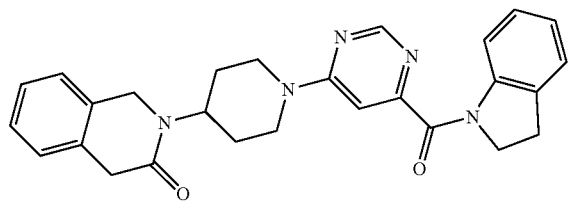 [SMILES: O=C(c1cc(N2CCC(N3Cc4ccccc4CC3=O)CC2)ncn1)N1CCc2ccccc21]<br>1-[4'-(3-cyclopropylmethyl-2,3-dihydro-indole-1-carbonyl)-3,4,5,6-tetrahydro-2H-[1,2']bipyridinyl-4-yl]-1,3-dihydro-imidazo-[4,5b]pyridin-2-one | 35 mg (0.2 mmol) 3-cyclopropyl-methyl-2,3-dihydro-1H-indole 40 mg (46% of theory) | ESI-MS: m/z = 495 [M + H]$^+$ R$_f$= 1.43 min (method C) |

Example 179

2-{1-[6-(2,3-dihydro-indole-1-carbonyl)-pyrimidin-4-yl]-piperidin-4-yl}-1,4-dihydro-2H-isoquinolin-3-one 0.10 g (0.39 mmol) (6-chloro-pyrimidin-4-yl)-(2,3-dihydro-indol-1-yl)-methanone and 100 μL (0.58 mmol) DIPEA were placed in 10 mL DMF. 95 mg (0.41 mmol) 2-piperidin-4-yl-1,4-dihydro-2H-isoquinolin-3-one were added. The reaction mixture was stirred for 2 h at RT. Then the reaction mixture was mixed with water and stirred again. The precipitated solid was suction filtered, washed with methanol and dried.

Yield: 125 mg (72% of theory)
ESI-MS: m/z=454 (M+H)$^+$
R$_f$: 0.67 (silica gel, DCM/cyclohexane/MeOH/NH$_4$OH 70:15:15:2)

Example 180

3-{1-[6-(5-fluoro-2,3-dihydro-indole-1-carbonyl)-pyrimidin-4-yl]-piperidin-4-yl}-1H-quinolin-2-one 80 mg (0.23 mmol) 6-[4-(2-oxo-1,2-dihydroquinolin-3-yl)-piperidin-1-yl]-pyrimidine-4-carboxylic acid, 35 mg (0.26 mmol) 5-fluoro-2,2-dihydro-(1H)-indole, 70 μL (0.5 mmol) and 90 mg (0.28 mmol) TBTU were stirred in 3 mL DMF overnight at RT. The reaction mixture was purified by HPLC. The product-containing fractions were combined and freeze-dried.

Yield: 30 mg (28% of theory)
ESI-MS: m/z=470 (M+H)$^+$
R$_t$ (HPLC-MS): 1.49 min (method C)

Analogously to 3-{1-[6-(5-fluoro-2,3-dihydro-indole-1-carbonyl)-pyrimidin-4-yl]-piperidin-4-yl}-1H-quinolin-2-one the following compounds were prepared from in each case 0.23 mmol 6-[4-(2-oxo-1,2-dihydro-quinolin-3-yl)-piperidin-1-yl]-pyrimidine-4-carboxylic acid, 2.2 to 3.1 eq triethylamine, 1.2 eq TBTU and 1.1 equivalents of the respective amine in 3 mL DMF:

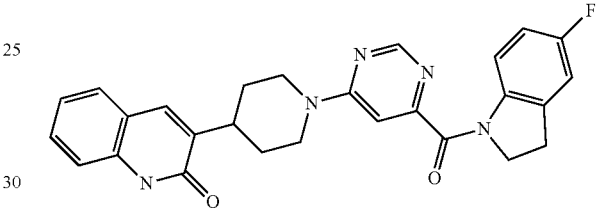

| Example | Structure Name | [Amount of amine] Amine Yield | Analytical data |
|---|---|---|---|
| 181 | 3-{1-[6-(4-fluoro-2,3-dihydro-indole-1-carbonyl)-pyrimidin-4-yl]-piperidin-4-yl}-1H-quinolin-2-one | 35 mg (0.26 mmol) 4-fluoro-2,3-dihydro-1H-indole 15 mg (14% of theory) | ESI-MS: m/z = 470 [M + H]$^+$ R$_t$ = 1.5 min (method C) |

-continued

| Example | Structure Name | [Amount of amine] Amine Yield | Analytical data |
|---|---|---|---|
| 182 | 3-{1-[6-(3-methyl-2,3-dihydro-indole-1-carbonyl)-pyrimidin-4-yl]-piperidin-4-yl}-1H-quinolin-2-one | 35 mg (0.26 mmol) 3-methyl-2,3-dihydroindole 35 mg (33% of theory) | ESI-MS: m/z = 466 [M + H]⁺ $R_t$ = 1.51 min (method C) |
| 183 | 3-{1-[6-(4,5,7,8-tetrahydro-thieno[2,3-d]azepine-6-carbonyl)-pyrimidin-4-yl]-piperidin-4-yl}-1H-quinolin-2-one | 60 mg (0.26 mmol) 5,6,7,8-tetrahydro-4H-thieno[2,3-d]-azepine hydrobromide 5 mg (5% of theory) | ESI-MS: m/z = 486 [M + H]⁺ $R_t$ = 1.42 min (method C) |
| 184 | 3-{1-[6-(2,3-dihydro-indole-1-carbonyl)-pyrimidin-4-yl]-piperidin-4-yl}-1H-quinolin-2-one | 28 µL (0.25 mmol) indoline 35 mg (34% of theory) | ESI-MS: m/z = 452 [M + H]⁺ $R_t$ = 1.45 min (method C) |
| 185 | 3-{1-[6-(4,5-difluoro-2,3-dihydro-indole-1-carbonyl)-pyrimidin-4-yl]-piperidin-4-yl}-1H-quinolin-2-one | 50 mg (0.26 mmol) 4,5-difluoroindoline hydrochloride 13 mg (12% of theory) | ESI-MS: m/z = 488 [M +H]⁺ $R_t$ = 1.54 min (method C) |
| 186: | 3-{1-[6-(7,7-dimethyl-1,4,6,7-tetrahydro-pyrazolo[4,3-c]pyridine-5-carbonyl)-pyrimidin-4-yl]-piperidin-4-yl}-1H-quinolin-2-one | 55 mg (0.26 mmol) 7,7-dimethyl-4,5,6,7-tetrahydro-1H-pyrazolo[4,3-c]-pyridine dihydrochloride 2 mg (2% of theory) | ESI-MS: m/z = 484 [M + H]⁺ $R_t$ = 1.16 min (method C) |

| Example | Structure Name | [Amount of amine] Amine Yield | Analytical data |
|---|---|---|---|
| 187 | 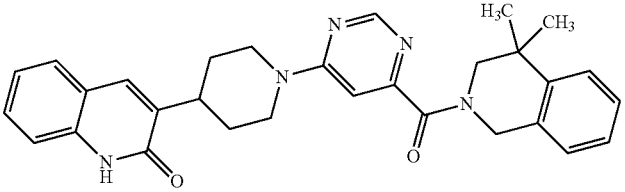 [SMILES: CC1(C)CN(C(=O)c2cc(N3CCC(c4cc5ccccc5[nH]c4=O)CC3)ncn2)Cc2ccccc21]

3-{1-[6-(4,4-dimethyl-3,4-dihydro-1H-isoquinoline-2-carbonyl)-pyrimidin-4-yl]-piperidin-4-yl}-1 H-quinolin-2-one | 50 mg (0.25 mmol) 4,4-dimethyl-1,2,3,4-tetrahydro-isoquinoline hydrochloride 23 mg (20% of theory) | ESI-MS: m/z = 494 [M + H]+ $R_t$ = 1.5 min (method C) |

Example 188

1-{1-[6-(5-fluoro-3-methyl-2,3-dihydro-indole-1-carbonyl)-pyrimidin-4-yl]-piperidin-4-yl}-1,3-dihydro-imidazo[4,5-b]pyridin-2-one

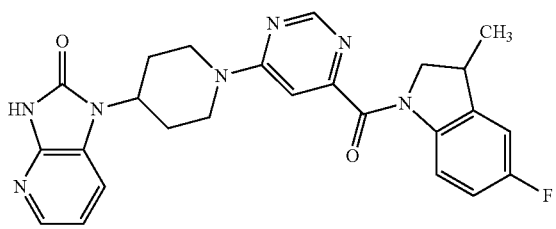 [SMILES: CC1CN(C(=O)c2cc(N3CCC(n4c(=O)[nH]c5ncccc54)CC3)ncn2)c2ccc(F)cc21]

80 mg (0.24 mmol) 6-[4-(2-oxo-2,3-dihydro-imidazo[4,5-b]pyridin-1-yl)-piperidin-1-yl]-pyrimidine-4-carboxylic acid, 36 mg (0.24 mmol) 5-fluoro-3-methyl-2,3-dihydro-1H-indole, 70 μL (0.5 mmol) TEA and 90 mg (0.28 mmol) TBTU were stirred in 1.8 mL DMF overnight at RT. The reaction mixture was purified by HPLC. The product-containing fractions were combined and freeze-dried.

Yield: 75 mg (67% of theory)
ESI-MS: m/z=474 (M+H)+
$R_t$ (HPLC-MS): 3.2 min (method K)

Example 189

6-[4-(2-oxo-2,3-dihydro-imidazo[4,5-b]pyridin-1-yl)-piperidin-1-yl]-pyrimidine-4-carboxylic acid-[2-(2-fluoro-phenyl)-ethyl]-amide

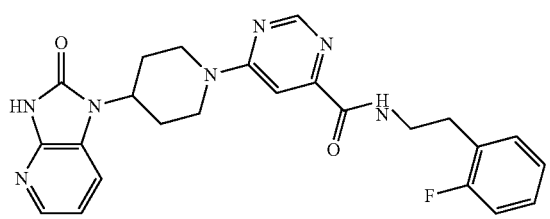 [SMILES: O=C(NCCc1ccccc1F)c1cc(N2CCC(n3c(=O)[nH]c4ncccc43)CC2)ncn1]

0.10 mg (0.29 mmol) 6-[4-(2-oxo-2,3-dihydro-imidazo[4,5-b]pyridin-1-yl)-piperidin-1-yl]-pyrimidine-4-carboxylic acid, 40 μL (0.31 mmol) 2-fluorophenethylamine, 45 μL (0.32 mmol) TEA and 100 mg (3.1 mmol) TBTU were stirred in 10 mL DMF overnight at RT. The reaction mixture was purified by HPLC. The product-containing fractions were combined and freeze-dried.

Yield: 70 mg (52% of theory)
ESI-MS: m/z=462 (M+H)+
$R_f$: 0.73 (silica gel, DCM/cyclohexane/MeOH/NH4OH 70:15:15:2)

Example 190

1-[4'-(5-fluoro-3,3-dimethyl-2,3-dihydro-indole-1-carbonyl)-6'-methoxy-3,4,5,6-tetrahydro-2H-[1,2']bipyridinyl-4-yl]-1,3-dihydro-imidazo[4,5-b]pyridin-2-one

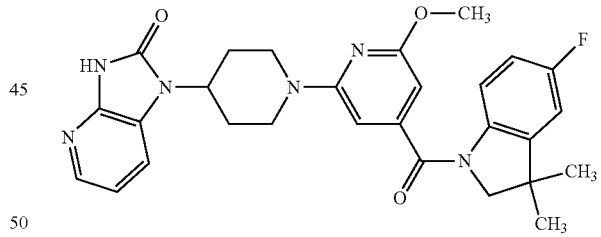

0.26 g (0.9 mmol) 1-piperidin-4-yl-1,3-dihydroimidazo[4,5-b]pyridin-2-one dihydrochloride, 0.30 g (0.9 mmol) (2-chloro-6-methoxy-pyridin-4-yl)-(5-fluoro-3,3-dimethyl-2,3-dihydro-indol-1-yl)-methanone and 0.37 g (2.7 mmol) potassium carbonate were stirred in 3 mL NMP for 12 h at 130° C. The reaction mixture was purified by HPLC. The product-containing fractions were combined and freeze-dried.

Yield: 40 mg (9% of theory)
ESI-MS: m/z=517 (M+H)+
$R_t$ (HPLC-MS): 1.62 min (method C)

Example 191

1-[6'-(5-fluoro-2,3-dihydro-indole-1-carbonyl)-2'-methoxy-3,4,5,6-tetrahydro-2H-[1,4']bipyridinyl-4-yl]-1,3-dihydro-imidazo[4,5-b]pyridin-2-one

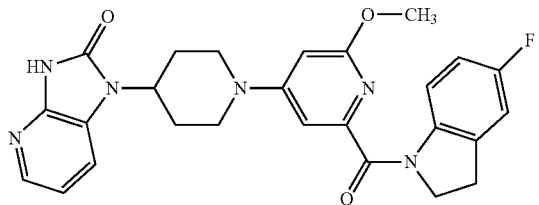 [SMILES: COc1cc(N2CCC(n3c(=O)[nH]c4ncccc43)CC2)cc(C(=O)N2CCc3cc(F)ccc32)n1]

436 mg (2.00 mmol) 1-piperidin-4-yl-1,3-dihydro-imidazo[4,5-b]pyridin-2-one and 200 mg (0.652 mmol) (4-chloro-6-methoxy-pyridin-2-yl)-(5-fluoro-2,3-dihydro-indol-1-yl)-methanone were stirred in 2 mL NMP overnight at 120° C. The reaction mixture was purified by preparative HPLC. The product-containing fractions were combined and evaporated down using the rotary evaporator.

Yield: 62 mg (20% of theory)
ESI-MS: m/z=487 (M−H)⁻
R$_t$ (HPLC): 1.7 min (method C)

Example 192

N-[4'-(5-fluoro-2,3-dihydro-indole-1-carbonyl)-4-(2-oxo-2,3-dihydro-imidazo[4,5-b]pyridin-1-yl)-3,4,5,6-tetrahydro-2H-[1,2']bipyridinyl-6'-yl]-N-methyl-methanesulphonamide

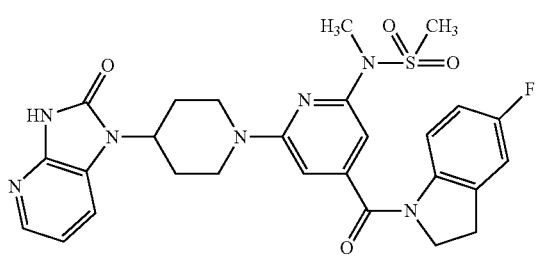 [SMILES: CN(c1cc(C(=O)N2CCc3cc(F)ccc32)cc(N2CCC(n3c(=O)[nH]c4ncccc43)CC2)n1)S(C)(=O)=O]

0.25 g (0.89 mmol) 1-piperidin-4-yl-1,3-dihydroimidazo[4,5-b]pyridin-2-one dihydrochloride, 0.34 g (0.89 mmol) N-[6-chloro-4-(5-fluoro-2,3-dihydro-indole-1-carbonyl)-pyridin-2-yl]-N-methyl-methanesulphonamide and 0.37 g (2.7 mmol) potassium carbonate were stirred in 3 mL of NMP for 4 h at 130° C. The reaction mixture was purified by HPLC. The product-containing fractions were combined and acetonitrile was eliminated by rotary evaporation. The precipitated substance was suction filtered and dried.

Yield: 160 mg (32% of theory)
ESI-MS: m/z=566 (M+H)⁺
R$_t$ (HPLC-MS): 1.4 min (method C)

Example 193

1-[4'-(4,5-difluoro-2,3-dihydro-indole-1-carbonyl)-6'-methoxy-3,4,5,6-tetrahydro-2H-[1,2']bipyridinyl-4-yl]-1,3-dihydro-imidazo[4,5-b]pyridin-2-one

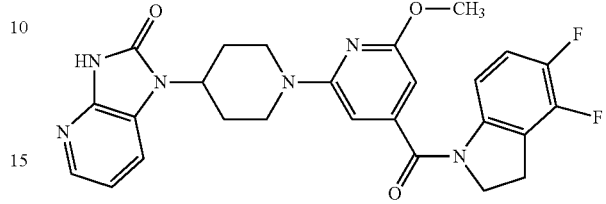

0.98 g (4.5 mmol) 1-piperidin-4-yl-1,3-dihydroimidazo[4,5-b]pyridin-2-one and 0.50 g (1.5 mmol) (2-chloro-6-methoxy-pyridin-4-yl)-(4,5-difluoro-2,3-dihydro-indol-1-yl)-methanone were stirred in 3 mL NMP for 12 h at 130° C. The reaction mixture was purified by HPLC. The product-containing fractions were combined and freeze-dried.

Yield: 0.25 g (32% of theory)
ESI-MS: m/z=507 (M+H)⁺
R$_t$ (HPLC-MS): 1.59 min (method C)

Example 194

3-(1-(6-((4aR,8aS)-decahydroisoquinoline-2-carbonyl)pyrimidin-4-yl)piperidin-4-yl)-7-methoxy-4,5-dihydro-1H-benzo[d][1,3]diazepin-2(3H)-one

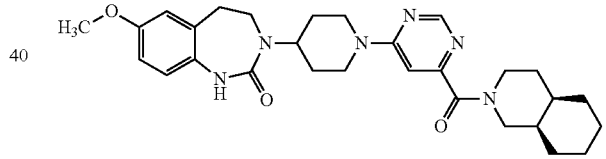

1.7 mg (12 µmol) (4aR,8aS)-decahydroisoquinoline and 1.6 mg (12 µmol) DIPEA were placed in 350 µL DMF. 4.0 mg (10 µmol) 6-[4-(7-methoxy-2-oxo-1,2,4,5-tetrahydro-1,3-benzodiazepin-3-yl)-piperidin-1-yl]-pyrimidine-4-carboxylic acid and 10 µmol DIPEA in 100 µL DMF were activated with 3.5 mg (11 µmol) TBTU in 50 µL DMF and then added dropwise. The reaction mixture was stirred overnight and then combined with 15 µL of an aqueous 2M potassium carbonate solution. After 1 h stirring the precipitate formed was allowed to settle. The supernatant solution was pipetted off and concentrated to dryness by rotary evaporation.

Yield: 5.1 mg
ESI-MS: m/z=519 (M+H)⁺

Analogously to decahydroisoquinoline-2-carbonyl)pyrimidin-4-yl)piperidin-4-yl)-7-methoxy-4,5-dihydro-1H-benzo[d][1,3]diazepin-2(3H)-one the following compounds were prepared from 4.0 mg (10 µmol) 6-[4-(7-methoxy-2-oxo-1,2,4,5-tetrahydro-1,3-benzodiazepin-3-yl)-piperidin-1-yl]-pyrimidine-4-carboxylic acid, 3.6 mg (11 µmol) TBTU, 12 µmol of the corresponding amine and 3.9 µL DIPEA in 350 µL DMF:

| Example | Structure | Amine Yield | Analytical data |
|---|---|---|---|
| 195 | 3-(1-(6-((4aS,8aS)-decahydro-isoquinoline-2-carbonyl)-pyrimidin-4-yl)-piperidin-4-yl)-7-methoxy-4,5-dihydro-1H-benzo[d][1,3]-diazepin-2(3H)-one | (4aS,8aS)-decahydro-isoquinoline 5 mg | ESI-MS: m/z = 519 [M + H]+ |
| 196 | 6-[4-(7-methoxy-2-oxo-1,2,4,5-tetrahydro-1,3-benzodiazepin-3-yl)-piperidin-1-yl]-pyrimidine-4-carboxylic acid (2-oxo-1.2.5,6,7,8-hexahydro-quinolin-5-yl)-amide | 5-amino-5,6,7,8-tetra-hydro-1H-quinolin-2-one-dihydrochloride 1.3 mg | ESI-MS: m/z = 544 [M + H]+ |
| 197 | 3-{1-[6-(6.7-dihydro-4H-thieno-[3,2-c]pyridine-5-carbonyl)-pyrimidin-4-yl]-piperidin-4-yl}-7-methoxy-1,3,4,5-tetrahydro-1,3-benzodiazepin-2-one | 4,5,6,7-tetrahydro-thieno[3,2-c]pyridine 5.2 mg | ESI-MS: m/z = 519 [M + H]+ |
| 198 | 7-methoxy-3-{1-[6-(4,5,7,8-tetra-hydro-thieno[2,3-d]azepine-6-carbonyl)-pyrimidin-4-yl]-piperidin-4-yl}-1,3,4,5-tetrahydro-benzo[d][1,3]diazepin-2-one | 5,6,7,8-tetrahydro-4H-thieno[2,3-d] azepine 6 mg | ESI-MS: m/z = 533 [M + H]+ |
| 199 | 7-methoxy-3-{1-[6-(octahydro-isoquinoline-2-carbonyl)-pyrimidin-4-yl]-piperidin-4-yl}-1,3,4,5-tetrahydro-1,3-benzodiazepin-2-one | decahydro-isoquiniline 5 mg | ESI-MS: m/z = 519 [M + H]+ |
| 200 | 7-methoxy-3-{1-[6-(1,2,4,5-tetra-hydro-benzo[d]azepine-3-carbonyl)-pyrimidin-4-yl]-piperidin-4-yl}-1,3,4,5-tetrahydro-1,3-benzodiazepin-2-one | 2.3.4,5-tetrahydro-2H-benzo[d]azepine 3.1 mg | ESI-MS: m/z = 527 [M + H]+ |

Example 201

6-[4-(7-methoxy-2-oxo-1,2,4,5-tetrahydro-1,3-benzodiazepin-3-yl)-piperidin-1-yl]-pyrimidine-4-carboxylic acid methyl-(4-oxo-3,4-dihydro-quinazolin-2-ylmethyl)-amide

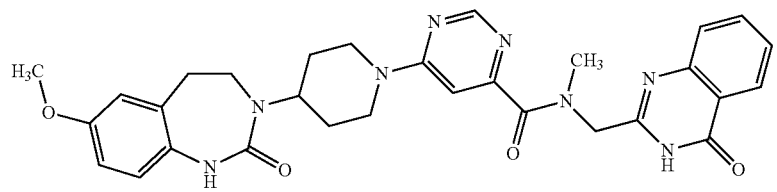 [SMILES: COc1ccc2c(c1)CCN(C1CCN(c3cc(C(=O)N(C)Cc4nc5ccccc5c(=O)[nH]4)ncn3)CC1)C(=O)N2]

2.3 mg (12 μmol) 2-methylaminomethyl-3H-quinazolin-4-one and 1.6 mg (12 μmol) DIPEA were placed in 350 μL DMF. 4.0 mg (10 μmol) of 6-[4-(7-methoxy-2-oxo-1,2,4,5-tetra-hydro-1,3-benzodiazepin-3-yl)-piperidin-1-yl]-pyrimidine-4-carboxylic acid and 1.3 mg (10 μmol) DIPEA in 100 μL DMF were activated with 3.5 mg (11 μmol) TBTU in 50 μL DMF and then added dropwise. The reaction mixture was stirred overnight. 15 μL of an aqueous 2M potassium carbonate solution were added and the mixture was stirred for a further hour. The precipitate formed was allowed to settle and the supernatant solution was pipetted off and concentrated to dryness by rotary evaporation.

Yield: 2.2 mg
ESI-MS: m/z=569 (M+H)+

Example 202

3-{1-[6-(7,7-dimethyl-3-trifluoromethyl-1,4,6,7-tetrahydro-pyrazolo[4,3-c]pyridine-5-carbonyl)-pyrimidin-4-yl]-piperidin-4-yl}-7-methoxy-1,3,4,5-tetrahydro-benzo[d][1,3]diazepin-2-one

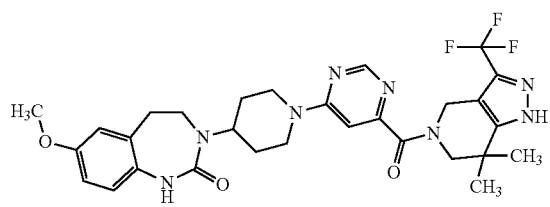 [SMILES: COc1ccc2c(c1)CCN(C1CCN(c3cc(C(=O)N4Cc5c(C(F)(F)F)n[nH]c5C(C)(C)C4)ncn3)CC1)C(=O)N2]

0.11 g (0.28 mmol) TBTU were added to 0.10 g (0.25 mmol) 6-[4-(7-methoxy-2-oxo-1,2,4,5-tetrahydro-1,3-benzodiazepin-3-yl)-piperidin-1-yl]-pyrimidine-4-carboxylic acid, 90 mg (0.32 mmol) 7,7-dimethyl-3-trifluoromethyl-4,5,6,7-tetrahydro-1H-pyrazolo[4,3-c]pyridine hydrochloride and 0.12 mL TEA in 1.0 mL DMF and the mixture was stirred for 4 h at RT. Then the reaction mixture was purified by preparative HPLC-MS. The product-containing fractions were combined and freeze-dried.

Yield: 40 mg (25% of theory)
ESI-MS: m/z=599 (M+H)+
$R_t$ (HPLC-MS): 3.11 min (method E)

Example 203

3-(5-fluoroindoline-1-carbonyl)-5-(4-(7-methoxy-2-oxo-4,5-dihydro-1H-benzo[d][1,3]-diazepin-3(2H)-yl)piperidin-1-yl)pyridine-1-oxide

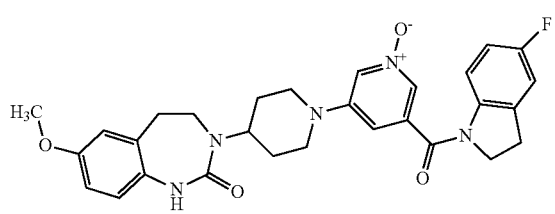 [SMILES: COc1ccc2c(c1)CCN(C1CCN(c3cc(C(=O)N4CCc5cc(F)ccc54)c[n+]([O-])c3)CC1)C(=O)N2]

Under an argon atmosphere 5.0 mg (0.02 mmol) palladium (II)acetate and 14 mg (20 μmol) BINAP were added to 69 mg (0.25 mmol) 7-methoxy-3-piperidin-4-yl-1,3,4,5-tetrahydro-1,3-benzodiazepin-2-one, 84 mg (0.25 mmol) 3-bromo-5-(5-fluoroindoline-1-carbonyl)-pyridine-1-oxide and 0.12 g (0.38 mmol) caesium carbonate in 4.0 mL dioxane and the mixture was stirred overnight at 120° C. The reaction mixture was then evaporated down and the residue was dissolved in DMF/MeOH and purified by preparative HPLC-MS. The product-containing fractions were combined, the organic solvent was evaporated down and the residue was made alkaline with a 1N aqueous sodium hydroxide solution. The precipitate formed was suction filtered, washed with water and dried under HV.

Yield: 40 mg (30% of theory)
ESI-MS: m/z=532 (M+H)+
$R_t$ (HPLC-MS): 1.44 min (method C)

Example 204

1-[2'-(5-fluoro-2,3-dihydro-indole-1-carbonyl)-5'-(3-hydroxy-prop-1-ynyl)-3,4,5,6-tetrahydro-2H-[1,4']bipyridinyl-4-yl]-1,3-dihydro-imidazo[4,5-b]pyridin-2-one

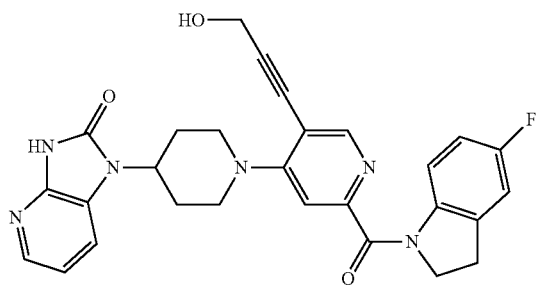 [SMILES: O=C(c1cc(N2CCC(n3c(=O)[nH]c4ncccc43)CC2)c(C#CCO)cn1)N1CCc2cc(F)ccc21]

Under an argon atmosphere 44 mg (0.34 mmol) 3-trimethylsilanyl-prop-2-yn-1-ol, 50 μL TEA, 13 mg 1,1'-bis(diphenylphosphine)ferrocene dichloropalladium (II) and 3 mg (20 μmol) copper(I) iodide were added to 0.10 g (0.17 mmol) 1-[2'-(5-fluoro-2,3-dihydro-indole-1-carbonyl)-5'-iodo-3,4,5,6-tetrahydro-2H-[1,4']bipyridinyl-4-yl]-1,3-dihydro-imidazo[4,5-b]pyridin-2-one in 4.0 mL 1,4-dioxane. Then 0.36 mL (0.36 mmol) of a 1 molar tetrabutylammonium fluoride solution in THF were added dropwise and the mixture was then stirred for 4 h at 80° C. The reaction mixture was mixed with water and the precipitate formed was suction filtered. The precipitate was stirred in 6 mL DMF and suction filtered. The filtrate was purified by preparative HPLC-MS. The product-containing fractions were combined and freeze-dried.

Yield: 0.4 mg (0.5% of theory)
ESI-MS: m/z=513 (M+H)$^+$
R$_t$ (HPLC-MS): 1.44 min (method C)

Example 205

6'-(5-fluoro-2,3-dihydro-indole-1-carbonyl)-4-(7-methoxy-2-oxo-1,2,4,5-tetrahydro-benzo-[d][1,3]diazepin-3-yl)-3,4,5,6-tetrahydro-2H-[1,4']bipyridinyl-3'-carbonitrile

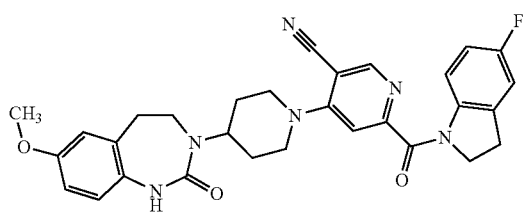 [SMILES: COc1ccc2c(c1)CCN(C1CCN(c3cc(C(=O)N4CCc5cc(F)ccc54)ncc3C#N)CC1)C(=O)N2]

150 mg (0.50 mmol) 4-chloro-6-(5-fluoro-2,3-dihydro-indole-1-carbonyl)-nicotinonitrile, 137 mg (0.50 mmol) 7-methoxy-3-piperidin-4-yl-1,3,4,5-tetrahydro-1,3-benzodiazepin-2-one and 103 mg (0.75 mmol) potassium carbonate in 2 mL DMF were stirred for 10 h at 130° C. Then the reaction mixture was diluted with 4 mL DMF and the precipitate formed was suction filtered. The filtrate was purified by preparative HPLC-MS. The product-containing fractions were combined and freeze-dried.

Yield: 10 mg (4% of theory)
ESI-MS: m/z=541 (M+H)$^+$
R$_t$ (HPLC-MS): 1.68 min (method C)

Example 206

3-{1-[6-(3-hydroxymethyl-2,3-dihydro-indole-1-carbonyl)-pyrimidin-4-yl]-piperidin-4-yl}-7-methoxy-1,3,4,5-tetrahydro-benzo[d][1,3]diazepin-2-one

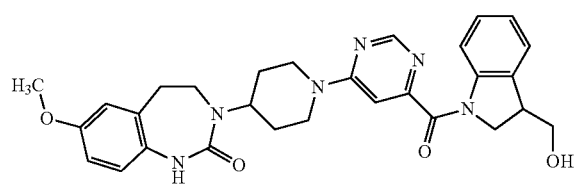 [SMILES: COc1ccc2c(c1)CCN(C1CCN(c3cc(C(=O)N4CC(CO)c5ccccc54)ncn3)CC1)C(=O)N2]

100 mg (0.25 mmol) of 6-[4-(7-methoxy-2-oxo-1,2,4,5-tetrahydro-1,3-benzodiazepin-3-yl)-piperidin-1-yl]-pyrimidine-4-carboxylic acid and 50 mg (0.32 mmol) (2,3-dihydro-1H-indol-3-yl)-methanol in 50 μL (0.27 mmol) TEA and 0.90 mL DMF were combined with 85 mg (0.27 mmol) TBTU and the mixture was stirred for 5 h at RT. Then the reaction mixture was purified by preparative HPLC-MS. The product-containing fractions were combined and evaporated down by roughly half. The precipitated solid was suction filtered and dried.

Yield: 69 mg (52% of theory)
ESI-MS: m/z=529 (M+H)$^+$
R$_t$ (HPLC-MS): 2.87 min (method E)

Example 207

3-[6'-(5-fluoro-2,3-dihydro-indole-1-carbonyl)-2'-methyl-3,4,5,6-tetrahydro-2H-[1,4']bipyridinyl-4-yl]-7-methoxy-1,3,4,5-tetrahydro-benzo[d][1,3]diazepin-2-one

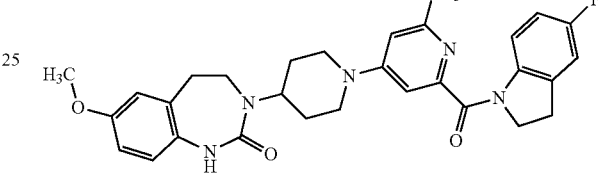

125 mg (0.43 mmol) (4-chloro-6-methyl-pyridin-2-yl)-(5-fluoro-2,3-dihydro-indol-1-yl)-methanone, 118 mg (0.43 mmol) 7-methoxy-3-piperidin-4-yl-1,3,4,5-tetrahydro-1,3-benzodiazepin-2-one and 89 mg (0.65 mmol) potassium carbonate in 2.0 mL NMP were stirred for 10 h at 130° C. Then the reaction mixture was purified by preparative HPLC-MS. The product-containing fractions were combined and freeze-dried.

Yield: 33 mg (14% of theory)
ESI-MS: m/z=530 (M+H)$^+$
R$_t$ (HPLC-MS): 3.07 min (method B)

Example 208

3-{1-[6-(5-fluoro-2,3-dihydro-indole-1-carbonyl)-pyrimidin-4-yl]-piperidin-4-yl}-6-methoxy-1H-quinolin-2-one

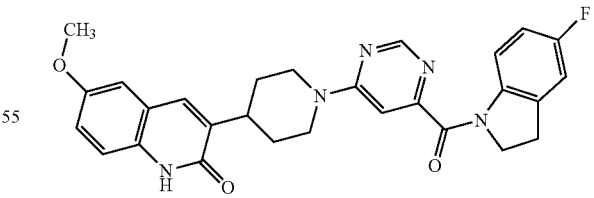

25 mg (70 μmol) 6-methoxy-3-piperidin-4-yl-1H-quinolin-2-one, 20 mg (70 μmol) (6-chloro-pyrimidin-4-yl)-(5-fluoro-2,3-dihydro-indol-1-yl)-methanone and 50 μL (0.29 mmol) DIPEA were stirred in 2 mL DMF overnight at RT. Then the reaction mixture was diluted with DMF and purified by preparative HPLC-MS. The product-containing fractions were combined and freeze-dried.

Yield: 4 mg (11% of theory)

ESI-MS: m/z=500 (M+H)+

$R_t$ (HPLC-MS): 1.56 min (method C)

Example 209

3-{1-[6-(6-fluoro-2,3-dihydro-indole-1-carbonyl)-pyrimidin-4-yl]-piperidin-4-yl}-7-methoxy-1,3,4,5-tetrahydro-benzo[d][1,3]diazepin-2-one

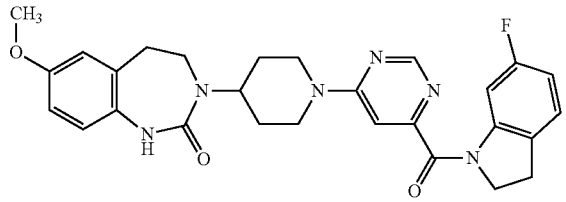 [SMILES: COc1ccc2c(c1)CCN(C1CCN(c3cc(C(=O)N4CCc5ccc(F)cc54)ncn3)CC1)C(=O)N2]

100 mg (0.25 mmol) 6-[4-(7-methoxy-2-oxo-1,2,4,5-tetrahydro-1,3-benzodiazepin-3-yl)-piperidin-1-yl]-pyrimidine-4-carboxylic acid and 35 mg (0.26 mmol) 6-fluoro-2,3-dihydro-1H-indole in 0.10 mL (0.71 mmol) TEA and 1.5 mL DMF were combined with 90 mg (0.28 mmol) TBTU and stirred for 1 h at RT. Then the reaction mixture was purified by preparative HPLC-MS. The product-containing fractions were combined and freeze-dried.

Yield: 58 mg (44% of theory)

ESI-MS: m/z=517 (M+H)+

$R_t$ (HPLC-MS): 1.56 min (method C)

Example 210

3-{1-[6-(5-fluoro-2,3-dihydro-indole-1-carbonyl)-pyrimidin-4-yl]-piperidin-4-yl}-3,4-dihydro-1H-pyrido[4,3-d]pyrimidin-2-one

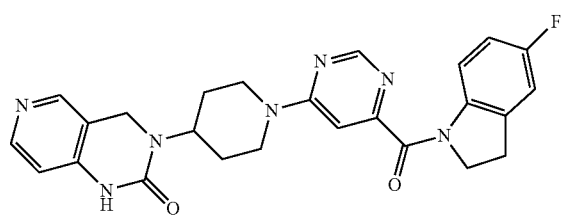 [SMILES: O=C(c1cc(N2CCC(N3Cc4cnccc4NC3=O)CC2)ncn1)N1CCc2cc(F)ccc21]

70 mg (0.25 mmol) (6-chloro-pyrimidin-4-yl)-(5-fluoro-2,3-dihydro-indol-1-yl)-methanone, 60 mg (0.26 mmol) 3-piperidin-4-yl-3,4-dihydro-1H-pyrido[4,3-d]pyrimidin-2-one and 50 µL (0.30 mmol) DIPEA in 5.0 mL DMF were shaken for 2 h at RT. Then the reaction mixture was poured onto water, stirred and the precipitate formed was suction filtered. This was washed with diisopropylether and dried.

Yield: 26 mg (22% of theory)

ESI-MS: m/z=474 (M+H)+

$R_t$ (HPLC-MS): 1.20 min (method C)

Example 211

3-[5'-ethynyl-2'-(5-fluoro-2,3-dihydro-indole-1-carbonyl)-3,4,5,6-tetrahydro-2H-[1,4']-bipyridinyl-4-yl]-7-methoxy-1,3,4,5-tetrahydro-benzo[d][1,3]diazepin-2-one

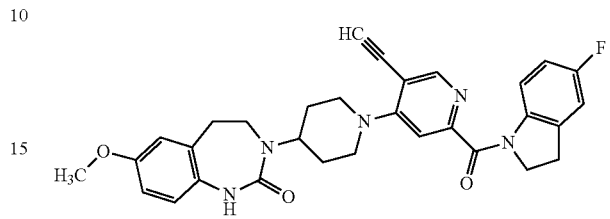

86 µL (86 µmol) of a 1N tetrabutylammonium fluoride solution in THF were added to 35 mg (57 mol) 3-[2'-(5-fluoro-2,3-dihydro-indole-1-carbonyl)-5'-trimethylsilanyl-ethynyl-3,4,5,6-tetrahydro-2H-[1,4']bipyridinyl-4-yl]-7-methoxy-1,3,4,5-tetrahydro-benzo[d][1,3]-diazepin-2-one in 1.5 mL THF and the mixture was stirred for 3 h at RT. Then the reaction mixture was combined with a 0.1 molar aqueous hydrochloric acid solution and the precipitate formed was suction filtered.

Yield: 8 mg (26% of theory)

ESI-MS: m/z=540 (M+H)+

$R_t$ (HPLC-MS): 1.56 min (method C)

Example 212

1-[6'-chloro-4'-(5-fluoro-2,3-dihydro-indole-1-carbonyl)-3,4,5,6-tetrahydro-2H-[1,2']bipyridinyl-4-yl]-1,3-dihydro-imidazo[4,5-b]pyridin-2-one

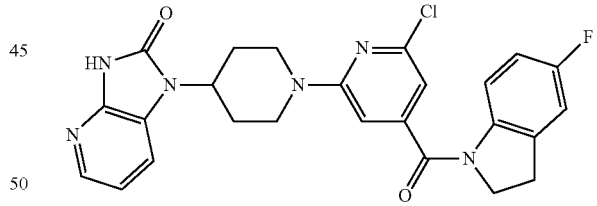

0.74 g (3.4 mmol) 1-piperidin-4-yl-1,3-dihydroimidazo[4,5-b]pyridin-2-one, 1.0 g (3.2 mmol) (2,6-dichloro-pyridin-4-yl)-(5-fluoro-2,3-dihydro-indol-1-yl)-methanone and 0.65 mL (3.8 mmol) DIPEA in 10 mL DMF were stirred for 2 h at RT. Then the reaction mixture was evaporated down, the residue was mixed with water and stirred for 30 min at RT. The precipitated solid was suction filtered, stirred with diisopropylether and isopropanol and suction filtered again. After drying the crude product was purified by preparative HPLC-MS. The product-containing fractions were combined and freeze-dried.

Yield: 350 mg (22% of theory)

ESI-MS: m/z=493 (M+H)+

$R_t$ (HPLC-MS): 1.73 min (method O)

Example 213

3-{1-[6-(5-fluoro-2,3-dihydro-indole-1-carbonyl)-pyrimidin-4-yl]-piperidin-4-yl}-3,4-dihydro-1H-pyrido[2,3-d]pyrimidin-2-one

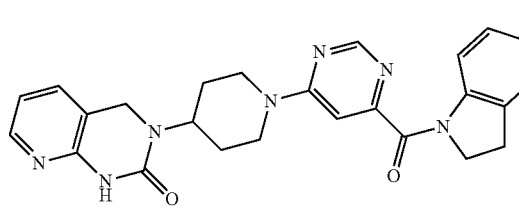

70 mg (0.25 mmol) (6-chloro-pyrimidin-4-yl)-(5-fluoro-2,3-dihydro-indol-1-yl)-methanone, 60 mg (0.26 mmol) 3-piperidin-4-yl-3,4-dihydro-1H-pyrido[2,3-d]pyrimidin-2-one and 52 µL (0.30 mmol) DIPEA in 5.0 mL DMF were shaken for 2 h at RT. Then the reaction mixture was poured onto water, stirred and the precipitate formed was suction filtered. This was washed with diisopropylether and dried.

Yield: 99 mg (83% of theory)
ESI-MS: m/z=474 (M+H)$^+$
R$_t$ (HPLC-MS): 1.43 min (method C)

Example 214

1-[4-(7-methoxy-2-oxo-1,2,4,5-tetrahydro-benzo[d][1,3]diazepin-3-yl)-3,4,5,6-tetrahydro-2H-[1,4']bipyridinyl-2'-carbonyl]-1,2,2a,5-tetrahydro-3H-pyrrolo[4,3,2-de]quinolin-4-one

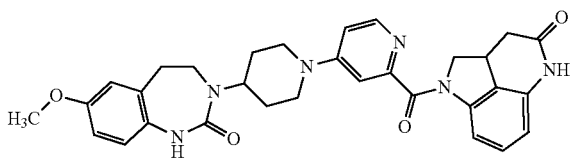 [SMILES: COc1ccc2c(c1)CCN(C1CCN(c3ccnc(C(=O)N4CC5CC(=O)Nc6cccc4c65)c3)CC1)C(=O)N2]

67 mg (0.17 mmol) 4-(7-methoxy-2-oxo-1,2,4,5-tetrahydro-benzo[d][1,3]diazepin-3-yl)-3,4,5,6-tetrahydro-2H-[1,4']bipyridinyl-2'-carboxylic acid and 30 mg (0.17 mmol) 1,2,2a,5-tetrahydro-3H-pyrrolo[4,3,2-de]quinolin-4-one in 56 µL (0.40 mmol) TEA and 1.8 mL DMF were combined with 58 mg (0.18 mmol) TBTU and stirred overnight at RT. Then the reaction mixture was purified by preparative HPLC-MS. The product-containing fractions were combined and freeze-dried.

Yield: 70 mg (75% of theory)
ESI-MS: m/z=553 (M+H)$^+$
R$_t$ (HPLC-MS): 2.84 min (method E)

Example 215

1-[4-(7-methoxy-2-oxo-1,2,4,5-tetrahydro-benzo[d][1,3]diazepin-3-yl)-3,4,5,6-tetrahydro-2H-[1,2']bipyridinyl-4'-carbonyl]-1,2,2a,5-tetrahydro-3H-pyrrolo[4,3,2-de]quinolin-4-one

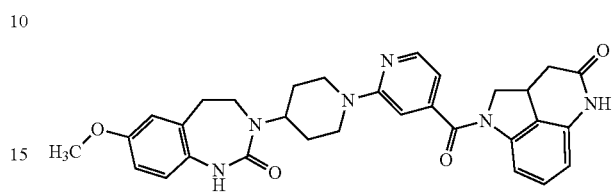

67 mg (0.17 mmol) 4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid and 30 mg (0.17 mmol) 1,2,2a,5-tetrahydro-3H-pyrrolo[4,3,2-de]quinolin-4-one in 56 µL (0.40 mmol) TEA and 1.8 mL DMF were combined with 58 mg (0.18 mmol) TBTU and stirred overnight at RT. Then the reaction mixture was purified by preparative HPLC-MS. The product-containing fractions were combined and freeze-dried.

Yield: 44 mg (47% of theory)
ESI-MS: m/z=553 (M+H)$^+$
R$_t$ (HPLC-MS): 3.00 min (method E)

Example 216

3-[6'-chloro-4'-(5-fluoro-2,3-dihydro-indole-1-carbonyl)-3,4,5,6-tetrahydro-2H-[1,2']bipyridinyl-4-yl]-7-methoxy-1,3,4,5-tetrahydro-benzo[d][1,3]diazepin-2-one

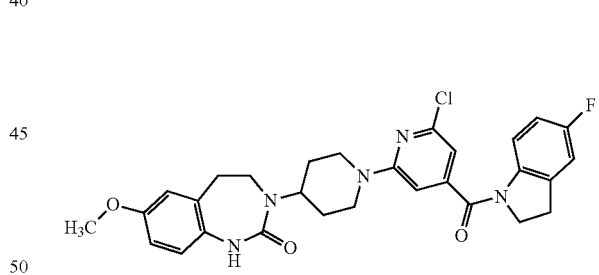

1.0 g (3.2 mmol) 7-methoxy-3-piperidin-4-yl-1,3,4,5-tetrahydro-1,3-benzodiazepin-2-one, 0.94 g (3.4 mmol) (2,6-dichloro-pyridin-4-yl)-(5-fluoro-2,3-dihydro-indol-1-yl)-methanone and 0.65 mL (3.8 mmol) DIPEA in 10 mL DMF were stirred for 2 h at RT. Then the reaction mixture was evaporated down, the residue was mixed with water and stirred for 30 min at RT. The precipitated solid was suction filtered, stirred with diisopropylether and isopropanol and suction filtered again. After drying the crude product was purified by preparative HPLC-MS. The product-containing fractions were combined and freeze-dried.

Yield: 750 mg (42% of theory)
ESI-MS: m/z=550 (M+H)$^+$
R$_t$ (HPLC-MS): 1.96 min (method O)

Example 217

3-{-[6-(5-hydroxymethyl-4.7-dihydro-5H-thieno[2,3-c]pyridin-6-carbonyl)-pyrimidin-4-yl]-piperidin-4-yl}-7-methoxy-1,3,4,5-tetrahydro-benzo[d][1,3]diazepin-2-one

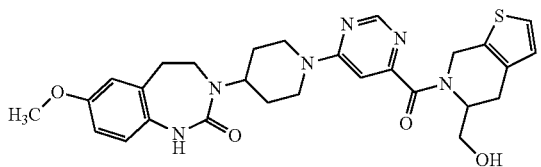 [SMILES: COc1ccc2c(c1)CCN(C1CCN(c3cc(C(=O)N4Cc5sccc5CC4CO)ncn3)CC1)C(=O)N2]

100 mg (0.25 mmol) 4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid and 50 mg (0.28 mmol) (4,5,6,7-tetrahydro-thieno[2,3-c]pyridin-5-yl)-methanol in 50 µL (0.36 mmol) TEA and 0.90 mL DMF were combined with 85 mg (0.27 mmol) TBTU and the mixture was stirred for 5 h at RT. Then the reaction mixture was purified by preparative HPLC-MS. The product-containing fractions were combined and evaporated down roughly by half. The precipitate formed was suction filtered and dried.

Yield: 40 mg (29% of theory)
ESI-MS: m/z=549 (M+H)$^+$
R$_t$ (HPLC-MS): 2.89 min (method E)

Example 218

4-(5-fluoro-2,3-dihydro-indole-1-carbonyl)-2-[4-(2-oxo-2,3-dihydro-imidazo[4,5-b]pyridin-1-yl)-piperidin-1-yl]-benzonitrile

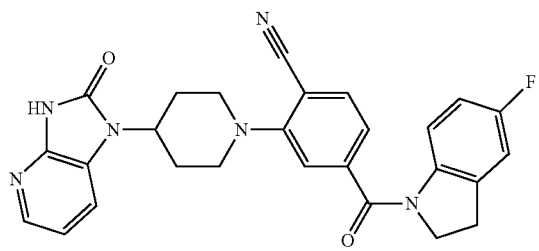 [SMILES: N#Cc1ccc(C(=O)N2CCc3cc(F)ccc32)cc1N1CCC(n2c(=O)[nH]c3ncccc32)CC1]

70 mg (0.19 mmol) 4-cyano-3-[4-(2-oxo-2,3-dihydro-imidazo[4,5-b]pyridin-1-yl)-piperidin-1-yl]-benzoic acid and 30 mg (0.21 mmol) 5-fluoro-2,3-dihydro-(1H)-indole in 0.10 mL (0.72 mmol) TEA and 1.5 mL DMF were mixed with 65 mg (0.20 mmol) TBTU and the mixture was stirred for 1 h at RT. Then the reaction mixture was purified by preparative HPLC-MS. The product-containing fractions were combined and freeze-dried.

Yield: 4 mg (4% of theory)
ESI-MS: m/z=483 (M+H)$^+$
R$_t$ (HPLC-MS): 1.64 min (method C)

Example 219

1-{1-[6-(3-hydroxymethyl-2,3-dihydro-indole-1-carbonyl)-pyrimidin-4-yl]-piperidin-4-yl}-1,3-dihydro-imidazo[4,5-b]pyridin-2-one

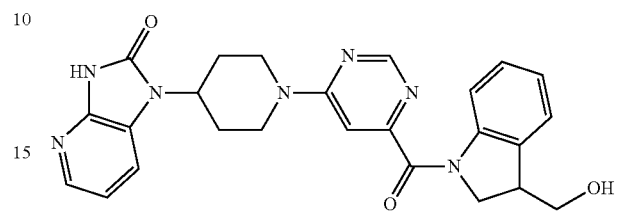

85 mg (0.25 mmol) 6-[4-(2-oxo-2,3-dihydroimidazo[4,5-b]pyridin-1-yl)-piperidin-1-yl]-pyrimidine-4-carboxylic acid and 50 mg (0.32 mmol) (2,3-dihydro-1H-indol-3-yl)-methanol in 50 µL (0.36 mmol) TEA and 0.90 mL DMF were combined with 85 mg (0.27 mmol) TBTU and stirred for 5 h at RT. Then the reaction mixture was purified by preparative HPLC-MS. The product-containing fractions were combined and freeze-dried.

Yield: 57 mg (46% of theory)
ESI-MS: m/z=472 (M+H)$^+$
R$_t$ (HPLC-MS): 1.11 min (method C)

Example 220

6-[4-(7-methoxy-2-oxo-1,2,4,5-tetrahydro-benzo[d][1,3]diazepin-3-yl)-piperidin-1-yl]-pyrimidine-4-carboxylic acid(1H-indazol-4-yl)-amide

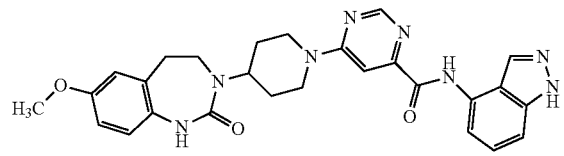 [SMILES: COc1ccc2c(c1)CCN(C1CCN(c3cc(C(=O)Nc4cccc5[nH]ncc45)ncn3)CC1)C(=O)N2]

100 mg (0.25 mmol) 4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid and 34 mg (0.25 mmol) 4-amino-indazole in 74 mµL (0.53 mmol) TEA and 1.5 mL DMF were combined with 89 mg (0.28 mmol) TBTU and the mixture was stirred overnight at RT. Then the reaction mixture was purified by preparative HPLC-MS. The product-containing fractions were combined and freeze-dried.

Yield: 24 mg (19% of theory)
ESI-MS: m/z=513 (M+H)$^+$
R$_t$ (HPLC-MS): 1.35 min (method C)

Example 221

3-{1-[3-(5-fluoro-2,3-dihydro-indole-1-carbonyl)-phenyl]-piperidin-4-yl}-7-methoxy-1,3,4,5-tetrahydro-benzo[d][1,3]diazepin-2-one

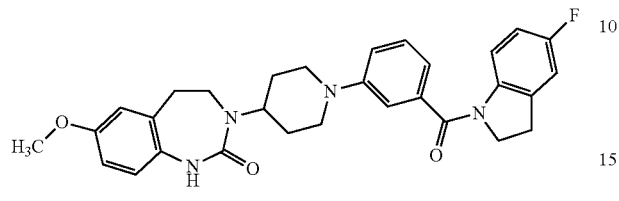

Under an argon atmosphere 7 mg (31 µmol) palladium(II) acetate and 20 mg (32 µmol) BINAP were added to 86 mg (0.31 mmol) 7-methoxy-3-piperidin-4-yl-1,3,4,5-tetrahydro-1,3-benzodiazepin-2-one, 0.10 g (0.31 mmol) (3-bromo-phenyl)-(5-fluoro-2,3-dihydro-indol-1-yl)-methanone and 0.16 g (0.48 mmol) caesium carbonate in 4.0 mL dioxane, and the mixture was stirred overnight at 120° C. The reaction mixture was then evaporated down and the residue was dissolved in DMF/MeOH and purified by preparative HPLC-MS.

The product-containing fractions were combined and freeze-dried.

Yield: 10 mg (5% of theory)

ESI-MS: m/z=515 (M+H)$^+$

R$_t$ (HPLC-MS): 1.69 min (method C)

Example 222

7-methoxy-3-{1-[6-(4,5,7,8-tetrahydro-thiazolo[4,5-d]azepine-6-carbonyl)-pyrimidin-4-yl]-piperidin-4-yl}-1,3,4,5-tetrahydro-benzo[d][1,3]diazepin-2-one

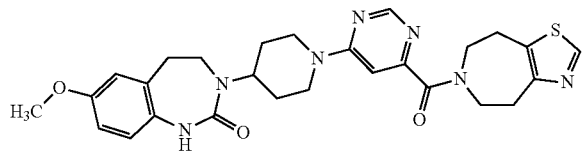 [SMILES: COc1ccc2c(c1)CCN(C1CCN(c3cc(C(=O)N4CCc5ncsc5CC4)ncn3)CC1)C(=O)N2]

83 mg (0.21 mmol) 4-(7-methoxy-2-oxo-1,2,4,5-tetrahydro-benzo[d][1,3]diazepin-3-yl)-3,4,5,6-tetrahydro-2H-[1,2']bipyridinyl-4'-carboxylic acid and 37 mg (0.24 mmol) 5,6,7,8-tetrahydro-4H-thiazolo[4,5-d]azepine in 0.13 mL (0.72 mmol) DIPEA and 1.0 mL DMF were combined with 77 mg (0.24 mmol) TBTU and the mixture was stirred overnight at RT. Then the reaction mixture was purified by preparative HPLC-MS. The product-containing fractions were combined and freeze-dried.

Yield: 14 mg (12% of theory)

ESI-MS: m/z=534 (M+H)$^+$

R$_t$ (HPLC-MS): 1.30 min (method C)

Example 223

1-{6-[4-(2-oxo-1,2,4,5-tetrahydro-benzo[d][1,3]diazepin-3-yl)-piperidin-1-yl]-pyrimidine-4-carbonyl}-1,2,2a,5-tetrahydro-3H-pyrrolo[4,3,2-de]quinolin-4-one

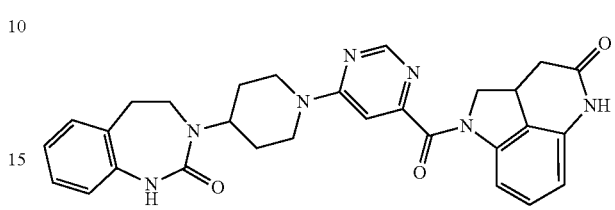

63mg (0.17 mmol) 6-[4-(2-oxo-1,2,4,5-tetrahydro-1,3-benzodiazepin-3-yl)-piperidin-1-yl]-pyrimidine-4-carboxylic acid and 30 mg (0.17 mmol) 1,2,2a,5-tetrahydro-3H-pyrrolo-[4,3,2-de]quinolin-4-one in 56 µL (0.40 mmol) TEA and 1.8 mL DMF were mixed with 58 mg (0.18 mmol) TBTU and the mixture was stirred overnight at RT. Then the reaction mixture was purified by preparative HPLC-MS. The product-containing fractions were combined and freeze-dried.

Yield: 60 mg (67% of theory)

ESI-MS: m/z=524 (M+H)$^+$

R$_t$ (HPLC-MS): 3.20 min (method E)

Example 224

7-methoxy-3-(1-(6-(1'-methyl-2',3'-dihydro-1'H-spiro[cyclopentan-1,4'-isoquinolin]-2'-yl-carbonyl)-pyrimidin-4-yl)piperidin-4-yl)-4,5-dihydro-1H-benzo[d][1,3]diazepin-2(3H)-one

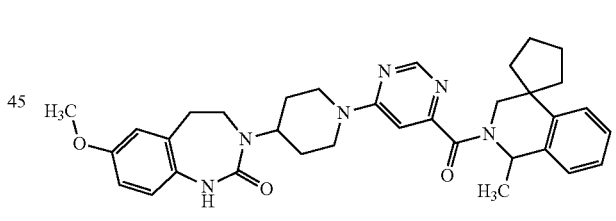

42 mg (0.11 mmol) 6-[4-(7-methoxy-2-oxo-1,2,4,5-tetrahydro-1,3-benzodiazepin-3-yl)-piperidin-1-yl]pyrimidine-4-carboxylic acid and 25 mg (0.11 mmol) 1'-methyl-2',3'-dihydro-1'H-spiro[cyclopentan-1,4'-isoquinoline hydrochloride in 63 µL (0.36 mmol) DIPEA and 1.0 mL DMF were combined with 39 mg (0.12 mmol) TBTU and the mixture was stirred overnight at RT. Then the reaction mixture was purified by preparative HPLC-MS. The product-containing fractions were combined and partially evaporated down. The precipitate formed was suction filtered and dried. The filtrate was freeze-dried. The residue remaining was identical to the precipitate.

Yield: 33 mg (54% of theory)

ESI-MS: m/z=581 (M+H)$^+$

R$_t$ (HPLC-MS): 1.74 min (method C)

Example 225

3-{1-[6-(2-hydroxymethyl-2,3-dihydro-indole-1-carbonyl)-pyrimidin-4-yl]-piperidin-4-yl}-7-methoxy-1,3,4,5-tetrahydro-benzo[d][1,3]diazepin-2-one

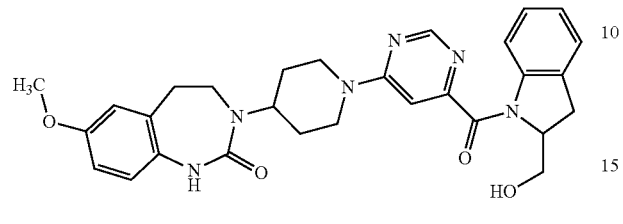

100 mg (0.25 mmol) 6-[4-(7-methoxy-2-oxo-1,2,4,5-tetrahydro-1,3-benzodiazepin-3-yl)-piperidin-1-yl]-pyrimidine-4-carboxylic acid and 45 mg (0.30 mmol) (2,3-dihydro-1H-indole-2-yl)-methanol in 50 µL (0.36 mmol) TEA and 0.90 mL DMF were combined with 85 mg (0.27 mmol) TBTU and stirred overnight at RT. Then the reaction mixture was purified by preparative HPLC-MS. The product-containing fractions were combined and partially evaporated down. The precipitate formed was suction filtered and dried.

Yield: 45 mg (30% of theory)
ESI-MS: m/z=529 (M+H)+
$R_t$ (HPLC-MS): 2.97 min (method E)

Example 226

3-{1-[6-(3,4-dihydro-1H-pyrrolo[1,2-a]pyrazine-2-carbonyl)-pyrimidin-4-yl]-piperidin-4-yl}-7-methoxy-1,3,4,5-tetrahydro-benzo[d][1,3]diazepin-2-one

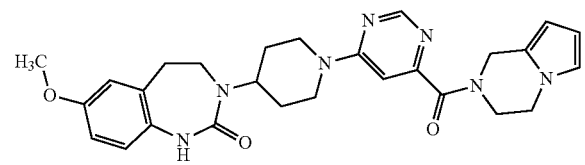 [SMILES: COc1ccc2c(c1)CCN(C1CCN(c3cc(C(=O)N4CCn5cccc5C4)ncn3)CC1)C(=O)N2]

83 mg (0.21 mmol) 6-[4-(7-methoxy-2-oxo-1,2,4,5-tetrahydro-1,3-benzodiazepin-3-yl)-piperidin-1-yl]-pyrimidine-4-carboxylic acid and 37 mg (0.24 mmol) 1,2,3,4-tetrahydro-pyrrolo[1,2-a]pyrazine in 0.10 mL (0.72 mmol) TEA and 2.0 mL DMF were mixed with 77 mg (0.24 mmol) TBTU and the mixture was stirred overnight at RT. Then the reaction mixture was purified by preparative HPLC-MS. The product-containing fractions were combined, the acetonitrile was evaporated down and the residue was dried.

Yield: 43 mg (41% of theory)
ESI-MS: m/z=502 (M+H)+
$R_t$ (HPLC-MS): 1.32 min (method C)

Example 227

1-{1-[6-(5-hydroxymethyl-4.7-dihydro-5H-thieno[2,3-c]pyridin-6-carbonyl)-pyrimidin-4-yl]-piperidin-4-yl}-1,3-dihydro-imidazo[4,5-b]pyridin-2-one

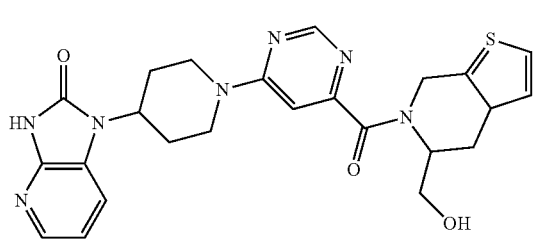

85 mg (0.25 mmol) 6-[4-(2-oxo-2,3-dihydroimidazo[4,5-b]pyridin-1-yl)-piperidin-1-yl]-pyrimidine-4-carboxylic acid and 50 mg (0.32 mmol) (4,5,6,7-tetrahydro-thieno[2,3-c]pyridin-5-yl)-methanol in 50 µL (0.36 mmol) TEA and 0.90 mL DMF were combined with 80 mg (0.25 mmol) TBTU and the mixture was stirred for 5 h at RT. Then the reaction mixture was purified by preparative HPLC-MS. The product-containing fractions were combined and freeze-dried.

Yield: 25 mg (20% of theory)
ESI-MS: m/z=492 (M+H)+
$R_t$ (HPLC-MS): 1.12 min (method C)

Example 228

6-[4-(2-oxo-2,3-dihydro-imidazo[4,5-b]pyridin-1-yl)-piperidin-1-yl]-pyrimidine-4-carboxylic acid(1H-indazol-4-yl)-amide

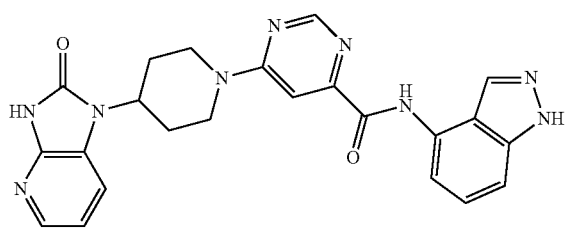 [SMILES: O=C(Nc1cccc2[nH]ncc12)c1cc(N2CCC(n3c(=O)[nH]c4ncccc43)CC2)ncn1]

100 mg (0.29 mmol) 6-[4-(2-oxo-2,3-dihydroimidazo[4,5-b]pyridin-1-yl)-piperidin-1-yl]-pyrimidine-4-carboxylic acid and 39 mg (0.29 mmol) 1H-indazole-4-ylamine in 87 mL (0.62 mmol) TEA and 1.5 mL DMF were combined with 104 mg (0.32 mmol) TBTU and stirred overnight at RT. Then the reaction mixture was purified by preparative HPLC-MS. The product-containing fractions were combined and freeze-dried.

Yield: 6 mg (5% of theory)
ESI-MS: m/z=456 (M+H)+
$R_t$ (HPLC-MS): 1.10 min (method C)

Example 229

1-{1-[6-(2-hydroxymethyl-2,3-dihydro-indole-1-carbonyl)-pyrimidin-4-yl]-piperidin-4-yl}-1,3-dihydro-imidazo[4,5-b]pyridin-2-one

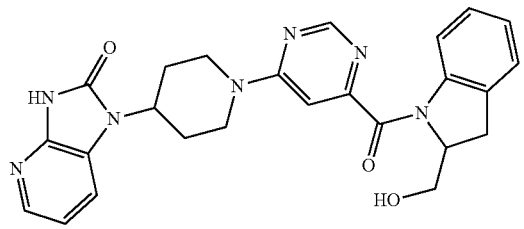 [SMILES: O=C(c1cc(N2CCC(n3c(=O)[nH]c4ncccc43)CC2)ncn1)N1c2ccccc2CC1CO]

85 mg (0.25 mmol) 6-[4-(2-oxo-2,3-dihydroimidazo[4,5-b]pyridin-1-yl)-piperidin-1-yl]-pyrimidine-4-carboxylic acid and 45 mg (0.30 mmol) (2,3-dihydro-1H-indol-2-yl)-methanol in 50 μL (0.36 mmol) TEA and 0.90 mL DMF were combined with 85 mg (0.27 mmol) TBTU and stirred overnight at RT. Then the reaction mixture was purified by preparative HPLC-MS. The product-containing fractions were combined and freeze-dried.

Yield: 36 mg (29% of theory)

ESI-MS: m/z=472 (M+H)$^+$ $R_t$ (HPLC-MS): 2.44 min (method E)

Example 230

3-(1-{6-[2-(3,5-difluoro-phenyl)-5,5-dimethyl-piperidine-1-carbonyl]-pyrimidin-4-yl}-piperidin-4-yl)-7-methoxy-1,3,4,5-tetrahydro-benzo[d][1,3]diazepin-2-one

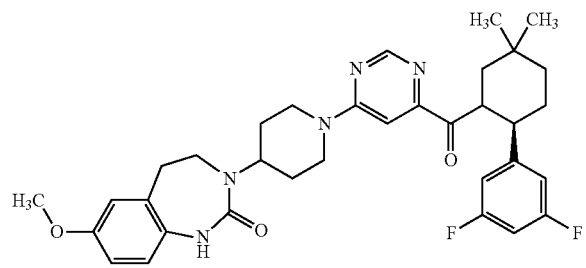 [SMILES: COc1ccc2c(c1)CCN(C1CCN(c3cc(C(=O)C4CC(C)(C)CC[C@H]4c4cc(F)cc(F)c4)ncn3)CC1)C(=O)N2]

65 mg (0.16 mmol) 6-[4-(7-methoxy-2-oxo-1,2,4,5-tetrahydro-1,3-benzodiazepin-3-yl)-piperidin-1-yl]-pyrimidine-4-carboxylic acid and 70 mg (0.16 mmol) (S)-2-(3,5-difluorophenyl)-5,5-dimethylpiperidine in 0.04 mL (0.72 mmol) DIPEA and 0.80 mL DMF were combined with 65 mg (0.17 mmol) HATU and stirred overnight at RT. Then the reaction mixture was purified by preparative HPLC-MS. The product-containing fractions were combined and freeze-dried.

Yield: 40 mg (43% of theory)

ESI-MS: m/z=605 (M+H)$^+$

Example 231

3-(1-(6-(1,4,5,6,7,8-hexahydropyrazolo[4,3-d]azepine-6-carbonyl)pyrimidin-4-yl)piperidin-4-yl)-7-methoxy-4,5-dihydro-1H-benzo[d][1,3]diazepin-2(3H)-one

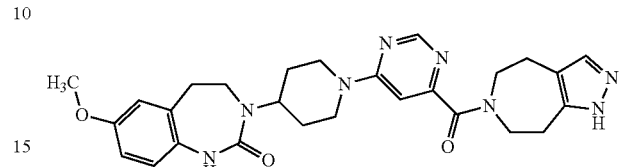

65 mg (0.16 mmol) 6-[4-(7-methoxy-2-oxo-1,2,4,5-tetrahydro-1,3-benzodiazepin-3-yl)-piperidin-1-yl]-pyrimidine-4-carboxylic acid and 35 mg (0.20 mmol) 1,4,5,6,7,8-hexahydro-pyrazolo[4,3-d]azepine hydrochloride in 80 μL (0.57 mmol) TEA and 0.80 mL DMF were combined with 68 mg (0.18 mmol) HATU and the mixture was stirred overnight at RT. Then the reaction mixture was purified twice by preparative HPLC-MS. The product-containing fractions were combined and freeze-dried.

Yield: 21 mg (25% of theory)

ESI-MS: m/z=517 (M+H)$^+$ $R_t$ (HPLC-MS): 3.29 min (method B)

Example 232

7-methoxy-3-{1-[6-(6-methoxy-2,3-dihydro-indole-1-carbonyl)-pyrimidin-4-yl]-piperidin-4-yl}-1,3,4,5-tetrahydro-benzo[d][1,3]diazepin-2-one

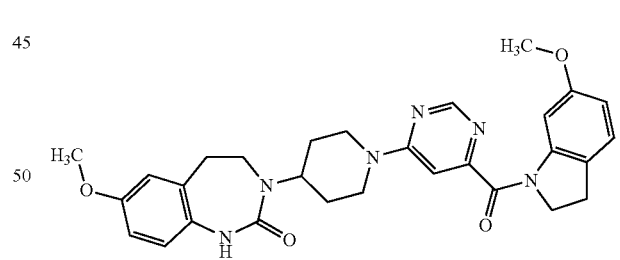

80 mg (0.20 mmol) 6-[4-(7-methoxy-2-oxo-1,2,4,5-tetrahydro-1,3-benzodiazepin-3-yl)-piperidin-1-yl]pyrimidine-4-carboxylic acid and 30 mg (0.20 mmol) 6-methoxy-2,3-dihydro-1H-indole in 50 μL (0.36 mmol) TEA and 1.5 mL DMF were combined with 70 mg (0.22 mmol) TBTU and the mixture was stirred for 1 h at RT. Then the reaction mixture was purified by preparative HPLC-MS. The product-containing fractions were combined and freeze-dried.

Yield: 35 mg (33% of theory)

ESI-MS: m/z=529 (M+H)$^+$ $R_t$ (HPLC-MS): 1.55 min (method C)

Example 233

6-[4-(2-oxo-2,3-dihydro-imidazo[4,5-b]pyridin-1-yl)-piperidin-1-yl]-pyrimidine-4-carboxylic acid(1H-indazol-5-yl)-amide

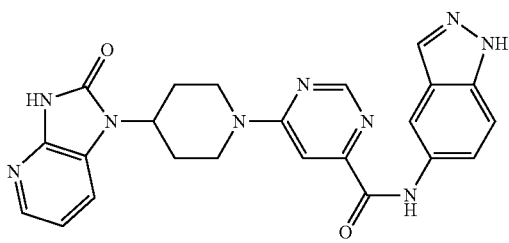 [SMILES: O=C(Nc1ccc2[nH]ncc2c1)c1cc(N2CCC(n3c(=O)[nH]c4ncccc43)CC2)ncn1]

100 mg (0.29 mmol) 6-[4-(2-oxo-2,3-dihydroimidazo[4,5-b]pyridin-1-yl)-piperidin-1-yl]-pyrimidine-4-carboxylic acid and 39 mg (0.29 mmol) 5-aminobenzopyrrazole in 87 µL (0.62 mmol) TEA and 1.5 mL DMF were combined with 104 mg (0.32 mmol) TBTU and the mixture was stirred overnight at RT. Then the reaction mixture was purified by preparative HPLC-MS. The product-containing fractions were combined and freeze-dried.

Yield: 45 mg (34% of theory)

ESI-MS: m/z=456 (M+H)$^+$ $R_t$ (HPLC-MS): 1.18 min (method ?)

Example 234

3-{1-[6-(2-ethyl-2,3-dihydro-indole-1-carbonyl)-pyrimidin-4-yl]-piperidin-4-yl}-7-methoxy-1,3,4,5-tetrahydro-benzo[d][1,3]diazepin-2-one

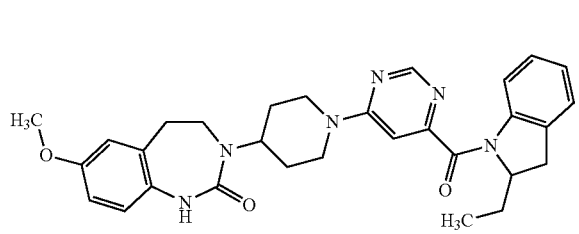 [SMILES: CCC1Cc2ccccc2N1C(=O)c1cc(N2CCC(N3CCc4cc(OC)ccc4NC3=O)CC2)ncn1]

110 mg (0.40 mmol) 7-methoxy-3-piperidin-4-yl-1,3,4,5-tetrahydro-1,3-benzodiazepin-2-one, 103 mg (0.36 mmol) (6-chloro-pyrimidin-4-yl)-(2-ethyl-2,3-dihydro-indol-1-yl)-methanone and 0.14 mL (0.80 mmol) DIPEA in 3.0 mL DMF were stirred overnight at RT. Then the reaction mixture was purified by preparative HPLC-MS. The product-containing fractions were combined, the organic solvent was evaporated down and the residue was neutralised with 1N aqueous sodium hydroxide solution. The precipitate formed was suction filtered, washed with water and dried under HV.

Yield: 110 mg (52% of theory)

ESI-MS: m/z=527 (M+H)$^+$ $R_t$ (HPLC-MS): 1.62 min (method C)

Example 235

6-[4-(7-methoxy-2-oxo-1,2,4,5-tetrahydro-benzo[d][1,3]diazepin-3-yl)-piperidin-1-yl]-pyrimidine-4-carboxylic acid(7-methyl-1H-indazol-5-yl)-amide

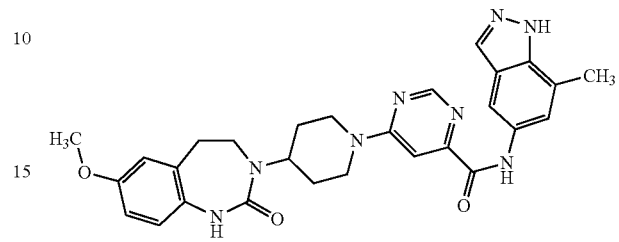

100 mg (0.25 mmol) 6-[4-(7-methoxy-2-oxo-1,2,4,5-tetrahydro-1,3-benzodiazepin-3-yl)-piperidin-1-yl]-pyrimidine-4-carboxylic acid and 37 mg (0.25 mmol) 7-methyl-1H-indazol-5-amine in 74 µL (0.53 mmol) TEA and 1.5 mL DMF were combined with 89 mg (0.28 mmol) TBTU and stirred overnight at RT. Then the reaction mixture was purified by preparative HPLC-MS. The product-containing fractions were combined and freeze-dried.

Yield: 7 mg (5% of theory)

ESI-MS: m/z=527 (M+H)$^+$ $R_t$ (HPLC-MS): 2.07 min (method S)

Example 236

7-methoxy-3-{1-[6-(5-oxo-octahydro-pyrrolo[3,2-b]pyridine-1-carbonyl)-pyrimidin-4-yl]-piperidin-4-yl}-1,3,4,5-tetrahydro-benzo[d][1,3]diazepin-2-one

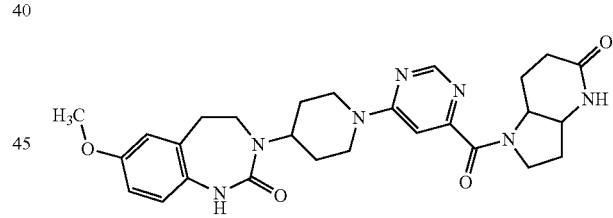

0.17 g (0.28 mmol) 3-{(1-[6-(5-benzyloxy-pyrrolo[3,2-b]pyridine-1-carbonyl)-pyrimidin-4-yl]-piperidin-4-yl}-7-methoxy-1,3,4,5-tetrahydro-benzo[d][1,3]diazepin-2-one and 50 mg palladium (Pd/C 5%) in 20 ml EtOH were hydrogenated for several hours at RT in a hydrogen atmosphere. As no reaction took place an additional 10 ml THF were added and hydrogenation was continued at 50° C. Then the catalyst was eliminated by suction filtering and the filtrate was evaporated down. The residue was purified by preparative HPLC-MS. The product-containing fractions were combined and freeze-dried.

Yield: 16 mg (11% of theory)

ESI-MS: m/z=520 (M+H)$^+$ $R_t$ (HPLC-MS): 2.17 min (method E)

The following Examples describe the preparation of pharmaceutical formulations that contain as active substance any desired compound of general formula I:

Example I

Capsules for Powder Inhalation Containing 1 Mg of Active Ingredient
Composition:
1 capsule for powder inhalation contains:

| active ingredient | 1.0 mg |
|---|---|
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient
Composition:
1 puff contains:

| active ingredient | 1.0 mg |
|---|---|
| benzalkonium chloride | 0.002 mg |
| disodium edetate | 0.0075 mg |
| purified water ad | 15.0 µl |

Method of Preparation:

The active ingredient and benzalkonium chloride are dissolved in water and transferred into Respimat® cartridges.

Example III

Inhalable Solution for Nebulisers Containing 1 mg of Active Ingredient
Composition:
1 vial contains:

| active ingredient | 0.1 g |
|---|---|
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient
Composition:
1 puff contains:

| active ingredient | 1.0 mg |
|---|---|
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient
Composition:

| active ingredient | 1.0 mg |
|---|---|
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml
Composition:

| active substance | 5 mg |
|---|---|
| glucose | 250 mg |
| human serum albumin | 10 mg |
| glycofurol | 250 mg |
| water for injections ad | 5 ml |

Preparation:

Glycofurol and glucose are dissolved in water for injections (WfI); human serum albumin is added; active ingredient is dissolved with heating; made up to specified volume with WfI; transferred into ampoules under nitrogen gas.

Example VII

Injectable Solution Containing 100 mg of Active Substance Per 20 ml
Composition:

| active substance | 100 mg |
|---|---|
| monopotassium dihydrogen phosphate = $KH_2PO_4$ | 12 mg |
| disodium hydrogen phosphate = $Na_2HPO_4 * 2H_2O$ | 2 mg |
| sodium chloride | 180 mg |
| human serum albumin | 50 mg |
| Polysorbate 80 | 20 mg |
| water for injections ad | 20 ml |

Preparation:

Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate Containing 10 mg of Active Substance

Composition:

| Active substance | 10 mg |
|---|---|
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:

Polysorbate 80 and mannitol are dissolved in water for injections (WfI); transferred into ampoules.

Example IX

Tablets Containing 20 mg of Active Substance

Composition:

| active substance | 20 mg |
|---|---|
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| active substance | 20 mg |
|---|---|
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| active substance | 50 mg |
|---|---|
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:

1. A compound of the formula I $$\text{(I)}$$

wherein $R^1$ denotes a group of general formula II $$\text{(II)}$$

wherein

G-L denotes N, N—$C(R^{5.1})_2$, C=$C(R^{5.1})$, C=N, $C(R^{5.1})$, $C(R^{5.1})$—$C(R^{5.1})_2$, $C(R^{5.1})$—$C(R^{5.1})_2$—$C(R^{5.1})_2$, C=$C(R^{5.1})$—$C(R^{5.1})_2$, $C(R^{5.1})$—$C(R^{5.1})$=$C(R^{5.1})$, $C(R^{5.1})$—$C(R^{5.1})_2$—$N(R^{5.2})$, C=$C(R^{5.1})$—$N(R^{5.2})$, $C(R^{5.1})$—$C(R^{5.1})$=N, $C(R^{5.1})$—$N(R^{5.2})$—$C(R^{5.1})_2$, C=N—$C(R^{5.1})_2$, $C(R^{5.1})$—N=$C(R^{5.1})$, $C(R^{5.1})$—N($R^{5.2}$)—$N(R^{5.2})$, C=N—$N(R^{5.2})$, N—$C(R^{5.1})_2$—$C(R^{5.1})_2$, N—$C(R^{5.1})$=$C(R^{5.1})$, N—$C(R^{5.1})_2$—$N(R^{5.2})$, N—$C(R^{5.1})$=N, N—$N(R^{5.2})$—$C(R^{5.1})_2$ or N—N=C($R^{5.1}$), Q-T denotes $C(R^6)_2$—$C(R^6)_2$, $C(R^6)$=$C(R^6)$, N=$C(R^6)$, $C(R^6)_2$—C(=O), C(=O)—$C(R^6)_2$, $C(R^6)_2$—$S(O)_m$ or $C(R^6)_2$—$N(R_6)$, while a group $C(R^6)_2$ contained in Q-T may also denote a cyclic group that is selected from among $C_{3-6}$-cycloalkyl, $C_{5-6}$-cycloalkenyl or heterocyclyl, or in a group $C(R^6)_2$—$C(R^6)_2$, $C(R^6)$=$C(R^6)$ or $C(R^6)_2$—$N(R^6)$ contained in Q-T in each case a group $R^6$ together with an adjacent group $R^6$ and the atoms to which these groups are attached may also denote a $C_{3-6}$-cycloalkyl, $C_{5-6}$-cycloalkenyl, heterocyclyl-, aryl- or heteroaryl group which may be substituted independently of one another by 1, 2 or 3 substituents $R^{6.1}$, $R^2$ denotes
(a) H,
(b) F, —CN, $C_{1-3}$-alkyl, —$CO_2$—$R^{2.1}$ or
(c) a $C_{1-3}$-alkyl group wherein each methylene group is substituted by up to two fluorine atoms and each methyl group is substituted by up to three fluorine atoms, R2.1 denotes H or $C_{1-6}$-alkyl, $R^3$ denotes
(a) H,
(b) $C_{1-6}$-alkylene-$R^{3.1}$,
(c) a $C_{3-6}$-cycloalkyl group substituted by one or two groups $R^{3.2}$,
(d) a $C_{5-7}$-cycloalkenyl group substituted by one or two groups $R^{3.2}$,
(e) an aryl group substituted by one or two groups $R^{3.2}$,
(f) a heterocyclyl group substituted by one or two groups $R^{3.2}$,
(g) a $C_{5-7}$-cycloalkyl group which may be fused to an aryl or heteroaryl group and is additionally substituted by one or two groups $R^{3.2}$,
(h) a heteroaryl group substituted by one or two groups $R_{3.2}$,
(i) a $C_{1-3}$-alkyl group wherein each methylene group is substituted by up to two fluorine atoms and each methyl group is substituted by up to three fluorine atoms, $R^{3.1}$ denotes
(a) H,
(b) an aryl group substituted by the groups $R^{3.1.1}$ and $R^{3.1.2}$,
(c) a heteroaryl group substituted by the groups $R^{3.1.1}$ and $R^{3.1.2}$, $R^{3.1.1}$ denotes
(a) H,
(b) halogen, $C_{1-3}$-alkyl, —OH, —CN, —O—$C_{1-3}$-alkyl, —O—C(O)—$C_{1-3}$-alkyl, —$NR^{3.1.1.1}R^{3.1.1.2}$, —$S(O)_m$—$C_{1-3}$-alkyl, —$NR^{3.1.1,1}$—C(O)—$C_{1-3}$-alkyl, —C(O)—$NR^{3.1.1.1}R^{3.1.1.2}$, —C(O)—O—$R^{3.1.1.3}$, —$NR^{3.1.1,1}$—C(O)—O—$C_{1-3}$-alkyl, —O—C(O)—$NR^{3.1.1.1}R^{3.1.1.2}$,
(c) a $C_{1-3}$-alkyl- or —O—$C_{1-3}$-alkyl group wherein each methylene group is substituted by up to two fluorine atoms and each methyl group is substituted by up to three fluorine atoms, $R^{3.1.1.1}$ denotes H, $C_{1-3}$-alkyl and
$R^{3.1.1.2}$ denotes H, $C_{1-3}$-alkyl, or
$R^{3.1.1.1}$ and $R^{3.1.1.2}$ together with the nitrogen atom to which they are bound also denote a group selected from among morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{3.1.1.3}$ denotes H, $C_{1-3}$-alkyl, R3.1.2 denotes
(a) H,
(b) halogen, $C_{1-3}$-alkyl, —OH, —CN, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, or $R^{3.2}$ independently of one another denote
(a) H,
(b) halogen, $C_{1-3}$-alkyl, —OH, —CN, —O—$C_{1-3}$-alkyl, —O—C(O)—$C_{1-3}$-alkyl, —$NR^{3.2.1}R^{3.2.2}$, —$S(O)_m$—$C_{1-3}$-alkyl, —$NR^{3.2.1}$—C(O)—$C_{1-3}$-alkyl, —C(O)—$NR^{3.2.1}R^{3.2.2}$, —C(O)—O—$R^{3.2.3}$, —$NR^{3.2.1}$—C(O)—O—$C_{1-3}$-alkyl, —O—C(O)—$NR^{3.2.1}R^{3.2.2}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{3.2.1}$ denotes H, $C_{1-3}$-alkyl and
$R^{3.2.2}$ denotes H, $C_{1-3}$-alkyl, or
$R^{3.2.1}$ and $R^{3.2.2}$ together with the nitrogen atom to which they are bound also denote a group selected from among morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —$OCF_3$, $C_{1-3}$-alkyl and $CF_3$, $R^{3.2.3}$ denotes H, $C_{1-3}$-alkyl, $R^4$ denotes
(a) H,
(b) $C_{1-6}$-alkylene-$R^{4.1}$,
(c) a $C_{3-6}$-cycloalkyl group substituted by one or two groups $R^{4.2}$,
(d) a $C_{5-7}$-cycloalkenyl group substituted by one or two groups $R^{4.2}$,
(e) an aryl group substituted by one or two groups $R^{4.2}$,
(f) a heterocyclyl group substituted by one or two groups $R^{4.2}$,
(g) a $C_{5-7}$-cycloalkyl group which may be fused to an aryl or heteroaryl group and is additionally substituted by one or two groups $R^{4.2}$,
(h) a heteroaryl group substituted by one or two groups $R^{4.2}$,
(i) a $C_{1-3}$-alkyl group wherein each methylene group is substituted by up to two fluorine atoms and each methyl group is substituted by up to three fluorine atoms, $R^{4.1}$ denotes
(a) H,
(b) an aryl group substituted by the groups $R^{4.1.1}$ and $R^{4.1.2}$,
(c) a heteroaryl group substituted by the groups $R^{4.1.1}$ and $R^{4.1.2}$, $R^{4.1.1}$ denotes
(a) H,
(b) halogen, $C_{1-3}$-alkyl, —OH, —CN, —O—$C_{1-3}$-alkyl, —O—C(O)—$C_{1-3}$-alkyl, —$NR^{4.1.1.1}R^{4.1.1.2}$, —$S(O)_m$—$C_{1-3}$-alkyl, —$NR^{4.1.1,1}$—C(O)—$C_{1-3}$-alkyl, —C(O)—$NR^{4.1.1.1}R^{4.1.1.2}$, —C(O)—O—$R^{4.1.1.3}$, —$NR^{4.1.1,1}$—C(O)—O—$C_{1-3}$-alkyl, —O—C(O)—$NR^{4.1.1.1}R^{4.1.1.2}$, (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl and $R^{4.1.1.2}$ denotes H, $C_{1-3}$-alkyl, or $R^{4.1.1.1}$ and $R^{4.1.1.2}$ together with the nitrogen atom to which they are bound also denote a group selected from among morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{4.1.1.3}$ denotes H, $C_{1-3}$-alkyl, $R^{4.1.2}$ denotes
  (a) H,
  (b) halogen, $C_{1-3}$-alkyl, —OH, —CN, —O—$C_{1-3}$-alkyl,
  (c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ independently of one another denote
  (a) H,
  (b) halogen, $C_{1-3}$-alkyl, —OH, —CN, —O—$C_{1-3}$-alkyl, —O—C(O)—$C_{1-3}$-alkyl, —NR$^{4.2.1}$R$^{4.2.2}$, —S(O)$_m$—$C_{1-3}$-alkyl, —NR$^{4.2.1}$—C(O)—$C_{1-3}$-alkyl, —C(O)—NR$^{4.2.1}$R$^{4.2.2}$, —C(O)—O—R$^{4.2.3}$, —NR$^{4.2.1}$—C(O)—O—$C_{1-3}$-alkyl, —O—C(O)—NR$^{4.2.1}$R$^{4.2.2}$,
  (c) a $C_{1-3}$-alkyl- or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and $R^{4.2.2}$ denotes H, $C_{1-3}$-alkyl, or $R^{4.2.1}$ and $R^{4.2.1}$ together with the nitrogen atom to which they are bound also denote a group selected from among morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{4.2.3}$ denotes H, $C_{1-3}$-alkyl, $R^3$ and $R^4$ together with the nitrogen atom to which they are bound denote:
  (a) a saturated 5-, 6- or 7-membered heterocyclic group which is substituted at a carbon atom by a group $R^{4.3}$ or by two groups $R^{4.3}$ and $R^{4.4}$,
  (b) a saturated 5-, 6- or 7-membered heterocyclic group which is substituted at two adjacent carbon atoms by a group $R^{4.3}$ and $R^{4.4}$ in each case,
  (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocyclyl group is substituted by 1, 2 or 3 groups $R^{4.5}$,
  (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
  (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
  (f) a heteroaryl group which is substituted at 1, 2 or 3 carbon atoms by a group $R^{4.5}$ in each case, $R^{4.3}$ independently of one another denote
  (a) H, $C_{1-3}$-alkyl, $C_{2-4}$-alkenyl, $C_{2-6}$-alkynyl, aryl, —$C_{1-3}$-alkylene-$R^{4.3.1}$, $C_{1-3}$-alkyl-O—C(O)—, HO—C(O)—, F, —O—$C_{1-3}$-alkyl, —OH, —CN,
  (b) a $C_{1-3}$-alkyl- or —O—$C_{1-3}$-alkyl group wherein each methylene group is substituted by up to two fluorine atoms and each methyl group is substituted by up to three fluorine atoms,
  (c) a 5- or 6-membered heteroaryl group,
  (d) aryl, $R^{4.3.1}$ denotes H, HO, $C_{1-3}$-alkyl-O—, $C_{1-3}$-alkyl-O—C(O)—, CN, —NH$_2$, ($C_{1-4}$-alkyl)-NH—, ($C_{1-4}$-alkyl)$_2$N—, $C_{3-6}$-cycloalkyl-, heterocyclyl, heteroaryl, aryl, $R^{4.4}$ denotes
  (a) H, $C_{1-3}$-alkyl, —OH, —O—$C_{1-3}$-alkyl or
  (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached may also denote a $C_{3-6}$-cycloalkyl, $C_{5-6}$-cycloalkenyl or heterocyclyl group, $R^{4.5}$ independently of one another denote
  (a) H,
  (b) halogen, $C_{1-3}$-alkyl, —OH, —O—$C_{1-3}$-alkyl, —S(O)$_m$—$C_{1-3}$-alkyl, —NR$^{4.5.2}$R$^{4.5.3}$, —CN, —C(O)—O—R$^{4.5.1}$, —C(O)—NR$^{4.5.2}$R$^{4.5.3}$,
  (c) a $C_{1-3}$-alkyl- or —O—$C_{1-3}$-alkyl group wherein each methylene group is substituted by up to two fluorine atoms and each methyl group is substituted by up to three fluorine atoms,
  (d) aryl, heteroaryl, $R^{4.5.1}$ denotes H, $C_{1-3}$-alkyl, $R^{4.5.2}$ denotes H, $C_{1-3}$-alkyl, $R^{4.5.3}$ denotes H, $C_{1-3}$-alkyl, or $R^{4.5.2}$ and $R^{4.5.3}$ together with the nitrogen atom to which they are bound also denote a group selected from among morpholinyl, thiomorpholinyl, piperidinyl, piperidonyl, piperazinyl, pyrrolidinyl and azetidinyl, while the group may additionally be substituted by one or two substituents selected from F, —OH, —O—$C_{1-3}$-alkyl, —OCF$_3$, $C_{1-3}$-alkyl and CF$_3$, $R^{5.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms, $R^{5.2}$ denotes H or $C_{1-6}$-alkyl, $R^6$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{6.2}$, wherein the substituents $R^{6.2}$ may be identical or different,
  (c) a heteroaryl group optionally substituted by 1, 2 or 3 substituents $R^{6.2}$, wherein the substituents $R^{6.2}$ may be identical or different,
  (d) a heterocyclic group optionally substituted by 1, 2 or 3 substituents $R^{6.2}$, wherein the substituents $R^{6.2}$ may be identical or different, $R^{6.1}$ denotes
(a) H, halogen, $C_{1-6}$-alkyl, $C_{3-6}$-cycloalkyl,
(b) —O—$C_{1-6}$-alkylene -$NR^8R^9$, —O—$R^7$, —O—$(CH_2)_s$—O—$R^7$, —$CO_2$—$R^7$, —C(O)—$NR^8R^9$, —O—C(O)—$NR^8R^9$, —$NR^7$—C(O)—$NR^8R^9$, —$NR^8$—C(O)—$R^9$, —$NR^8$—C(O)—O—$R^9$, —$SO_2$—$NR^8R^9$, —$NR^8$—$SO_2$—$R^9$, —$S(O)_m$—$R^8$, —CN, —$NR^8R^9$, —$NR^7$—C(O)—$NR^8R^9$, —O—C(O)—$R^7$,
(c) a $C_{1-3}$-alkyl- or $C_{1-3}$-alkyl-O— group wherein each methylene group is substituted by up to two fluorine atoms and each methyl group is substituted by up to three fluorine atoms,
(d) an aryl group substituted by 1, 2 or 3 substituents $R^7$, wherein the substituents $R^7$ may be identical or different,
(e) a heteroaryl group substituted by 1, 2 or 3 substituents $R^7$, wherein the substituents $R^7$ may be identical or different,
(f) a heterocyclic group substituted by 1, 2 or 3 substituents $R^7$, wherein the substituents $R^7$ may be identical or different, $R^{6.2}$ denotes
(a) halogen, $C_{1-6}$-alkyl, $C_{3-6}$-cycloalkyl,
(b) —O—$R^7$, —O—$(CH_2)_s$—O—$R^7$, —$CO_2R^7$, —C(O)—$NR^8R^9$, —O—(CO)—$NR^8R^9$, —$N(R^7)$—C(O)—$NR^8R^9$, —$N(R^8)$—C(O)—$R^9$, —$N(R^8)$—C(O)—O—$R^9$, —$SO_2$—$NR^8R^9$, —$N(R^8)$—$SO_2$—$R^9$, —$S(O)_m$—$R^8$, —CN, —$NR^8R^9$, —$N(R^7)$—C(O)—$NR^8R^9$, —O—C(O)—$R^7$ or
(c) a $C_{1-3}$-alkyl group wherein each methylene group is substituted by up to two fluorine atoms and each methyl group is substituted by up to three fluorine atoms, $R^7$ denotes
(a) H,
(b) $C_{1-6}$-alkyl, $C_{3-6}$-cycloalkyl, aryl, heteroaryl, benzyl which may be substituted by a group $R^{7.1}$, or
(c) a $C_{1-3}$-alkyl group wherein each methylene group is substituted by up to two fluorine atoms and each methyl group is substituted by up to three fluorine atoms, $R^{7.1}$ denotes halogen, HO— or $C_{1-6}$-alkyl-O—, $R^8$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^9$ denotes
(a) H,
(b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$ or fluorine, wherein the substituents $R^7$ are independent of one another, m denotes one of the numbers 0, 1 or 2,
s denotes one of the numbers 1, 2 or 3,
U denotes N,
V denotes C—$R^{11}$,
X denotes N,
Y denotes C—$R^{13}$,
$R^{11}$ denotes H, Cl, $C_{1-3}$-alkyl, —$NR^{11.1}R^{11.2}$ or —O—$C_{1-3}$-alkyl,
$R^{11.1}$ denotes H or $C_{1-6}$-alkyl,
$R^{11.2}$ denotes H or —$SO_2$—$C_{1-3}$-alkyl,
$R^{13}$ denotes H, halogen or $C_{1-3}$-alkyl,
or a tautomer or salt thereof.

2. A compound of the formula I according to claim 1, wherein
$R^1$ denotes a group of general formula II

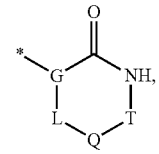

(II)

wherein
G-L denotes N, N—$C(R^{5.1})_2$, $C=C(R^{5.1})$, C=N, $C(R^{5.1})$, $C(R^{5.1})$—$C(R^{5.1})_2$, $C(R^{5.1})$—$C(R^{5.1})_2$—$C(R^{5.1})_2$, $C=C(R^{5.1})$—$C(R^{5.1})_2$, $C(R^{5.1})$—$C(R^{5.1})$=$C(R^{5.1})$, $C(R^{5.1})$—$C(R^{5.1})_2$—$N(R^{5.2})$, $C=C(R^{5.1})$—$N(R^{5.2})$, $C(R^{5.1})$—$C(R^{5.1})$=N, $C(R^{5.1})$—$N(R^{5.2})$—$C(R^{5.1})_2$, C=N—$C(R^{5.1})_2$, $C(R^{5.1})$—N=$C(R^{5.1})$, $C(R^{5.1})$—N$(R^{5.2})$—$N(R^{5.2})$, C=N—$N(R^{5.2})$, N—$C(R^{5.1})_2$—$C(R^{5.1})_2$, N—$C(R^{5.1})$=$C(R^{5.1})$, N—$C(R^{5.1})_2$—$N(R^{5.2})$, N—$C(R^{5.1})$=N, N—$N(R^{5.2})$—$C(R^{5.1})_2$ or N—N=$C(R^{5.1})$, Q-T denotes $C(R^6)_2$—$C(R^6)_2$, $C(R^6)$=$C(R^6)$, N=$C(R^6)$, $C(R^6)_2$—C(=O), C(=O)—$C(R^6)_2$, $C(R^6)_2$—$S(O)_m$ or $C(R^6)_2$—$N(R^6)$, while a $C(R^6)_2$ contained in Q-T group may also denote a cyclic group that is selected from among cyclobutyl, cyclopentyl, cyclohexyl, cyclopentenyl, cyclohexenyl, dioxanyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl and piperazinyl, or in a group $C(R^6)^2$-$C(R^6)_2$, $C(R^6)$=$C(R^6)$ or $C(R^6)_2$—N$(R^6)$ contained in Q-T in each case a group $R^6$ together with an adjacent group $R^6$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, 1H-quinolinyl-2-on, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{6.1}$, $R^{5.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms,
$R^{5.2}$ denotes H or $C_{1-6}$-alkyl,
$R^6$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{6.2}$, wherein the substituents $R^{6.2}$ may be identical or different,
  (c) a heteroaryl group optionally substituted by 1, 2 or 3 substituents $R^{6.2}$, wherein the substituents $R^{6.2}$ may be identical or different,
  (d) a heterocyclic group optionally substituted by 1, 2 or 3 substituents $R^{6.2}$, wherein the substituents $R^{6.2}$ may be identical or different,
$R^{6.1}$ denotes
  (a) H, halogen, $C_{1-6}$-alkyl, $C_{3-6}$-cycloalkyl,
  (b) —O—$C_{1-6}$-alkylene-$NR^8R^9$, —O—$R^7$, —O—$(CH_2)_s$—O—$R^7$, —$CO_2$—$R^7$, $C(O)$—$NR^8R^9$, —O—$C(O)$—$NR^8R^9$, —$NR^7$—$C(O)$—$NR^8R^9$, —$NR^8$—$C(O)$—$R^9$, —$NR^8$—$C(O)$—O—$R^9$, —$SO_2$—$NR^8R^9$, —$NR^8$—$SO_2$—$R^9$, —$S(O)_m$—$R^8$, —CN, —$NR^8R^9$, —$NR^7$—$C(O)$—$NR^8R^9$, —O—$C(O)$—$R^7$,
  (c) a $C_{1-3}$-alkyl or $C_{1-3}$-alkyl-O— group wherein each methylene group is substituted by up to two fluorine atoms and each methyl group is substituted by up to three fluorine atoms,
  (d) an aryl group with 1, 2 or 3 substituents $R^7$, wherein the substituents $R^7$ may be identical or different,
  (e) a heteroaryl group substituted by 1, 2 or 3 substituents $R^7$, wherein the substituents $R^7$ may be identical or different,
  (f) a heterocyclic group substituted by 1, 2 or 3 substituents $R^7$, wherein the substituents $R^7$ may be identical or different,
R6.2 denotes
  (a) halogen, $C_{1-6}$-alkyl, $C_{3-6}$-cycloalkyl,
  (b) —O—$R^7$, —O—$(CH_2)_s$—O—$R^7$, —$CO_2R^7$, —$C(O)$—$NR^8R^9$, —O—$(CO)$—$NR^8R^9$, —$N(R^7)$—$C(O)$—$NR^8R^9$, —$N(R^8)$—$C(O)$—$R^9$, —$N(R^8)$—$C(O)$—O—$R^9$, —$SO_2$—$NR^8R^9$, —$N(R^8)$—$SO_2$—$R^9$, —$S(O)_m$—$R^8$, CN, $NR^8R^9$, —$N(R^7)$—$C(O)$—$NR^8R^9$, —O—$C(O)$—$R^7$ or
  (c) a $C_{1-3}$-alkyl group wherein each methylene group is substituted by up to two fluorine atoms and each methyl group is substituted by up to three fluorine atoms,
$R^7$ denotes
  (a) H,
  (b) $C_{1-6}$-alkyl, $C_{3-6}$-cycloalkyl, aryl, heteroaryl, benzyl which may be substituted by a group $R^{7.1}$, or
  (c) a $C_{1-3}$-alkyl group wherein each methylene group is substituted by up to two fluorine atoms and each methyl group is substituted by up to three fluorine atoms,
$R^{7.1}$ denotes halogen, HO- or $C_{1-6}$-alkyl-O—,
$R^8$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms,
$R^9$ denotes
  (a) H,
  (b) $C_{1-6}$-alkyl, $C_{3-6}$-cycloalkyl, aryl, heteroaryl or benzyl, wherein the groups may be unsubstituted or substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or
$R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$ or fluorine, wherein the substituents $R^7$ are independent of one another,
m denotes one of the numbers 0, 1 or 2 and
s denotes one of the numbers 1, 2 or 3,
or a tautomer or salt thereof.

3. A compound of the formula I according to claim 1, wherein
$R^1$ denotes a group of general formulae

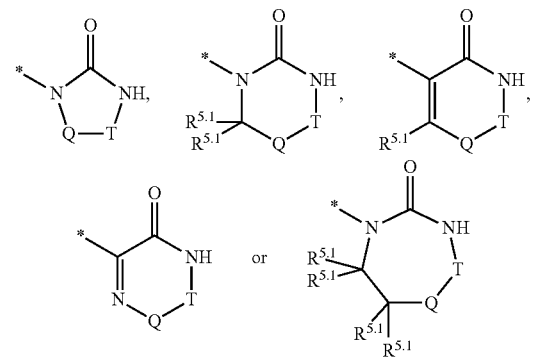

wherein
Q-T denote $C(R^6)_2$—$C(R^6)_2$, $C(R^6)$=$C(R^6)$, N=$C(R^6)$, $C(R^6)_2$—$C$(=O), $C$(=O)—$C(R^6)_2$, $C(R^6)_2$—$S(O)_m$ or $C(R^6)_2$—$N(R^6)$,
  while in a group $C(R^6)_2$—$C(R^6)_2$, $C(R^6)$=$C(R^6)$ or $C(R^6)_2$—$N(R^6)$ contained in Q-T in each case a group $R^6$ together with an adjacent group $R^6$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholinyl-S-oxide, thiomorpholinyl-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents R6.1,
$R^{5.1}$ denotes
  (a) H,
  (b) $C_{1-6}$-alkyl, —CN, —OH, —O—$C_{1-3}$-alkyl, (c) a $C_{1-3}$-alkyl- or $C_{1-3}$-alkyl-O— group wherein each methylene group is substituted by up to two fluorine atoms and each methyl group is substituted by up to three fluorine atoms, $R^6$ independently of one another denote
(a) H, $C_{1-6}$-alkyl, $C_{2-6}$-alkenyl, $C_{2-6}$-alkynyl, $C_{3-6}$-cycloalkyl,
(b) an aryl group optionally substituted by 1, 2 or 3 substituents $R^{6.2}$, wherein the substituents $R^{6.2}$ may be identical or different,
(c) a heteroaryl group optionally substituted by 1, 2 or 3 substituents $R^{6.2}$, wherein the substituents $R^{6.2}$ may be identical or different,
(d) a heterocyclic group optionally substituted by 1, 2 or 3 substituents $R^{6.2}$, wherein the substituents $R^{6.2}$ may be identical or different, $R^{6.1}$ denotes
(a) H, halogen, $C_{1-6}$-alkyl, $C_{3-6}$-cycloalkyl,
(b) —O—$C_{1-6}$-alkylene-$NR^8R^9$, —O—$R^7$, —$CO_2R^7$, —C(O)$NR^8R^9$, —$SO_2$—$NR^8R^9$, —N($R^8$)—$SO_2$—$R^9$, —S(O)$_m$—$R^8$, —CN, —$NR^8R^9$, —O—C(O)—$R^7$ or
(c) a $C_{1-3}$-alkyl group wherein each methylene group is substituted by up to two fluorine atoms and each methyl group is substituted by up to three fluorine atoms, $R^{6.2}$ denotes
(a) halogen, $C_{1-6}$-alkyl, $C_{3-6}$-cycloalkyl,
(b) —O—$R^7$, —O—(CH$_2$)$_s$—O—$R^7$, —$CO_2R^7$, —S(O)$_m$—$R^8$, —CN, —O—C(O)—$R^7$ or
(c) a $C_{1-3}$-alkyl group wherein each methylene group is substituted by up to two fluorine atoms and each methyl group is substituted by up to three fluorine atoms, $R^7$ denotes
(a) H,
(b) $C_{1-6}$-alkyl, $C_{3-6}$-cycloalkyl, aryl, heteroaryl, benzyl which may be substituted by a group $R^{7.1}$, or
(c) a $C_{1-3}$-alkyl group wherein each methylene group is substituted by up to two fluorine atoms and each methyl group is substituted by up to three fluorine atoms, $R^{7.1}$ denotes halogen, HO— or $C_{1-6}$-alkyl-O—, $R^8$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^9$ denotes
(a) H,
(b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$, wherein the substituents $R^7$ are independent of one another, m denotes one of the numbers 0, 1 or 2 and
s denotes one of the numbers 1, 2 or 3,
or a tautomer or salt thereof.

4. A compound of the formula I according to claim 1, wherein
$R^1$ denotes a group of general formulae

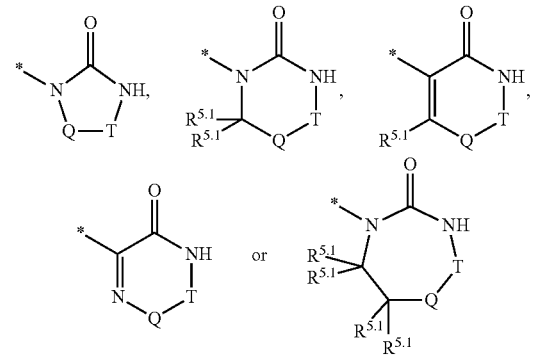

wherein
Q-T denotes C($R^6$)$_2$—C($R^6$)$_2$, C($R^6$)=C($R^6$), N=C($R^6$), C($R^6$)$_2$—C(=O), C(=O)—C($R^6$)$_2$, C($R^6$)$_2$—S(O)$_m$ or C($R^6$)$_2$—N($R^6$),
while in a group C($R^6$)$_2$—C($R^6$)$_2$, C($R^6$)=C($R^6$) or C($R^6$)$_2$—N($R^6$) contained in Q-T in each case a group $R^6$ together with an adjacent group $R^6$ and the atoms to which these groups are attached may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another by 1, 2 or 3 substituents $R^{6.1}$, $R^{5.1}$ denotes
(a) H,
(b) $C_{1-6}$-alkyl, —CN, —OH, —O—$C_{1-3}$-alkyl,
(c) a $C_{1-3}$-alkyl or $C_{1-3}$-alkyl-O— group wherein each methylene group is substituted by up to two fluorine atoms and each methyl group is substituted by up to three fluorine atoms, $R^6$ denotes
(a) H, $C_{1-6}$-alkyl, $C_{3-6}$-cycloalkyl,
(b) an aryl group optionally substituted by 1, 2 or 3 substituents $R^{6.2}$, wherein the substituents $R^{6.2}$ may be identical or different,
(c) a heteroaryl group optionally substituted by 1, 2 or 3 substituents $R^{6.2}$, wherein the substituents $R^{6.2}$ may be identical or different,
(d) a heterocyclic group optionally substituted by 1, 2 or 3 substituents $R^{6.2}$, wherein the substituents $R^{6.2}$ may be identical or different, $R^{6.1}$ denotes
(a) H, halogen, $C_{1-6}$-alkyl, $C_{3-6}$-cycloalkyl,
(b) —O—$C_{1-6}$-alkylene-$NR^8R^9$, —O—$R^7$, —$CO_2R^7$, —C(O)—$NR^8R^9$, —$SO_2$—$NR^8R^9$, —$NR^8$—$SO_2$—$R^9$, —S(O)$_m$—$R^8$, —CN, —$NR^8R^9$, —O—C(O)—$R^7$ or
(c) a $C_{1-3}$-alkyl group wherein each methylene group is substituted by up to two fluorine atoms and each methyl group is substituted by up to three fluorine atoms, $R^{6.2}$ denotes (a) halogen, $C_{1-6}$-alkyl, $C_{3-6}$-cycloalkyl, (b) —O—$R^7$, —O—$(CH_2)_s$—$OR^7$, —$CO_2R^7$, —$S(O)_m$—$R^8$, —CN, —O—C(O)—$R^7$ or (c) a $C_{1-3}$-alkyl group wherein each methylene group is substituted by up to two fluorine atoms and each methyl group is substituted by up to three fluorine atoms, $R^7$ denotes (a) H, (b) $C_{1-6}$-alkyl, $C_{3-6}$-cycloalkyl, aryl, heteroaryl, benzyl which may be substituted by a group $R^{7.1}$, or (c) a $C_{1-3}$-alkyl group wherein each methylene group is substituted by up to two fluorine atoms and each methyl group is substituted by up to three fluorine atoms, $R^{7.1}$ denotes halogen, HO— or $C_{1-6}$-alkyl-O—, $R^8$ denotes (a) H, (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or (c) a $C_{1-3}$-alkyl group wherein each methylene group is substituted by up to two fluorine atoms and each methyl group is substituted by up to three fluorine atoms, $R^9$ denotes (a) H, (b) $C_{1-6}$-alkyl, $C_{3-6}$-cycloalkyl, aryl, heteroaryl, or benzyl, wherein the groups may be unsubstituted or substituted by halogen, HO— or $C_{1-6}$-alkyl-O—, or (c) a $C_{1-3}$-alkyl group wherein each methylene group is substituted by up to two fluorine atoms and each methyl group is substituted by up to three fluorine atoms, or $R^8$ and $R^9$ together may also form a ring which is selected from among azetidinyl, pyrrolidinyl, piperidinyl, piperazinyl and morpholinyl, wherein the ring may be unsubstituted or substituted by 1, 2 or 3 substituents $R^7$, wherein the substituents $R^7$ are independent of one another, m denotes one of the numbers 0, 1 or 2 and s denotes one of the numbers 1, 2 or 3, or a tautomer or salt thereof.

5. A compound of the formula I according to claim 1, wherein $R^1$ denotes a group of formulae wherein $R^{5.1}$ denotes (a) H, (b) $C_{1-3}$-alkyl, —OH, —O—$C_{1-3}$-alkyl, (c) a $C_{1-3}$-alkyl- or $C_{1-3}$-alkyl-O- group wherein each methylene group is substituted by up to two fluorine atoms and each methyl group is substituted by up to three fluorine atoms, $R^6$ independently of one another denote
  (a) H, $C_{1-6}$-alkyl, $C_{3-6}$-cycloalkyl,
  (b) a phenyl group optionally substituted by 1, 2 or 3 substituents $R^{6.2}$, wherein the substituents $R^{6.2}$ may be identical or different,
  (c) a heteroaryl group optionally substituted by 1, 2 or 3 substituents $R^{6.2}$ which is selected from among benzimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents $R^{6.2}$ may be identical or different,
  (d) a heterocyclic group optionally substituted by 1, 2 or 3 substituents $R^{6.2}$, wherein the substituents $R^{6.2}$ may be identical or different,
$R^{6.1}$ denotes
  (a) H, halogen, $C_{1-6}$-alkyl, $C_{3-6}$-cycloalkyl,
  (b) —O—$C_{1-6}$-alkylene-$NR^8R^9$, —O—$R^7$, —$CO_2R^7$, —C(O)—$NR^8R^9$, —$SO_2$—$NR^8R^9$, —$NR^8$—$SO_2$—$R^9$, —$S(O)_m$—$R^8$, —CN, —$NR^8R^9$, —O—C(O)—$R^7$ or
  (c) a $C_{1-3}$-alkyl or $C_{1-3}$-alkyl-O— group wherein each methylene group is substituted by up to two fluorine atoms and each methyl group is substituted by up to three fluorine atoms,
$R^{6.2}$ denotes
  (a) halogen, $C_{1-6}$-alkyl, $C_{3-6}$-cycloalkyl,
  (b) —O—$R^7$, —O—$(CH_2)_s$—O—$R^7$, —$CO_2R^7$, —$S(O)_m$—$R^8$, —CN, —O—C(O)—$R^7$ or
  (c) a $C_{1-3}$-alkyl group wherein each methylene group is substituted by up to two fluorine atoms and each methyl group is substituted by up to three fluorine atoms,
$R^7$ denotes
  (a) H,
  (b) $C_{1-6}$-alkyl, $C_{3-6}$-cycloalkyl, aryl, heteroaryl, benzyl which may be substituted by a group $R^{7.1}$, or
  (c) a $C_{1-3}$-alkyl group wherein each methylene group is substituted by up to two fluorine atoms and each methyl group is substituted by up to three fluorine atoms,
$R^{7.1}$ denotes HO— or $C_{1-6}$-alkyl-O—,
$R^8$ denotes
  (a) H,
  (b) $C_{1-3}$-alkyl, phenyl or benzyl, wherein the groups may be unsubstituted or substituted by halogen, HO— or $H_3C$—O—,
$R^9$ denotes
  (a) H,
  (b) $C_{1-3}$-alkyl, phenyl or benzyl, wherein the groups may be unsubstituted or substituted by halogen, HO— or $H_3C$—O—, or
$R^8$ and $R^9$ together may also form a ring which is selected from among azetidinyl, pyrrolidinyl, piperidinyl, piperazinyl and morpholinyl, wherein the ring may be unsubstituted or substituted by a substituent $R^7$,
m denotes one of the numbers 0, 1 or 2, and
s denotes one of the numbers 1, 2 or 3,
or a tautomer or salt thereof.

6. A compound of the formula I according to claim 1, wherein
$R^1$ denotes

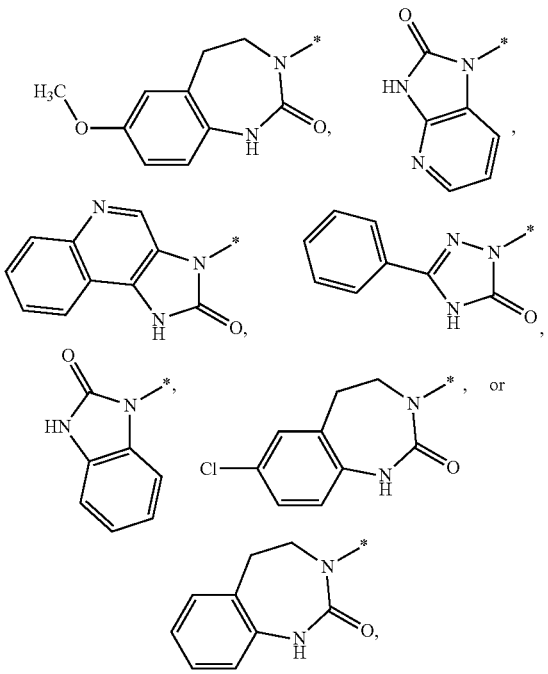

or a tautomer or salt thereof.

7. A compound of the formula I according to claim 1, wherein $R^2$ denotes a hydrogen atom,
or a tautomer or salt thereof.

8. A compound of the formula I according to claim 1, wherein
$R^3$ denotes
  (a) H,
  (b) $C_{1-6}$-alkyl,
  (c) a $C_{3-6}$-cycloalkyl group substituted by one or two groups $R^{3.2}$,
  (d) a $C_{1-3}$-alkyl group wherein each methylene group is substituted by up to two fluorine atoms and each methyl group is substituted by up to three fluorine atoms,
$R^{3.2}$ independently of one another denote
  (a) H,
  (b) halogen, $C_{1-3}$-alkyl, —OH, —O—$C_{1-3}$-alkyl,
  (c) a $C_{1-3}$-alkyl or —O—$C_{1-3}$-alkyl group wherein each methylene group is substituted by up to two fluorine atoms and each methyl group is substituted by up to three fluorine atoms,
$R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$,
  (f) a $C_{5-7}$-cycloalkyl group which may be fused to an aryl group and is additionally substituted by one or two groups $R^{4.2}$, or
  (g) a heteroaryl group substituted by one or two groups $R^{4.2}$,
$R^{4.1}$ denotes
  (a) H,
  (b) a phenyl group substituted by the groups $R^{4.1.1}$ and $R^{4.1.2}$, (c) a heteroaryl group substituted by the groups $R^{4.1.1}$ and $R^{4.1.2}$, $R^{4.1.1}$ denotes
- (a) H,
- (b) halogen, $C_{1-3}$-alkyl, —OH, —CN, —O—$C_{1-3}$-alkyl, —NR$^{4.1.1.1}$R$^{4.1.1.2}$, —S—$C_{1-3}$-alkyl, —NR$^{4.1.1.131}$C(O)—$C_{1-3}$-alkyl, —C(O)—NR$^{4.1.1.1}$R$^{4.1.1.2}$, —C(O)—O—R$^{4.1.1.3}$,
- (c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.1}$ denotes H, $C_{1-3}$-alkyl, $R^{4.1.1.2}$ denotes H, $C_{1-3}$-alkyl, or $R^{4.1.1.1}$ and $R^{4.1.1.2}$ together with the nitrogen atom to which they are bound may also denote a group selected from morpholinyl, thiomorpholinyl, piperidinyl, piperazinyl, pyrrolidinyl and azetidinyl, $R^{4.1.1.3}$ denotes H, $C_{1-3}$-alkyl, $R^{4.1.2}$ denotes
- (a) H,
- (b) halogen, $C_{1-3}$-alkyl, —OH, —O—$C_{1-3}$-alkyl,
- (c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote
- (a) H,
- (b) halogen, $C_{1-3}$-alkyl, —OH, —CN, —O—$C_{1-3}$-alkyl, —NR$^{4.2.1}$R$^{4.2.2}$, —S—$C_{1-3}$-alkyl, —NR4.2.1—C(O)—$C_{1-3}$-alkyl, —C(O)—NR$^{4.2.1}$R$^{4.2.2}$, —C(O)—O—R$^{4.2.3}$,
- (c) a $C_{1-3}$-alkyl- or —O—$C_{1-3}$-alkyl group wherein each methylene group is substituted by up to two fluorine atoms and each methyl group is substituted by up to three fluorine atoms, $R^{4.2.1}$ denotes H, $C_{1-3}$-alkyl and $R^{4.2.2}$ denotes H, $C_{1-3}$-alkyl, or $R^{4.2.1}$ and $R^{4.2.2}$ together with the nitrogen atom to which they are bound may also denote a group which is selected from among morpholinyl, thiomorpholinyl, piperidinyl, piperidonyl, piperazinyl, pyrrolidinyl and azetidinyl, and which may additionally be substituted by one or two groups selected from F, —OH, —O—$C_{1-3}$-alkyl, —OCF$_3$, $C_{1-3}$-alkyl and CF$_3$, $R^{4.2.3}$ denotes H, $C_{1-3}$-alkyl, $R^3$ and $R^4$ together with the nitrogen atom to which they are bound denote:
- (a) a saturated 5-, 6- or 7-membered heterocyclic group which is substituted at a carbon atom by a group $R^{4.3}$ or by two groups $R^{4.3}$ and $R^{4.4}$,
- (b) a saturated 5-, 6- or 7-membered heterocyclic group which is substituted at two adjacent carbon atoms by in each case a group $R^{4.3}$ and $R^{4.4}$,
- (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocycyl group is substituted by 1, 2 or 3 groups $R^{4.5}$,
- (d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
- (e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$, or
- (f) a heteroaryl group which is substituted at 1, 2 or 3 carbon atoms by a group $R^{4.5}$, $R^{4.3}$ denotes H, $C_{1-3}$-alkyl, phenyl, —$C_{1-3}$-alkylene-R$^{4.3.1}$, $C_{1-3}$-alkyl-O—C(O)—, HO—C(O)—, F, —O—$C_{1-3}$-alkyl, —OH, —CN $R^{4.3.1}$ denotes H, HO, $C_{1-3}$-alkyl-O—, cyclopropyl, $C_{1-3}$-alkyl-O—C(O)—, CN, —NH$_2$, ($C_{1-4}$-alkyl)-NH—, ($C_{1-4}$-alkyl)$_2$N, heterocyclyl, $R^{4.4}$ denotes
- (a) H, $C_{1-3}$-alkyl, —OH, —O—$C_{1-3}$-alkyl or
- (b) a $C_{1-3}$-alkyl or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached may also denote a $C_{3-6}$-cycloalkyl-, $C_{5-6}$-cycloalkenyl- or heterocyclyl group, $R^{4.5}$ independently of one another denote
- (a) H,
- (b) halogen, $C_{1-3}$-alkyl, —OH, —O—$C_{1-3}$-alkyl, —NH$_2$, —CN, —C(O)—O—R$^{4.5.1}$, —C(O)—NR$^{4.5.2}$R$^{4.5.3}$,
- (c) a $C_{1-3}$-alkyl or —O—-$C_{1-3}$-alkyl group wherein each methylene group is substituted by up to two fluorine atoms and each methyl group is substituted by up to three fluorine atoms,
- (d) phenyl, $R^{4.5.1}$ denotes H, $C_{1-3}$-alkyl, $R^{4.5.2}$ denotes H, $C_{1-3}$-alkyl and $R^{4.5.3}$ denotes H, $C_{1-3}$-alkyl, or a tautomer or salt thereof.

9. A compound of the formula I according to claim 1, wherein $R^3$ denotes
- (a) H,
- (b) $C_{1-6}$-alkyl,
- (c) a $C_{3-6}$-cycloalkyl substituted by one or two groups $R^{3.2}$, or
- (d) a $C_{1-3}$-alkyl group wherein each methylene group is substituted by up to two fluorine atoms and each methyl group is substituted by up to three fluorine atoms, $R^{3.2}$ independently of one another denote
- (a) H,
- (b) halogen, $C_{1-3}$-alkyl, —OH, —O—$C_{1-3}$-alkyl,
- (c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes
- (a) H,
- (b) $C_{1-6}$-alkylene-R$^{4.1}$,
- (c) a $C_{3-6}$-cycloalkyl group substituted by one or two groups $R^{4.2}$,
- (d) a $C_{5-7}$-cycloalkenyl group substituted by one or two groups $R^{4.2}$,
- (e) an aryl group substituted by one or two groups $R^{4.2}$,
- (f) a $C_{5-6}$-cycloalkyl group which may be fused to a phenyl group and which is additionally substituted by one or two groups $R^{4.2}$, $R^{4.1}$ denotes
(a) H,
(b) a phenyl group substituted by the groups $R^{4.1.1}$ and $R^{4.1.2}$, $R^{4.1.1}$ denotes
(a) H,
(b) halogen, $C_{1-3}$-alkyl, —OH, —O—$C_{1-3}$-alkyl, —CN, —C(O)—O—$R^{4.1.1.3}$,
(c) a $C_{1-3}$-alkyl- or —O—$C_{1-3}$-alkyl group wherein each methylene group is substituted by up to two fluorine atoms and each methyl group is substituted by up to three fluorine atoms, $R^{4.1.1.3}$ denotes H, $C_{1-3}$-alkyl, $R^{4.12}$ denotes
(a) H,
(b) halogen, $C_{1-3}$-alkyl, —OH, —O—$C_{1-3}$-alkyl,
(c) a $C_{1-3}$-alkyl- or —O—$C_{1-3}$-alkyl group wherein each methylene group is substituted by up to two fluorine atoms and each methyl group is substituted by up to three fluorine atoms, or $R^{4.2}$ independently of one another denote
(a) H,
(b) halogen, $C_{1-3}$-alkyl, —OH, —O—$C_{1-3}$-alkyl, —CN, —O—C(O)—$C_{1-3}$-alkyl,
(c) a $C_{1-3}$-alkyl- or —O—$C_{1-3}$-alkyl group wherein each methylene group is substituted by up to two fluorine atoms and each methyl group is substituted by up to three fluorine atoms, $R^3$ and $R^4$ together with the nitrogen atom to which they are bound denote:
(a) a saturated 5- or 6-membered heterocyclic group which is substituted at a carbon atom by a group $R^{4.3}$ or by two groups $R^{4.3}$ and $R^{4.4}$,
(b) a saturated 5- or 6-membered heterocyclic group which is substituted at two adjacent carbon atoms by a group $R^{4.3}$ and $R^{4.4}$ in each case,
(c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, while the fused-on cycloalkyl or heterocycyl group is substituted by 1, 2 or 3 groups $R^{4.5}$,
(d) a monounsaturated 5-, 6- or 7-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
(e) a monounsaturated 5-, 6- or 7-membered heterocyclic group which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

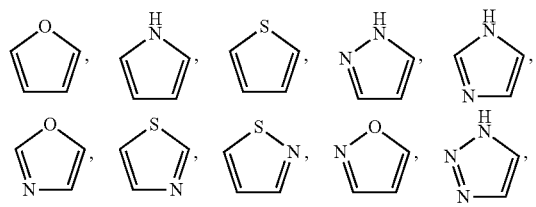

-continued

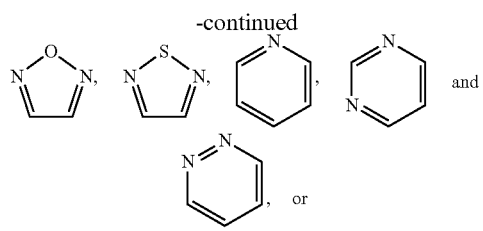

(f) a heteroaryl group which is substituted at 1, 2 or 3 carbon atoms by in each case a group $R^{4.5}$, $R^{4.3}$ denotes H, $C_{1-3}$-alkyl, phenyl, —$C_{1-3}$-alkylene-$R^{4.3.1}$, $C_{1-3}$-alkyl—O—C(O)—, HO—C(O)—, F, —O—$C_{1-3}$-alkyl, —OH, —CN $R^{4.3.1}$ denotes H, HO, $C_{1-3}$-alkyl-O, cyclopropyl, $C_{1-3}$-alkyl-O—C(O)—, CN, —NH$_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
(a) H, $C_{1-3}$-alkyl, —OH, —O—$C_{1-3}$-alkyl or
(b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atoms to which they are attached may also denote a $C_{3-6}$-cycloalkyl or heterocyclyl group, and $R^{4.5}$ independently of one another denote
(a) H,
(b) halogen, $C_{1-3}$-alkyl, —OH, —O—$C_{1-3}$-alkyl, —NH$_2$, —CN,
(c) a $C_{1-3}$-alkyl- or —O—$C_{1-3}$-alkyl group wherein each methylene group is substituted by up to two fluorine atoms and each methyl group is substituted by up to three fluorine atoms, or
(d) denotes phenyl,
or a tautomer or salt thereof.

10. A compound of the formula I according to claim 1, wherein $R^3$ denotes
(a) H,
(b) $C_{1-6}$-alkyl,
(c) a $C_{3-6}$-cycloalkyl group substituted by one or two groups $R^{3.2}$, or
(d) a $C_{1-3}$-alkyl group wherein each methylene group is substituted by up to two fluorine atoms and each methyl group is substituted by up to three fluorine atoms, $R^{3.2}$ independently of one another denote
(a) H,
(b) halogen, $C_{1-3}$-alkyl, —OH, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, $R^4$ denotes
(a) H,
(b) $C_{1-6}$-alkylene-$R^{4.1}$,
(c) a $C_{3-6}$-cycloalkyl group substituted by one or two groups $R^{4.2}$,
(d) a $C_{5-7}$-cycloalkenyl group substituted by one or two groups $R^{4.2}$,
(e) a phenyl group substituted by one or two groups $R^{4.2}$,
(f) a $C_{5-6}$-cycloalkyl group which may be fused to a phenyl group and is additionally substituted by one or two groups $R^{4.2}$, $R^{4.1}$ denotes
(a) H,
(b) a phenyl group substituted by the groups $R^{4.1.1}$ and $R^{4.1.2}$, $R^{4.1.1}$ denotes
(a) H,
(b) halogen, $C_{1-3}$-alkyl, —OH, —O—$C_{1-3}$-alkyl, —CN, —C(O)—O—$R^{4.1.1.3}$,
(c) a $C_{1-3}$-alkyl or —O—$C_{1-3}$-alkyl group wherein each methylene group is substituted by up to two fluorine atoms and each methyl group is substituted by up to three fluorine atoms, $R^{4.1.1.3}$ denotes H, $C_{1-3}$-alkyl, $R^{4.1.2}$ denotes
(a) H,
(b) halogen, $C_{1-3}$-alkyl, —OH, —O—$C_{1-3}$-alkyl,
(c) a $C_{1-3}$-alkyl or —O—$C_{1-3}$-alkyl group wherein each methylene group is substituted by up to two fluorine atoms and each methyl group is substituted by up to three fluorine atoms, or $R^{4.2}$ denotes
(a) H,
(b) halogen, $C_{1-3}$-alkyl, —OH, —O—$C_{1-3}$-alkyl, —CN,
(c) a $C_{1-3}$-alkyl or —O—$C_{1-3}$-alkyl group wherein each methylene group is substituted by up to two fluorine atoms and each methyl group is substituted by up to three fluorine atoms, or $R^3$ and $R^4$ together with the nitrogen atom to which they are attached denote:
(a) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$,
(b) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at two adjacent carbon atoms by a group $R^{4.3}$ and $R^{4.4}$ in each case,
(c) a saturated 5-, 6- or 7-membered heterocyclic group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, while the fused-on cycloalkyl or heterocyclyl group is substituted by 1, 2 or 3 groups $R^{4.5}$,
(d) a monounsaturated 5-, 6- or 7-membered heterocyclic group, which is selected from among

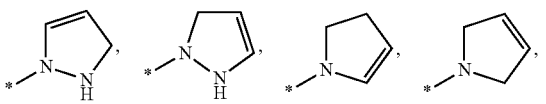

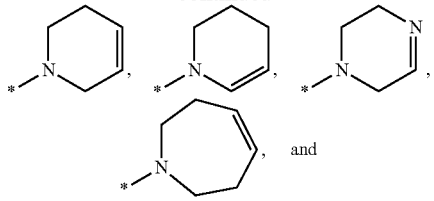

and which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, (e) a monounsaturated 5-, 6- or 7-membered heterocyclic group, which is selected from among

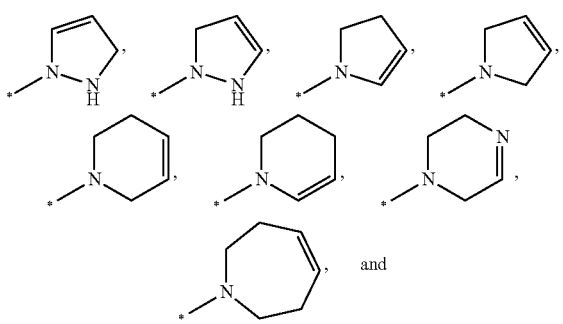

and which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

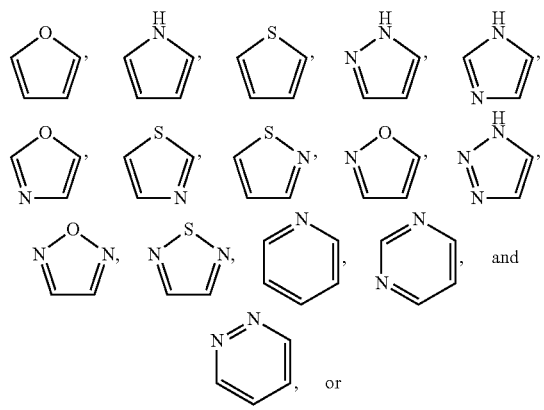

(f) a heteroaryl group, which is selected from among indole, isoindole, azaindole, indazole and benzimidazole, and which is substituted at 1, 2 or 3 carbon atoms by a group $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, HO, $C_{1-3}$-alkyl-O—, cyclopropyl, $C_{1-3}$-alkyl-O—C(O)—, CN, —NH$_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
 (a) H, $C_{1-3}$-alkyl, —OH, —O—$C_{1-3}$-alkyl or
 (b) a $C_{1-3}$-alkyl- or —O—$C_{1-3}$-alkyl group wherein each methylene group is substituted by up to two fluorine atoms and each methyl group is substituted by up to three fluorine atoms, $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denotes
 (a) H,
 (b) halogen, $C_{1-3}$-alkyl, —OH, —O—$C_{1-3}$-alkyl, —NH$_2$, —CN,
 (c) a $C_{1-3}$-alkyl- or —O—$C_{1-3}$-alkyl group wherein each methylene group is substituted by up to two fluorine atoms and each methyl group is substituted by up to three fluorine atoms, or
 (d) phenyl, or a tautomer or salt thereof.

11. A compound of the formula I according to claim 1, wherein $R^3$ denotes
 (a) H,
 (b) $C_{1-3}$-alkyl,
 (c) a $C_{1-3}$-alkyl group wherein each methylene group is substituted by up to two fluorine atoms and each methyl group is substituted by up to three fluorine atoms, and $R^4$ denotes H or a group selected from

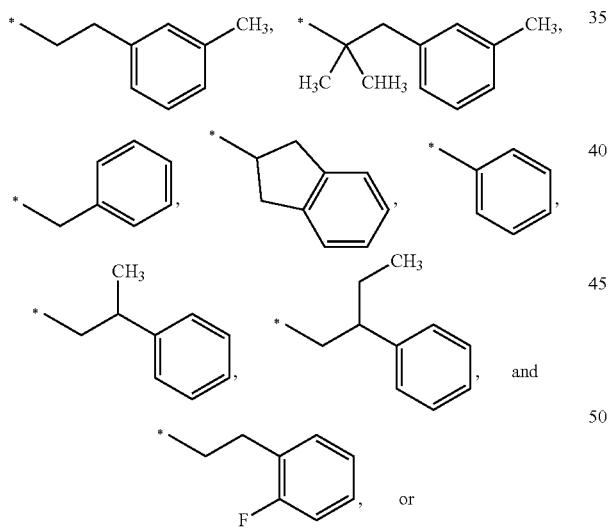

$R^3$ and $R^4$ together with the nitrogen atom to which they are attached denote a group selected from

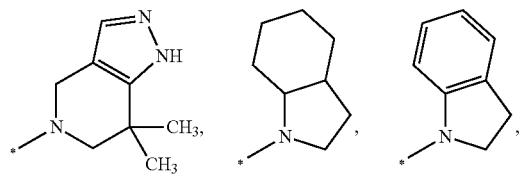

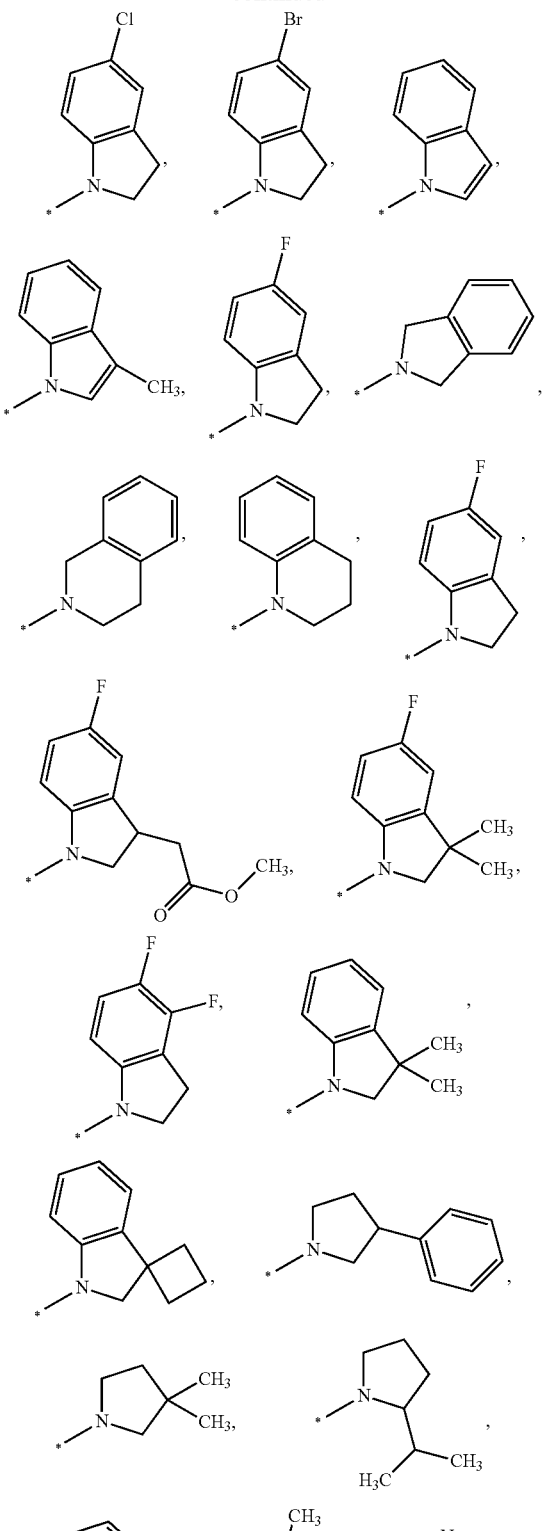

-continued
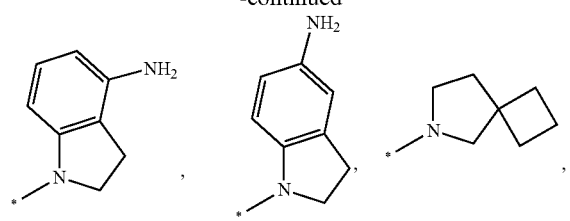
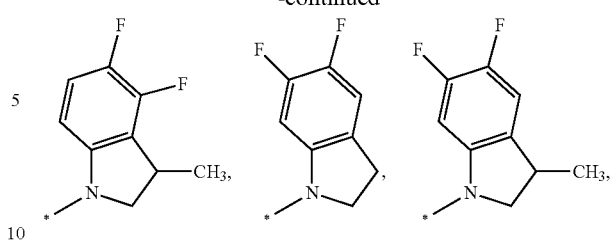
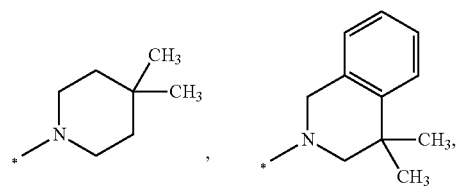
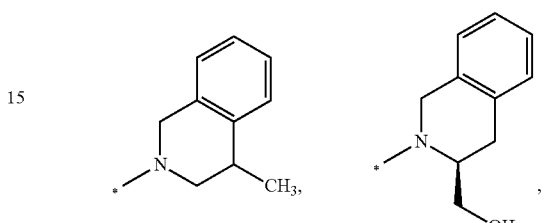
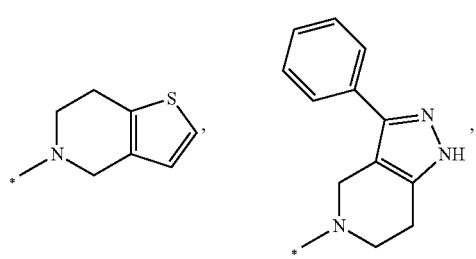
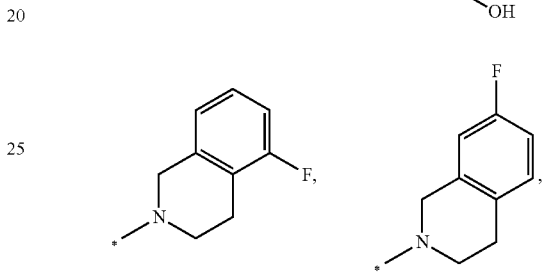
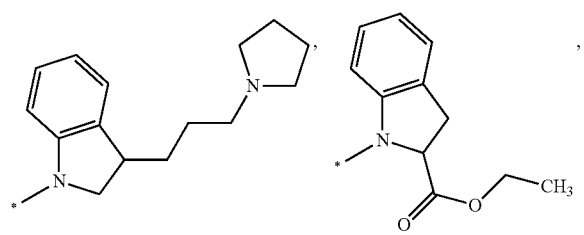
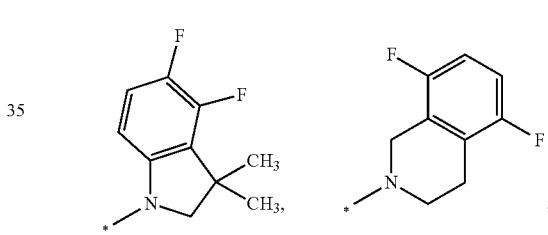
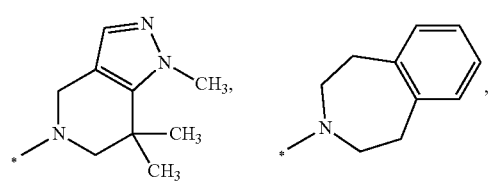
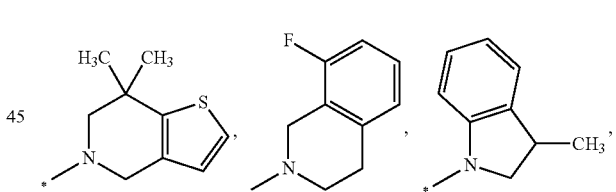
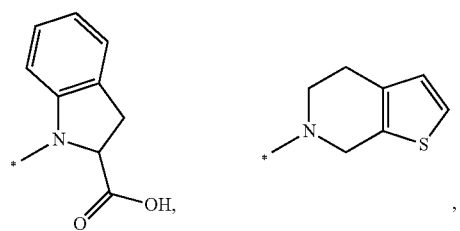
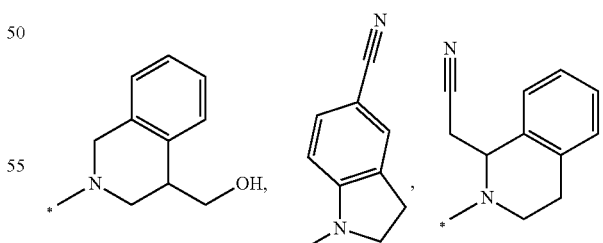
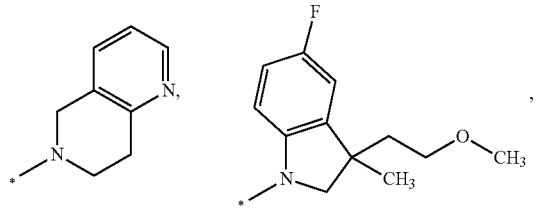
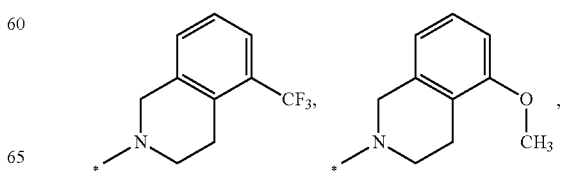

387
-continued
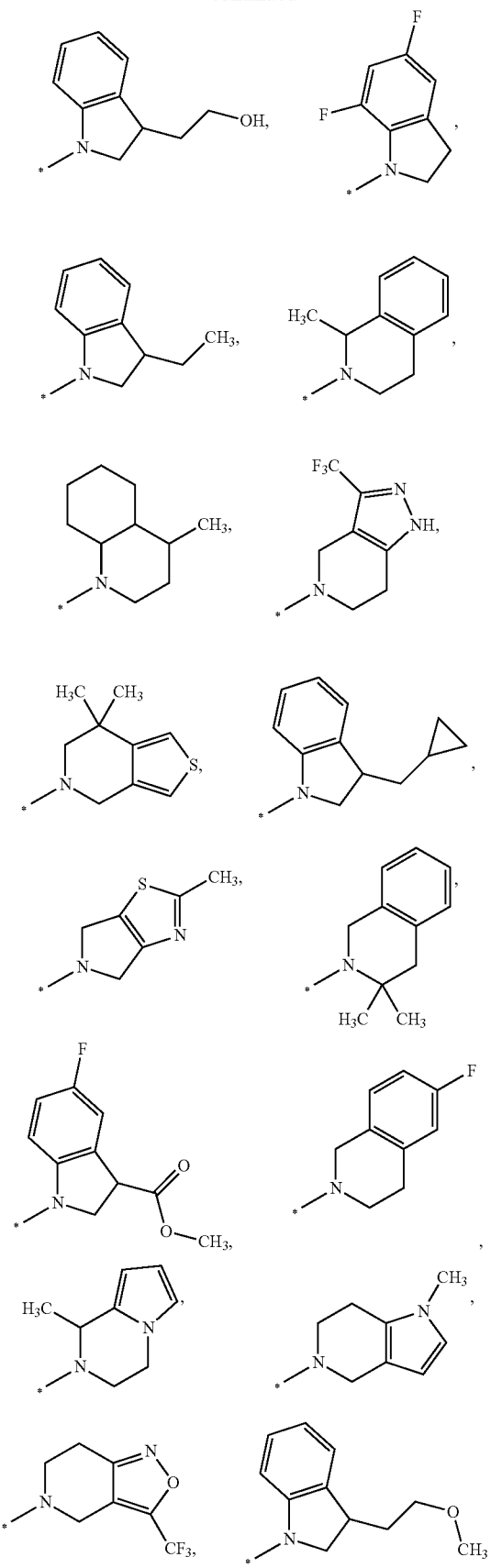
388
-continued
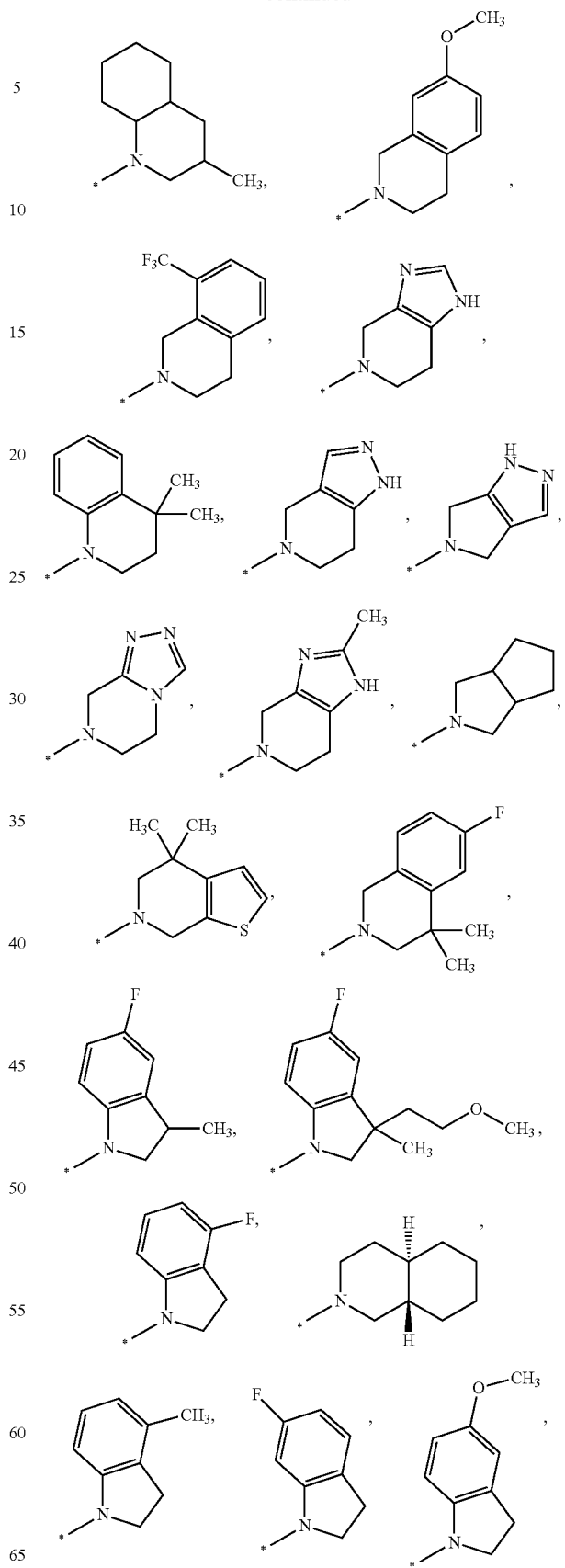

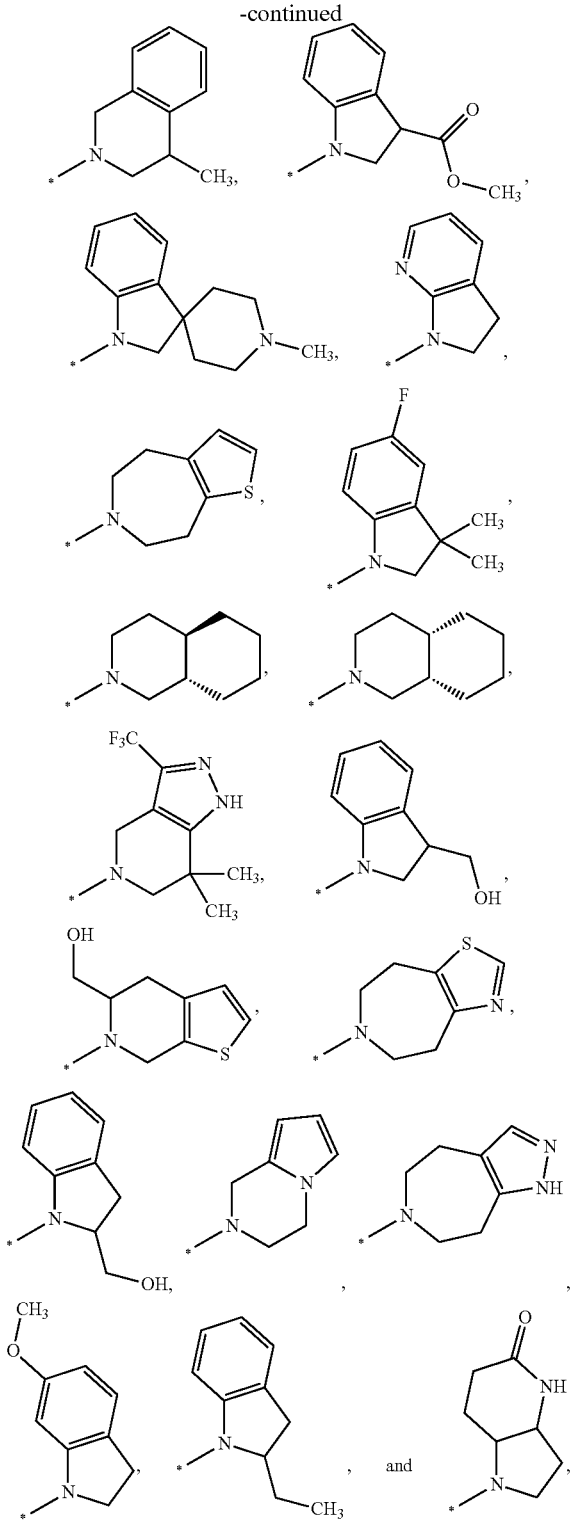

or a tautomer or salt thereof.

12. A compound of the formula I according to claim 1, wherein
R$^3$ and R$^4$ together with the nitrogen atom to which they are attached denote a monounsaturated 5-membered heterocyclic group, which is substituted at a carbon atom by a group R$^{4.3}$ or by two groups R$^{4.3}$ and R$^{4.4}$ and is additionally fused to a phenyl group, while the fused-on phenyl group is substituted by 1, 2 or 3 groups R$^{4.5}$, R$^{4.3}$ denotes H, C$_{1-3}$-alkyl, phenyl, —C$_{1-3}$-alkylene-R$^{4.3.1}$, C$_{1-3}$-alkyl-O—C(O)—, HO—C(O)—, F, —O—C$_{1-3}$-alkyl, —OH, —CN, R$^{4.3.1}$ denotes H, HO, C$_{1-3}$-alkyl-O—, C$_{1-3}$-alkyl-O—C(O)—, cyclopropyl, CN, —NH$_2$, (C$_{1-4}$-alkyl)-NH—, (C$_{1-4}$-alkyl)$_2$N—, morpholinyl, thiomorpholinyl, piperidinyl, pyrrolidinyl, azetidinyl, R$^{4.4}$ denotes
(a) H, C$_{1-3}$-alkyl, —OH, —O—C$_{1-3}$-alkyl or
(b) a C$_{1-3}$-alkyl- or —O—C$_{1-3}$-alkyl group wherein each methylene group is substituted by up to two fluorine atoms and each methyl group is substituted by up to three fluorine atoms, or R$^{4.3}$ and R$^{4.4}$ together with the carbon atom to which they are attached also denote a C$_{3-6}$-cycloalkyl group or a heterocyclyl group which is selected from among azetidinyl, pyrrolidinyl, piperidinyl and azepanyl, and R$^{4.5}$ independently of one another denotes
(a) H,
(b) halogen, C$_{1-3}$-alkyl, —OH, —O—C$_{1-3}$-alkyl, —NH$_2$, —CN, NO$_2$,
(c) a C$_{1-3}$-alkyl- or —O—C$_{1-3}$-alkyl group wherein each methylene group is substituted by up to two fluorine atoms and each methyl group is substituted by up to three fluorine atoms, or
(d) phenyl, or a tautomer or salt thereof.

13. A compound of the formula I according to claim 1, wherein
R$^3$ and R$^4$ together with the nitrogen atom to which they are attached denote a group of general formula IIIa or IIIb

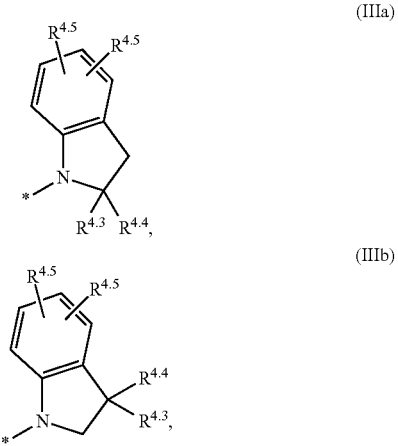

R$^{4.3}$ denotes H, C$_{1-3}$-alkyl, phenyl, —C$_{1-3}$-alkylene-R$^{4.3.1}$, C$_{1-3}$-alkyl-O—C(O)—, HO—C(O)—, F, —O—C$_{1-3}$-alkyl, —OH, —CN, R$^{4.3.1}$ denotes H, HO, C$_{1-3}$-alkyl-O, C$_{1-3}$-alkyl-O—C(O), CN, —NH$_2$, (C$_{1-4}$-alkyl)-NH, (C$_{1-4}$-alkyl)$_2$N, morpholinyl, thiomorpholinyl, piperidinyl, pyrrolidinyl, azetidinyl, R$^{4.4}$ denotes
(a) H, C$_{1-3}$-alkyl, —OH, —O—C$_{1-3}$-alkyl or
(b) a C$_{1-3}$-alkyl- or —O—C$_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denotes (a) H, (b) halogen, $C_{1-3}$-alkyl, —OH, —O—$C_{1-3}$-alkyl, —$NH_2$, —CN, $NO_2$, (c) a $C_{1-3}$-alkyl- or —O—$C_{1-3}$-alkyl group wherein each methylene group is substituted by up to two fluorine atoms and each methyl group is substituted by up to three fluorine atoms, or (d) phenyl, or a tautomer or salt thereof.

14. A compound of the Compounds of general formula I according to claim 1, wherein $R^3$ and $R^4$ together with the nitrogen atom to which they are attached denote a group selected from

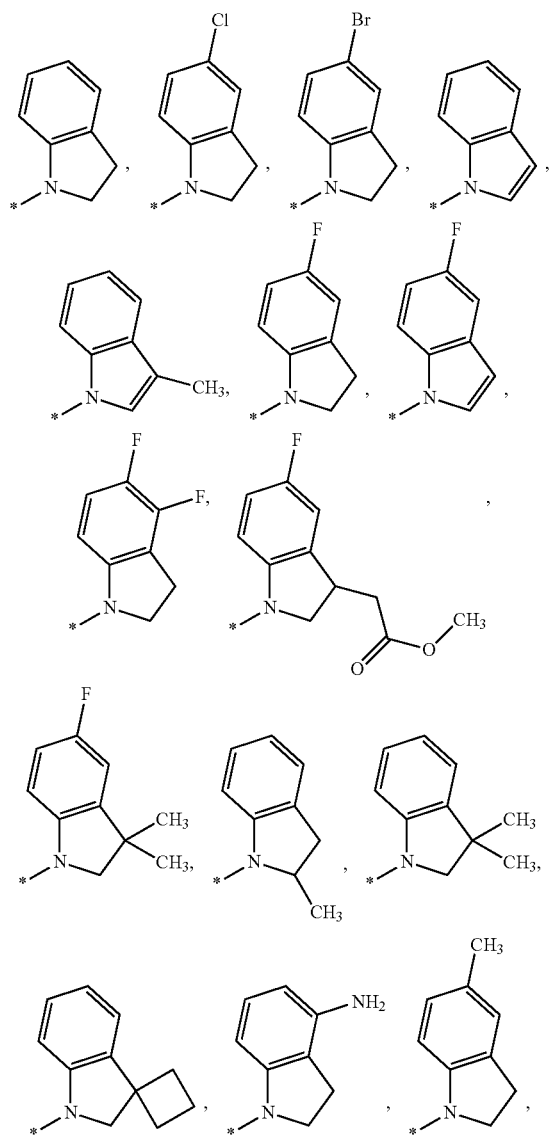

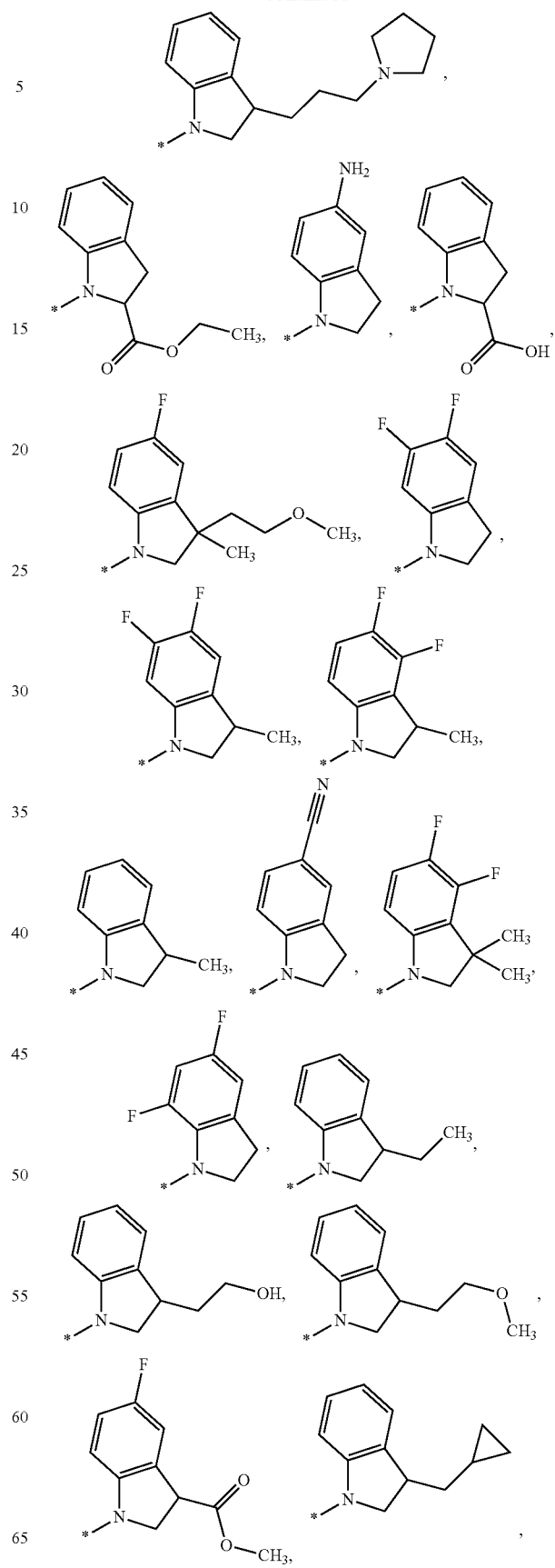

-continued

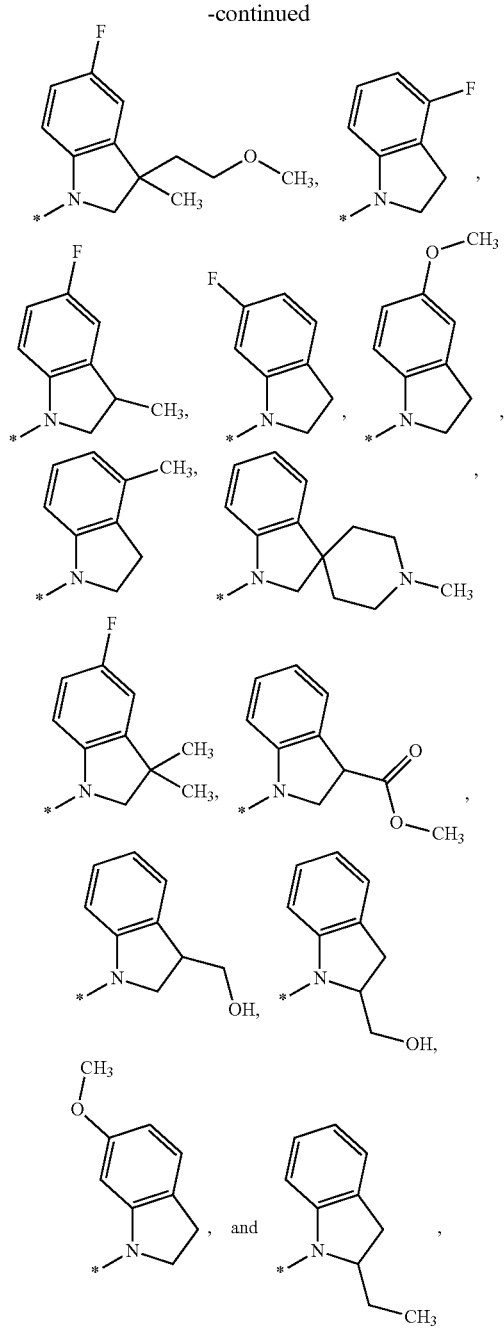

or a tautomer or salt thereof.

15. A compound of the formula I according to claim 1, wherein

U—V—X denotes a group selected from —N═(C—R$^{11}$)—N═,

R$^{11}$ denotes H, —NR$^{11.1}$R$^{11.2}$ or —O—C$_{1-3}$-alkyl,

R$^{11.1}$ denotes H or C$_{1-6}$-alkyl,

R$^{11.2}$ denotes H or —SO$_2$—C$_{1-3}$-alkyl, and

Y denotes N or CH, or a tautomer or salt thereof.

16. A compound of the formula I according to claim 1, wherein the ring

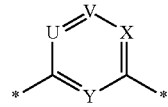

denotes the group

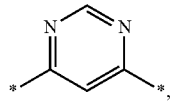

or a tautomer or salt thereof.

17. A compound of the formula I according to claim 1, wherein

R$^1$ denotes a group selected from

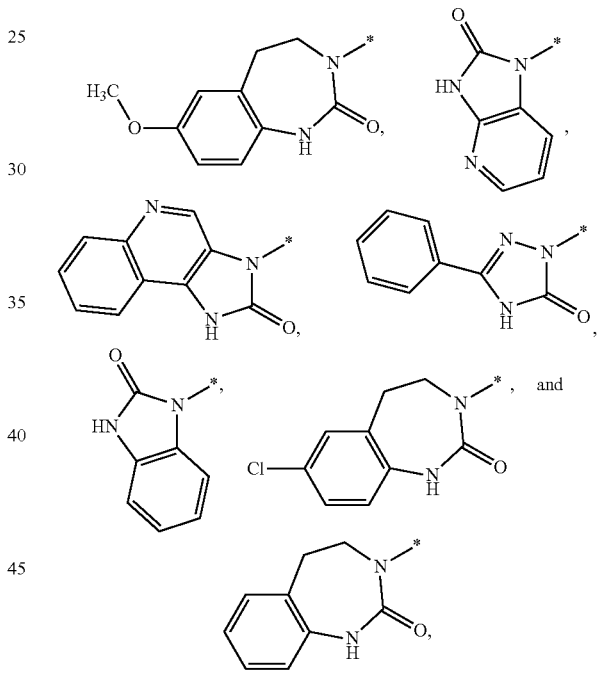

R$^2$ denotes H,

R$^3$ denotes (a) H, (b) C$_{1-3}$-alkyl, (c) a C$_{1-3}$-alkyl group wherein each methylene group is substituted by up to two fluorine atoms and each methyl group is substituted by up to three fluorine atoms, and R$^4$ denotes H or a group selected from

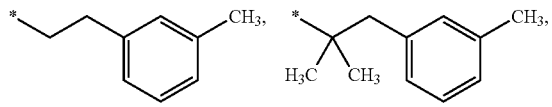

395
-continued
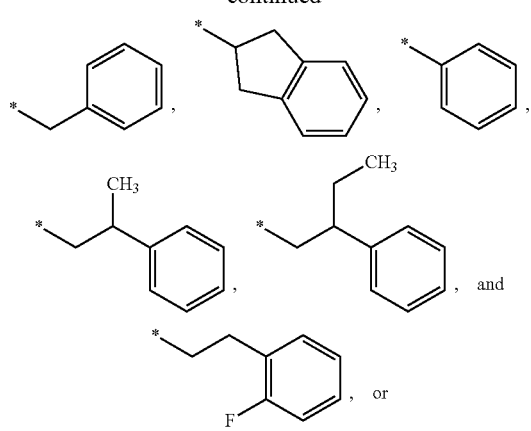
R³ and R⁴ together with the nitrogen atom to which they are attached denote a group selected from
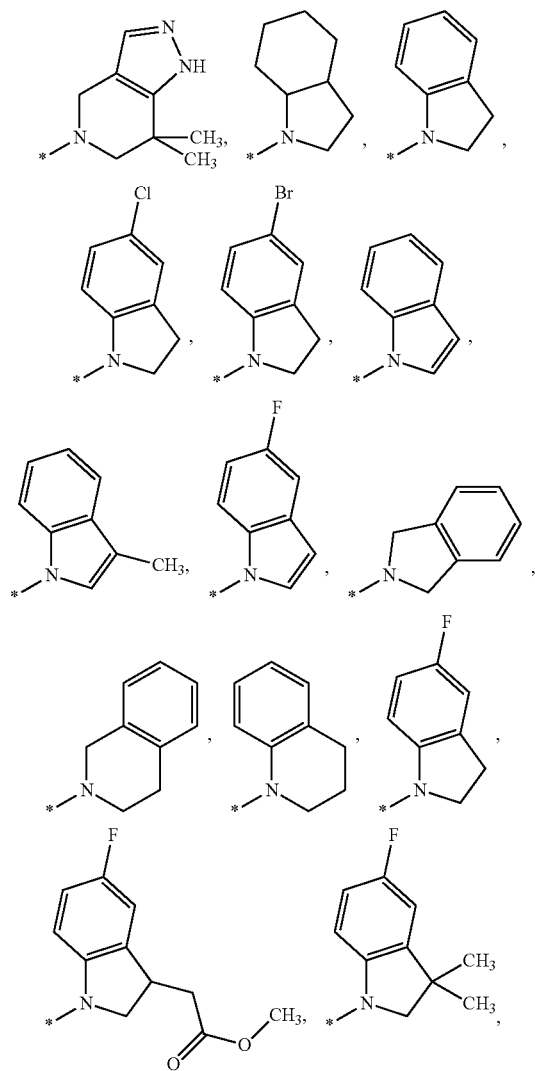
396
-continued
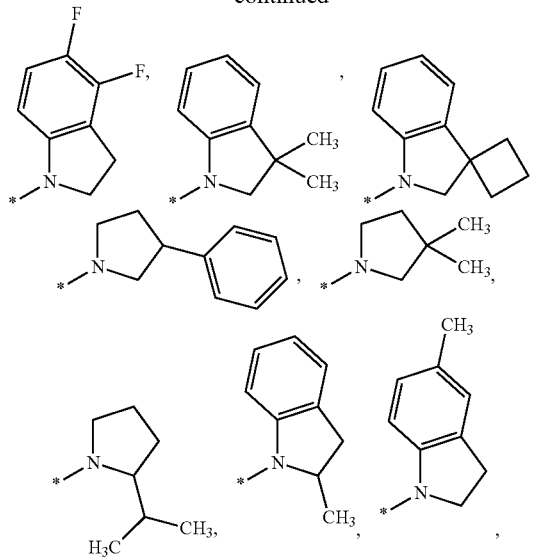

397
-continued
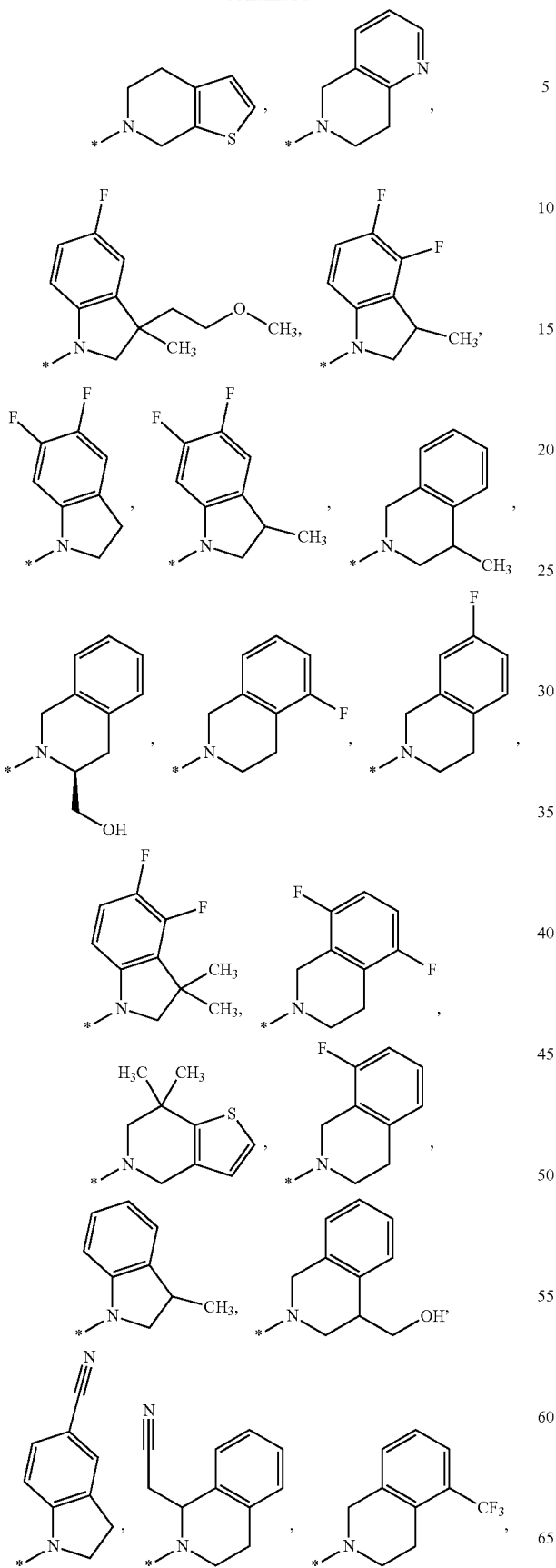
398
-continued
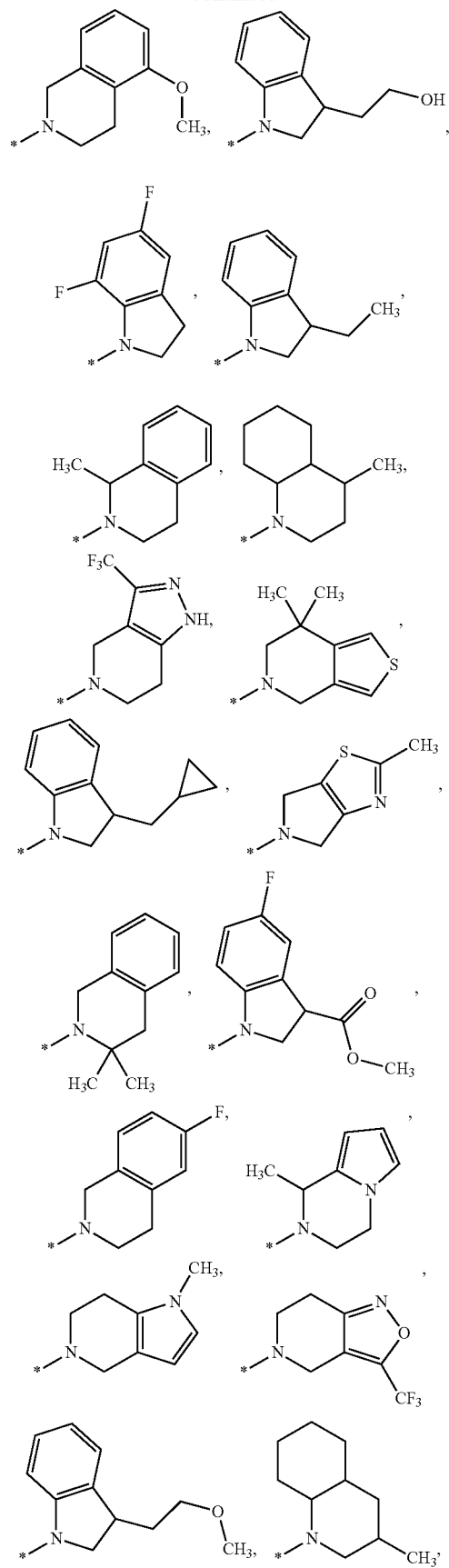

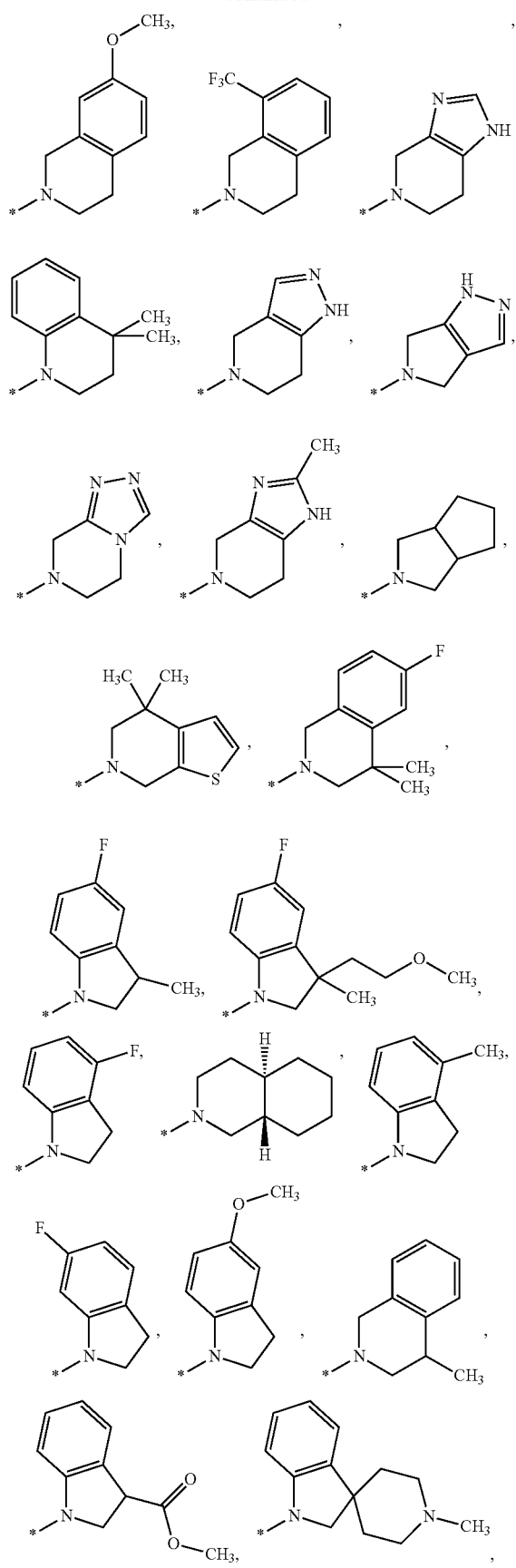
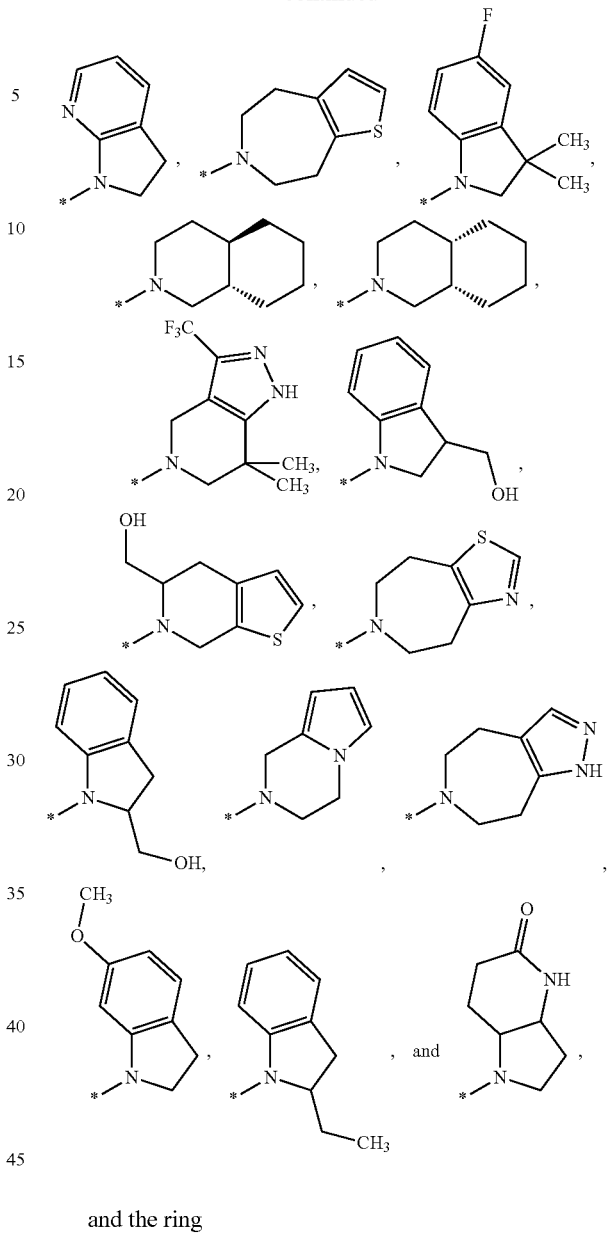
and the ring
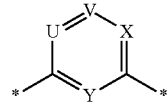
denotes the group
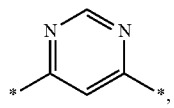
or a tautomer or salt thereof.
18. A compound of the formula I according to claim 1, wherein $R^1$ denotes a group selected from
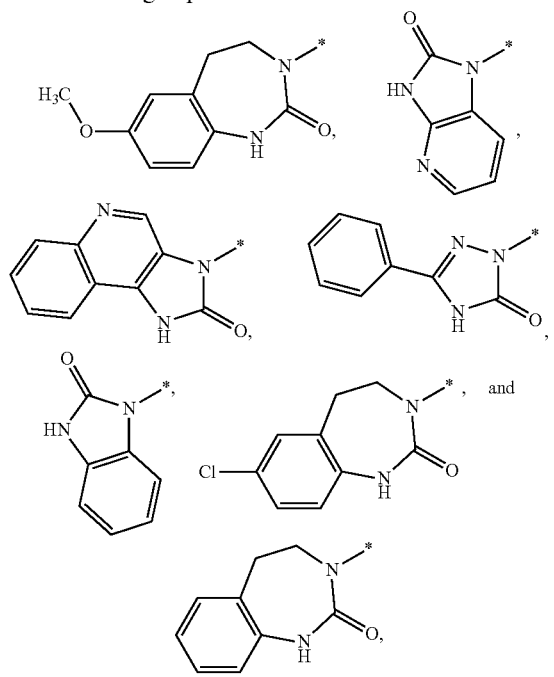
$R^3$ and $R^4$ together with the nitrogen atom to which they are attached denote a group selected from
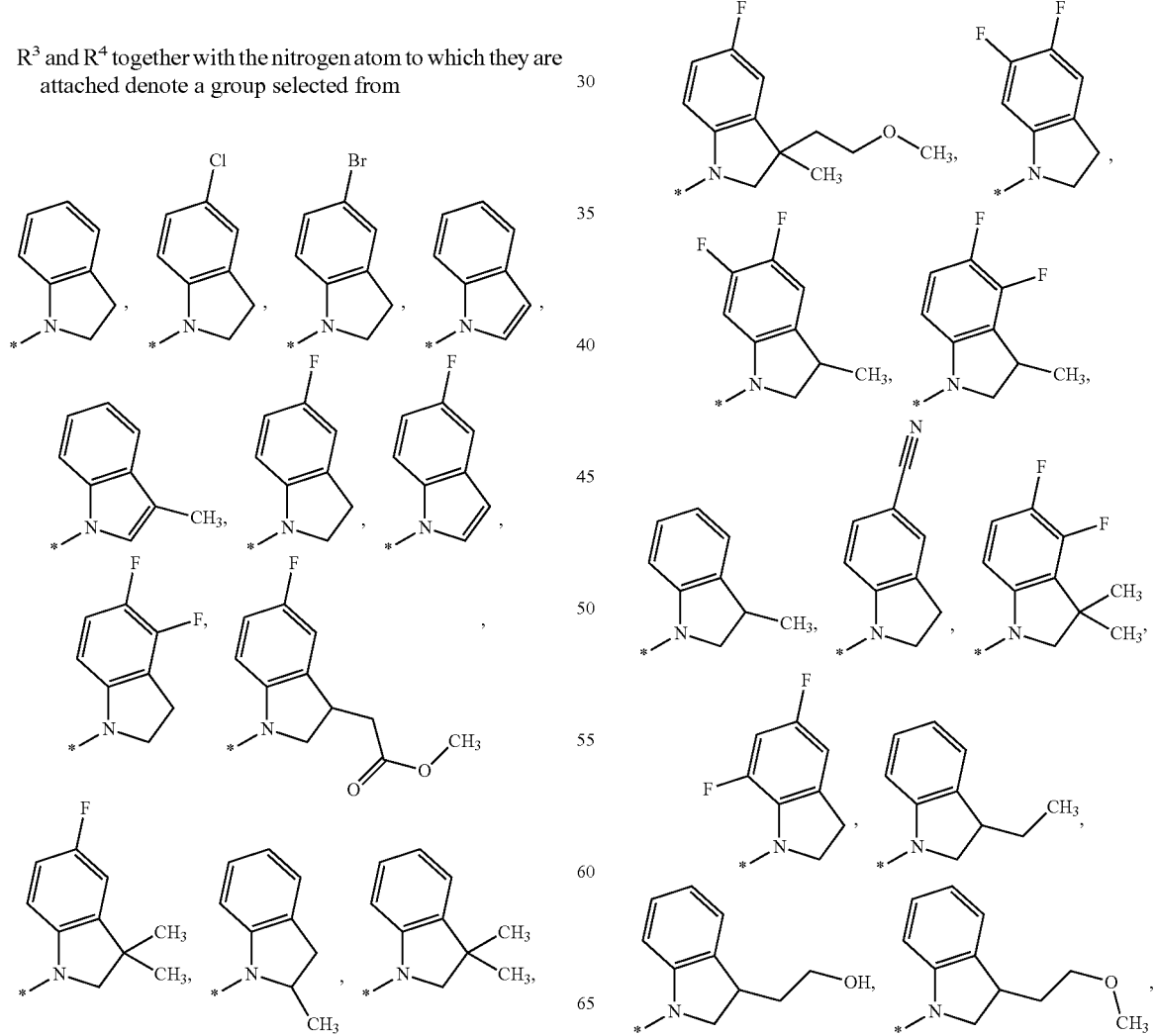
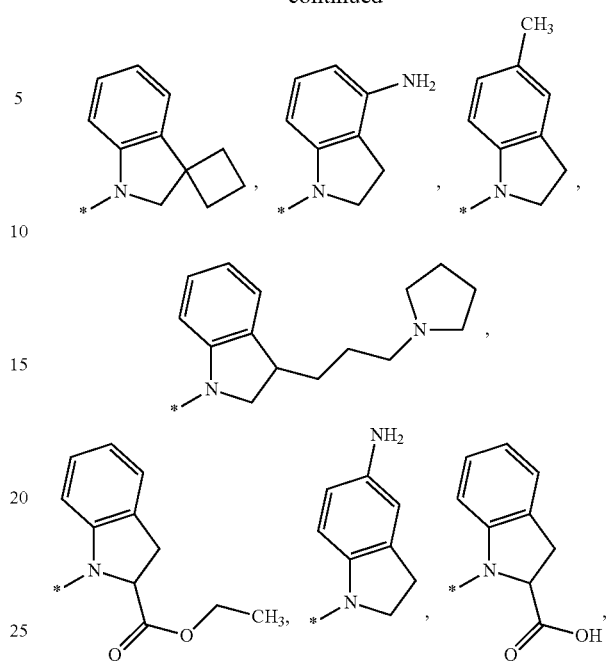

-continued
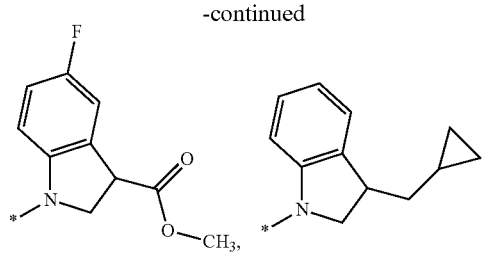
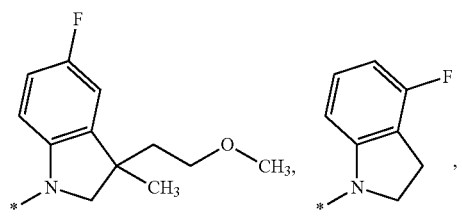
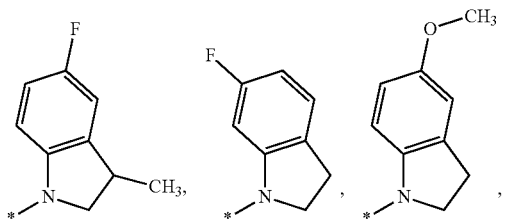
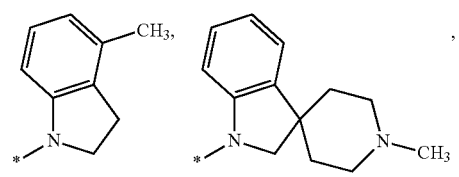
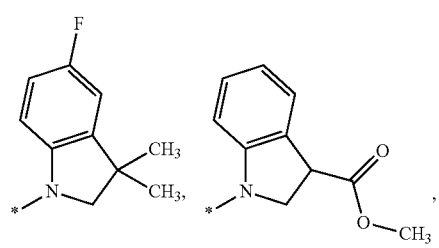
-continued
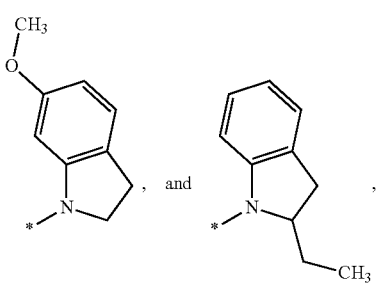
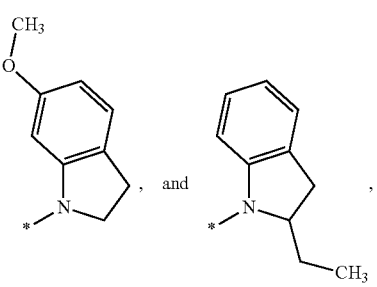
and the ring
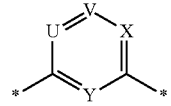
denotes the group
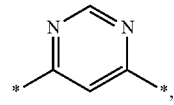
or a tautomer or salt thereof.
19. A compound of the formula I according to claim 1, selected from the group consisting of:
| No. | Structure |
|---|---|
| (7) | 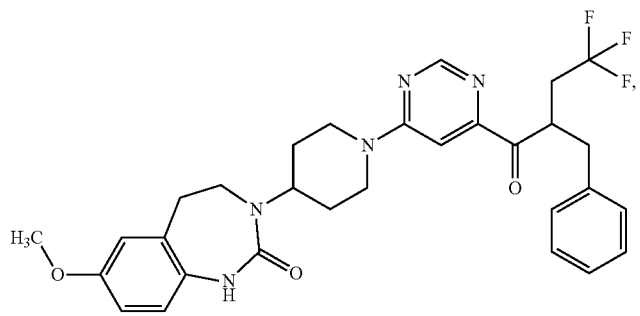 [SMILES: COc1ccc2c(c1)CCN(C1CCN(c3cc(C(=O)C(Cc4ccccc4)CC(F)(F)F)ncn3)CC1)C(=O)N2] |

-continued
| No. | Structure |
|---|---|
| (8) | 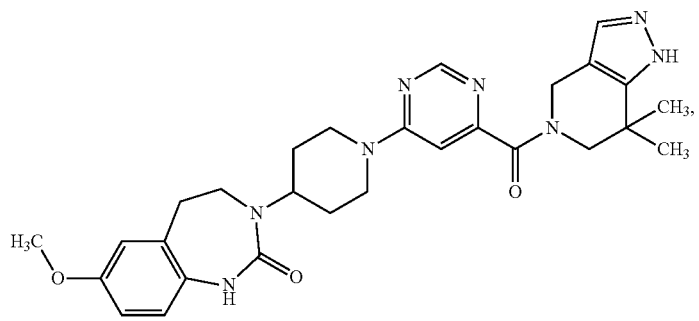 [SMILES: COc1ccc2c(c1)CCN(C1CCN(c3cc(C(=O)N4Cc5cn[nH]c5C(C)(C)C4)ncn3)CC1)C(=O)N2] |
| (9) | 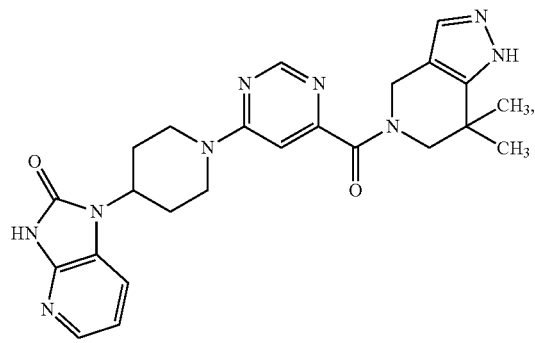 [SMILES: CC1(C)CN(C(=O)c2cc(N3CCC(n4c(=O)[nH]c5ncccc54)CC3)ncn2)Cc2cn[nH]c21] |
| (10) | 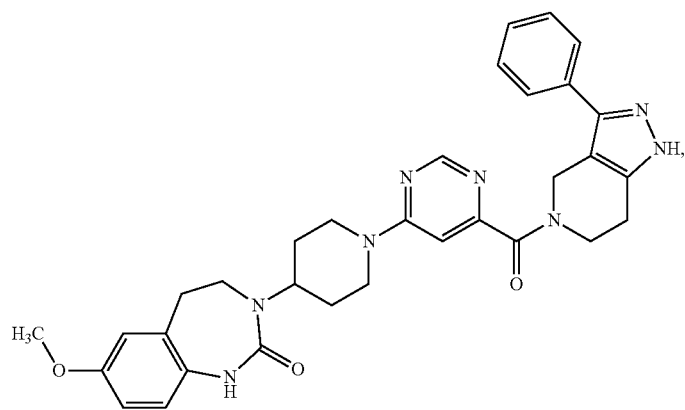 [SMILES: COc1ccc2c(c1)CCN(C1CCN(c3cc(C(=O)N4CCc5[nH]nc(-c6ccccc6)c5C4)ncn3)CC1)C(=O)N2] |
| (11) | 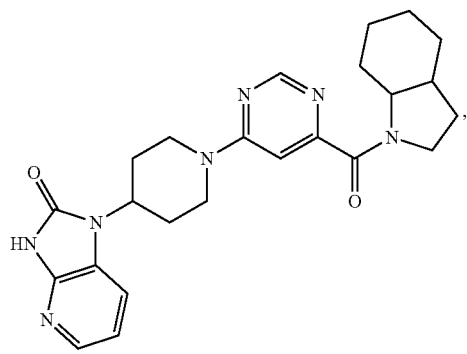 [SMILES: O=C(c1cc(N2CCC(n3c(=O)[nH]c4ncccc43)CC2)ncn1)N1CCC2CCCCC21] |

| No. | Structure |
|---|---|
| (12) | 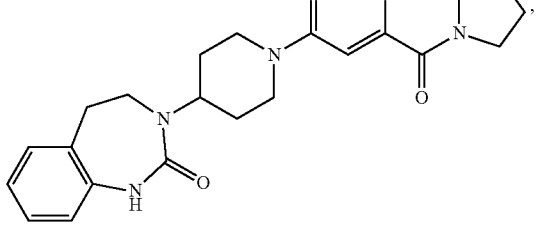 |
| (13) | 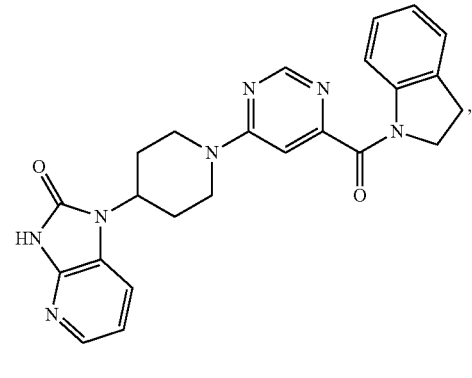 |
| (14) | 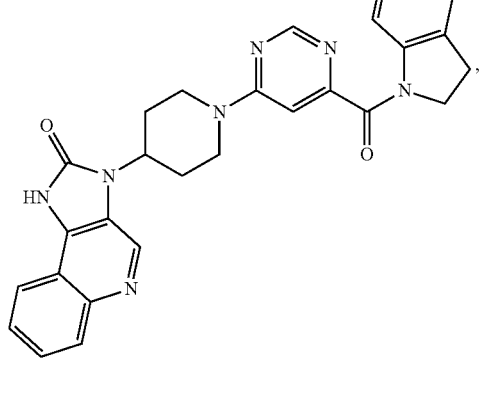 |
| (15) | 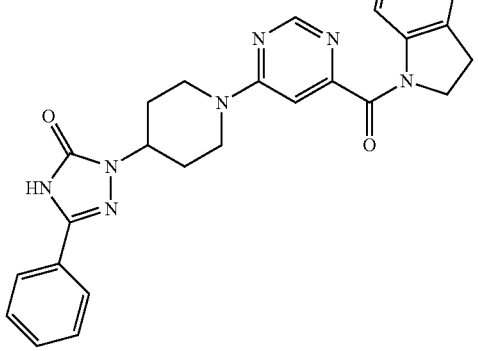 |

| No. | Structure |
|---|---|
| (16) | 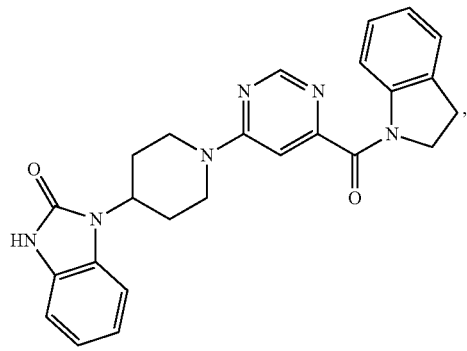 [SMILES: O=C(c1cc(N2CCC(n3c(=O)[nH]c4ncccc43)CC2)ncn1)N1CCc2ccccc21] |
| (17) | 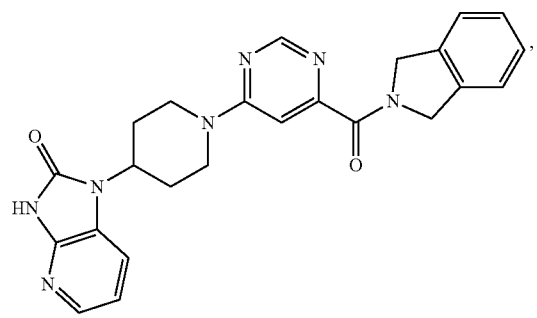 [SMILES: O=C(c1cc(N2CCC(n3c(=O)[nH]c4ncccc43)CC2)ncn1)N1Cc2ccccc2C1] |
| (18) | 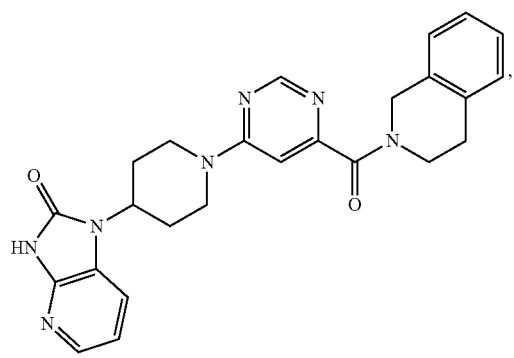 [SMILES: O=C(c1cc(N2CCC(n3c(=O)[nH]c4ncccc43)CC2)ncn1)N1CCc2ccccc2C1] |
| (19) | 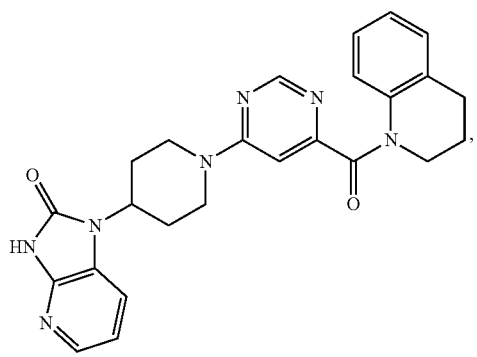 [SMILES: O=C(c1cc(N2CCC(n3c(=O)[nH]c4ncccc43)CC2)ncn1)N1CCCc2ccccc21] |

| No. | Structure |
|---|---|
| (20) | 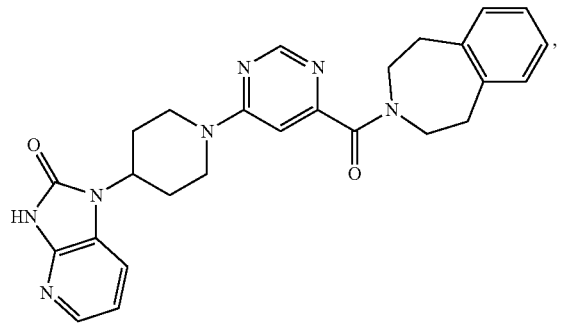 [SMILES: O=C(c1cc(N2CCC(n3c(=O)[nH]c4ncccc43)CC2)ncn1)N1CCc2ccccc2CC1] |
| (21) | 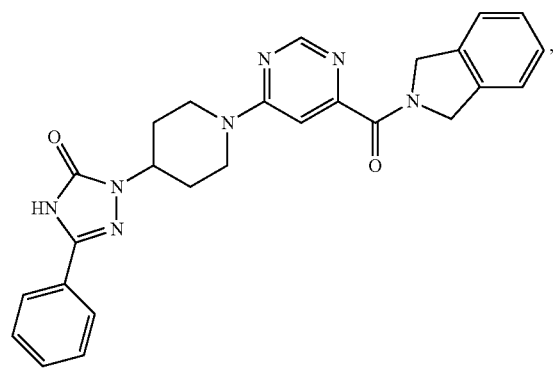 [SMILES: O=C(c1cc(N2CCC(n3nc(-c4ccccc4)[nH]c3=O)CC2)ncn1)N1Cc2ccccc2C1] |
| (22) | 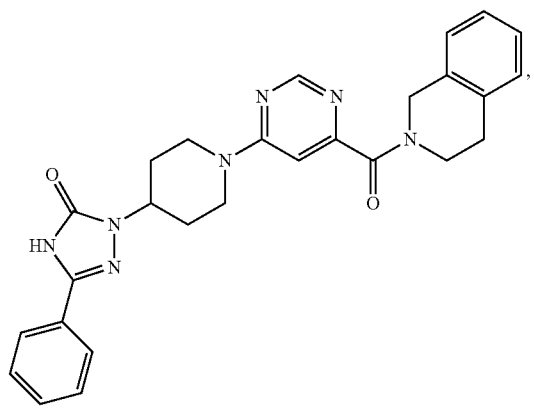 [SMILES: O=C(c1cc(N2CCC(n3nc(-c4ccccc4)[nH]c3=O)CC2)ncn1)N1CCc2ccccc2C1] |
| (23) | 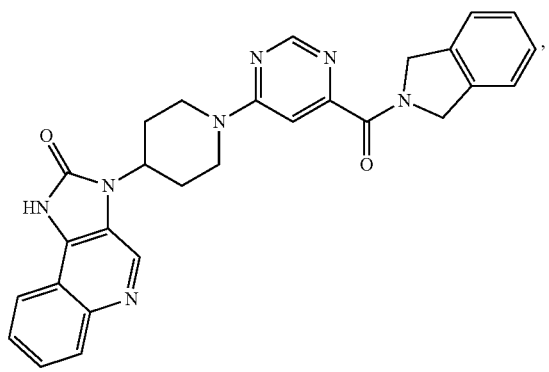 [SMILES: O=C(c1cc(N2CCC(n3c(=O)[nH]c4c5ccccc5ncc43)CC2)ncn1)N1Cc2ccccc2C1] |

-continued
| No. | Structure |
|---|---|
| (24) | 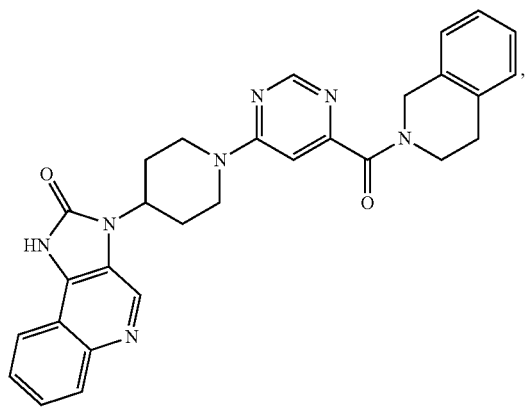 [SMILES: O=C(c1cc(N2CCC(n3c(=O)[nH]c4c5ccccc5ncc43)CC2)ncn1)N1CCc2ccccc2C1] |
| (25) | 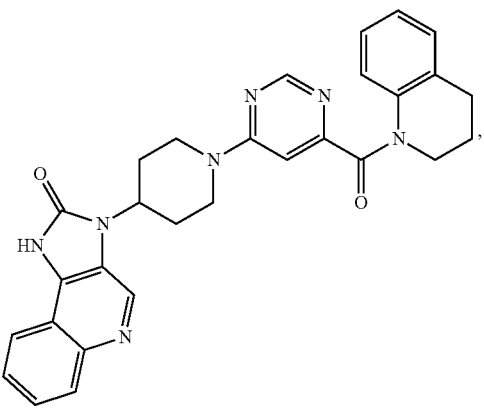 [SMILES: O=C(c1cc(N2CCC(n3c(=O)[nH]c4c5ccccc5ncc43)CC2)ncn1)N1CCCc2ccccc21] |
| (26) | 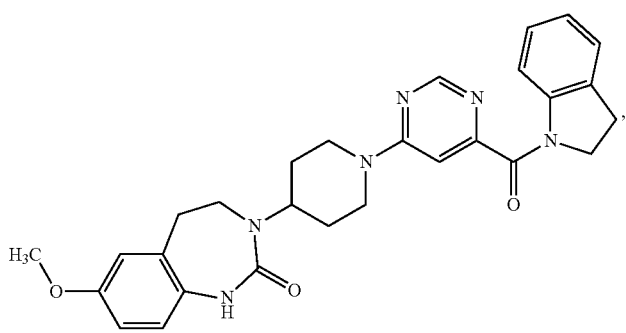 [SMILES: COc1ccc2c(c1)CCN(C1CCN(c3cc(C(=O)N4CCc5ccccc54)ncn3)CC1)C(=O)N2] |
| (27) | 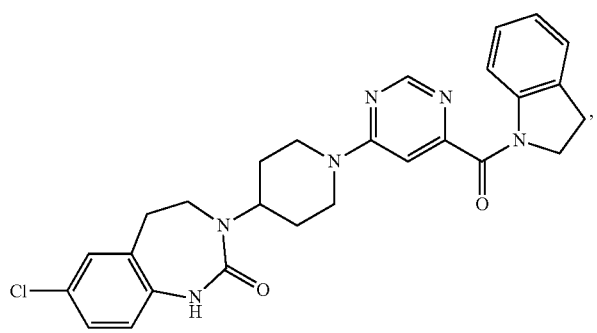 [SMILES: O=C(c1cc(N2CCC(N3CCc4cc(Cl)ccc4NC3=O)CC2)ncn1)N1CCc2ccccc21] |

-continued
| No. | Structure |
|---|---|
| (28) | 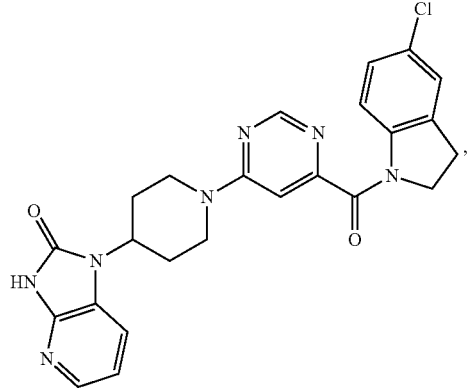 |
| (29) | 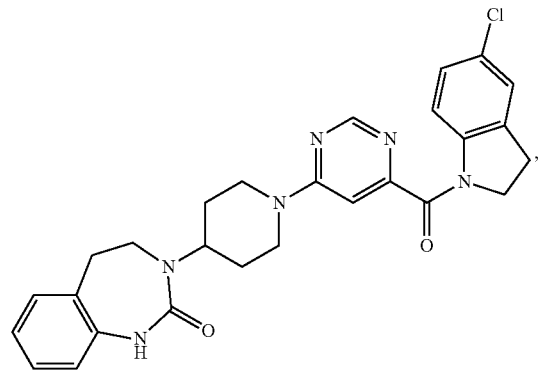 [SMILES: O=C(c1cc(N2CCC(N3CCc4ccccc4NC3=O)CC2)ncn1)N1CCc2cc(Cl)ccc21] |
| (30) | 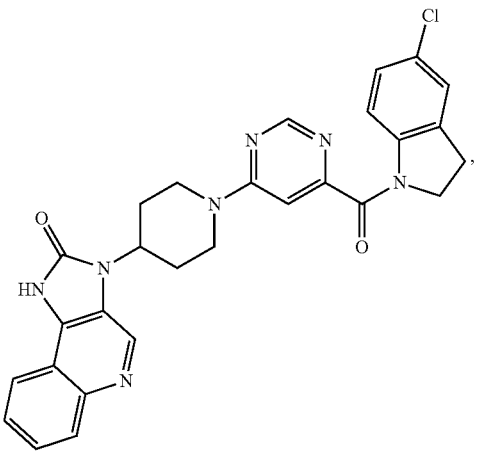 [SMILES: O=C(c1cc(N2CCC(n3c(=O)[nH]c4c5ccccc5ncc43)CC2)ncn1)N1CCc2cc(Cl)ccc21] |

-continued
| No. | Structure |
|---|---|
| (31) | 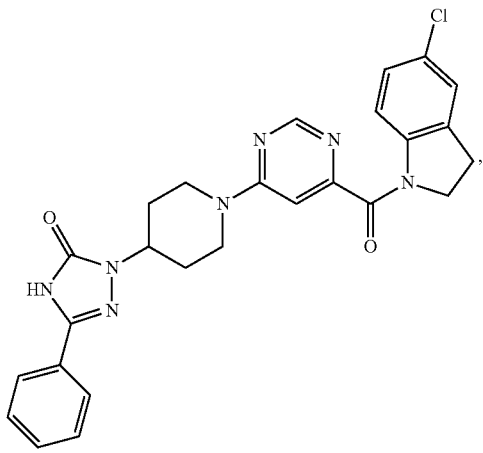 [SMILES: O=C(c1cc(N2CCC(n3nc(-c4ccccc4)[nH]c3=O)CC2)ncn1)N1CCc2cc(Cl)ccc21] |
| (32) | 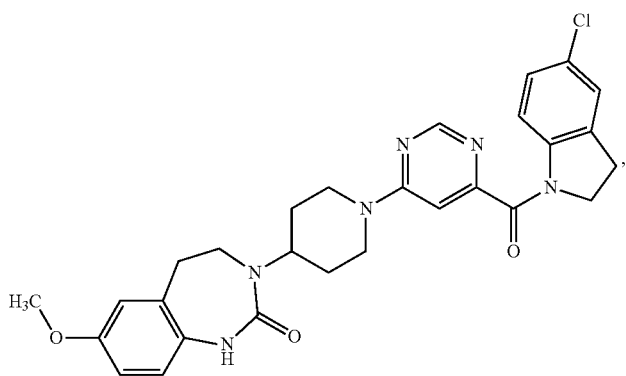 [SMILES: COc1ccc2c(c1)CCN(C1CCN(c3cc(C(=O)N4CCc5cc(Cl)ccc54)ncn3)CC1)C(=O)N2] |
| (33) | 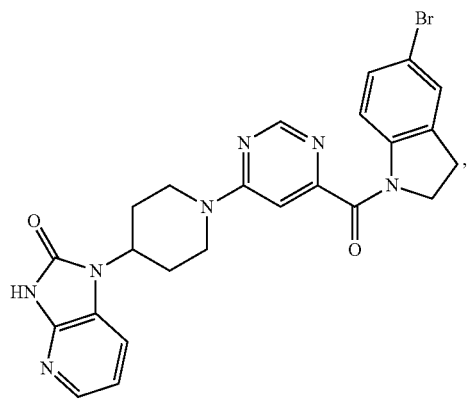 |

-continued
| No. | Structure |
|---|---|
| (34) | 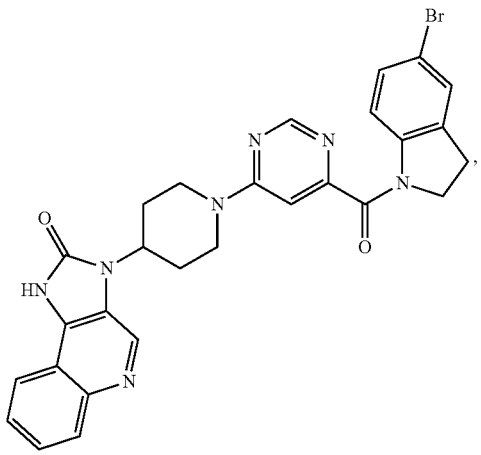 [SMILES: O=C(c1cc(N2CCC(n3c(=O)[nH]c4c5ccccc5ncc43)CC2)ncn1)N1CCc2cc(Br)ccc21] |
| (35) | 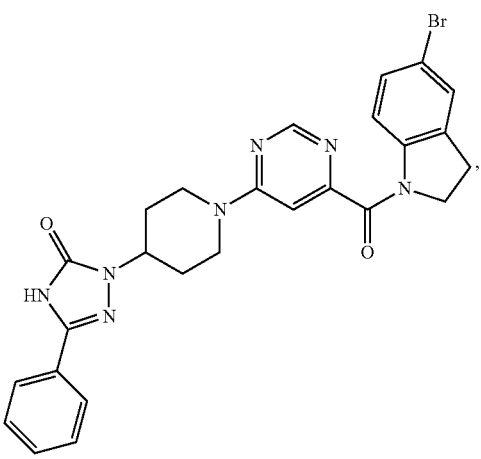 |
| (36) | 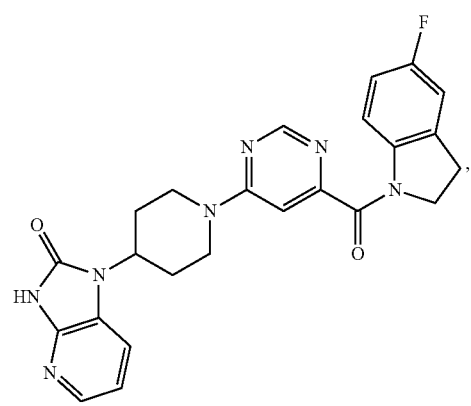 |

| No. | Structure |
|---|---|
| (37) | 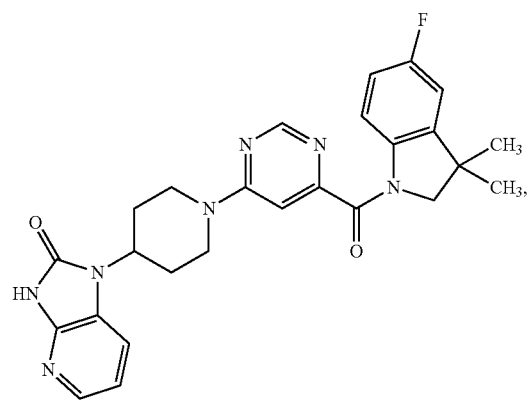 [SMILES: CC1(C)CN(C(=O)c2cc(N3CCC(n4c(=O)[nH]c5ncccc54)CC3)ncn2)c2ccc(F)cc21] |
| (38) | 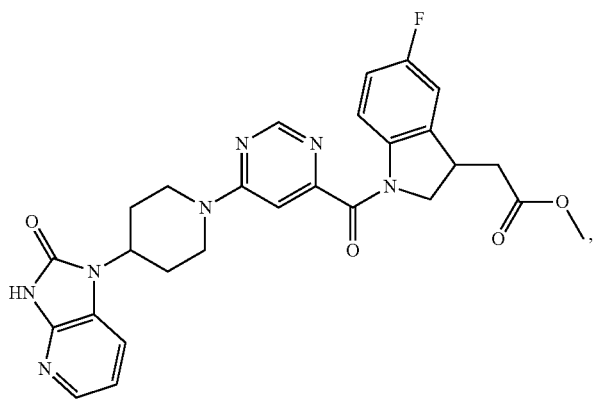 [SMILES: COC(=O)CC1CN(C(=O)c2cc(N3CCC(n4c(=O)[nH]c5ncccc54)CC3)ncn2)c2ccc(F)cc21] |
| (39) | 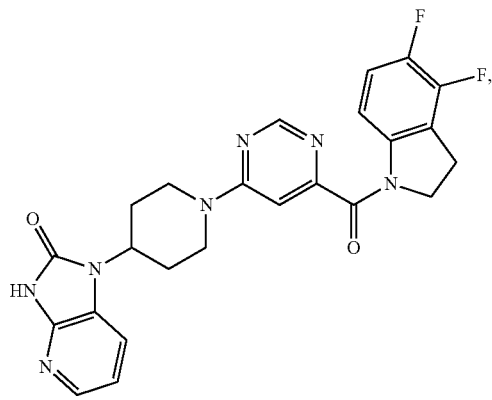 [SMILES: O=C(c1cc(N2CCC(n3c(=O)[nH]c4ncccc43)CC2)ncn1)N1CCc2c1ccc(F)c2F] |
| (40) | 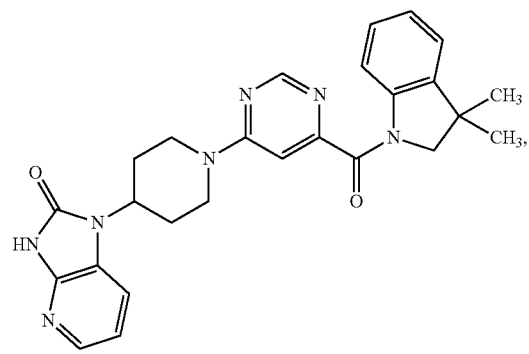 [SMILES: CC1(C)CN(C(=O)c2cc(N3CCC(n4c(=O)[nH]c5ncccc54)CC3)ncn2)c2ccccc21] |

| No. | Structure |
|---|---|
| (41) | 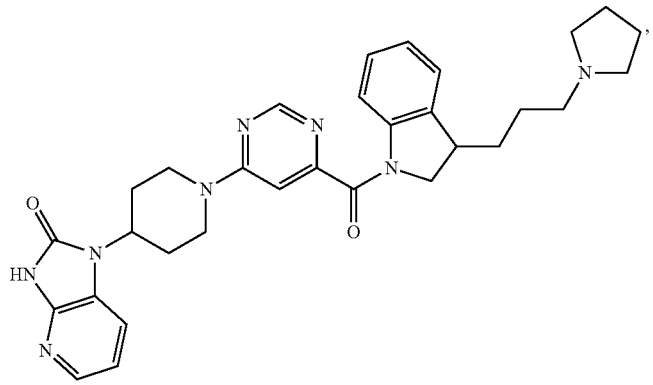 [SMILES: O=C(c1cc(N2CCC(n3c(=O)[nH]c4ncccc43)CC2)ncn1)N1CC(CCCN2CCCC2)c2ccccc21] |
| (42) | 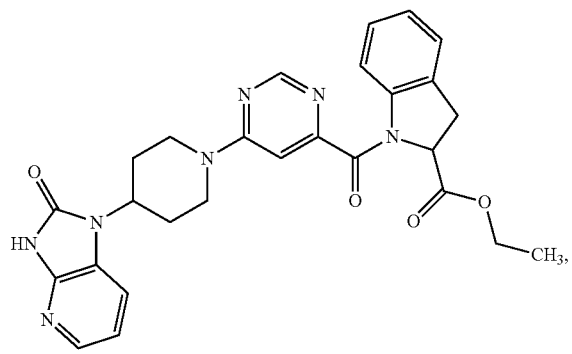 [SMILES: CCOC(=O)C1Cc2ccccc2N1C(=O)c1cc(N2CCC(n3c(=O)[nH]c4ncccc43)CC2)ncn1] |
| (43) | 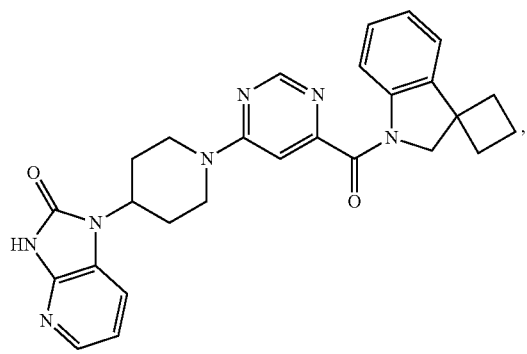 [SMILES: O=C(c1cc(N2CCC(n3c(=O)[nH]c4ncccc43)CC2)ncn1)N1CC2(CCC2)c2ccccc21] |
| (44) | 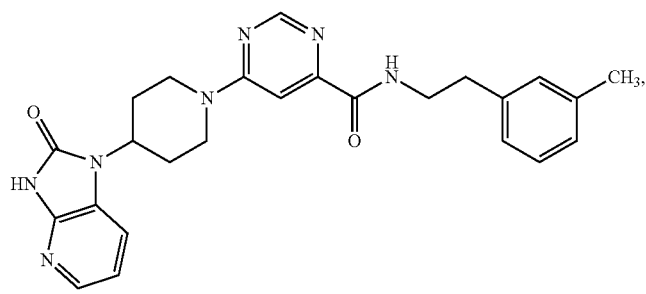 [SMILES: Cc1cccc(CCNC(=O)c2cc(N3CCC(n4c(=O)[nH]c5ncccc54)CC3)ncn2)c1] |

| No. | Structure |
|---|---|
| (45) | 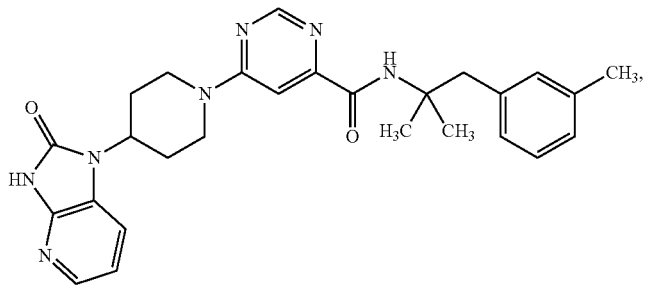 [SMILES: Cc1cccc(CC(C)(C)NC(=O)c2cc(N3CCC(n4c(=O)[nH]c5ncccc54)CC3)ncn2)c1] |
| (46) | 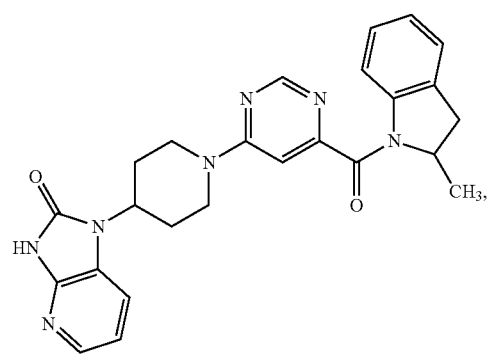 [SMILES: CC1Cc2ccccc2N1C(=O)c1cc(N2CCC(n3c(=O)[nH]c4ncccc43)CC2)ncn1] |
| (47) | 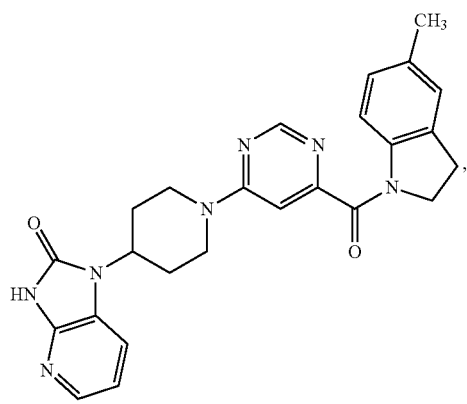 [SMILES: Cc1ccc2c(c1)CCN2C(=O)c1cc(N2CCC(n3c(=O)[nH]c4ncccc43)CC2)ncn1] |
| (48) | 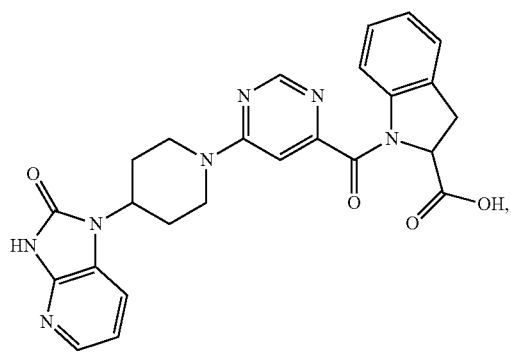 [SMILES: O=C(O)C1Cc2ccccc2N1C(=O)c1cc(N2CCC(n3c(=O)[nH]c4ncccc43)CC2)ncn1] |

-continued
| No. | Structure |
|---|---|
| (49) | 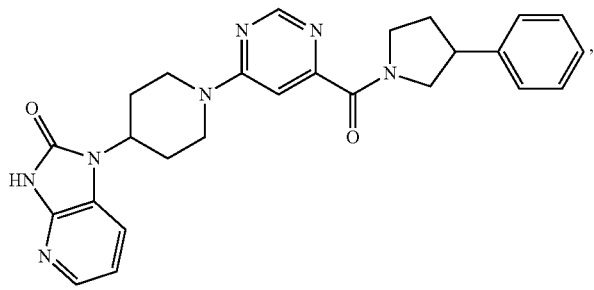 [SMILES: O=C(c1cc(N2CCC(n3c(=O)[nH]c4ncccc43)CC2)ncn1)N1CCC(c2ccccc2)C1 ; ","] |
| (50) | 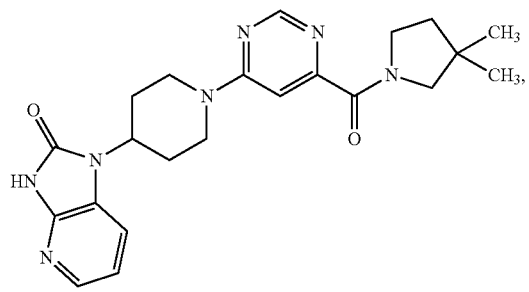 [SMILES: CC1(C)CCN(C(=O)c2cc(N3CCC(n4c(=O)[nH]c5ncccc54)CC3)ncn2)C1] |
| (51) | 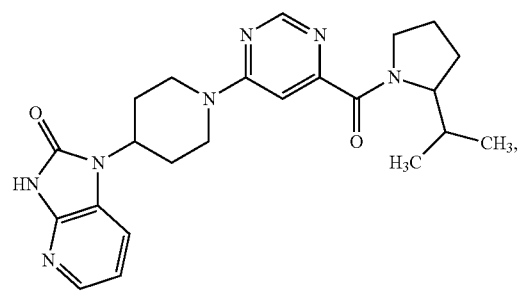 [SMILES: CC(C)C1CCCN1C(=O)c1cc(N2CCC(n3c(=O)[nH]c4ncccc43)CC2)ncn1] |
| (52) | 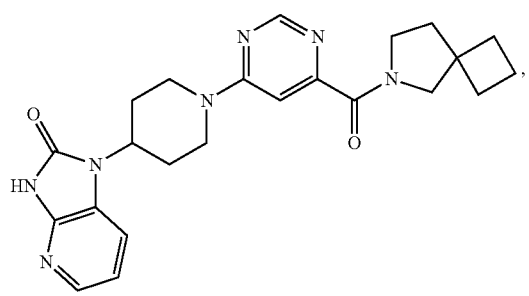 [SMILES: O=C(c1cc(N2CCC(n3c(=O)[nH]c4ncccc43)CC2)ncn1)N1CCC2(CCC2)C1 ; ","] |
| (53) | 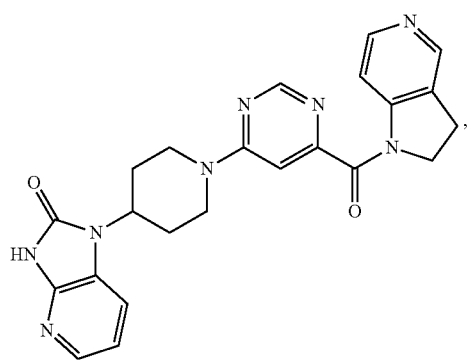 [SMILES: O=C(c1cc(N2CCC(n3c(=O)[nH]c4ncccc43)CC2)ncn1)N1CCc2cnccc21 ; ","] |

| No. | Structure |
|---|---|
| (54) | 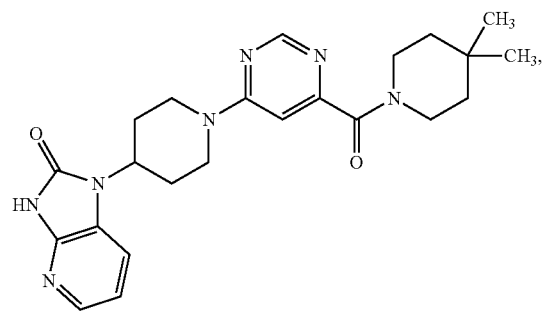 [SMILES: CC1(C)CCN(C(=O)c2cc(N3CCC(n4c(=O)[nH]c5ncccc54)CC3)ncn2)CC1] |
| (55) | 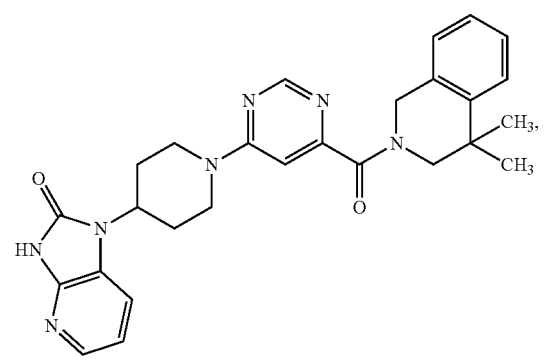 [SMILES: CC1(C)CN(C(=O)c2cc(N3CCC(n4c(=O)[nH]c5ncccc54)CC3)ncn2)Cc2ccccc21] |
| (56) | 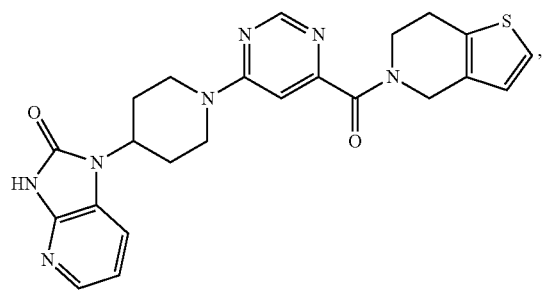 [SMILES: O=C(c1cc(N2CCC(n3c(=O)[nH]c4ncccc43)CC2)ncn1)N1CCc2sccc2C1 ; ","] |
| (57) | 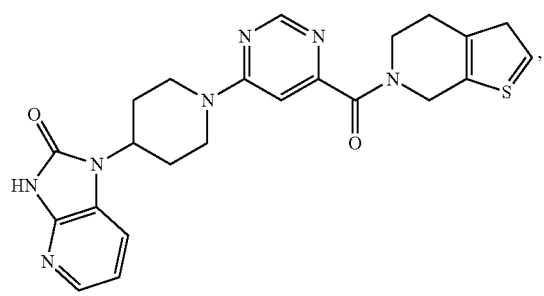 |
| (58) | 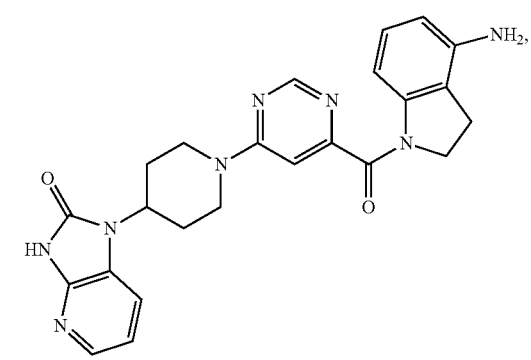 [SMILES: Nc1cccc2c1CCN2C(=O)c1cc(N2CCC(n3c(=O)[nH]c4ncccc43)CC2)ncn1] |

| No. | Structure |
|---|---|
| (59) | 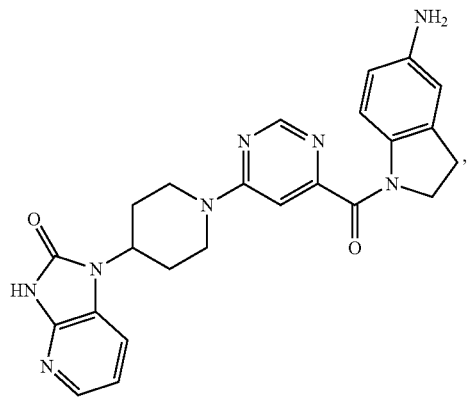 [SMILES: Nc1ccc2c(c1)CCN2C(=O)c1cc(N2CCC(n3c(=O)[nH]c4ncccc43)CC2)ncn1 ; ","] |
| (60) | 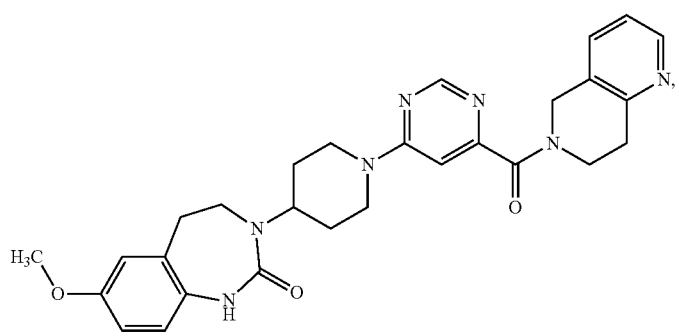 [SMILES: COc1ccc2c(c1)CCN(C1CCN(c3cc(C(=O)N4CCc5ncccc5C4)ncn3)CC1)C(=O)N2] |
| (61) | 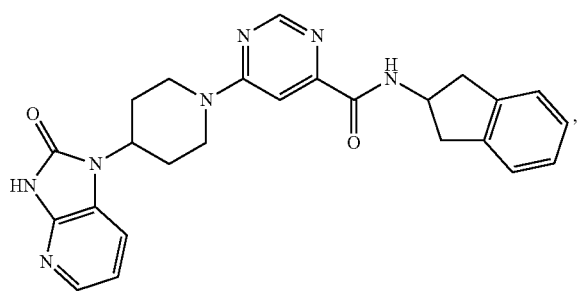 [SMILES: O=C(NC1Cc2ccccc2C1)c1cc(N2CCC(n3c(=O)[nH]c4ncccc43)CC2)ncn1] |
| (62) | 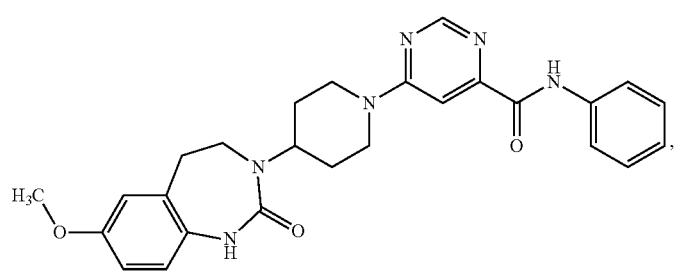 [SMILES: COc1ccc2c(c1)CCN(C1CCN(c3cc(C(=O)Nc4ccccc4)ncn3)CC1)C(=O)N2] |

| No. | Structure |
|---|---|
| (63) | 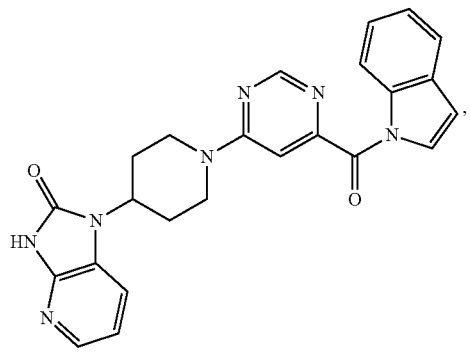 [SMILES: O=C(c1cc(N2CCC(n3c(=O)[nH]c4ncccc43)CC2)ncn1)n1ccc2ccccc21 ; ","] |
| (64) | 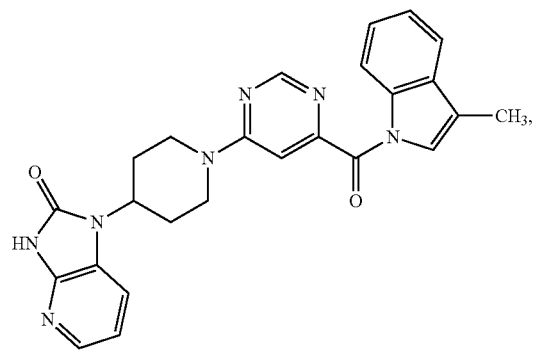 [SMILES: Cc1cn(C(=O)c2cc(N3CCC(n4c(=O)[nH]c5ncccc54)CC3)ncn2)c2ccccc12] |
| (65) | 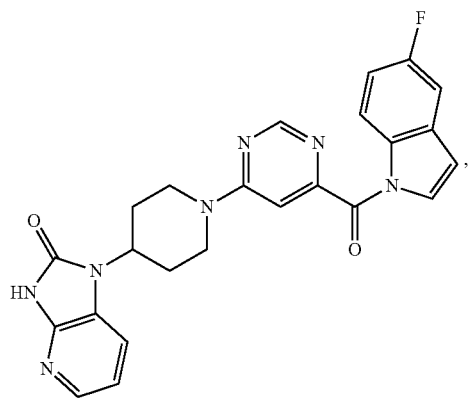 [SMILES: O=C(c1cc(N2CCC(n3c(=O)[nH]c4ncccc43)CC2)ncn1)n1ccc2cc(F)ccc21 ; ","] |
| (66) | 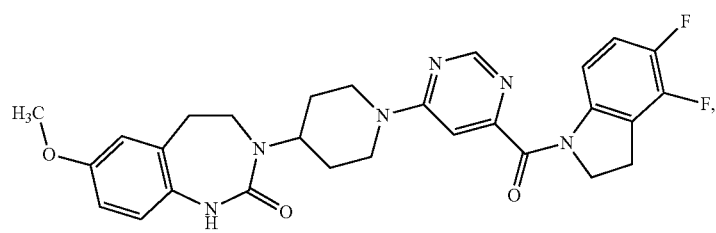 [SMILES: COc1ccc2c(c1)CCN(C1CCN(c3cc(C(=O)N4CCc5c4ccc(F)c5F)ncn3)CC1)C(=O)N2] |

| No. | Structure |
|---|---|
| (67) | 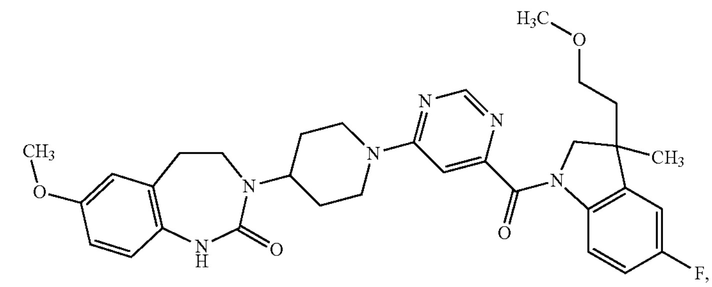 [SMILES: COCCC1(C)CN(C(=O)c2cc(N3CCC(N4CCc5cc(OC)ccc5NC4=O)CC3)ncn2)c2ccc(F)cc21] |
| (68) | 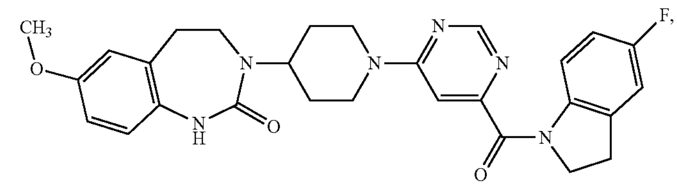 [SMILES: COc1ccc2c(c1)CCN(C1CCN(c3cc(C(=O)N4CCc5cc(F)ccc54)ncn3)CC1)C(=O)N2] |
| (69) | 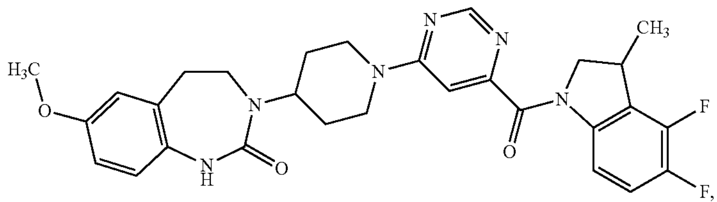 [SMILES: COc1ccc2c(c1)CCN(C1CCN(c3cc(C(=O)N4CC(C)c5c4ccc(F)c5F)ncn3)CC1)C(=O)N2] |
| (70) | 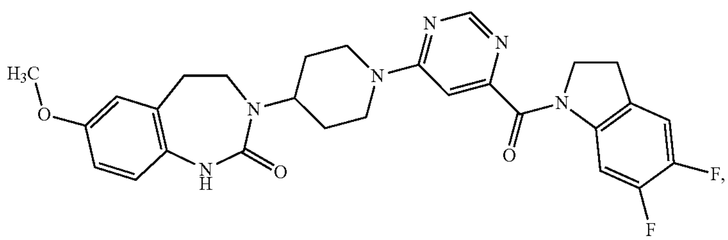 [SMILES: COc1ccc2c(c1)CCN(C1CCN(c3cc(C(=O)N4CCc5cc(F)c(F)cc54)ncn3)CC1)C(=O)N2] |
| (71) | 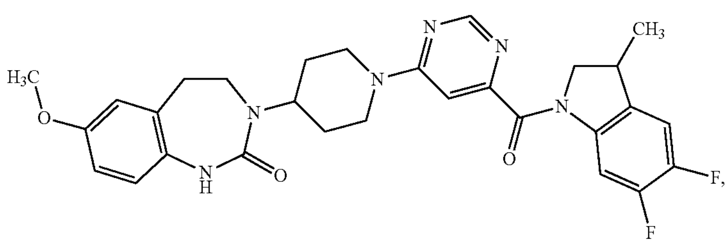 [SMILES: COc1ccc2c(c1)CCN(C1CCN(c3cc(C(=O)N4CC(C)c5cc(F)c(F)cc54)ncn3)CC1)C(=O)N2] |
| (72) | 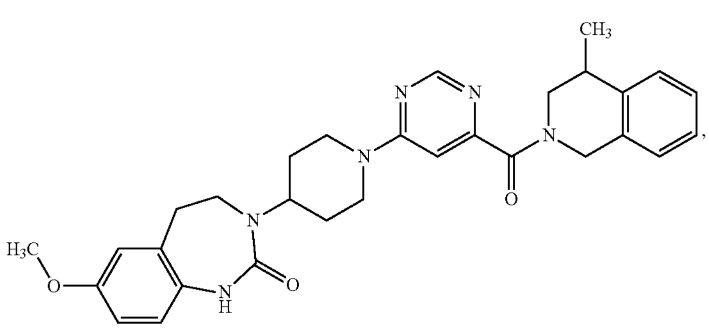 [SMILES: COc1ccc2c(c1)CCN(C1CCN(c3cc(C(=O)N4Cc5ccccc5C(C)C4)ncn3)CC1)C(=O)N2] |

-continued
| No. | Structure |
|---|---|
| (73) | 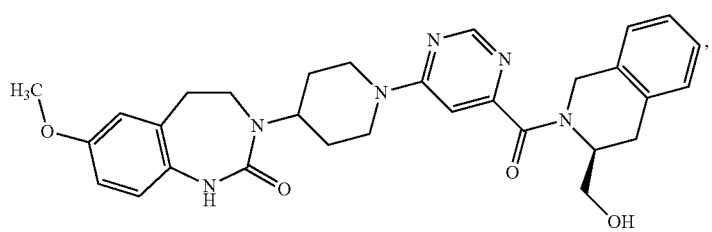 [SMILES: COc1ccc2c(c1)CCN(C1CCN(c3cc(C(=O)N4Cc5ccccc5C[C@H]4CO)ncn3)CC1)C(=O)N2] |
| (74) | 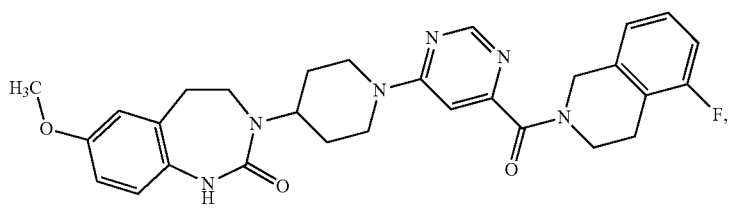 [SMILES: COc1ccc2c(c1)CCN(C1CCN(c3cc(C(=O)N4CCc5c(F)cccc5C4)ncn3)CC1)C(=O)N2] |
| (75) | 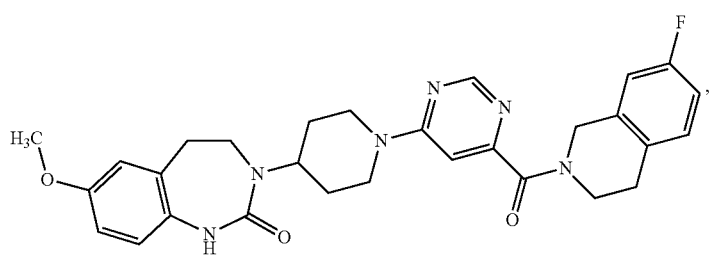 [SMILES: COc1ccc2c(c1)CCN(C1CCN(c3cc(C(=O)N4CCc5ccc(F)cc5C4)ncn3)CC1)C(=O)N2 ; ","] |
| (76) | 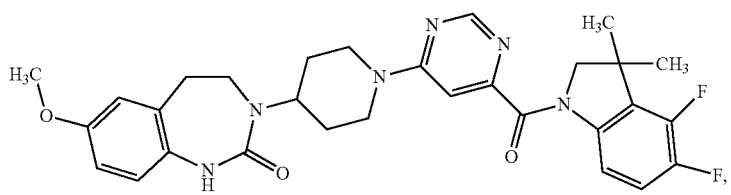 [SMILES: COc1ccc2c(c1)CCN(C1CCN(c3cc(C(=O)N4CC(C)(C)c5c4ccc(F)c5F)ncn3)CC1)C(=O)N2] |
| (77) | 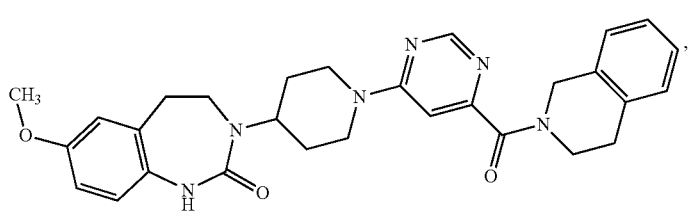 [SMILES: COc1ccc2c(c1)CCN(C1CCN(c3cc(C(=O)N4CCc5ccccc5C4)ncn3)CC1)C(=O)N2 ; ","] |
| (78) | 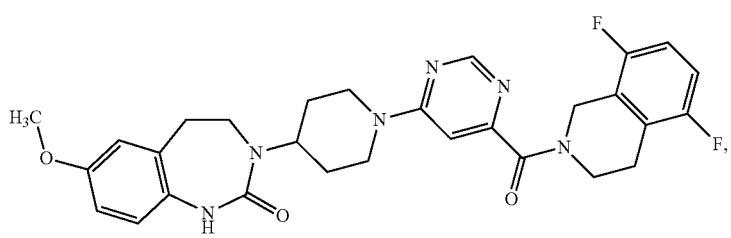 [SMILES: COc1ccc2c(c1)CCN(C1CCN(c3cc(C(=O)N4CCc5c(F)ccc(F)c5C4)ncn3)CC1)C(=O)N2] |
| (79) | 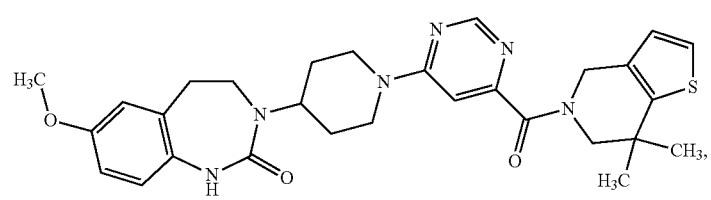 [SMILES: COc1ccc2c(c1)CCN(C1CCN(c3cc(C(=O)N4Cc5ccsc5C(C)(C)C4)ncn3)CC1)C(=O)N2] |

| No. | Structure |
|---|---|
| (80) | 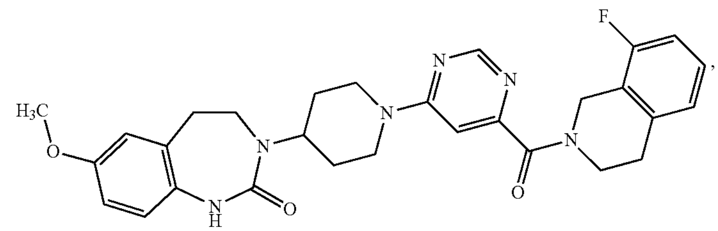 [SMILES: COc1ccc2c(c1)CCN(C1CCN(c3cc(C(=O)N4CCc5cccc(F)c5C4)ncn3)CC1)C(=O)N2] |
| (81) | 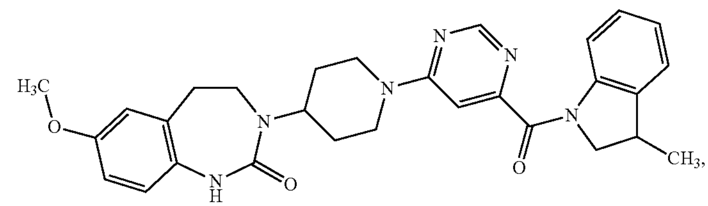 [SMILES: COc1ccc2c(c1)CCN(C1CCN(c3cc(C(=O)N4CC(C)c5ccccc54)ncn3)CC1)C(=O)N2] |
| (82) | 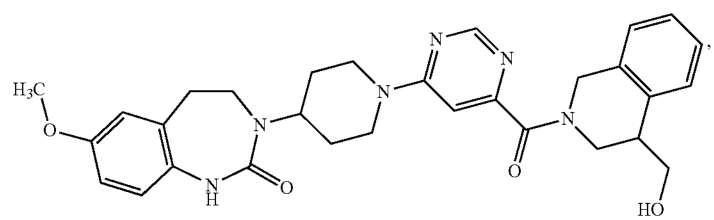 [SMILES: COc1ccc2c(c1)CCN(C1CCN(c3cc(C(=O)N4Cc5ccccc5C(CO)C4)ncn3)CC1)C(=O)N2] |
| (83) | 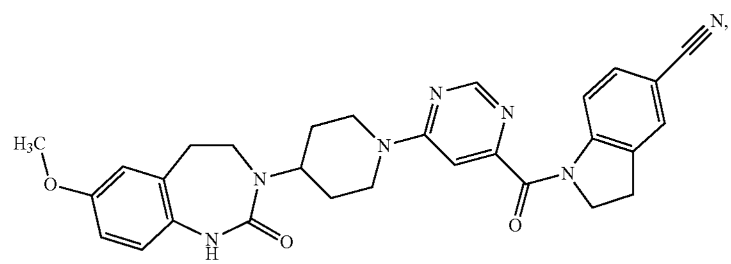 [SMILES: COc1ccc2c(c1)CCN(C1CCN(c3cc(C(=O)N4CCc5cc(C#N)ccc54)ncn3)CC1)C(=O)N2] |
| (84) | 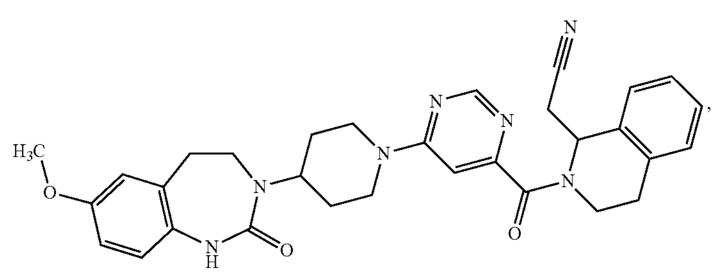 [SMILES: COc1ccc2c(c1)CCN(C1CCN(c3cc(C(=O)N4CCc5ccccc5C4CC#N)ncn3)CC1)C(=O)N2] |
| (85) | 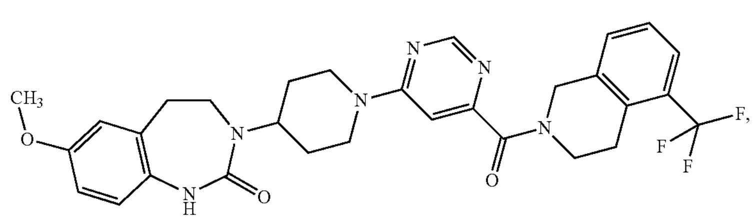 [SMILES: COc1ccc2c(c1)CCN(C1CCN(c3cc(C(=O)N4CCc5c(cccc5C(F)(F)F)C4)ncn3)CC1)C(=O)N2] |

| No. | Structure |
|---|---|
| (86) | 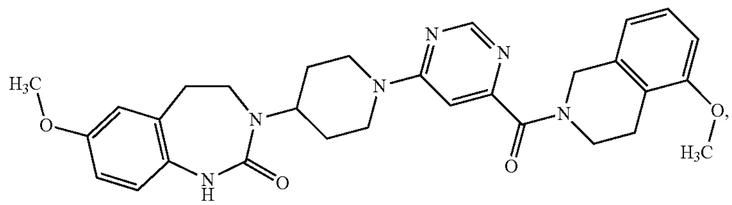 [SMILES: COc1ccc2c(c1)CCN(C1CCN(c3cc(C(=O)N4CCc5c(cccc5OC)C4)ncn3)CC1)C(=O)N2] |
| (87) | 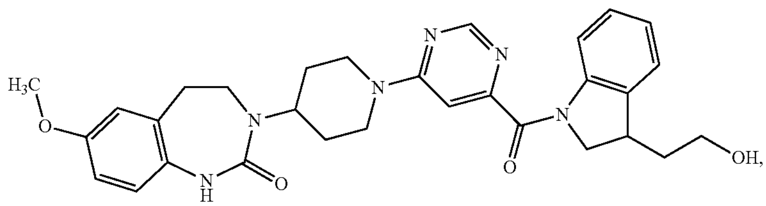 [SMILES: COc1ccc2c(c1)CCN(C1CCN(c3cc(C(=O)N4CC(CCO)c5ccccc54)ncn3)CC1)C(=O)N2] |
| (88) | 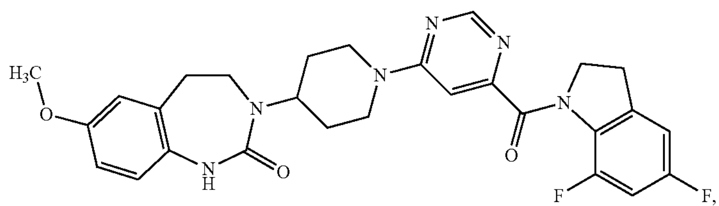 [SMILES: COc1ccc2c(c1)CCN(C1CCN(c3cc(C(=O)N4CCc5cc(F)cc(F)c54)ncn3)CC1)C(=O)N2] |
| (89) | 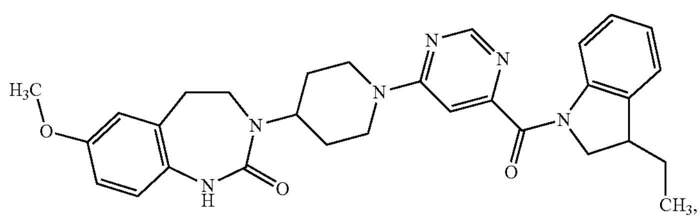 [SMILES: CCC1CN(C(=O)c2cc(N3CCC(N4CCc5cc(OC)ccc5NC4=O)CC3)ncn2)c2ccccc21] |
| (90) | 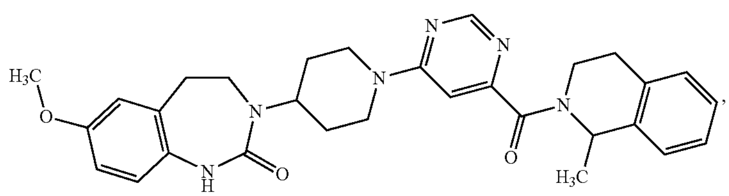 [SMILES: COc1ccc2c(c1)CCN(C1CCN(c3cc(C(=O)N4CCc5ccccc5C4C)ncn3)CC1)C(=O)N2] |
| (91) | 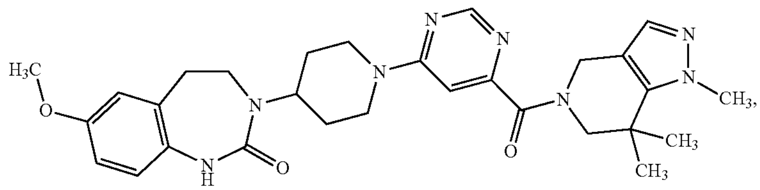 [SMILES: COc1ccc2c(c1)CCN(C1CCN(c3cc(C(=O)N4Cc5cnn(C)c5C(C)(C)C4)ncn3)CC1)C(=O)N2] |
| (92) | 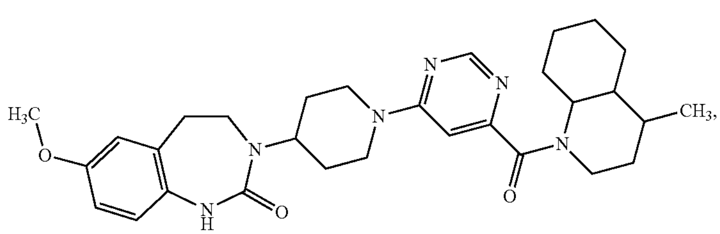 [SMILES: COc1ccc2c(c1)CCN(C1CCN(c3cc(C(=O)N4CCC(C)C5CCCCC54)ncn3)CC1)C(=O)N2] |

| No. | Structure |
|---|---|
| (93) | 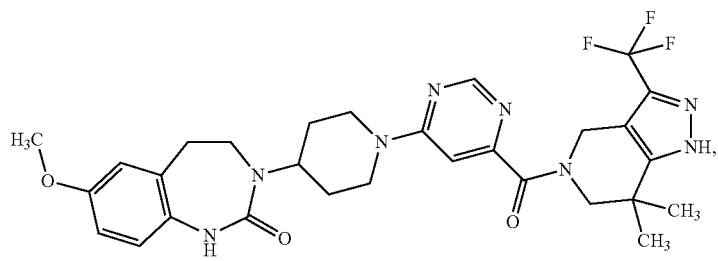 [SMILES: COc1ccc2c(c1)CCN(C1CCN(c3cc(C(=O)N4Cc5c(C(F)(F)F)n[nH]c5C(C)(C)C4)ncn3)CC1)C(=O)N2] |
| (94) | 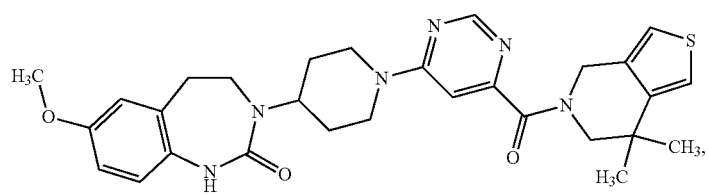 [SMILES: COc1ccc2c(c1)CCN(C1CCN(c3cc(C(=O)N4Cc5cscc5C(C)(C)C4)ncn3)CC1)C(=O)N2] |
| (95) | 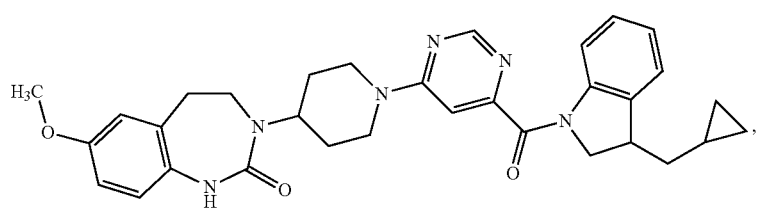 [SMILES: COc1ccc2c(c1)CCN(C1CCN(c3cc(C(=O)N4CC(CC5CC5)c5ccccc54)ncn3)CC1)C(=O)N2] |
| (96) | 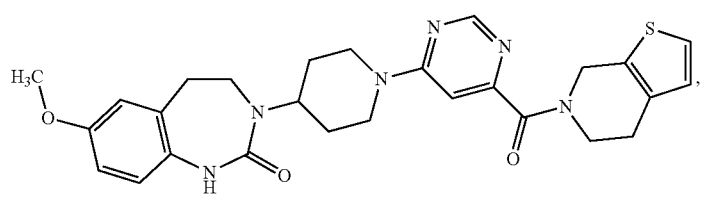 [SMILES: COc1ccc2c(c1)CCN(C1CCN(c3cc(C(=O)N4CCc5ccsc5C4)ncn3)CC1)C(=O)N2] |
| (97) | 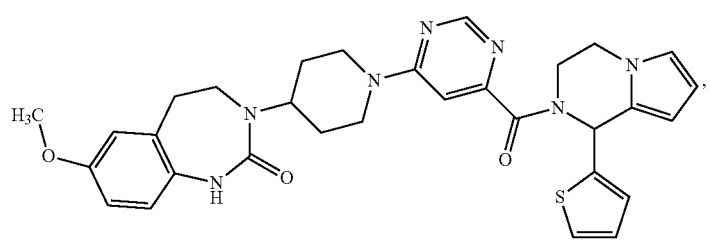 [SMILES: COc1ccc2c(c1)CCN(C1CCN(c3cc(C(=O)N4CCn5cccc5C4c4cccs4)ncn3)CC1)C(=O)N2] |
| (98) | 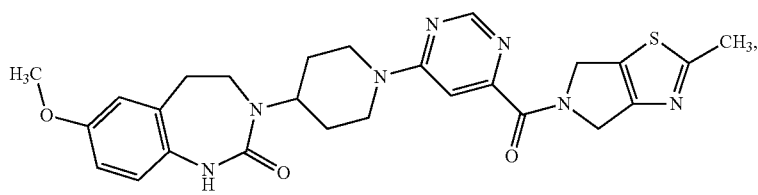 [SMILES: COc1ccc2c(c1)CCN(C1CCN(c3cc(C(=O)N4Cc5nc(C)sc5C4)ncn3)CC1)C(=O)N2] |
| (99) | 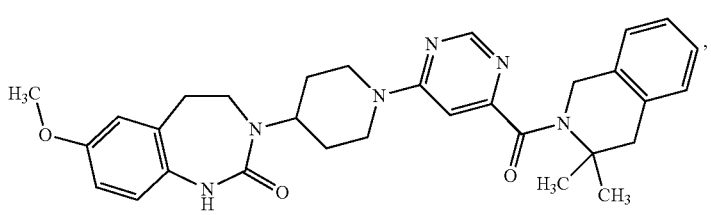 [SMILES: COc1ccc2c(c1)CCN(C1CCN(c3cc(C(=O)N4Cc5ccccc5CC4(C)C)ncn3)CC1)C(=O)N2] |

| No. | Structure |
|---|---|
| (100) | 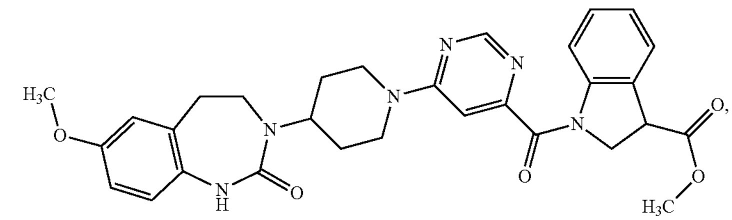 [SMILES: COC(=O)C1CN(C(=O)c2cc(N3CCC(N4CCc5cc(OC)ccc5NC4=O)CC3)ncn2)c2ccccc21] |
| (101) | 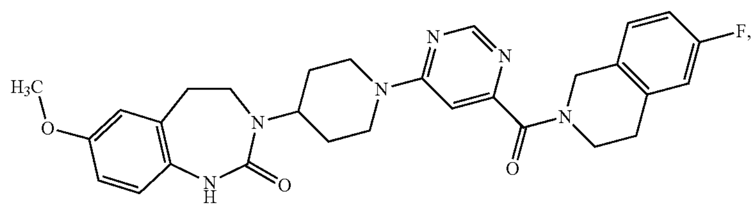 [SMILES: COc1ccc2c(c1)CCN(C1CCN(c3cc(C(=O)N4CCc5cc(F)ccc5C4)ncn3)CC1)C(=O)N2] |
| (102) | 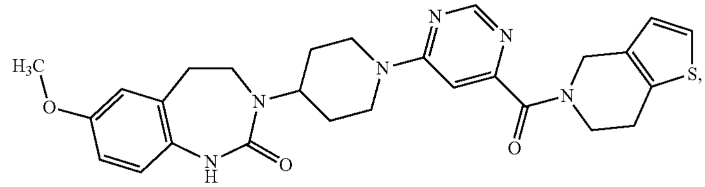 [SMILES: COc1ccc2c(c1)CCN(C1CCN(c3cc(C(=O)N4CCc5sccc5C4)ncn3)CC1)C(=O)N2] |
| (103) | 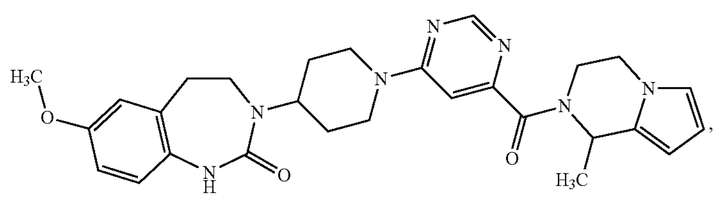 [SMILES: COc1ccc2c(c1)CCN(C1CCN(c3cc(C(=O)N4CCn5cccc5C4C)ncn3)CC1)C(=O)N2] |
| (104) | 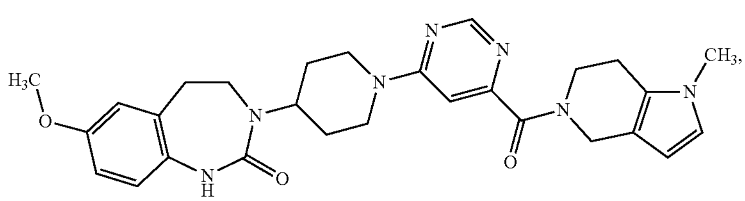 [SMILES: COc1ccc2c(c1)CCN(C1CCN(c3cc(C(=O)N4CCc5c(ccn5C)C4)ncn3)CC1)C(=O)N2] |
| (105) | 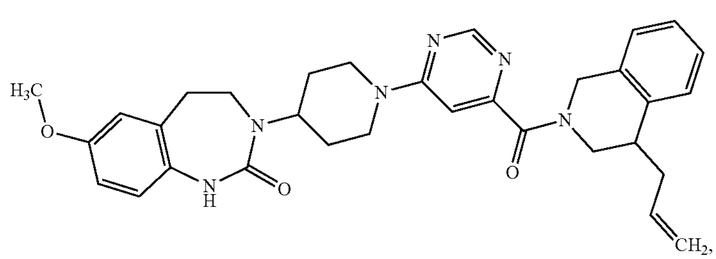 [SMILES: C=CCC1CN(C(=O)c2cc(N3CCC(N4CCc5cc(OC)ccc5NC4=O)CC3)ncn2)Cc2ccccc21] |
| (106) | 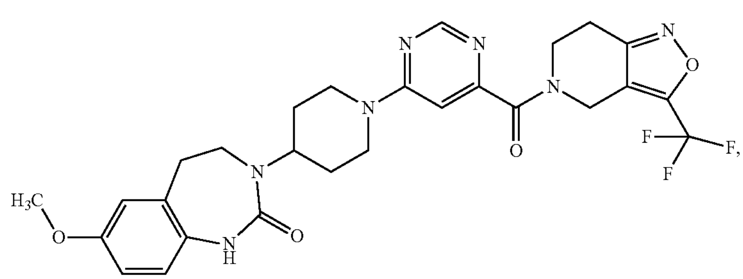 [SMILES: COc1ccc2c(c1)CCN(C1CCN(c3cc(C(=O)N4CCc5noc(C(F)(F)F)c5C4)ncn3)CC1)C(=O)N2] |

-continued

| No. | Structure |
|---|---|
| (107) | 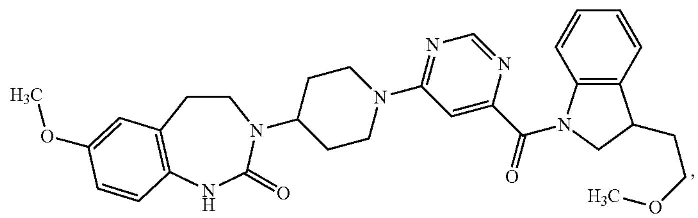 [SMILES: COCCC1CN(C(=O)c2cc(N3CCC(N4CCc5cc(OC)ccc5NC4=O)CC3)ncn2)c2ccccc21] |
| (108) | 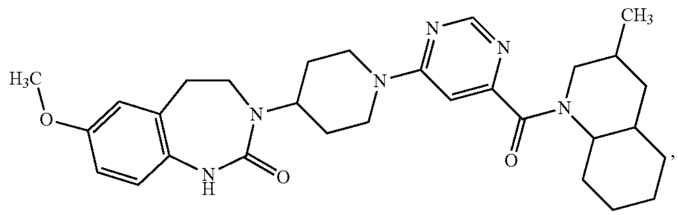 [SMILES: COc1ccc2c(c1)CCN(C1CCN(c3cc(C(=O)N4CC(C)CC5CCCCC54)ncn3)CC1)C(=O)N2] |
| (109) | 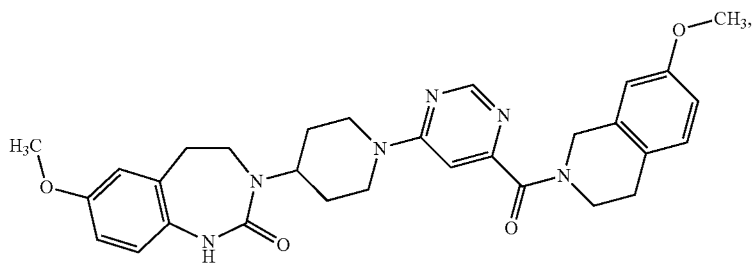 [SMILES: COc1ccc2c(c1)CN(C(=O)c1cc(N3CCC(N4CCc5cc(OC)ccc5NC4=O)CC3)ncn1)CC2] |
| (110) | 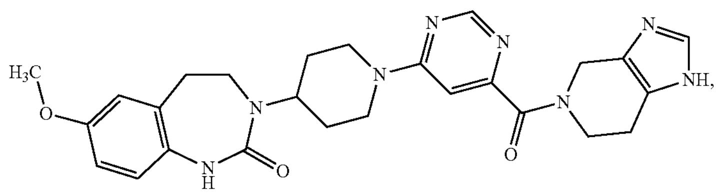 [SMILES: COc1ccc2c(c1)CCN(C1CCN(c3cc(C(=O)N4CCc5[nH]cnc5C4)ncn3)CC1)C(=O)N2] |
| (111) | 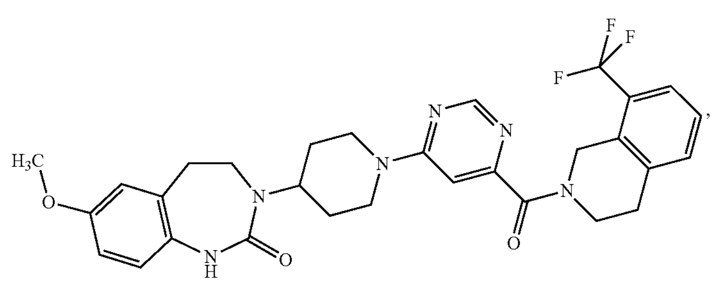 [SMILES: COc1ccc2c(c1)CCN(C1CCN(c3cc(C(=O)N4CCc5cccc(C(F)(F)F)c5C4)ncn3)CC1)C(=O)N2] |
| (112) | 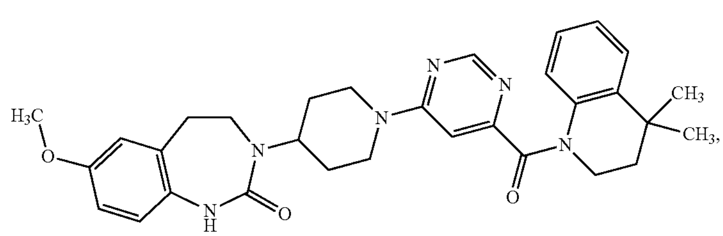 [SMILES: COc1ccc2c(c1)CCN(C1CCN(c3cc(C(=O)N4CCC(C)(C)c5ccccc54)ncn3)CC1)C(=O)N2] |
| (113) | 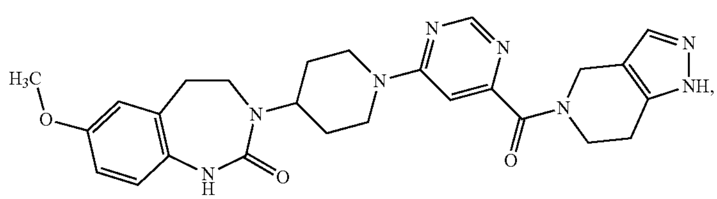 [SMILES: COc1ccc2c(c1)CCN(C1CCN(c3cc(C(=O)N4CCc5[nH]ncc5C4)ncn3)CC1)C(=O)N2] |

| No. | Structure |
|---|---|
| (114) | 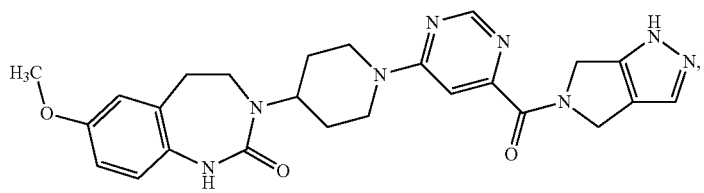 [SMILES: COc1ccc2c(c1)CCN(C1CCN(c3cc(C(=O)N4Cc5cn[nH]c5C4)ncn3)CC1)C(=O)N2] |
| (115) | 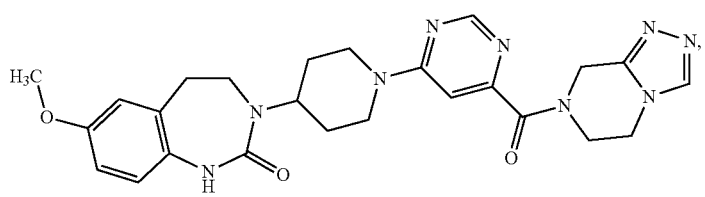 [SMILES: COc1ccc2c(c1)CCN(C1CCN(c3cc(C(=O)N4CCn5cnnc5C4)ncn3)CC1)C(=O)N2] |
| (116) | 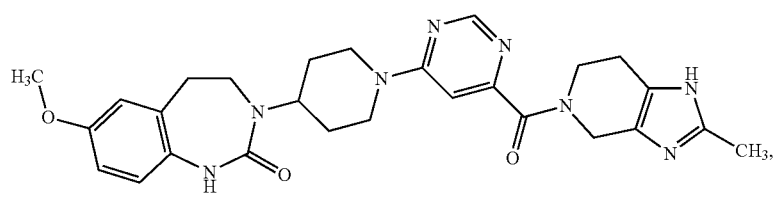 [SMILES: COc1ccc2c(c1)CCN(C1CCN(c3cc(C(=O)N4CCc5[nH]c(C)nc5C4)ncn3)CC1)C(=O)N2] |
| (121) | 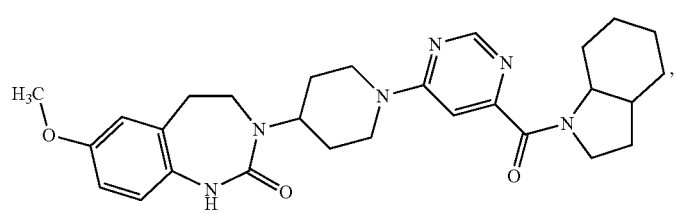 [SMILES: COc1ccc2c(c1)CCN(C1CCN(c3cc(C(=O)N4CCC5CCCCC54)ncn3)CC1)C(=O)N2 ; ","] |
| (123) | 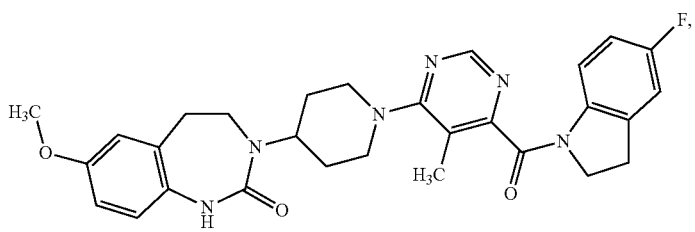 [SMILES: COc1ccc2c(c1)CCN(C1CCN(c3ncnc(C(=O)N4CCc5cc(F)ccc54)c3C)CC1)C(=O)N2] |
| (126) | 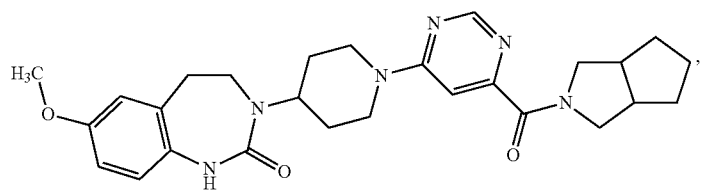 [SMILES: COc1ccc2c(c1)CCN(C1CCN(c3cc(C(=O)N4CC5CCCC5C4)ncn3)CC1)C(=O)N2] |
| (127) | 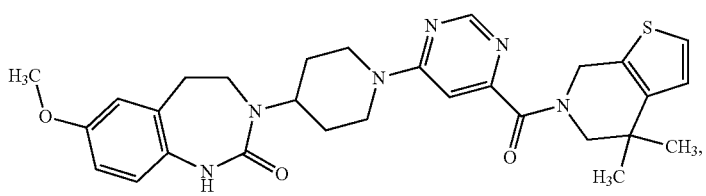 [SMILES: COc1ccc2c(c1)CCN(C1CCN(c3cc(C(=O)N4Cc5sccc5C(C)(C)C4)ncn3)CC1)C(=O)N2] |

| No. | Structure |
|---|---|
| (128) | 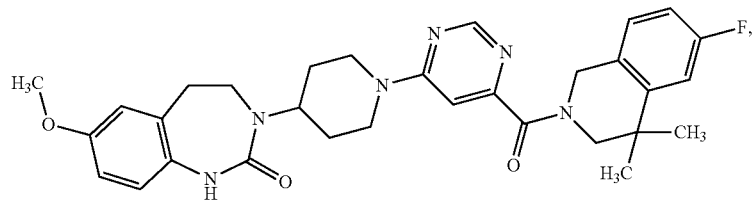 [SMILES: COc1ccc2c(c1)CCN(C1CCN(c3cc(C(=O)N4Cc5ccc(F)cc5C(C)(C)C4)ncn3)CC1)C(=O)N2] |
| (129) | 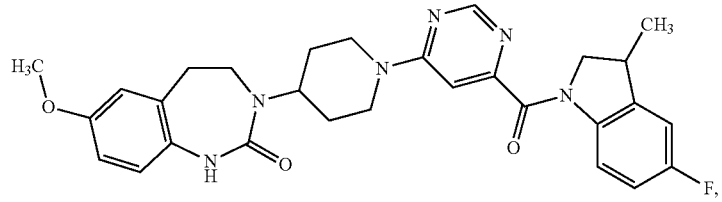 |
| (130) | 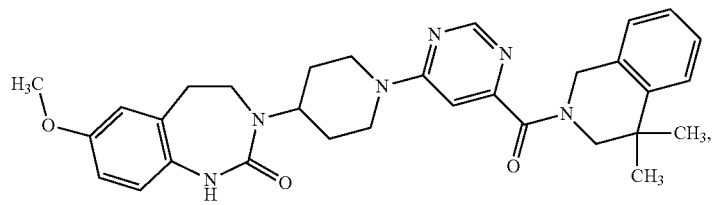 [SMILES: COc1ccc2c(c1)CCN(C1CCN(c3cc(C(=O)N4Cc5ccccc5C(C)(C)C4)ncn3)CC1)C(=O)N2] |
| (131) | 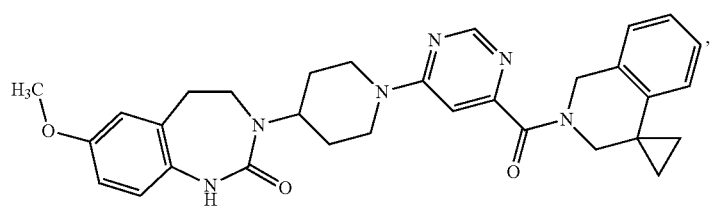 [SMILES: COc1ccc2c(c1)CCN(C1CCN(c3cc(C(=O)N4Cc5ccccc5C5(CC5)C4)ncn3)CC1)C(=O)N2] |
| (132) | 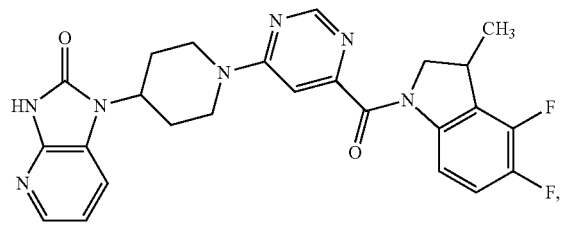 [SMILES: CC1CN(C(=O)c2cc(N3CCC(n4c(=O)[nH]c5ncccc54)CC3)ncn2)c2ccc(F)c(F)c21] |
| (133) | 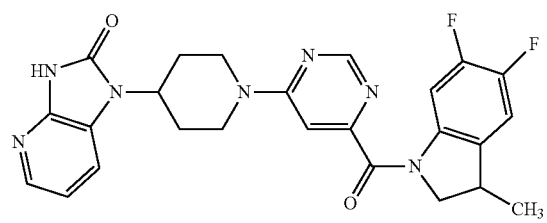 [SMILES: CC1CN(C(=O)c2cc(N3CCC(n4c(=O)[nH]c5ncccc54)CC3)ncn2)c2cc(F)c(F)cc21] |
| (134) | 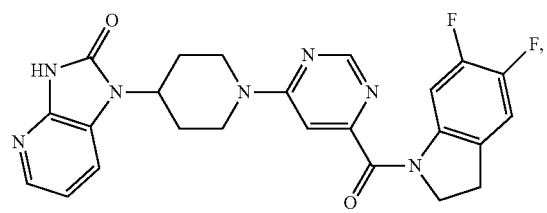 [SMILES: O=C(c1cc(N2CCC(n3c(=O)[nH]c4ncccc43)CC2)ncn1)N1CCc2cc(F)c(F)cc21] |

| No. | Structure |
|---|---|
| (135) | 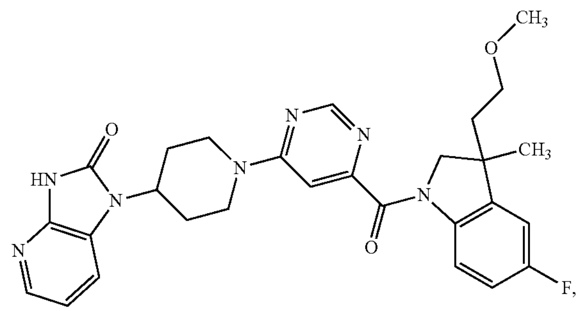 [SMILES: COCCC1(C)CN(C(=O)c2cc(N3CCC(n4c(=O)[nH]c5ncccc54)CC3)ncn2)c2ccc(F)cc21] |
| (136) | 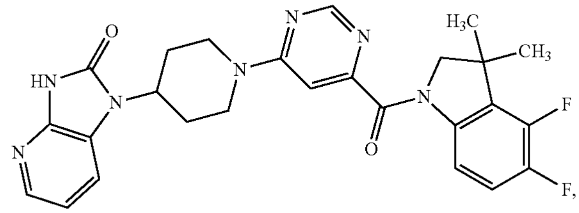 [SMILES: CC1(C)CN(C(=O)c2cc(N3CCC(n4c(=O)[nH]c5ncccc54)CC3)ncn2)c2ccc(F)c(F)c21] |
| (137) | 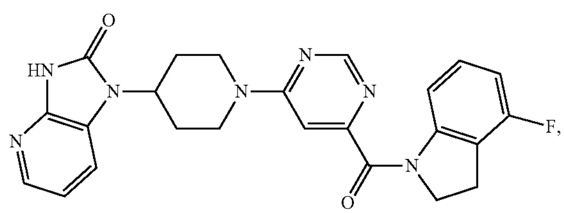 [SMILES: O=C(c1cc(N2CCC(n3c(=O)[nH]c4ncccc43)CC2)ncn1)N1CCc2c(F)cccc21] |
| (138) | 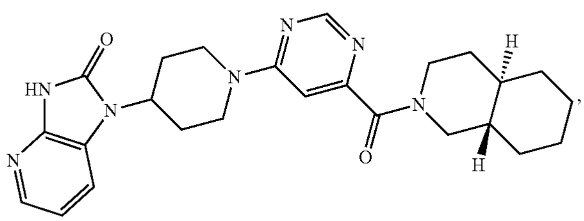 [SMILES: O=C(c1cc(N2CCC(n3c(=O)[nH]c4ncccc43)CC2)ncn1)N1CC[C@H]2CCCC[C@@H]2C1] |
| (139) | 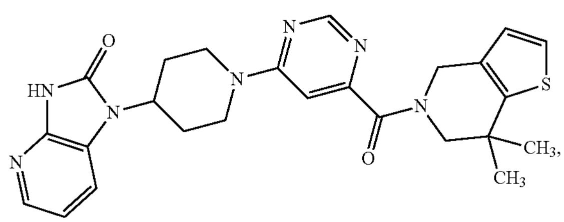 [SMILES: CC1(C)CN(C(=O)c2cc(N3CCC(n4c(=O)[nH]c5ncccc54)CC3)ncn2)Cc2ccsc21] |
| (140) | 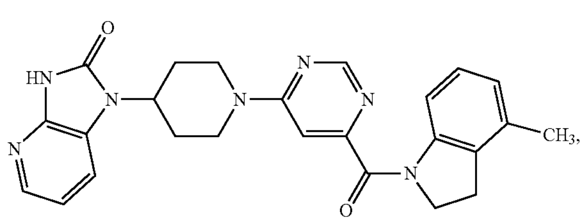 [SMILES: Cc1cccc2c1CCN2C(=O)c1cc(N2CCC(n3c(=O)[nH]c4ncccc43)CC2)ncn1] |

| No. | Structure |
|---|---|
| (141) | 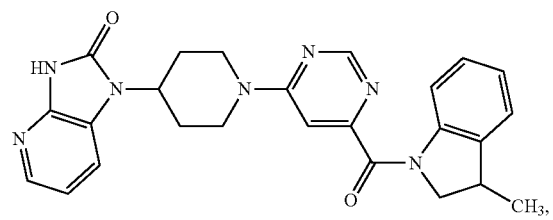 [SMILES: CC1CN(C(=O)c2cc(N3CCC(n4c(=O)[nH]c5ncccc54)CC3)ncn2)c2ccccc21] |
| (142) | 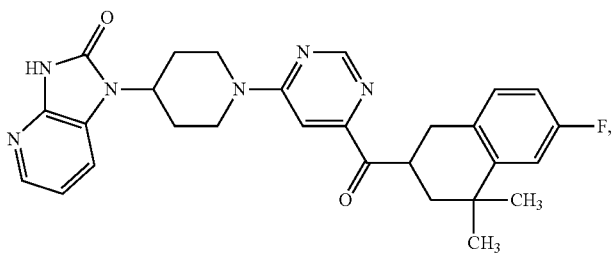 [SMILES: CC1(C)CC(C(=O)c2cc(N3CCC(n4c(=O)[nH]c5ncccc54)CC3)ncn2)Cc2ccc(F)cc21] |
| (143) | 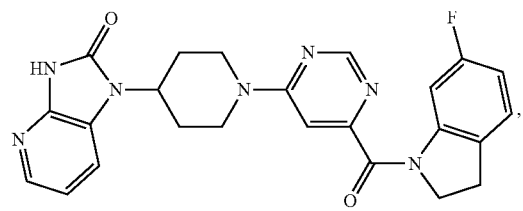 [SMILES: O=C(c1cc(N2CCC(n3c(=O)[nH]c4ncccc43)CC2)ncn1)N1CCc2ccc(F)cc21] |
| (144) | 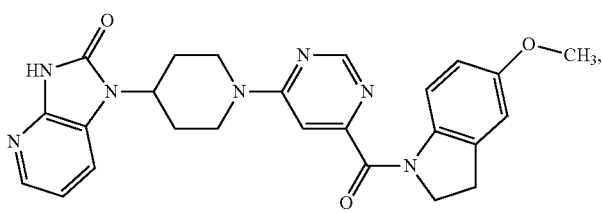 [SMILES: COc1ccc2c(c1)CCN2C(=O)c1cc(N2CCC(n3c(=O)[nH]c4ncccc43)CC2)ncn1] |
| (145) | 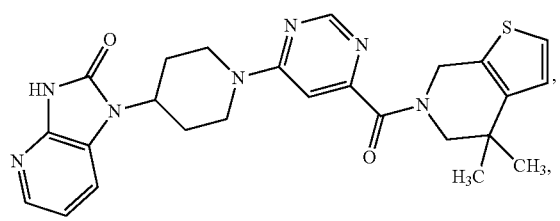 [SMILES: CC1(C)CN(C(=O)c2cc(N3CCC(n4c(=O)[nH]c5ncccc54)CC3)ncn2)Cc2sccc21] |
| (146) | 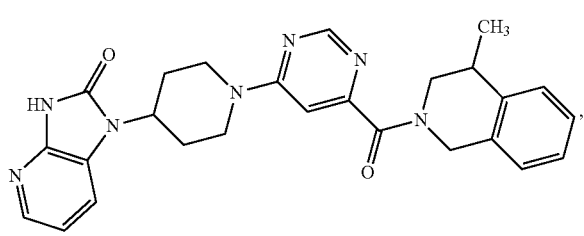 [SMILES: CC1CN(C(=O)c2cc(N3CCC(n4c(=O)[nH]c5ncccc54)CC3)ncn2)Cc2ccccc21] |
| (147) | 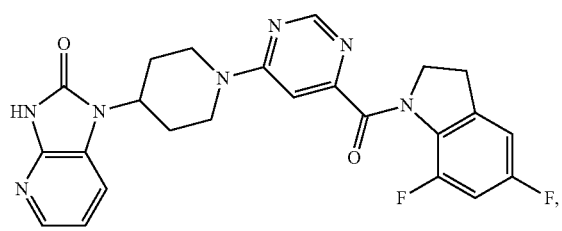 [SMILES: O=C(c1cc(N2CCC(n3c(=O)[nH]c4ncccc43)CC2)ncn1)N1CCc2cc(F)cc(F)c21] |

| No. | Structure |
|---|---|
| (148) | 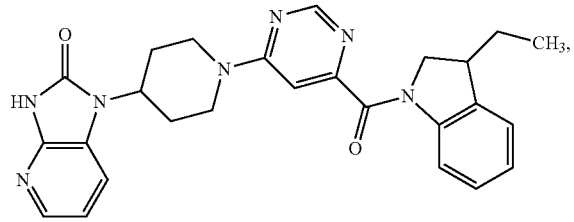 [SMILES: CCC1CN(C(=O)c2cc(N3CCC(n4c(=O)[nH]c5ncccc54)CC3)ncn2)c2ccccc21] |
| (149) | 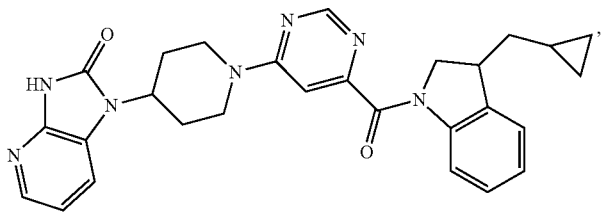 [SMILES: O=C(c1cc(N2CCC(n3c(=O)[nH]c4ncccc43)CC2)ncn1)N1CC(CC2CC2)c2ccccc21] |
| (150) | 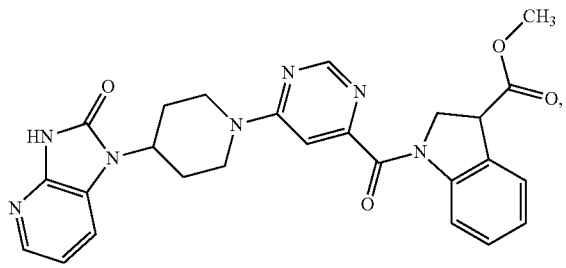 [SMILES: COC(=O)C1CN(C(=O)c2cc(N3CCC(n4c(=O)[nH]c5ncccc54)CC3)ncn2)c2ccccc21] |
| (151) | 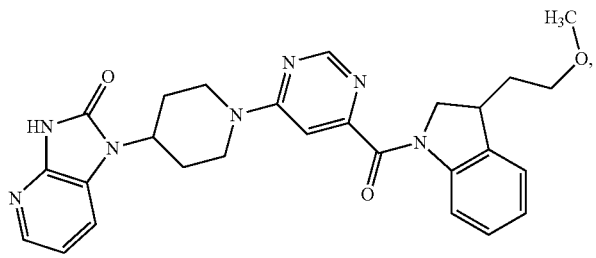 [SMILES: COCCC1CN(C(=O)c2cc(N3CCC(n4c(=O)[nH]c5ncccc54)CC3)ncn2)c2ccccc21] |
| (152) | 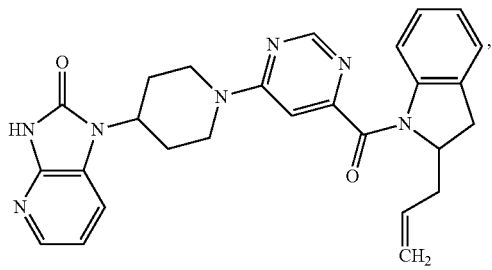 [SMILES: C=CCC1Cc2ccccc2N1C(=O)c1cc(N2CCC(n3c(=O)[nH]c4ncccc43)CC2)ncn1] |
| (153) | 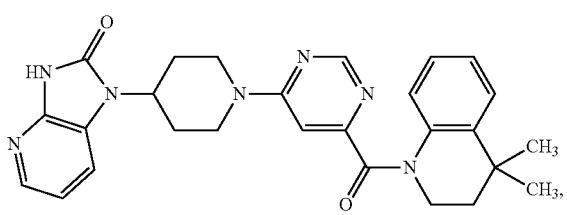 [SMILES: CC1(C)CCN(C(=O)c2cc(N3CCC(n4c(=O)[nH]c5ncccc54)CC3)ncn2)c2ccccc21] |

| No. | Structure |
|---|---|
| (154) | 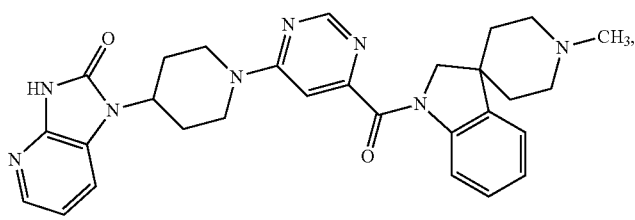 [SMILES: CN1CCC2(CC1)CN(C(=O)c1cc(N3CCC(n4c(=O)[nH]c5ncccc54)CC3)ncn1)c1ccccc12] |
| (155) | 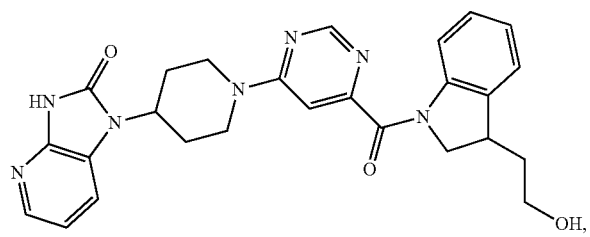 [SMILES: O=C(c1cc(N2CCC(n3c(=O)[nH]c4ncccc43)CC2)ncn1)N1CC(CCO)c2ccccc21] |
| (156) | 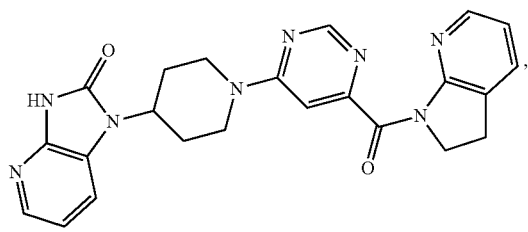 [SMILES: O=C(c1cc(N2CCC(n3c(=O)[nH]c4ncccc43)CC2)ncn1)N1CCc2cccnc21 ; ","] |
| (157) | 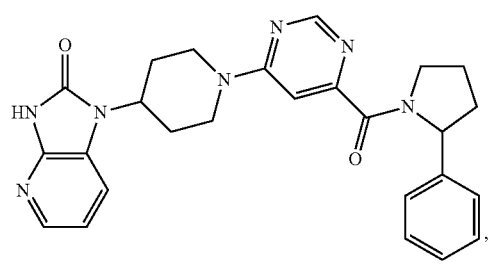 [SMILES: O=C(c1cc(N2CCC(n3c(=O)[nH]c4ncccc43)CC2)ncn1)N1CCCC1c1ccccc1] |
| (158) | 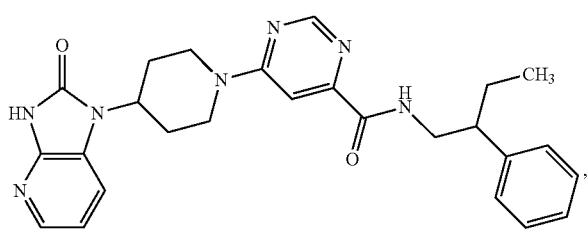 [SMILES: CCC(CNC(=O)c1cc(N2CCC(n3c(=O)[nH]c4ncccc43)CC2)ncn1)c1ccccc1] |
| (159) | 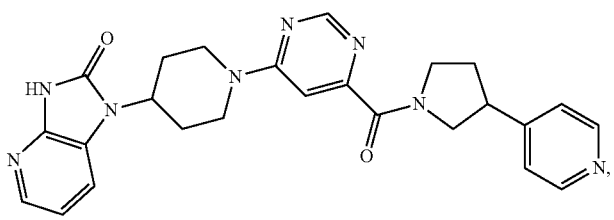 [SMILES: O=C(c1cc(N2CCC(n3c(=O)[nH]c4ncccc43)CC2)ncn1)N1CCC(c2ccncc2)C1] |

| No. | Structure |
|---|---|
| (160) | 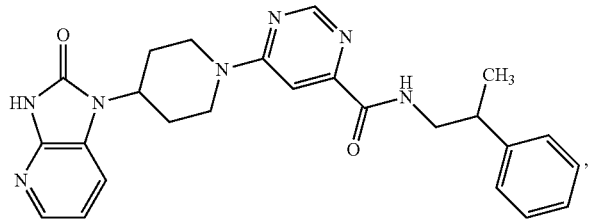 [SMILES: CC(CNC(=O)c1cc(N2CCC(n3c(=O)[nH]c4ncccc43)CC2)ncn1)c1ccccc1] |
| (178) | 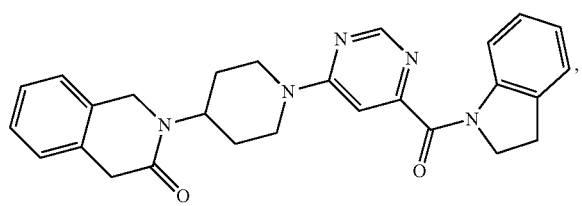 [SMILES: O=C(c1cc(N2CCC(N3Cc4ccccc4CC3=O)CC2)ncn1)N1CCc2ccccc21] |
| (179) | 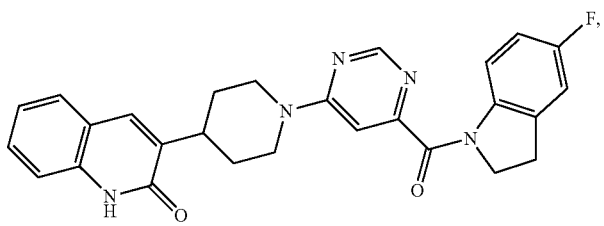 [SMILES: O=C(c1cc(N2CCC(c3cc4ccccc4[nH]c3=O)CC2)ncn1)N1CCc2cc(F)ccc21] |
| (180) | 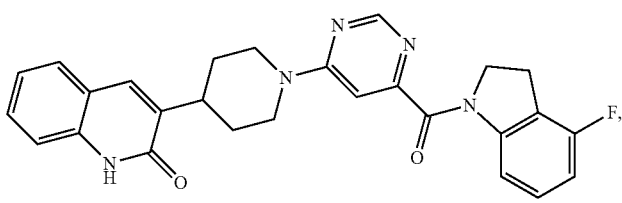 [SMILES: O=C(c1cc(N2CCC(c3cc4ccccc4[nH]c3=O)CC2)ncn1)N1CCc2c(F)cccc21] |
| (181) | 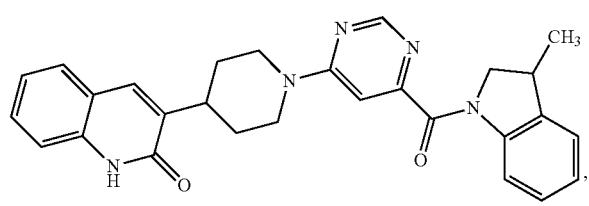 [SMILES: CC1CN(C(=O)c2cc(N3CCC(c4cc5ccccc5[nH]c4=O)CC3)ncn2)c2ccccc21 ; ","] |
| (182) | 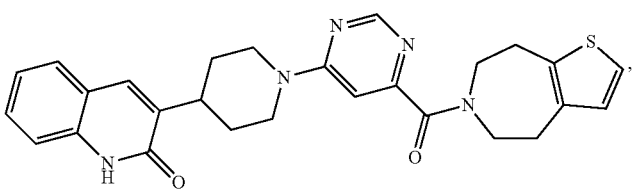 [SMILES: O=C(c1cc(N2CCC(c3cc4ccccc4[nH]c3=O)CC2)ncn1)N1CCc2ccsc2CC1] |
| (183) | 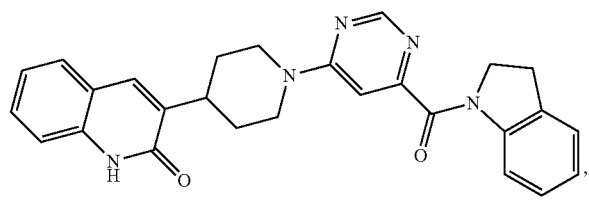 [SMILES: O=C(c1cc(N2CCC(c3cc4ccccc4[nH]c3=O)CC2)ncn1)N1CCc2ccccc21 ; ","] |

| No. | Structure |
|---|---|
| (184) | 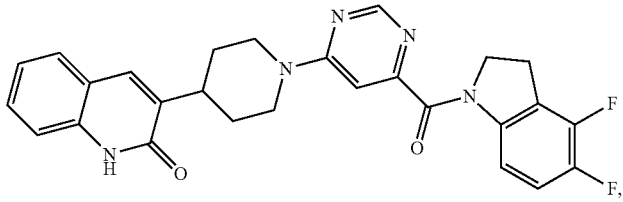 [SMILES: O=C(c1cc(N2CCC(c3cc4ccccc4[nH]c3=O)CC2)ncn1)N1CCc2c1ccc(F)c2F] |
| (185) | 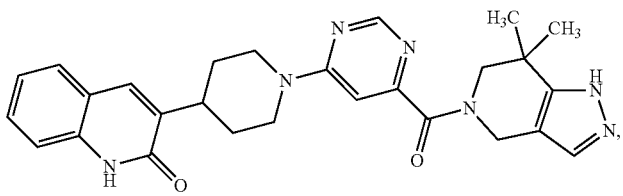 [SMILES: CC1(C)CN(C(=O)c2cc(N3CCC(c4cc5ccccc5[nH]c4=O)CC3)ncn2)Cc2cn[nH]c21] |
| (186) | 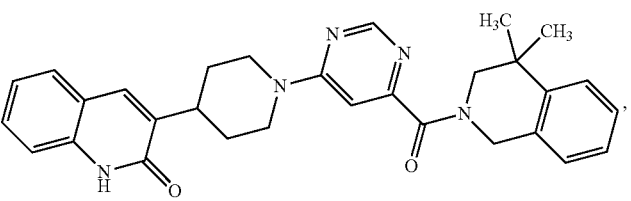 [SMILES: CC1(C)CN(C(=O)c2cc(N3CCC(c4cc5ccccc5[nH]c4=O)CC3)ncn2)Cc2ccccc21] |
| (187) | 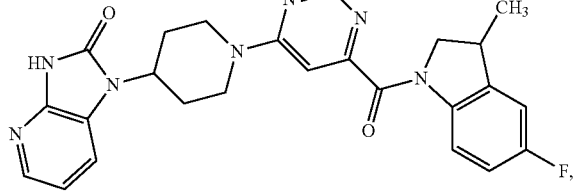 |
| (188) | 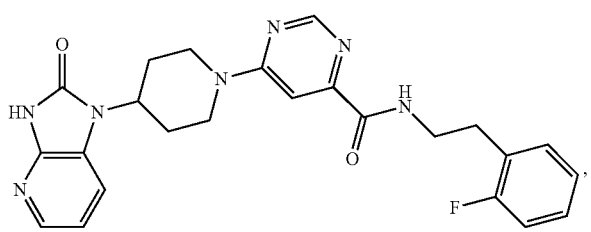 [SMILES: O=C(NCCc1ccccc1F)c1cc(N2CCC(n3c(=O)[nH]c4ncccc43)CC2)ncn1] |
| (193) | 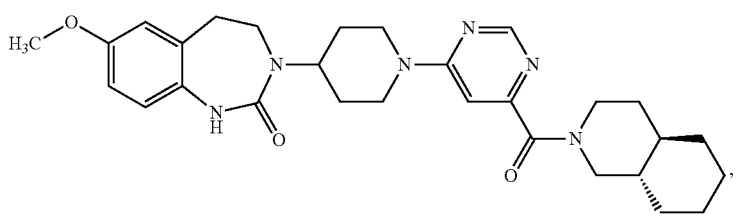 |
| (194) | 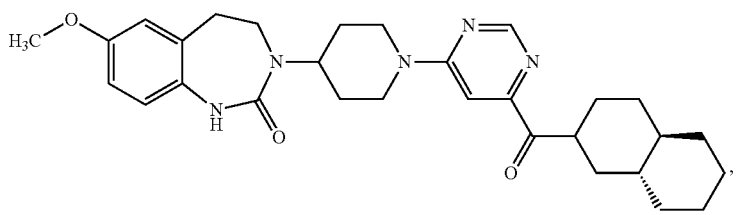 [SMILES: COc1ccc2c(c1)CCN(C1CCN(c3cc(C(=O)C4CC[C@H]5CCCC[C@@H]5C4)ncn3)CC1)C(=O)N2] |

| No. | Structure |
|---|---|
| (195) | 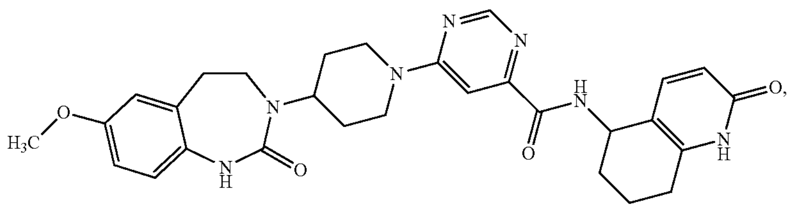 [SMILES: COc1ccc2c(c1)CCN(C1CCN(c3cc(C(=O)NC4CCCc5[nH]c(=O)ccc54)ncn3)CC1)C(=O)N2] |
| (196) | 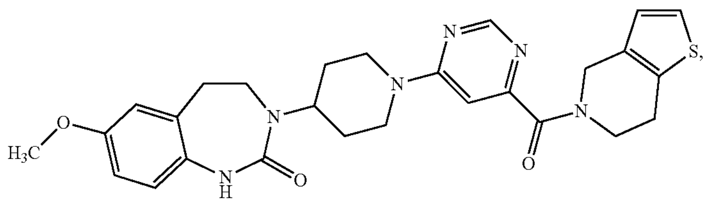 [SMILES: COc1ccc2c(c1)CCN(C1CCN(c3cc(C(=O)N4CCc5sccc5C4)ncn3)CC1)C(=O)N2] |
| (197) | 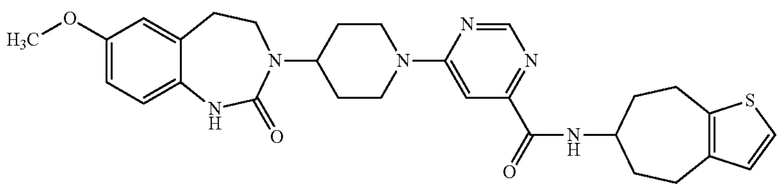 |
| (198) | 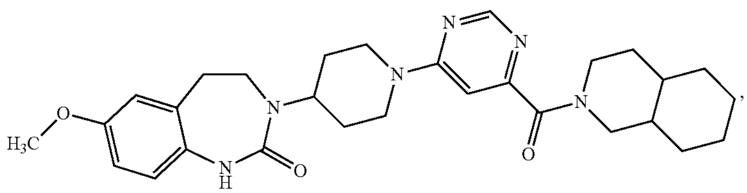 [SMILES: COc1ccc2c(c1)CCN(C1CCN(c3cc(C(=O)N4CCC5CCCCC5C4)ncn3)CC1)C(=O)N2] |
| (199) | 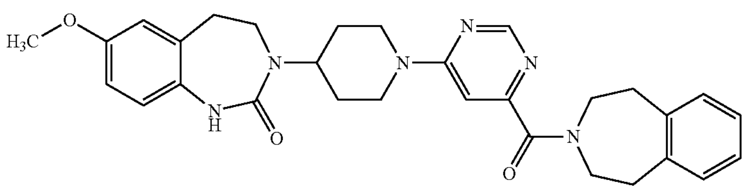 [SMILES: COc1ccc2c(c1)CCN(C1CCN(c3cc(C(=O)N4CCc5ccccc5CC4)ncn3)CC1)C(=O)N2] |
| (200) | 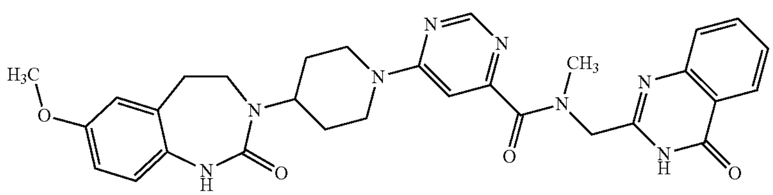 |
| (201) | 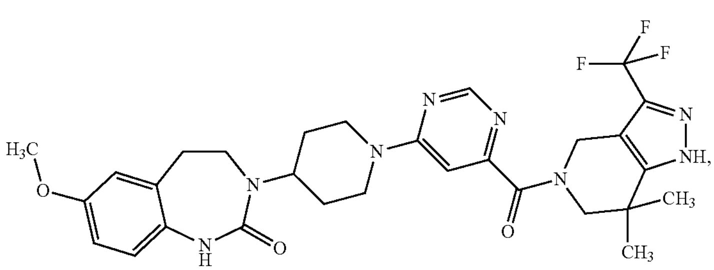 [SMILES: COc1ccc2c(c1)CCN(C1CCN(c3cc(C(=O)N4Cc5c(C(F)(F)F)n[nH]c5C(C)(C)C4)ncn3)CC1)C(=O)N2] |

-continued
| No. | Structure |
|---|---|
| (205) | 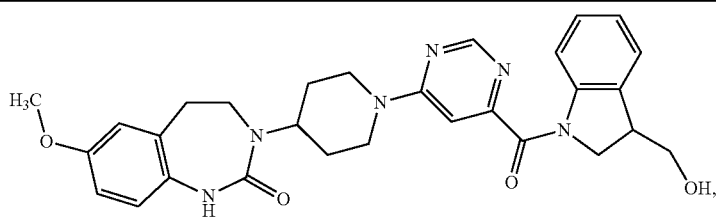 |
| (207) | 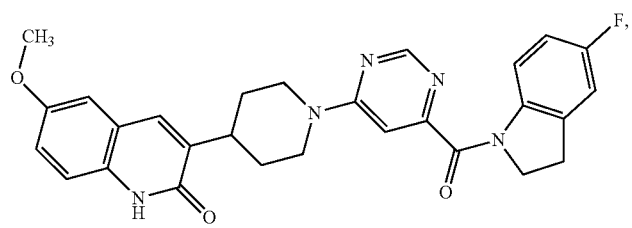 [SMILES: COc1ccc2[nH]c(=O)c(C3CCN(c4cc(C(=O)N5CCc6cc(F)ccc65)ncn4)CC3)cc2c1] |
| (208) | 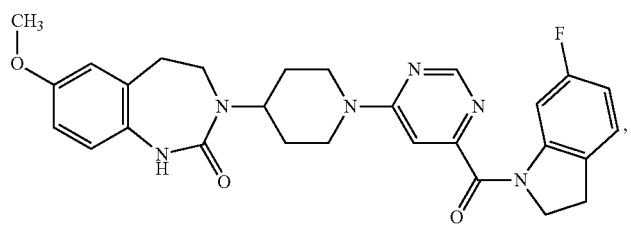 [SMILES: COc1ccc2c(c1)CCN(C1CCN(c3cc(C(=O)N4CCc5ccc(F)cc54)ncn3)CC1)C(=O)N2] |
| (209) | 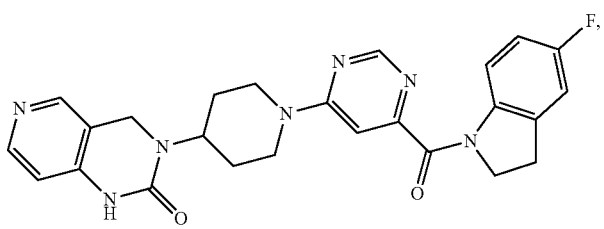 [SMILES: O=C(c1cc(N2CCC(N3Cc4cnccc4NC3=O)CC2)ncn1)N1CCc2cc(F)ccc21] |
| (212) | 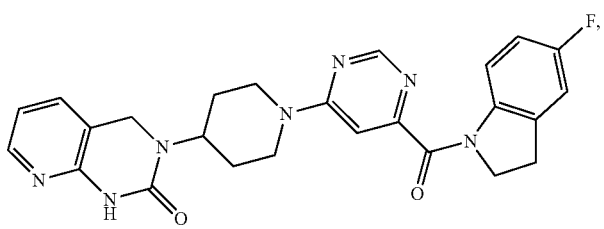 [SMILES: O=C(c1cc(N2CCC(N3Cc4cccnc4NC3=O)CC2)ncn1)N1CCc2cc(F)ccc21] |
| (214) | 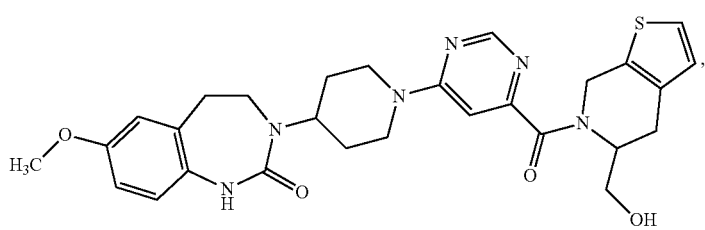 [SMILES: COc1ccc2c(c1)CCN(C1CCN(c3cc(C(=O)N4Cc5sccc5CC4CO)ncn3)CC1)C(=O)N2] |
| (216) | 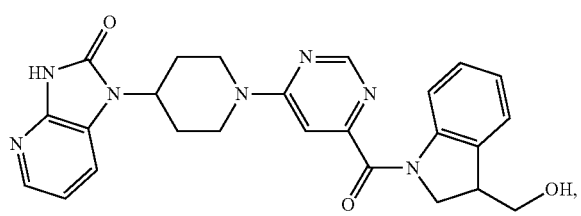 [SMILES: O=C(c1cc(N2CCC(n3c(=O)[nH]c4ncccc43)CC2)ncn1)N1CC(CO)c2ccccc21] |

| No. | Structure |
|---|---|
| (217) | 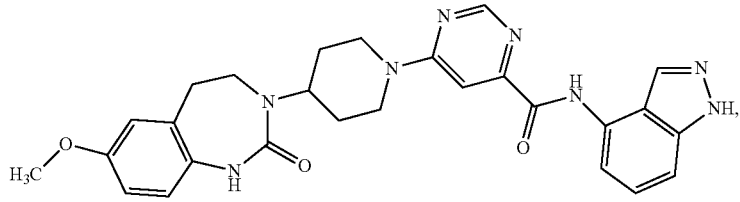 [SMILES: COc1ccc2c(c1)CCN(C1CCN(c3cc(C(=O)Nc4cccc5[nH]ncc45)ncn3)CC1)C(=O)N2] |
| (219) | 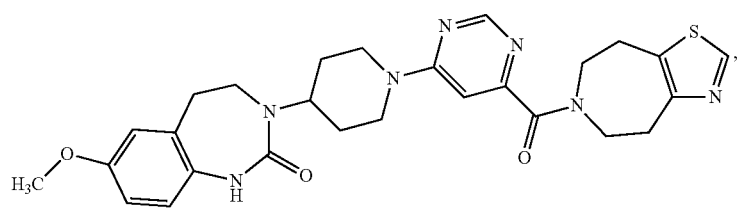 [SMILES: COc1ccc2c(c1)CCN(C1CCN(c3cc(C(=O)N4CCc5ncsc5CC4)ncn3)CC1)C(=O)N2] |
| (220) | 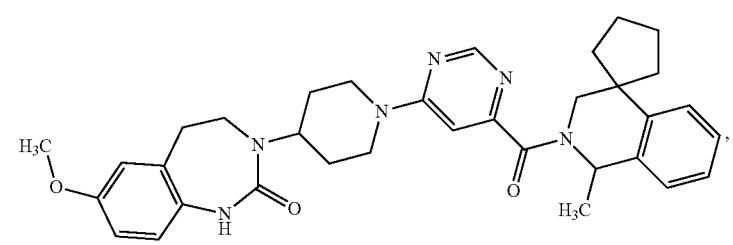 [SMILES: COc1ccc2c(c1)CCN(C1CCN(c3cc(C(=O)N4CC5(CCCC5)c5ccccc5C4C)ncn3)CC1)C(=O)N2] |
| (221) | 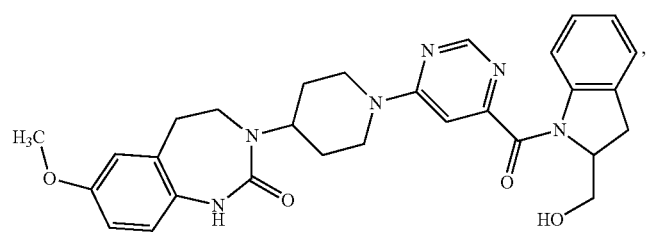 [SMILES: COc1ccc2c(c1)CCN(C1CCN(c3cc(C(=O)N4c5ccccc5CC4CO)ncn3)CC1)C(=O)N2] |
| (222) | 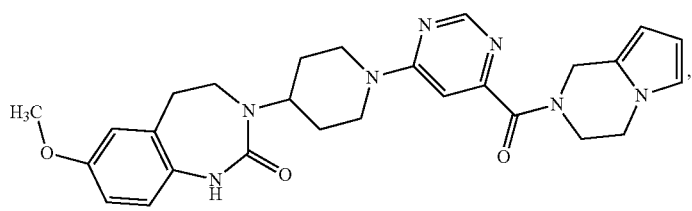 [SMILES: COc1ccc2c(c1)CCN(C1CCN(c3cc(C(=O)N4CCn5cccc5C4)ncn3)CC1)C(=O)N2] |
| (223) | 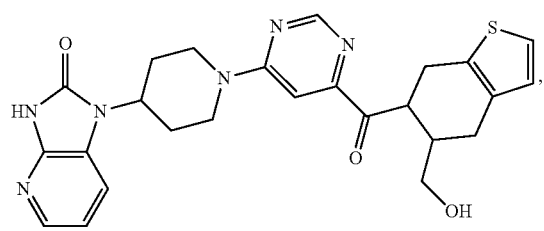 [SMILES: O=C(c1cc(N2CCC(n3c(=O)[nH]c4ncccc43)CC2)ncn1)C1Cc2sccc2CC1CO] |
| (224) | 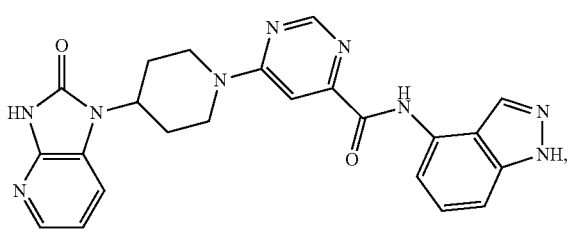 [SMILES: O=C(Nc1cccc2[nH]ncc12)c1cc(N2CCC(n3c(=O)[nH]c4ncccc43)CC2)ncn1] |

-continued
| No. | Structure |
|---|---|
| (225) | 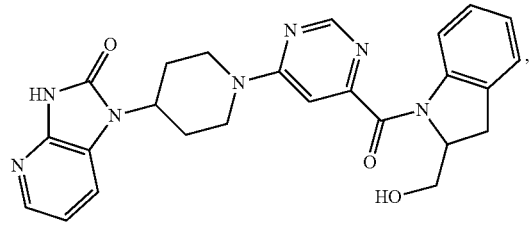 [SMILES: O=C(c1cc(N2CCC(n3c(=O)[nH]c4ncccc43)CC2)ncn1)N1c2ccccc2CC1CO] |
| (226) | 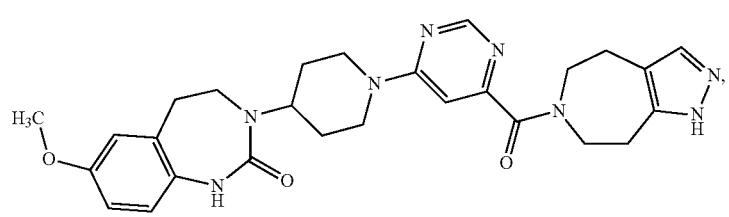 [SMILES: COc1ccc2c(c1)CCN(C1CCN(c3cc(C(=O)N4CCc5cn[nH]c5CC4)ncn3)CC1)C(=O)N2] |
| (227) | 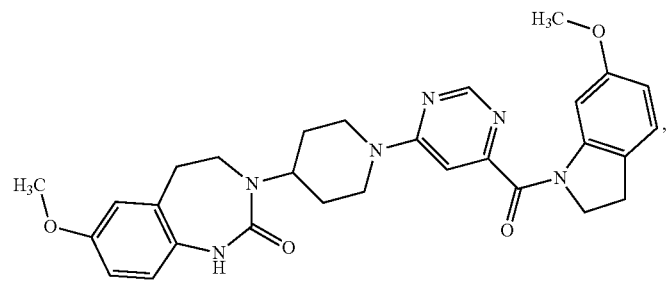 [SMILES: COc1ccc2c(c1)CCN(C1CCN(c3cc(C(=O)N4CCc5ccc(OC)cc54)ncn3)CC1)C(=O)N2] |
| (228) | 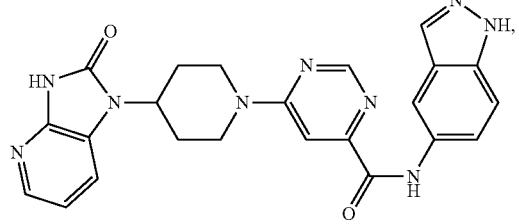 |
| (229) | 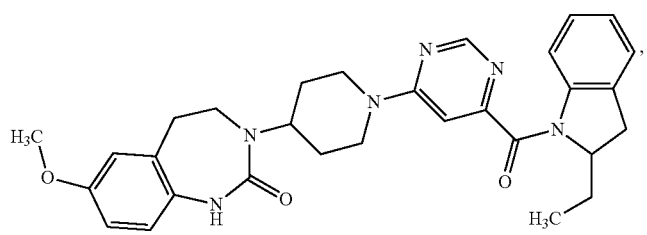 [SMILES: CCC1Cc2ccccc2N1C(=O)c1cc(N2CCC(N3CCc4cc(OC)ccc4NC3=O)CC2)ncn1] |
| (230) | 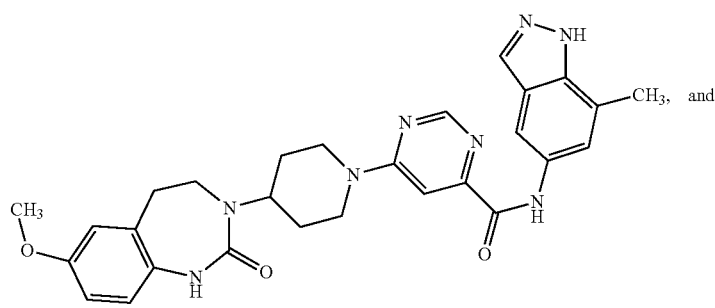 [SMILES: COc1ccc2c(c1)CCN(C1CCN(c3cc(C(=O)Nc4cc(C)c5[nH]ncc5c4)ncn3)CC1)C(=O)N2] |

| No. | Structure |
|---|---|
| (231) | 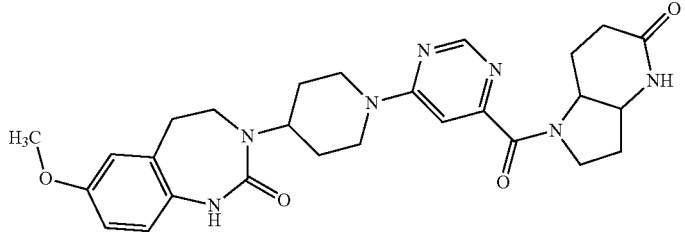 [SMILES: COc1ccc2c(c1)CCN(C1CCN(c3cc(C(=O)N4CCC5NC(=O)CCC54)ncn3)CC1)C(=O)N2] | or a tautomer or salt thereof.

20. A physiologically acceptable salt of a compound according to any one of claims 1-19.

21. A pharmaceutical composition comprising a compound according to any one of claims 1-19, or a physiologically acceptable salt thereof, and a carrier or diluent.

22. A method for inhibiting CGRP, wherein the diseases treatable by such inhibition include migraine and cluster headache which comprises administering to a host in need of such treatment a therapeutically effective amount of a compound according to any one of claims 1-19, or a physiologically acceptable salt thereof.

* * * * *